United States Patent
Acton et al.

(10) Patent No.: US 7,045,532 B2
(45) Date of Patent: May 16, 2006

(54) ACE-2 MODULATING COMPOUNDS AND METHODS OF USE THEREOF

(75) Inventors: Susan L. Acton, Lexington, MA (US); Timothy D. Ocain, Framingham, MA (US); Alexandra E. Gould, Cambridge, MA (US); Natalie A. Dales, Arlington, MA (US); Bing Guan, Brighton, MA (US); James A. Brown, Framingham, MA (US); Michael Patane, Andover, MA (US); Vivek J. Kadambi, Boxboro, MA (US); Michael Solomon, Medford, MA (US); Alain Stricker-Krongrad, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 302 days.

(21) Appl. No.: 09/999,781

(22) Filed: Oct. 31, 2001

(65) Prior Publication Data

US 2004/0082496 A1    Apr. 29, 2004

Related U.S. Application Data

(63) Continuation-in-part of application No. 09/870,382, filed on May 29, 2001, now abandoned, which is a continuation-in-part of application No. 09/704,216, filed on Nov. 1, 2000, now abandoned, which is a continuation-in-part of application No. 09/635,501, filed on Aug. 9, 2000, which is a continuation-in-part of application No. 09/561,759, filed on Apr. 28, 2000, now Pat. No. 6,632,830.

(60) Provisional application No. 60/371,741, filed on Oct. 19, 2001, provisional application No. 60/171,052, filed on Dec. 16, 1999, provisional application No. 60/132,034, filed on Apr. 30, 1999.

(51) Int. Cl.
  A61K 31/194    (2006.01)
  A61K 31/198    (2006.01)
  A61K 31/39     (2006.01)
  A61K 31/415    (2006.01)
  A61K 31/4172   (2006.01)

(52) U.S. Cl. ............ 514/311; 514/357; 514/359; 514/361; 514/365; 514/367; 514/374; 514/376; 514/378; 514/392; 514/400; 514/406; 514/423; 514/438; 514/443; 514/466; 514/471; 514/561; 514/563; 514/564; 546/173; 546/334; 548/127; 548/163; 548/204; 548/217; 548/221; 548/228; 548/235; 548/247; 548/255; 548/324.5; 548/339.1; 548/339.5; 548/375.1; 548/531; 548/540; 548/557

(58) Field of Classification Search ........... 514/311, 514/357, 359, 361, 365, 367, 374, 378, 392, 514/400, 406, 423, 438, 443, 466, 471, 561, 514/563, 564, 376; 546/173, 334; 548/127, 548/163, 204, 217, 221, 235, 247, 255, 324.5, 548/339.1, 339.5, 375.1, 531, 540, 557, 228; 549/58, 76, 444, 493

See application file for complete search history.

(56) References Cited

U.S. PATENT DOCUMENTS

| | | | |
|---|---|---|---|
| 4,591,648 A | 5/1986 | Jones et al. | 548/334 |
| 4,833,128 A * | 5/1989 | Solomon et al. | 514/23 |
| 5,110,799 A | 5/1992 | Tolman et al. | 514/19 |
| 5,155,118 A | 10/1992 | Carini et al. | 514/381 |
| 5,338,649 A | 8/1994 | Inaba et al. | 430/430 |
| 5,481,018 A | 1/1996 | Athey et al. | 558/442 |
| 5,665,371 A | 9/1997 | Hoermann | 424/423 |
| 5,744,157 A * | 4/1998 | Droge | 424/450 |
| 5,827,820 A | 10/1998 | du Moulin et al. | 514/2 |
| 6,194,556 B1 * | 2/2001 | Acton et al. | 536/23.2 |
| 6,201,021 B1 | 3/2001 | Ohuchida et al. | 514/558 |
| 6,632,830 B1 * | 10/2003 | Acton et al. | 514/365 |

FOREIGN PATENT DOCUMENTS

| | | |
|---|---|---|
| DE | 3219113 | 11/1983 |
| WO | WO 91/00724 | 1/1991 |
| WO | WO 00/18899 | 4/2000 |
| WO | WO-00/66104 A2 * | 11/2000 |

OTHER PUBLICATIONS

Roberts et al., *Basic Principles of Organic Chemistry*, 2nd ed. Menlo Park: W.A. Benjamin, Inc., pp. 1208-1210 (1977).

* cited by examiner

Primary Examiner—Jeffrey Edwin Russel
(74) Attorney, Agent, or Firm—Fish & Richardson P.C.

(57) ABSTRACT

ACE-2 inhibitors for the treatment of body weight and related disorders are disclosed. ACE-2 inhibitors include peptides and small molecules. Examples of small molecule ACE-2 inhibitors include compounds of formula (I):

$$Z\text{-}A \qquad (I)$$

Wherein Z is a zinc coordinating moiety and A is an amino-acid mimicking moiety, and pharmaceutically acceptable salts thereof. Methods of using the inhibitors and pharmaceutical compositions containing the inhibitors to treat a body weight disorder, to decrease appetite, to increase muscle mass, to decrease body fat, to treat diabetes and to treat a state associated with altered lipid metabolism, are also described.

40 Claims, 1 Drawing Sheet

ACE-2 MODULATING COMPOUNDS AND METHODS OF USE THEREOF

RELATED APPLICATIONS

This application is a continuation-in-part of U.S. patent application Ser. No. 09/870,382, filed on May 29, 2001, (Now Abandoned), which is a continuation-in-part of U.S. patent application Ser. No. 09/704,216, filed on Nov. 1, 2000, (Now Abandoned), which is a continuation-in-part of U.S. patent application Ser. No. 09/561,759, filed on Apr. 28, 2000, (Now U.S. Pat. No. 6,632,830), which claims the benefit of U.S. Provisional Application Serial No. 60/171,052, entitled "ACE-2 Inhibiting Compounds and Methods of Use Thereof," filed on Dec. 16, 1999 and U.S. Provisional Application Serial No. 60/132,034, entitled "ACE-2 Inhibiting Compounds and Methods of Use Thereof," filed on Apr. 30, 1999; this application also claims the benefit of U.S. Provisional Application Serial No. 60/371,741 entitled "ACE-2 Modulating Compounds and Methods of Use Thereof," filed on Oct. 19, 2001; this application is also a continuation-in-part of U.S. patent application Ser. No. 09/635,501, entitled "Angiotensin Converting Enzyme Homolog and Uses Therefor," filed Aug. 9, 2000; the entire contents of each of the aforementioned applications are hereby expressly incorporated herein by reference.

BACKGROUND OF THE INVENTION

Obesity is generally defined as the excessive accumulation of body fat. A body weight 20% over that in standard height-weight tables is widely accepted as an obese condition (except for certain heavily muscled persons). Since 1985 obesity has been recognized as a chronic disease, and is the second leading cause of preventable death in the United States.

The increasing prevalence of obesity and preobesity, or overweight, is a major public health issue in the United States. Approximately one third of adults are estimated to be obese. According to the U.S. Bureau of the Census, approximately 58 million American adults (26 million men and 32 million women) are obese. Socioepidemiologic studies suggest that age, socioeconomic status, and genetics may be important risk factors. For example, there is a two-fold increase in the prevalence of obesity between the ages of 20 and 55. Obesity is also far more common among black than white women, occurring in about 60% of middle-aged black women ("The Merck Manual of Diagnosis and Therapy", Berkow et al., 16th Edition, 1992, Merck Research Laboratories).

Obesity has important medical consequences. Studies suggest a relationship between obesity and an increased risk of cardiovascular disease, including coronary heart disease and stroke, and hypertension. Hypertension, or high blood pressure, is the most important risk factor predisposing to stroke and is an important risk factor predisposing to coronary atherosclerosis.

One important system involved in regulating blood pressure is the renin-angiotensin-aldosterone system (RAS). In this system, renin, a proteolytic enzyme formed in the granules of the juxtaglomerular apparatus cells of the kidney, catalyzes the conversion of angiotensinogen (a plasma protein) into angiotensin I, a decapeptide. This inactive product is then hydrolyzed by angiotensin converting enzyme (ACE) to an octapeptide, angiotensin II, which is a potent vasoconstrictor and also stimulates the release of aldosterone. Aldosterone is an adrenal cortex hormone that promotes the retention of salt and water by the kidneys, and thus increases plasma volume, resulting in an increase in blood pressure.

ACE is produced in the endothelium of somatic tissues and in the testis. It is expressed ubiquitously in the vasculature, including highly vascularized organs such as the lung, heart, pancreas, and kidney. ACE, also referred to as peptidyl dipeptidase A (EC 3.4.15.1) and kininase II, is a metallopeptidase, more particularly, a zinc dipeptidase which, in addition to angiotensin I, can also hydrolyze other biologically active polypeptides, such as kinins, e.g., bradykinin. Bradykinin is a vasodilator, which acts, at least in part, by inducing the release of vasodilator prostaglandins, and which is inactivated upon hydrolysis by ACE. Hence, ACE activity regulates blood pressure, at least in part by producing angiotensin II, a vasoconstrictor, and by inactivating bradykinin, a vasodilator.

Given its wide tissue distribution and its broad substrate specificity, ACE plays a pivotal role in the RAS regulation of blood pressure.

SUMMARY OF INVENTION

Recently, an ACE-like peptidase, termed ACE-2 (GenBank Accession No. AF291820), has been described (Donoghue, et al. (2000) Circ. Res. 87:e1–e9). Although this enzyme, like ACE, can cleave angiotensin I, ACE-2 differs from ACE in being a carboxypeptidase and the angiotensin I cleavage product is a nonapeptide (Ang1–9). Also unlike ACE, ACE-2 expression is highly restricted to the heart, kidney, large intestine, small intestine, adipose tissue and testis. ACE-2, however, is also produced by the endothelium like ACE.

The invention pertains, at least in part, to the treatment of ACE-2 associated states, such as body weight disorders, e.g., diabetes, such as obesity, anorexia, and cachexia, by targeting the expression or activity of an ACE homologue, referred to herein as ACE-2. The invention also relates to compounds that modulate ACE-2 associated states, (e.g., body weight disorders, etc.) via ACE-2 activity.

Another aspect of the invention comprises administering, e.g., systemically (.eg., orally) or locally to a subject, an effective amount of an ACE-2 modulating compound. Depending on the ACE-2 associated state, the ACE-2 modulating compound can be an ACE-2 agonist, an ACE-2 inverse agonist, or an ACE-2 antagonist. In an embodiment, an ACE-2 inhibitor (e.g., antagonist) is administered to a subject with a body weight disorder such as obesity, such that the body weight disorder is treated. In another example, an ACE-2 activator (e.g., agonist) is administered to a subject with a body weight disorder such as anorexia or cachexia, such the body weight disorder is treated.

The invention also encompasses methods of treatment using ACE-2 modulating compounds such as activators (e.g., agonists), inverse agonists, and inhibitors (e.g., antagonists) of ACE-2. Examples of ACE-2 modulating compounds include small molecules, and organic and inorganic compounds.

In an embodiment, the invention pertains, at least in part, to a method for the treatment of a body weight disorder in a subject. The method includes administering to a subject an effective amount of an ACE-2 modulating compound, such that the body weight disorder in the subject is treated.

In another embodiment, the invention pertains, at least in part, to a method for decreasing the appetite of a subject. The method includes administering to the subject an effective amount of an ACE-2 modulating compound, such that the appetite of the subject is decreased.

In another embodiment, the invention includes a method for increasing muscle mass in a subject. The method includes administering to a subject an effective amount of an ACE-2 modulating compound, such that the muscle mass of the subject is increased.

In yet another embodiment, the invention pertains to a method for decreasing the body fat content of a subject. The method includes administering to the subject an effective amount of an ACE-2 modulating compound, such that the amount of fatty tissue of the subject is decreased.

In a further embodiment, the invention pertains, at least in part, to a method of promoting weight gain in a subject, by administering to the subject an effective amount of an ACE-2 activator (e.g., agonist). The subject may be suffering from anorexia or cachexia.

In another further embodiment, the invention also pertains at least in part, to a method of reducing body fat in a subject, by administering to the subject an effective amount of an ACE-2 inhibitor (e.g., antagonist).

In yet another embodiment, the invention pertains to a method for treating diabetes in a subject. The method includes administering to the subject an effective amount of an ACE-2 modulating compound.

In another further embodiment, the invention also includes a method for treating a state associated with lipid metabolism in a subject. The method includes administering to the subject an effective amount of an ACE-2 modulating compound, such that the state is treated.

In another embodiment, the invention also pertains to a method for treating atherosclerosis in a subject. The method includes administering to the subject an effective amount of an ACE-2 modulating compound.

Another aspect of the invention features transgenic non-human animals which include (and preferably express) a heterologous form of an ACE-2 gene described herein, or which misexpress an endogenous ACE-2 gene (e.g., an animal in which expression of one or more of the subject ACE-2 genes is disrupted, e.g., a "knock-out" mouse). Such transgenic animals can serve as in vivo models for studying cellular and/or tissue disorders comprising mutated or mis-expressed ACE-2 alleles or for use in drug screening, e.g., to identify modulators of the invention. Alternatively, such transgenic animals can be useful for expressing recombinant ACE-2 polypeptides.

As demonstrated herein, mice completely lacking functional ACE-2 protein exhibit a significantly lower percentage of body fat and a lower body weight compared to similarly aged wild-type males of the same strain. In particular, knock-out mice in which the gene encoding ACE-2 is not biologically active exhibit a significantly lower percentage of body fat and a lower body weight compared to similarly aged wild-type males of the same strain.

The invention also relates to assays designed to screen for compounds or compositions that modulate ACE-2 activity, i.e., compounds or compositions that act as activators (e.g., agonists), inhibitors (e.g., antagonists), or inverse agonists of ACE-2, and thereby identify modulators of the invention, e.g., useful for treating body weight disorders. To this end, cell-based assays or non-cell-based assays, including, e.g., cell lysate assays, can be used to detect compounds that interact with, e.g., act as a ligand or substrate, of ACE-2. The cell-based assays are advantageous in that they are useful in the identification of compounds that affect ACE-2 biological activity, but do not necessarily interact directly with ACE-2.

The invention also relates to assays designed to screen for compounds or compositions that modulate ACE-2 gene expression and thereby identify modulators of the invention. For example, cell-based assays or cell lysate assays (e.g., in vitro transcription or translation assays) can be used to screen for compounds or compositions that modulate ACE-2 transcription (e.g., compounds that modulate the expression, production, or activity of transcription factors involved in ACE-2 gene expression; or polynucleotides that form triple helical structures with an ACE-2 regulatory region and inhibit transcription of the ACE-2 gene). Alternatively, cell-based assays or cell-lysate assays can be used to screen for compounds or compositions that modulate translation of ACE-2 transcripts (e.g., antisense and ribozyme molecules).

In yet another embodiment, the cell-based assays or cell-lysate assays can be used to test polynucleotide constructs designed to modify the expression of the ACE-2 gene in vivo. Such constructs include polynucleotide constructs designed for gene therapy useful for the methods described, e.g., expression constructs or gene replacement constructs that place the ACE-2 gene under the control of an inducible promoter system or a constitutive promoter system.

The present invention includes the use of ACE-2 therapeutics and/or ACE-2 modulating compounds for treating ACE-2 associated states, such as body weight disorders, which are described in more detail below. ACE-2 therapeutics or ACE-2 modulating compounds include activators (e.g., agonists), inverse agonists, and inhibitors (e.g., antagonists) of ACE-2. Examples of ACE-2 modulating compounds include small molecules, organic and inorganic compounds, and peptides and antibodies, as well as nucleotide sequences that can be used to inhibit ACE-2 gene expression (e.g., antisense, triplex DNA, and ribozyme molecules), and gene or regulatory sequence replacement constructs designed to enhance ACE-2 gene expression (e.g., expression constructs that place the ACE-2 gene under the control of a strong promoter system).

In a further embodiment, the invention also pertains to a method for modulating ACE-2, by contacting ACE-2 with an ACE-2 modulating compound, such that ACE-2 is modulated. The ACE-2 modulating compound may be any compound described herein.

The invention also encompasses the use of such compounds and compositions, including gene therapy approaches, that modulate ACE-2 activity or ACE-2 gene expression to treat body weight disorders, and other ACE-2 associated states.

DETAILED DESCRIPTION OF THE INVENTION

Figure 1:
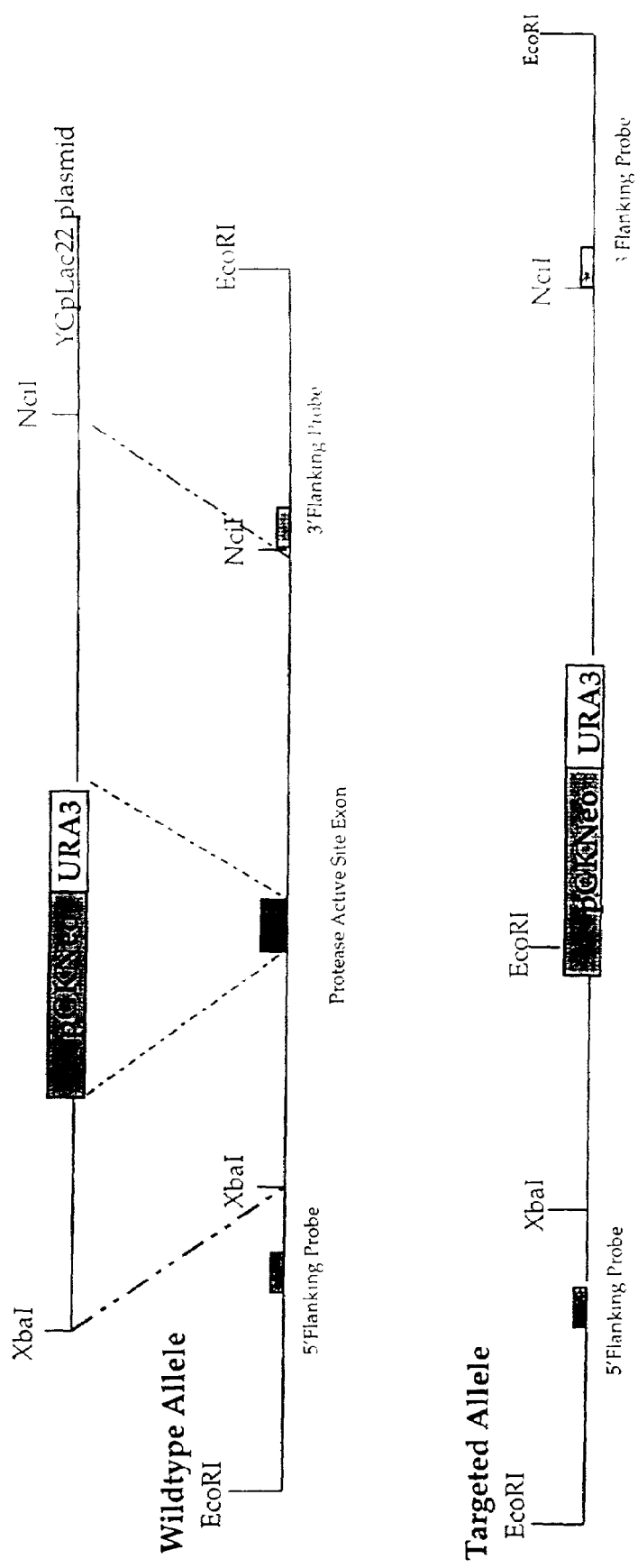
FIG. 1 is a schematic diagram of the construction of the ACE-2 targeting vector. To generate the targeted allele, the exon encoding the active site of ACE-2 was replaced with a pGKNEO/URA3 cassette by homologous recombination in yeast. The 5' flanking probe identified the presence of wild type and targeted alleles using Southern analysis.

Given its limited tissue expression and ACE-like catalytic activity, as well as the relationship between hypertension and obesity, ACE-2 is a target for the development of methods of treating body weight disorders, and other ACE-2 associated states.

The invention pertains, at least in part, to a method for the treatment of an ACE-2 associated states, e.g., a body weight disorder in a subject. The method includes administering to a subject an effective amount of an ACE-2 modulating compound, such that the ACE-2 associated state in the subject is treated. The invention also pertains to compounds and methods which inhibit the activity of ACE-2.

The invention is based at least in part on the discovery of a specific role for ACE-2 in body weight regulation and other processes. The ACE-2 gene (GenBank Accession No. 291820) encodes a protein having regions which are significantly homologous to regions of known angiotensin converting enzymes (ACEs). The genes and proteins used in the methods disclosed herein are referred to as Angiotensin Converting Enzyme 2 (ACE-2) genes and proteins, which are described in U.S. Pat. No. 6,194,556, and Donoghue, et al., supra, each of which is incorporated herein by reference in its entirety.

ACE-2 is a protein having regions which are significantly homologous to regions of known angiotensin converting enzymes (ACEs). The sequence of the full length cDNA encoding ACE-2 was determined from a clone obtained from a cDNA library prepared from mRNA of a human heart of a subject who had congestive heart failure. The cDNA encoding the full length human ACE-2 protein and comprising 5' and 3' untranslated regions is 3396 nucleotides long (SEQ ID NO: 1). The mature ACE-2 protein is 787 amino acids in length (amino acid residues 19 to 805 of the full length peptide shown in SEQ ID NO: 2).

The ACE-2 polypeptide is an angiotensin converting enzyme homologue and shares sequence identity with endothelial ACE and testicular ACE. The ACE-2 protein further comprises functional domains shared by ACEs. For example, ACE-2 contains a single catalytic domain from about amino acids 147 to 555 of SEQ ID NO:2, which is encoded by the nucleotide sequence from residues 520 to 1746 of SEQ ID NO:1, and referred to herein as the ACE-2 catalytic domain. This domain is approximately 42% identical to each of the two catalytic domains in endothelial ACE (Donoghue, et al. supra). ACE-2 also comprises a zinc binding domain (ZBD) within the catalytic domain from about amino acid 374 to amino acid 378 of SEQ ID NO:2, which is encoded by the nucleotide sequence from nucleotide 1201 to 1215 of SEQ ID NO:1, and referred to herein as a minimum zinc binding domain. It is likely that at least some of the adjacent amino acids participate in binding zinc. The sequence of the minimum zinc binding domain is identical to the zinc binding domain that is present in all ACE proteins which have been identified as being located in the catalytic site of the enzyme (Lattion et al. (1989) FEBS Letters 252:99). As the sequence encompassing amino acids 372 to 381 of SEQ ID NO:2 are conserved in all ACE proteins, it is likely that amino acids 372, 373, 379, 380, and 381 of SEQ ID NO:2 are involved in binding zinc. In addition, all the amino acids which have been reported as interacting with the zinc atom or involved in catalysis in ACE proteins are present in ACE-2. Thus, by analogy, His 374, 378 and Glu 402 are probably the amino acids coordinating the zinc atom, and Glu 375, His 417, and Glu 406 are involved in the catalytic activity of ACE-2.

ACE-2 has a hydrophobic region in its C-terminal domain from about amino acid 741 to about amino acid 765. This hydrophobic region is thought to be a transmembrane domain, similar to that present in ACE proteins. A BLAST search (Altschul et al. J. Mol Biol. (1990) 215:403) of the nucleic acid and the amino acid sequences of ACE-2 revealed that certain portions of the ACE-2 protein and cDNA have a significant homology to certain regions of previously identified angiotensin converting enzymes. Two forms of ACE proteins have been described previously: a larger form, referred to as endothelial or somatic ACE, since it is present in numerous somatic tissues, including vascular endothelium, renal tubular epithelium, ciliated gut epithelium, stimulated macrophages, areas of the brain and testis. The smaller form of ACE is referred to as the testicular form, since it is found essentially only in developing sperm cells in the testis.

The specific role of the ACE-2 protein in vivo was investigated by engineering ACE-2 "knock out" mice in which most of the endogenous ACE-2 gene coding sequence was deleted, thereby creating mice which are unable to produce biologically active ACE-2 protein.

To produce the ACE-2 knock out mice, human ACE-2 gene sequences were utilized to isolate and clone the murine ACE-2 gene. A murine ACE-2 targeting construct was then generated which was designed to delete the majority of the murine ACE-2 coding sequence upon homologous recombination with the endogenous murine ACE-2 gene. Embryonic stem (ES) cells containing the disrupted ACE-2 gene were produced, isolated and microinjected into murine blastocysts to yield mice chimeric for cells containing a disrupted ACE-2 gene. Offspring of the chimeric mice resulting from germline transmission of the ES genome were obtained and animals heterozygous for the disrupted ACE-2 were identified.

To assess the role of ACE-2 in vivo, the animals heterozygous for the ACE-2 disrupted gene were bred together to produce mice homozygous for the ACE-2 mutation. Inactivation of the ACE-2 by gene targeting resulted in, at least in part, male mice that have a higher ratio of lean to fat tissue, a lower percentage of overall body fat tissue, and a lower overall body weight than wild type counterparts. These knock-out experiments are described in greater detail in Example 16 below.

ACE-2 is capable of hydrolyzing angiotensin I (1–10) by cleaving the C-terminal amino acid (i.e., leucine) from angiotensin I. The resulting 9-amino acid peptide ("Ang. (1–9)") can be further hydrolyzed by ACE into a 5-amino acid peptide containing the first five amino acids from angiotensin I. ACE-2 is also capable of cleaving angiotensin II (1–8) to angiotensin 1–7 with a much higher catalytic activity than with angiotensin I as a substrate. ACE-2 also catalyzes the hydrolysis of other peptides, such as (des-Arg9)-bradykinin and Lys-(des-Arg9)-bradykinin, and thus may be involved in regulating blood pressure in a similar manner as endothelial ACE protein. Other biologically active peptides which can be hydrolyzed by ACE-2 include apelin-13 and apelin-36, β-casomorphin, dynorphin A 1–13, ghrelin, and neurotensin. All of the ACE-2 hydrolytic activity has been found to be carboxypeptidase activity only. Kinetic characterization of the hydrolytic activity of ACE-2 is described in Example 38.

Apelin is a peptide that appears to be an endogenous ligand of the G-protein coupled receptor APJ, also known as the angiotensin receptor AT(1), and may play a role in body fluid homeostasis, blood pressure, circadian rhythm, and food and water intake. β-casomorphin, a hepta-peptide produced during the hydrolysis of casein, has been shown to stimulate food intake in experimental animals. Dynorphin A is an opioid peptide that may have both physiological and pathological roles in acute and chronic pain states. Ghrelin is a recently discovered hormone which appears to be an important regulator of growth hormone secretion and energy homeostasis, and thus may play an important role in obesity and cachexia as well as in the regulation of growth processes. Neurotensin is a tridecapeptide that exhibits selective anatomic and neurochemical interactions with dopaminergic systems and appears to be involved in some of the behavioral properties of psychostimulants.

ACE-2 is characterized by the presence of a transmembrane domain in the carboxy terminal portion of the protein. Thus, ACE-2 can be in a membrane bound form. ACE proteins have also been found in a soluble form, which may result either from leakage of the protein from the surface or, from specific hydrolysis by a protease, or the soluble form may be encoded by a differentially spliced mRNA. Accordingly, ACE-2 is believed also to exist in a soluble form.

The terms "ACE-2 associated state" and "ACE-2 associated disorder" include those states which are associated with ACE-2, ACE-2 substrates, or the products of an ACE-2 metabolic pathway. ACE-2 associated states and disorders also include states and disorders which are characterized by aberrant levels of ACE-2 activity, and/or levels of ACE-2 substrate and/or ACE-2 metabolic products. ACE-2 associated states and disorders may include, for example, high blood pressure, high blood pressure related diseases and disorders, and, in particular, arterial hypertension. Other ACE-2 associated states include congestive heart failure (CHF), body weight disorders, neurodegenerative disorders, and diseases associated with peptide hormones or cytokine processing.

Blood pressure refers to the pressure exerted by the blood upon the walls of the blood vessels, e.g., arteries, and is usually measured on the radial artery by means of a sphygmomanometer, and expressed in millimeters of mercury. The following ranges of blood pressure are usually used as a standard for normal versus abnormal blood pressure: a normal blood pressure corresponds to a diastolic blood pressure of less than 85 mm Hg; a high normal blood pressure corresponds to a diastolic blood pressure between 85 and 89 mm Hg; a mild hypertension corresponds to a diastolic blood pressure between 90–104 mm Hg; a moderate hypertension corresponds to a diastolic blood pressure between 105 and 114 mm Hg; and severe hypertension corresponds to a diastolic blood pressure higher than 115 mm Hg. Abnormal blood pressure can also be determined based on the systolic blood pressure (when the diastolic pressure is less than 90 mm Hg). Thus, a normal blood pressure corresponds to a systolic blood pressure of less than 140 mm Hg; a borderline systolic hypertension corresponds to a systolic blood pressure between 140 and 159 mm Hg; and isolated systolic hypertension corresponds to a systolic blood pressure higher than 160 mm Hg. This classification is borrowed from *Cecil: Essentials of Medicine*, Third Edition by Andreoli et al. W.B. Saunders Company (1993). A diagnosis of hypertension, also referred to herein as "abnormally high blood pressure", is usually made in an adult over 18 years of age if the average of two or more blood pressure measurements on at least two subsequent visits is 90 mm Hg or higher diastolic or 140 mm Hg systolic. Since children and pregnant women have a lower blood pressure, a blood pressure over 120/80 (i.e., 120 mm Hg systolic blood pressure/80 mm Hg diastolic blood pressure), is considered abnormal. Isolated systolic hypertension (ISH) refers to a condition in which the systolic blood pressure is greater than 160 mm Hg and the diastolic blood pressure is less than 85 mm Hg. ISH is associated with enhanced morbidity.

ACE-2 associated states also include other blood pressure related diseases or conditions, e.g., CHF (congestive heart failure), chronic heart failure, left ventricular hypertrophy, acute heart failure, myocardial infarction, and cardiomyopathy.

One ACE-2 associated state is CHF. CHF is characterized by the inability of the left ventricle to maintain a normal blood pressure. This results in a baroflex-mediated reflex increase in sympathetic discharge, which stimulates the myocardium to beat faster and stronger, yet increases peripheral vasoconstriction so that the afterload rises and the load on the failing myocardium augments (Lionel H. Opie, Drugs for the Heart, Third Edition, W.B. Saunders Co., 1991). Excess adrenergic activity also results in enhanced activity of the renin-angiotensin system, further increasing peripheral vascular resistance and contributing to fluid retention (edema) by stimulation of the secretion of aldosterone. In addition, angiotensin promotes the release of vasopressin to contribute to abnormal volume regulation and hyponatremia in severe CHF. Overloading of the left ventricle also results in hypertrophy of the ventricular muscle, resulting in a decrease in its contractility, further contributing to the condition.

Previously it has been discovered that vasodilators such as ACE-inhibitors are efficient in treating CHF and reducing mortality. The present invention contemplates therapeutic methods and compositions in which ACE-inhibiting compounds are administered to a subject concurrently or separately with ACE-2 modulating compounds. ACE inhibiting compounds are particularly preferred therapeutics for treating CHF since they are able to inhibit the deleterious neurohumoral viscious circle involving angiotensin-renin-aldosterone. Thus, it is believed that ACE-2 modulating, e.g., inhibiting, compounds, which also modulate angiotensin hydrolysis, will also be useful for treating and preventing CHF.

The term "neurodegenerative disorders" includes neuropathies, Alzheimer disease, Parkinson's disease, Huntington's disease, amyotropic lateral sclerosis, motor neuron disease, traumatic nerve injury, multiple sclerosis, acute disseminated encephalomyelitis, acute necrotizing hemorrhagic leukoencephalitis, dysmyelination disease, mitochondrial disease, migrainous disorder, stroke, aging, dementia, peripheral nervous system diseases and mental disorders such as depression and schizophrenia. The term includes disorders which can be treated by administering an effective amount of a compound of the invention.

ACE-2 associated states also include states which are associated with regulating cell proliferation, such as smooth cell proliferation. Smooth muscle cell proliferation in the intima of muscular arteries is a primary cause of vascular stenosis in atherosclerosis, after vascular surgery, and after coronary angioplasty. Several animal studies have indicated that the renin-angiotensin system plays an important role in this vascular response to injury. The stimulatory effect of angiotensin II on cell growth and replication in the cardiovascular system, which may result in myocardial hypertrophy and hypertrophy or hyperplasia of conduit and resistance vessels in certain subjects is mediated through angiotensin II receptors (subtype AT1) (Rosendorff C. *J. Am. Coll. Cardiol.* (1996)28: 803). The importance of ACE in atherosclerosis is further described, e.g., in Malik et al. *Am. Heart J.* (1997) 134:514. It has also been shown, that angiotensin caused myocyte hypertrophy and fibroblast proliferation associated with the induction of mRNA for several early response genes (c-fos, c-jun, jun B, Egr-1 and c-myc), angiotensinogen and transforming growth factor beta (TGFβ) (Rosendorff *J. Am. Coll. Cardiol.* (1996) 28: 803–12; Paquet et al. *J. Hypertens.* (1990) 8: 565–72).

Accordingly, in one embodiment, the invention pertains to methods for reducing or inhibiting smooth muscle cell proliferation, comprising administering to a subject an efficient amount of a composition by administering an ACE-2 modulating, e.g., inhibiting, compound. ACE-2 modulating, e.g., inhibiting, compounds may be administered systemically or locally, e.g., at a site of vascular injury.

Other examples of ACE-2 associated states include kidney diseases or disorders, e.g., renal failure. Angiotensin and ACEs are important in the development and for the maintenance of the functional and structural integrity of the adult kidney (see, e.g., Hilgers et al. *Semin. Nephrol* (1997) 17:492). Chronic renal disease evolves to end-stage renal failure through events, including enhanced intraglomerular pressure and plasma protein ultrafiltration, mediated at least in part by angiotensin II. It has been reported that ACE inhibitors reduce intracapillary pressure and ameliorate glomerular size-selective function (see, e.g., Ruggenenti and Remuzzi *Curr. Opin. Nephrol. Hypertens.* (1997) 6:489). Thus, based at least in part on the fact that ACE-2 is expressed in kidney and is homologous to ACE, ACE-2 modulating compounds may be used for treating and preventing renal diseases or disorders, either alone or in combination with known ACE inhibitors.

ACE-2 associated states also include various other hyperadrenergic states, such as acute myocardial infarction (AMI) and some ventricular arrthythmias. The invention further provides methods for treating kinetensin associated conditions. As described herein, ACE-2 cleaves the C-terminal amino acid (leucine) from kinetensin. Kinetensin is a nine amino acid peptide having the sequence IARRHPYFL (SEQ ID NO:3), which has been reported to induce a dose-dependent release of histamine from mast cells, as well as induce a dose-dependent increase in vascular permeability when injected intradermally (Sydbom et al. *Agents Actions* (1989) 27: 68) into rats. Accordingly, modulating the plasma and/or tissue level of kinetensin, such as by modulating the hydrolysis of the C-terminal amino acid from kinetensin, should be useful for treating conditions that are caused by, or contributed to by, an abnormal kinetensin level. Such conditions include those caused by, or contributed to by, an abnormal histamine release from mast cells and/or by an abnormal vascular permeability. Since excessive histamine release is associated with local or systemic allergic reactions, including exzema, asthma, anaphylactic shock, these conditions are included in the definition of "ACE-2 associated states."

Other examples of ACE-2 associated states include, for example, SIRS (Systemic Inflammatory Response Syndromes), sepsis, polytrauma, inflammatory bowel disease, acute and chronic pain, bone destruction in rheumatoid and osteo arthritis and periodontal disease, dysmenorrhea, premature labor, brain edema following focal injury, diffuse axonal injury, stroke, reperfusion injury and cerebral vasospasm after subarachnoid hemorrhage, allergic disorders including asthma, adult respiratory distress syndrome, wound healing and scar formation.

The term "body weight disorder" includes disorders or states associated with growth or metabolism of fat tissue including, but not limited to, rapid weight loss or weight gain, obesity, anorexia, cachexia, bulimia, diabetes, generalized or familial partial lipodystrophy (peripheral fat wasting), hypercholesterolemia, hyperlipidemia, and other diseases of aberrant metabolic rate. A symptom of a body weight disorder is an abnormal body weight which can be determined according to the body mass index (BMI), which is the ratio of.[body weight in kg] divided by [height in m]$^2$. As defined herein, an individual's body weight is defined as being underweight (BMI<18.5), normal (BMI=18.5–24.9), overweight (preobese; BMI=25.0–29.9), moderately overweight (grade 1 obesity; BMI=30.0–34.9), severely overweight (grade 2 obesity; BMI=35.0–39.9), or massively or morbidly obese (grade 3 obesity; BMI=≧40). Ranges intermediate to the above-recited values, e.g., 18.5–24.9, 25.0–29.9, 30.0–34.9, 35.0–39.9, and ≧40, and to the below recited values are also intended to be encompassed by the invention. Body weight disorders also include abnormal and/or undesirable percentages of body fat. In one embodiment, the percent body fat of said subject is 5% or less, 8% or less, 10% or less, 15% or less, 5% or greater, 10% or greater, 12.5% or greater, 15% or greater, 17.5% or greater, 20% or greater, 25% or greater, 30% or greater, 35% or greater, 40% or greater, etc.

Based at least on the presence of ACE-2 in testis, ACE-2 associated states may also include infertility or other disorders relating to gamete maturation. In addition, ACE-2 associated states may also include cognitive disorders, and disorders associated with bradykinin and des-Arg bradykinin.

The invention also pertains to a method for treating a blood pressure related disease or disorder in a subject. The invention involves administering a compound of the invention, e.g., a compound of any one of formulae I–VIII, e.g., an ACE-2 modulating, e.g., ACE-2 inhibiting, compound, to the subject, such that the blood pressure related disease or disorder is treated.

The invention also pertains to a method of treating chronic heart failure in a subject. The invention includes administering to the subject an effective amount of a compound of the invention, e.g., a compound of any one of formulae I–VIII, e.g., an ACE-2 modulating, e.g., ACE-2 inhibiting, compound, such that the chronic heart failure in the subject is treated.

The invention also pertains to a method of treating left ventricular hypertrophy in a subject. The method includes administering to the subject an effective amount of a compound of the invention, e.g., a compound of any one of formulae I–VIII, e.g., an ACE-2 modulating, e.g., ACE-2 inhibiting, compound, such that the left ventricular hypertrophy in said subject is treated.

The invention also pertains to a method of treating acute heart failure in a subject. The method includes administering to the subject an effective amount of a compound of the invention, e.g., a compound of any one of formulae I–VIII, e.g., an ACE-2 modulating, e.g., ACE-2 inhibiting, compound, such that said acute heart failure in the subject is treated.

The invention also pertains to a method of treating cardiomyopathy in a subject. The method includes administering to the subject an effective amount of a compound of the invention, e.g., a compound of any one of formulae I–VIII, e.g., an ACE-2 modulating, e.g., ACE-2 inhibiting, compound, such that the cardiomyopathy in the subject is treated.

The invention also pertains to a method of treating congestive heart failure in a subject. The method involves administering to the subject a compound of the invention, e.g., a compound of any one of formulae I–VIII, e.g., an ACE-2 modulating, e.g., ACE-2 inhibiting, compound, such that the congestive heart failure in the subject is treated.

The invention also pertains to a method of treating arterial hypertension in a subject. The method includes administering to the subject, an effective amount of a compound of the invention, e.g., a compound of any one of formulae I–VIII, e.g., an ACE-2 modulating, e.g., ACE-2 inhibiting, compound, such that the arterial hypertension in the subject is treated.

The invention also pertains to a method of treating myocardial infarction in a subject. The method includes administering to the subject an effective amount of a compound of the invention, e.g., a compound of any one of formulae I–VIII, e.g., an ACE-2 modulating, e.g., ACE-2 inhibiting, compound, such that myocardial infarction in the subject is treated.

The invention also pertains to a method for treating a cell proliferation disorder in a subject. The method includes administering to the subject an effective amount of a compound of the invention, e.g., a compound of any one of formulae I–VIII, e.g., an ACE-2 modulating, e.g., ACE-2 inhibiting, compound, such that the cell proliferation disorder in the subject is treated. Examples of cell proliferation disorders include, for example, cancer. In one embodiment the cell proliferation disorder is a smooth cell proliferation disorder.

The invention also pertains to a method for treating vascular stenosis in a subject. The method includes administering to a subject an effective amount of a compound of the invention, e.g., a compound of any one of formulae I–VIII, e.g., an ACE-2 modulating, e.g., ACE-2 inhibiting, compound, such that the vascular stenosis in the subject is treated.

The invention also pertains to a method of treating a kidney disease or disorder in a subject. The method includes administering to a subject an effective amount of a compound of the invention, e.g., a compound of any one of formulae I–VIII, e.g., an ACE-2 modulating, e.g., ACE-2 inhibiting, compound, such that the kidney disease or disorder in the subject is treated.

The invention also pertains to a method of treating a kinetensin associated disorder in a subject. The method includes administering to the subject an effective amount of a compound of the invention, e.g., a compound of any one of formulae I–VIII, e.g., an ACE-2 modulating, e.g., ACE-2 inhibiting, compound, such that the kinentensin associated disorder in the subject is treated. Examples of kinetensin associated disorders include those caused by, for example, abnormal vascular permeability, local and systemic allergic reactions, exzema, asthma, and anaphylactic shock.

The invention also pertains to a method of treating a state associated with inflammation. The method includes administering to a subject an effective amount of a compound of the invention, e.g., a compound of any one of formulae I–VIII, e.g., an ACE-2 modulating, e.g., ACE-2 inhibiting, compound, such that the state associated with inflammation in the subject is treated. Examples of states associated with inflammation include SIRS, polytrauma, inflammatory bowel disease, acute and chronic pain, bone destruction in rheumatoid and osteo arthritis, periodontal disease, dysmeorrhea, premature labor, brain edema following focal injury, diffuse axonal injury, allergic disorders, wound healing, and scar formation.

The invention also pertains to a method for treating a neurodegenerative disorder in a subject. The method includes administering to the subject an effective amount of a compound of the invention, e.g., a compound of any one of formulae I–VIII, e.g., an ACE-2 modulating, e.g., ACE-2 inhibiting, compound, such that the neurodegenerative disease in the subject is treated. Examples of neurodegenerative disorder include neuropathy, Alzheimer's disease, Parkinson's disease, Huntington's disease, amyotropic lateral sclerosis, motor neuron disease, traumatic nerve injury, multiple sclerosis, acute disseminated encephalomyelitis, acute necrotizing hemorrhagic leukoencephalitis, dysmyelination disease, mitochondrial disease, migrainous disorder, stroke, aging, dementia, peripheral nervous system diseases and mental disorders. In one embodiment, the neurodegenerative disorder is Alzheimer's disease.

The invention also pertains to a method for treating a subject for a stroke. The method includes administering to the subject an effective amount of a compound of the invention, e.g., a compound of any one of formulae I–VIII, e.g., an ACE-2 modulating, e.g., ACE-2 inhibiting, compound, such that the subject is treated for the stroke.

The invention also pertains to a method for treating heart disease in a subject. The method includes administering to the subject an effective amount of a compound of the invention, e.g., a compound of any one of formulae I–VIII, e.g., an ACE-2 modulating, e.g., ACE-2 inhibiting, compound, such that the subject is treated for heart disease.

In yet another embodiment, the invention pertains to a method for treating diabetes in a subject. The method includes administering to the subject an effective amount of an ACE-2 modulating compound. The diabetes may be or may not be related to a body weight disorder in the subject.

In another further embodiment, the invention also includes a method for treating a state associated with lipid metabolism in a subject. The method includes administering to the subject an effective amount of an ACE-2 modulating compound, such that the state is treated.

The term "state associated with lipid metabolism" includes disorders and states which are caused or modulated (e.g., increased) by aberrant, normal, or undesirable (elevated or depressed) levels of lipid metabolism. In certain embodiments, states associated lipid metabolism include, for example, obesity, lipidosis, a lipodystrophy, e.g., hyperlipenia, hyperlipidemia, hyperproteinemia, hyperliposis, lipoidosis, and lipolipoidosis.

In another embodiment, the invention also pertains to a method for treating atherosclerosis in a subject. The method includes administering to the subject an effective amount of an ACE-2 modulating compound.

The invention also pertains to a method for treating a disease or state associated with a peptide hormone in a subject. The method includes administering to the subject an effective amount of a compound of the invention, e.g., a compound of any one of formulae I–VIII, e.g., an ACE-2 modulating, e.g., ACE-2 inhibiting, compound, such that the disease associated with a peptide hormone is treated. Examples of diseases or states associated with peptide hormones include inflammation, blood pressure effects, kidney disease, and preterm labor.

The invention also pertains to a method for treating a disease associated with cytokine processing in a subject. The method involves administering to a subject an effective amount of a compound of the invention, e.g., a compound of any one of formulae I–VIII, e.g., an ACE-2 modulating, e.g., ACE-2 inhibiting, compound, such that said disease associated with cytokine processing is treated in said subject.

The invention also pertains to the methods of treating any of the above mentioned diseases and disorders by further administering in combination with the compounds of the invention, an ACE inhibitor. Examples of ACE inhibitors include captopril, enalapril, enalaprilat, zofenopril, ceroanapril, alacepril, benazepril, delapril, quinapril, quinaprilat, moexipril, rentiapril, spirapril, cilazapril, perindopril, fosinopril, linsinopril, ramipril, and trandolapril.

The compounds of the invention are also useful for treating ACE associated disorders and diseases.

In a particular embodiment, the compounds of the invention which are dual inhibitors of ACE and ACE-2 can be administered to a subject suffering from an ACE associated disorder, such that said ACE associated disorder is treated.

The terms "treatment," "treating," or "treat," includes the application or administration of a therapeutic agent (e.g., ACE-2 modulating compounds) to a subject, or application or administration of a therapeutic agent to an isolated tissue or cell line from a subject, who has a disease or disorder (e.g., an ACE-2 associated state) or a symptom of a disease or disorder, such that the disease or disorder (or at least one symptom of the disease or disorder) is cured, healed, prevented, alleviated, relieved, altered, remedied, ameliorated, improved or otherwise affected, preferably in an advantageous manner. Therapeutic agents include, but are not limited to ACE-2 modulating compounds such as small molecules, organic compounds, inorganic compounds, peptides, antibodies, ribozymes and antisense oligonucleotides.

The term "administering" includes routes of administration which allow the ACE-2 modulating compound to perform its intended function, e.g. modulating, e.g., inhibiting, the function of ACE-2 and/or treating an ACE-2 associated state, e.g., a body weight disorder, etc. Examples of routes of administration which can be used include parental injection (e.g., subcutaneous, intravenous, and intramuscular), intraperitoneal injection, rectal, occullar, oral, inhalation, and transdermal. The injection can administered by bolus injection or by continuous infusion. Depending on the route of administration, the ACE-2 modulating, e.g., inhibiting, compound can be coated with or disposed in a selected material to protect it from natural conditions which may detrimentally effect its ability to perform its intended function. The ACE-2 modulating, e.g., inhibiting, compound can be administered alone or with a pharmaceutically acceptable carrier. Further, the ACE-2 modulating, e.g., inhibiting, compound can be administered as a mixture of ACE-2 modulating, e.g., inhibiting, compounds, which also can be coadministered with a pharmaceutically acceptable carrier. The ACE-2 modulating, e.g., inhibiting, compound can be administered prior to the onset of an ACE-2 mediated state, or after the onset of a ACE-2 mediated state. The ACE-2 modulating, e.g., inhibiting, compound also can be administered as a prodrug which is converted to another form in vivo. In certain embodiments, the ACE-2 modulating compound may be administered such that the compound is exposed to the lower gastrointestinal tract (e.g., small and large intestines, bowel, etc.) and has limited systemic absorbtion.

In an embodiment, the invention includes methods and compositions for modifying body weight and/or the percentage of body fat and treating body weight disorders, including but not limited to, obesity, cachexia, diabetes, and anorexia, by administering to the subject an effective amount of an ACE-2 modulating compound, such that the body weight disorder is treated or prevented in the subject. An approach which may be used to ameliorate body weight disorders is the administration of ACE-2 modulating compounds, such as ACE-2 inhibitors (e.g., antagonists), activators (e.g., agonists) or inverse agonists, such as, but not limited to compounds of any one of Formulae I–VIII.

Because a reduction of the level of normal ACE-2 protein activity promotes development of a lower body weight and/or reduces the percentage of body fat, an increase in ACE-2 protein activity, or activation of the ACE-2 pathway (e.g., downstream activation) can stimulate a normal body weight state (e.g., a BMI=18.5–24.9 kg/m$^2$) in underweight individuals (e.g., an anorexic or cachexic phenotype) exhibiting a deficient level of ACE-2 gene expression and/or ACE-2 protein activity.

Thus, symptoms of certain body weight disorders such as, for example, cachexia or anorexia, which involve an underweight (e.g., a BMI<18.5 kg/m$^2$) phenotype, can be ameliorated by increasing the level of ACE-2 gene expression and/or ACE-2 protein activity, and/or increasing the availability of ACE-2 substrates to the proteolytic activity of ACE-2.

In an embodiment of the invention, activators (e.g., agonists) of ACE-2 protein activity can be used therapeutically to promote weight gain and/or increase the percentage of body fat in subjects with an underweight phenotype, e.g., anorexia or cachexia.

Alternatively, symptoms of certain body weight disorders such as, for example, obesity, overweight, and diabetes, which involve an overweight (e.g., a BMI=25.0–29.9 kg/m$^2$) or obese (e.g., a BMI=30.0–34.9, 35.0–39.9, or $\geq$40 kg/m$^2$) phenotype, can be ameliorated by decreasing the level of ACE-2 gene expression and/or ACE-2 protein activity, and/or decreasing the availability of ACE-2 substrates to the proteolytic activity of ACE-2.

In an embodiment of the invention, inhibitors (e.g., antagonists) of ACE-2 protein activity can be used therapeutically to reduce weight gain, enhance weight loss and/or decrease the percentage of body fat in subjects with an overweight or obese phenotype.

In an embodiment, activators (e.g., agonists) of ACE-2 activity can be used therapeutically to promote weight gain and/or increase the percentage of body fat in subjects with an underweight phenotype, e.g., anorexia or cachexia. Inhibitors (e.g., antagonists) of ACE-2 activity can be used to reduce weight gain, enhance weight loss, and/or reduce the percentage of body fat in subjects with an obese phenotype.

The invention also pertains to methods for increasing muscle mass of a subject by administering to the subject an effective amount of an ACE-2 modulating compound, such that the muscle mass of the subject is increased.

The language "effective amount" of the compound is that amount necessary or sufficient to treat or prevent an ACE-2 associated state, e.g. prevent or treat the various morphological and somatic symptoms of an ACE-2 associated state, e.g., a body weight disorder. The effective amount can vary, depending on such factors as the size and weight of the subject, the type of illness, or the particular ACE-2 modulating, e.g., inhibiting, compound. For example, the choice of the ACE-2 modulating, e.g., inhibiting, compound can affect what constitutes an "effective amount". One of ordinary skill in the art would be able to study the aforementioned factors and make the determination regarding the effective amount of the ACE-2 modulating, e.g., inhibiting, compound without undue experimentation.

The effective amount can be determined through consideration of the toxicity and therapeutic efficacy of the ACE-2 modulating, e.g., inhibiting, compounds by standard pharmaceutical procedures in cell cultures or experimental animals, e.g., for determining the $LD_{50}$ (dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies are useful in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The term "subject" or "patient" includes animals (e.g., mammals, e.g., cats, dogs, horses, pigs, cows, sheep, rodents, rabbits, squirrels, bears, primates (e.g., chimpanzees, gorillas, and humans) which are capable of suffering from an ACE-2 associated disorder, e.g., a body weight disorder, etc.

In a further embodiment, the subject is normal weight, under weight, or over weight subjects as well as transgenic subjects. In one embodiment, the subject has a BMI of 18 or less, 18 or greater, 19 or greater, 20 or greater, 21 or greater, 22 or greater, 23 or greater, 24 or greater, 25 or greater, 26 or greater, 27 or greater, 28 or greater, 29 or greater, 30 or greater, 31 or greater, 32 or greater, 33 or greater, 34 or greater, 35 or greater, 36 or greater, 37 or greater, 38 or greater, 39 or greater, 40 or greater, 41 or greater, 42 or greater, 43 or greater, 44 or greater, or 45 or greater.

The invention described in the subsections below encompasses screening methods (e.g., assays) for the identification of ACE-2 therapeutics and/or ACE-2 modulating compounds that can be used to treat body weight disorders. The terms ACE-2 therapeutic and ACE-2 modulating compound are used interchangeably herein. The invention also encompasses activators (e.g., agonists), inverse agonists, and inhibitors (e.g., antagonists) of ACE-2, including small molecules, organic and inorganic compounds, peptides and antibodies, as well as nucleotide sequences that can be used to inhibit ACE-2 gene expression (e.g., antisense and ribozyme molecules), and gene or regulatory sequence replacement constructs designed to enhance ACE-2 gene expression (e.g., expression constructs that place the ACE-2 gene under the control of a strong promoter system). Such compounds are useful for the treatment of ACE-2 associated states, such as body weight disorders.

The invention also pertains to a method of treating an ACE-2 associated state in a subject, by administering to the subject a therapeutically effective amount of an ACE-2 modulating, e.g., inhibiting, compound, such that the ACE-2 associated state is treated. The invention also pertains, at least in part, to each of the ACE-2 modulating compounds disclosed herein, as well as each of the intermediates and other compounds described in the synthesis of the ACE-2 modulating compounds. The invention also pertains, per se, to pharmaceutical compositions comprising ACE-2 modulating compounds of the invention in combination with a pharmaceutically acceptable carrier.

Examples of ACE-2 modulating compounds include peptides, antibodies, ribozymes, antisense oligonucleotides, and small molecules. Examples of small molecule ACE-2 modulating compounds, include compounds of the formula (I):

$$Z-\Lambda \quad (I)$$

wherein Z is a zinc coordinating moiety and Λ is an amino-acid mimicking moiety, and pharmaceutically acceptable salts thereof.

The language "ACE-2 modulating compound" refers to organic compounds, inorganic compounds, peptides, antibodies, ribozymes, antisense oligonucleotides, and small molecules, which modulate, e.g., inhibit, activate, promote, or otherwise alter the activity of ACE-2. ACE-2 modulating compounds include both ACE-2 activators (e.g., agonists), inverse agonists and inhibitors (e.g., antagonists). The term includes, but is not limited to, compounds of formulae I, II, III, IV, V, VI, VII and VIII.

The language "ACE-2 inhibiting compound" includes compounds which reduce the activity of ACE-2, e.g., the ability of ACE-2 to hydrolyze substrate, in vivo or in vitro. Preferably, the ACE-2 inhibiting compounds are ACE-2 antagonists or inverse agonists.

The language "zinc coordinating moiety" includes moieties which interact with metals, e.g., zinc, associated with ACE-2. Although not wishing to be bound by theory, it is thought that the zinc coordinating moiety interacts with at least one zinc atom which is associated with the zinc binding domain of ACE-2, as discussed above. Examples of zinc coordinating moieties include, for example, groups which are either capable of coordinating to zinc (e.g., electron donating groups, e.g., an ester, a guanidine, a carboxylic acid, hydroxyalkyl, an alkyl group, an amide, an amine, a hydroxyl, a thiol, a ketone, an aldehyde, carboxylate, sulfonate, sulfide, imidazolyl, or other heterocyclic moieties) or are capable of being converted into groups capable to coordinating to zinc, e.g., cleavable prodrug moieties, cleavable carboxylic acid prodrug moieties, protecting prodrug moieties or ester prodrug capable of releasing the free acid upon administration. Furthermore, in certain embodiments, the zinc-coordinating moiety may be a hydrogen atom. The language "zinc coordinating moiety" includes all moieties which coordinate to zinc or other metal atoms associated with ACE-2 and allow the compounds of the invention to perform their intended function, e.g., modulating ACE-2 activity.

The term "interact" includes any interactions which allow the compound to perform its intended function. Examples of interactions include ionic interactions, hydrophobic interactions, covalent interactions, hydrogen bond interactions, and combinations thereof.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The language "cleavable prodrug moieties" includes moieties which can be metabolized in vivo to a group capable of coordinating to zinc or another enzyme binding site. The prodrug moieties may be metabolized in vivo by esterases or by other mechanisms. Examples of prodrugs and their uses are well known in the art (See, e.g., Berge et al. (1977) "Pharmaceutical Salts", *J. Pharm. Sci.* 66:1–19). The prodrugs can be prepared in situ during the final isolation and purification of the compounds, or by separately reacting the purified compound in its free acid form with a suitable derivatizing agent. For example, carboxylic acids can be converted into esters via treatment with an alcohol in the presence of a catalyst. Examples of cleavable prodrug moieties include substituted and unsubstituted, branched or unbranched lower alkyl ester moieties, (e.g., ethyl esters, propyl esters, butyl esters, pentyl esters, cyclopentyl esters, hexyl esters, cyclohexyl esters), lower alkenyl esters, dilower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, dilower alkyl amides, and hydroxy amides. In certain embodiments of the invention, the prodrug moiety itself may coordinate to the zinc without being converted prior to coordination. In a further embodiment, cleavable prodrug moieties may comprise protecting prodrug moieties.

The term "substituted" includes substituents which can be placed on the moiety and which allow the molecule to perform its intended function. Examples of substituents include alkyl, alkenyl, alkynyl, aryl, NR'R", CN, $NO_2$, F, Cl, Br, I, $CF_3$, $CCl_3$, $CHF_2$, $CHCl_2$, CONR'R", $S(O)_{1-2}NR'R"$, CHO, $O(CR'R")_{0-3}CF_3$, $S(O)_{0-2}R'$, $O(CR'R")_{0-3}CCl_3$, $SCF_3$, $SCCl_3$, COR', $CO_2R'$, and OR' wherein R' and R" are each independently hydrogen, $C_1$–$C_4$ alkyl, $C_2$–$C_4$ alkenyl, $C_2$–$C_4$ alkynyl or optionally substituted aryl. Preferably, substitutions enhance the ability of the ACE-2 modulating compound to perform its intended function, e.g., modulate ACE-2 activity.

The language "protecting prodrug moiety" includes moieties attached by a linkage, e.g., a cleavable linkage, to the ACE-2 modulating compound and which can be metabolized in vivo to yield an active drug. Examples of protecting prodrug moieties include amino acids (e.g., glycine, alanine), branched or unbranched, substituted or unsubstituted lower alkyls (e.g., methyl, ethyl, propyl groups), lower alkenyl groups, di-lower amino-lower alkyl groups, acylamino lower alkyl groups, acyloxy lower alkyl groups, aryl groups, aryl lower alkyl groups, and substituted aryl and aryl lower alkyl groups.

One example of a zinc coordinating moiety of the invention is a moiety of the formula (X):

(X)

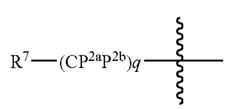

wherein:

$R^7$ is hydrogen, carboxylic acid, unsubstituted or substituted lower alkyl esters, lower alkenyl esters, dilower alkyl amino esters, arylaminocarbonyl, aroyl, aryl, alkylaminocarbonyl, aminocarbonyl, lower alkyl amides, dilower alkyl amides, alkenylaminocarboxy, hydroxy, ether, thio, amino, $(CH_2)_{1-4}SR^{7'}$, a heterocycle, or a cleavable prodrug moiety;

$R^{7'}$ is alkyl, alkenyl, alkynyl, aryl or hydrogen;

$P^{2a}$ and $P^{2b}$ are each independently selected for each occurrence each independently hydrogen, substituted or unsubstituted, branched, straight chain or cyclic $C_1$–$C_5$ alkyl;

and q is 0, 1, 2, or 3.

In a further embodiment, $R^7$ includes moieties of the formulae (XI and XII):

(XI)

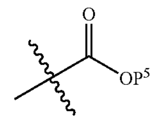

(XII)

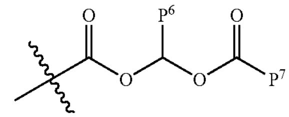

wherein $P^5$, $P^6$, and $P^7$ are each independently selected from the group consisting of substituted and unsubstituted alkyl, benzyl, phenyl, cycloalkyl, alkenyl, and alkynyl. Examples of $P^5$ include ethyl, cyclopentyl and butyl. Examples of $P^7$ include t-butyl, and examples of $P^6$ include hydrogen or methyl. $P^5$, $P^6$, and $P^7$ can be substituted with any substituent which allows the compound of the invention to perform its intended function, e.g., bind or interact with ACE-2. In a further embodiment, $P^5$, $P^6$, and $P^7$ are selected such that the compound is capable of performing its intended function after being administered to a subject. For example, $P^5$, $P^6$, and $P^7$ may be selected such that the compound of the invention is capable of being absorbed by the digestive system after being administered orally. In another embodiment, $P^5$, $P^6$, and $P^7$ include moieties which allow the compound to perform its intended function in vivo. In one embodiment, the $R^7$ group may be cleaved in vivo to yield a carboxylic acid or carboxylate. Therefore, in one embodiment, $P^5$, $P^6$, and $P^7$ may be selected such that they are cleaved in vivo to yield a compound which is capable of performing its intended function, e.g., interact with ACE-2.

The language "amino acid mimicking moiety" ("Λ") includes moieties which are the same or are structurally similar to an N-linked terminal natural or unnatural amino acid (e.g., leucine, histidine) and which interact with ACE-2 resulting in inhibition or modulation of ACE-2 activity. Although not wishing to be bound by theory, it is thought that the amino acid mimicking moiety may interact with a binding pocket region of ACE-2. In one embodiment, the amino acid mimicking moiety is comprised of at least one natural or unnatural amino acid, or a derivative thereof, containing, for example, a charged, an uncharged, a polar or non-polar side chain (e.g., the side chains of alanine, valine, arginine, leucine, isoleucine, phenylalanine, tryptophan, methionine, glycine, serine, proline, threonine, cysteine, tyrosine, histidine, asparagine, glutamine, lysine, glutamic acid, and aspartic acid).

In certain embodiments, the amino acid mimicking moiety may be comprised of two or more amino acids which interact with ACE-2. These amino acid mimicking moieties may be linked by a functional group, for example, an amine group. For example, in a further embodiment, the amino acid mimicking moiety may comprise a side chain pocket binding moiety (J-D) and an auxiliary pocket binding moiety (G-M) linked by a group (Q).

The group Q may be, for example, a bond, O, S, $(CR^3R^{3a})_{1-3}$, $CR^3OR^{3a}$ (e.g., CHOH), $CR^3SH$ (e.g., CHSH), $CR^3NR^{3a}R^{3b}$ (e.g., $CR^3NHR^{3a}$, $CHNH_2$, $CHNHR^3$, $CHNR^3R^{3a}$) $NR^3$ (e.g., NH), $O(CR^3R^{3a})_n$, $(CR^3R^{3a})_nO$ $(CR^{3b}R^{3c})_n$, (e.g., $(CH_2)_nO(CH_2)_n$) wherein n is either 0, 1, 2, or 3, and $R^3$, $R^{3a}$, $R^{3b}$, and $R^{3c}$ are each independently hydrogen, substituted or unsubstituted $C_1$–$C_5$ branched or straight chain alkyl, $C_2$–$C_5$ branched or straight chain alkenyl, aryloxycarbonyl, arylaminocarbonyl, arylalkylsulfonyl, arylalkyl, substituted or unsubstituted acyl, aryl, $C_3$–$C_8$ ring, optionally substituted with up to four heteroatoms. Preferably, Q is NH or $NR^3$. In other embodiments, the $R^3$ side chain may be bonded to the J or D groups or alternatively bonded to the G or M group to form a cyclic structure.

The term "side chain pocket" includes a region of ACE-2 which interacts with side chain pocket binding moieties.

The language "side chain pocket binding moiety" includes moieties which interact with the side chain pocket. Examples of possible side chain pocket binding moieties include hydrogen, branched or straight chain, substituted or unsubstituted lower alkyl, lower alkenyl, lower alkynyl, aryl, or heteroaryl moieties or amino acid side chains of a natural or unnatural amino acids. Examples of preferred side chain pocket binding moieties include substituted or unsubstituted, branched or straight chain alkyl groups, and uncharged or charged amino acid side chains such as those of alanine, valine, leucine, isoleucine, phenylalanine, tryptophan, methionine, glycine, serine, threonine, cysteine, tyrosine, asparagine, proline, arginine, glutamic acid, aspartic acid, lysine, histidine and glutamine. Also included are non-natural amino acid side chains, e.g., derived from substituted natural amino acids, analogs of natural amino acids, derivatives of natural amino acids, and other non-naturally occurring amino acids. The side chain pocket binding moieties may also include substituted or unsubstituted heterocyclic moieties which may include imidazoles, thiazoles, pyrazoles, and benzimidiazoles.

Furthermore, the side chain pocket binding moiety may be of the formula (XIII):

(XIII)

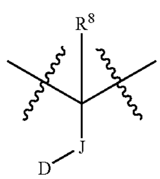

wherein $R^8$ is hydrogen, or alkyl, and optionally may be linked to form a cyclic structure with the D group;

J is selected from the group consisting of a bond, O, S, $CR^4SH$ (e.g., CHSH), $CR^4OH$ (e.g., CHOH), $CR^{4b}NR^4R^{4a}$ (e.g., $CHNH_2$), $NR^4$ (e.g., NH), $(CR^4R^{4a})_n$, (e.g., $(CH_2)_n$), $O(CR^4R^{4a})_n$ (e.g., $O(CH_2)_n$), $(CR^4R^{4a})_pO(CR^{4a}R^{4b})_n$, (e.g., $(CH_2)_pO(CH_2)_n$), a chain of 1 to 5 atoms (e.g., carbon) optionally substituted by $C_1$–$C_6$ alkyl, halogens, wherein n is either 0, 1, 2, or 3, and p is 0, 1, 2, or 3; and $R^4$, $R^{4a}$, $R^{4b}$, and $R^{4c}$ are each independently substituted or unsubstituted $C_1$–$C_6$ branched or straight chain alkyl, $C_2$–$C_6$ branched or straight chain alkenyl, substituted or unsubstituted acyl, alkynyl, arylalkyl, aryl, $C_3$–$C_8$ ring, optionally substituted with up to four heteroatoms; and D is hydrogen, alkoxy, alkyl, alkenyl, amine, hydroxy, alkynyl, aryl, or heteroaryl, any of which optionally may be branched or substituted. Examples of substituted D groups include alkyl amino, alkylhydroxy, alkylthio, alkylphenyl, alkylcycloalkyl, and alkylacetylene. Furthermore, D may be linked to form a ring with G, M, or Q.

In one embodiment, J is a bond and D is alkyl (e.g., methyl, ethyl, isopropyl, n-propyl, isobutyl, n-butyl, t-butyl, pentyl, etc.) or alkynyl. Furthermore, D may be phenyl, or heteroaryl, e.g., pyridinyl or imidazolyl. In certain embodiments, J and D are unsubstituted alkyl, alkynyl, aryl, or alkenyl.

The term "auxiliary pocket" includes a region of ACE-2 which interacts with auxiliary pocket binding moieties.

The term "auxiliary pocket binding moiety" includes moieties which interact with the auxiliary pocket of ACE-2. Examples of possible auxiliary pocket binding moieties include hydrogen, branched or straight chain, substituted or unsubstituted alkyl, aryl, arylalkyl, heteroarylalkyl, alkenyl, alkynyl, or heteroaryl moieties, or amino acid side chains of a natural or unnatural amino acid. In certain embodiments, auxiliary pocket binding moieties may interact with metals associated with ACE-2, e.g., zinc.

Examples of "auxiliary pocket binding moieties" include moieties of the formula (XIV):

(XIV)

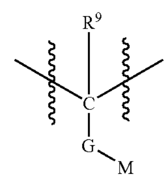

wherein $R^9$ is lower alkyl, or preferably, hydrogen, G is a linking moiety; and M is anchor moiety.

The term "linking moiety" or "G" includes moieties which link the anchor moiety with the ACE-2 modulating compound. For example, the term "linking moiety" includes covalent bonds, $C_1$–$C_6$ alkyl, alkenyl, alkynyl, ether, ester, thioether, amine, and carbonyl moieties. In another embodiment, the linking moiety is a covalent bond, amine $C_1$–$C_6$, $C_1$–$C_5$, $C_1$–$C_4$, $C_1$–$C_3$, or $C_1$–$C_2$ alkyl. The linking moiety may be substituted with up to three, four, five, or six heteroatoms.

The term "anchor moiety" or "M" includes moieties which interact with the auxiliary binding pocket of ACE-2. In certain embodiments, these moieties may also interact with metals, e.g., zinc, associated with ACE-2. The term "anchor moiety" includes moieties which allow the ACE-2 interacting compound to perform its intended function. Examples of anchor moieties include, for example, hydrogen atoms, unsubstituted or substituted alkyl, alkenyl, alkynyl, carbocyclic groups, e.g., substituted or unsubstituted phenyl, naphthyl or heterocyclic (including heteroaryl), e.g., substituted or unsubstituted furanyl, imidazolyl, benzothiophenyl, benzofuranyl, quinolinyl, isoquinolinyl, benzodioxazolyl, benzoxazolyl, benzothiazolyl, benzoimidazolyl, thiazolyl, isothiazolyl, oxazolyl, isooxazolyl, methylenedioxyphenyl, indolyl, thienyl, pyrimidyl, pyrazinyl, pyrazolyl, purinyl, deazapurinyl, napthridinyl, or indolizinyl. Examples of substituents include alkyl, alkenyl, alkynyl, aryl, NR'R", CN, $NO_2$, F, Cl, Br, I, $CF_3$, $CCl_3$, $CHF_2$, $CHCl_2$, CONR'R", $S(O)_2NR'R"$, CHO, $S(O)_{0-2}R'$, $O(CR'R")_{0-2}CF_3$, $OCCl_3$, $SCF_3$, $SCCl_3$, COR', $CO_2R'$, and OR' and wherein R' and R" are each independently hydrogen, $C_1$–$C_6$ alkyl, $C_2$–$C_6$ alkenyl, $C_2$–$C_6$ alkynyl or optionally substituted aryl. In one advantageous embodiment, the anchor moiety ("M") is substituted with at least one subanchor moiety and/or auxiliary subanchor moiety. Each subanchor moiety ("L") or auxiliary subanchor moiety ("V")

may optionally be linked to the anchor moiety through a sublinking moiety ("K") or auxiliary sublinking moiety ("W"). Auxiliary subanchor and sublinking moieties include all moieties described below for linking and sublinking moieties. Auxiliary sublinking and auxiliary subanchor moieties, generally, are connected to M through at least one heteroatom of M. In contrast, sublinking and subanchor moieties, generally, but not necessarily, are connected to M through a carbon atom of M.

The term "subanchor moiety" or "L" includes hydrogen, alkyl, alkenyl, alkynyl, carbocyclic groups, aryl groups, e.g., substituted or unsubstituted phenyl, biphenyl, or heterocyclic, heteroaryl groups e.g., substituted or unsubstituted furanyl, imidazolyl, benzothiophenyl, benzofuranyl, quinolinyl, isoquinolinyl, benzodioxazolyl, benzoxazolyl, benzothiazolyl, benzoimidazolyl, thiazolyl, isothiaozolyl, oxazolyl, isooxazolyl, methylenedioxyphenyl, indolyl, thienyl, pyrimidyl, pyrazinyl, purinyl, or deazapurinyl. biphenyl, naphthyl, indazolyl, napthridinyl, or indolizinyl. In one advantageous embodiment, the subanchor moiety is aliphatic or aromatic, e.g., unsubstituted or substituted carbocyclic, heterocyclic, or phenyl. Preferably, the subanchor moiety allows the ACE-2 modulating, e.g., inhibiting, compound to perform its intended function, e.g., inhibit ACE-2 function. In certain embodiments, a molecule of the invention may comprise one or more subanchor moieties.

Examples of sublinking-subanchor moieties ("L-K") include moieties of the formulae:

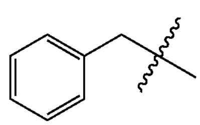

,

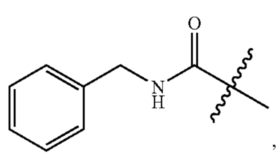

,

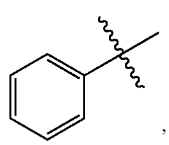

,

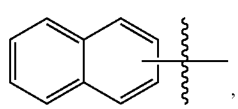

,

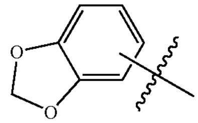

,

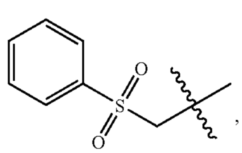

,

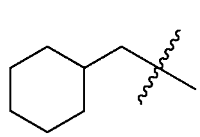

,

,

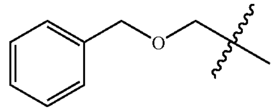

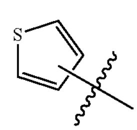

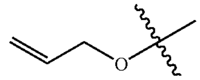

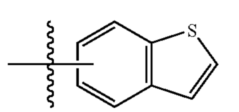

-continued 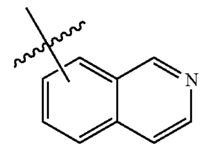 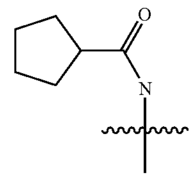 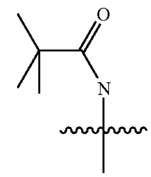 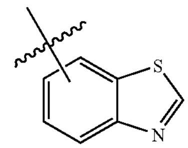 and 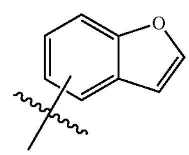 wherein said sublinking and subanchor moieties can be substituted at any position capable of substitution with alkyl, alkenyl, alkynyl, aryl, NR'R", CN, $NO_2$, F, Cl, Br, I, $CF_3$, $CCl_3$, $CHF_2$, $CHCl_2$, CONR'R", $S(O)_2NR'R"$, CHO, $S(O)_{0-2}R'$, $O(CR'R")_{0-2}CF_3$, $OCCl_3$, $SCF_3$, $SCCl_3$, COR', $CO_2R'$, and OR' and wherein R' and R" are each independently hydrogen, $C_1$–$C_6$ alkyl, $C_2$–$C_6$ alkenyl, $C_2$–$C_6$ alkynyl or optionally substituted aryl.

Examples of subanchor moieties include, for example, 4-chlorophenyl, biphenyl, 3-chlorophenyl, 3,5-dichlorophenyl, 3-methylphenyl, 3,5-dimethylphenyl, 3-$CF_3$-phenyl, 2,5-dichlorophenyl, m-fluorophenyl, m-iodophenyl, methylenedioxyphenyl, m-trifluoromethylphenyl, 2,3-dichlorophenyl, 2,3-difluorophenyl, 2,3-dimethoxyphenyl, p-fluorophenyl, p-nitrophenyl, p-t-butylphenyl, p-isopropyl phenyl, p-trifluoromethoxyphenyl, 3,4-dimethylphenyl, 4-cyanophenyl, 3,4-chlorophenyl, 4-methylphenyl, and 4-trifluoromethylphenyl.

The term "sublinking moiety" or "K" includes moieties which link the subanchor moiety with the anchor moiety. For example, the term "sublinking moiety" includes covalent bonds, $C_1$–$C_6$ alkyl, alkenyl, alkynyl, ether, ester, thioether, amine, amide and carbonyl moieties. In another embodiment, the linking moiety is a covalent bond, amine or $C_1$–$C_6$ alkyl. A subanchor moiety may be connected to the anchor moiety through one or more sublinking moieties. Examples of sublinking moieties also include O, S, $CR^{K}OH$ (e.g., CHOH), $(CR^{K}R^{K1})_n$—$SO_2$, $CR^{K}NR^{K1}R^{K2}$ (e.g., $CHNHR^{K1}$, $CHNR^{K1}R^{K2}$, NH, $NR^{K}$, $(CR^{K}R^{K1})_n$ (e.g.,$(CH_2)_n$), $O(CR^{K}R^{K1})_n$ (e.g., $O(CH_2)_n$), $(CR^{K}R^{K1})_nO(CR^{K2}R^{K3})_n$, (e.g., $(CH_2)_nO(CH_2)_n$), a chain of 1 to 5 atoms optionally substituted by $C_1$–$C_6$ alkyl, halogens, wherein n is either 0, 1, 2, or 3, and $R^{K}$, $R^{K1}$, $R^{K2}$, and $R^{K3}$ are hydrogen, each independently substituted or unsubstituted $C_1$–$C_6$ branched or straight chain alkyl, aryl, arylalkyl, substituted or unsubstituted acyl, $C_3$–$C_8$ ring, optionally substituted with up to four heteroatoms. In a further embodiment, the sublinking moiety is a covalent bond, an ether, an amine, or $C_1$–$C_3$ alkyl (e.g., —$CH_2$—, —$CH_2CH_2$—, etc.). In another embodiment, sublinking moieties include $CONR^{K2}CR^{K}R^{K1}$, $CR^{K}R^{K1}$—$S(O_2)$, $(CR^{K}R^{K1})_{0-3}$, and $(CR^{K}R^{K1})_{0-2}O(CR^{K2}R^{K3})_{0-2}$, wherein $R^{K}$, $R^{K1}$, $R^{K2}$, and $R^{K3}$ are selected from the group consisting of halogens, hydrogen, and alkyl. In a further embodiment, K is $(CH_2)$, $CONHCH_2$, $CH_2$—$S(O_2)$, $(CH_2)_2$, or $(CH_2)O(CH_2)$.

For example, in one embodiment, the anchor moiety includes cyclic moieties of the formula (XV):

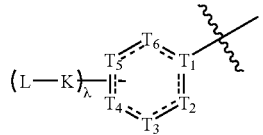

(XV)

wherein

λ is 0, 1, 2, 3, 4, or 5;

$T_1$, $T_2$, $T_3$, $T_4$, and $T_5$ are each independently carbon, nitrogen, sulfur, or oxygen, optionally bound to hydrogen or oxygen (e.g., to form a carbonyl or sulfonyl group);

$T_6$ is carbon, nitrogen, sulfur, oxygen or a covalent bond (such that a five membered ring is formed), optionally bound to hydrogen or oxygen (e.g., forming a carbonyl or sulfonyl group)

each K is an independently selected sublinking moiety; and each L is an independently selected subanchor moiety. The sublinking and subanchor moieties may be attached to any available atom of the aromatic or heteroaromatic ring. Furthermore, two or more sublinking moieties may be attached to the same subanchor moiety, forming a bicyclic or tricyclic ring system.

Examples of anchor moieties include moieties wherein $T_2$ and $T_4$ are nitrogen, $T_1$, $T_3$ and $T_5$ are carbon and $T_6$ is a covalent bond. Another example of an anchor moiety includes the moiety wherein $T_2$ and $T_3$ are nitrogen, $T_1$, $T_4$, $T_5$ are each carbon, and $T_6$ is a covalent bond. Another example of an anchor moiety includes the moiety wherein $T_1$, $T_3$, and $T_5$ are each carbon, $T_2$ is nitrogen, and $T_4$ is sulfur.

Examples of anchor moieties ("M-K-L") also include:

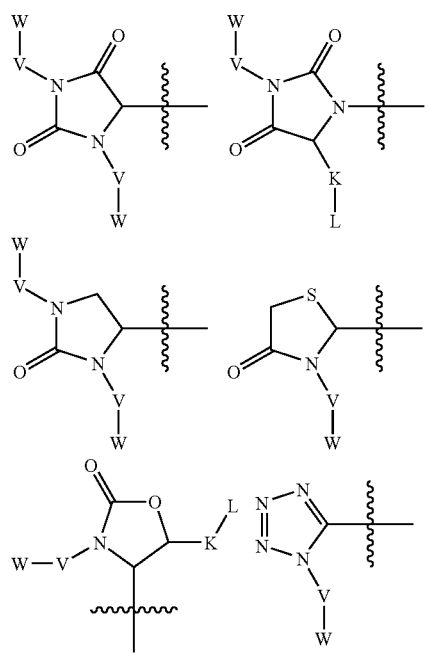

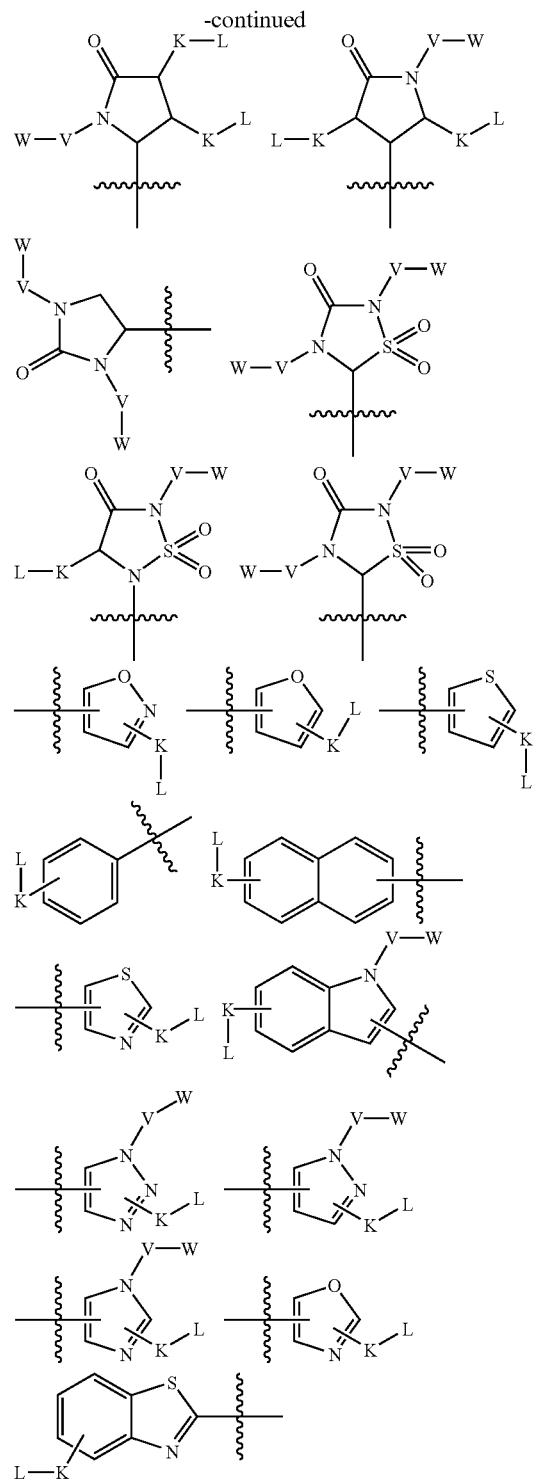

wherein each K and L are independently selected sublinking and subanchor moieties for each position capable of substitution. In one embodiment, K is a covalent bond and L is a hydrogen atom. V and W are each independently selected auxiliary sublinking and auxiliary subanchor moieties, respectively.

The term "auxiliary sublinking moiety" or "V" includes sublinking moieties as described previously that when bonded to a heteroatom (e.g., nitrogen, oxygen, sulfur, phosphorous, etc.) result in a compound of the invention which is capable of performing its intended function (e.g., modulate ACE-2). The term "auxiliary subanchor moieties" include, but are not limited to sublinking moieties as described above.

Examples of auxiliary sublinking moieties (or "V") include covalent bonds, $CONR^{V2}CR^{V}R^{V1}$, $CR^{V}R^{V1}$—$S(O_2)$, $(CR^{V}R^{V1})_{0-3}$, and $(CR^{V}R^{V1})_{0-2}O(CR^{V2}R^{V3})_{0-2}$, wherein $R^{V}$, $R^{V1}$, $R^{V2}$, and $R^{V3}$ are selected from the group consisting of halogens, hydrogen, and alkyl. In a further embodiment, V is $(CH_2)$, $CONHCH_2$, $CH_2$—$S(O_2)$, $(CH_2)_2$, or $(CH_2)O(CH_2)$. In another embodiment, V is a covalent bond.

The term "auxiliary subanchor moiety" (or "W") includes, but is not limited to, subanchor moieties as described previously. It also includes moieties that when bonded to auxiliary subanchor moieties result in a compound of the invention which is capable of performing its intended function (e.g., modulate ACE-2).

For example, in one embodiment, the anchor moiety is substituted or unsubstituted pyrazolyl, thioazolyl, or oxazolyl or imidazolyl. In a further embodiment, the imidazolyl anchor moiety is substituted with one or more subanchor moieties ("L"), linked to the imidazolyl anchor moiety through sublinking moieties ("K"). In one embodiment, the imidazolyl anchor moiety is represented by the formula (XVI):

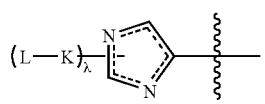

(XVI)

wherein

λ is 0, 1, 2, 3, or 4;

each K is an independently selected sublinking moiety; and each L is an independently selected subanchor moiety. The sublinking and subanchor moieties may be attached to any available atom of the imidazole ring. Furthermore, two or more sublinking moieties may be attached to the same subanchor moiety, forming a bicyclic or tricyclic ring system. In a further embodiment, when K-L is bonded directly to a heteroatom (e.g., the nitrogen), the K-L may be replaced by V—W, which represents auxiliary sublinking and auxiliary anchor moieties, respectfully.

In one embodiment, the imidazolyl anchor moiety is of the formula (XVII):

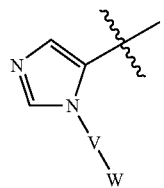

(XVII)

wherein V and W are, respectively, auxiliary sublinking and auxiliary subanchor moieties as described above. In a further embodiment, V is alkyl, and W is cycloalkyl.

In an embodiment, K is a covalent bond, aminocarbonyl, $(CH_2)_n$ or $(CH_2)_pO(CH_2)_n$, wherein n is 0, 1, 2, 3, 4, or 5 and p is 0, 1, 2, 3, 4, or 5. In another embodiment, L is a subanchor moiety, such as, but not limited to, unsubstituted or substituted phenyl, alkyl or cyclic alkyl. L, e.g., phenyl or another subanchor moiety, can be substituted with one or more substituents that allow the compound to perform its intended function, e.g., modulate ACE-2 activity. Examples of substituents include alkyl, alkenyl, alkynyl, aryl, NR'R", CN, $NO_2$, F, Cl, Br, I, $CF_3$, $CCl_3$, $CHF_2$, $CHCl_2$, CONR'R", $S(O)_{1-2}NR'R"$, CHO, $O(CR'R")_{0-3}CF_3$, $S(O)_{0-2}R'$, $O(CR'R")_{0-3}CCl_3$, $SCF_3$, $SCCl_3$, COR', $CO_2R'$, and OR' wherein R' and R" are each independently hydrogen, $C_1$–$C_4$ alkyl, $C_2$–$C_4$ alkenyl, $C_2$–$C_4$ alkynyl or optionally substituted aryl. In one embodiment, L is phenyl and is substituted with a nitro group. In other embodiments, L is 4-chlorophenyl, biphenyl, 3-chlorophenyl, 3,5-dichlorophenyl, 3-methylphenyl, 3,5-dimethylphenyl, 3-$CF_3$-phenyl, 2,5-dichlorophenyl, m-fluorophenyl, m-iodophenyl, methylenedioxyphenyl, m-trifluoromethylphenyl, 2,3-dichlorophenyl, 2,3-difluorophenyl, 2,3-dimethoxyphenyl, p-fluorophenyl, p-nitrophenyl, p-t-butylphenyl, p-isopropyl phenyl, p-trifluoromethoxyphenyl, 3,4-dimethylphenyl, 4-cyanophenyl, 3,4-chlorophenyl, 4-methylphenyl, and 4-trifluoromethylphenyl.

In another embodiment, the anchor moiety is of the formula (XVIII):

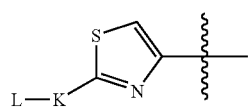

(XVIII)

wherein K and L are, respectively, sublinking and subanchor moieties as described above.

In an embodiment, K is a covalent bond, aminocarbonyl, $(CR^{K}R^{K1})_n$ (e.g., $(CH_2)_n$) or $(CR^{K}R^{K1})_pO(CR^{K2}R^{K3})_n$ (e.g., $(CH_2)_pO(CH_2)_n$) wherein n is 0, 1, 2, 3, 4, or 5 and p is 0, 1, 2, 3, 4, or 5.

In another embodiment, L is a subanchor moiety, such as, but not limited to, unsubstituted or substituted phenyl, alkyl or cyclic alkyl. L, e.g., phenyl or another subanchor moiety, can be substituted with one or more substituents that allow the compound to perform its intended function, e.g., modulate ACE-2 activity. Examples of substituents include alkyl, alkenyl, alkynyl, aryl, NR'R", CN, $NO_2$, F, Cl, Br, I, $CF_3$, $CCl_3$, $CHF_2$, $CHCl_2$, CONR'R", $S(O)_{1-2}NR'R"$, CHO, $O(CR'R")_{0-3}CF_3$, $S(O)_{0-2}R'$, $O(CR'R")_{0-3}CCl_3$, $SCF_3$, $SCCl_3$, COR', $CO_2R'$, and OR' wherein R' and R" are each independently hydrogen, $C_1$–$C_4$ alkyl, $C_2$–$C_4$ alkenyl, $C_2$–$C_4$ alkynyl or optionally substituted aryl.

In another embodiment, the phenyl anchor moiety is of the formula (XIX):

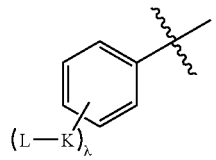

(XIX)

wherein K, L, and λ are as described above.

In one embodiment, K is a covalent bond, alkoxy, or oxy and L is substituted or unsubstituted aryl, e.g., phenyl, benzothiophenyl, benzofuranyl, pyridiyl, quinoline, isoquinoline, etc. In a further embodiment, L is substituted phenyl, e.g., halogen substituted or alkyl (e.g., methyl).

In another embodiment, the anchor moiety is of the formula (XX):

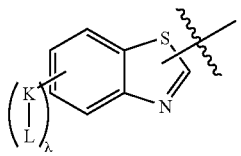

(XX)

wherein K, L, and λ are as described above.

In yet another embodiment, the anchor moiety is of the formula (XXI):

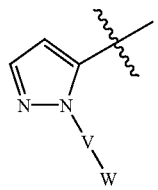

(XXI)

wherein V and W are, respectively, auxiliary sublinking and auxiliary subanchor moieties as described above.

In one embodiment, the anchor moiety and/or other portions of the ACE-2 modulating, e.g., inhibiting, compound may be selected such that the compound is less toxic, e.g., less toxic as measured in the Toxicity Assay.

In another embodiment, the anchor moiety and/or other portions of the ACE-2 modulating, e.g., inhibiting, compound is selected such that the compound is not substantially metabolized before performing its intended function. For example, in one embodiment, the ACE-2 compound may comprise a carbon-carbon bond linking the anchor moiety to the subanchor or sublinking moiety. The effect of metabolism on a particular compound can be determined through the use of assays known in the art. For example, the compounds of the invention may be exposed to serum from a subject, and the effect of the serum on the compound of the invention may be monitored.

The term "substantially metabolized" includes metabolism of the ACE-2 modulating, e.g., inhibiting, compound which prevents the modulating compound from performing its intended function. The term does not include cleavage or other alteration of prodrug moieties which do not prevent the ACE-2 modulating, e.g., inhibiting, compound from performing its intended function.

The ACE-2 modulating compound of the invention, e.g., ACE-2 inhibitors, may be identified through assays which determine the compound's $K_i$. An example of such an assay is the ACE-2 Competitive Substrate Assay (ACS Assay). The ACS assay determines the ability of a compound to inhibit the activity of ACE-2 by having a test compound compete with a known ACE-2 substrate and determining the amount of known substrate converted by ACE-2 to its cleaved products. The ACE-2 assay is described in greater detail in Example 11. The invention includes ACE-2 modulating, e.g., inhibiting, compounds which interact with ACE-2 with a $K_i$ of 50 μM or less, 40 μM or less, 20 μM or less, 10 μM or less, 1 μM or less, 0.75 μM or less, 0.1 μM or less, 0.50 μM or less, 0.25 μM or less. 0.10 μM or less, 0.075 μM or less, 0.050 μM or less, 0.040 μM or less, 0.030 μM or less, 0.025 μM or less, 0.01 μM or less, 0.0075 μM or less, 0.005 μM or less, 0.0025 μM or less, or, advantageously, 0.0015 μM or less.

The invention also pertains to an ACE-2 modulating, e.g., inhibiting, compound of the formula (II):

Z-A-B-E (II)

wherein Z is a zinc coordinating moiety, E is an enzyme coordinating moiety, A is an auxiliary pocket binding moiety; and B is a side chain binding pocket moiety. In one embodiment, the compound is an ACE-2 inhibiting compound.

The language "enzyme coordinating moiety" or "E" includes, preferably, carboxylic acids, hydrogen, and cleavable prodrug moieties. It includes electron rich moieties which are able to coordinate to the enzyme to facilitate inhibition of ACE-2. The enzyme coordinating moiety also includes prodrugs which can be hydrolyzed in vivo to an active form. The language "enzyme coordinating moiety" includes any moiety, which, in vivo and/or in vitro, allows for interactions to occur between the ACE- 2 modulating compound and ACE-2. In one embodiment, E is a carboxylic acid or a carboxylic acid equivalent.

The language "carboxylic acid equivalent" includes moieties which allow the ACE-2 modulating compound to perform its intended function, e.g., modulate ACE-2 function. Examples of carboxylic acid equivalents include, for example, $SO_3H$, $PO_3H$, $SO_2NH_2$, $SO_2NHCH_3$, $CONHSO_2R^5$, $SO_2NHCF_3$, $NHSO_2CH_3$, $NHSO_2CF_3$, CONHOH, CONHCN, and other carboxylic acid isoteres. In one embodiment, E is $CO_2R^5$ (e.g., $CO_2H$), $CONR^5R^{5'}$ (e.g., $CONH_2$, $CONHR^5$) or hydrogen, wherein $R^5$ and $R^{5'}$ are each hydrogen, independently substituted or unsubstituted $C_1$–$C_5$ branched or straight chain alkyl, $C_2$–$C_5$ branched or straight chain alkenyl, aryl, $C_3$–$C_8$ ring, optionally substituted with up to four heteroatoms. The term "carboxylic acid equivalent" also includes certain heterocycles which allow the ACE-2 modulating compound to perform its intended function. Examples of heterocyclic carboxylic acid equivalents include tetrazole.

In a further embodiment, E comprises $P^4$, linked to Z through a linker comprising $(CP^{3a}P^{3b})_q$. Examples of $P^4$ groups include substituted lower alkyl esters, unsubstituted lower alkyl esters, branched lower alkyl esters, lower unsubstituted alkenyl esters, lower substituted alkenyl esters, dilower alkyl amino esters, acyl amino esters, acyloxy lower alkyl esters, unsubstituted aryl esters, substituted aryl esters, aryl lower alkyl esters, substituted aryl lower alkyl esters, amides, lower alkyl amides, dilower alkyl amides, lower alkenyl amides, dilower alkenyl amides, and aryl amides. Other examples of $P^4$ include carboxylic acids and $(CH_2)_{1\text{-}4}SP^{4'}$. $P^{4'}$ is alkyl, alkenyl, alkynyl, or hydrogen. In one embodiment, $P^4$ is a hydrogen, carboxylic acid, $(CH_2)_{1\text{-}4}SP^{4'}$, a cleavable prodrug moiety, carboxylic acid, $COOP^{4'}$, or $CONP^{4'}P^{4''}$, wherein $P^{4'}$ and $P^{4''}$ are each independently hydrogen, $C_1$–$C_6$ alkyl, $C_2$–$C_6$ alkenyl, $C_2$–$C_6$ alkynyl, or optionally substituted aryl.

Examples of $P^{3a}$ and $P^{3b}$ include hydrogen, substituted or unsubstituted, branched, straight chain and cyclic $C_1$–$C_5$ alkyl, each independently selected for each occurrence. Examples of values of q include 0, 1, 2, and 3. In one embodiment, $P^{3a}$ and $P^{3b}$ are hydrogen atoms for each occurrence. In another embodiment q is 0.

In another further embodiment, $P^4$ is a carboxylic acid,

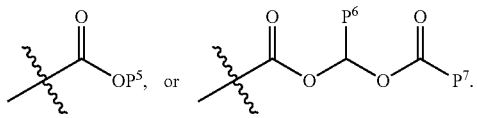

In one particular embodiment, $P^4$ is not a carboxylic acid. $P^5$, $P^6$, and $P^7$ are each independently selected from the group consisting of substituted and unsubstituted alkyl, benzyl, phenyl, cycloalkyl, alkenyl, and alkynyl. $P^5$, $P^6$, and $P^7$ are any substituent which allows the compound of the invention to perform its intended function, e.g., bind or interact with ACE-2. In a further embodiment, $P^5$, $P^6$, and $P^7$ are selected such that the compound is capable of performing its intended function after being administered to a subject. For example, $P^5$, $P^6$, and $P^7$ may be selected such that the compound of the invention is capable of being absorbed by the digestive system after being administered orally. In another embodiment, $P^5$, $P^6$, and $P^7$ include moieties which allow the compound to perform its intended function in vivo. In one embodiment, $P^4$ groups may be cleaved in vivo to yield a carboxylic acid or carboxylate. Therefore, in one embodiment, $P^5$, $P^6$, and $P^7$ may be selected such that $P^4$ is cleaved in vivo to yield a compound which is capable of performing its intended function.

In one embodiment, the invention pertains to compounds of the formula (III):

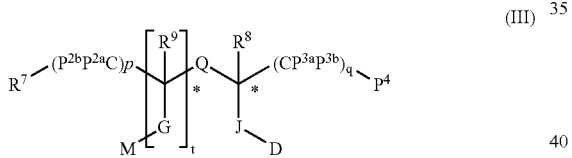

wherein $P^4$ is selected from the group consisting of a carboxylic acid, cleavable prodrug moieties, $COOP^{4'}$, $(CH_2)_{1-4}SP^{4'}$, or $C(O)NP^{4'}P^{4''}$;

$R^7$ is hydrogen, carboxylic acid, unsubstituted or substituted lower alkyl esters, lower alkenyl esters, dilower alkyl amino esters, arylaminocarbonyl, aroyl, aryl, alkylaminocarbonyl, aminocarbonyl, $COOR^{7'}$, $CONR^{7'}R^{7''}$, hydroxy, ether, thio, amino, $(CH_2)_{1-4}SR^{7'}$, a heterocycle, or a cleavable prodrug moiety;

$P^{4'}$, $P^{4''}$, $R^{7'}$ and $R^{7'}$ are each independently hydrogen, $C_1$–$C_6$ alkyl, $C_2$–$C_6$ alkenyl, $C_2$–$C_6$ alkynyl or optionally substituted aryl;

$R^8$ is selected from the group consisting of hydrogen, alkyl and a covalent bond to D;

$R^9$ is lower alkyl or hydrogen;

Q is a bond, O, S, $CR^3OH$ (e.g., CHOH), $(CR^3R^{3a})_n$ (e.g., $(CH_2)_n$), $CR^3SH$ (e.g., CHSH), $CR^3NR^{3a}R^{3b}$ (e.g., $CR^3NH_2$, $CHNHR^3$, $CHNH_2$, $CR^3NHR^{3a}$), $NR^3$, $O(CR^3R^{3a})_n$ (e.g., $O(CH_2)_n$), $CR^3R^{3a})_nO(CR^{3b}R^{3c})_n$ (e.g., $(CH_2)_nO(CH_2)_n$), wherein n is either 0, 1, 2, or 3, and $R^3$, $R^{3a}$, $R^{3b}$, and $R^{3c}$ are each independently hydrogen, substituted or unsubstituted $C_1$–$C_5$ branched or straight chain alkyl, $C_2$–$C_6$ branched or straight chain alkenyl, aryloxycarbonyl, arylaminocarbonyl, arylalkylsulfonyl, arylalkyl, substituted or unsubstituted acyl, aryl, $C_3$–$C_8$ ring, optionally substituted with up to four heteroatoms;

$P^{2a}$, $P^{2b}$, $P^{3a}$ and $P^{3b}$ are each independently hydrogen, substituted or unsubstituted, branched, straight chain or cyclic $C_1$–$C_5$ alkyl, G is a linking moiety;

M is an anchor moiety, heterocyclic, carbocyclic, or CONR'R'', wherein R' and R'' are each independently hydrogen, $C_1$–$C_6$ alkyl, $C_2$–$C_6$ alkenyl, $C_2$–$C_6$ alkynyl or optionally substituted aryl;

J is selected from the group consisting of a bond, substituted or unsubstituted alkyl, alkenyl, and alkynyl;

D is hydrogen, alkoxy, alkyl, alkenyl, alkynyl, aryl, or optionally linked to G, M, or Q to form a ring;

t is 0 or 1;

p is 0, 1, 2, 3, 4, or 5;

q is 1, 2, or 3; and enantiomers, diastereomers, mixtures of enantiomers, mixtures of diastereomers, and pharmaceutically acceptable salts thereof. In a further embodiment, the * carbons are in the S,S configuration.

In one embodiment, $P^4$ is a carbonyl moiety bound to $R^6$. Examples of $R^6$ include hydroxyl and protecting prodrug moieties. In another further embodiment, Each or $P^{2a}$, $P^{2b}$, $P^{3a}$, and $P^{3b}$ are hydrogen. In another further embodiment, $R^7$ is hydrogen or a carboxylic acid, $R^8$ is hydrogen, p is 0, t is 1, q is 0, and Q is NH.

In another embodiment, the invention pertains to a compound of the formula (IV):

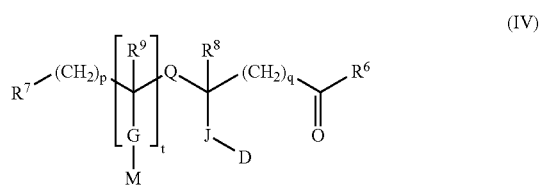

wherein $R^6$ is hydroxyl or a protecting prodrug moiety;

$R^7$ is an hydrogen atom, carboxylic acid, unsubstituted or substituted, arylaminocarboxy, aroyl, alkylaminocarboxy, aminocarboxy, alkenylaminocarboxy, a protecting prodrug moiety, hydroxyl, heterocycle, alkoxy, ether, thiol, an amine lower alkyl esters, lower alkenyl esters, dilower alkyl amino, aryl, $(CH_2)_{1-4}SR^{7'}$, a heterocycle, or a cleavable prodrug moiety, $COOR^{7'}$, $CONR^{7'}R^{7''}$, $(CH_2)_{1-4}SR^{7'}$, a heterocycle, or a cleavable prodrug moiety;

$R^{7'}$ and $R^{7''}$ are each independently hydrogen, $C_1$–$C_6$ alkyl, $C_2$–$C_6$ alkenyl, $C_2$–$C_6$ alkynyl or optionally substituted aryl;

$R^8$ is hydrogen, or alkyl, and optionally linked to D to form a ring;

$R^9$ is lower alkyl or hydrogen;

Q is a bond, O, S, $CR^3OH$, $CR^3SH$, $CR^3NH_2$, $CR^3NR^{3a}R^{3b}$, $NR^3$, $(CR^3R^{3a})_n$, $O(CR^3R^{3a})_n$, $CR^3R^{3a})_nO$ $(CR^{3b}R^{3c})_n$, wherein n is either 0, 1, 2, or 3, and $R^3$, $R^{3a}$, $R^{3b}$, and $R^{3c}$ are each independently hydrogen, substituted or unsubstituted $C_1$–$C_5$ branched or straight chain alkyl, $C_2$–$C_6$ branched or straight chain alkenyl, aryloxycarbonyl, arylaminocarbonyl, arylalkylsulfonyl, arylalkyl, substituted or unsubstituted acyl, aryl, $C_3$–$C_8$ ring, optionally substituted with up to four heteroatoms.

G is a linking moiety;

M is an anchor moiety;

J is a bond, a substituted or unsubstituted alkyl, alkenyl, or alkynyl moiety;

D is hydrogen, alkoxy, alkyl, alkenyl, alkynyl, aryl, or heteroaryl, optionally linked to G, M or Q to form a ring;

t is 0 or 1;

p is 0, 1, 2, 3, 4, or 5; and q is 0, 1, 2, or 3.

In a further embodiment, $R^6$ is hydroxyl, an amino acid (e.g., glycine, alanine), branched or unbranched, substituted or unsubstituted lower alkyls (e.g., methyl, ethyl, propyl groups), lower alkenyl groups (e.g., ethenenyl, propenyl, butenyl, pentenyl), di-lower amino-lower alkyl groups (dimethylamino, diethylamino, diisopropylamino, di-n-propylamino, methylethylamino, methylpropylamino, etc.) acylamino lower alkyl groups, acyloxy lower alkyl groups, aryl groups (e.g., phenyl, furanyl, biphenyl, napthridinyl, pyrazolyl, etc.), aryl lower alkyl groups, and substituted aryl or aryl lower alkyl groups.

In a further embodiment, $R^8$ is hydrogen, or alkyl (e.g., methyl, ethyl, propyl, butyl), optionally linked to D to form a ring.

In a further embodiment, $R^9$ is lower alkyl (e.g., methyl, ethyl, propyl, or butyl) or hydrogen.

In a further embodiment, Q is $CH_2$, O, or $NR^3$. $R^3$ is, for example, hydrogen, substituted or unsubstituted cyclic, branched or straight chain $C_1$–$C_5$ alkyl, $C_1$–$C_5$ alkenyl, acyl, aryloxycarbonyl, arylaminocarbonyl, arylalkylsulfonyl, or aryl.

In a further embodiment, G is a bond, $C_1$, $C_2$, $C_3$, $C_4$, $C_5$ or $C_6$ alkyl, alkenyl, alkynyl, ether, ester, thioether, amine, or carbonyl, optionally substituted with up to three, four, five, or six heteroatoms.

In a further embodiment, M is a hydrogen atom, alkyl (straight, branched or cycloalkyl), alkenyl, alkynyl, heterocyclic, carbocyclic, aryl, e.g., phenyl, biphenyl, heteroaryl, e.g., furanyl, imidazolyl, benzothiophenyl, benzofuranyl, quinolinyl, isoquinolinyl, benzodioxazolyl, benzoxazolyl, benzothiazolyl, benzoimidazolyl, thiazolyl, isothiazolyl, oxazolyl, benzothiazolyl, isooxazolyl, methylenedioxyphenyl, indolyl, thienyl, pyrimidyl, pyrazinyl, pyrazolyl, purinyl, deazapurinyl, naphthyl, napthridinyl, or indolizinyl, wherein in M is optionally substituted with, for example, alkyl, alkenyl, alkynyl, aryl, NR'R", CN, $NO_2$, F, Cl, Br, I, $CF_3$, $CCl_3$, $CHF_2$, $CHCl_2$, CONR'R", $S(O)_{1-2}NR'R"$, CHO, $O(CR'R")_{0-3}CF_3$, $S(O)_{0-2}R'$, $O(CR'R")_{0-3}CCl_3$, $SCF_3$, $SCCl_3$, COR', $CO_2R'$, and OR' wherein R' and R" are each independently hydrogen, $C_1$–$C_4$ alkyl, $C_2$–$C_4$ alkenyl, $C_2$–$C_4$ alkynyl or optionally substituted aryl.

Various groups can be linked to form rings. For example, in a further embodiment, $R^8$ and $R^9$ are hydrogen or alkyl. In another further embodiment, $R^8$ is alkyl and is linked to D to form a ring. In another further embodiment, $R^9$ is alkyl and is linked with M to form a ring. In yet another further embodiment, D and Q are linked to form a ring.

In one embodiment, the compounds of formula (IV) are ACE-2 modulating compounds, e.g., ACE-2 inhibiting compounds.

The invention also pertains to compound wherein $R^7$ is hydrogen or a carboxylic acid; $R^8$ is hydrogen and $R^9$ is hydrogen, p is 0, t is 1, q is 0.

In a further embodiment, compounds of the invention include compounds of the formula (VII):

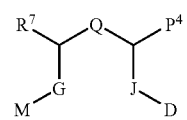

(VII)

wherein

Q is $CH_2$, O, or $NR^3$;

$R^3$ is hydrogen, substituted or unsubstituted, branched, cyclic, or straight chain $C_1$–$C_5$ alkyl, $C_1$–$C_5$ alkenyl, acyl, arylalkyl, aryloxycarbonyl, arylaminocarbonyl, arylalkylsulfonyl, or aryl;

$P^4$ is a carboxylic acid, substituted or unsubstituted, branched, cyclic, or straight chain, lower alkyl esters, alkenyl esters, dilower alkyl amino esters, $(CH_2)_{1-4}SP^{4'}$, $COOP^{4'}$, or $CONP^{4'}P^{4''}$;

$P^{4'}$ and $P^{4''}$ are each independently hydrogen, $C_1$–$C_6$ alkyl, $C_2$–$C_6$ alkenyl, $C_2$–$C_6$ alkynyl or optionally substituted aryl;

$R^7$ is hydrogen, carboxylic acid, unsubstituted or substituted lower alkyl esters, lower alkenyl esters, dilower alkyl amino esters, arylaminocarbonyl, aroyl, aryl, alkylaminocarbonyl, aminocarbonyl, lower alkyl amides, dilower alkyl amides, alkenylaminocarboxy, hydroxy, ether, thio, amino, $(CH_2)_{1-4}SR^{7'}$, a heterocycle, cleavable prodrug moiety, $COOR^{7'}$, $CONR^{7'}R^{7''}$, a heterocycle, or a cleavable prodrug moiety;

$R^{7'}$ and $R^{7''}$ are each independently hydrogen, $C_1$–$C_6$ alkyl, $C_2$–$C_6$ alkenyl, $C_2$–$C_6$ alkynyl or optionally substituted aryl;

$R^{7'}$ is alkyl, alkenyl, alkynyl, aryl, or hydrogen;

G is a linking moiety, such as, for example, a covalent bond, substituted or unsubstituted, $C_1$–$C_6$ (e.g., $C_1$, $C_2$, $C_3$, $C_4$, $C_5$ or $C_6$) alkyl, alkenyl, alkynyl, heterocyclic, ether, thioether, amine or carbonyl moiety, optionally substituted with up to three, four, five or six heteroatoms;

M is an anchor moiety, such as for example, alkyl, hydrogen, heterocyclic, or carbocyclic;

J is a bond, substituted or unsubstituted alkyl, alkenyl, or alkynyl; and

D is alkyl, alkenyl, alkynyl, aryl, alkoxy, heteroaryl, or optionally linked to Q, G or M to form a ring, and enantiomers, diastereomers, mixtures of enantiomers, mixtures of diastereomers, and pharmaceutically acceptable salts thereof.

In another embodiment, the invention pertains to compounds wherein $P^4$ comprises a carbonyl group bonded to $R^6$. Certain compounds of this embodiment are represented by the formula (VIII):

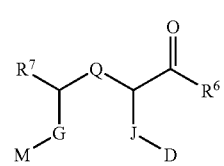

(VIII)

wherein $R_6$ is —OH or a protecting prodrug moiety; $R_7$ is an hydrogen atom, carboxylic acid, an amide, a protecting prodrug moiety, hydroxyl, thiol, heterocycle (e.g., imidazole, thiazole, oxazole), ether, alkoxy, or an amine; Q is CH$_2$, O, NH, or NR$^3$; G is a linking moiety as described above, a covalent bond, C$_1$–C$_5$ alkyl, alkenyl, alkynyl, ether, thioether, amine, or carbonyl; M is an anchor moiety as described above, alkyl, hydrogen, aryl, heteroaryl, heterocyclic, or carbocyclic; J is a bond, substituted or substituted alkyl, alkenyl, or alkynyl moiety; and D is alkyl, alkoxy, alkenyl, alkynyl, aryl, or heteroaryl, optionally linked to G or M to form a ring. In a further embodiment, M comprises a subanchor moiety, as defined above.

In an embodiment, R$^7$ is a carboxylic acid group; G is a covalent bond, C$_1$–C$_3$ alkyl, or aminoalkyl; and M is phenyl, or heteroaryl (e.g., thienyl, triazolyl, thiazolyl, or imidazolyl). In another embodiment, J is a covalent bond or alkynyl. D may be alkyl (e.g., n-propyl, methyl, isopropyl, ethyl, cycloalkyl, or butyl), a side chain of a natural or unnatural amino acid, or heteroaryl (e.g., pyridinyl or imidozlyl).

Examples of compounds of the invention which may be prodrugs include compounds of the formula (V):

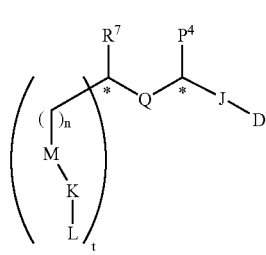

(V)

wherein

M is carbocyclic, heterocyclic, CONR'R'', wherein R' and R'' are each independently hydrogen, C$_1$–C$_6$ alkyl, C$_2$–C$_6$ alkenyl, C$_2$–C$_6$ alkynyl or optionally substituted aryl;

Q is a bond, O, S, CR$^3$OH, CR$^3$SH, CR$^3$NR$^{3a}$R$^{3b}$, NR$^3$, (CR$^3$R$^{3a}$)$_n$, O(CR$^3$R$^{3b}$)$_n$, and (CR$^3$R$^{3a}$)$_n$O(CR$^{3b}$R$^{3c}$)$_n$, wherein n is 0, 1, 2, or 3 and R$^3$, R$^{3a}$, R$^{3b}$, and R$^{3c}$ are each independently hydrogen, substituted or unsubstituted, branched, cyclic, or straight chain C$_1$–C$_6$ alkyl, C$_2$–C$_6$ alkenyl, acyl, arylalkyl, aryloxycarbonyl, arylaminocarbonyl, arylalkylsulfonyl, or aryl;

K is an independently selected sublinking moiety for each position capable of substitution of M;

L is an independently selected subanchor moiety selected for each position capable of substitution of M;

P$^4$ is a hydrogen, carboxylic acid, (CH$_2$)$_{1-4}$SP$^{4'}$, a cleavable prodrug moiety, carboxylic acid, COOP$^{4'}$, or CONP$^{4'}$P$^{4''}$;

R$^7$ is hydrogen, carboxylic acid, aroyl, aryl, COOR$^{7'}$, C(O)NR$^{7'}$R$^{7''}$, hydroxy, ether, thio, (CH$_2$)$_{1-4}$SR$^{7'}$, a heterocycle, or a cleavable prodrug moiety;

P$^{4'}$, P$^{4''}$, R$^{7'}$ and R$^{7''}$ independently hydrogen, C$_1$–C$_6$ alkyl, C$_2$–C$_6$ alkenyl, C$_2$–C$_6$ alkynyl or optionally substituted aryl; alkyl, alkenyl, alkynyl, or hydrogen;

n is 0, 1, 2, 3, or 4;

J is a bond, substituted or unsubstituted alkyl, alkenyl, or alkynyl;

D is hydrogen, alkyl, alkenyl, amine, alkoxy, hydroxy, alkynyl, aryl, or heteroaryl, any of which optionally may be branched or substituted;

t is 0 or 1; and enantiomers, diastereomers, mixtures of enantiomers, mixtures of diastereomers, and pharmaceutically acceptable salts thereof.

In one embodiment, Q is O, CR$^3$R$^{3a}$, NR$^3$, or S.

M includes anchor moieties, as described previously, such as, for example, moieties of the formulae:

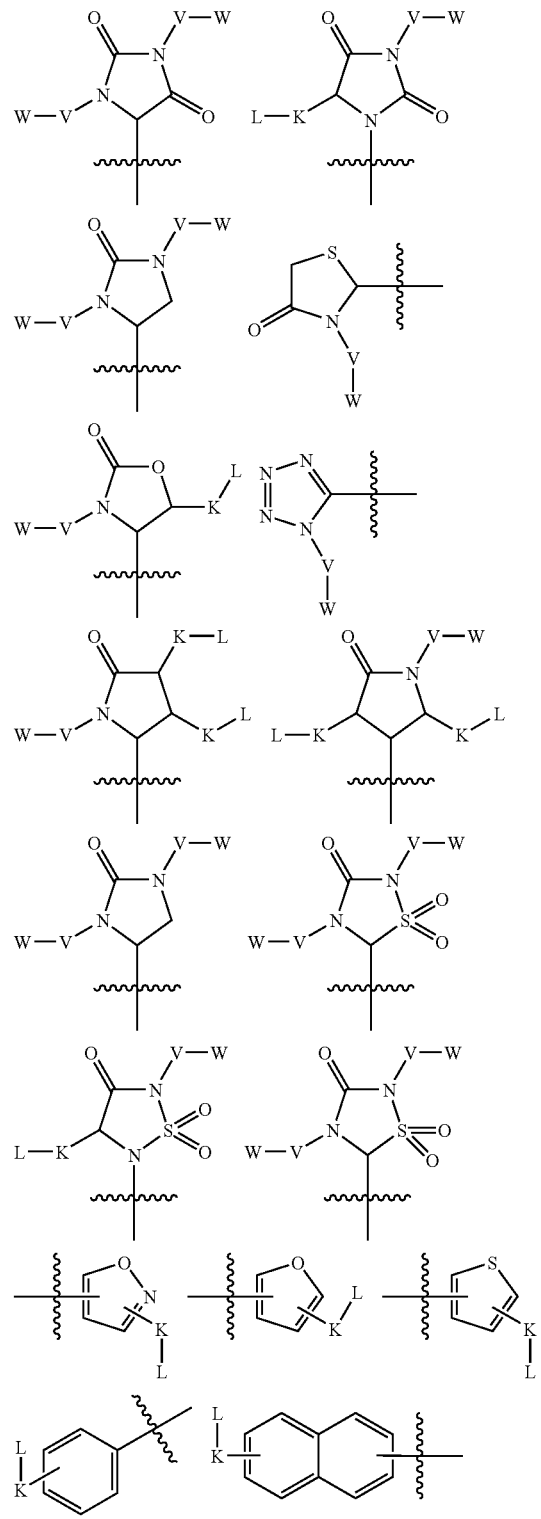

-continued

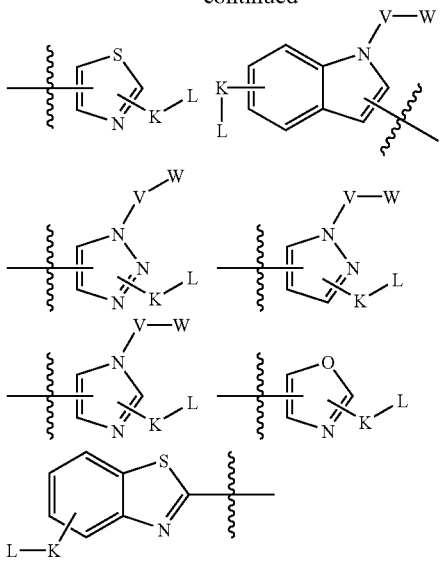

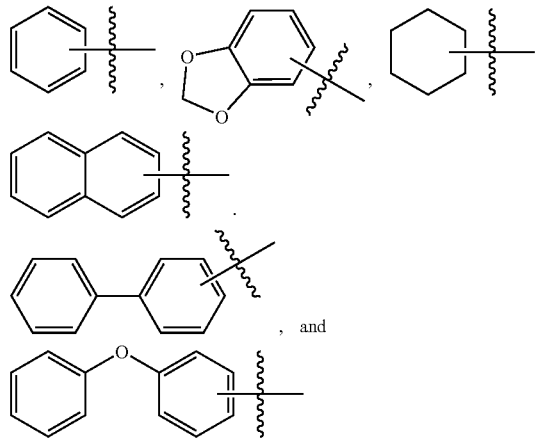

wherein

K is selected independently for each position capable of substitution from the subanchor moieties described previously;

L is selected independently for each position capable of substitution from the subanchor moieties described previously;

V is an auxiliary sublinking moiety; and

W is an auxiliary subanchor moiety.

The term "carbocyclic" includes both cycloalkyl, cycloalkenyl, aryl, biaryl and any ring system which includes one ring composed of carbon atoms bonded to each other. The carbon atoms may be bonded to atoms which are not carbon, as long as at least one ring is formed with the carbon atoms.

The term "heterocyclic" includes heteroaryls as well as any ring formed which incorporate a heteroatom or an atom which is not carbon. The ring may be saturated or unsaturated and may contain one or more double bonds.

The term "auxiliary sublinking moiety" or "V" includes sublinking moieties as described previously that when bonded to a heteroatom (e.g., nitrogen, oxygen, sulfur, phosphorous, etc.) result in a compound of the invention which is capable of performing its intended function (e.g., modulate ACE-2). The term "auxiliary subanchor moieties" include, but are not limited to sublinking moieties as described above.

Examples of auxiliary sublinking moieties (or "V") include covalent bonds, $CONR^{V2}CR^{V}R^{V1}$, $CR^{V}R^{V1}$—$S(O_2)$, $(CR^{V}R^{V1})_{0-3}$, and $(CR^{V}R^{V1})_{0-2}O(CR^{V2}R^{V3})_{0-2}$, wherein $R^{V}$, $R^{V1}$, $R^{V2}$, and $R^{V3}$ are selected from the group consisting of halogens, hydrogen, and alkyl. In a further embodiment, V is $(CH_2)$, $CONHCH_2$, $CH_2$—$S(O_2)$, $(CH_2)_2$, or $(CH_2)O(CH_2)$. In another embodiment, V is a covalent bond.

The term "auxiliary subanchor moiety" (or "W") includes, but is not limited to, subanchor moieties as described previously. It also includes moieties that when bonded to auxiliary subanchor moieties result in a compound of the invention which is capable of performing its intended function (e.g., modulate ACE-2).

Examples of auxiliary subanchor moieties (or "W") include, for example, alkyl, alkenyl, alkynyl,

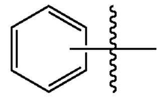

,

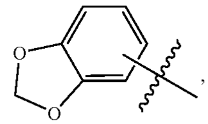

,

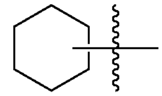

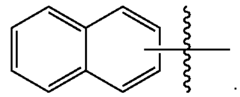

.

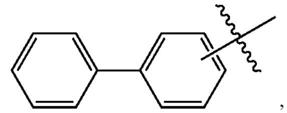

, and

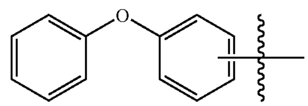

The auxiliary subanchor moiety can be substituted at any position that allows the auxiliary subanchor moiety to perform its intended function, e.g., allows the compound of the invention to interact with ACE-2. Examples of substituents of V and W include hydrogen, chlorine, bromine, fluorine, iodine, nitro, carboxy, substituted or unsubstituted alkoxy, alkyl, and aryl.

In a further embodiment, V—W is or

In a further embodiment, M-K-L is or

In yet another further embodiment, M-K-L is or

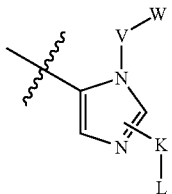

Examples of sublinking moieties (or "K") include covalent bonds, $CONR^{K2}CR^KR^{K1}$, $CR^KR^{K1}-S(O_2)$, $(CR^KR^{K1})_{0-3}$, and $(CR^KR^{K1})_{0-2}O(CR^{K2}R^{K3})_{0-2}$, wherein $R^K$, $R^{K1}$, $R^{K2}$, and $R^{K3}$ are selected from the group consisting of halogens, hydrogen, and alkyl. In a further embodiment, K is $(CH_2)$, $CONHCH_2$, $CH_2-S(O_2)$, $(CH_2)_2$, or $(CH_2)O(CH_2)$. Other sublinking moieties include $NR^K$, O, and S.

In one embodiment, the subanchor moiety (or "L") is selected from the group consisting of hydrogen, $NH_2$, and substituted and unsubstituted alkyl, aryl, arylalkyl, and arylalkylamino. L can be substituted at any position which allows it to perform its intended function. L can be substituted at any position capable of being substituted. Examples of possible substituents include, but are not limited to, hydrogen, chlorine, bromine, fluorine, iodine, nitro, carboxy, substituted or unsubstituted alkoxy, alkyl, and aryl.

In a further embodiment, M is:

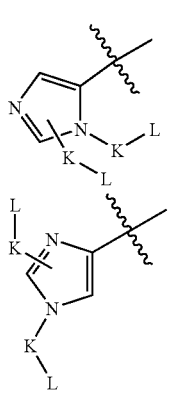
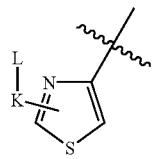

wherein

K and L are chosen independently for each position capable of substitution. Examples of K include covalent bonds, alkyl, alkenyl, alkynyl, or aryl. Examples of L include hydrogen atoms, substituted and unsubstituted alkyl, aryl, arylalkylamino, arylalkyl,

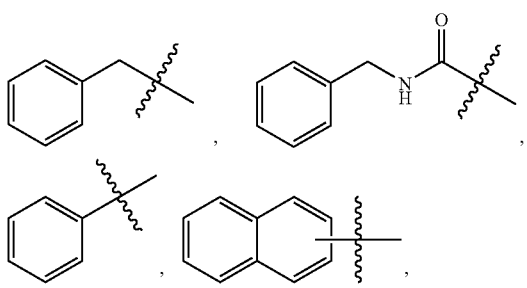

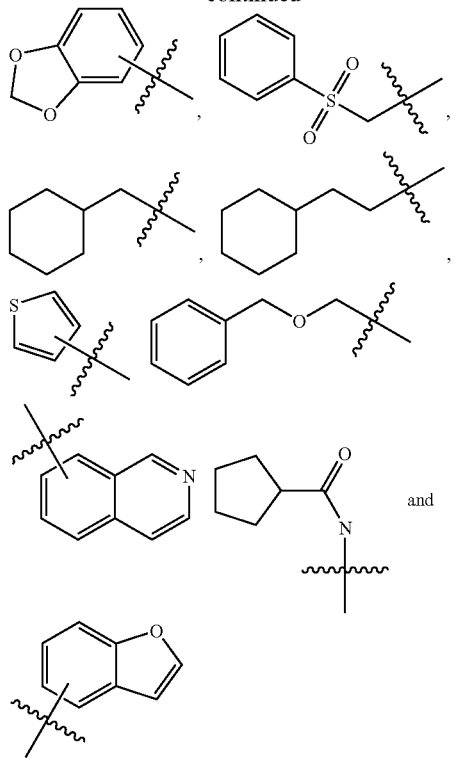

and

Each of the subanchor and sublinking moieties shown above can be substituted at each position capable of substitution. Examples of possibly advantageous substituents of the subanchor and sublinking moieties include chlorine, bromine, fluorine, iodine, nitro, alkoxy (substituted or unsubstituted), cyano, fluoroalkoxy ($OCF_3$), alkyl (substituted or unsubstituted), carboxy, fluoroalkyl ($CF_3$), and substituted or unsubstituted aryl, e.g., benzyl.

In a further embodiment, M is linked to K and/or L through a carbon-carbon bond. In a further embodiment, K is a covalent bond and L is a hydrogen atom. In another, K is a covalent bond and L is alkyl.

In another further embodiment, n is 1. In yet another embodiment, Q is NH. In another, J is a bond.

In another further embodiment, D is alkyl (e.g., substituted alkyl, e.g., alkyl amino, alkylhydroxy, alkylthio, alkylphenyl, alkylcycloalkyl, or alkylacetylene) or alkoxy. For example, in one further embodiment D is alkyl, e.g., $C_1-C_8$, e.g., isobutyl.

In another further embodiment, $P^4$ and $R^7$ are each carboxylic acids,

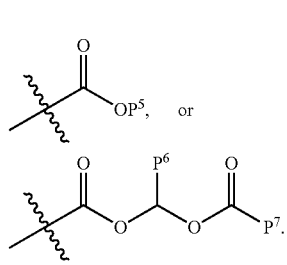

In one particular embodiment, both $P^4$ and $R^7$ are not both carboxylic acids. $P^5$, $P^6$, and $P^7$ are each independently selected from the group consisting of substituted and unsubstituted alkyl, benzyl, phenyl, cycloalkyl, alkenyl, and alkynyl. $P^5$, $P^6$, and $P^7$ are any substituent which allows the compound of the invention to perform its intended function, e.g., bind or interact with ACE-2. In a further embodiment, $P^5$, $P^6$, and $P^7$ are selected such that the compound is capable of performing its intended function after being administered to a subject. For example, $P^5$, $P^6$, and $P^7$ may be selected such that the compound of the invention is capable of being absorbed by the digestive system after being administered orally. In another embodiment, $P^5$, $P^6$, and $P^7$ include moieties which allow the compound to perform its intended function in vivo. In one embodiment, $P^4$ and $R^7$ groups may be cleaved in vivo to yield a carboxylic acid or carboxylate. Therefore, in one embodiment, $P^5$, $P^6$, and $P^7$ may be selected such that in vivo $P^4$ and/or $R^7$ are selected such that they are cleaved in vivo to yield a compound which is capable of performing its intended function.

The invention also pertains to compounds wherein, the * carbons are of the S configuration. The following diagram shows the stereochemistry of four possible stereoisomers:

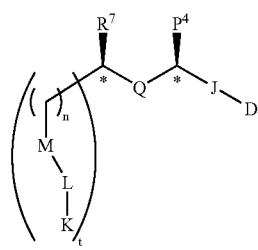

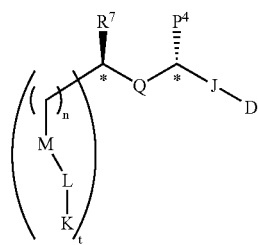

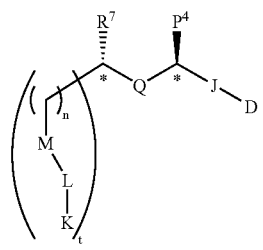

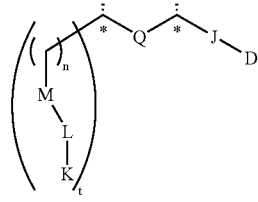

Examples of compounds of the invention of formula (V) include:

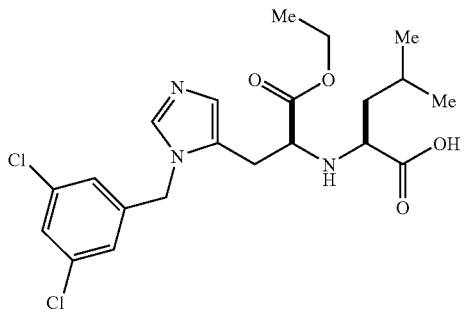

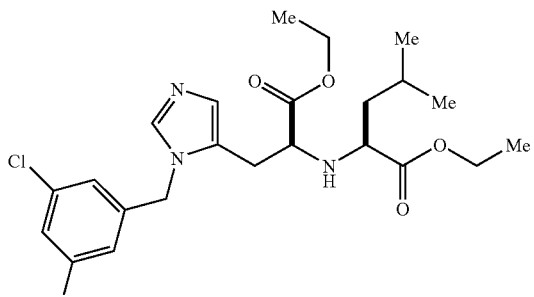

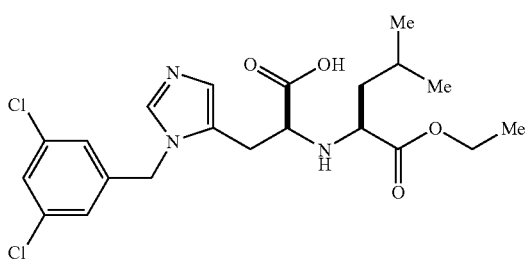

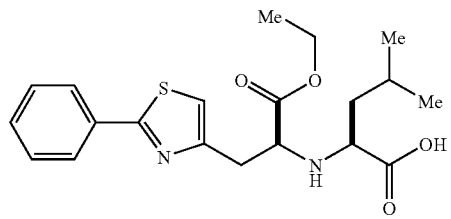

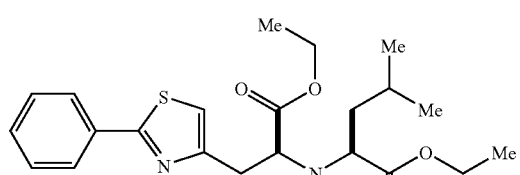

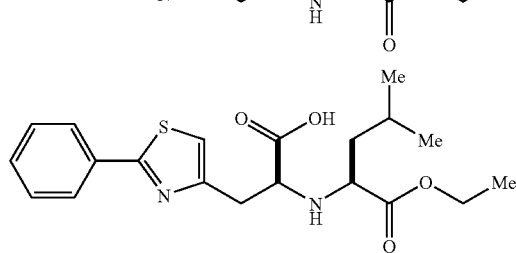

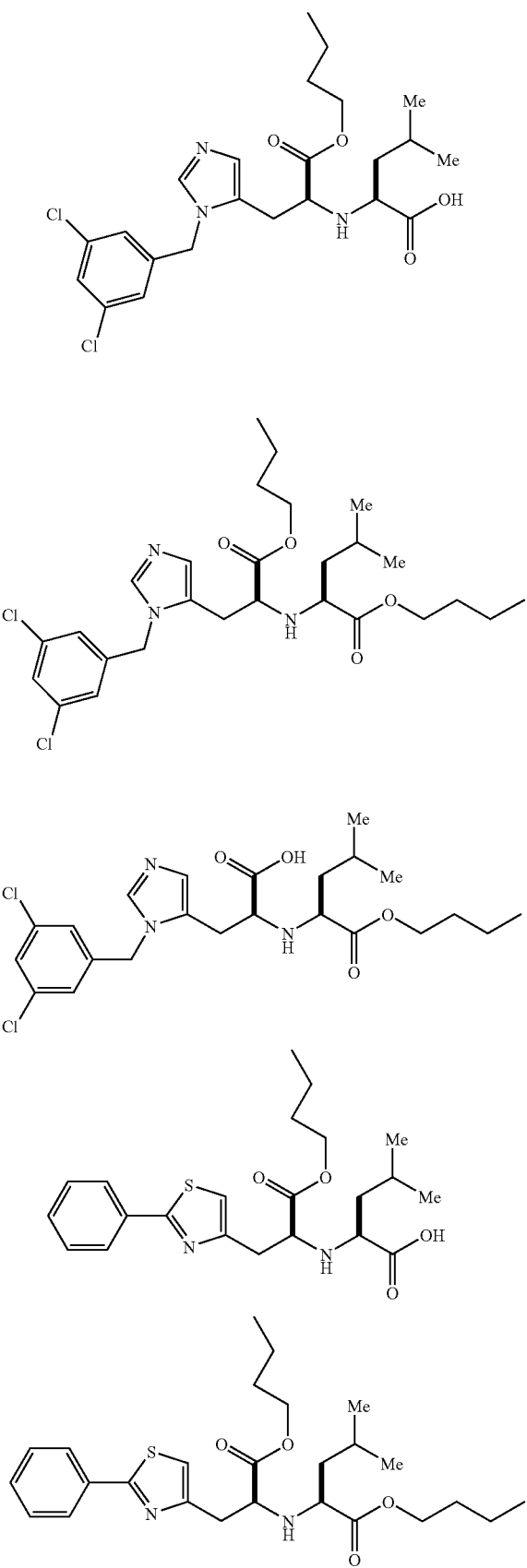
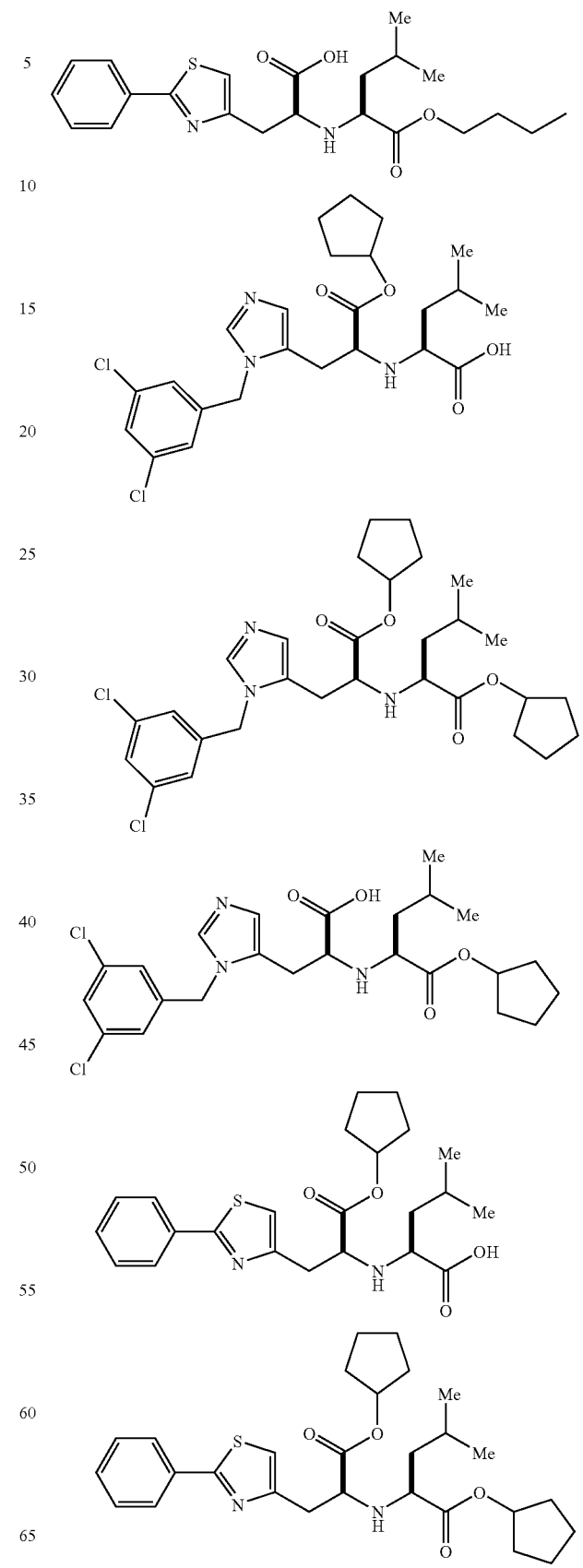

-continued
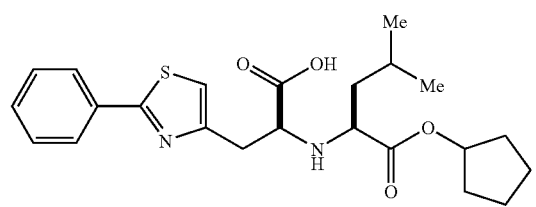
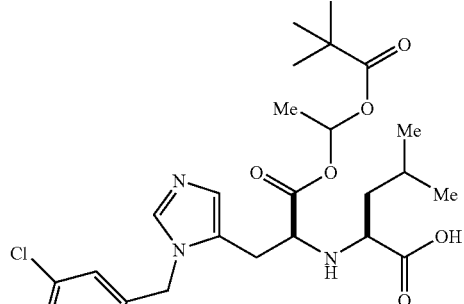
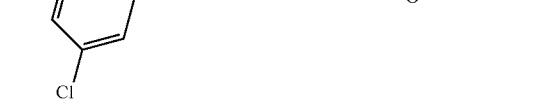
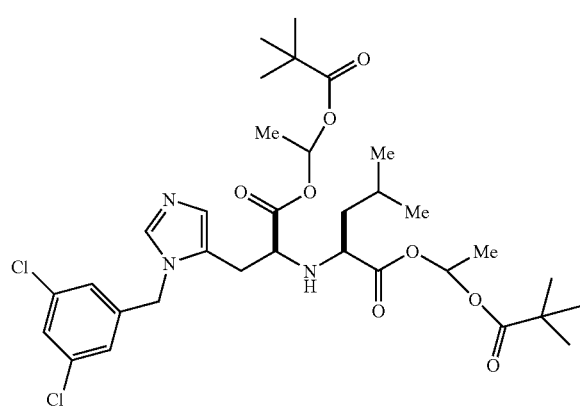
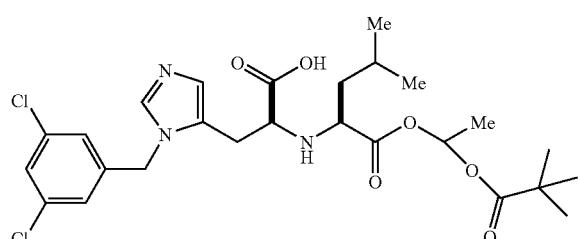
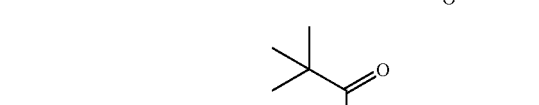
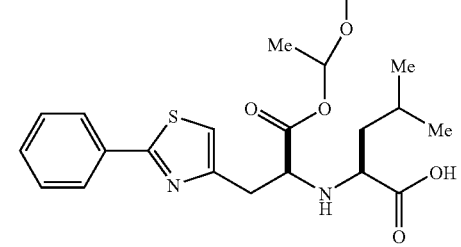
-continued
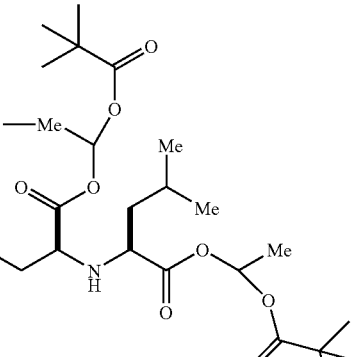
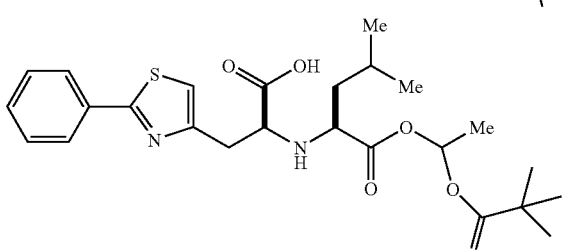
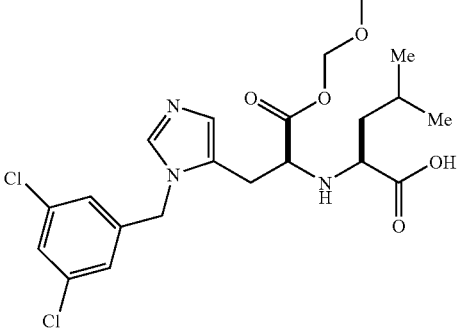
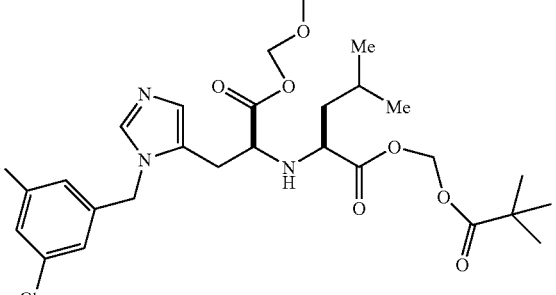
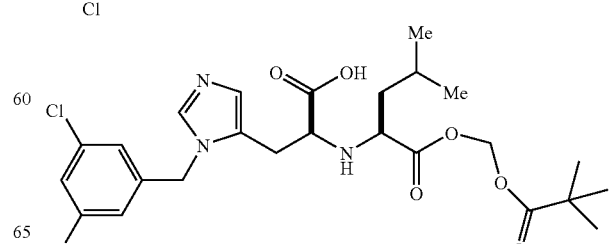

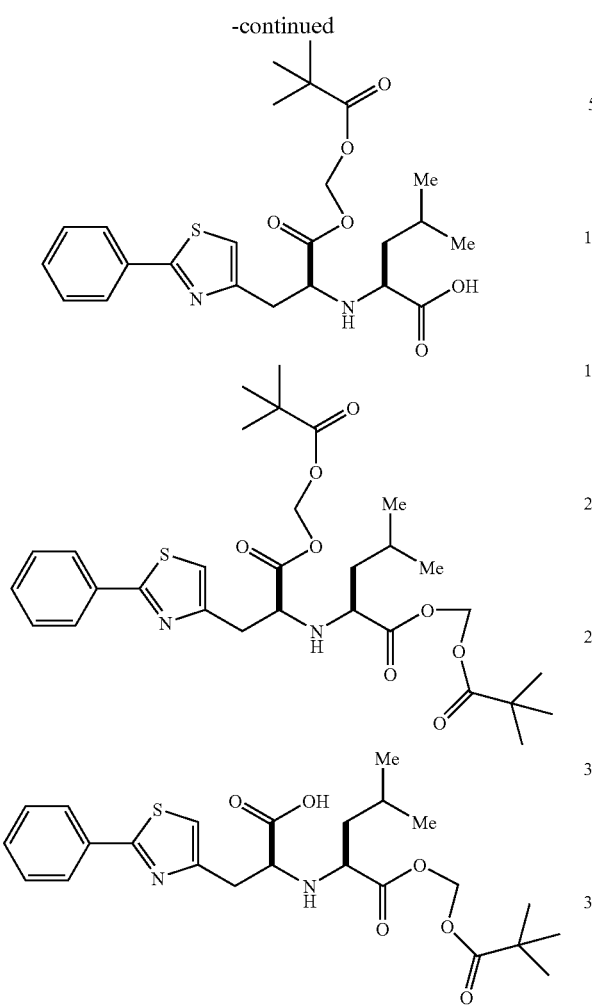

Compounds of the invention of formula V include, but are not limited to, 2-{2-[3-(3,5-Dichloro-benzyl)-3H-imidazol-4-yl]-1-ethoxycarbonyl-ethylamino}-4-methyl-pentanoic acid; 2-{2-[3-(3,5-Dichloro-benzyl)-3H-imidazol-4-yl]-1-ethoxycarbonyl-ethylamino}-4-methyl-pentanoic acid ethyl ester; 2-{1-Carboxy-2-[3-(3,5-dichloro-benzyl)-3H-imidazol-4-yl]-ethylamino}-4-methyl-pentanoic acid ethyl ester; 2-[1-Ethoxycarbonyl-2-(2-phenyl-thiazol-4-yl)-ethylamino]-4-methyl-pentanoic acid; 2-[1-Ethoxycarbonyl-2-(2-phenyl-thiazol-4-yl)-ethylamino]-4-methyl-pentanoic acid ethyl ester; and 2-[1-Carboxy-2-(2-phenyl-thiazol-4-yl)-ethylamino]-4-methyl-pentanoic acid ethyl ester.

The compounds of the invention also include prodrugs. Prodrugs of the invention may or may not be able to interact with ACE-2 prior to being metabolized in vivo. However, once the compounds of the invention which are prodrugs are metabolized in vivo or in vitro, they are capable of performing their intended function, e.g., bind or interact with ACE-2. In one embodiment, the compounds of the invention are capable of performing their intended function after being orally administered. In order to perform their intended function after oral administration, it is believed that the compounds must be absorbed by a portion of the digestive tract. In one embodiment of the invention, the compounds of the invention are capable of being absorbed by the digestive tract.

In another embodiment, the prodrug compound is metabolized in vivo or in vitro to yield a compound which is capable of performing its intended function, e.g., bind or interact with ACE-2. The ability of a compound to be metabolized in vivo or in vitro can be determined using methods known in the art. Examples of these methods include exposing the compound of the invention to reactive components present in a subject and analyzing the results of the interaction of the compound of the invention with the reactive components. Examples of reactive components include, for example, enzymes present in vivo, and other species present in vivo which are capable of interacting with and altering the compound of the invention.

The compounds of formula VI below, may be converted to compounds which are included in formula I–V, VII, and VIII, above, after being metabolized in vivo, in vitro, or ex vivo. In one embodiment, the invention pertains to a method for treating a subject by administering to the subject an effective amount of a compound which is metabolized in vivo to a compound capable of interacting with ACE-2. In a further embodiment, the compound capable of interacting with ACE-2 is of any one of formulas I–VIII.

The invention also pertains to compounds of the formula (VI):

(VI)

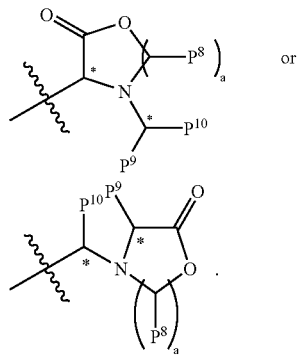

wherein II is

M is heterocyclic, carbocyclic, or CONR'R", wherein R' and R" are each independently hydrogen, $C_1$–$C_6$ alkyl, $C_2$–$C_6$ alkenyl, $C_2$–$C_6$ alkynyl or optionally substituted aryl;

K is an independently selected subanchor moiety for each position of M which is capable of substitution;

L is an independently selected subanchor moiety for each position of M which is capable of substitution;

$P^8$ is hydrogen or alkyl;

$P^9$ is carboxylic acid, unsubstituted or substituted lower alkyl esters, $(CH_2)_{1-4}SP^{9'}$, lower alkenyl esters, dilower alkyl amino esters, amides (lower alkylaminocarbonyl, lower dialkylaminocarbonyl, aminocarbonyl, alkenylaminocarbonyl, dialkenylaminocarbonyl, arylaminocarbonyl, arylalkyl aminocarbonyl, etc.) lower alkyl amides, dilower alkyl amides, or lower alkyl amides;

$P^{10}$ is carboxylic acid, unsubstituted or substituted lower alkyl esters, $(CH_2)_{1-4}SP^{10'}$, lower alkenyl esters, dilower alkyl amino esters, amides (lower alkylaminocarbonyl, lower dialkylaminocarbonyl, aminocarbonyl, alkenylaminocarbonyl, dialkenylaminocarbonyl, arylaminocarbonyl, arylalkylaminocarbonyl, etc.), lower alkyl amides, dilower alkyl amides, or lower alkyl amides;

$P^{9'}$ and $P^{10'}$ are each independently alkyl, alkenyl, alkynyl, aryl, or hydrogen;

a is 1, 2, or 3;

b is 0 or 1; and x is 0, 1, 2, 3, or 4, and enantiomers, diastereomers, mixtures of enantiomers, mixtures of diastereomers, and pharmaceutically acceptable salts thereof.

Examples of M include anchor moieties include those described above, such as, for example, substituted or unsubstituted aryl, heteroaryl, carbocyclic, heterocyclic or amidyl moieties. In a further embodiment, M includes moieties of the formula:

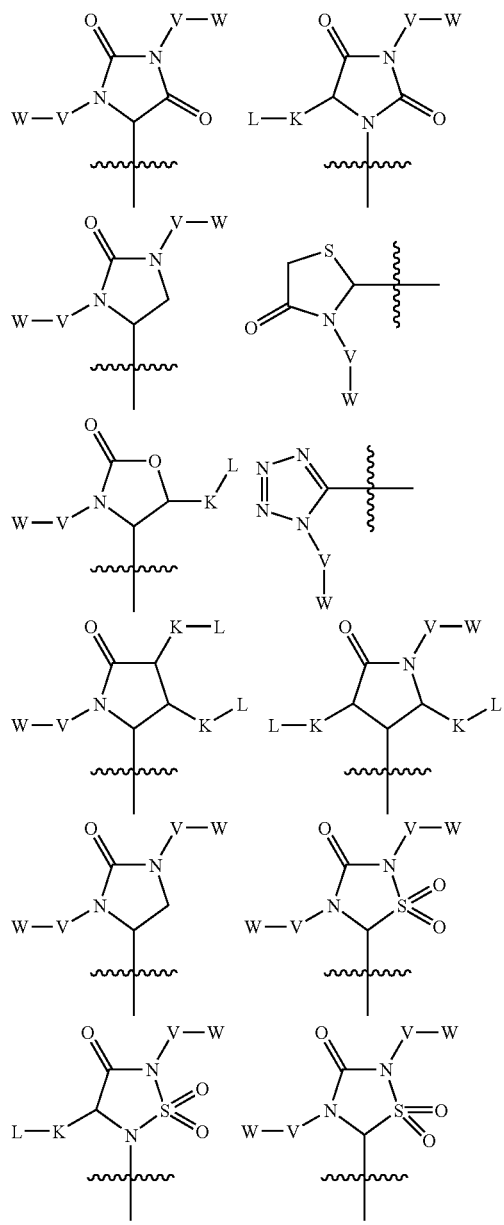

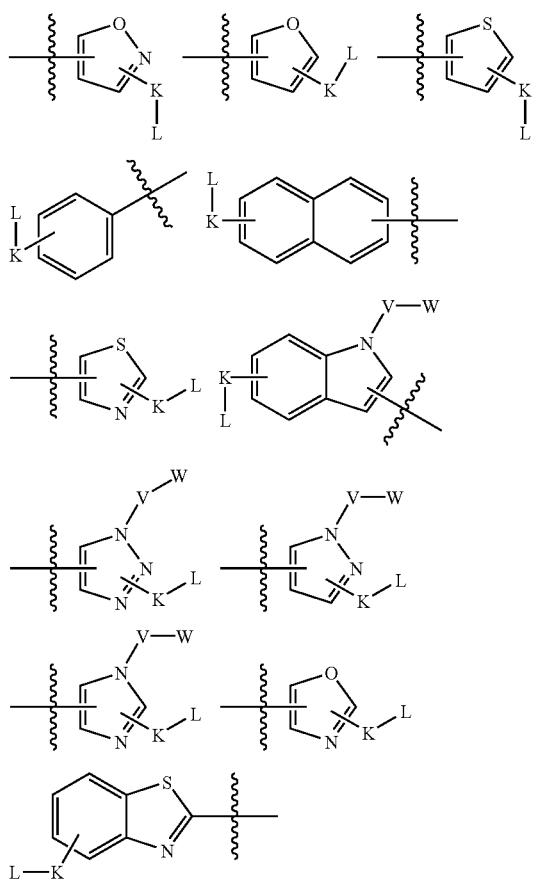

wherein K and L are each independently selected subanchor and sublinking moieties as described above. V and W are each independently selected auxiliary subanchor and sublinking moieties as described above.

Examples of auxiliary sublinking moieties (or "V") include covalent bonds, $CONR^{V2}CR^{V}R^{V1}$, $CR^{V}R^{V1}$—$S(O_2)$, $(CR^{V}R^{V1})_{0-3}$, and $(CR^{V}R^{V1})_{0-2}O(CR^{V2}R^{V3})_{0-2}$, wherein $R^{V}$, $R^{V1}$, $R^{V2}$, and $R^{V3}$ are selected from the group consisting of halogens, hydrogen, and alkyl. In a further embodiment, V is $(CH_2)$, $CONHCH_2$, $CH_2$—$S(O_2)$, $(CH_2)_2$, or $(CH_2)O(CH_2)$. In another embodiment, V is a covalent bond.

Examples of auxiliary subanchor moieties (or "W") include, for example, alkyl, alkenyl, alkynyl,

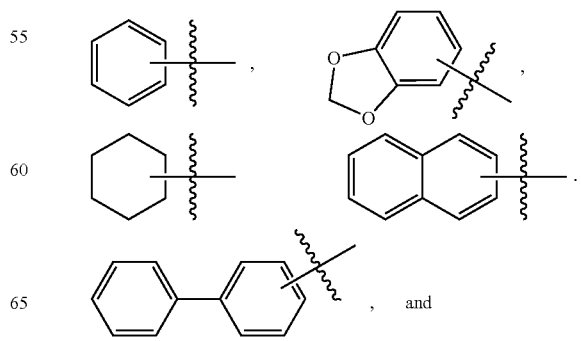

and

-continued
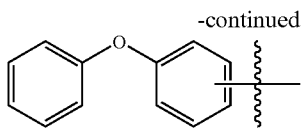
The auxiliary subanchor moiety can be substituted at any position that allows the auxiliary subanchor moiety to perform its intended function, e.g., allows the compound of the invention to interact with ACE-2. Examples of substituents of V and W include hydrogen, chlorine, bromine, fluorine, iodine, nitro, carboxy, substituted or unsubstituted alkoxy, alkyl, and aryl.

In a further embodiment, V—W is or

In a further embodiment, M-K-L is or

In yet another further embodiment, M-K-L is or

Examples of sublinking moieties (or "K") include covalent bonds, $CONR^{K2}CR^{K}R^{K1}$, $CR^{K}R^{K1}—S(O_2)$, $(CR^{K}R^{K1}K)_{0-3}$, and $(CR^{K}R^{K1})_{0-2}O(CR^{K2}R^{K3})_{0-2}$, wherein $R^{K}$, $R^{K1}$, $R^{K2}$, and $R^{K3}$ are selected from the group consisting of halogens, hydrogen, and alkyl. In a further embodiment, K is $(CH_2)$, $CONHCH_2$, $CH_2—S(O_2)$, $(CH_2)_2$, or $(CH_2)O(CH_2)$. Other sublinking moieties include $NR^{K}$, O, and S.

In one embodiment, the subanchor moiety (or "L") is selected from the group consisting of hydrogen, $NH_2$, and substituted and unsubstituted alkyl, aryl, arylalkyl, and arylalkylamino. L can be substituted at any position which allows it to perform its intended function. L can be substituted at any position capable of being substituted. Examples of possible substituents include, but are not limited to, hydrogen, chlorine, bromine, fluorine, iodine, nitro, carboxy, substituted or unsubstituted alkoxy, alkyl, and aryl.

In a further embodiment, M is:

wherein

K and L are chosen independently for each position capable of substitution. Examples of K include covalent bonds, alkyl, alkenyl, alkynyl, or aryl. Examples of L include hydrogen atoms, substituted and unsubstituted alkyl, aryl, arylalkylamino, arylalkyl,

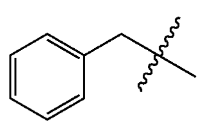

,

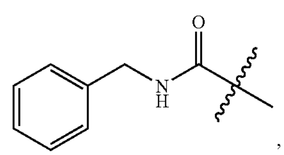

,

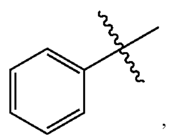

,

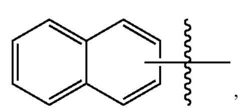

,

,

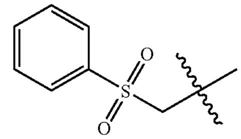

,

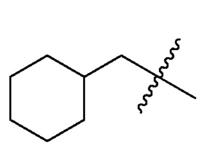

,

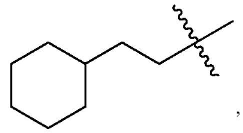

,

-continued

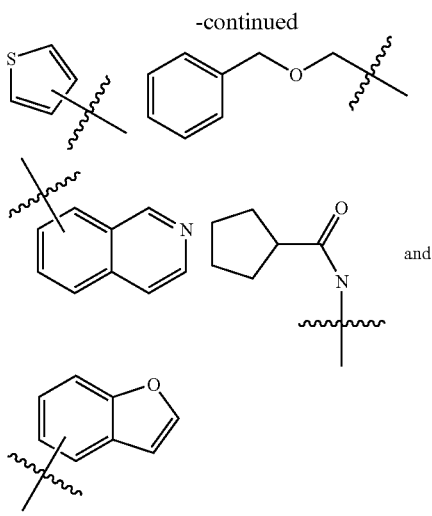

and

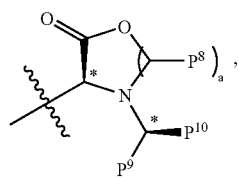

In a further embodiment, M is linked to K and/or L through a carbon-carbon bond. In a further embodiment, K is a covalent bond and L is a hydrogen atom. In another, K is a covalent bond and L is alkyl.

Each of the subanchor, sublinking, auxiliary subanchor, and auxiliary sublinking moieties shown above can be substituted at each position capable of substitution. Examples of possibly advantageous substituents of the subanchor and sublinking moieties include chlorine, bromine, fluorine, iodine, nitro, alkoxy (e.g., OR', unsubstituted or substituted, e.g., halogenated, e.g., fluoroalkoxy, $O(CR'R'')_{0-3}CF_3$, $O(CR'R'')_{0-3}CCl_3$), cyano, alkyl (unsubstituted or substituted, e.g., halogenated, e.g., fluoroalkyl, e.g., $(CR'R'')_{0-3}CF_3$, $(CR'R'')_{0-3}CCl_3$, $(CR'R'')_{0-3}CHF_2$, $(CR'R'')_{0-3}CHCl_2$, etc.), carboxy (e.g., CONR'R'', CHO, $CO_2R'$, COR', etc.), $S(O)_{0-2}R'$, $S(O)_{1-2}NR'R'$, thioethers (e.g., alkylthiols, e.g., substituted or unsubstituted, e.g., $SCF_3$, $SCCl_3$) and substituted or unsubstituted aryl, alkenyl, alkynyl, e.g., benzyl. Other examples of substituents for the subanchor and the sublinking moieties include other substituents described supra wherein R' and R'' are each independently hydrogen, $C_1$–$C_6$ alkyl, $C_2$–$C_6$ alkenyl, $C_2$–$C_6$ alkynyl or optionally substituted aryl.

In one embodiment, M is bound to the subanchor or sublinking moiety through a carbon atom, e.g., through a carbon-carbon bond, or through another bond which is substantially metabolically stable.

In another further embodiment, x is 1. In another, a is 1. In yet another, $P^9$ is substituted or unsubstituted alkyl (e.g., $C_1$–$C_8$ alkyl, e.g., methyl, ethyl, propyl, t-butyl, isobutyl, pentyl, hexyl, etc.), alkylamino, alkylhydroxy, alkyl thio, alkenylphenyl, alkylcycloalkyl, and alkylacetylene.

In another further embodiment, II is

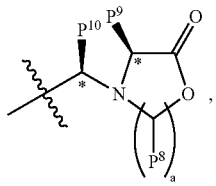

and the * carbons are of the S configuration (as shown).

In yet another further embodiment, II is

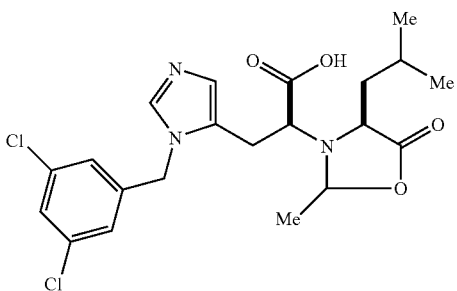

and the * carbons are of the S configuration (as shown).

Examples of compounds of the invention of formula (VI) include:

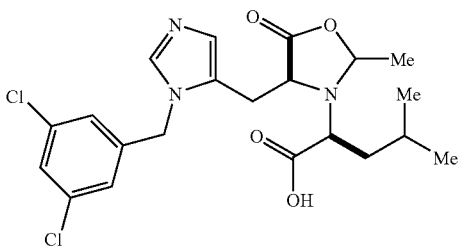

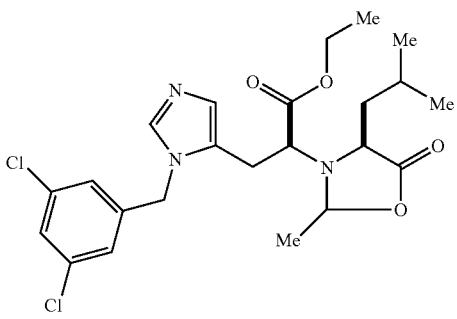

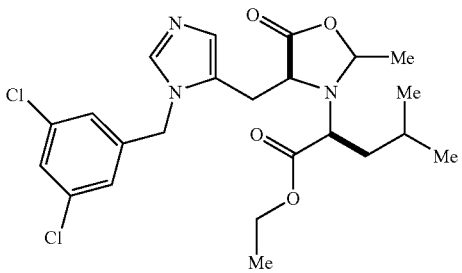

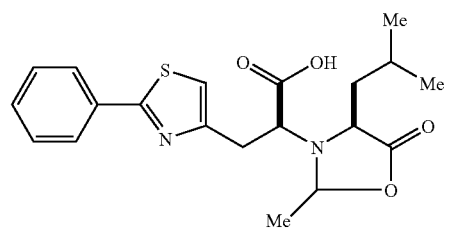
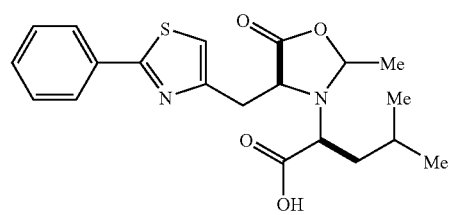
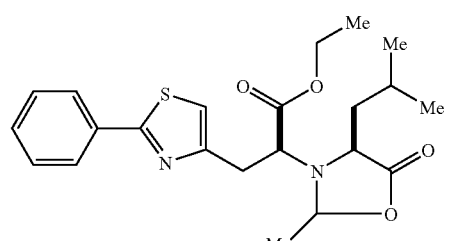
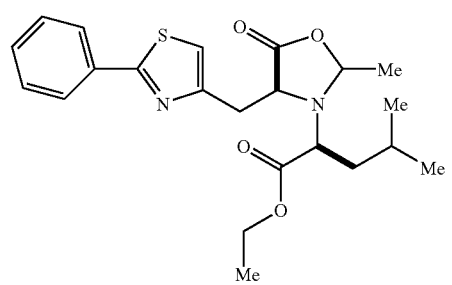
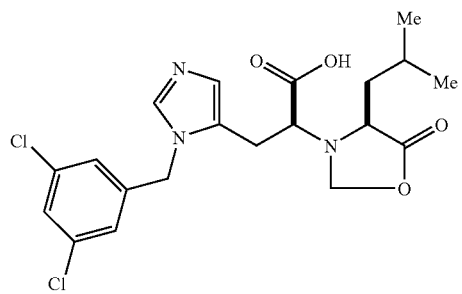
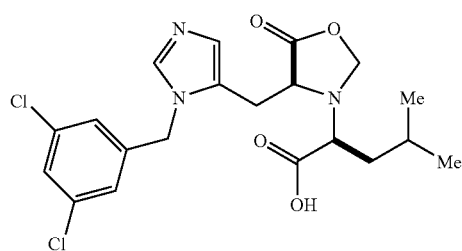
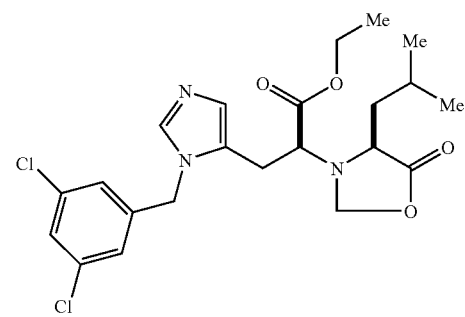
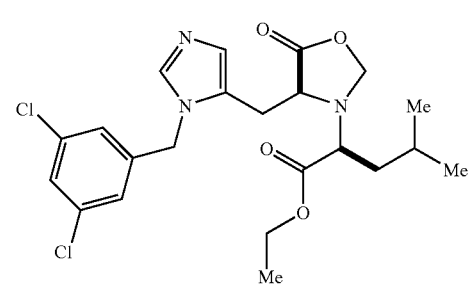
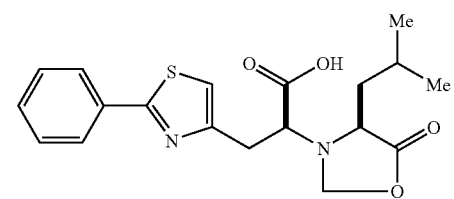
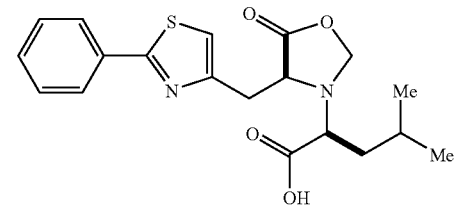
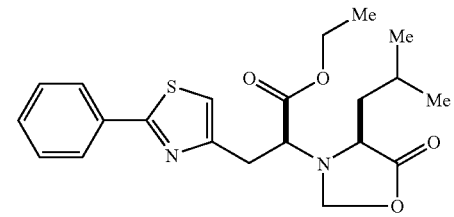
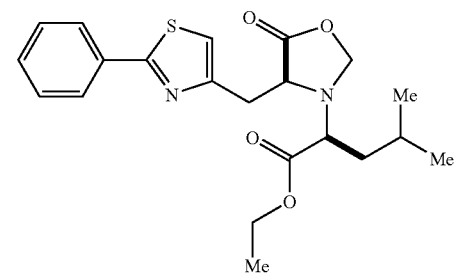
Examples of compounds of formula VI of the invention include, but are not limited to, 3-[3-(3,5-Dichloro-benzyl)-

3H-imidazol-4-yl]-2-(4-isobutyl-2-methyl-5-oxo-oxazolidin-3-yl)-propionic acid; 2-{4-[3-(3,5-Dichloro-benzyl)-3H-imidazol-4-ylmethyl]-2-methyl-5-oxo-oxazolidin-3-yl}-4-methyl-pentanoic acid; 3-[3-(3,5-Dichloro-benzyl)-3H-imidazol-4-yl]-2-(4-isobutyl-2-methyl-5-oxo-oxazolidin-3-yl)-propionic acid ethyl ester; 2-{4-[3-(3,5-Dichloro-benzyl)-3H-imidazol-4-ylmethyl]-2-methyl-5-oxo-oxazolidin-3-yl}-4-methyl-pentanoic acid ethyl ester; 2-(4-Isobutyl-2-methyl-5-oxo-oxazolidin-3-yl)-3-(2-phenyl-thiazol-4-yl)-propionic acid; 4-Methyl-2-[2-methyl-5-oxo-4-(2-phenyl-thiazol-4-ylmethyl)-oxazolidin-3-yl]-pentanoic acid; 2-(4-Isobutyl-2-methyl-5-oxo-oxazolidin-3-yl)-3-(2-phenyl-thiazol-4-yl)-propionic acid ethyl ester; and 4-Methyl-2-[2-methyl-5-oxo-4-(2-phenyl-thiazol-4-ylmethyl)-oxazolidin-3-yl]-pentanoic acid ethyl ester.

In one embodiment, the ACE-2 compounds of the invention do not include compounds A, G, H, I, J, or L. In another embodiment, the ACE-2 compounds of the invention do not include BD, 2-(1-carboxy-ethylamino)-3-(1H-imidazol-4-yl)-propionic acid.

Examples of compounds of the invention include:
2-{1-Carboxy-2-[3-(3-nitro-benzyl)-3H-imidazol-4-yl]-ethylamino}-4-methyl-pentanoic acid;
2-[2-(3-Benzyl-3H-imidazol-4-yl)-1-carboxy-ethylamino]-hexanoic acid;
2-[2-(3-Benzyl-3H-imidazol-4-yl)-1-carboxy-ethylamino]-4-methyl-pentanoic acid;
2-[1-Carboxy-2-(1H-imidazol-4-yl)-ethylamino]-4-phenyl-butyric acid;
2-[2-(3-Benzyloxymethyl-3H-imidazol-4-yl)-1-carboxy-ethylamino]-4-methyl-pentanoic acid;
2-[1-Carboxy-2-(methyl-phenyl-amino)-ethylamino]-4-methyl-pentanoic acid;
2-[1-Carboxy-2-(1H-imidazol-4-yl)-ethylamino]-4-methyl-pentanoic acid;
2-[2-(1-Benzyl-1H-imidazol-4-yl)-1-carboxy-ethylamino]-4-methyl-pentanoic acid;
2-(1-Carboxy-2-phenyl-ethylamino)-3-(3H-imidazol-4-yl)-propionic acid;
2-[1-Carboxy-2-(1H-imidazol-4-yl)-ethylamino]-4-methyl-pentanoic acid;
2-[1-Carboxy-2-(4-hydroxy-phenyl)-ethylamino]-3-(1H-imidazol-4-yl)-propionic acid;
2-[1-Carboxy-2-(1H-imidazol-4-yl)-ethylamino]-4-phenyl-butyric acid;
2-[1-Carboxy-2-(1H-imidazol-4-yl)-ethylamino]-pentanoic acid;
2-[2-(1H-Imidazol-4-yl)-1-methoxycarbonyl-ethylamino]-4-methyl-pentanoic acid;
2-(1-Carboxy-3-phenyl-propylamino)-5-pyridin-2-yl-pent-4-ynoic acid;
2-{1-Carboxy-2-[1-(4-chloro-benzyl)-1H-imidazol-4-yl]-ethylamino}-4-methyl-pentanoic acid;
2-[2-(1-Benzyl-1H-imidazol-4-yl)-1-carboxy-ethylamino]-4-methyl-pentanoic acid;
2-[1-Carboxy-2-(1H-imidazol-4-yl)-ethylamino]-pentanoic acid;
2-[1-Carboxy-2-(1H-imidazol-4-yl)-ethylamino]-hexanoic acid;
2-(1-Carboxy-2-thiophen-2-yl-ethylamino)-4-methyl-pentanoic acid;
6-Amino-2-(1-carboxy-3-phenyl-propylamino)-hexanoic acid;
2-[1-Carboxy-2-(1H-imidazol-4-yl)-ethylamino]-3-methyl-pentanoic acid;
2-[(Carboxy-phenyl-methyl)-amino]-4-methyl-pentanoic acid;
2-{1-Carboxy-2-[1-(2,4-dinitro-phenyl)-1H-imidazol-4-yl]-ethylamino}-4-methyl-pentanoic acid;
2-(1-Carboxy-2-thiazol-2-yl-ethylamino)-4-methyl-pentanoic acid;
2-(1-Carboxy-2-pyridin-2-yl-ethylamino)-4-methyl-pentanoic acid;
2-(1-Carboxy-ethylamino)-3-(1H-imidazol-4-yl)-propionic acid;
2-(1-Carboxy-3-methylsulfanyl-propylamino)-4-phenyl-butyric acid;
2-(1-Carboxy-3-methyl-butylamino)-succinic acid;
2-(1-Carboxy-3-methyl-butylamino)-hexanoic acid;
2-(1-Carboxy-3-methylsulfanyl-propylamino)-4-methyl-pentanoic acid;
2-[1-Carboxy-2-(3-methyl-3H-imidazol-4-yl)-ethylamino]-4-methyl-pentanoic acid;
2-(1-Carboxy-3-phenyl-propylamino)-4-methyl-pentanoic acid;
2-(1-Carboxy-2-phenyl-ethylamino)-4-methyl-pentanoic acid;
2-(1-Carboxy-2-phenyl-ethylamino)-pentanoic acid;
2-(1-Carboxy-2-phenyl-ethylamino)-4-phenyl-butyric acid;
2-(1-Carboxy-3-phenyl-propylamino)-4,4-dimethyl-pentanoic acid;
2-(1-Carboxy-ethylamino)-3-(1H-imidazol-4-yl)-propionic acid;
2-(1-Carboxy-2-thiophen-2-yl-ethylamino)-pentanoic acid;
2-[1-Carboxy-2-(1H-[1,2,4]triazol-3-yl)-ethylamino]-4-methyl-pentanoic acid;
2-(1-Carboxy-2-cyclopropyl-ethylamino)-4-phenyl-butyric acid;
2-[1-Carboxy-2-(4-hydroxy-phenyl)-ethylamino]-3-(1H-imidazol-4-yl)-propionic acid;
2-[2-(1-Benzyl-1H-imidazol-4-yl)-1-carboxy-ethylamino]-4-methyl-pentanoic acid;
2-(1-Carboxy-2-cyclohexyl-ethylamino)-4-phenyl-butyric acid;
2-(1-Carboxy-3-phenyl-propylamino)-5-phenyl-pent-4-ynoic acid;
2-[2-(1H-Imidazol-4-yl)-1-methoxycarbonyl-ethylamino]-4-methyl-pentanoic acid;
2-{1-Carboxy-2-[1-(4-methoxy-benzyl)-1H-imidazol-4-yl]-ethylamino}-4-methyl-pentanoic acid;
2-{1-Carboxy-2-[1-(4-trifluoromethyl-benzyl)-1H-imidazol-4-yl]-ethylamino}-4-methyl-pentanoic acid;
2-[(Carboxy-phenyl-methyl)-amino]-4-methyl-pentanoic acid;
2-(1-Carboxy-propylamino)-4-methylsulfanyl-butyric acid; and
2-(1-Carboxy-2-phenyl-ethylamino)-4-methyl-pentanoic acid;
2-[2-(1H-Imidazol-4-yl)-1-methoxycarbonyl-ethylamino]-4-methyl-pentanoic acid;
2-{1-Carboxy-2-[1-(4-methoxy-benzyl)-1H-imidazol-4-yl]-ethylamino}-4-methyl-pentanoic acid;
2-{1-Carboxy-2-[1-(4-trifluoromethyl-benzyl)-1H-imidazol-4-yl]-ethylamino}-4-methyl-pentanoic acid;
2-[(Carboxy-phenyl-methyl)-amino]-4-methyl-pentanoic acid;
2-(1-Carboxy-propylamino)-4-methylsulfanyl-butyric acid;
2-(1-Carboxy-3-phenyl-propylamino)-5-pyridin-2-yl-pent-4-ynoic acid;
2-{1-Carboxy-2-[3-(4-trifluoromethyl-benzyl)-3H-imidazol-4-yl]-ethylamino}-4-methyl-pentanoic acid;
2-[1-Carboxy-2-(3-naphthalen-1-ylmethyl-3H-imidazol-4-yl)-ethylamino]-4-methyl-pentanoic acid;

2-{1-Carboxy-2-[3-(4-chloro-benzyl)-3H-imidazol-4-yl]-ethylamino}-4-methyl-pentanoic acid;
4-{5-[2-Carboxy-2-(1-carboxy-3-methyl-butylamino)-ethyl]-imidazol-1-ylmethyl}-benzoic acid;
4-{5-[2-Carboxy-2-(1-carboxy-3-methyl-butylamino)-ethyl]-imidazol-1-ylmethyl}-benzoic acid;
2-[1-Carboxy-2-(2-phenyl-thiazol-4-yl)-ethylamino]-4-methyl-pentanoic acid;
2-[2-(1-Benzyl-1H-benzoimidazol-2-yl)-1-carboxy-ethylamino]-4-methyl-pentanoic acid;
2-[2-(Benzyl-phenyl-amino)-1-carboxy-ethylamino]-4-methyl-pentanoic acid;
2-[2-(2-Amino-thiazol-4-yl)-1-carboxy-ethylamino]-4-methyl-pentanoic acid;
2-{1-Carboxy-2-[3-(3,4-dichloro-benzyl)-3H-imidazol-4-yl]-ethylamino}-4-methyl-pentanoic acid;
2-[1-Carboxy-2-(2-methyl-thiazol-4-yl)-ethylamino]-4-methyl-pentanoic acid;
2-{1-Carboxy-2-[3-(4-cyano-benzyl)-3H-imidazol-4-yl]-ethylamino}-4-methyl-pentanoic acid;
2-{1-Carboxy-2-[3-(3-chloro-benzyl)-3H-imidazol-4-yl]-ethylamino}-4-methyl-pentanoic acid;
'2-{1-Carboxy-2-[3-(3,5-dichloro-benzyl)-3H-imidazol-4-yl]-ethylamino}-4-methyl-pentanoic acid
2-{1-Carboxy-2-[3-(4-methyl-benzyl)-3H-imidazol-4-yl]-ethylamino}-4-methyl-pentanoic acid;
2-{2-[3-(4-Butyl-benzyl)-3H-imidazol-4-yl]-1-carboxy-ethylamino}-4-methyl-pentanoic acid;
2-{1-Carboxy-2-[3-(3,4-dimethyl-benzyl)-3H-imidazol-4-yl]-ethylamino}-4-methyl-pentanoic acid;
2-[2-(2-Benzylamino-thiazol-4-yl)-1-carboxy-ethylamino]-4-methyl-pentanoic acid;
2-{1-Carboxy-2-[3-(3-methyl-benzyl)-3H-imidazol-4-yl]-ethylamino}-4-methyl-pentanoic acid;
2-{1-Carboxy-2-[3-(3,5-dimethyl-benzyl)-3H-imidazol-4-yl]-ethylamino}-4-methyl-pentanoic acid;
2-{1-Carboxy-2-[3-(4-trifluoromethoxy-benzyl)-3H-imidazol-4-yl]-ethylamino}-4-methyl-pentanoic acid;
2-{1-Carboxy-2-[3-(4-isopropyl-benzyl)-3H-imidazol-4-yl]-ethylamino}-4-methyl-pentanoic acid;
2-{1-Carboxy-2-[3-(2-methyl-benzyl)-3H-imidazol-4-yl]-ethylamino}-4-methyl-pentanoic acid;
2-{2-[3-(4-tert-Butyl-benzyl)-3H-imidazol-4-yl]-1-carboxy-ethylamino}-4-methyl-pentanoic acid;
2-{2-[3-(2-Benzenesulfonylmethyl-benzyl)-3H-imidazol-4-yl]-1-carboxy-ethylamino}-4-methyl-pentanoic acid;
2-{1-Carboxy-2-[3-(4-nitro-benzyl)-3H-imidazol-4-yl]-ethylamino}-4-methyl-pentanoic acid;
2-[2-(3-Biphenyl-2-ylmethyl-3H-imidazol-4-yl)-1-carboxy-ethylamino]-4-methyl-pentanoic acid;
'2-{2-[3-(3,5-Bis-trifluoromethyl-benzyl)-3H-imidazol-4-yl]-1-carboxy-ethylamino}-4-methyl-pentanoic acid;
2-{1-Carboxy-2-[3-(4-fluoro-benzyl)-3H-imidazol-4-yl]-ethylamino}-4-methyl-pentanoic acid;
2-{1-Carboxy-2-[3-(4-fluoro-benzyl)-3H-imidazol-4-yl]-ethylamino}-4-methyl-pentanoic acid;
2-[1-Carboxy-2-(2-phenyl-thiazol-4-yl)-ethylamino]-4-methyl-pentanoic acid;
2-[1-Carboxy-2-(5-methyl-isoxazol-3-yl)-ethylamino]-4-methyl-pentanoic acid;
2-[2-(1-Benzyl-1H-pyrazol-3-yl)-1-carboxy-ethylamino]-4-methyl-pentanoic acid;
2-{1-Carboxy-2-[3-(2,3-dimethoxy-benzyl)-3H-imidazol-4-yl]-ethylamino}-4-methyl-pentanoic acid;
2-{1-Carboxy-2-[3-(2-methyl-biphenyl-3-ylmethyl)-3H-imidazol-4-yl]-ethylamino}-4-methyl-pentanoic acid;
'2-{1-Carboxy-2-[3-(2-methoxy-naphthalen-1-ylmethyl)-3H-imidazol-4-yl]-ethylamino}-4-methyl-pentanoic acid;
2-{1-Carboxy-2-[3-(2,3-difluoro-benzyl)-3H-imidazol-4-yl]-ethylamino}-4-methyl-pentanoic acid;
2-{1-Carboxy-2-[1-(2,3-difluoro-benzyl)-1H-imidazol-4-yl]-ethylamino}-4-methyl-pentanoic acid;
2-{1-Carboxy-2-[3-(2,3-dichloro-benzyl)-3H-imidazol-4-yl]-ethylamino}-4-methyl-pentanoic acid;
'2-{1-Carboxy-2-[3-(3-trifluoromethyl-benzyl)-3H-imidazol-4-yl]-ethylamino}-4-methyl-pentanoic acid;
2-{1-Carboxy-2-[3-(2,5-dichloro-benzyl)-3H-imidazol-4-yl]-ethylamino}-4-methyl-pentanoic acid; and
2-{1-Carboxy-2-[3-(2,6-dichloro-benzyl)-3H-imidazol-4-yl]-ethylamino}-4-methyl-pentanoic acid.
4-Methyl-2-[1-methylcarbamoyl-2-(3-phenylamino-3H-imidazol-4-yl)-ethylamino]-pentanoic acid;
2-[2-(4-Benzyl-furan-3-yl)-1-carboxy-ethylamino]-4-methyl-pentanoic acid;
2-[1-Carboxy-2-(3-phenyl-3H-imidazol-4-yl)-ethylamino]-4-methyl-pentanoic acid;
2-[1-Carboxy-2-(3-phenethyl-3H-imidazol-4-yl)-ethylamino]-4-methyl-pentanoic acid;
2-{1-Carboxy-2-[3-(pyridin-3-yloxy)-3H-imidazol-4-yl]-ethylamino}-4-methyl-pentanoic acid;
2-{1-Carboxy-2-[3-(4-nitro-phenoxy)-3H-imidazol-4-yl]-ethylamino}-4-methyl-pentanoic acid;
2-[1-Carboxy-2-(3-phenoxy-3H-imidazol-4-yl)-ethylamino]-4-methyl-pentanoic acid;
2-{1-Carboxy-2-[3-(2-nitro-benzyl)-3H-imidazol-4-yl]-ethylamino}-4-methyl-pentanoic acid;
2-{1-Carboxy-2-[3-(3-nitro-benzyl)-3H-imidazol-4-yl]-ethylamino}-4-methyl-pentanoic acid;
2-{1-Carboxy-2-[3-(2-trifluoromethyl-benzyl)-3H-imidazol-4-yl]-ethylamino}-4-methyl-pentanoic acid;
2-{1-Carboxy-2-[3-(3-trifluoromethyl-benzyl)-3H-imidazol-4-yl]-ethylamino}-4-methyl-pentanoic acid;
2-{1-Carboxy-2-[3-(2-methyl-benzyl)-3H-imidazol-4-yl]-ethylamino}-4-methyl-pentanoic acid;
2-{1-Carboxy-2-[3-(3-methyl-benzyl)-3H-imidazol-4-yl]-ethylamino}-4-methyl-pentanoic acid;
2-{1-Carboxy-2-[3-(2-chloro-benzyl)-3H-imidazol-4-yl]-ethylamino}-4-methyl-pentanoic acid;
2-{1-Carboxy-2-[3-(3-chloro-benzyl)-3H-imidazol-4-yl]-ethylamino}-4-methyl-pentanoic acid;
2-{1-Carboxy-2-[3-(2-hydroxy-benzyl)-3H-imidazol-4-yl]-ethylamino}-4-methyl-pentanoic acid;
2-{1-Carboxy-2-[3-(3-hydroxy-benzyl)-3H-imidazol-4-yl]-ethylamino}-4-methyl-pentanoic acid;
2-{1-Carboxy-2-[3-(2-fluoro-benzyl)-3H-imidazol-4-yl]-ethylamino}-4-methyl-pentanoic acid;
2-[2-(3-Benzyl-3H-imidazol-4-yl)-1-carboxy-ethylamino]-4-methyl-pentanoic acid;
2-[1-Carboxy-2-(3-phenylamino-3H-imidazol-4-yl)-ethylamino]-4-methyl-pentanoic acid;
2-{[2,3-Dioxo-1-(3-phenylamino-3H-imidazol-4-ylmethyl)-butyl]-methyl-amino}-4-methyl-pentanoic acid;
2-{[2,3-Dioxo-1-(4-phenylamino-furan-3-ylmethyl)-butyl]-methyl-amino}-4-methyl-pentanoic acid;
2-[2,3-Dioxo-1-(4-phenylamino-furan-3-ylmethyl)-butylamino]-4-methyl-pentanoic acid;
2-[1-Carboxy-2-(4-phenylamino-furan-3-yl)-ethylamino]-4-methyl-pentanoic acid;
2-[1-Carboxy-2-(2-o-tolyl-2H-isoindol-1-yl)-ethylamino]-4-methyl-pentanoic acid;
2-[2-(2-Benzyl-2H-isoindol-1-yl)-1-carboxy-ethylamino]-4-methyl-pentanoic acid;

2-[1-Carboxy-2-(2-phenyl-2H-isoindol-1-yl)-ethylamino]-4-methyl-pentanoic acid;
2-[1-Carboxy-2-(2-pyridin-2-yl-2H-isoindol-1-yl)-ethylamino]-4-methyl-pentanoic acid;
2-{1-Carboxy-2-[2-(3-nitro-phenyl)-2H-isoindol-1-yl]-ethylamino}-4-methyl-pentanoic acid;
2-{1-Carboxy-2-[2-(4-nitro-phenyl)-2H-isoindol-1-yl]-ethylamino}-4-methyl-pentanoic acid;
2-{1-Carboxy-2-[2-(4-nitro-benzyl)-2H-isoindol-1-yl]-ethylamino}-4-methyl-pentanoic acid;
2-({Carboxy-[3-(4-nitro-phenyl)-naphthalen-1-yl]-methyl}-amino)-4-methyl-pentanoic acid;
2-({Carboxy-[3-(4-nitro-benzyl)-naphthalen-1-yl]-methyl}-amino)-4-methyl-pentanoic acid;
'2-{1-Carboxy-2-[3-(3-trifluoromethyl-benzyl)-3H-imidazol-4-yl]-ethylamino}-4-methyl-pentanoic acid;
2-{1-Carboxy-2-[3-(2,5-dichloro-benzyl)-3H-imidazol-4-yl]-ethylamino}-4-methyl-pentanoic acid;
2-{1-Carboxy-2-[3-(2,6-dichloro-benzyl)-3H-imidazol-4-yl]-ethylamino}-4-methyl-pentanoic acid;
2-[1-Carboxy-2-(3-cyclohexylmethyl-3H-imidazol-4-yl)-ethylamino]-4-methyl-pentanoic acid;
2-[1-Carboxy-2-(3-phenethyl-3H-imidazol-4-yl)-ethylamino]-4-methyl-pentanoic acid;
2-{1-Carboxy-2-[3-(2-ethyl-butyl)-3H-imidazol-4-yl]-ethylamino}-4-methyl-pentanoic acid;
2-{1-Carboxy-2-[3-(3-iodo-benzyl)-3H-imidazol-4-yl]-ethylamino}-4-methyl-pentanoic acid;
2-{1-Carboxy-2-[3-(3-fluoro-benzyl)-3H-imidazol-4-yl]-ethylamino}-4-methyl-pentanoic acid;
2-{1-Carboxy-2-[3-(3-fluoro-benzyl)-3H-imidazol-4-yl]-ethylamino}-4-methyl-pentanoic acid;
2-[1-Carboxy-2-(2-phenylethynyl-1H-imidazol-4-yl)-ethylamino]-4-methyl-pentanoic acid;
2-[1-Carboxy-2-(1-methyl-2-phenylethynyl-1H-imidazol-4-yl)-ethylamino]-4-methyl-pentanoic acid;
2-[1-Carboxy-2-(2-phenethyl-1H-imidazol-4-yl)-ethylamino]-4-methyl-pentanoic acid;
2-[1-Carboxy-3-(3-phenyl-3H-imidazol-4-yl)-propylamino]-4-methyl-pentanoic acid;
2-[1-Carboxy-2-(3-phenyl-3H-imidazol-4-yl)-ethylamino]-4-methyl-pentanoic acid;
2-[2-(3-Benzyl-2,5-dimethyl-3H-imidazol-4-yl)-1-carboxy-ethylamino]-4-methyl-pentanoic acid;
2-[1-Carboxy-4-(3-phenyl-3H-imidazol-4-yl)-butylamino]-4-methyl-pentanoic acid;
2-[2-(2-Benzyl-thiazol-4-yl)-1-carboxy-ethylamino]-4-methyl-pentanoic acid;
2-[1-Carboxy-2-(2-phenyl-oxazol-4-yl)-ethylamino]-4-methyl-pentanoic acid;
2-{1-Carboxy-2-[2-(3,5-dichloro-phenyl)-oxazol-4-yl]-ethylamino}-4-methyl-pentanoic acid;
2-{1-Carboxy-2-[2-(3,5-dimethyl-phenyl)-oxazol-4-yl]-ethylamino}-4-methyl-pentanoic acid;
2-[2-(2-Benzyl-oxazol-4-yl)-1-carboxy-ethylamino]-4-methyl-pentanoic acid;
2-{1-Carboxy-2-[2-(3,5-dichloro-benzyl)-oxazol-4-yl]-ethylamino}-4-methyl-pentanoic acid;
2-{1-Carboxy-2-[2-(3,5-dimethyl-benzyl)-oxazol-4-yl]-ethylamino}-4-methyl-pentanoic acid;
2-{1-Carboxy-2-[2-(2-cyclohexyl-ethyl)-oxazol-4-yl]-ethylamino}-4-methyl-pentanoic acid;
2-[1-Carboxy-2-(4-phenyl-oxazol-2-yl)-ethylamino]-4-methyl-pentanoic acid;
2-{1-Carboxy-2-[4-(3,5-dichloro-phenyl)-oxazol-2-yl]-ethylamino}-4-methyl-pentanoic acid;
2-{1-Carboxy-2-[4-(3,5-dimethyl-phenyl)-oxazol-2-yl]-ethylamino}-4-methyl-pentanoic acid;
2-[2-(4-Benzyl-oxazol-2-yl)-1-carboxy-ethylamino]-4-methyl-pentanoic acid;
2-{1-Carboxy-2-[4-(3,5-dichloro-benzyl)-oxazol-2-yl]-ethylamino}-4-methyl-pentanoic acid;
2-{1-Carboxy-2-[4-(3,5-dimethyl-benzyl)-oxazol-2-yl]-ethylamino}-4-methyl-pentanoic acid;
2-{1-Carboxy-2-[4-(2-cyclohexyl-ethyl)-oxazol-2-yl]-ethylamino}-4-methyl-pentanoic acid;
2-{2-[5-(1H-Benzoimidazol-2-yl)-isoxazol-3-yl]-1-carboxy-ethylamino}-4-methyl-pentanoic acid;
2-{1-Carboxy-2-[1-(3-phenyl-propyl)-1H-[1,2,3]triazol-4-yl]-ethylamino}-4-methyl-pentanoic acid;
2-[1-Carboxy-2-(4-pyridin-4-yl-oxazol-2-yl)-ethylamino]-4-methyl-pentanoic acid;
2-{1-Carboxy-2-[2-(3,5-dichloro-phenyl)-thiazol-4-yl]-ethylamino}-4-methyl-pentanoic acid;
2-{1-Carboxy-2-[2-(3,5-dimethyl-phenyl)-thiazol-4-yl]-ethylamino}-4-methyl-pentanoic acid;
2-[2-(2-Benzyl-thiazol-4-yl)-1-carboxy-ethylamino]-4-methyl-pentanoic acid;
2-{1-Carboxy-2-[2-(3,5-dimethyl-benzyl)-thiazol-4-yl]-ethylamino}-4-methyl-pentanoic acid;
2-{1-Carboxy-2-[2-(3,5-dichloro-benzyl)-thiazol-4-yl]-ethylamino}-4-methyl-pentanoic acid;
2-[1-Carboxy-2-(4-phenyl-thiazol-2-yl)-ethylamino]-4-methyl-pentanoic acid;
2-{1-Carboxy-2-[2-(2-cyclohexyl-ethyl)-thiazol-4-yl]-ethylamino}-4-methyl-pentanoic acid;
2-{1-Carboxy-2-[4-(3,5-dimethyl-phenyl)-thiazol-2-yl]-ethylamino}-4-methyl-pentanoic acid;
2-{1-Carboxy-2-[4-(3,5-dichloro-phenyl)-thiazol-2-yl]-ethylamino}-4-methyl-pentanoic acid;
2-[1-Carboxy-2-(2-pyridin-4-yl-thiazol-4-yl)-ethylamino]-4-methyl-pentanoic acid;
2-[2-(4-Benzyl-thiazol-2-yl)-1-carboxy-ethylamino]-4-methyl-pentanoic acid;
2-{1-Carboxy-2-[4-(3,5-dichloro-benzyl)-thiazol-2-yl]-ethylamino}-4-methyl-pentanoic acid;
2-{1-Carboxy-2-[4-(3,5-dimethyl-benzyl)-thiazol-2-yl]-ethylamino}-4-methyl-pentanoic acid;
2-{1-Carboxy-2-[4-(2-cyclohexyl-ethyl)-thiazol-2-yl]-ethylamino}-4-methyl-pentanoic acid;
2-[1-Carboxy-2-(4-pyridin-4-yl-thiazol-2-yl)-ethylamino]-4-methyl-pentanoic acid;
2-[(3-Benzo[1,3]dioxol-5-yl-propyl)-(2-mercapto-ethyl)-amino]-4-methyl-pentanoic acid;
2-[Cyclohexanecarbonyl-(2-mercapto-ethyl)-amino]-4-methyl-pentanoic acid;
2-[(Benzo[1,2,5]thiadiazol-5-ylmethanesulfonyl)-(2-mercapto-ethyl)-amino]-4-methyl-pentanoic acid;
2-[But-3-enyloxycarbonyl-(2-mercapto-ethyl)-amino]-4-methyl-pentanoic acid;
2-[N'-(1-Benzyl-pyrrolidin-3-yl)-N-(2-mercapto-ethyl)-guanidino]-4-methyl-pentanoic acid;
2-[1-(2-Mercapto-ethyl)-3-(1-phenyl-ethyl)-ureido]-4-methyl-pentanoic acid;
2-[3-Furan-2-ylmethyl-1-(2-mercapto-ethyl)-thioureido]-4-methyl-pentanoic acid;
2-{1-Carboxy-2-[2-(3-trifluoromethyl-phenyl)-thiazol-4-yl]-ethylamino}-4-methyl-pentanoic acid;
2-(1-Carboxy-3-methylamino-propylamino)-4-methyl-pentanoic acid; compound with 3-phenyl-propionaldehyde;
2-{1-Carboxy-3-[2-(4-chloro-phenoxy)-acetylamino]-propylamino}-4-methyl-pentanoic acid;

2-[3-(Biphenyl-4-sulfonylamino)-1-carboxy-propylamino]-4-methyl-pentanoic acid;
2-{3-[(Biphenyl-4-carbonyl)-amino]-1-carboxy-propylamino}-4-methyl-pentanoic acid;
2-{1-Carboxy-3-[(naphthalene-2-carbonyl)-amino]-propylamino}-4-methyl-pentanoic acid;
2-[1-Carboxy-3-(4-methoxy-benzenesulfonylamino)-propylamino]-4-methyl-pentanoic acid;
2-[1-Carboxy-3-(naphthalene-2-sulfonylamino)-propylamino]-4-methyl-pentanoic acid;
2-[3-(3,5-Bis-trifluoromethyl-benzoylamino)-1-carboxy-propylamino]-4-methyl-pentanoic acid;
2-[3-(3,5-Bis-trifluoromethyl-benzoylamino)-1-carboxy-propylamino]-4-methyl-pentanoic acid;
2-[2-(5-Benzyl-2-methyl-thiazol-4-yl)-1-carboxy-ethylamino]-4-methyl-pentanoic acid;
2-{1-Carboxy-2-[2-(3-trifluoromethyl-phenyl)-thiazol-4-yl]-ethylamino}-4-methyl-pentanoic acid;
2-{1-Carboxy-3-[(naphthalene-2-carbonyl)-amino]-propylamino}-4-methyl-pentanoic acid;
2-[3-(Biphenyl-4-sulfonylamino)-1-carboxy-propylamino]-4-methyl-pentanoic acid;
2-{1-Carboxy-2-[2-(2,4-dichloro-phenyl)-thiazol-4-yl]-ethylamino}-4-methyl-pentanoic acid;
2-{1-Carboxy-2-[2-(2,3-dihydro-benzofuran-5-yl)-thiazol-4-yl]-ethylamino}-4-methyl-pentanoic acid;
2-{1-Carboxy-2-[2-(3-chloro-4-fluoro-phenyl)-thiazol-4-yl]-ethylamino}-4-methyl-pentanoic acid;
2-[1-Carboxy-2-(2-p-tolyl-thiazol-4-yl)-ethylamino]-4-methyl-pentanoic acid;
2-[1-Carboxy-2-(5-phenyl-isoxazol-3-yl)-ethylamino]-4-methyl-pentanoic acid;
2-(2-Mercapto-3-phenyl-propionylamino)-4-methyl-pentanoic acid;
2-[1-Carboxy-3-(4'-chloro-biphenyl-4-sulfonylamino)-propylamino]-4-methyl-pentanoic acid;
2-[1-Carboxy-3-(3-methoxy-benzoylamino)-propylamino]-4-methyl-pentanoic acid;
2-[1-Carboxy-3-(3-chloro-benzoylamino)-propylamino]-4-methyl-pentanoic acid;
2-[2-(4-Benzyloxy-phenyl)-1-carboxy-ethylamino]-4-methyl-pentanoic acid;
2-[1-Carboxy-2-(4-cyclohexylmethoxy-phenyl)-ethylamino]-4-methyl-pentanoic acid
2-{1-Carboxy-2-[4-(3,5-dichloro-benzyloxy)-phenyl]-ethylamino}-4-methyl-pentanoic acid;
2-{1-Carboxy-2-[4-(3,5-dimethyl-benzyloxy)-phenyl]-ethylamino}-4-methyl-pentanoic acid;
2-{1-Carboxy-2-[3-(3,4-dichloro-benzyl)-2-oxo-2,3-dihydro-imidazol-1-yl]-ethylamino}-4-methyl-pentanoic acid;
2-[2-(Benzothiazol-2-ylcarbamoyl)-1-carboxy-ethylamino]-4-methyl-pentanoic acid;
2-(1-Carboxy-3-{4-[(4-chloro-phenyl)-phenyl-methyl]-piperazin-1-yl}-3-oxo-propylamino)-4-methyl-pentanoic acid;
2-{2-[3-(3,5-Dichloro-benzyl)-3H-imidazol-4-yl]-1-methoxycarbonyl-ethylamino}-4-methyl-pentanoic acid;
2-({1-Carboxy-2-[3-(3,5-dichloro-benzyl)-3H-imidazol-4-yl]-ethyl}-formyl-amino)-4-methyl-pentanoic acid;
2-{2-[3-(3,5-Dichloro-benzyl)-3H-imidazol-4-yl]-1-methoxycarbonyl-ethylamino}-4-methyl-pentanoic acid benzyl ester;
2-{1-Benzyloxycarbonyl-2-[3-(3,5-dichloro-benzyl)-3H-imidazol-4-yl]-ethylamino}-4-methyl-pentanoic acid;
2-{1-Benzyloxycarbonyl-2-[3-(3,5-dichloro-benzyl)-3H-imidazol-4-yl]-ethylamino}-4-methyl-pentanoic acid;
2-{1-Butoxycarbonyl-2-[3-(3,5-dichloro-benzyl)-3H-imidazol-4-yl]-ethylamino}-4-methyl-pentanoic acid;
2-{1-Carboxy-2-[3-(3,5-dichloro-benzyl)-2-oxo-2,3-dihydro-imidazol-1-yl]-ethylamino}-4-methyl-pentanoic acid
2-{1-Carboxy-2-[3-(3,5-difluoro-benzyl)-2-oxo-2,3-dihydro-imidazol-1-yl]-ethylamino}-4-methyl-pentanoic acid;
2-{1-Carboxy-2-[2-oxo-3-(1-phenyl-ethyl)-2,3-dihydro-imidazol-1-yl]-ethylamino}-4-methyl-pentanoic acid;
2-[1-Carboxy-2-(3-chloro-benzoylamino)-ethylamino]-4-methyl-pentanoic acid;
2-[1-Carboxy-2-(3,4-dichloro-benzoylamino)-ethylamino]-4-methyl-pentanoic acid;
2-[2-(3-Hydroxy-phenyl)-1-methoxycarbonyl-ethylamino]-4-methyl-pentanoic acid benzyl ester;
2-[2-(3-Hydroxy-phenyl)-1-methoxycarbonyl-ethylamino]-4-methyl-pentanoic acid benzyl ester;
2-[1-Carboxy-2-(2-phenyl-oxazol-4-yl)-ethylamino]-4-methyl-pentanoic acid;
2-{1-Carboxy-2-[2-(3,5-dichloro-phenyl)-oxazol-4-yl]-ethylamino}-4-methyl-pentanoic acid;
2-{1-Carboxy-2-[2-(3,5-dichloro-phenyl)-thiazol-4-yl]-ethylamino}-4-methyl-pentanoic acid;
2-{1-Carboxy-2-[1-(3,5-dichloro-benzyl)-1H-pyrazol-3-yl]-ethylamino}-4-methyl-pentanoic acid;
2-{1-Cyclopentyloxycarbonyl-2-[3-(3,5-dichloro-benzyl)-3H-imidazol-4-yl]-ethylamino}-4-methyl-pentanoic acid;
2-{1-Carboxy-2-[3-(3,5-difluoro-benzyl)-2-oxo-imidazolidin-1-yl]-ethylamino}-4-methyl-pentanoic acid;
2-[2-(3-Benzyl-2-oxo-2,3-dihydro-imidazol-1-yl)-1-carboxy-ethylamino]-4-methyl-pentanoic acid;
2-[1-Carboxy-2-(4-phenethyloxy-phenyl)-ethylamino]-4-methyl-pentanoic acid;
2-[2-(4-tert-Butoxy-phenyl)-1-carboxy-ethylamino]-4-methyl-pentanoic acid;
2-{1-Carboxy-2-[4-(pyridin-4-ylmethoxy)-phenyl]-ethylamino}-4-methyl-pentanoic acid;
2-[2-(4-Allyloxy-phenyl)-1-carboxy-ethylamino]-4-methyl-pentanoic acid;
2-{1-Carboxy-2-[4-(pyridin-3-ylmethoxy)-phenyl]-ethylamino}-4-methyl-pentanoic acid;
2-[1-Carboxy-2-(4'-methyl-biphenyl-3-yl)-ethylamino]-4-methyl-pentanoic acid;
2-[1-Carboxy-2-(3-methoxy-benzoylamino)-ethylamino]-4-methyl-pentanoic acid;
2-{1-Carboxy-2-[(naphthalene-1-carbonyl)-amino]-ethylamino}-4-methyl-pentanoic acid;
2-[1-Carboxy-2-(6-chloro-benzothiazol-2-ylcarbamoyl)-ethylamino]-4-methyl-pentanoic acid;
2-[1-Carboxy-2-(5,6-dimethyl-benzothiazol-2-ylcarbamoyl)-ethylamino]-4-methyl-pentanoic acid;
2-[1-Carboxy-2-(4-chloro-benzothiazol-2-ylcarbamoyl)-ethylamino]-4-methyl-pentanoic acid;
2-{1-Carboxy-2-[3-(2-cyclohexyl-ethyl)-2-oxo-2,3-dihydro-imidazol-1-yl]-ethylamino}-4-methyl-pentanoic acid;
2-{1-Carboxy-2-[2-oxo-3-(1-phenyl-ethyl)-2,3-dihydro-imidazol-1-yl]-ethylamino}-4-methyl-pentanoic acid;
2-[1-Carboxy-2-(5,6-dichloro-benzothiazol-2-ylcarbamoyl)-ethylamino]-4-methyl-pentanoic acid;
2-[1-Carboxy-2-(3-cyclopropylmethyl-2-oxo-2,3-dihydro-imidazol-1-yl)-ethylamino]-4-methyl-pentanoic acid;
2-[1-Carboxy-2-(3',5'-dichloro-biphenyl-3-yl)-ethylamino]-4-methyl-pentanoic acid;
2-[1-Carboxy-2-(3-thiophen-3-yl-phenyl)-ethylamino]-4-methyl-pentanoic acid;

2-[1-Carboxy-2-(3',5'-dimethoxy-biphenyl-3-yl)-ethylamino]-4-methyl-pentanoic acid;
3-[2-(1-Benzyloxycarbonyl-3-methyl-butylamino)-2-methoxycarbonyl-ethyl]-pyrazole-1-carboxylic acid tert-butyl ester;
2-{2-[3-(3,5-Dichloro-benzyl)-3H-imidazol-4-yl]-1-methoxycarbonyl-ethylamino}-4-methyl-pentanoic acid methyl ester;
2-[1-Carboxy-2-(3-cyclohexyl-2-oxo-2,3-dihydro-imidazol-1-yl)-ethylamino]-4-methyl-pentanoic acid;
2-[1-Carboxy-2-(6-methoxy-benzothiazol-2-ylcarbamoyl)-ethylamino]-4-methyl-pentanoic acid;
2-[1-Carboxy-2-(6-ethoxy-benzothiazol-2-ylcarbamoyl)-ethylamino]-4-methyl-pentanoic acid;
2-[1-Carboxy-2-(6-fluoro-benzothiazol-2-ylcarbamoyl)-ethylamino]-4-methyl-pentanoic acid
2-[2-(6-Bromo-benzothiazol-2-ylcarbamoyl)-1-carboxy-ethylamino]-4-methyl-pentanoic acid
2-{1-Carboxy-2-[3-(3,5-difluoro-phenyl)-2-oxo-2,3-dihydro-imidazol-1-yl]-ethylamino}-4-methyl-pentanoic acid;
2-{1-Carboxy-2-[(naphthalene-2-carbonyl)-amino]-ethylamino}-4-methyl-pentanoic acid;
2-[1-Carboxy-2-(naphthalene-2-sulfonylamino)-ethylamino]-4-methyl-pentanoic acid;
2-{1-Carboxy-2-[2-(3,5-dichloro-benzyl)-2H-pyrazol-3-yl]-ethylamino}-4-methyl-pentanoic acid;
2-[1-Carboxy-2-(3-naphthalen-1-yl-phenyl)-ethylamino]-4-methyl-pentanoic acid;
2-[1-Carboxy-2-(3-naphthalen-1-yl-phenyl)-ethylamino]-4-methyl-pentanoic acid;
2-{1-Carboxy-2-[3-(3,5-dichloro-benzyl)-3H-imidazol-4-yl]-ethylamino}-4-methyl-pentanoic acid;
2-{1-Carboxy-2-[3-(3,5-difluoro-benzyloxy)-phenyl]-ethylamino}-4-methyl-pentanoic acid;
2-[2-(3-Allyloxy-phenyl)-1-carboxy-ethylamino]-4-methyl-pentanoic acid;
2-{1-Carboxy-2-[3-(3,5-difluoro-phenyl)-2-oxo-imidazolidin-1-yl]-ethylamino}-4-methyl-pentanoic acid;
2-{1-Carboxy-2-[(5-chloro-1H-indole-2-carbonyl)-amino]-ethylamino}-4-methyl-pentanoic acid;
2-{1-Carboxy-2-[3-(3,5-dichloro-benzyl)-2-oxo-oxazolidin-4-yl]-ethylamino}-4-methyl-pentanoic acid;
2-[1-Carboxy-2-(4-thiophen-3-yl-phenyl)-ethylamino]-4-methyl-pentanoic acid;
2-[1-Carboxy-2-(3',5'-dichloro-biphenyl-4-yl)-ethylamino]-4-methyl-pentanoic acid;
2-[1-Carboxy-2-(4'-methyl-biphenyl-4-yl)-ethylamino]-4-methyl-pentanoic acid;
2-{1-Carboxy-2-[3-(4-iodo-benzyl)-3H-imidazol-4-yl]-ethylamino}-4-methyl-pentanoic acid;
2-{1-Carboxy-2-[3-(3,5-difluoro-benzyl)-3H-imidazol-4-yl]-ethylamino}-4-pentanoic acid;
2-(1-Carboxy-2-{3-[2-(4-fluoro-phenyl)-ethyl]-2-oxo-2,3-dihydro-imidazol-1-yl}-ethylamino)-4-methyl-pentanoic acid;
2-[1-Carboxy-2-(3-cyclohexylmethyl-2-oxo-2,3-dihydro-imidazol-1-yl)-ethylamino]-4-methyl-pentanoic acid;
2-{1-Carboxy-2-[3-(3,5-dichloro-benzyl)-3H-imidazol-4-yl]-ethylamino}-4-methyl-pentanoic acid tert-butyl ester;
2-{1-Carboxy-2-[3-(3,5-dichloro-benzyl)-2-oxo-oxazolidin-4-yl]-ethylamino}-4-methyl-pentanoic acid;
2-[1-Carboxy-2-(5-p-tolyl-furan-2-yl)-ethylamino]-4-methyl-pentanoic acid;
2-(1-Carboxy-2-{3-[2-(3-fluoro-phenyl)-ethyl]-2-oxo-2,3-dihydro-imidazol-1-yl}-ethylamino)-4-methyl-pentanoic acid 2-[1-Carboxy-2-(5-phenyl-furan-2-yl)-ethylamino]-4-methyl-pentanoic acid;
2-{1-Carboxy-2-[5-(3,5-dichloro-phenyl)-furan-2-yl]-ethylamino}-4-methyl-pentanoic acid;
2-{1-Carboxy-2-[5-(3,5-dimethyl-phenyl)-furan-2-yl]-ethylamino}-4-methyl-pentanoic acid;
2-{1-Carboxy-2-[5-(3,5-difluoro-phenyl)-furan-2-yl]-ethylamino}-4-methyl-pentanoic acid;
2-[1-Carboxy-2-(5-thiophen-3-yl-furan-2-yl)-ethylamino]-4-methyl-pentanoic acid;
2-[1-Carboxy-2-(6-methyl-benzothiazol-2-ylcarbamoyl)-ethylamino]-4-methyl-pentanoic acid;
2-[1-Carboxy-2-(4-hydroxy-phenyl)-ethylamino]-4-methyl-pentanoic acid;
2-{1-Carboxy-2-[3-(3,5-dichloro-benzyloxy)-phenyl]-ethylamino}-4-methyl-pentanoic acid;
2-{1-Carboxy-2-[3-(pyridin-4-ylmethoxy)-phenyl]-ethylamino}-4-methyl-pentanoic acid;
2-{1-Carboxy-2-[3-(3,5-dimethyl-benzyloxy)-phenyl]-ethylamino}-4-methyl-pentanoic acid;
2-{1-Carboxy-2-[3-(4-chloro-benzyloxy)-phenyl]-ethylamino}-4-methyl-pentanoic acid;
2-{2-[3-(2,4-Bis-trifluoromethyl-benzyloxy)-phenyl]-1-carboxy-ethylamino}-4-methyl-pentanoic acid;
2-[1-Carboxy-2-(1-phenyl-1H-pyrazol-3-yl)-ethylamino]-4-methyl-pentanoic acid;
2-{1-Carboxy-2-[3-(3-chloro-benzyl)-2-oxo-2,3-dihydro-imidazol-1-yl]-ethylamino}-4-methyl-pentanoic acid;
2-{1-Carboxy-2-[4-(3,5-dichloro-benzyl)-phenyl]-ethylamino}-4-methyl-pentanoic acid;
2-[2-(4-Benzyl-phenyl)-1-carboxy-ethylamino]-4-methyl-pentanoic acid;
2-[1-Carboxy-2-(4-phenyl-thiazol-2-ylcarbamoyl)-ethylamino]-4-methyl-pentanoic acid;
2-{1-Carboxy-2-[5-(4-methoxy-phenyl)-furan-2-yl]-ethylamino}-4-methyl-pentanoic acid;
2-[2-(5-Benzo[1,3]dioxol-5-yl-furan-2-yl)-1-carboxy-ethylamino]-4-methyl-pentanoic acid
2-[1-Carboxy-2-(5-naphthalen-1-yl-furan-2-yl)-ethylamino]-4-methyl-pentanoic acid;
2-{1-Carboxy-2-[5-(4-chloro-phenyl)-furan-2-yl]-ethylamino}-4-methyl-pentanoic acid;
2-{1-Carboxy-2-[5-(4-trifluoromethyl-phenyl)-furan-2-yl]-ethylamino}-4-methyl-pentanoic acid;
2-[1-Carboxy-2-(3-isobutoxy-phenyl)-ethylamino]-4-methyl-pentanoic acid;
2-{1-Carboxy-2-[3-(3-chloro-benzyloxy)-phenyl]-ethylamino}-4-methyl-pentanoic acid;
2-{1-Carboxy-2-[3-(2-chloro-benzyloxy)-phenyl]-ethylamino}-4-methyl-pentanoic acid;
2-[3-(4-Benzyloxy-phenyl)-1-carboxy-propylamino]-4-methyl-pentanoic acid;
2-[3-(4-Benzyloxy-phenyl)-1-carboxy-propylamino]-4-methyl-pentanoic acid;
2-{1-Carboxy-2-[5-(3-chloro-phenyl)-furan-2-yl]-ethylamino}-4-methyl-pentanoic acid
2-{1-Carboxy-2-[3-(3-fluoro-benzyl)-2-oxo-2,3-dihydro-imidazol-1-yl]-ethylamino}-4-methyl-pentanoic acid;
2-{1-Carboxy-2-[3-(3,4-difluoro-benzyl)-2-oxo-2,3-dihydro-imidazol-1-yl]-ethylamino}-4-methyl-pentanoic acid;
2-[1-Carboxy-3-(6-fluoro-benzothiazol-2-ylcarbamoyl)-propylamino]-4-methyl-pentanoic acid;
2-{1-Carboxy-2-[3-(2,5-difluoro-benzyl)-2-oxo-2,3-dihydro-imidazol-1-yl]-ethylamino}-4-methyl-pentanoic acid;

2-{1-Carboxy-2-[4-(3,5-difluoro-benzoylamino)-phenyl]-ethylamino}-4-methyl-pentanoic acid;
2-[1-Carboxy-2-(4'-fluoro-biphenyl-4-yl)-ethylamino]-4-methyl-pentanoic acid;
2-[2-(4-Benzo[1,3]dioxol-5-yl-phenyl)-1-carboxy-ethylamino]-4-methyl-pentanoic acid;
2-[2-(4-Benzo[b]thiophen-3-yl-phenyl)-1-carboxy-ethylamino]-4-methyl-pentanoic acid;
2-[2-(3-Benzyl-phenyl)-1-carboxy-ethylamino]-4-methyl-pentanoic acid;
2-[1-Carboxy-2-(4'-trifluoromethyl-biphenyl-4-yl)-ethylamino]-4-methyl-pentanoic acid;
2-(1-Carboxy-2-{3-[2-(3-chloro-phenyl)-ethyl]-2-oxo-2,3-dihydro-imidazol-1-yl}-ethylamino)-4-methylpentanoic acid;
2-{2-[3-(4-Bromo-benzyl)-3H-imidazol-4-yl]-1-carboxy-ethylamino}-4-methyl-pentanoic acid;
2-[2-(4-Benzenesulfonylamino-phenyl)-1-carboxy-ethylamino]-4-methyl-pentanoic acid
2-{1-Carboxy-2-[3-(3-chloro-benzyl)-phenyl]-ethylamino}-4-methyl-pentanoic acid
2-{1-Carboxy-2-[3-(3,5-dichloro-benzyl)-phenyl]-ethylamino}-4-methyl-pentanoic acid
2-{1-Carboxy-2-[3-(5-chloro-benzo[b]thiophen-3-ylmethoxy)-phenyl]-ethylamino}-4-methyl-pentanoic acid;
2-[1-Carboxy-2-(4-pyridin-2-yl-phenyl)-ethylamino]-4-methyl-pentanoic acid;
2-[1-Carboxy-2-(4-pyridin-3-yl-phenyl)-ethylamino]-4-methyl-pentanoic acid;
2-[1-Carboxy-2-(4-pyridin-4-yl-phenyl)-ethylamino]-4-methyl-pentanoic acid;
2-(1-Carboxy-ethylamino)-3-[3-(3,5-dichloro-benzyl)-3H-imidazol-4-yl]-propionic acid;
2-(1-Carboxy-ethylamino)-3-[3-(3,5-dichloro-benzyl)-3H-imidazol-4-yl]-propionic acid;
2-{1-Carboxy-2-[3-(3,5-dichloro-benzyl)-3H-imidazol-4-yl]-ethylamino}-4-phenyl-butyric acid;
2-{1-Carboxy-2-[3-(3,5-dichloro-benzyl)-3H-imidazol-4-yl]-ethylamino}-4-phenyl-butyric acid;
2-(1-Carboxy-2-{3-[2-(2-fluoro-phenyl)-ethyl]-2-oxo-2,3-dihydro-imidazol-1-yl}-ethylamino)-4-methyl-pentanoic acid;
2-[1-Carboxy-2-(4-pyrrol-1-yl-phenyl)-ethylamino]-4-methyl-pentanoic acid;
2-(1-Carboxy-3-methyl-butylamino)-5-(3,5-dichloro-phenyl)-pent-4-ynoic acid;
2-{1-Carboxy-2-[4-(3,5-difluoro-phenoxy)-phenyl]-ethylamino}-4-methyl-pentanoic acid;
2-[1-Carboxy-2-(3',5'-dichloro-biphenyl-2-yl)-ethylamino]-4-methyl-pentanoic acid;
4-[2-Carboxy-2-(1-carboxy-3-methyl-butylamino)-ethyl]-benzoic acid tert-butyl ester;
2-(1-Carboxy-3-methyl-butylamino)-5-(3,5-dichloro-phenyl)-pent-4-enoic acid;
2-{1-Carboxy-2-[3-(3,5-difluoro-benzyl)-2,5-dioxo-imidazolidin-1-yl]-ethylamino}-4-methyl-pentanoic acid;
2-{1-Carboxy-2-[3-(3,5-dichloro-benzyl)-2,5-dioxo-imidazolidin-1-yl]-ethylamino}-4-methyl-pentanoic acid;
2-{2-[3-(2,4-Bis-trifluoromethyl-benzyl)-2,5-dioxo-imidazolidin-1-yl]-1-carboxy-ethylamino}-4-methyl-pentanoic acid;
2-{1-Carboxy-2-[4-(5-methyl-pyridin-2-yl)-phenyl]-ethylamino}-4-methyl-pentanoic acid;
2-{1-Carboxy-2-[4-(4-methyl-pyridin-2-yl)-phenyl]-ethylamino}-4-methyl-pentanoic acid;
2-{1-Carboxy-2-[4-(3-chloro-4-ethoxy-pyridin-2-yl)-phenyl]-ethylamino}-4-methyl-pentanoic acid;
2-[1-Carboxy-2-(4-quinolin-3-yl-phenyl)-ethylamino]-4-methyl-pentanoic acid;
2-{1-Carboxy-2-[4-(3,5-difluoro-benzylcarbamoyl)-phenyl]-ethylamino}-4-methyl-pentanoic acid;
2-{1-Carboxy-2-[4-(3,5-dichloro-phenylcarbamoyl)-phenyl]-ethylamino}-4-methyl-pentanoic acid;
2-[1-Carboxy-2-(4-phenylcarbamoyl-phenyl)-ethylamino]-4-methyl-pentanoic acid;
2-[1-Carboxy-2-(4-cyclohexylcarbamoyl-phenyl)-ethylamino]-4-methyl-pentanoic acid;
2-[1-Carboxy-2-(2-cyano-phenyl)-ethylamino]-4-methyl-pentanoic acid;
2-[1-Carboxy-2-(4-phenoxy-phenyl)-ethylamino]-4-methyl-pentanoic acid;
2-{1-Carboxy-2-[4-(5-chloro-benzo[b]thiophen-3-ylmethoxy)-phenyl]-ethylamino}-4-methyl-pentanoic acid;
2-{1-Carboxy-2-[5-(3,4-dichloro-phenyl)-isoxazol-3-yl]-ethylamino}-4-methyl-pentanoic acid;
2-{1-Carboxy-2-[4-(3,5-dichloro-phenoxy)-phenyl]-ethylamino}-4-methyl-pentanoic acid;
2-{1-Carboxy-2-[2-(3,5-dichloro-phenoxy)-phenyl]-ethylamino}-4-methyl-pentanoic acid;
2-{1-Carboxy-2-[2-(3-chloro-benzyloxy)-phenyl]-ethylamino}-4-methyl-pentanoic acid;
2-{1-Carboxy-2-[4-(4-fluoro-phenoxy)-phenyl]-ethylamino}-4-methyl-pentanoic acid;
2-[1-Carboxy-2-(1-p-tolyl-1H-pyrazol-3-yl)-ethylamino]-4-methyl-pentanoic acid;
2-{1-Carboxy-2-[4-(cyclopentanecarbonyl-amino)-phenyl]-ethylamino}-4-methyl-pentanoic acid;
2-{1-Carboxy-2-[4-(2,2-dimethyl-propionylamino)-phenyl]-ethylamino}-4-methyl-pentanoic acid;
2-{1-Carboxy-2-[2-(5-chloro-benzo[b]thiophen-3-ylmethoxy)-phenyl]-ethylamino}-4-methyl-pentanoic acid;
2-{1-Carboxy-2-[5-(4-chloro-phenyl)-isoxazol-3-yl]-ethylamino}-4-methyl-pentanoic acid;
2-{1-Carboxy-2-[5-(2-chloro-phenyl)-isoxazol-3-yl]-ethylamino}-4-methyl-pentanoic acid;
2-{1-Carboxy-2-[4-(5-fluoro-2,3-dihydro-benzofuran-3-ylmethoxy)-phenyl]-ethylamino}-4-methyl-pentanoic acid;
2-{2-[4-(Benzo[b]thiophen-3-ylmethoxy)-phenyl]-1-carboxy-ethylamino}-4-methyl-pentanoic acid;
5-[2-Carboxy-2-(1-carboxy-3-methyl-butylamino)-ethyl]-1-(3,5-dichloro-benzyl)-1H-pyrrole-2-carboxylic acid;
2-{1-Carboxy-2-[1-(2-cyclohexyl-ethyl)-5-(2,2,2-trifluoro-acetyl)-1H-pyrrol-2-yl]-ethylamino}-4-methyl-pentanoic acid;
2-[1-Carboxy-2-(4-nitro-phenyl)-ethylamino]-4-methyl-pentanoic acid;
2-{1-Carboxy-2-[4-(2-methoxy-benzoylamino)-phenyl]-ethylamino}-4-methyl-pentanoic acid;
2-[1-Carboxy-2-(2-trifluoromethyl-phenyl)-ethylamino]-4-methyl-pentanoic acid;
2-(2-{4-[Bis-(3,5-difluoro-benzyl)-amino]-phenyl}-1-carboxy-ethylamino)-4-methyl-pentanoic acid;
2-[1-Carboxy-2-(2-p-tolyl-thiazol-4-yl)-ethylamino]-4-phenyl-butyric acid;
2-[1-Carboxy-2-(4-dimethylcarbamoyl-phenyl)-ethylamino]-4-methyl-pentanoic acid;
2-{1-Carboxy-2-[4-(3,5-dimethyl-phenylcarbamoyl)-phenyl]-ethylamino}-4-methyl-pentanoic acid;
2-[2-(4-tert-Butylcarbamoyl-phenyl)-1-carboxy-ethylamino]-4-methyl-pentanoic acid;
4-Methyl-2-{[pyrimidin-2-yl-(2-p-tolyl-thiazol-4-ylmethyl)-amino]-methyl}-pentanoic acid;
2-{1-Carboxy-2-[1-(3,5-dichloro-benzyl)-1H-pyrrol-2-yl]-ethylamino}-4-methyl-pentanoic acid;

2-[1-Carboxy-2-(4-isopropylcarbamoyl-phenyl)-ethylamino]-4-methyl-pentanoic acid;
2-{1-Carboxy-2-[4-(morpholine-4-carbonyl)-phenyl]-ethylamino}-4-methyl-pentanoic acid; and
2-{1-Carboxy-2-[4-(3,4-dihydro-1H-isoquinoline-2-carbonyl)-phenyl]-ethylamino}-4-methyl-pentanoic acid.
Examples compounds of the invention include those having the structures shown below:
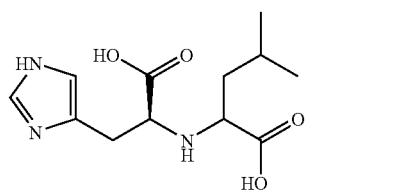
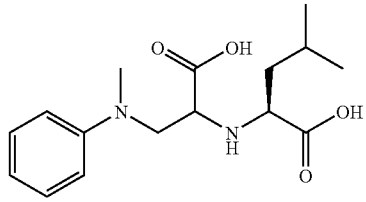
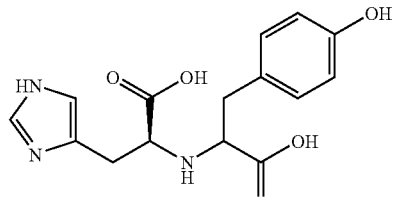
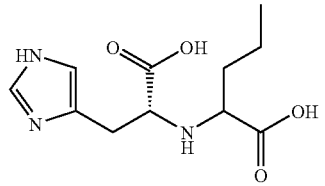
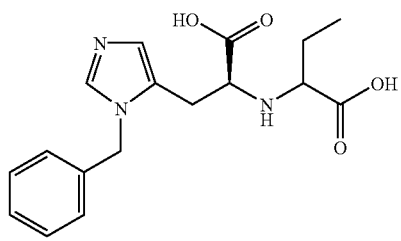
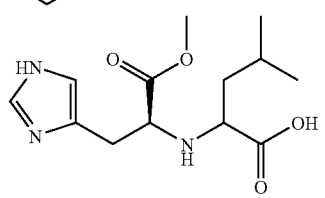
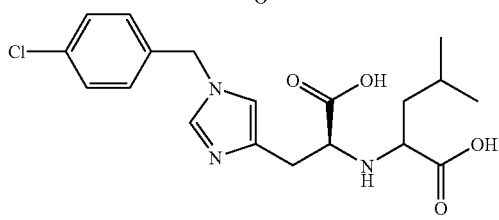
-continued
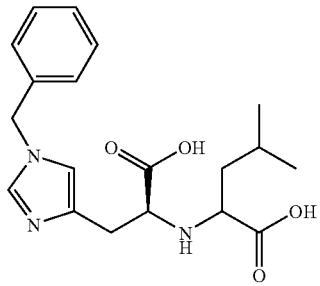
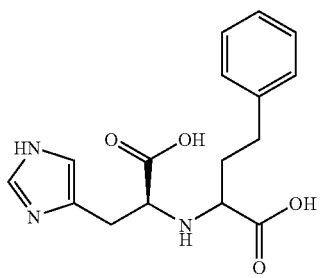
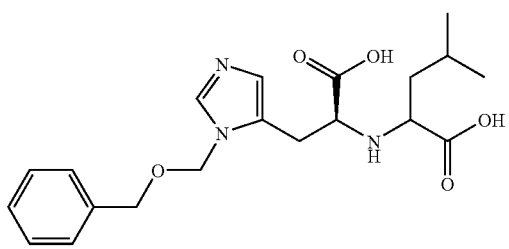
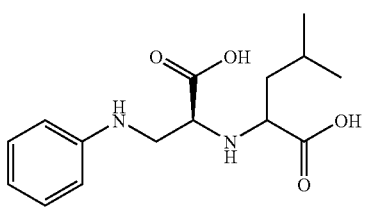
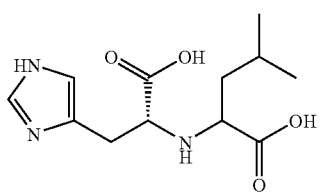
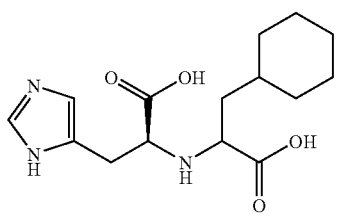

-continued
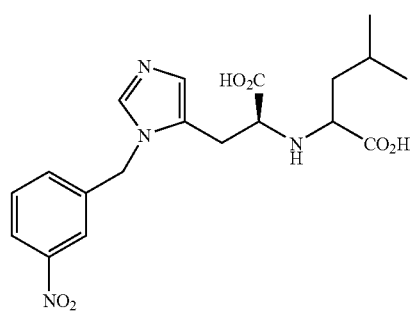
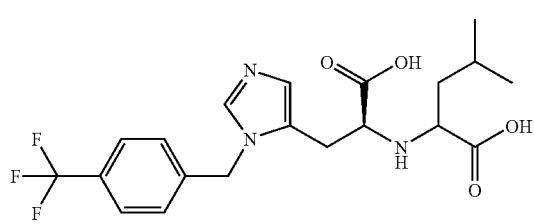
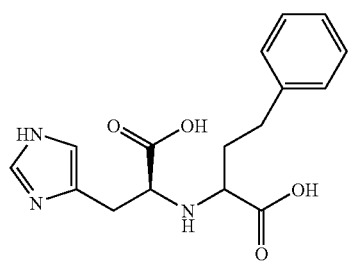
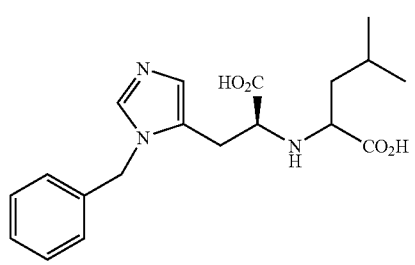
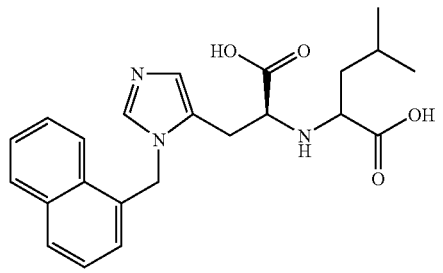
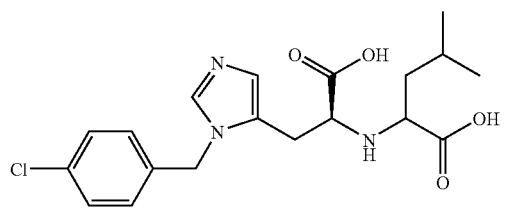
-continued
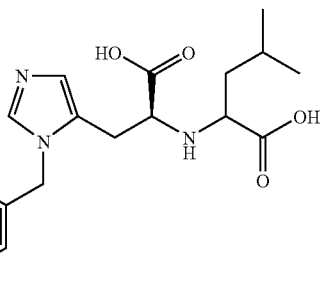
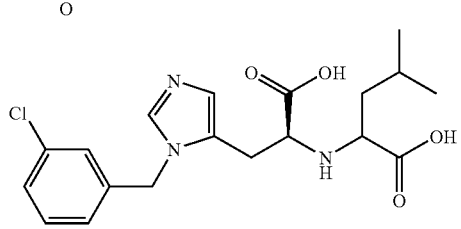
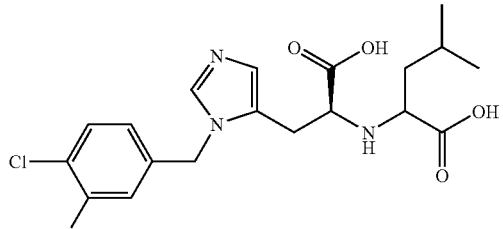
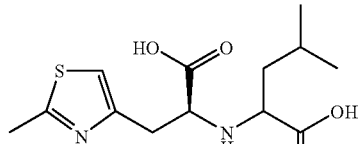
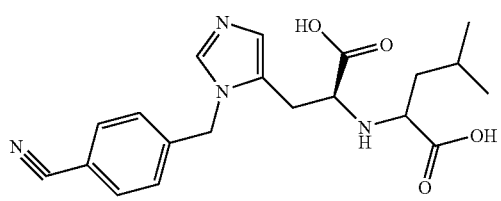
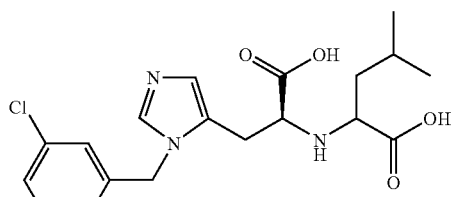
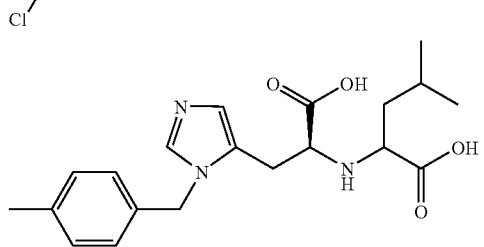

-continued
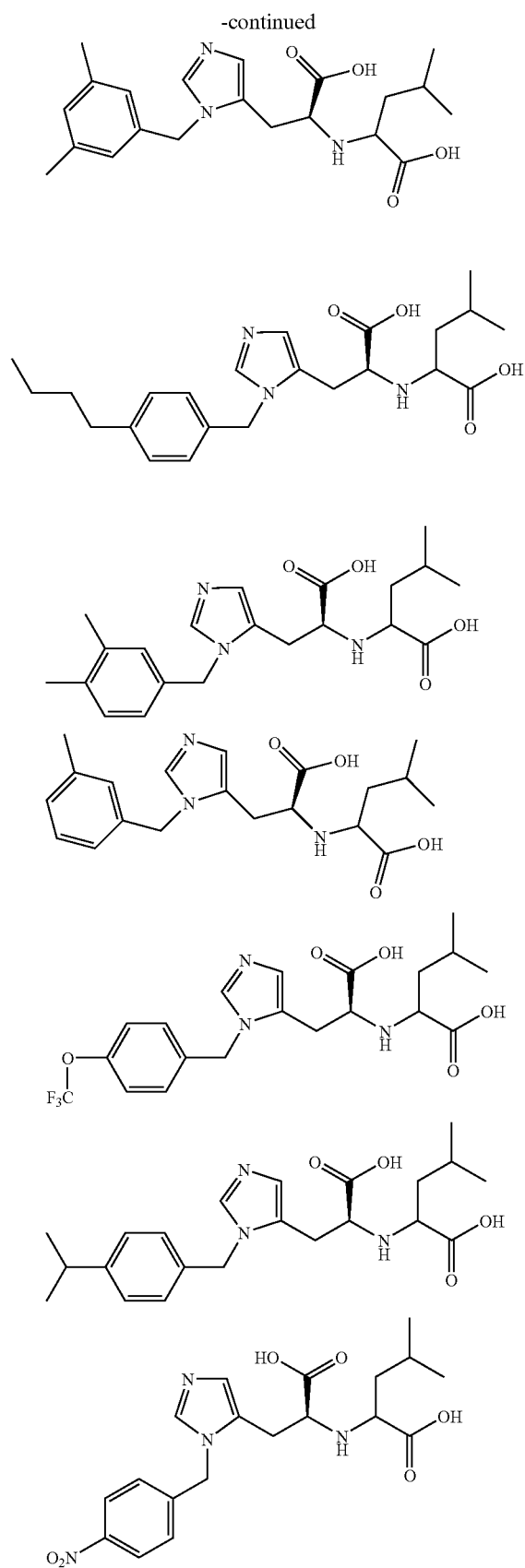
-continued
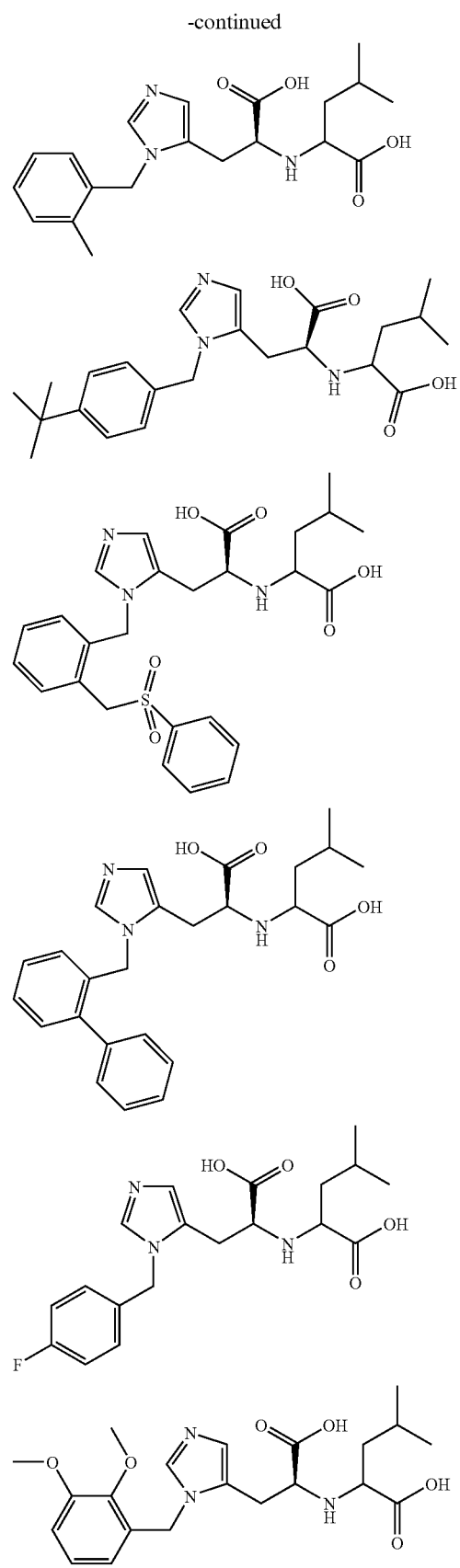

-continued
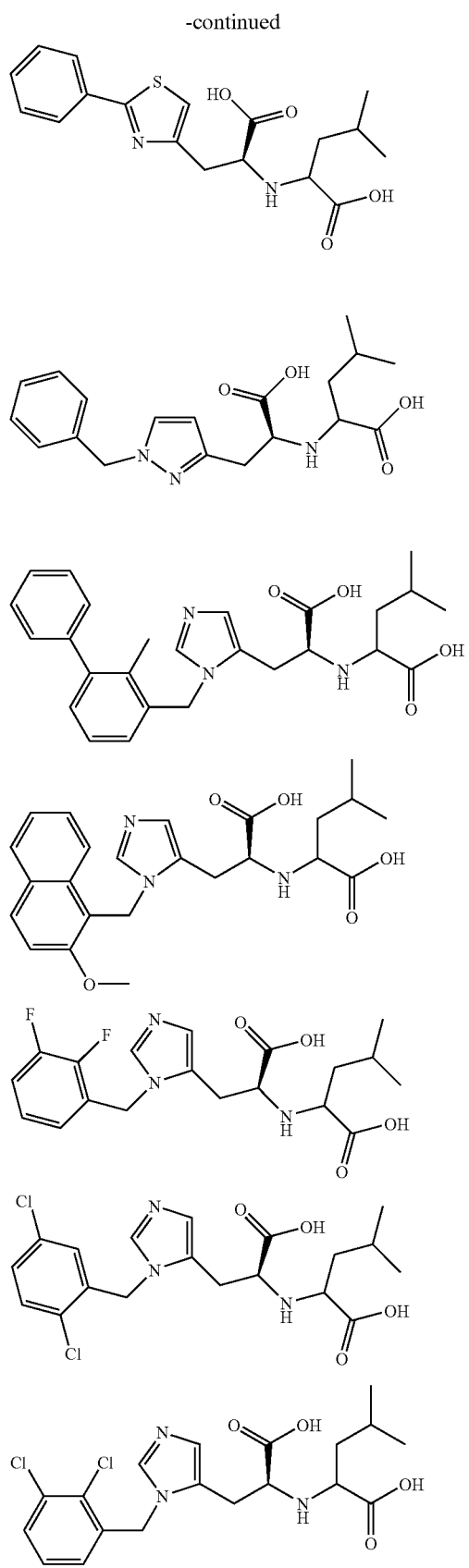
-continued
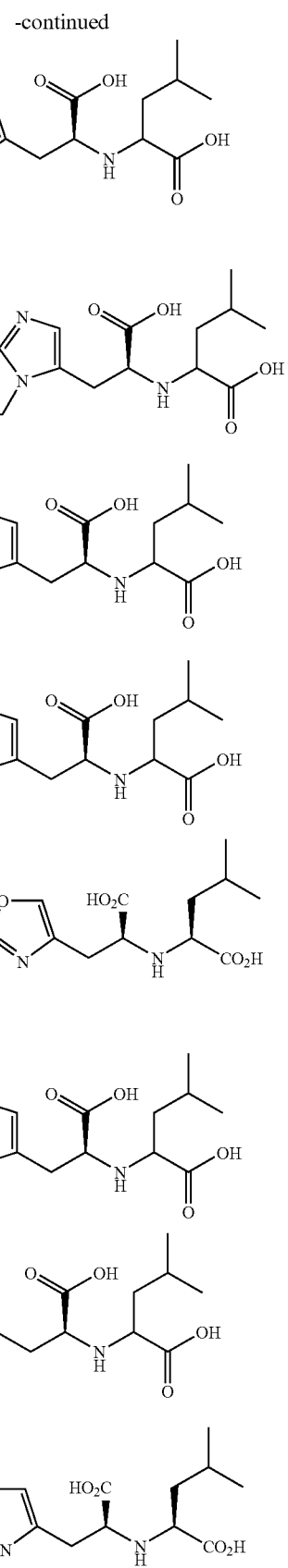

-continued
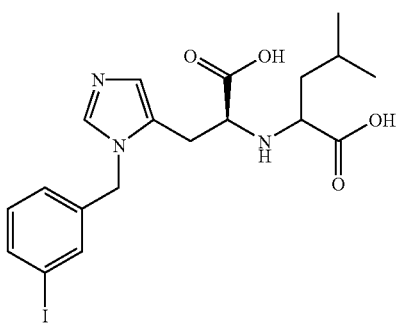
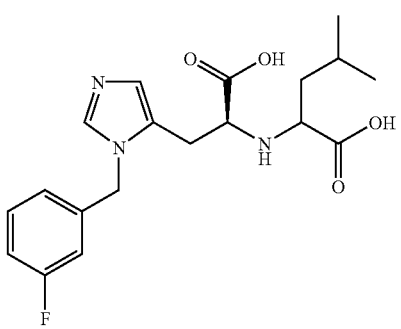
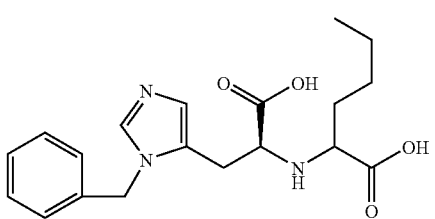
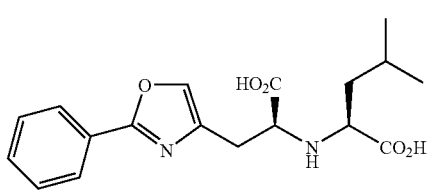
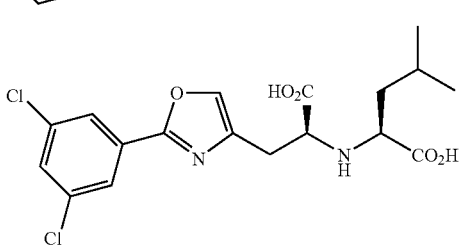
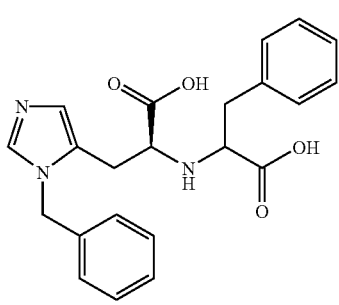
-continued
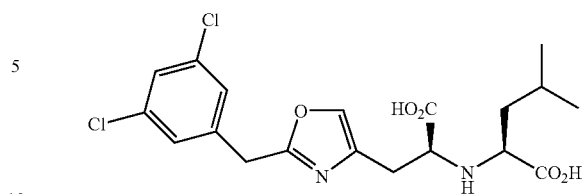
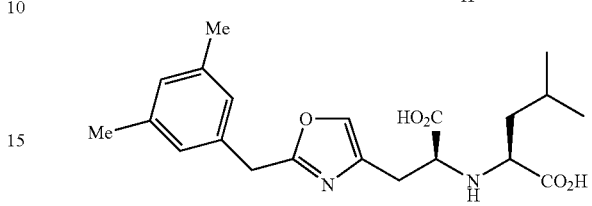
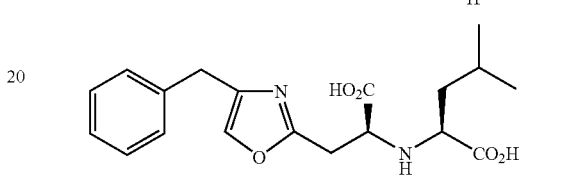
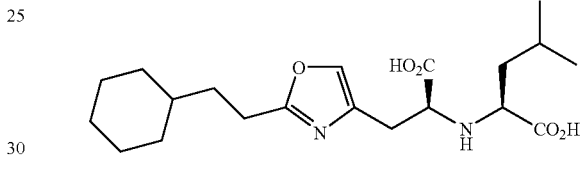
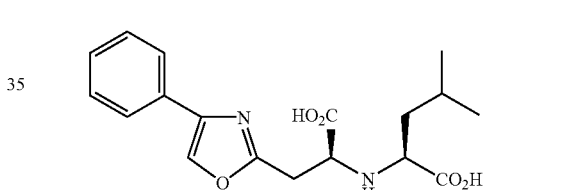
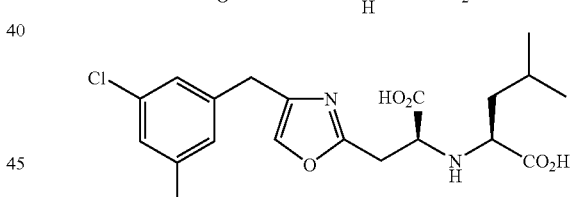
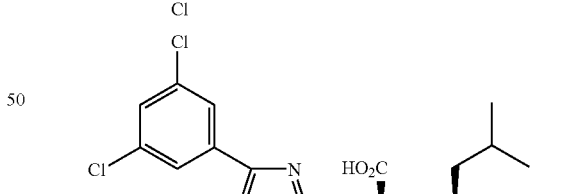
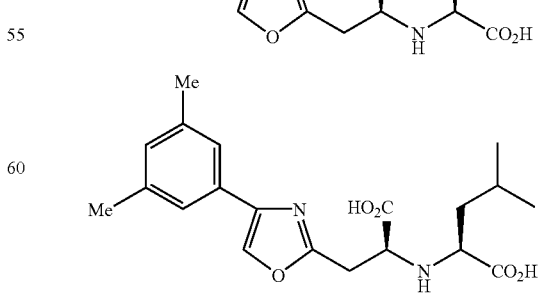

-continued
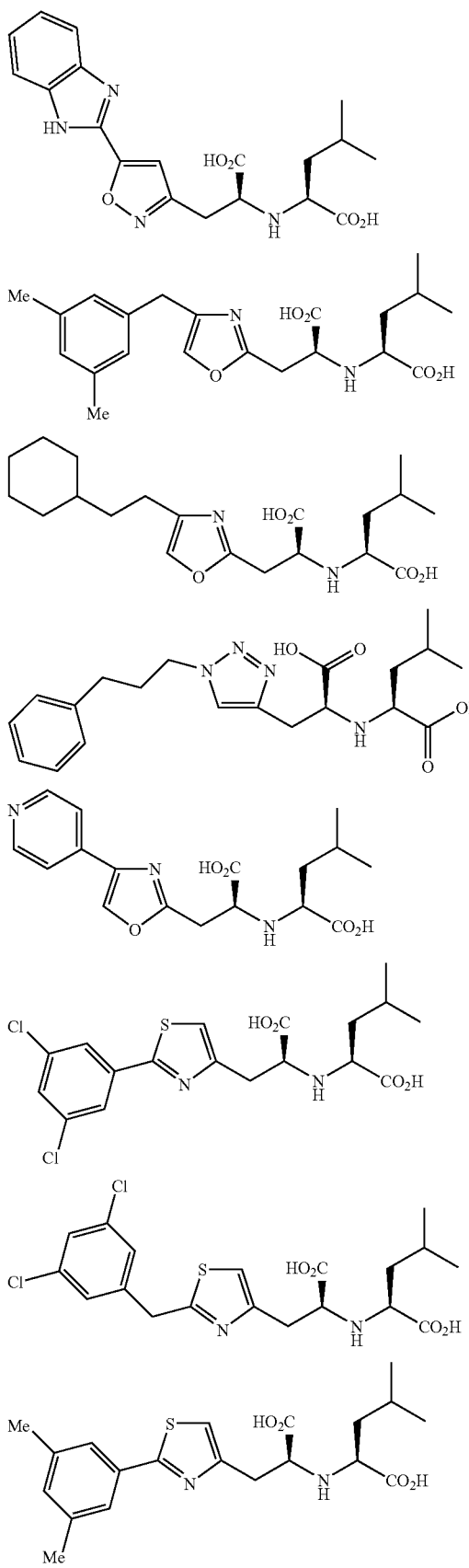
-continued
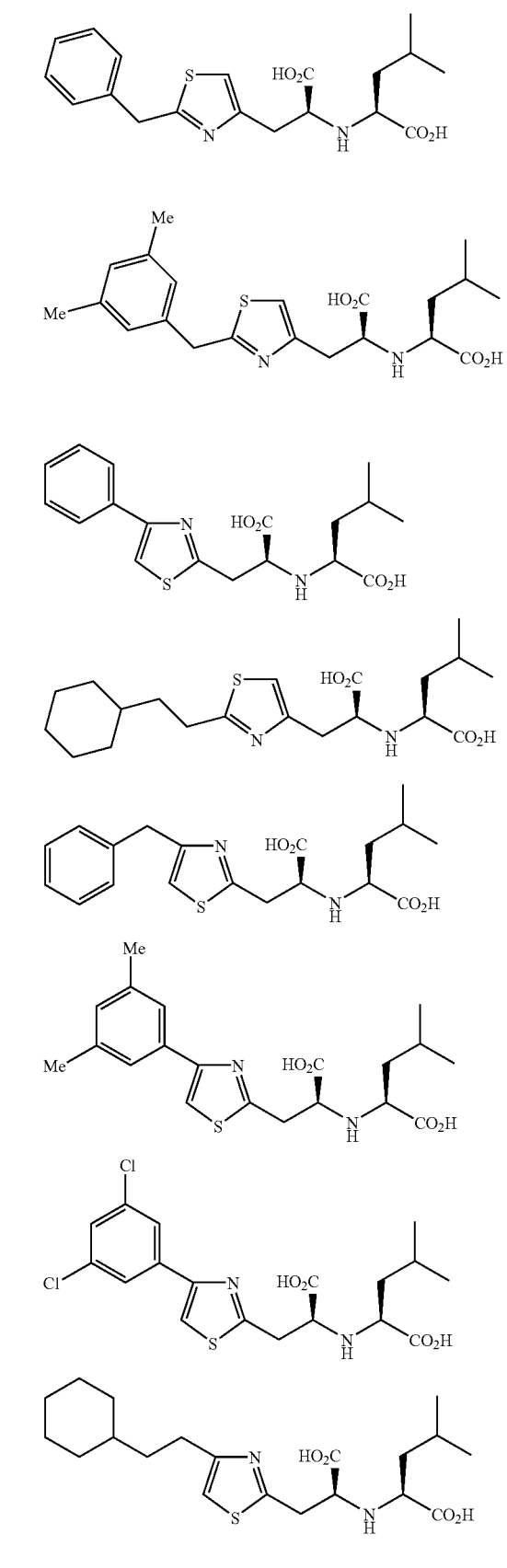

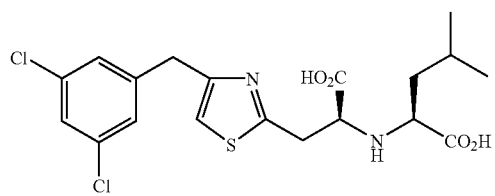
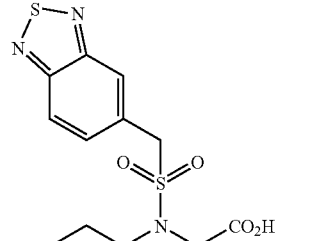
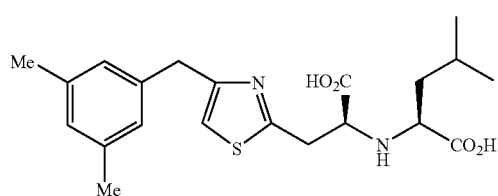
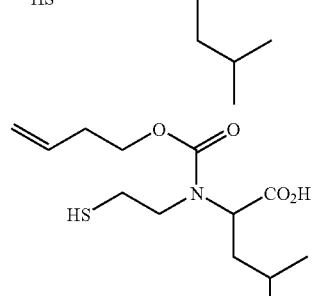
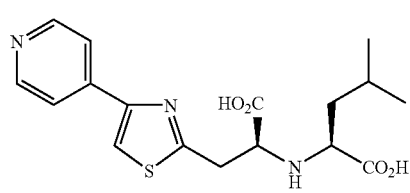
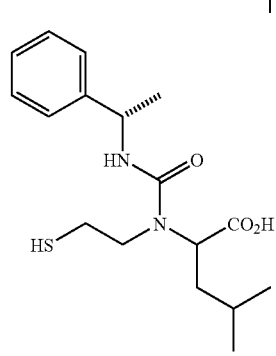
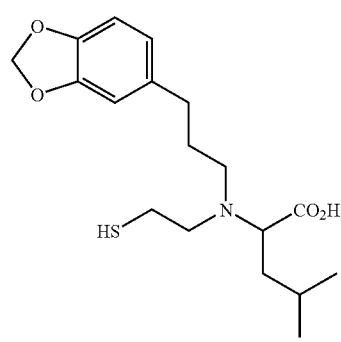
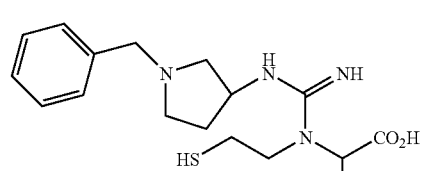
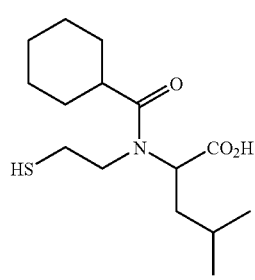
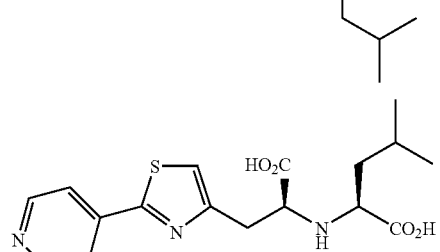
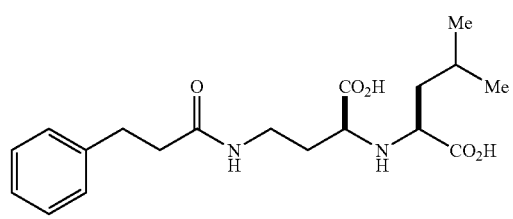
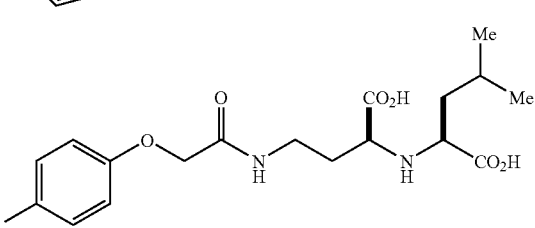

81
-continued
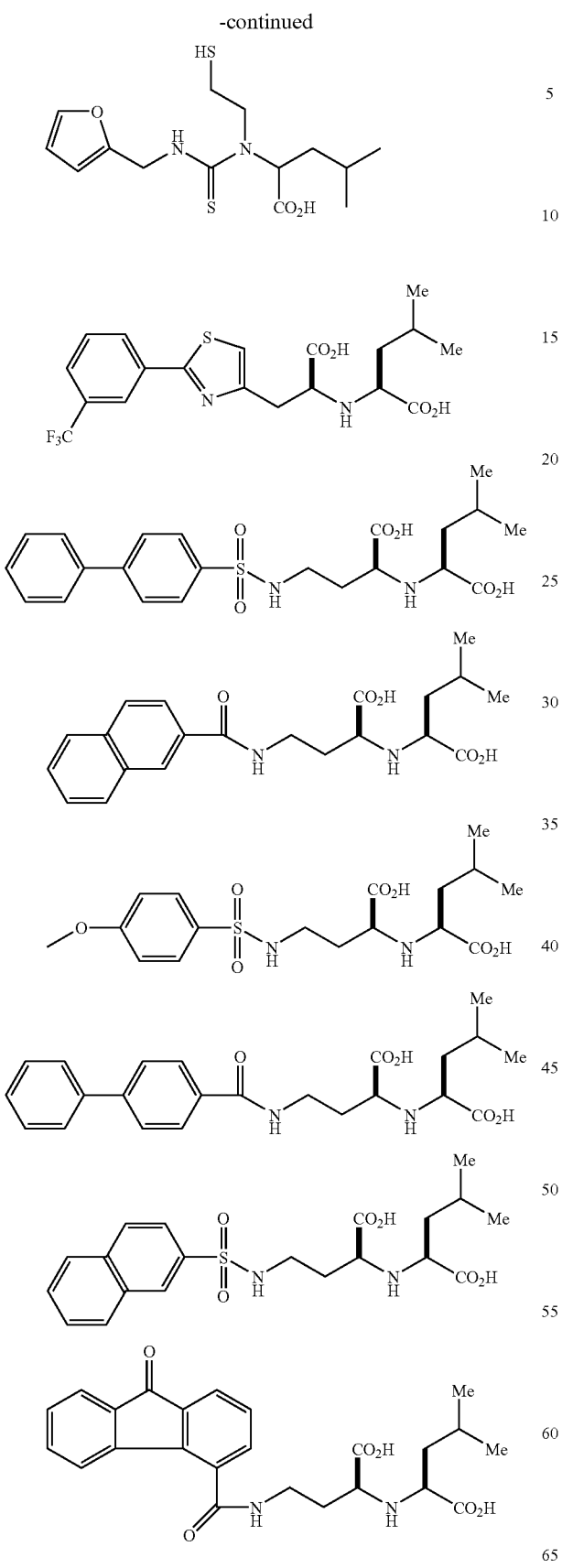
82
-continued
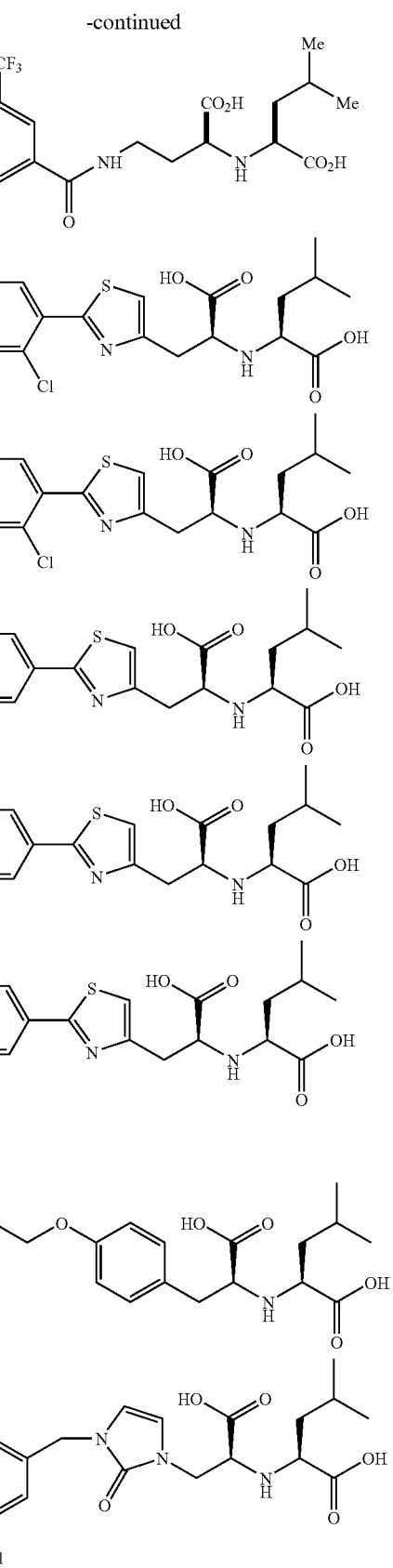

83 84
-continued -continued
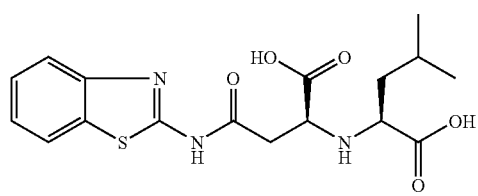
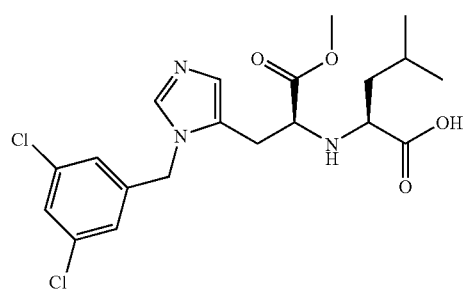
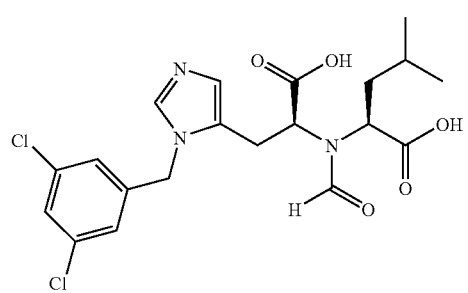
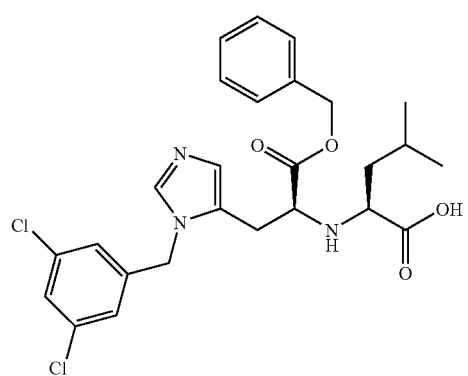
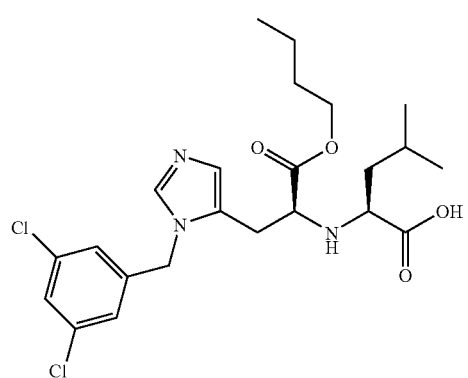
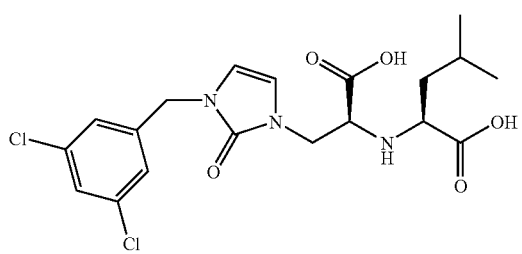
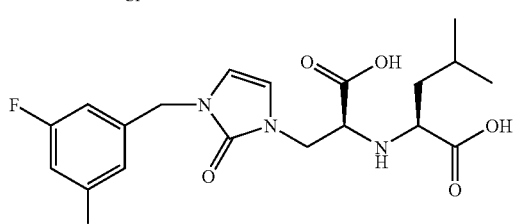
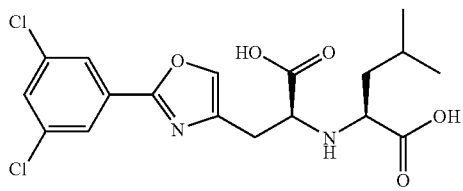
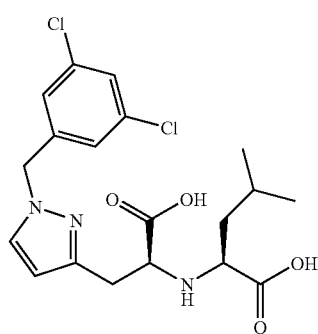
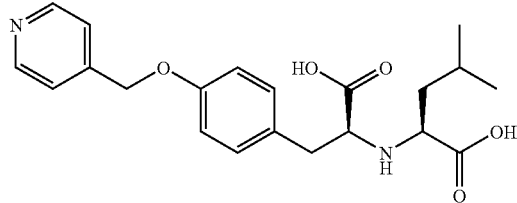
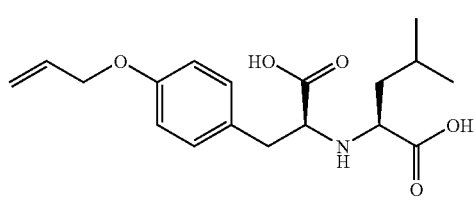
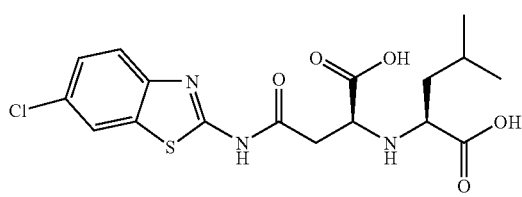

85
-continued
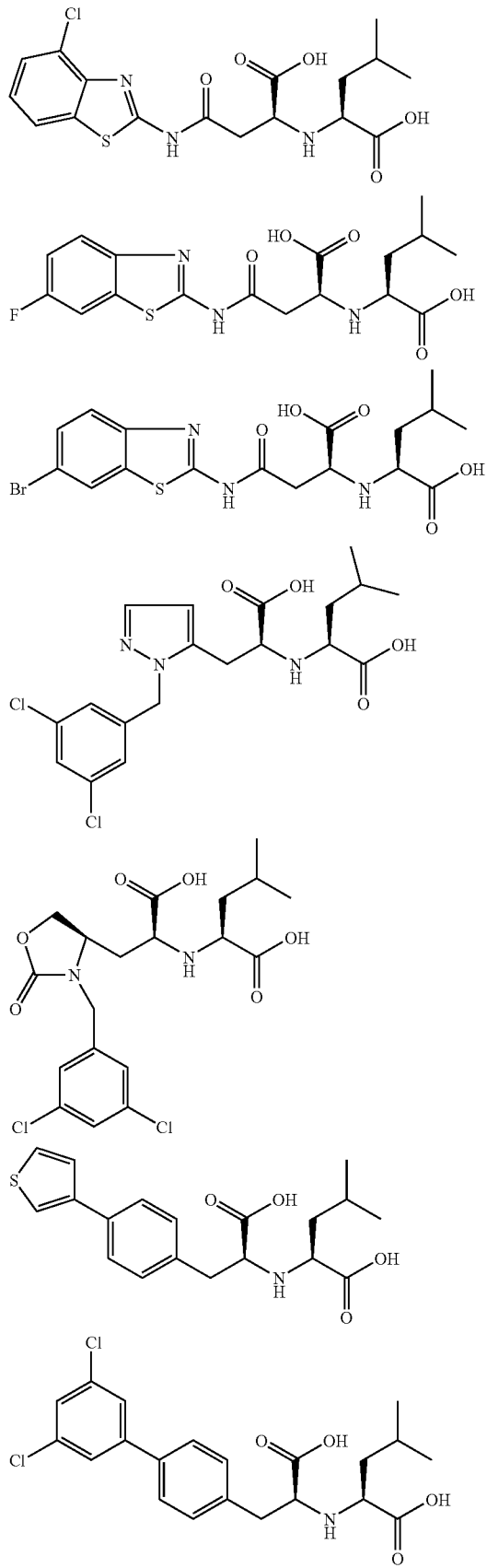
86
-continued
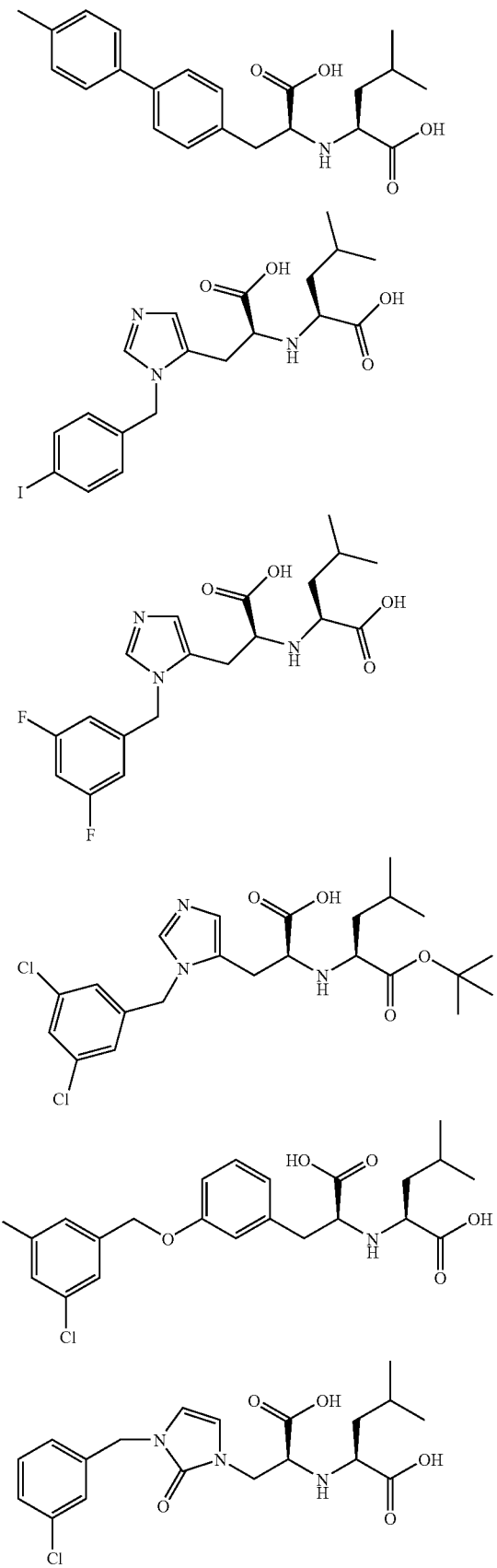

-continued
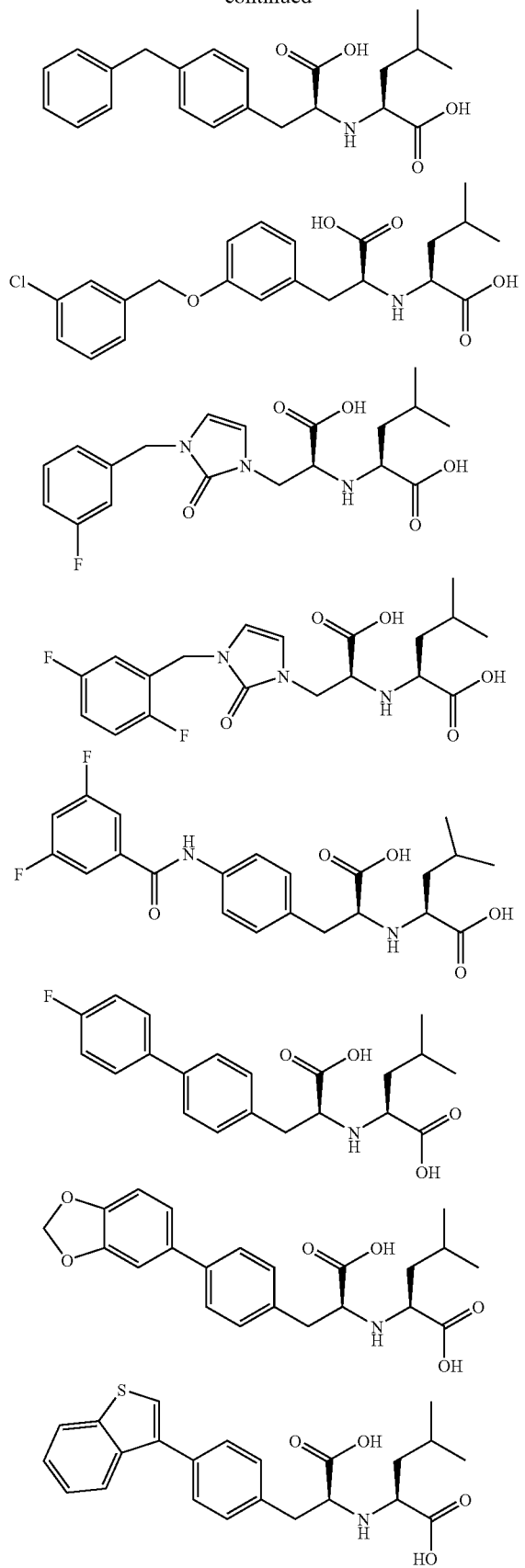
-continued
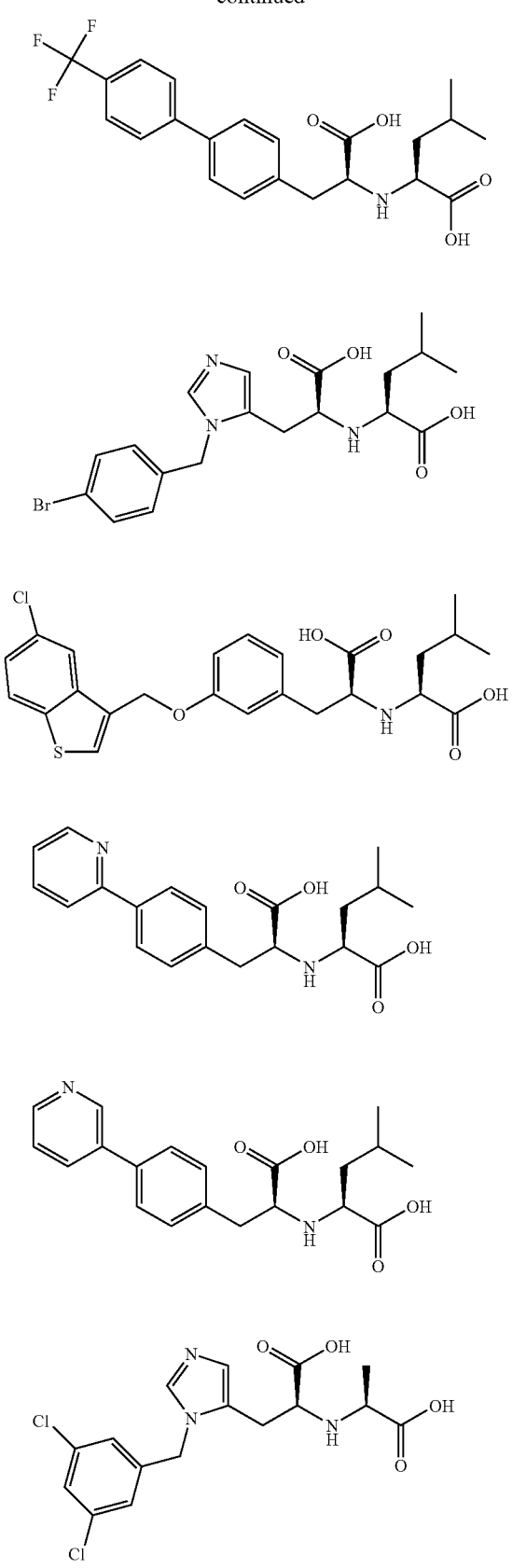

-continued
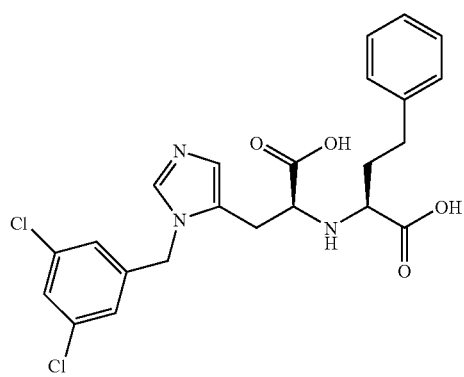
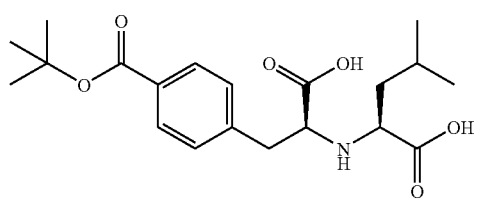
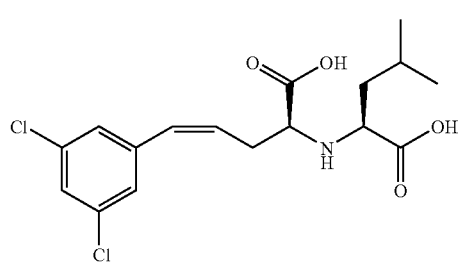
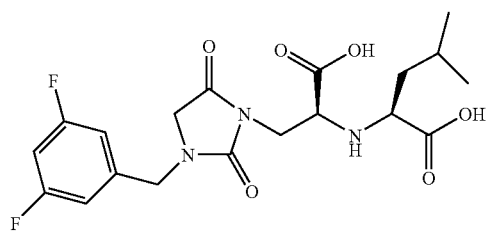
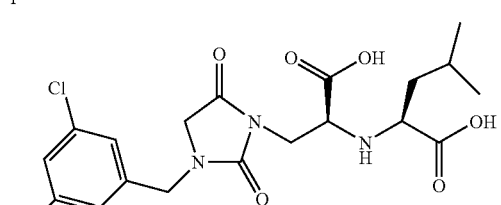
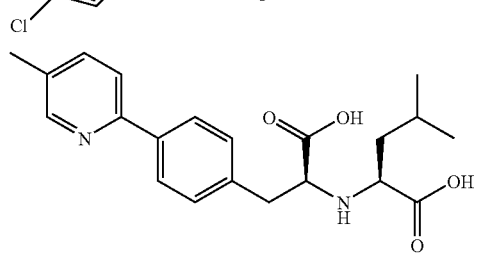
-continued
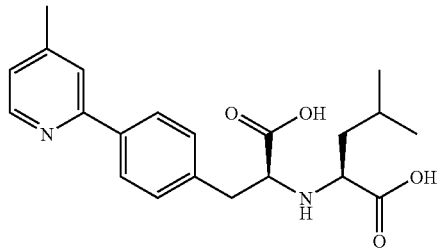
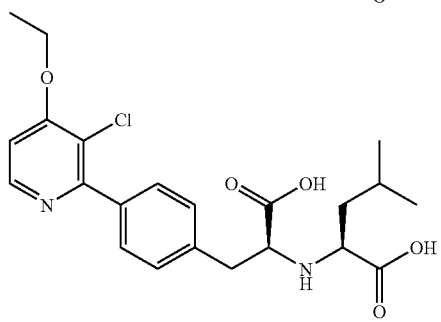
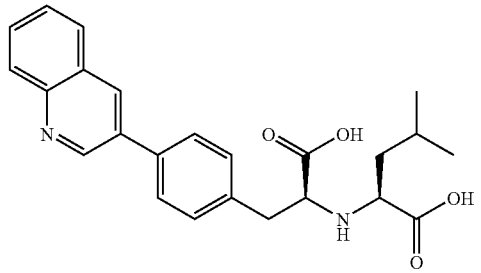
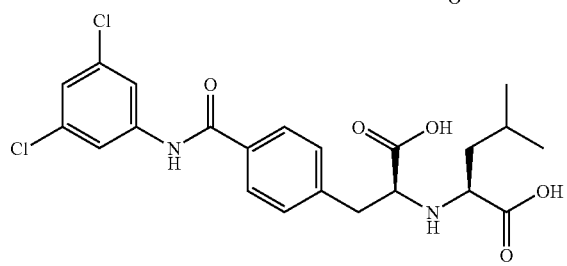
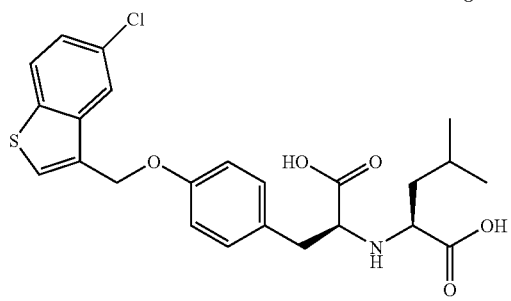
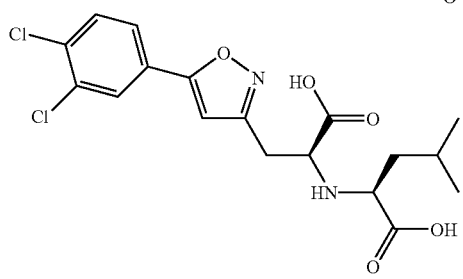

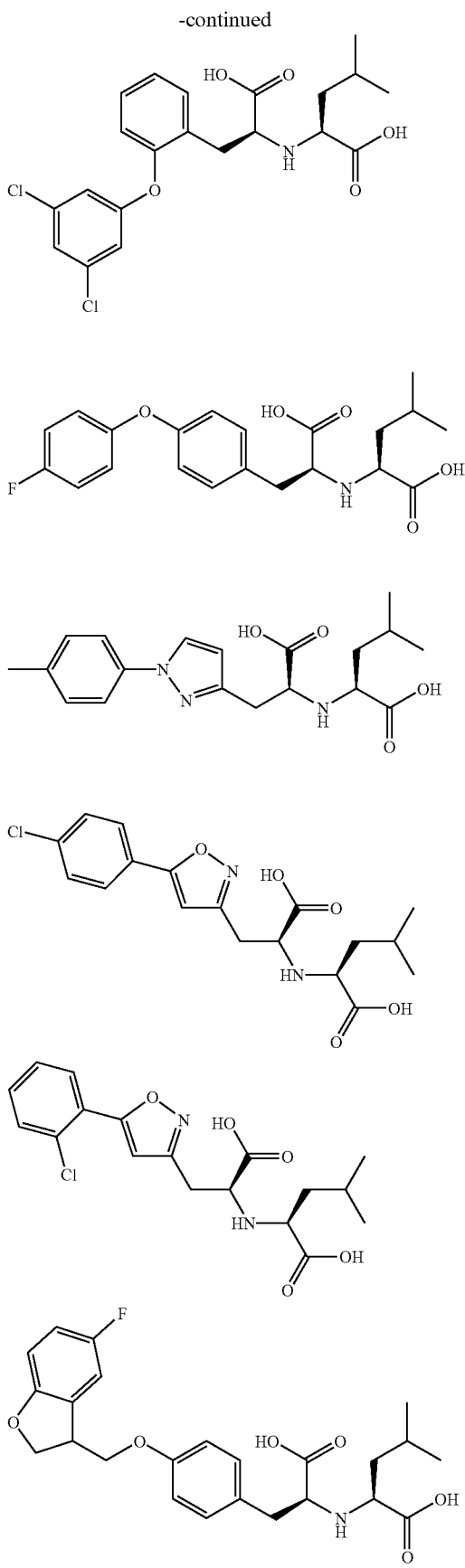

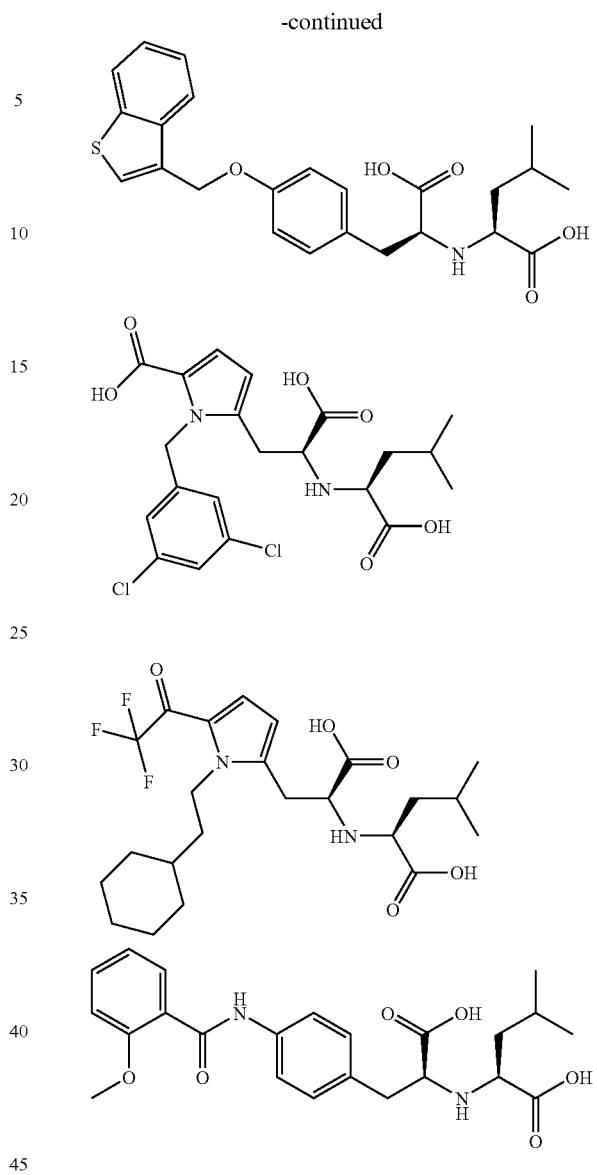

Other exemplary compounds are discussed in the Example section and Table 2.

The term "small molecules" includes molecules which are capable of being used as therapeutic agents e.g., peptides, peptidomimetics (e.g., peptoids), amino acids, amino acid analogs, polynucleotides, polynucleotide analogs, nucleotides, nucleotide analogs, organic (including, e.g., heteroorganic and organometallic compounds) and inorganic compounds. The term includes compounds which have a molecular weight of about, for example, 10,000 grams per mole or less, 5,000 grams per mole or less, 2,000 grams per mole or less, or 1,000 g/mol grams per mole or less. In a further embodiment, the small molecule is an organic compound. Examples of small molecules include those described in Formulae 1–VIII and in Table 2. Organic compounds comprise one or more carbon atoms. In another embodiment, the compound is an inorganic compound. Inorganic compounds include compounds which do not comprise a carbon atom.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (e.g., isopropyl, tert-butyl, isobutyl, etc.), cycloalkyl (alicyclic) groups (e.g., cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 3–8 carbon atoms in their ring structure, and more preferably have 5 or 6 carbons in the ring structure. The term $C_1$–$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$–$C_6$ for straight chain, $C_3$–$C_6$ for branched chain). Likewise, cycloalkenyl groups may have from 3–8 carbon atoms in their ring structure, and more preferably have 5 or 6 carbons in the ring structure. The term $C_2$–$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$–$C_6$ for straight chain, $C_3$–$C_6$ for branched chain). The term $C_2$–$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including, e.g., alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2–5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —$O^-X^+$, where $X^+$ is a counterion.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The compounds of the invention can be synthesized by methods known to those of skill in the art from compounds which are commercially available. Scheme 1 depicts a general method of synthesizing compounds of the invention, wherein Q is NH.

Resin bound FMOC protected amino acids are commercially available from Novabiochem. The amino terminus is deprotected by treatment with 20% piperidine in DMF for 30 minutes (Scheme 1). The amine (1-1) is then treated with acetic acid in DMF and various commercially available α-ketoesters. The resulting Schiff base is then treated with a hydride agent such as NaBH$_3$CN to be converted into the corresponding secondary amine. The acids are removed from the resin through treatment with a strong acid, e.g., trifluoroacetic acid. The resulting acid (1-2) is esterified through treatment with the corresponding alcohol (1-3). The diastereomers prepared here are separated by conventional means. The thiol compounds of the invention, wherein Q is CH$_2$SH, are synthesized by methods well known in the art. A sample synthesis is outlined below in Scheme 2.

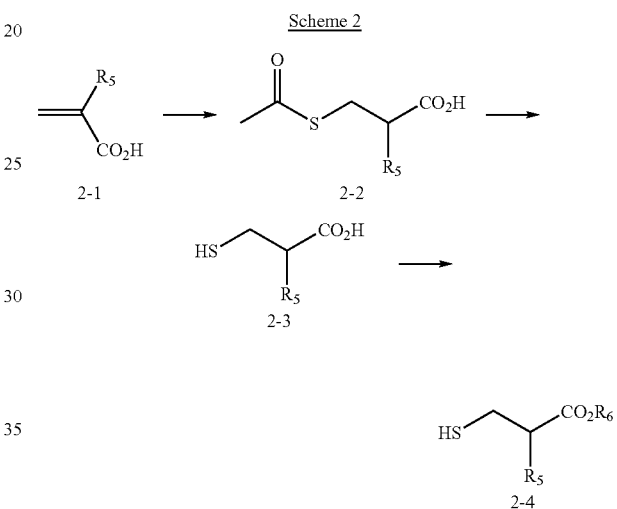

In scheme 2, the thiol is synthesized, for example, by heating thiolacetic acid with an appropriately substituted acrylic acid (2-1) to form the thioester (2-2). The thioester is hydrolyzed to the thiol by treatment with base to give the thiol (2-3). The ester is formed by treating the acid compound with the appropriate alcohol to form the desired ester (2-4). One of skill in the art can separate resulting enantiomers through conventional means such as, for example, chiral HPLC chromatography.

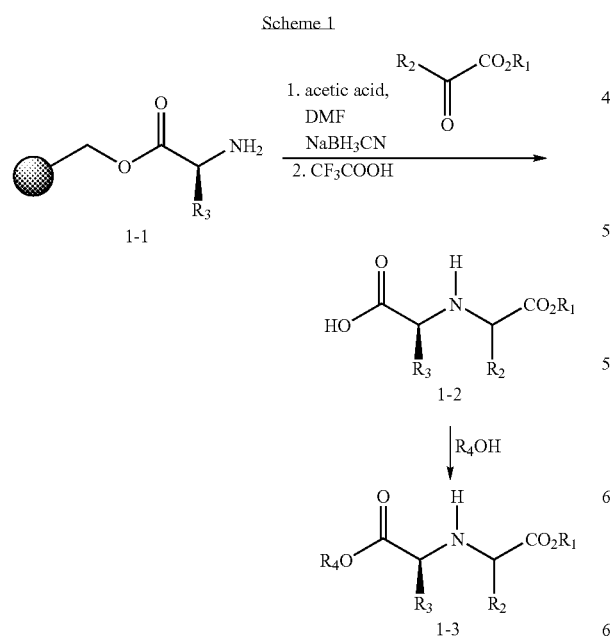

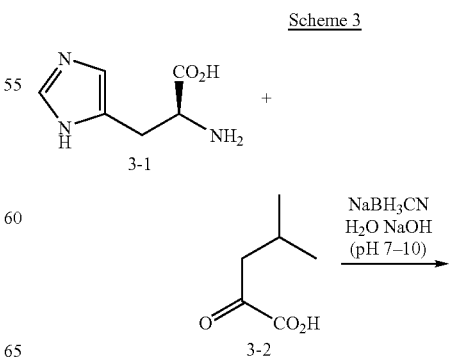

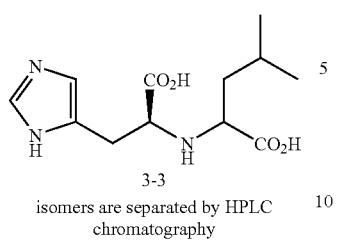

3-3
isomers are separated by HPLC chromatography

The imidazole compounds of the invention are synthesized using the procedure outlined in Scheme 3. In a neutral to basic solution, the amine (3-1) reacts with the carbonyl of the α-ketoacid (3-2) to form the Schiff base, which is readily converted into the secondary amine (3-3) by a reducing agent. Substituted imidazole compounds of the invention are synthesized, for example, by treating α-protected histidine with a suitable halogenenated compound, such as benzyl bromide. The substituted histidine derivatives are then used in place of histidine in the synthesis shown in Scheme 3.

Compounds of the invention are synthesized using the procedure outlined in Scheme 4. In Scheme 4, a phenyl ACE-2 modulating compound is synthesized by treating an ethyl ester (4-1) with triflic anhydride and 2,6-lutidine in methylene chloride at –78° C. To this mixture, leucine methyl ester can be added forming the secondary amine (4-2). The ester is then treated with aqueous base to form the resulting diacid (4-3). Further synthetic examples are given in the Example section.

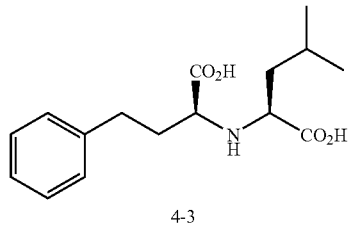

4-3

Benzylpyrazole compounds of the invention are synthesized using the methods outlined in Scheme 5. In particular, commercially available 3-methylpyrazole (5-1) was oxidized to pyrazole-3-carboxylic acid and then treated with 2 equivalents of benzyl bromide (Jones, R. G. *J. Am. Chem. Soc.* 1949, 71, 3994). The resulting 1-benzylpyrazole-3-carboxylic acid benzyl ester was then reduced with LiAlH$_4$ and converted to bromide 5-2. Alkylation of Scholkopf's dihydropyrazine with this bromide provided 5-3 as a mixture of diastereomers (3–4 to 1 trans:cis) (Scholkopf, U. et al. *Angew. Chem. Int. Ed. Engl.* 1981, 20, 798). Hydrolysis of the dihydropyrazine provided amino ester 5-4, which was then alkylated with triflate 5-5. The resulting diester was hydrolyzed to give diacid 5-6 as a mixture of diastereomers, which were separated by reverse phase HPLC.

Scheme 3

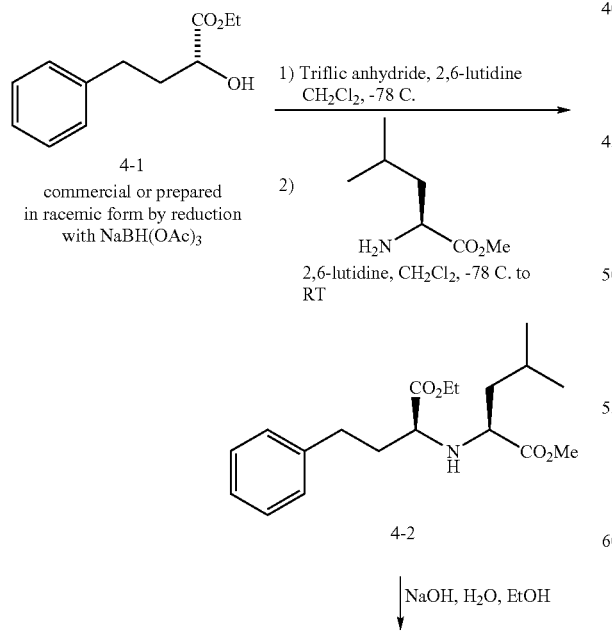

Scheme 5

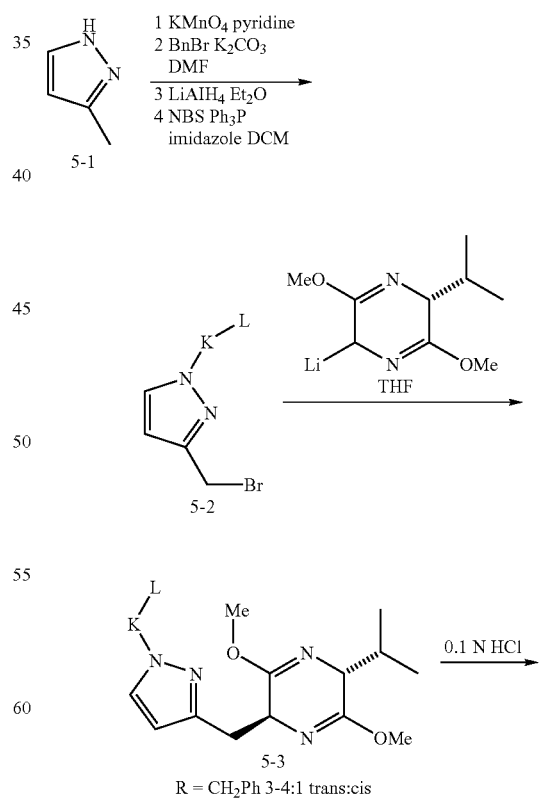

-continued

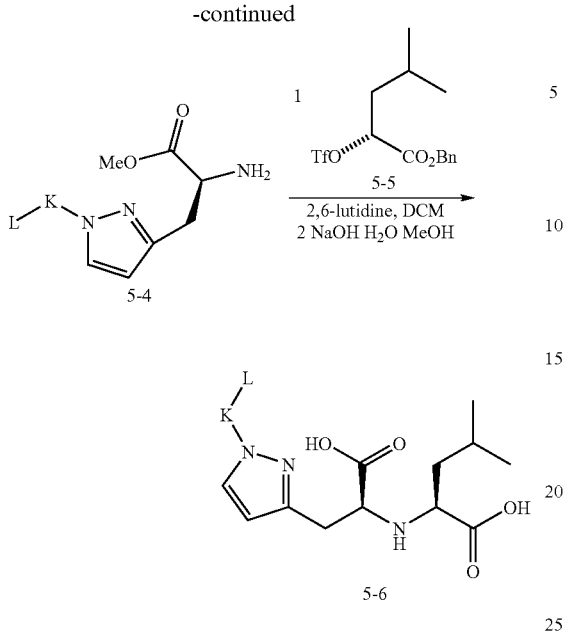

Phenylthiazole compounds of the invention are synthesized by preparing amino esters 6-1 and subsequently alkylating the esters with the trifluoromethane sulfonate of leucic acid methyl ester (6-3) (Svete, J.; et al. *J. Heterocyclic Chem.* 1994, 31, 1259.) Hydrolysis of the esters provides the diacids 6-2 (Scheme 6).

Scheme 6

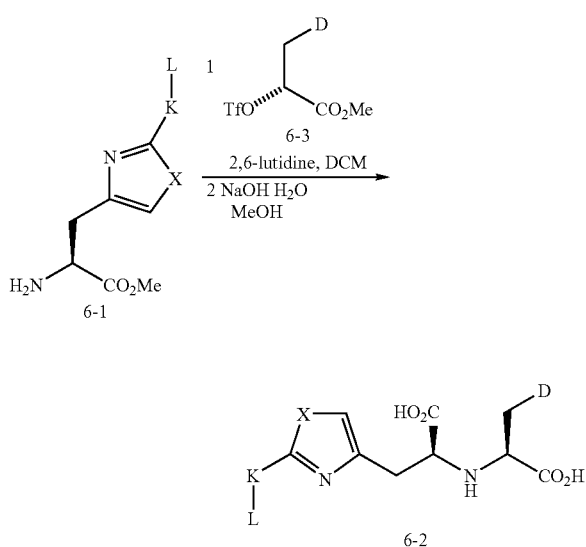

X = O, S
K—L = alkyl, aryl, heteroaryl, arylalkyl, etc.

Thiazoles and oxazoles of the invention are prepared by the method shown in Scheme 7. The amino ester 7-1 (X=O) is treated with an appropriate α-bromoketone in methanol to give, following removal of the Boc group with TFA, the amino ester 7-2. Amino ester 7-2 is alkylated with the triflate of an appropriate alcohol ester in the presence of 2,6-lutidine, and treated with NaOH in MeOH to provide the diacid 7-3. Thioamide 7-1 (X=S) is prepared by treating asparagine with Lawesson's reagent. This thioamide is treated as described above to provide thiazoles 7-3.

Scheme 7

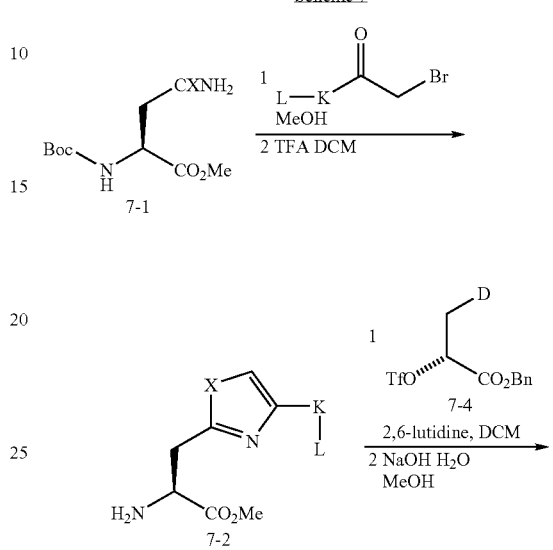

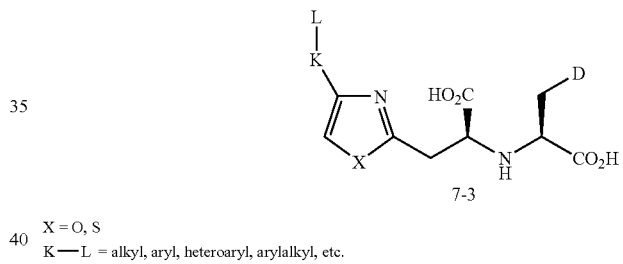

X = O, S
K—L = alkyl, aryl, heteroaryl, arylalkyl, etc.

Isoxazolyl compounds of the invention are synthesized, for example, by using the method shown in Scheme 8. In Scheme 8, the methyl ester of 2-tert-butoxycarbonylamino-4-oxobutyric acid (8-1) is reacted with hydroxylamine hydrochloride, then with NCS, and finally with an appropriate alkyne in the presence of triethylamine to provide the amino ester 8-3 (Gosselin, F. et al. *J. Org. Chem.* 1998, 63, 7463; Aicher, T. D. et al. *J. Med. Chem.* 1998, 41, 4556). This amino ester is then reacted as described previously with an appropriate trifluoromethane sulfonate (8-5). Ester hydrolysis then provides the diacid 8-4.

Scheme 8

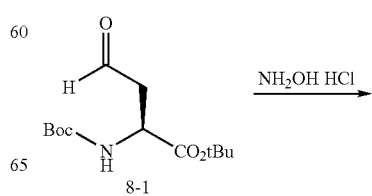

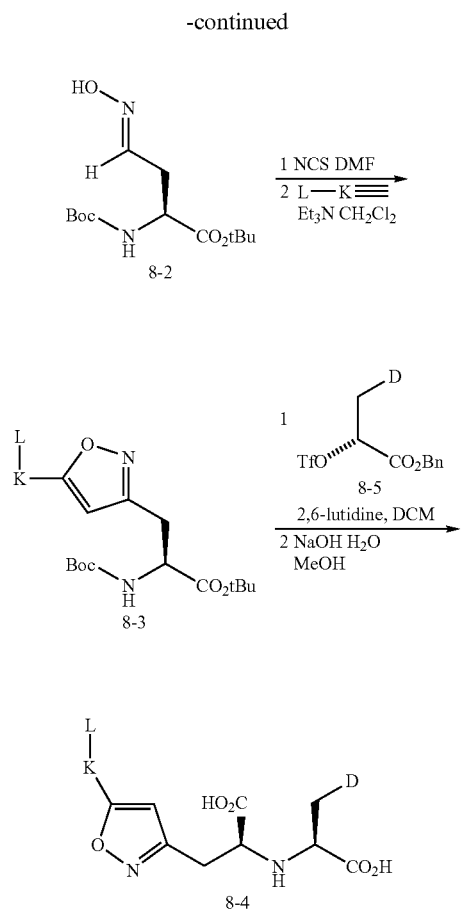

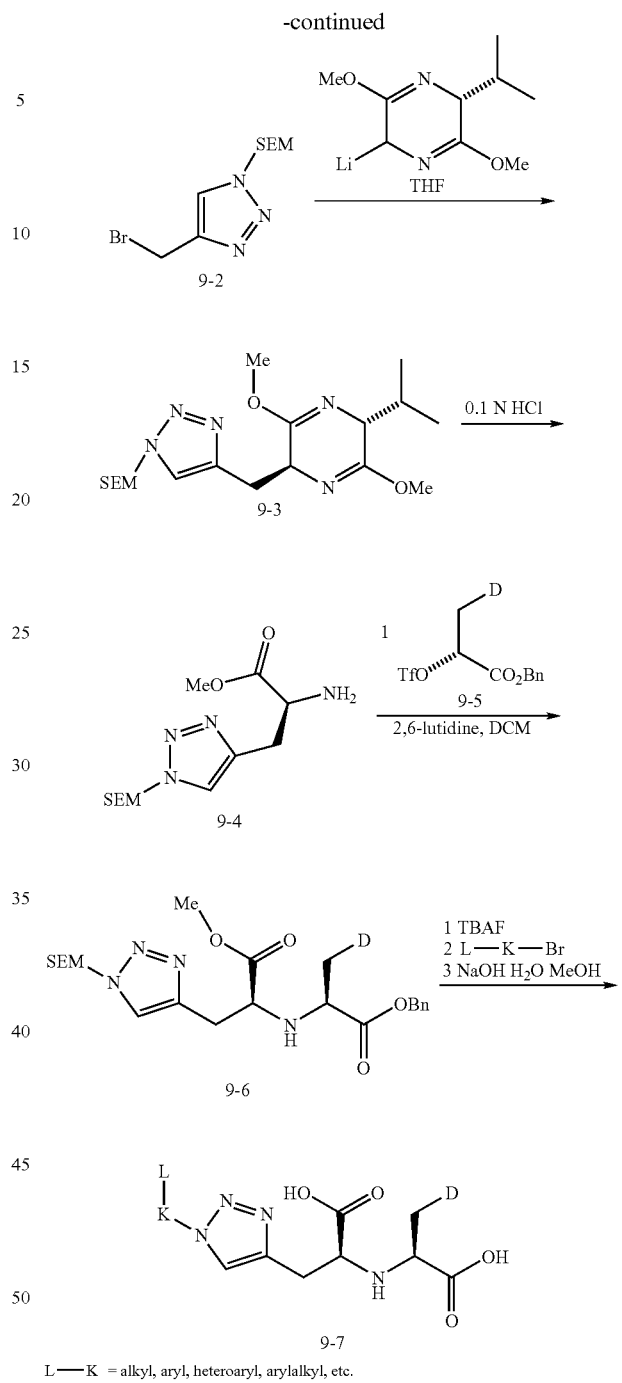

Triazolyl compounds of the invention are synthesized, for example, by the method shown in Scheme 9. Triazole 9-1 is reduced to the alcohol and then converted to the bromide 9-2 (WO 99/43677). Alkylation of Scholkopf's dihydropyrazine with this bromide, hydrolysis of the dihydropyrazine, and reaction with the appropriate triflate as previously described provides diester 9-6. Removal of the SEM protecting group, alkylation with an appropriate alkyl bromide, and ester hydrolysis gives the diacid 9-7.

Scheme 9

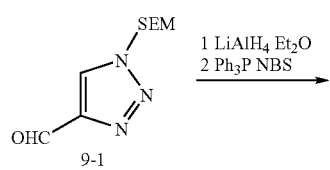

Mercaptoethyl amine compounds of the invention are synthesized using the method shown in Scheme 10. Commercially available N-Boc mercaptoethylamine (10-1) is protected as the 9-fluorenylmethyl ether. (Bodansky, M. et al. *Int. J. Pept. Protein Res.* 1982, 20, 434). The Boc group is removed with HCl in dioxane to provide amine 10-2, which is then treated with the appropriate ketoester in the presence of NaB(OAc)$_3$H to provide the secondary amine 10-3. Further treatment of this amine with a variety of electrophiles (see conditions i–vii Scheme 10, and Sellier, C. et al. *Liebigs Ann. Chem.* 1992, 4, 317) provides compounds 10-4.

Scheme 10

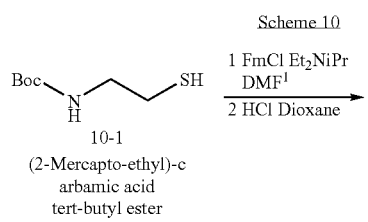

10-1
(2-Mercapto-ethyl)-carbamic acid tert-butyl ester

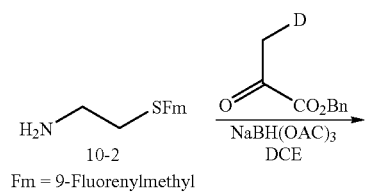

Fm = 9-Fluorenylmethyl

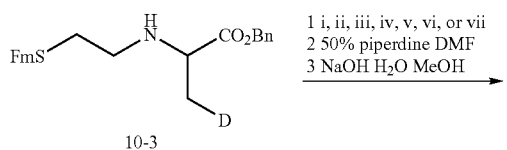

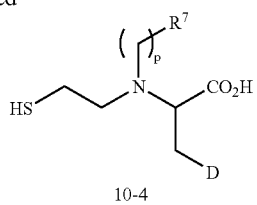

10-4 i RCOCl, iPrNEt$_2$, DCM
ii RBr, RI, RCl, or ROTf, DMF
iii RSO$_2$Cl, iPrNEt$_2$, DCM
iv ROCOCl, iPrNEt$_2$, DCM
v RNCO, iPrNEt$_2$, DCM
vi RNCS, iPrNEt$_2$, DCM
vii RNH$_2$, (PhO)$_2$CNHBoc, MeCN$^2$ In Scheme 11, a method for synthesizing diacids is shown. The free amine (11-1) was reacted with 1.1 eq of the triflate 11-2 (*Tetrahedron*, 1995, 51, 10513) in dichloromethane at −78° C. rising to room temperature overnight. The Boc group is cleaved using 50:50 TFA/DCM and basified using NaHCO$_3$ to give the free amine (11-3). The free amine (11-3) is then reacted with acid chlorides in the presence of TEA to give the amides which are saponified using NaOH/MeOH to afford the desired diacids (11-5).

Scheme 11

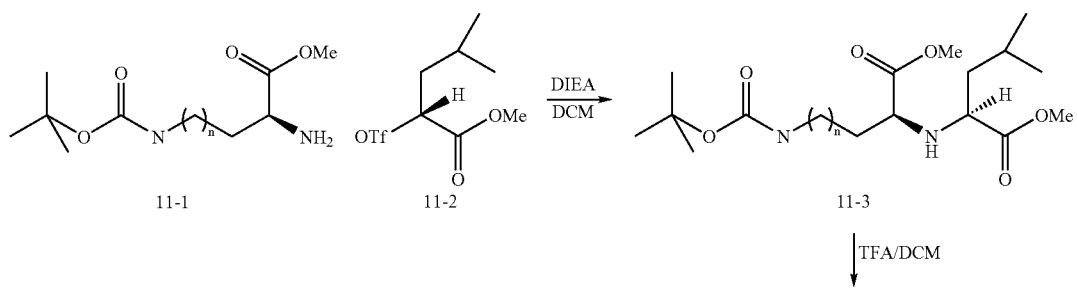

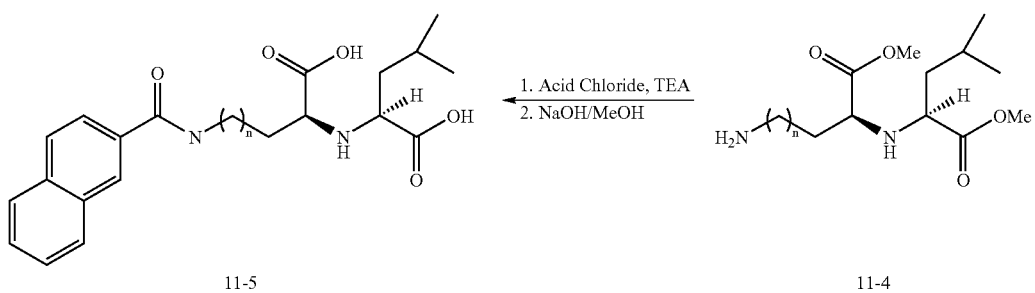

Another method of synthesizing the diacid is shown in Scheme 12. The free amine (12-1) is reacted with the triflate 11-2 to give the diester 12-2. The tert-butyl ester is then cleaved using TFA/DCM to give free acid 12-3, which is coupled with a free amine, such as benzyl amine, using standard HOBT/EDCI conditions to give an amide. Hydrolysis of the diester as in Scheme 11 provides the diacid compounds of the invention (12-4).

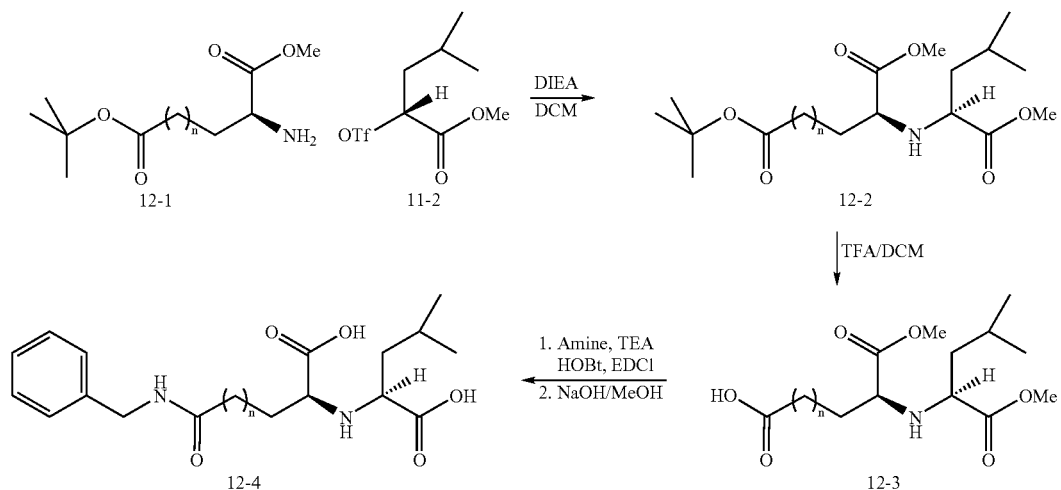

Another method of synthesizing the compounds of the invention is shown in Scheme 13. The free amine (11-4) is reacted with 1 equivalent of an isocyanate, such as benzyl isocyanate, in the presence of 1 eq. TEA to yield ureas, which are hydrolysed to give diacids (13-1).

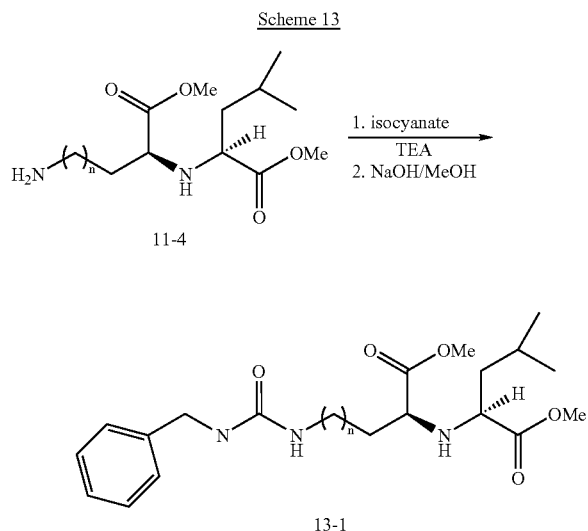

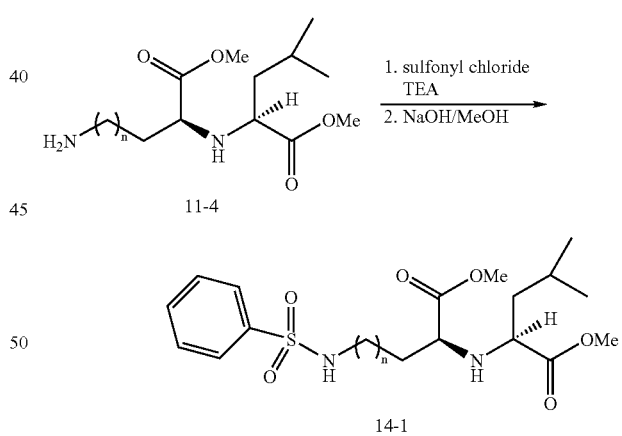

In Scheme 14, an example of a method for the synthesis of sulfonamides is shown. The free amine (11-4) is reacted with 1 eq of a sulfonyl chlorides, such as phenylsulfonyl chloride, to give a sulfonamide, which is hydrolysed to give diacid (14-1).

In Scheme 15, an example for the synthesis of acetylthioalkanoic acid compounds of the invention is shown. The alpha-hydroxy ester (15-1) is first converted to the mesylate (15-2) which is displaced with inversion via the cesium salt of thiolacetic acid (*JOC,* 1986, 51, 3664) to give thiol ester (15-3). Next, the allyl ester is removed using standard palladium conditions to give the 2-(acetylthio)alkanoic acids (15-4). Alternatively, the 2-(acetylthio)alkanoic acid compounds of the invention (e.g., 15-4) can be synthesized via the alpha bromo acids as described in the literature (*JMC,* 1996, 39, 2594).

Scheme 15

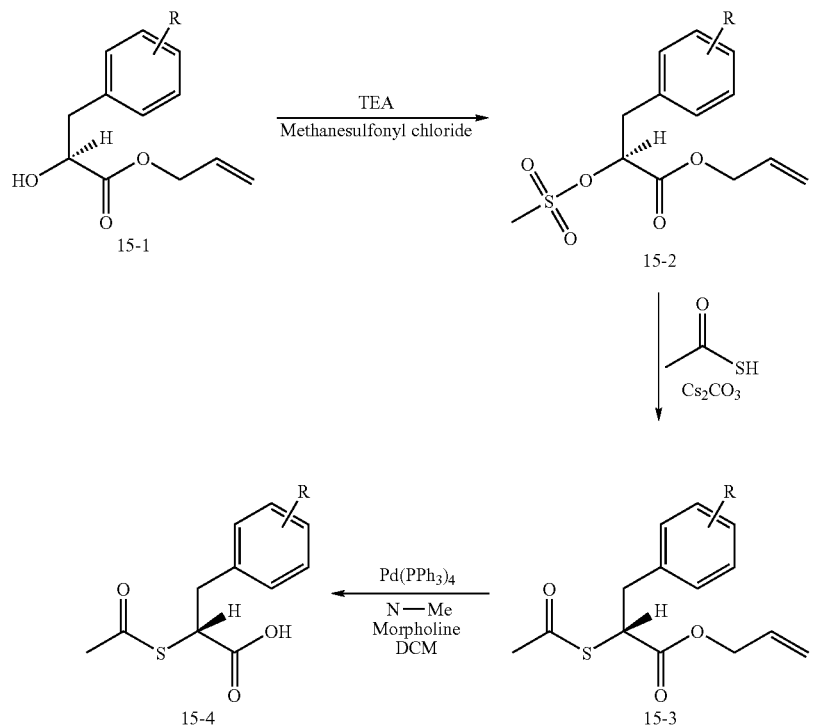

In Scheme 16, a method for synthesizing thiol alkanoic acids is depicted. The thio acids (15-4) are coupled to alpha amino esters (16-1) using PyBOP in dichloromethane to give the amides (16-2). Hydrolysis of both the methyl ester and acetyl group is accomplished via aqueous sodium hydroxide treatment to give the thiol compounds (16-3).

Scheme 16

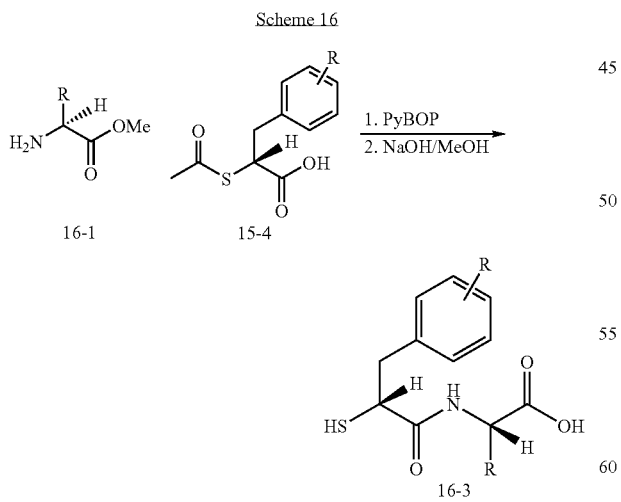

In Scheme 17, a method for synthesizing thiol alkanoic acids compounds of the invention is shown. Alpha-amino esters are coupled to compound 17-1 using PyBOP provides amides, which are hydrolysed to the free acid and thiol using basic sodium hydroxide conditions (Biorg. Med. Chem. Lett., 1996, 6, 2317).

Scheme 17

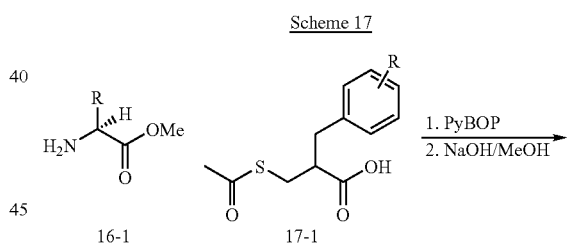

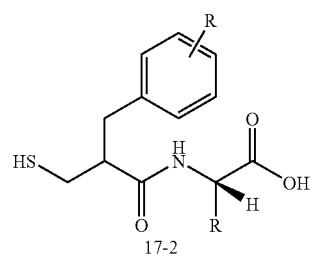

Scheme 18 depicts another method for synthesizing the thiol alkanoic acids compounds of the invention. Compound 18-1 (*JOC*, 1995, 60, 5157) is reacted with triflate (11-2, as described in Scheme 11 above) to give compound 18-2, which upon hydrolysis with sodium hydroxide produces the thiol alkanoic acid compound of the invention, 18-3.

Scheme 18

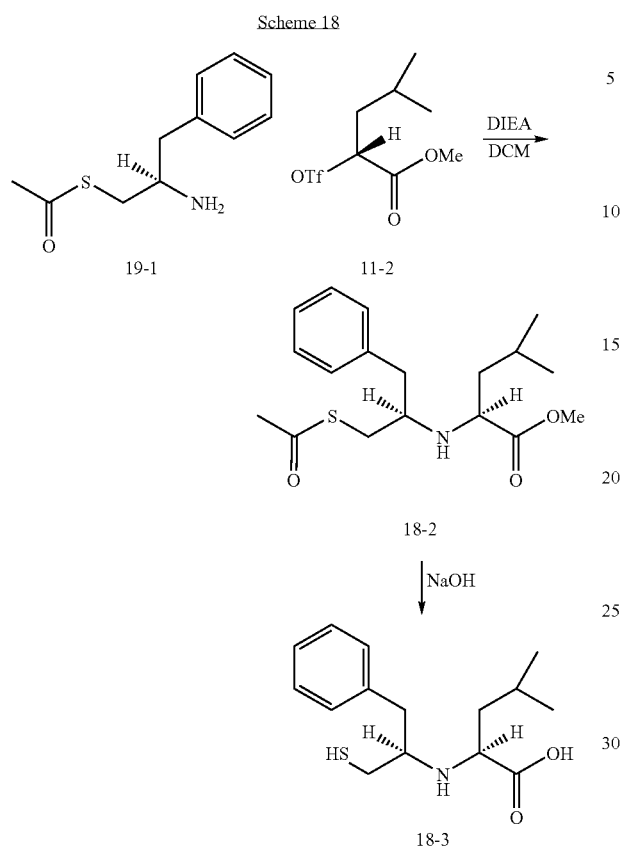

In Scheme 19, a method for synthesizing amidyl diacids are shown. Leucine methyl ester (19-1) is reacted with ethyl iodoacetate (19-2) in dimethylformamide (DMF) to give the diester, 19-3. The diester, 19-3, is then reacted with an acid and PyBrop to give compound, 19-4. Compound 19-4 is hydrolysed with aqueous sodium hydroxide to give the di-acid, 19-5.

Scheme 19

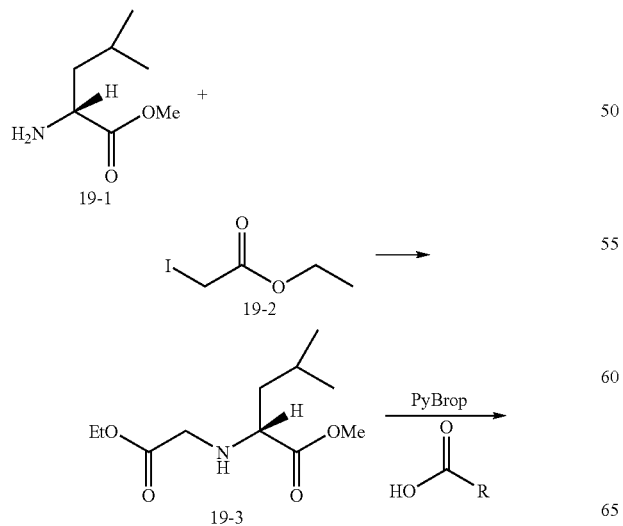

-continued

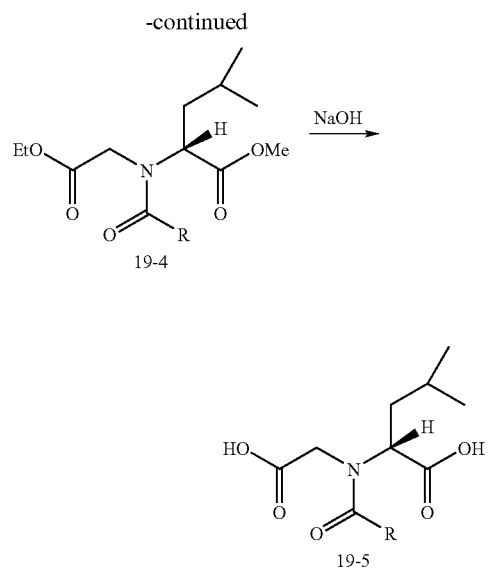

Sulfonamide compounds of the invention can be synthesized using the method depicted in Scheme 20. Leucine methyl ester, 19-1, is reacted with a sulfonyl chloride in the presence of triethyl amine (TEA) in dichloromethane (DCM) to give sulfonamide (20-1). 20-1 is then reacted with ethyl iodoacetate and silver oxide in DMF to yield sulfonamide, 20-2. The sulfonamide, 20-2, is then hydrolysed with aqueous sodium hydroxide to give the di-acid, 20-3.

Scheme 20

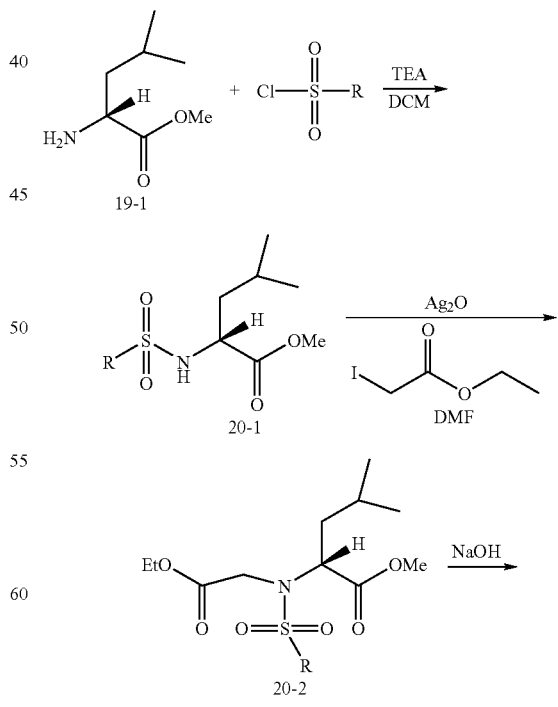

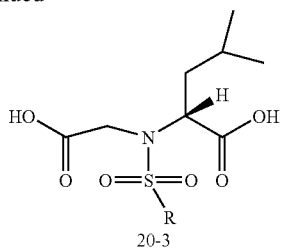

In Scheme 21, a method for synthesizing compounds of the invention with formyl-hydroxy amino groups is shown. Compound 21-1 (*J. Med. Chem.* 1985, 28, 1158.) is condensed with leucine benzyl ester 21-2 to give the diester, 21-3. The diester, 21-3, is hydrogenated over Pd/C to give a formyl-hydroxy amino compound of the invention, 21-4.

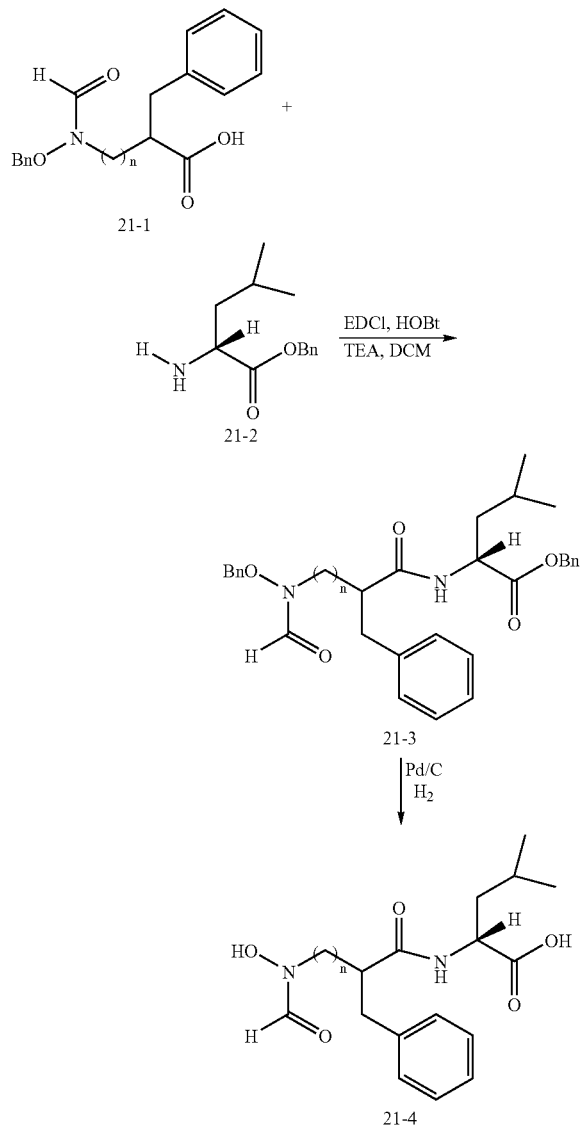

In Scheme 22, a method for preparing urea compounds of the invention is shown. Diester 19-3 is reacted with phosgene in dichloromethane. The urea, 22-1, is formed by addition of an amine. Hydrolysis with aqueous sodium hydroxide produces the di-acid, 22-2.

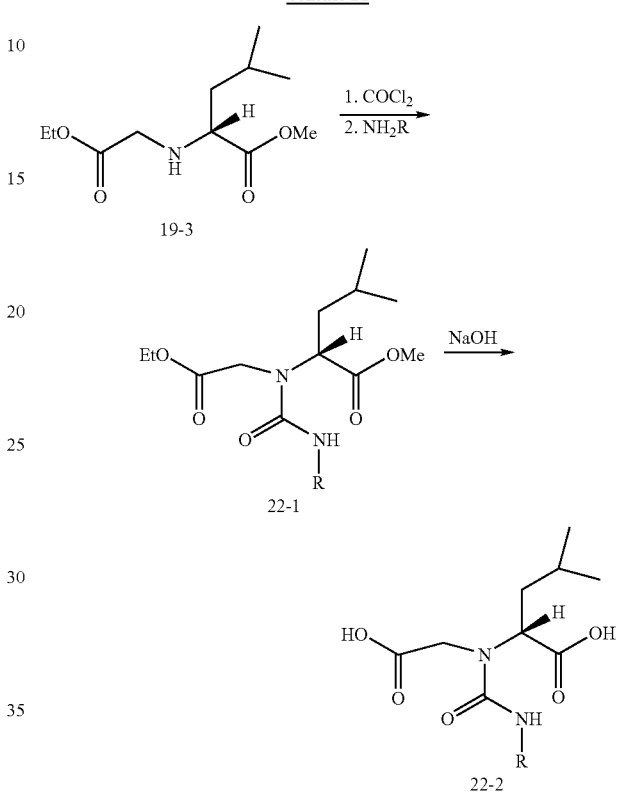

The N-3 alkylated imidazolyl compounds of the invention are synthesized by the route shown in Scheme 23. $Boc_2O$ (2 eq) is added to a solution of histidine methyl ester 23-1 (1 eq,) in MeOH (0.4 M) and triethylamine (2 eq). After 24 hours, the reaction mixture is concentrated and the residue is dissolved in dichloromethane (DCM) and $H_2O$. The layers are separated and the organic layer are washed with brine, dried over $Na_2SO_4$, filtered and concentrated to provide a yellow oil. This oil is triturated from hexane to provide the di-Boc protected imidazole 23-2 as white solid.

A solution of benzyl alcohol 23-3 (1.1 eq) in DIEA (1.1 eq) and dichloromethane (0.6 M) is added slowly to a cooled solution (−78° C.) of triflic anhydride (1.1 eq) in dichloromethane (0.3 M) under argon. After 30 minutes, a solution of the di-Boc protected histidine 23-3 (1 eq) in dichloromethane (0.6 M) was added slowly to the triflate. The reaction mixture warmed to room temperature overnight. After 20 hours, the reaction mixture is concentrated completely and re-dissolved in methanol (0.5 M) and heated for 1 hour. The reaction mixture is then concentrated again and diluted with DCM or EtOAc and washed with $NaHCO_3$ (3×) and brine (1×) then dried over $Na_2SO_4$, filtered and concentrated. The resulting oil is purified by column chromatography (MeOH/DCM) to give the N-3 alkylated imidazole derivative 23-4.

The Boc protection is removed from the imidazole derivative 23-4 using HCl in dioxane. Trituration of the resulting di-HCl salt from ethyl acetate (EtOAc) provides a white solid which is suspended in dichloroethane (0.1 M). The keto-ester 23-5 (2 eq) is added to this suspension and stirred for 1 hour. After 1 hour, NaB(OAc)$_3$H (3 eq) is added slowly. After 24 hours, sodium carbonate (NaHCO$_3$) is added to quench the reaction (the pH of the reaction mixture is raised to 8 with saturated NaHCO$_3$ and stirred for 1 hour). The layers are separated and the aqueous layer is extracted with EtOAc twice. The combined organic layers were dried over sodium sulfate (Na$_2$SO$_4$), filtered and concentrated to give a yellow oil. Column chromatography (EtOAc/hexane; EtOAc; MeOH/EtOAc) provides the diester as a mixture of diastereomers. The diester is then hydrolyzed overnight using 1 N NaOH (10 eq) in ethanol (EtOH) to provide the diacid 23-6 as the disodium salt and a mixture of diastereomers (40:60). The diastereomers were separated and purified using HPLC and crystallization.

derivative 23-4 is hydrolyzed using NaOH to give the acid (Scheme 24). The acid is then alkylated using Cs$_2$CO$_3$ (or another appropriate base) and an alkyl or aryl halide (R—X) such as benzyl bromide to give ester 24-1. After the Boc group is removed using HCl in dioxane, the resulting amine is subjected to reductive amination at pH 7 to give the ester prodrug 24-2. Depending on the solubility of the amino ester, volatile co-solvents such as MeOH, EtOH, MeCN or dioxane may be used to speed the reaction progress. Once the reaction is complete, any volatile co-solvent is evaporated and the mixture is acidified to pH 3–4 using 6N HCl. In most cases, upon acidification the desired mono-ester 24-2 forms a precipitate or a gum. This material is separated, dried and purified either on a flash column or by HPLC.

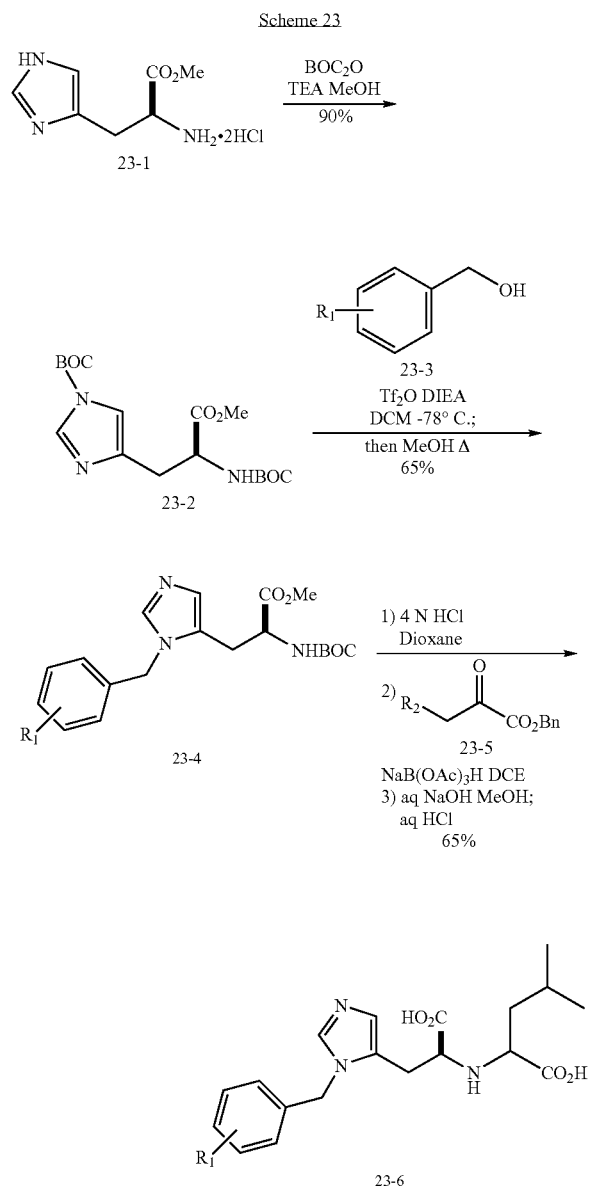

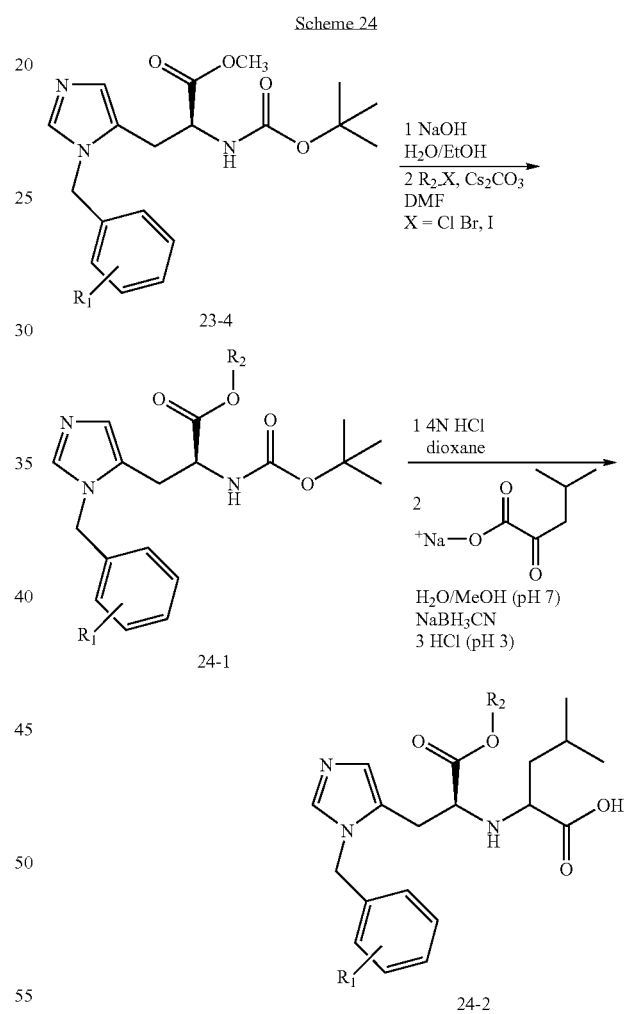

Prodrugs of the invention are synthesized using an intermediate from Scheme 23. The N3-alkylated Boc-His-OMe Scheme 25 depicts the synthesis of mono-esters such as 25-4 from intermediate 25-1. Standard hydrolysis of the ester 25-1 followed by Boc removal provides the amino acid 25-2. Reductive amination, at neutral pH, between amine 25-2 and the keto-ester 25-3 provides the mono-ester 25-4. The keto-ester 25-3 is prepared from the keto-acid via a similar procedure as shown in Scheme 24 (Cs$_2$CO$_3$ and the appropriate alkyl or aryl halide in dimethylformamide (DMF)).

Scheme 25

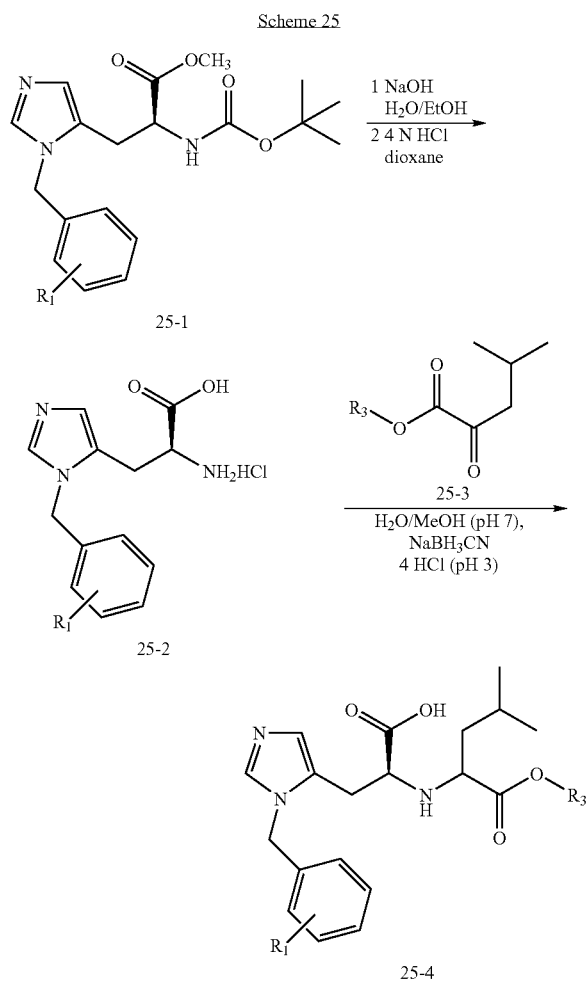

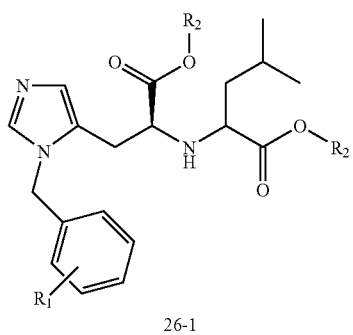

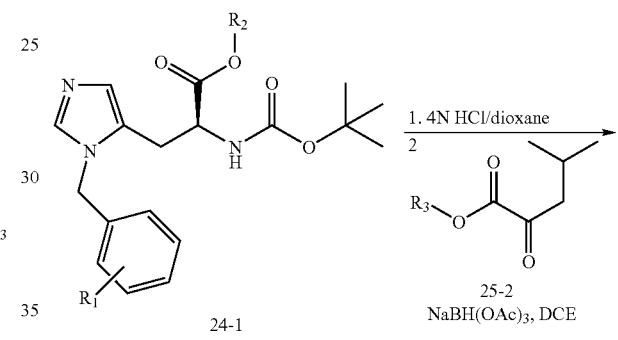

Di-ester prodrugs such as 26-1 are prepared from the diacid 23-5 via esterification as in Scheme 26 (base such as Cs$_2$CO$_3$ and an alkyl or aryl halide in DMF). Alternatively, differentially substituted di-esters are prepared via reductive amination of the appropriately substituted coupling partners (Scheme 27). For example, the amino ethyl ester 25-1 is reacted with the benzyl ester of the keto acid 24-2 to give the di-ester 27-1.

Scheme 26

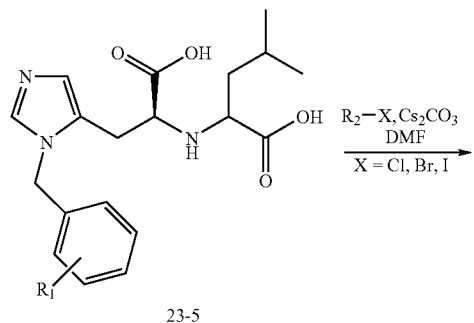

Lactone prodrugs such as 28-1 and 28-2 are synthesized from the diacid 23-5 (Scheme 28). Reaction of 23-5 with an aldehyde (such as formaldehyde) provides a mixture of prodrug lactones 28-1 and 28-2. Alternatively, a mono-ester such as 24-2 or 25-4 is treated with an aldehyde such as formaldehyde to give a fully protected prodrugs 29-1 and 29-2 (Scheme 29). (Ref: King, G. A. et al. *Org. Prep. Proced. Int.* (1997) 29:177–184; Paleo, M. et al. *J. Org. Chem.* (1997) 62:6862–6869).

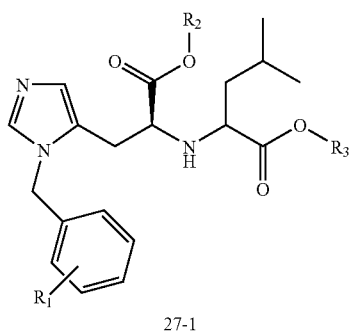

Scheme 28

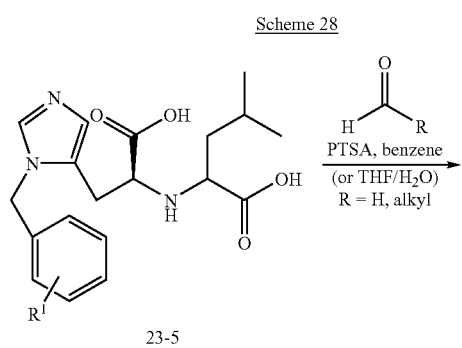

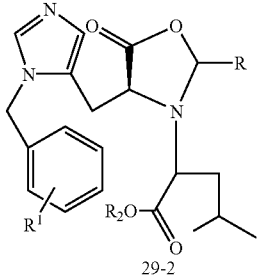

Scheme 29

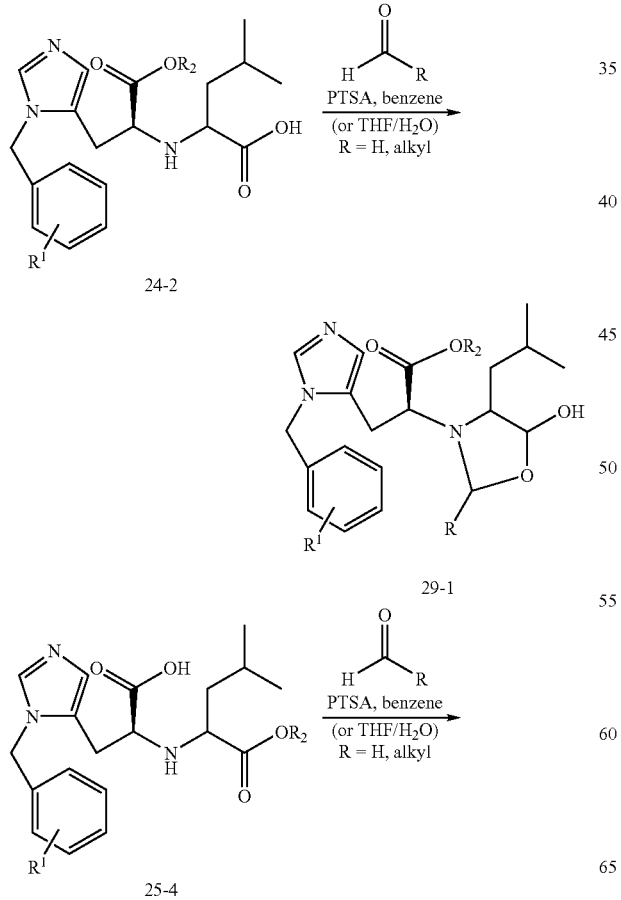

Scheme 30 depicts methods of synthesizing aromatic and phenyl derivatives of the compounds of the invention. Alkylated tyrosine derivatives (30-1 (p), 30-2 (m), 30-3 (o)) are obtained from the tyrosine-leucine derivatives such as 30-6 (Scheme 30) tyrosine methyl ester 30-4 is reacted with the triflate of the leucic ester alcohol 30-5 in DCM and lutidine at −78 C. to provide the amino diester 30-6. Alkylation of 30-6 with an alkyl or benzyl halide (such as 3,5 dichlorobenzyl bromide) in the presence of $CsCO_3$, $Na_2CO_3$, $K_2CO_3$ or NaH in DMF or other appropriate solvents provides the desired product 30-7 (Xu, T. J. et al. *Bioorg. Med. Chem. Lett.* (1999) 9:1933–1936). Hydrolysis of the esters using either NaOH, LiOH or KOH provides the diacid 30-8. Following acidification the diacid 30-8 is purified by HPLC or reverse phase column chromatography. Mitsunobu reactions can also be used to derivatize the phenolic oxygen (Cobb, J. E. et al. *J. Med. Chem.* (1998) 41:5055–5069). Meta and ortho substituted tyrosine derivatives can be prepared similarly via the appropriate starting materials.

Scheme 30

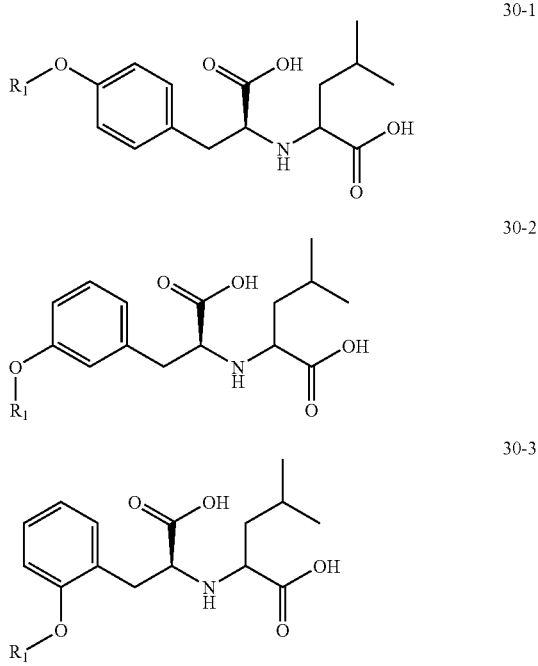

-continued

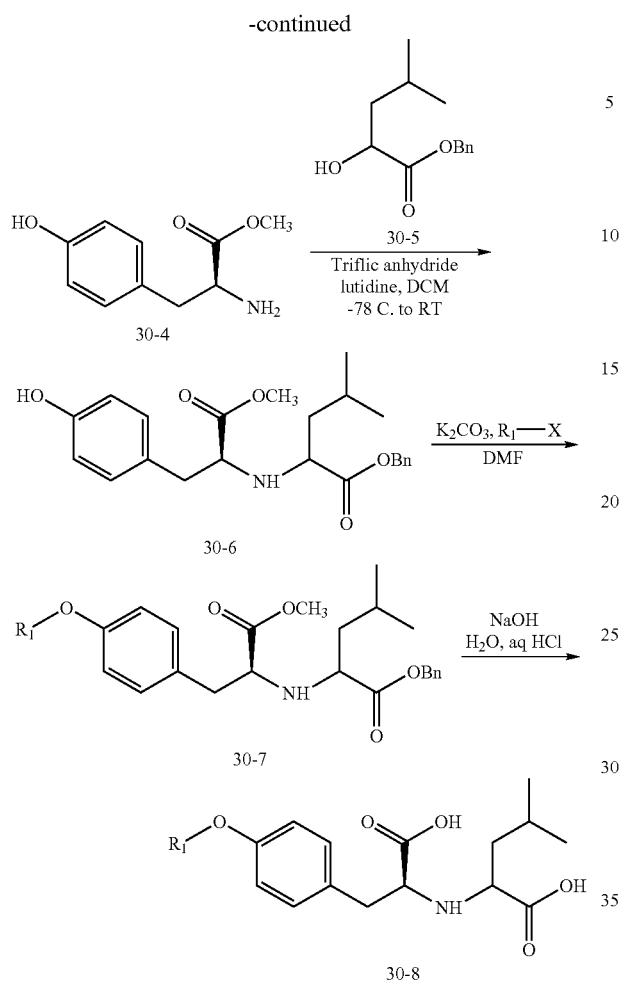

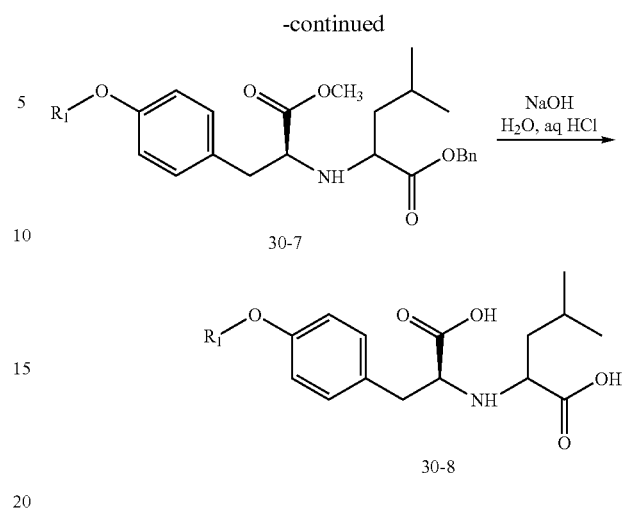

Alternatively, the substituted tyrosine derivative is assembled prior to triflate displacement (Scheme 31). Thus, alkylation of the protected tyrosine derivative 31-1 is performed using similar conditions as above, followed by amine deprotection, thus providing the amino ester 31-2. Triflate displacement, as above, provides the diester 30-7. Hydrolysis and purification provides diacid 30-8.

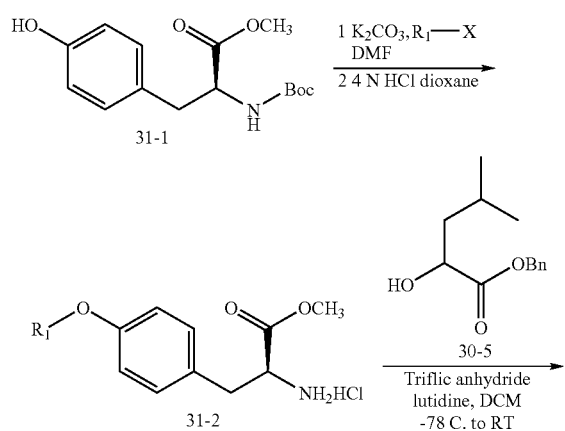

Diphenyl ether derivatives are synthesized according to Scheme 32. (Evans, D. A. et al. *Tetrahedron Lett.* (1998) 39:2937–2940). Boc-Tyr-OMe (32-1) is reacted with a boronic acid derivative (32-2) in the presence of Cu(OAc)$_2$, pyridine and 4 Å sieves to give the diphenyl either which, after Boc deprotection provides the amino ester 32-3. Reaction of the amine 32-3 with the triflate of the leucic ester alcohol (31-5) gives the amino diester 32-4. Hydrolysis of the esters affords the diacid 32-5 which is purified by HPLC. Meta and ortho substituted tyrosine derivatives are prepared similarly via the appropriate starting materials.

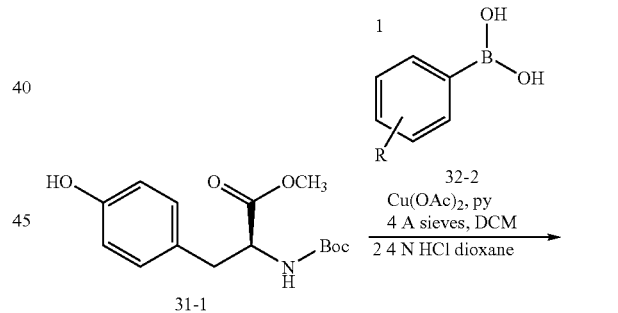

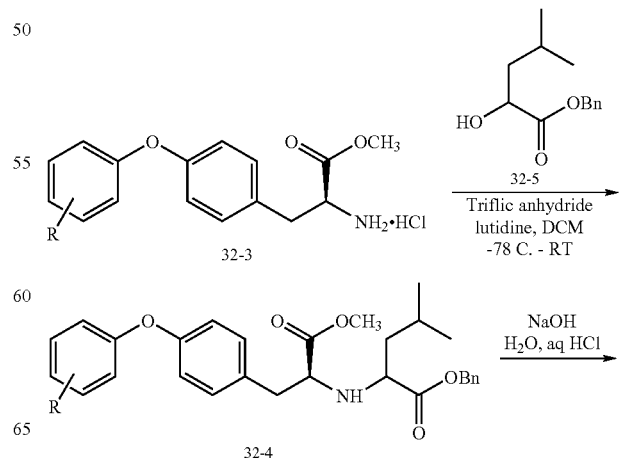

-continued

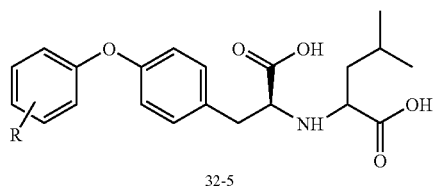

32-5

Substituted phenylalanine derivatives (33-1) are synthesized from the appropriate aryl halide starting material. Esterification of Boc-Phe(4-Br)—OH (33-4) (or Boc-Phe(4-I)—OH) using TMSCHN$_2$ followed by palladium catalyzed cross coupling provides the 4-substituted amino acid derivative 33-5 (Negishi, E.-I. and King, A. O. J. Org. Chem. (1977) 42:1821; Klement, I. et al Tetrahedron Lett. (1994) 35:1177). Boc deprotection followed by reaction with the triflate of the leucic ester alcohol, as before, provides the diester 33-6. Hydrolysis of the esters gives the diacid 33-1. 3-Substituted (33-2) and 2-substituted (33-3) phenylalanine derivatives are prepared in a similar manner. Other metal mediated cross coupling reactions can also be used. For example, biaryl derivatives such as 33-7 can be synthesized via Suzuki or Stille couplings (Firooznia, F. et al. Tetrahedron Lett. (1999) 40:213–216; Firooznia, F. et al. Tetrahedron Lett. (1998) 39: 3985–3988; Morera, E. and Ortar, G. Synlett (1997) 12:1403–1405)

Scheme 33

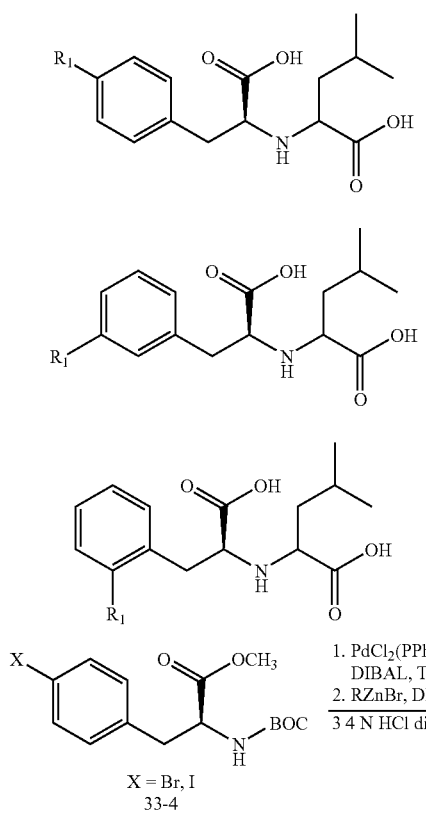

-continued

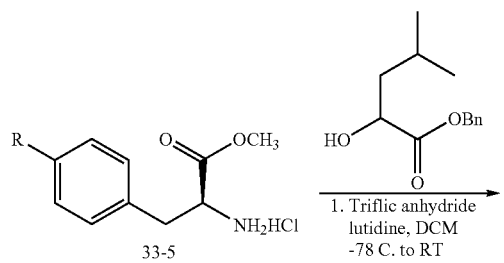

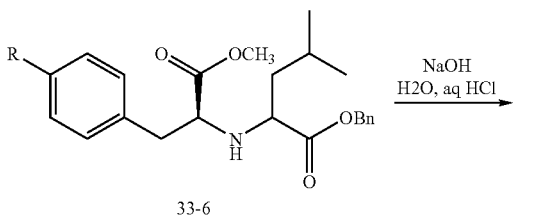

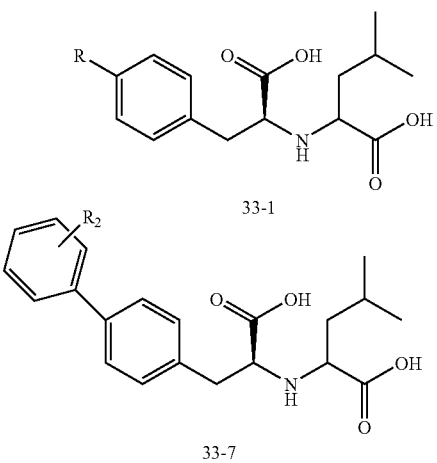

1-Napthylalanine (34-1) and 2-napthylalanine (34-2) derivatives are available via the routes shown in Schemes 30–33. Similarly, substituted naphthalene derivatives (34-3, 34-4) are synthesized from the halogenated (or hydroxyl) naphthalene amino acid derivatives (34-5, 34-6). Amino acid synthesis is achieved via a number of methods (Ref: Hagiwara, D. et al. J. Med. Chem. (1994) 37:2090–2099; Myers, A. G. and Gleason, J. L. Org. Syn (1999) 76:57–76; Myers, A. G., and Yoon, T. Tetrahedron Lett. (1995) 36:9429–9432; Burk, M. J. et al. J. Am. Chem. Soc. (1994)116:10847–10848; Mulzer, J. and Funk G. Synthesis (1995) 1:101–112).

Scheme 34

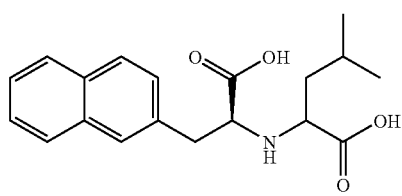

34-1

-continued

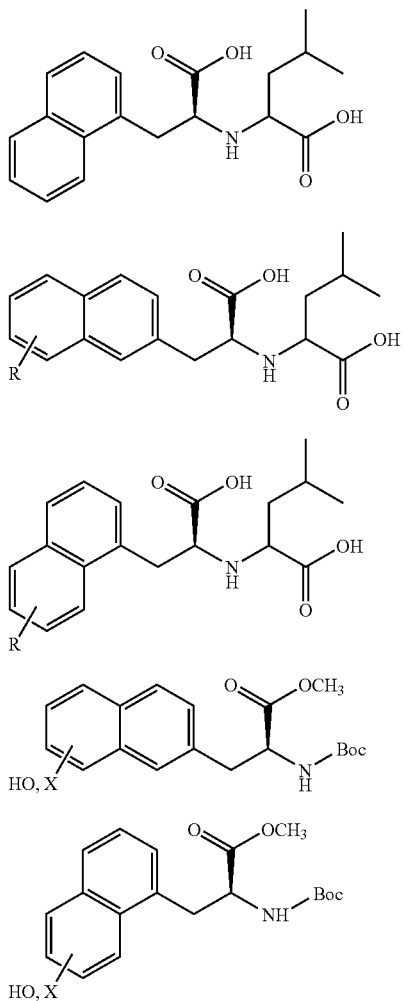

The invention also pertains to a method of treating an ACE-2 associated state, for example, which is a method for treating a body weight disorder or a state associated with body mass. The method involves administering to a subject a therapeutically effective amount of an ACE-2 modulating, e.g., inhibiting, compound, such that the ACE-2 associated state is treated (e.g., at least one symptom is alleviated).

Examples of states associated with body mass include lipodystrophy, cachexia (e.g., cachexia associated with disorders such as cancer, autoimmune disorders (such as AIDS)), old age, space travel. The ACE-2 inhibitors can be used to increase muscle mass, and/or decrease body fat. The ACE-2 inhibitors can be administered to healthy individuals or to individuals who wish to alter their body composition, e.g., subjects who wish to increase their body mass. ACE-2 inhibitors can also be used to treat disorders such as obesity and diabetes.

The language "in combination with" another therapeutic agent includes co-administration of the ACE-2 modulating compound, (e.g., inhibitor) and another therapeutic agent, administration of the ACE-2 modulating compound first, followed by the other therapeutic agent and administration of the other therapeutic agent first, followed by the ACE-2 modulating, e.g., inhibiting, compound. The other therapeutic agent may be any agent which is known in the art to treat, prevent, or reduce the symptoms of a ACE-2 associated state, e.g., a body weight disorder. Furthermore, the other therapeutic agent may be any agent of benefit to the subject when administered in combination with the administration of an ACE-2 modulating, e.g., inhibiting, compound. The other therapeutic agent may also be an ACE-2 modulating compound. Furthermore, ACE-2 compounds can also be administered in combination with other known therapies for ACE-2 associated states. Other methods of treating ACE-2 associated states, e.g., body weight disorders, are known to those skilled in the art. In one embodiment, the other therapeutic agent may be an ACE inhibitor. In certain embodiments, the ACE-2 inhibitor may be a dual inhibitor of ACE and ACE-2.

The term "dual inhibitors" include compounds and combinations of compounds which inhibit both ACE and ACE-2 gene expression or protein activity. Dual inhibitors can be compounds which bind to both ACE and ACE-2 equally well, compounds which bind to ACE preferentially over ACE-2, and compounds which bind to ACE-2 preferentially over ACE. For example, in one embodiment, a dual inhibitor has a $K_i$ for ACE of 5 µM or less (e.g. 4 µM or less, 3 µM or less, 2 µM or less, or, preferably, 1 µM or less), and a $K_i$ of 5 µM or less for ACE-2. In one embodiment, the dual inhibitor compounds of the invention are compounds in Table 2 which are identified by *** in the Human ACE-2 Activity column and * in the ACE Activity column.

Furthermore, the selection of a dual inhibitor may be subject specific, based on the needs of a particular subject. For example, for a particular condition in a particular subject, it may be advantageous to treat the subject's condition by administering to the subject a dual inhibitor which inhibits ACE and ACE-2 equally. For another subject, it may be advantageous to administer to the subject a dual inhibitor which inhibits ACE at a higher rate than ACE-2. Alternatively, for yet another subject it may be advantageous to administer to the subject a dual inhibitor which inhibits ACE-2 at a higher rate than ACE.

In one embodiment, the selection of a particular dual inhibitor for a particular subject is based on the response of the subject to an ACE-2 inhibitor, ACE inhibitor, or dual inhibitor. For example, based on the subject's response to an ACE-2 inhibitor, a person skilled in the art may determine that a dual inhibitor and/or ACE inhibitor may be effective to treat a subject's condition. Similarly, based on a subject's response to an ACE inhibitor, a person skilled in the art may determine that a dual inhibitor or a ACE-2 inhibitor may be more effective to treat a subject's condition. Furthermore, based on a subject's response to a dual inhibitor, a person of skill in the art may determine that a particular subject may benefit from increased ACE or ACE-2 inhibition to treat the subject's condition.

In a further embodiment, the response of a subject to a particular dual inhibitor, ACE inhibitor, or ACE-2 inhibitor can be predicted, e.g., by pharmacogenomics. Pharmacogenomics predicts a subject's response to a particular drug based on the subject's genotype. For example, based on a subject's genotype, an effective dual inhibitor to treat the subject's condition will be administered. The ratio of inhibition of ACE and ACE-2 can be tailored to each subject to increase the efficacy of each subject's treatment.

The invention also pertains to a method for increasing body muscle, e.g., increasing muscle mass, in a subject. The method includes administering to the subject an effective amount of a compound of the invention, e.g., a compound of any one of formulae I–VIII, e.g., an ACE-2 modulating, e.g., ACE-2 inhibiting, compound, such that the body muscle of a subject is increased. In one embodiment, the subject is suffering from cachexia, e.g., cachexia resulting from a disease, e.g., cancer or an autoimmune disease, e.g., AIDS. In one embodiment, the subject is not suffering from cachexia and desires greater muscle mass, e.g., a person who desires greater muscle mass, e.g., an athlete or body builder. In one embodiment, the subject is suffering from decreased muscle mass. The decreased body muscle mass may be due to old age, inactivity, space travel, obesity, etc. In an embodiment, the muscle mass of said subject is increased about 1% or greater, about 5% or greater, about 10% or greater, about 15% or greater, about 20% or greater, about 25% or greater, about 30% or greater, about 35% or greater, about 40% or greater, about 45% or greater, about 50% or greater, about 60% or greater, about 70% or greater, about 80% or greater, about 90% or greater, about 100% or greater, about 120% or greater, about 140% or greater, about 160% or greater, about 180% or greater, or about 200% or greater, as compared to the muscle mass of the subject prior to administration of the compound of the invention.

The invention also pertains to a method for decreasing body fat in a subject. The method includes administering to the subject an effective amount of a compound of the invention, e.g., a compound of any one of formulae I–VIII, e.g., an ACE-2 modulating, e.g., ACE-2 inhibiting, compound, so that the body fat in the subject is decreased. In one embodiment, the subject is of normal or above average weight and desires decreased body fat. In another embodiment, the subject is obese. In another embodiment, the subject is suffering from a disorder of lipid metabolism, e.g., a lipodystrophy or a lipidosis. In an embodiment, the percent body fat of the subject is decreased about 1% or greater, about 5% or greater, about 10% or greater, about 15% or greater, about 20% or greater, about 25% or greater, about 30% or greater, about 35% or greater, about 40% or greater, about 45% or greater, about 50% or greater, about 55% or greater, about 60% or greater, about 65% or greater, about 70% or greater, about 85% or greater, about 90% or greater, about 95% or greater, about 100% or greater, about 125% or greater, about 150% or greater, about 175% or greater, about 200% or greater, about 250% or greater, about 300% or greater, etc. as compared to the body fat percentage of the subject prior to administration of the ACE-2 modulating compound of the invention.

In another embodiment, the invention pertains, at least in part, to a method for decreasing the appetite of a subject. The method includes administering to the subject an effective amount of an ACE-2 modulating compound of the invention such that the appetite of the subject is decreased, e.g., suppressed.

The invention also relates to a pharmaceutical composition containing a pharmaceutically acceptable carrier and an effective amount of an ACE-2 modulating, e.g., inhibiting, compound to treat an ACE-2 associated state. The invention pertains to pharmaceutical compositions comprising a compound of any one of formulae I–VIII, as described above.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the subject. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In an embodiment, the pharmaceutically acceptable carrier is selected such that the ACE-2 modulating compound of the invention has low systemic absorbtion and relatively high exposure to the gastrointestinal tract (e.g., lower gastrointestinal tract, e.g., bowel, large and small and intestines).

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the invention with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the invention, which may be used in a suitable hydrated form, and/or the pharmaceutical compositions of the invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

While it is possible for a compound of the invention to be administered alone, it is preferable to administer the compound as a pharmaceutical composition.

The regimen of administration can affect what constitutes an effective amount. The ACE-2 modulating, e.g., inhibiting, can be administered to the subject either prior to or after the onset of an ACE-2 associated state. Further, several divided dosages, as well as staggered dosages, can be administered daily or sequentially, or the dose can be continuously infused, or can be a bolus injection. Further, the dosages of the ACE-2 modulating, e.g., inhibiting, compound(s) can be proportionally increased or decreased as indicated by the exigencies of the therapeutic or prophylactic situation.

In particular, cell based and non-cell based assays are described that can be used to identify compounds that interact with the ACE-2 nucleic acid or protein, e.g., modulate the expression of the ACE-2 gene and/or activity of the ACE-2 polypeptide. The cell based assays can be used to identify compounds or compositions that affect the biological activity of the ACE-2 polypeptide, whether they bind to ACE-2, or act on ACE-2 target peptides, e.g., ligands or substrates, such as angiotensin I, bradykinin, neurotensin, and kinetensin. Such cell based assays of the invention utilize cells, cell lines, or engineered cells or cell lines that express the ACE-2 polypeptide. The cells can be further engineered to incorporate a reporter molecule linked to an ACE-2 ligand or substrate to aid in the identification of compounds that modulate ACE-2 enzymatic activity.

The invention also encompasses the use of cell based assays and cell lysate assays (e.g., in vitro transcription or translation assays) to screen for compounds or compositions that modulate ACE-2 gene expression and therefor can be used to identify ACE-2 modulating compounds useful for the methods described herein. To this end, constructs containing a reporter sequence linked to a regulatory element of the ACE-2 gene can be used in engineered cells, or in cell lysate extracts, to screen for compounds that modulate the expression of the reporter gene product at the level of transcription. For example, such assays can be used to identify compounds that modulate the expression or activity of transcription factors involved in ACE-2 gene expression, or to test the activity of triple helix polynucleotides. Alternatively, engineered cells or translation extracts can be used to screen for compounds (including antisense and ribozyme constructs) that modulate the translation of ACE-2 mRNA transcripts, and therefore, affect expression of the ACE-2 gene.

The invention also encompasses ACE-2 proteins, polypeptides (including soluble ACE-2 polypeptides or peptides), and biologically active fragments thereof, and ACE-2 fusion proteins for use in non-cellular screening assays, for use in generating antibodies, and for the diagnosis and/or treatment of body weight disorders.

ACE-2 protein products can also be used to treat body weight disorders, including, for example, obesity, anorexia or cachexia. Such ACE-2 protein products include, but are not limited to, soluble derivatives such as peptides or polypeptides corresponding to truncated ACE-2 polypeptides and ACE-2 fusion protein products (especially ACE-2-Ig fusion proteins, e.g., fusions of the ACE-2 polypeptide or a domain of the ACE-2 polypeptide, to an IgFc domain). Alternatively, antibodies to ACE-2 or anti-idiotypic antibodies that mimic or interfere with ACE-2 activity (including antigen-binding fragments, e.g., Fab, F(ab)'$_2$, or single chain antibodies, e.g., scFv), antagonists or agonists (including compounds that modulate ACE-2 target peptides, e.g., ACE-2 ligands or substrates, can be used to treat body weight disorders such as obesity, anorexia or cachexia.

For example, the administration of an effective amount of soluble ACE-2 polypeptide, or an ACE-2 fusion protein (e.g., ACE-2-IgFc) or an anti-idiotypic antibody (or an antigen-binding fragment thereof, e.g., an Fab, F(ab)'$_2$, or a single chain antibody, e.g., scFv) that mimics the ACE-2 activity would interact with and thereby "mop up" or "neutralize" endogenous ACE-2 ligand, and prevent or reduce ACE-2 activity, thereby leading to a weight loss or a reduction of a high BMI. In yet another approach, nucleotide constructs encoding such ACE-2 products can be used to genetically engineer host cells to express such ACE-2 products in vivo; these genetically engineered cells can function as "bioreactors" in the body delivering a continuous supply of an ACE-2 polypeptide, an ACE-2 polypeptide fragment, or an ACE-2 fusion protein that will "mop up" or neutralize an ACE-2 ligand.

"Gene therapy" approaches for the modulation of ACE-2 expression and/or activity in the treatment of body weight disorders are within the scope of the invention. For example, nucleotide constructs encoding functional ACE-2 polypeptides or polypeptide fragments, mutant ACE-2 polypeptides or polypeptide fragments, as well as antisense and ribozyme molecules can be used to modulate ACE-2 gene expression.

The invention also encompasses pharmaceutical formulations, methods for the prophylactic or therapeutic treatment of body weight disorders, and kits for the diagnosis or prognosis of body weight disorders.

The Role of ACE-2 in the Regulation of Body Weight

The specific role of the ACE-2 protein in vivo was investigated by engineering ACE-2 "knock out" mice in which most of the endogenous ACE-2 gene coding sequence was deleted, thereby creating mice which are unable to produce biologically active ACE-2 protein.

In order to produce the ACE-2 knock out mice, human ACE-2 gene sequences were utilized to isolate and clone the murine ACE-2 gene. A murine ACE-2 targeting construct was then generated which was designed to delete the majority of the murine ACE-2 coding sequence upon homologous recombination with the endogenous murine ACE-2 gene. Embryonic stem (ES) cells containing the disrupted ACE-2 gene were produced, isolated and microinjected into murine blastocysts to yield mice chimeric for cells containing a disrupted ACE-2 gene. Offspring of the chimeric mice resulting from germline transmission of the ES genome were obtained and animals heterozygous for the disrupted ACE-2 were identified.

In order to assess the role of ACE-2 in vivo, the animals heterozygous for the ACE-2 disrupted gene were bred together to produce mice homozygous for the ACE-2 mutation. Inactivation of the ACE-2 by gene targeting resulted in male mice that have a higher ratio of lean to fat tissue, a lower percentage of overall body fat tissue, and a lower overall body weight than wild type counterparts.

These knock-out experiments are described in greater detail in Example 13 below.

Screening Assays for Drugs Useful in Regulation of Body Weight

At least three different assay systems, described in the subsections below, can be designed and used to identify compounds or compositions that modulate ACE-2 activity or ACE-2 gene expression, and therefore, modulate body weight and/or the percentage of body fat.

The systems described herein are useful when formulated into kits. To this end, ACE-2 or cells expressing ACE-2 can be packaged in a variety of containers, e.g., vials, tubes, microtitre well plates, bottles, and the like. Other reagents can be included in separate containers and provided with the kit; e.g., positive controls samples, negative control samples, ACE-2 target peptides (including but not limited to), buffers, cell culture media, etc., and instructions for use.

A. Cell-Based Assays

In accordance with the invention, a cell-based assay system can be used to screen for compounds that modulate the activity of an ACE-2 protein or expression of an ACE-2 gene and thereby, modulate body weight and/or the percentage of body fat. To this end, cells that endogenously express ACE-2 can be used to screen for compounds. Alternatively, cell lines, such as 293 cells, COS cells, CHO cells, fibroblasts, and the like, genetically engineered to express ACE-2 can be used for screening purposes. Preferably, host cells genetically engineered to express a functional enzyme that catalyzes the cleavage of ACE-2 target peptides, e.g., ligands or substrates (e.g., angiotensin I, des-Arg bradykinin, neurotensin, and kinetensin), can be used in the assay; e.g., as measured by production of the cleavage product. For example, the cleavage product of angiotensin I is angiotensin 1–9.

To be useful in screening assays, the host cells expressing ACE-2, or a biologically active fragment thereof, should show significant catalysis of an ACE-2 substrate (e.g., angiotensin I, des-Arg bradykinin, neurotensin, or kinetensin). Host cells should preferably possess a number of characteristics, depending on the readout, to maximize the catalytic activity of ACE-2, for example, for detecting the generation of angiotensin 1–9 from the cleavage of angiotensin I.

In utilizing such cell systems, the cells expressing ACE-2 are exposed to a test compound or to vehicle controls (e.g., placebos). For example, in screening for compounds that can act as antagonists (e.g. inhibitors) of ACE-2, it is necessary to include ACE-2 substrates (e.g., angiotensin I, des-Arg bradykinin, neurotensin, or kinetensin) as a control in order to test for inhibition of ACE-2 catalytic activity by the test compound. After exposure, the cells can be assayed for the production of ACE-2 cleavage products and/or the reduction in the amount of ACE-2 substrate, by, for example, mass spectrometry.

In a specific embodiment of the invention, a construct encoding at least the catalytic domain of ACE-2 is linked to any of a variety of different reporter genes and introduced into an appropriate host cell. Examples of such reporter genes include, but are not limited to, chloramphenicol acetyltransferase (CAT), luciferase, GUS, growth hormone, and placental alkaline phosphatase (SEAP). Following exposure of the cell to the test compound, the level of reporter gene expression is quantitated to determine the ability of the test compound to modulate ACE-2 catalytic activity. Alkaline phosphatase assays are particularly useful in the practice of the invention as the enzyme is secreted from the cell. Therefore, tissue culture supernatant can be assayed for secreted alkaline phosphatase. In addition, alkaline phosphatase activity is measurable by calorimetric, bioluminescent or chemilumenscent assays such as those described in Bronstein, I. et al. (1994, Biotechniques 17: 172–177). Such assays provide a simple, sensitive, and easily automatable detection system for pharmaceutical screening.

To discriminate between ACE (e.g., human testicular ACE (GenBank Accession No. P22966) or human endothelial ACE (GenBank Accession No. P12822)) and ACE-2 and to identify compounds that selectively agonize or antagonize ACE-2, the assays described above can be conducted using a panel of host cells, each genetically engineered to express ACE or ACE-2. Such a panel is preferred for drug discovery purposes. To this end, host cells can be genetically engineered to express any of the amino acid sequences for known angiotensin converting enzymes. For example, the cloning and characterization of testicular and endothelial ACE have been described in Ehlers, et al. (1989) Proc. Natl. Acad. Sci. USA 86:7741–7745 and Soubrier, et al. (1988) Proc. Natl. Acad. Sci. USA 85:9386–9390), respectively, each of which is incorporated herein by reference in its entirety. Thus, each of the foregoing sequences can be utilized to engineer a cell or cell line that expresses one of the ACEs for use in screening assays described herein. To identify compounds that specifically or selectively regulate ACE-2 activity, the activation or inhibition of ACE-2 catalytic activity is compared to the effect of the test compound on the other ACEs.

Non-Cell Based Assays

In addition to cell based assays, non-cell based assay systems are useful in the identification of compounds that interact with, e.g., bind to, ACE-2. Such compounds may act as inhibitors (e.g., antagonists), inverse agonists, or activators (e.g., agonists) of ACE-2 activity and may be used in the treatment of body weight disorders.

Isolated membranes can be used to identify compounds that interact with ACE-2. For example, in a typical experiment using isolated membranes, CHO cells are genetically engineered to express ACE-2. Membranes are harvested by standard techniques and used in an in vitro enzymatic assay. An ACE-2 substrate (e.g., angiotensin I, a decapeptide; des-Arg bradykinin, an octapeptide; neurotensin, a 13-amino acid peptide; or kinetensin, a nonapeptide) is incubated with the membranes and the accumulation of cleavage products (e.g., angiotensin 1-9, des-Arg bradykinin septapeptide, neurotensin 12-amino acid peptide, or kinetensin octapeptide) and/or the reduction of substrate is measured, e.g., by mass spectrometry.

To identify other ACE-2 substrates, membranes can be incubated with a known substrate in the presence or absence of candidate substrate, and the reaction products analyzed by mass spectrometry. In samples containing compounds that compete with the known substrate the amount of the reaction product of the known substrate will be lower compared to the samples containing only the known substrate.

Alternatively, recombinantly expressed ACE-2 can be obtained as a secreted product (e.g., from the culture media of transfected cells expressing ACE-2) and utilized in non-cell based assays to identify candidate substrates of ACE-2. The recombinantly expressed ACE-2 polypeptides or fusion proteins containing at least the catalytic domain of ACE-2 can be used in the methods of the non-cell based screening assays described above.

In one aspect of the invention the screens may be designed to identify compounds that antagonize the ACE-2 hydrolysis of known ACE-2 substrates, such as angiotensin I, des-Arg bradykinin, neurotensin, and kinetensin.

Assays for Compounds or Compositions that Modulate Expression of ACE-2

In vitro cell based assays can be designed to screen for compounds that regulate ACE-2 expression at either the transcriptional or translational level.

In one embodiment, DNA encoding a reporter molecule can be linked to a regulatory element of the ACE-2 gene and used in appropriate intact cells, cell extracts, or lysates to identify compounds that modulate ACE-2 gene expression. Appropriate cells or cell extracts are prepared from any cell type that normally expresses the ACE-2 gene, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

To identify compounds that regulate ACE-2 translation, cells or cell lysates containing ACE-2 transcripts may be tested for modulation of ACE-2 mRNA translation. To assay for inhibitors of ACE-2 translation, test compounds are assayed for their ability to modulate the translation of ACE-2 mRNA in in vitro translation assays. Compounds that reduce the level of ACE-2 expression, either at the transcriptional or translational level, are useful in the treatment of body weight disorders associated with a BMI above normal, such as obesity. In contrast, those compounds that increase the expression of ACE-2 may be useful for treatment of disorders with a BMI below normal, such as anorexia or cachexia.

Compounds that can be Screened in Accordance with the Invention

The assays described above can identify compounds which affect ACE-2 activity, e.g., ACE-2 modulating compounds. For example, compounds that affect ACE-2 activity include, but are not limited to, compounds that (i) bind to ACE-2; (ii) inhibit or decrease binding of an ACE-2 substrate to ACE-2; (iii) stimulate, activate or enhance ACE-2 activity (agonists) or decrease or inhibit ACE-2 activity (inverse agonists and antagonists); and (iv) neutralize ACE-2 activity by binding to an ACE-2 substrate. Compounds that affect ACE-2 gene activity (e.g., by affecting ACE-2 gene expression), including molecules (e.g., proteins, peptides, and small molecules) that affect transcription or interfere with splicing events so that expression of the full length or a truncated form of ACE-2 is modulated) can also be identified in the screens of the invention. It should be noted that the assays described herein can also identify compounds that are indirectly modulated by ACE-2 activity. The identification and use of such compounds which affect other events that result from ACE-2 catalytic activity to thereby modulate effects of ACE-2 on the development of body weight disorders are within the scope of the invention. Such compounds can be used as part of a therapeutic method for the treatment of body weight disorders.

The compounds which can be screened in accordance with the invention include, but are not limited to peptides and antibodies, and fragments thereof, and other compounds or agents (e.g., peptidomimetics) that bind to the catalytic domain of ACE-2 and either mimic the activity triggered by an ACE-2 substrate (e.g., agonists, activators) or inhibit the activity triggered by the substrate (e.g., antagonists, inhibitors or inverse agonists); as well as peptides and antibodies, and fragments thereof, and other organic compounds that bind to and "neutralize" the ACE-2 substrate; i.e., prevents the substrate from being cleaved by ACE-2.

Compounds include, but are not limited to, peptides such as, for example, soluble peptides, including but not limited to members of random peptide libraries; (see, e.g., Lam, K. S. et al. (1991) Nature 354:82–84; Houghten, R. et al. (1991) Nature 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al. (1993) Cell 72:767–778), antibodies (including, but not limited to, polyclonal, monoclonal, humanized, anti-idiotypic, chimeric or single chain antibodies, and Fab, $F(ab')_2$, scFv, and Fab expression library fragments, and epitope-binding fragments thereof), and small organic or inorganic molecules.

Other compounds which can be screened in accordance with the invention include, but are not limited to, small molecules. The term "small molecules" includes molecules which are capable of being used as therapeutic agents e.g., peptides, peptidomimetics (e.g., peptoids), amino acids, amino acid analogs, polynucleotides, polynucleotide analogs, nucleotides, nucleotide analogs, organic (including, e.g., heteroorganic and organometallic compounds) and inorganic compounds. The term includes compounds which have a molecular weight of about, for example, 10,000 grams per mole or less, 5,000 grams per mole or less, 2,000 grams per mole or less, or 1,000 g/mol grams per mole or less, less than about 500 grams per mole, and salts, esters, and other pharmaceutically acceptable forms of such compounds. Small molecules include those as described above. In a further embodiment, the small molecule is an organic compound. Examples of small molecules include those described in Formulae 1–VIII and in Table 2. Organic compounds comprise one or more carbon atoms. In another embodiment, the compound is an inorganic compound. Inorganic compounds include compounds which do not comprise a carbon atom.

The test compounds of the invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) J. Med. Chem. 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233. Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner, U.S. Pat. No. 5,223, 409), spores (Ladner USP '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

Computer modeling and searching technologies permit identification of compounds, as well as improvement of already identified compounds, that can modulate ACE-2 expression or activity. Having identified such a compound or composition, the active sites or regions are identified. Such active sites can be substrate binding sites. The active site can be identified using computer modeling methods and searching techniques known in the art including, for example, methods and techniques based on the amino acid sequences of peptides, the nucleotide sequences of nucleic acids, and structures obtained from studies of complexes of the relevant compound or composition with its natural ligand. In the latter case, chemical or X-ray crystallographic methods are useful in the identification of the active site by determining the position of the complexed ligand on the factor.

Next, the three dimensional geometric structure of the active site is determined. This can be done by known methods, including X-ray crystallography, which can determine a complete molecular structure. Alternatively, solid or liquid phase NMR can be used to determine certain intramolecular distances. Any other experimental method of structure determination can be used to obtain partial or complete geometric structures. The geometric structures can be measured with a complexed ligand, natural or artificial to increase the accuracy of the active site structure determined.

If an incomplete or insufficiently accurate structure has been obtained, the methods of computer based numerical modeling can be used to complete or improve the accuracy of the structure. Any recognized modeling method can be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination of these, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. Compounds found from this type of search are potential ACE-2 modulating compounds.

Alternatively, these methods can be used to identify improved modulating compounds from an already known modulating compound or ligand. By modifying the composition of the known compound, the structural consequences of the modification can be determined using the experimental and computer modeling methods described above. The altered structure can then be compared to the active site structure of the compound to determine if an improved fit or interaction results. In this manner, systematic variations in composition, such as by varying side groups, can be quickly evaluated to obtain modified modulating compounds or ligands with a more desirable specificity or activity.

Further experimental and computer modeling methods useful in the identification of modulating compounds based upon identification of the active sites of ACE-2, and related transduction and transcription factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, (e.g., Rotivinen, et al. (1988) Acta Pharmaceutical Fennica 97:159–166; Ripka (1988) New Scientist 54–57; McKinaly and Rossmann (1989) Annu. Rev. Pharmacol. Toxiciol. 29:111–122; Perry and Davies, *QSAR: Quantitative Structure-Activity Relationships in Drug Design*, pp. 189–193, Alan R. Liss, Inc. 1989; Lewis and Dean (1989) Proc. R. Soc. Lond. 236: 125–140 and 141–162). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these programs were designed primarily to identify drugs specific to particular proteins, they can be adapted to design of drugs specific to regions of DNA or RNA, once the region of interest is identified.

Although described above with reference to the design and generation of compounds which alter or interfere with substrate or binding to its target molecule, one can also use the above described methods to screen libraries of known compounds, including natural products or synthetic chemicals, and biologically active materials, including proteins and peptides, for compounds which are inhibitors or activators.

Compounds identified using assays such as those described herein are useful, for example, in elaborating the biological function of ACE-2, in particular, in regulating body weight and/or modulating the percentage of body fat, and in methods of treatment for body weight disorders in human subjects. The in vivo efficacy of compounds identified in a screen described herein can be tested in animal model systems for body weight disorders to identify drugs, pharmaceuticals, therapeutic methods and compositions, and interventions that can be therapeutically effective. For example, a compound identified by the methods described herein can be tested in an animal model of body weight disorder to determine an effective concentration and treatment regimen to ameliorate the body weight disorder symptoms in the test animals. The response of the animals to the test compound can be monitored by assessing the reversal of symptoms or physiological conditions associated with the body weight disorder being tested.

To this end, transgenic animals that express the human ACE-2 polypeptides, or fragments thereof, are useful. Animals of any species, including, but not limited to, mice, rats, rabbits, guinea pigs, pigs, micro-pigs, goats, and non-human primates, e.g., baboons, monkeys, and chimpanzees are useful in the generation of transgenic animals. Any technique known in the art can be used to introduce the human ACE-2 transgene into animals to produce the founder lines of transgenic animals. Such techniques include, but are not limited to, pronuclear microinjection (Hoppe, P. C. and Wagner, 1989, U.S. Pat. No. 4,873,191); retrovirus mediated gene transfer into germ lines (Van der Putten et al. (1985) Proc. Natl. Acad. Sci. USA 82:6148–6152); gene targeting in embryonic stem cells (Thompson et al. (1989) Cell 56:313–321); electroporation of embryos (Lo (1983) Mol. Cell. Biol. 3:1803–1814); and sperm-mediated gene transfer (Lavitrano et al. (1989) Cell 57:717–723); etc. For a review of such techniques, see Gordon, 1989, "Transgenic Animals", Intl. Rev. Cytol. 115:171–229, which is incorporated by reference herein in its entirety.

The invention provides for transgenic animals that carry the ACE-2 transgene in all their cells, as well as animals which carry the transgene in some, but not all their cells, i.e., mosaic animals. The transgene can be integrated as a single transgene or in concatamers, e.g., head-to-head tandems or head-to-tail tandems. Alternatively, the transgene can be selectively introduced into and activated in a particular cell type by following, for example, the teaching of Lasko et al. ((1992) Proc. Natl. Acad. Sci. USA 89:6232–6236). The regulatory sequences required for such a cell-type specific activation will depend upon the particular cell type of interest, and will be apparent to those of skill in the art. When the ACE-2 transgene is to be integrated into the chromosomal site of the endogenous ACE-2 gene, the use of gene targeting techniques is preferred. Briefly, when such a technique is to be utilized, vectors containing nucleotide sequences homologous to the endogenous ACE-2 gene and/or sequences flanking the gene are designed for the purpose of integrating, via homologous recombination with chromosomal sequences, into and disrupting the function of the endogenous ACE-2 gene. In an alternative method, the transgene can be selectively expressed in a particular cell type with concomitant inactivation of the endogenous ACE-2 gene in only that cell type, by following, for example, the teaching of Gu et al. ((1994) Science 265: 103–106). The regulatory sequences required for such a cell-type specific recombination will depend upon the particular cell type of interest, and will be apparent to those of skill in the art.

Once founder animals have been generated, standard techniques such as Southern blot analysis or PCR techniques are used to analyze animal tissues to determine whether integration of the transgene has taken place. Alternatively, the level of mRNA expression of the transgene in the tissues of the founder animals can be assessed using techniques which include, but are not limited to, Northern blot analysis of tissue samples obtained from the animal, in situ hybridization analysis, and RT-PCR. Samples of ACE-2 gene-expressing tissue, can also be evaluated immunocytochemically using antibodies specific for the ACE-2 transgene product.

ACE-2 Proteins, Polypeptides, and Antibodies

ACE-2 protein, polypeptides and peptide fragments, mutated, truncated, or deleted forms of the ACE-2 and/or ACE-2 fusion proteins can be prepared for a variety of uses, including, but not limited to, the generation of antibodies, as reagents in diagnostic assays, the identification of other cellular gene products involved in the regulation of body weight, as reagents in assays for screening for compounds that can be used in the treatment of body weight disorders, and as pharmaceutical reagents useful in the treatment of body weight disorders related to aberrant ACE-2 gene expression or protein activity.

Production of ACE-2 Polypeptides

The amino acid sequence of ACE-2 is shown in SEQ ID NO: 2. Peptides corresponding to one or more domains of the ACE-2 (e.g., the catalytic domain, or the zinc binding domain), truncated ACE-2 (e.g., an ACE-2 polypeptide in which a fragment is deleted), as well as fusion proteins in which the full length ACE-2, an ACE-2 peptide, or truncated ACE-2 polypeptide is fused to an unrelated protein are also within the scope of the invention. Such soluble peptides, proteins, fusion proteins, and antibodies (including anti-idiotypic antibodies) that bind to and prevent or inhibit the proteolysis of an ACE-2 ligand by ACE-2, can be used as described herein to effectuate weight loss. To this end, peptides corresponding to biologically active fragments of ACE-2 (e.g., fragments containing the catalytic domain, or a fragment thereof) or the entire ACE-2 polypeptide can be fused to another polypeptide (e.g., an IgFc polypeptide). Fusion of an ACE-2 polypeptide, or a biologically active fragment thereof, to an IgFc polypeptide can increase the stability of the preparation, increase the half-life and activity of the ACE-2-Ig fusion protein in vivo, and can confer upon the fusion protein immunoglobulin effector functions (e.g., binding to an Ig receptor). In an alternative embodiment, the Fc region of the Ig portion of the fusion protein can be modified to reduce immunoglobulin effector function.

A variety of host expression vector systems are useful for the expression of nucleotide sequences encoding the appropriate regions of the ACE-2 to produce such polypeptides. Where the resulting peptide or polypeptide is a soluble derivative, the peptide or polypeptide can be recovered from the culture media. Where the polypeptide or protein is not secreted, the ACE-2 product can be recovered from the host cell itself. With regard to recombinant ACE-2 expressed in CHO cells, ACE-2 is synthesized as a transmembrane protein, some of which is cleaved posttranslationally to generate a secreted form in vivo and in cell culture (Donoghue, et al., supra).

The host-expression vector systems also encompass engineered host cells that express ACE-2, or biologically active equivalents, in situ, i.e., anchored in the cell membrane. Purification or enrichment of ACE-2 from such expression systems can be accomplished using appropriate detergents and lipid micelles and methods well known to those skilled in the art. However, such engineered host cells themselves are also useful in situations where it is important not only to retain the structural and functional characteristics of membrane-bound ACE-2, but to assess biological activity, e.g., in drug screening assays.

The host expression vector systems that are useful for purposes of the invention include, but are not limited to, microorganisms such as bacteria (e.g., *E. coli, B. subtilis*) transformed with recombinant bacteriophage DNA, plasmid DNA or cosmid DNA expression vectors containing ACE-2 nucleotide sequences; yeast (e.g., *Saccharomyces, Pichia*) transformed with recombinant yeast expression vectors containing the ACE-2 nucleotide sequences; insect cell systems infected with recombinant virus expression vectors (e.g., baculovirus) containing the ACE-2 sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing ACE-2 nucleotide sequences; and mammalian cell systems (e.g., COS, CHO, BHK, 293, and 3T3 cell lines) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the ACE-2 gene product being expressed. For example, when a large quantity of such a protein is to be produced for the generation of pharmaceutical compositions of ACE-2 protein or for raising antibodies to the ACE-2 protein, for example, vectors which direct the expression of high levels of fusion protein products that are readily purified may be desirable. Such vectors include, but are not limited to, the *E. coli* expression vector pUR278 (Ruther, et al. (1983) EMBO J. 2:1791), in which the ACE-2 coding sequence can be ligated individually into the vector in frame with the lacZ coding region so that a fusion protein is produced; pIN vectors (Inouye and Inouye (1985) Nucl. Acids Res. 13:3101–3109; Van Heeke and Schuster (1989) J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al. (1991) Proc. Natl. Acad. Sci. USA 88:8972–8976). In this system, the gene of interest is subcloned into a vaccinia recombination plasmid such that the open reading frame of the gene becomes translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

In an insect system,*Autographa californica* nuclear polyhedrosis virus (AcNPV) is used as a vector to express foreign genes. The virus grows in *Spodoptera frugiperda* cells. The ACE-2 coding sequence can be cloned individually into non-essential regions (e.g., the polyhedrin gene) of the virus and placed under control of an AcNPV promoter (e.g., the polyhedrin promoter). Successful insertion of the ACE-2 gene coding sequence will result in inactivation of the polyhedrin gene and production of non-occluded recombinant virus (i.e., virus lacking the proteinaceous coat coded for by the polyhedrin gene). The recombinant viruses are then used to infect cells in which the inserted gene is expressed. (See, e.g., Smith, et al. (1983) J. Virol. 46:584; Smith, U.S. Pat. No. 4,215,051.)

In mammalian host cells, there are a number of useful viral-based expression systems. In cases where an adenovirus is used as an expression vector, the ACE-2 polynucleotide sequence of interest can be ligated to an adenovirus transcription/translation control complex, e.g., the late promoter and tripartite leader sequence. This chimeric gene is then be inserted in the adenovirus genome by in vitro or in vivo recombination. Insertion in a non-essential region of the viral genome (e.g., region E1 or E3) will result in a recombinant virus that is viable and capable of expressing the ACE-2 gene product in infected hosts. (See, e.g., Logan and Shenk (1984) Proc. Natl. Acad. Sci. USA 81:3655–3659.) Specific initiation signals may also be required for efficient translation of inserted ACE-2 nucleotide sequences, including, e.g., the ATG initiation codon and adjacent sequences. In cases where an entire ACE-2 gene or cDNA, including its own initiation codon and adjacent sequences, is inserted into the appropriate expression vector, no additional translational control signals may be needed. However, in cases where only a portion of the ACE-2 coding sequence is inserted, exogenous translational control signals, including, e.g., the ATG initiation codon, must be provided. Furthermore, the initiation codon must be in frame with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See Bittner, et al. (1987) Methods in Enzymol. 153:516–544).

In addition, a host cell strain can be chosen which modulates the expression of the inserted sequences, or modifies and processes the gene product in the specific fashion desired. Such posttranslational modifications (e.g., glycosylation) and processing (e.g., cleavage) of protein products may be important for the function of the protein. Different host cells have characteristic and specific mechanisms for the posttranslational processing and modification of proteins and gene products. Appropriate cell lines or host systems can be chosen to ensure the correct modification and processing of the foreign protein expressed. Accordingly, it can be advantageous to use eukaryotic host cells which possess the cellular machinery to enable proper processing of the primary transcript, glycosylation, phosphorylation, or other posttranslational modifications of the gene product. Mammalian host cells which possess such capabilities include, but are not limited to, CHO, VERO, BHK, HeLa, COS, MDCK, 293, 3T3 and WI38 cell lines.

For long-term, high-yield production of recombinant proteins, stable expression is preferred. For example, cell lines which stably express the ACE-2 sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method is useful in engineering cell lines to express the ACE-2 gene product. Such engineered cell lines are particularly useful in screening and the evaluation of compounds that affect the endogenous activity of the ACE-2 gene product.

There are a number of such useful selection systems, including, but not limited to, the genes encoding the herpes simplex virus thymidine kinase (Wigler, et al. (1977) Cell 11:223), hypoxanthine-guanine phosphoribosyltransferase (Szybalska and Szybalski (1962) Proc. Natl. Acad. Sci. USA 48:2026), and adenine phosphoribosyltransferase (Lowy, et al. (1980) Cell 22:817) which can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al. (1980) Natl. Acad. Sci. USA 77:3567; O'Hare, et al. (1981) Proc. Natl. Acad. Sci. USA 78:1527); gpt, which confers resistance to mycophenolic acid (Mulligan and Berg (1981) Proc. Natl. Acad. Sci. USA 78:2072); neo, which confers resistance to the aminoglycoside G-418 (Colberre-Garapin, et al. (1981) *J. Mol. Biol.* 150:1); and hygro, which confers resistance to hygromycin (Santerre, et al. (1984) *Gene* 30:147).

Antibodies to ACE-2 Polypeptides

Antibodies that specifically recognize one or more epitopes of ACE-2 or conserved variants of ACE-2, or peptide fragments of ACE-2 are also encompassed by the invention. Such antibodies include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the aforementioned.

The antibodies of the invention are useful, for example, in the detection of the ACE-2 in a biological sample and therefore, can be utilized as part of a diagnostic or prognostic technique whereby subjects can be tested for abnormal amounts of ACE-2. Such antibodies are also useful in conjunction with, for example, compound screening schemes, e.g., as described herein, for the evaluation of the effect of test compounds on ACE-2 gene expression and/or activity of ACE-2 polypeptides. Additionally, such antibodies can be used in conjunction with the gene therapy techniques described, below, e.g., to evaluate the normal endogenous and/or engineered ACE-2-expressing cells prior to their introduction into the subject. Such antibodies are additionally useful as a reagent for the inhibition of abnormal ACE-2 activity. Such antibodies are therefore useful as part of weight disorder treatment methods.

The term "antibody" as used herein refers to an immunoglobulin molecule and immunologically active portions of immunoglobulin molecules, i.e., molecules that contain an antigen binding site which specifically binds (i.e., immunoreacts with) an antigen, such as a ACE-2 molecule. Examples of immunologically active portions of immunoglobulin molecules include scFV and dcFV fragments, Fab and F(ab')$_2$ fragments.

The antibody can be a polyclonal, monoclonal, recombinant, e.g., a chimeric, humanized, fully human, non-human (e.g., murine, rat, rabbit, or goat), or single chain antibody. In a preferred embodiment it has effector function and can fix complement. The antibody can be coupled to a toxin or imaging agent.

The term "monoclonal antibody" or "monoclonal antibody composition", as used herein, refers to a population of antibody molecules that contain only one species of an antigen binding site capable of immunoreacting with a particular epitope of ACE-2. A monoclonal antibody composition thus typically displays a single binding affinity for a particular ACE-2 protein with which it immunoreacts.

Polyclonal anti-ACE-2 antibodies can be prepared as described above by immunizing a suitable subject with a ACE.-2 immunogen. The anti-ACE-2 antibody titer in the immunized subject can be monitored over time by standard techniques, such as with an enzyme linked immunosorbent assay (ELISA) using immobilized ACE-2. If desired, the antibody molecules directed against ACE-2 can be isolated from the subject (e.g., from the blood) and further purified by well known techniques, such as protein A chromatography to obtain the IgG fraction. At an appropriate time after immunization, e.g., when the anti-ACE-2 antibody titers are highest, antibody-producing cells can be obtained from the subject and used to prepare monoclonal antibodies by standard techniques, such as the hybridoma technique originally described by Kohler and Milstein (1975) *Nature* 256:495–497 (see also Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75); the human B cell hybridoma technique (Kozbor et al. (1983) *Immunol Today* 4:72); the EBV-hybridoma technique (Cole et al. (1985), *Monoclonal Antibodies and Cancer Therapy*, Alan R. Liss, Inc., pp. 77–96); and trioma techniques. The technology for producing monoclonal antibody hybridomas is well known. (See generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; and M. L. Gefter et al. (1977) *Somatic Cell Genet.* 3:231–36.) Briefly, an immortal cell line (typically a myeloma cell line) is fused to lymphocytes (typically splenocytes) from a mammal immunized with a ACE-2 immunogen as described herein, and the culture supernatants of the resulting hybridoma cells are screened to identify a hybridoma producing a monoclonal antibody that binds ACE-2.

Any of the many well known protocols for fusing lymphocytes and immortalized cell lines can be used to generate an anti-ACE-2 monoclonal antibody (see, e.g., Galfre et al. (1977) *Nature* 266:55052; Gefter et al. *Somatic Cell Genet.*, supra; Lerner, *Yale J. Biol. Med.*, supra; Kenneth, *Monoclonal Antibodies*, supra). Moreover, the ordinarily skilled worker will appreciate that there are many variations of such methods which are useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (Manassas Va.). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells. Unfused splenocytes die after several days because they are not transformed. Hybridoma cells producing a monoclonal antibody of the invention are detected by screening the hybridoma culture supernatants for antibodies that bind ACE-2 , e.g., using a standard ELISA assay.

Alternative to preparing monoclonal antibody-secreting hybridomas, a monoclonal anti-ACE-2 antibody can be identified and isolated by screening a recombinant combinatorial immunoglobulin library (e.g., an antibody phage display library) with an ACE-2 polypeptide to thereby identify immunoglobulin library members that bind ACE-2. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody phage display libraries can be found in, for example, U.S. Pat. No. 5,223,409; PCT International Publication No. WO 92/18619; PCT International Publication No. WO 91/17271; PCT International Publication No. WO 92/20791; PCT International Publication No. WO 92/15679;

PCT International Publication No. WO 93/01288; PCT International Publication No. WO 92/01047; PCT International Publication No. WO 92/09690; PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, chimeric, humanized, and completely human antibodies are also within the scope of the invention. Chimeric, humanized, but most preferably, completely human antibodies are desirable for applications which include repeated administration, e.g., therapeutic treatment of human subjects, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in PCT International Application No. PCT/US86/02269; EPO Publication No. 184,187; EPO Publication No. 171,496; EPO Publication No. 173,494; PCT International Publication No. WO 86/01533; U.S. Pat. No. 4,816,567; EPO Publication No. 125,023; Better et al. (1988) *Science* 240:1041–1043; Liu et al. (1987) *Proc. Natl. Acad Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human subjects. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), are available to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903.

A full-length ACE-2 protein, or an antigenic fragment thereof, can be used as an immunogen or can be used to identify anti-ACE-2 antibodies made with other immunogens, e.g., cells, membrane preparations, and the like. The antigenic fragments of ACE-2 should include at least 8 amino acid residues of the amino acid sequence shown in SEQ ID NO:2 and encompass an epitope of ACE-2, respectively. Preferably, the antigenic peptide includes at least 10 amino acid residues, more preferably at least 15 amino acid residues, even more preferably at least 20 amino acid residues, and most preferably at least 30 amino acid residues.

Fragments of ACE-2 which include, e.g., amino acid residues 147 to 555 of SEQ ID NO:2, can be used as immunogens to make an antibody against the ACE-2 catalytic domain.

Antibodies reactive with, or specific for, any of this region, or other regions or domains described herein are provided.

In an alternative embodiment, the antibody fails to bind to an Fc receptor, e.g., it is of an immunoglobulin class which does not support Fc receptor binding or has been modified, e.g., by deletion or other mutation, such that is does not have a functional Fc receptor binding region.

Preferred epitopes encompassed by the antigenic peptide are regions of ACE-2 which are located on the surface of the protein, e.g., hydrophilic regions, as well as regions with high antigenicity. For example, an Emini surface probability analysis of the human ACE-2 protein sequence can be used to identify the regions that have a particularly high probability of being localized to the surface of the ACE-2 protein, and are thus likely to constitute surface residues useful for targeting antibody production.

In a preferred embodiment the antibody binds an epitope on any domain or region on ACE-2 proteins described herein.

The anti-ACE-2 antibody can be a single chain antibody. A single-chain antibody (scFV) may be engineered as described, for example, in Colcher, D. et al., (1999 ) *Ann. NY Acad. Sci.* 880: 263–80; and Reiter, Y. (1996) *Clin. Cancer Res.* 2:245 –52. The single chain antibody can be dimerized or multimerized to generate multivalent antibodies having specificities for different epitopes of the same target ACE-2 protein.

An anti-ACE-2 antibody can be used to detect ACE-2 protein (e.g., in a cellular lysate or cell supernatant) in order to evaluate the abundance and pattern of expression of the protein. Anti-ACE-2 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies to ACE-2 can, in turn, be utilized to generate anti-idiotype antibodies that "mimic" ACE-2, using techniques well known to those skilled in the art. (See, e.g., Greenspan and Bona (1993) FASEB J 7:437–444; and Nissinoff (1991) J. Immunol. 147:2429–2438.) For example, antibodies which bind to the ACE-2 catalytic site and competitively inhibit the binding of ACE-2 substrates can be used to generate anti-idiotypes that "mimic" the ACE-2 catalytic site and, therefore, bind and neutralize ACE-2 substrates. Such neutralizing anti-idiotypes, or fragments thereof, can be used in therapeutic regimens to reduce or inhibit ACE-2 activity and promote a reduction in body weight and/or the percentage of body fat.

Alternatively, antibodies to ACE-2 that can act as (e.g., agonists activators) of ACE-2 activity can be generated. Such antibodies that enhance ACE-2 catalytic activity are particularly useful for treating weight disorders such as anorexia and cachexia. Alternatively, antibodies that act as inhibitors (e.g., antagonists) or inverse agonists of ACE-2 activity and inhibit the catalytic activity of ACE-2 are useful in the treatment of weight disorders such as obesity.

Gene Therapy Approaches to Controlling ACE-2 Activity and Regulating Body Weight The expression of ACE-2 can be controlled in vivo (e.g., at the transcriptional or translational level) using gene therapy approaches to regulate ACE-2 activity and treat body weight disorders. Several approaches are described below.

Gene Replacement Therapy

Where an increase in the level of normal ACE-2 gene expression and/or ACE-2 gene product activity is desirable, ACE-2 nucleic acid sequences can be utilized, e.g., in the treatment of body weight disorders, including anorexia and cachexia. Where the cause is a defective ACE-2 gene, treatment can be administered, for example, in the form of gene replacement therapy. Specifically, one or more copies of a normal ACE-2 gene or a portion of the ACE-2 gene that directs the production of an ACE-2 gene product exhibiting normal function, can be inserted into the appropriate cells of a subject, using vectors which include, but are not limited to, adenovirus, adeno-associated virus, retrovirus, and herpes virus vectors, in addition to other particles that introduce DNA into cells, such as liposomes.

Because ACE-2 gene expression is limited to the heart (in particular, the endothelium of most intramyocardial vessels, including capillaries, venules, and medium-sized coronary arteries and arterioles), testis, small intestine, large intestine, adipose tissue, and kidney, (in particular, the endothelium and focally in rare smooth muscle cells of medium sized vessels, and proximal tubule epithelial cells), gene replacement therapy techniques can be used to deliver ACE-2 gene sequences to these cell types in subjects by direct administration of ACE-2 gene sequences to the site within these tissues where the ACE-2 gene sequences are expressed.

Alternatively, targeted homologous recombination can be utilized to correct the defective endogenous ACE-2 gene in the appropriate tissue. In animals, targeted homologous recombination can be used to correct the defect in ES cells in order to generate offspring with a corrected trait.

Additional methods which are useful in increasing the overall level of ACE-2 gene expression and/or ACE-2 activity include the introduction of appropriate ACE-2-expressing cells, preferably autologous cells, into a subject at positions and in numbers which are sufficient to ameliorate the symptoms of body weight disorders, such as anorexia and cachexia. Such cells can be either recombinant or non-recombinant. Among the cells which can be administered to increase the overall level of ACE-2 gene expression in a subject are normal cells, or cells which express the ACE-2 gene, such as the endothelium of most intramyocardial vessels, testis, small intestine, large intestine, adipose tissue, and the endothelium and focally in rare smooth muscle cells of medium sized vessels, and proximal tubule epithelial cells of the kidney. The cells can be delivered directly to the anatomical site, or as part of a tissue graft located at a different site in the body. Such cell-based gene therapy techniques are well known to those skilled in the art. (See, e.g., U.S. Pat. No. 5,399,349 and U.S. Pat. No. 5,460,959).

Finally, compounds, identified in the assays described above, that stimulate or enhance the proteolytic activity of ACE-2, can be used to achieve weight gain. The formulation and mode of administration will depend upon the physicochemical properties of the compound.

Inhibition of ACE-2 Expression

In an alternate embodiment, therapeutic methods to reduce body weight and/or the percentage of body fat can be designed to reduce the level of endogenous ACE-2 gene expression, e.g., using antisense or ribozyme approaches to inhibit or prevent translation of ACE-2 mRNA transcripts; triple helix approaches to inhibit transcription of the ACE-2 gene; or targeted homologous recombination to inactivate or "knock out" the ACE-2 gene or its endogenous promoter. Such gene therapy is useful in the treatment of body weight disorders such as obesity, where the inhibition of ACE-2 expression is designed to reduce body weight and/or the percentage of body fat. Because ACE-2 gene expression is limited to the heart, kidney, adipose tissue, small intestine, large intestine and testis, delivery techniques can be utilized which enable administration of the antisense, ribozyme or DNA constructs described herein directly to the tissue containing the target cells.

Antisense approaches involve the design of oligonucleotides (either DNA or RNA) that are complementary to mRNA. The antisense oligonucleotides will bind to the complementary mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

While antisense nucleotides complementary to the coding region sequence could be used, those complementary to the transcribed untranslated region are most preferred. Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs were recently shown to be effective at inhibiting translation of mRNAs as well. (See generally, Wagner, R. (1994) Nature 372:333–335.) Thus, oligonucleotides complementary to either the 5'- or 3'-non-translated, non-coding regions of ACE-2 can be used in an antisense approach to inhibit translation of endogenous ACE-2 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of ACE-2 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, the results obtained using the antisense oligonucleotide can be compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA. 86:6553–6556; Lemaitre et al. (1987) Proc. Natl. Acad. Sci. USA 84:648–652; and PCT International Publication No. WO 88/09810) or the blood-brain barrier (see, e.g., PCT International Publication No. WO 89/10134), hybridization-triggered cleavage agents (see, e.g., Krol et al. (1988) BioTechniques 6:958–976), or intercalating agents (see, e.g., Zon (1988) Pharm. Res. 5:539–549). To this end, the oligonucleotide can be conjugated to another molecule, e.g., a peptide, hybridization triggered cross-linking agent, transport agent, hybridization-triggered cleavage agent, etc.

The antisense oligonucleotide can comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al. (1987) Nucl. Acids Res. 15:6625–6641). The oligonucleotide is a 2'-0-methylribonucleotide (Inoue et al., (1987) Nucl. Acids Res. 15:6131–6148), or a chimeric RNA-DNA analogue (Inoue et al. (1987) FEBS Lett. 215:327–330).

Oligonucleotides of the invention can be synthesized by standard methods known in the art, e.g., by use of an automated DNA synthesizer (such as those commercially available from Biosearch, Applied Biosystems, etc.). As examples, phosphorothioate oligonucleotides can be synthesized by the method of Stein et al. ((1988) Nucl. Acids Res. 16:3209), and methylphosphonate oligonucleotides can be prepared by use of controlled pore glass polymer supports (Sarin et al. (1988) Proc. Natl. Acad. Sci. USA 85:7448–7451), etc.

The antisense molecules should be delivered to the cells which express the ACE-2 in vivo, e.g., heart (in particular, the endothelium of most intramyocardial vessels, including capillaries, venules, and medium-sized coronary arteries and arterioles), testis, small intestine, large intestine, adipose tissue, and kidney, (in particular, the endothelium and focally in rare smooth muscle cells of medium sized vessels, and proximal tubule epithelial cells). A number of methods have been developed for delivering antisense DNA or RNA to cells; e.g., antisense molecules can be injected directly into the tissue site, or modified antisense molecules, designed to target the desired cells (e.g., antisense molecules linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the subject will result in the transcription of sufficient amounts of single stranded RNAs that will form complementary base pairs with the endogenous ACE-2 transcripts and thereby prevent translation of the ACE-2 mRNA. For example, a vector can be introduced in vivo such that it is taken up by a cell and directs the transcription of an antisense RNA. Such a vector can be constructed to remain episomal or become chromosomally integrated, as long as it can be transcribed to produce the desired antisense RNA. Such vectors can be constructed by recombinant DNA technology methods standard in the art. Vectors can be plasmid, viral, or others known in the art used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist and Chambon (1981) Nature 290:304–310), the promoter contained in the 3' long terminal repeat of Rous sarcoma virus (Yamamoto, et al. (1980) Cell 22:787–797), the herpes thymidine kinase promoter (Wagner, et al. (1981) Proc. Natl. Acad. Sci. USA 78:1441–1445), the regulatory sequences of the metallothionein gene (Brinster, et al. (1982) Nature 296:39–42), etc. Any type of plasmid, cosmid, YAC or viral vector can be used to prepare the recombinant DNA construct which can be introduced directly into the tissue site (e.g., heart (in particular, the endothelium of most intramyocardial vessels, including capillaries, venules, and medium-sized coronary arteries and arterioles), small intestine, large intestine, adipose tissue, testis, and kidney, (in particular, the endothelium and focally in rare smooth muscle cells of medium sized vessels, and proximal tubule epithelial cells)). Alternatively, viral vectors can be used which selectively infect the desired tissue, in which case administration can be accomplished by another route (e.g., systemically).

Ribozyme molecules designed to catalytically cleave ACE-2 mRNA transcripts can also be used to prevent translation of ACE-2 mRNA and expression of ACE-2 polypeptide. (See, e.g., PCT International Publication No. WO 90/11364; and Sarver et al. (1990) Science 247:1222–1225). While ribozymes that cleave mRNA at site-specific recognition sequences can be used to destroy ACE-2 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature, 334:585–591. Preferably the ribozyme is engineered so that the cleavage recognition site is located near the 5' end of the ACE-2 mRNA; i.e., to increase efficiency and minimize the intracellular accumulation of non-functional mRNA transcripts.

The ribozymes of the invention also include RNA endoribonucleases (hereinafter "Cech-type ribozymes") such as the one which occurs naturally in *Tetrahymena Thermophila* (known as the IVS, or L-19 IVS RNA) and which has been extensively described by Thomas Cech and collaborators (Zaug, et al. (1984) Science, 224:574–578; Zaug and Cech (1986) Science, 231:470–475; Zaug, et al. (1986) Nature, 324:429–433; PCT publication No. WO 88/04300; and Been and Cech (1986) Cell, 47:207–216). The Cech-type ribozymes have an eight base pair active site which hybridizes to a target RNA sequence where after cleavage of the target RNA takes place. The invention encompasses those Cech-type ribozymes which target eight base-pair active site sequences that are present in ACE-2.

As in the antisense approach, the ribozymes can be composed of modified oligonucleotides (e.g. for improved stability, targeting, etc.) and should be delivered to cells which express the ACE-2 in vivo, e.g., heart, testis, small intestine, large intestine, adipose tissue, and kidney. A preferred method of delivery involves using a DNA construct "encoding" the ribozyme under the control of a strong constitutive pol III or pol II promoter, so that transfected cells will produce sufficient quantities of the ribozyme to destroy endogenous ACE-2 messages and inhibit translation. Because ribozymes unlike antisense molecules, are catalytic, a lower intracellular concentration is required for efficiency.

Endogenous ACE-2 gene expression can also be reduced by inactivating or "knocking out" the ACE-2 gene or its promoter using targeted homologous recombination (e.g., see Smithies, et al., (1985) Nature 317:230–234; Thomas and Capecchi (1987) Cell 51:503–512; and Thompson, et al. (1989) Cell 5:313–321; each of which is incorporated herein by reference in its entirety). For example, a mutant, non-functional ACE-2 (or a completely unrelated DNA sequence) flanked by DNA homologous to the endogenous ACE-2 gene can be used, with or without a selectable marker and/or a negative selectable marker, to transfect cells that express ACE-2 in vivo. Insertion of the DNA construct, via targeted homologous recombination, results in inactivation of the ACE-2 gene. Such approaches are particularly suited in the agricultural field where modifications to ES (embryonic stem) cells can be used to generate animal offspring with an inactive ACE-2 polypeptide (e.g., see Thomas and Capecchi (1987) and Thompson (1989), supra). However this approach can be adapted for use in humans provided the recombinant DNA constructs are directly administered or targeted to the required site in vivo using appropriate viral vectors.

Alternatively, endogenous ACE-2 gene expression can be reduced by targeting deoxyribonucleotide sequences complementary to the regulatory region of the ACE-2 gene (i.e., the ACE-2 promoter and/or enhancers) to form triple helical structures that prevent transcription of the ACE-2 gene in target cells in the body. (See generally, Helene, C. (1991) Anticancer Drug Des., 6:569–84; Helene, C., et al. (1992) Ann. N.Y. Acad. Sci. 660:27–36; and Maher, L. J. (1992) Bioassays 14:807–15).

Delivery of Soluble ACE-2 Polypeptides

Genetically engineered cells that express soluble ACE-2 polypeptides, or fragments thereof, or fusion proteins e.g. fusion Ig molecules can be administered in vivo where they can function as "bioreactors" that deliver a supply of the soluble molecules. Such soluble ACE-2 polypeptides and fusion proteins, when expressed at appropriate concentrations, should neutralize or "mop up" the native ligand for ACE-2. and thus act as inhibitors of ACE-2 activity and promote weight loss and/or reduce the percentage of body fat in a subject.

This invention is further illustrated by the following examples which should not be construed as limiting. The contents of all references and published patents and patent applications cited throughout the application are hereby incorporated by reference.

EXEMPLIFICATION OF THE INVENTION

Example 1

Production of ACE and ACE-2 Polypeptides

ACE and ACE-2 polypeptides were produced in CHO cells as follows. Full length ACE-2 expression vector (pFLA-2) was generated by ligating an EcroRI/Afl III fragment of a 5' RACE clone (cchr002) and an Afl III/Not I fragment of the original library clone into the EcoRI/Not I sites of pcDNA3.1 (Invitrogen). An expression vector for secreted ACE-2 (pMD37) was generated by subcloning into pACE-2 a small PCR fragment which has a stop codon inserted after the serine immediately preceding the transmembrane domain. Testicular ACE cDNA was obtained from James Riordan and was subcloned into pcDNA3.1 for expression. For the transfections, CHO K1 cells, which are maintained in serum-free Ultra CHO medium (Biowhittaker) at 37° C. in a humidified 5% $CO_2$ incubator, were seeded at $1\times10^6$ cells/10 cm dish on day 0 and transfected with lipofectamine on day 1 as per manufacturers' instructions. Briefly, 10 µg of DNA were combined with 40 µl of lipofectamine in Opti-MEM medium and the mixture was incubated on the cells for 5–6 hours. Ultra CHO medium was then added to the cells and they were incubated overnight at 37° C. On day 2, the medium was changed and on day 4 the media were collected. For the examples below, the conditioned media containing the secreted ACE-2 protein was concentrated in Centriplus 30 concentrators (Amicon).

Example 2

Purification of ACE-2

The following protocol is an example of a protocol that was used for the purification of ACE-2 for use in the subsequent examples.

ACE-2 CHOK1 cell supernatant was dialyzed into 50 mM BisTrisPropane/Tris HCl overnight at pH 6.5 and 4° C. The dialyzed supernatant was then filtered using a 0.2 µm filter unit. The filtrate was then loaded on to a MonoQ anion exchange column and eluted with a 0–250 mM NaCl gradient. The fractions containing ACE-2 (as determined by Coumassie Blue stained SDS-Page gel or Western blot) were pooled and 1M $Am_2SO_4$ was added until the final concentration was about 1M. The fractions were then centrifuged, and the supernatant was retained. The supernatant was then loaded on to a phenyl superose hydrophobic column and eluted with 1M–0.5M $Am_2SO_4$ reverse gradient in 100 mM NaPi at pH 7. The ACE-2 containing fractions were then pooled and dialyzed into 20 mM HEPES/15 mM NaCl at pH 7 at 4° C. overnight. The dialyzed fractions were then filtered for a final time through a 0.2 µm syringe.

Example 3

Synthesis of Compounds D and E

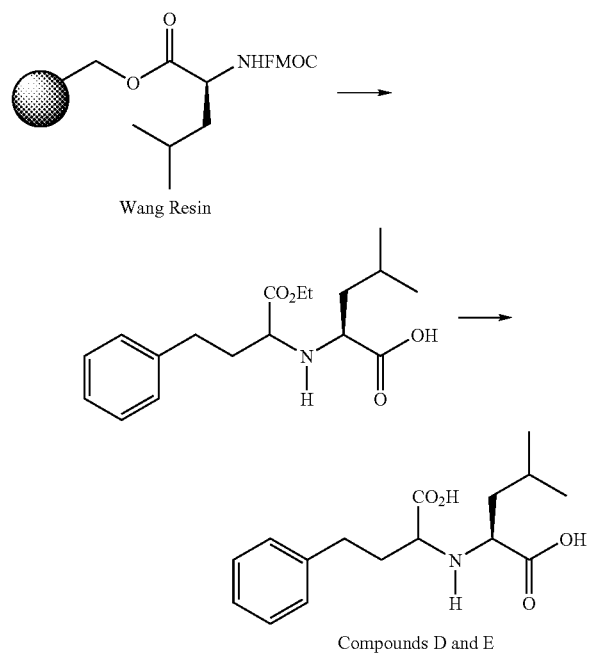

Compounds D and E

Fmoc-Leu-Wang resin (commercially available from Novabiochem, loading 0.8 mmol/g, 2.61 g, 2.09 mmol) was treated with 20% piperidine in DMF (ca. 100 mL) for thirty minutes. The resin was then filtered and washed well with DMF, THF, $CH_2Cl_2$, and methanol. The resin was then suspended in 52 mL of DMF, and acetic acid (6.5 mL) and ethyl 2-oxo-4-phenylbutyrate (9.8 mL, 52.20 mmol) were added. This slurry was shaken for 10 minutes and the $NaBH_3CN$ (5.26 g, 83.60 mmol) was added which resulted in the evolution of heat and gas (Blackburn et al. *Biorg. and Med. Chem. Lett.* (1997) 7(7):823–828). The reaction mixture was sealed and shaken for two days. The resin was then separated from the reaction mixture by filtration and was subsequently washed well with methanol, $CH_2Cl_2$, 10% acetic acid in THF, THF, DMF and methanol. The resin was then suspended in ca. 10 mL of 50% trifluoroacetic acid in $CH_2Cl_2$ and shaken for thirty minutes. The resin was separated from the reaction mixture by filtration, and the resin was again treated with 100 mL of 50% trifluoroacetic acid in $CH_2Cl_2$ for 30 minutes. After filtration, the resin was washed well with 50 mL 50% trifluoroacetic acid in $CH_2Cl_2$. Combined filtrates were concentrated to give a tan oil. Purification of this oil by column chromatography ($SiO_2$, 7.5:2:0.5, $CH_2Cl_2$:EtOAc:methanol with 0.1% acetic acid) provided 2 sets of material—172 mg of desired product and 192 mg of desired product contaminated with a material of higher Rf (desired product Rf: 0.45, contaminant Rf: 0.55 in 7:2:1 $CH_2Cl_2$:EtOAc:methanol with 0.1% acetic acid.) Both sets of material were clean by $^1$H NMR. The 172 mg of desired material was further purified by HPLC (C18 column, gradient elution starting with 100% of 95% $H_2O$, 1% acetonitrile, 0.1% formic acid, ending with 60% of 95% $H_2O$, 1% acetonitrile, 0.1% formic acid and 40% of 95% acetonitrile, 0.5% $H_2O$, 0.1% formic acid 30 mL/min.). This HPLC method separated the 2 diastereomers of the monoester to give 37 mg of a white powder (retention time 11.5 minutes,) and 58 mg of a white powder (retention time 13.2 minutes,). Both compounds are clean and single isomers by $^1$H NMR.

A round bottomed flask containing 18 mg of the earlier eluted monoester was dissolved in 1 mL of 95% ethanol, and 400 µL of aqueous 1N NaOH solution was added. The reaction mixture was stirred for eighteen hours. The reaction mixture was then dried in vacuo and redissolved in water. A 2N HCl solution was added dropwise until a pH of 1 was reached and a white precipitate had appeared. The white precipitate was triturated with water and ethyl acetate and then concentrated under vacuum to give 12 mg of white solid, Compound D).

A round-bottomed flask containing 18 mg of the later eluted monoester was dissolved in 1 mL of 95% ethanol and 200 µL of aqueous 1N NaOH solution was added. The reaction mixture was stirred for 18 hours and was not complete by TLC. Another 100 µL of aqueous NaOH was added, and the reaction mixture was stirred for 48 additional hours. The reaction mixture was then dried in vacuo and redissolved in water. 1N HCl solution was added until a pH of 1 was reached and a white precipitate had appeared. Ethyl acetate was added and the two phase mixture was extracted twice with ethyl acetate (containing 2.5% THF). The combined organic phases were extracted with brine, dried over $Na_2SO_4$, filtered and concentrated to give a white solid (Compound E).

Example 4

Synthesis of Compound G

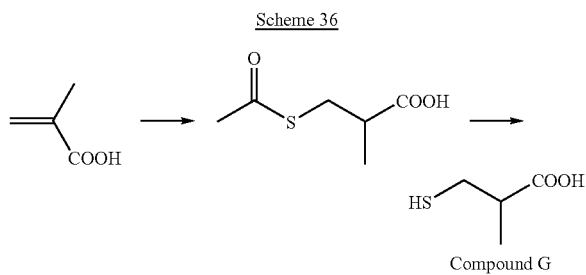

Scheme 36

Compound G was synthesized by heating thiolacetic acid with methacrylic acid to form the thioester (Neustadt et al., *J. Med. Chem.* (1994) 37:2461–2476). The thioester was then treated with 1N NaOH (aq) and MeOH and hydrolyzed to the thiol (Compound G).

Example 5

Synthesis of Compounds EA and EB

Propargyl glycine (1 equiv) was dissolved in a 50:50 mixture of benzene and methanol, and a solution of TMS diazomethane in hexane (2M, 1.5 equiv) was added to the reaction mixture dropwise. This reaction mixture was stirred at room temperature for 6 hours, and then it was concentrated. The residue was dissolved in dichloromethane, and the resulting solution was washed with saturated $NaHCO_3$ solution, dried over $MgSO_4$, filtered, and concentrated to give the desired ester as an oil.

Ethyl 4-phenyl-2-hydroxy-butyrate (prepared in racemic form from the $LiAlH_4$ reduction of ethyl 4-phenyl-2-oxo-butyrate) was dissolved in dichloromethane, and the solution was cooled to –78° C. Trifluoromethane sulfonic anhydride (1.05 equiv) and 2,6-lutidine (1.1 equiv) were then added dropwise. The reaction mixture was stirred at –78° C. for 1 hour and then allowed to warm to room temperature. Water was added to the reaction mixture, and the organic phase was separated, washed with brine, dried, filtered, and concentrated to give a yellow oil. This oil was purified by column chromatography (silica gel, 10% ethyl acetate/hexane) to give the desired triflate as an oil (Walker, *Tetrahedron*, (1997) 37:2461–2476).

The triflate prepared above was dissolved in dichloromethane, and the solution was cooled to –78° C. 2,6-Lutidine (1.1 equiv) was added and then a solution of the methyl ester of propargyl glycine (prepared above) in dichloromethane was added dropwise. The reaction mixture was stirred at –78° C. for 1 hour and then allowed to warm to room temperature and stirred overnight. Water was added to the reaction mixture, and the organic phase was separated, washed with water and brine, dried, filtered, and concentrated to give a yellow oil. This oil was purified by column chromatography (Biotage Quad 3, silica gel, 15% ethyl acetate/hexane) to give the desired secondary amine as an oil.

The secondary amine prepared above was dissolved in degassed DMF, and 2-bromopyridine (1.1 equiv) was added to this solution. Palladium tetrakistriphenylphosphine (0.05 equiv), triethyl amine (2.0 equiv), and copper iodide (0.2 equiv) were added sequentially. The reaction mixture was protected from the light and stirred for 3 hours. Water was added, and this mixture was extracted three times with ethyl acetate. Combined organic phases were washed with water and brine, dried, filtered, and concentrated to give a brown oil. This oil was purified by column chromatography (silica gel, 30% ethyl acetate/hexane) to give a yellow semi-solid. Further purification by column chromatography (silica gel, 50% ethyl acetate/hexane) gave the desired alkynylpyridine diester as a colorless oil (Wallace et al. *J. Med. Chem.* (1998) 41:1513–1523).

The diester prepared above was dissolved in ethanol, and a 1 N solution of NaOH (8.0 equiv) was added dropwise. The solution was stirred at room temperature for 1 hour. The reaction mixture was concentrated, and the residue was taken up in water. The solution was acidified to pH 1 with 2 N HCl solution and then concentrated to give a white solid. This solid was dissolved in water and purified by absorbing on to DOWEX resin (cationic, prewashed) and eluting first with water and then 2% pyridine/water to give a yellow solid upon concentration of the basic fractions. Further purification of this material by HPLC provided two diacids (EA and EB).

Example 6

Synthesis of Compounds EZ and FA

A suspension of Boc-His-OMe (0.92 mol, 25 g) in toluene (300 mL, 0.3 M) and triethylamine (1.1 mol, 15.5 mL) was treated with trityl chloride (28.5 g, 1.02 mol). The reaction was heated at 60° C. for 24 hours (Anthony, N. J., et al. *J. Med. Chem.*, (1999) 42:3356–3368; Kitajima, Y., et al. *Bull. Chem. Soc. Japan*, (1982)55:3870–3872). The reaction mixture was diluted with ethyl acetate and washed with saturated $NaHCO_3$ (3×) and brine (1×). A brown oil was obtained after drying ($MgSO_4$) and concentration in vacuo. Trituration from ether, hexane and methanol resulted in 37.6 g (80%) of the trityl protected histidine derivative as a white solid.

The trityl protected histidine derivative (5.0 g, 9.77 mmol) was suspended in anhydrous MeCN (10 mL, 1M) under a $N_2$ atmosphere and gently heated to 35° C. at which temperature the mixture became homogeneous. Benzyl bromide (9.77 mmol, 1.16 mL) was then added and the reaction temperature was increased to 55° C. After 15 hours, the reaction mixture was concentrated completely and redissolved in MeOH (60 mL, 0.16 M). This solution was refluxed for 1 hour then concentrated completely. The solid residue was dissolved in $CH_2Cl_2$ and washed with saturated $NaHCO_3$ (2×) and brine (1×) and dried over $MgSO_4$. The crude brown oil was purified by column chromatography (0–2% MeOH in $CH_2Cl_2$) to yield 2.1 g (58%) of the N-3 benzyl histidine derivative (N-3 alkylation was confirmed by ROESY NMR).

The N-3 benzyl histidine derivative (7.8 g, 22 mmol) was dissolved in 4N HCl in dioxane (85 mL) and reacted for 1 hour then concentrated completely. The resulting white solid was dissolved in 1 N NaOH (130 mL) and the pH was adjusted to 9–10 using 6 N HCl. α-Ketoisocaproic acid sodium salt (16.6 g, 109 mmol) was then added. After 15–30 minutes, $NaBH_3CN$ (4.1 g, 66 mmol) was added. After 48 hours, the pH was adjusted to 3 using 6 N HCl and the reaction mixture was filtered through a pad of Dowex (50WX2-200) eluting with water then $NH_4OH$. The product fractions were combined and purified to give EZ and FA.

Example 7

Purification of EZ and FA

The reaction mixture (21.4 g) containing salts, unreacted starting materials and diastereomers (EZ and FA) was dissolved in water (50 mL) and passed through a HP-20 column to remove the salts. The column was eluted with distilled water (500 mL) and finally washed with methanol (500 mL). Removal of the solvent yielded a residue (8.5 g) that was chromatographed over a column of RP-18 silica gel (MeOH:$H_2O$; 60:40). Several fractions were collected and monitored by TLC. Fractions containing diastereomers were pooled (3.2 g) and further purified by preparative HPLC (Varian, C-18 column, $H_2O$:ACN:0.1 HCOOH) to afford pure diastereomers EZ (1.02 g) and FA (1.78 g) as white colorless solids. The more active diastereomer (EZ) was passed through a column of Sephadex LH-20 to remove formate impurities. The product fractions were pooled to yield EZ as a colorless powder (0.93 g) that crystallized from a mixture of ethanol and methanol as colorless needles.

Example 8

Spectroscopy Data for Selected Compounds

Compound EN
$^1$H-NMR ($D_2O$): δ 8.33 (s, 1H); 7.41–7.48 (m, 5H); 7.26 (s, 1H); 5.68 (ABq, 2H, J=11.5 Hz, $δ_A$=5.69, $δ_B$=5.67); 4.71 (s, 2H); 3.84 (dd, 1H, J=7.3, 6.4 Hz); 3.57 (t, 1H, J=7.6, 6.3 Hz); 3.37–3.45 (m, 2H); 1.76–1.80 (m, 1H); 1.54–1.63 (m, 2H); 0.93 (d, 6H J=6.6 Hz).

Compound EZ
$^1$H NMR ($CD_3OD$) δ 8.58 (s, 1H), 7.48 (s, 1H), 7.32–7.45 (m, 3H), 7.24–7.31 (m, 2H), 3.72 (t, 1H, J=6.8 Hz), 3.60 (dd, 1H, J=7.6, 6.1 Hz), 3.13–3.21 (m, 2H), 1.88–1.97 (m, 1H), 1.64–1.78 (m, 2H), 0.98 (d, 6H, J=6.5 Hz), (8.12, s formic acid, 0.1 eq); N-3 alkylation confirmed by ROESY NMR.

Compound GA
$^1$H NMR ($CD_3OD$) δ 8.19 (bd, 1H, J=7.9 Hz), 8.06 (bs, 1H), 7.91 (bs, 1H), 7.63 (t, 1H, J=7.8 Hz), 7.57 (bd, 1H, J=7.8 Hz), 7.17 (bs, 1H), 5.46 (s, 2H), 3.63 (t, 1H, J=6.5 Hz), 3.55 (t, 1H, J=6.9 Hz), 3.10–3.16 (m, 2H), 1.89–1.94 (m, 1H), 1.70 (t, 2H, J=6.8 Hz), 0.97 (d, 6H, J=6.5 Hz), (1.97, s, acetic acid, 0.6 eq).

Compound GM
$^1$H NMR ($CD_3OD$) δ 8.28 (s, 1H); 7.39–7.32 (m, 3H); 7.27 (s, 1H); 7.16–7.14 (m, 1H); 5.36 (s, 2H); 3.69 (t, 1H, J=6 Hz); 3.57 (t, 1H, J=6 Hz); 3.16–3.13 (m, 2H); 1.99–1.86 (m, 1H); 1.71–1.65 (m, 2H); and 0.96 (d, 6H, J=6 Hz).

Compound HE
$^1$H NMR ($CD_3OD$) δ 8.37 (s, 1H); 7.42 (t, 1H, J=1.8 Hz); 7.36 (s, 1H); 7.21 (d, 2H, J=1.8 Hz); 5.37 (s, 2H); 3.70 (t, 1H, J=6 Hz); 3.59 (dd, 1H); 3.15–3.12 (m, 2H); 1.98–1.85 (m, 1H); 1.70–1.64 (m, 2H); and 0.96 (d, 6H, J=6 Hz).

Compound HO
$^1$H NMR ($CD_3OD$) δ 8.48 (s, 1H); 7.42–7.39 (m, 3H); 7.34 (s, 1H); 7.19–7.14 (m, 1H); 5.40 (s, 2H); 3.61–3.51 (m, 2H); 3.27 (d, 2H, J=6 Hz); 2.38 (s, 3H); 1.97–1.77 (m, 1H); 1.74–1.69 (m, 2H); and 0.99–0.96 (m, 6H).

Compound HQ
$^1$H NMR ($CD_3OD$) δ 8.47 (s, 1H); 7.41 (s, 1H); 7.19 (s, 1H); 6.99 (s, 2H); 5.36 (s, 2H); 3.63 (t, 1H, J=9Hz); 3.53 (t, 1H, J=6 Hz); 3.27 (d, 2H, J=9 Hz); 2.35 (s, 6H); 1.83–1.77 (m, 1H); 1.71–1.68 (m, 2H); and 0.98 (d, 6H).

Example 9

Synthesis of Benzylpyrazole Compounds

Scheme 37

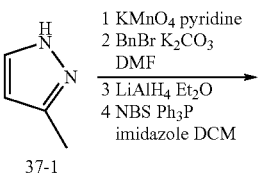

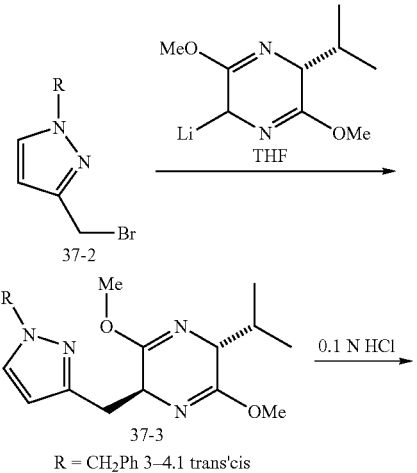

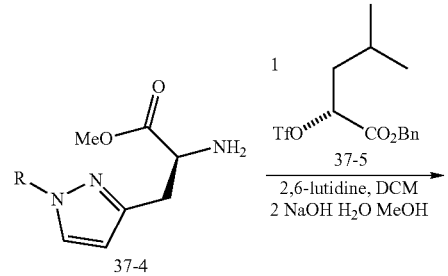

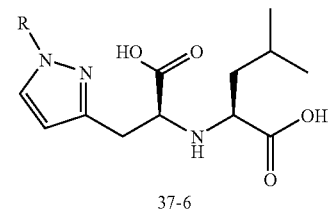

3-Methylpyrazole (2.0 g, 1.96 mL, 24.36 mmol) was dissolved in 92 mL of $H_2O$ and 46 mL of pyridine. This solution was warmed to reflux, and $KMnO_4$ (19.3 g, 121.79 mmol) was added in portions. The resulting mixture was heated at reflux for 45 minutes, cooled to room temperature, and filtered. The black precipitate was washed well with hot H₂O, and the filtrate was extracted twice with ethyl acetate (EtOAc). The aqueous phase was then concentrated to give a white solid. The mass of this material is well over 100% yield, and the $^1$H NMR spectrum is consistent with the desired pyrazole-3-carboxylic acid.

A portion of this white solid (3.18 g, estimated to be 1.13 g or 10.1 mmol of desired acid) was suspended in 100 mL of DMF. K₂CO₃ (6.98 g, 50.5 mmol) and benzyl bromide (2.34 mL, 20.2 mmol) were added. The reaction mixture was stirred overnight, and then diluted with H₂O and EtOAc. The aqueous phase was extracted with EtOAc. The combined organic phases were washed with H₂O and brine, dried over Na₂SO₄, filtered, and concentrated to give a pale yellow oil. Purification by column chromatography (SiO₂, 20% EtOAc in hexane) provided 1.06 g of the desired ester as a yellow oil that contains a small amount of DMF. $^1$H NMR spectrum is consistent with desired 1-benzylpyrazole-3-carboxylic acid benzyl ester.

1-Benzylpyrazole-3-carboxylic acid benzyl ester (1.06 g, 3.63 mmol) was then dissolved in 50 mL of Et₂O, and LiAlH₄ (334 mg, 9.06 mmol) was added in portions. This slurry was warmed to reflux, stirred overnight, and then cooled to room temperature. H₂O and MeOH were added carefully, and the resulting mixture was saturated with CO₂ gas. The slurry was then filtered, and the precipitate was washed well with MeOH. The filtrate was concentrated and purified by column chromatography (SiO₂, 50% EtOAc in hexane) to give 475 mg of the desired alcohol as a colorless oil (69% yield). $^1$H NMR spectrum is consistent with the desired (1-benzylpyrazol-3-yl) methanol.

This alcohol (1.0 g, 5.31 mmol) was dissolved in CH₂Cl₂ and 0.515 mL of pyridine. This solution was cooled to 0° C., and Ph₃P (3.90 g, 14.87 mmol) and NBS (2.84 g, 15.94 mmol) were added sequentially. The resulting brown mixture was stirred at 0° C. for 90 minutes, then diluted with EtOAc, and extracted with H₂O. The aqueous phase was extracted with EtOAc, and the combined organic phases were washed with brine, dried over Na₂SO₄, filtered, and concentrated to give a light brown solid. Purification by column chromatography (SiO₂, 5–10% EtOAc in hexane) provided the desired bromide (37-2) as a colorless oil (1.26 g, 95% yield). $^1$H NMR spectrum is consistent with the desired 1-benzyl-3-bromomethylpyrazole.

2-Isopropyl-3,6-dimethoxy-2,5-dihydropyrazine (0.324 mL, 1.81 mmol) was dissolved in 20 mL of THF, and the resulting solution was cooled to –78° C. n-BuLi (0.869 mL, 2.17 mmol, 2.5 M solution in hexane) was added dropwise via syringe, and the yellow solution was stirred for 30 minutes. A solution of the bromide (37-2, 500 mg, 1.99 mmol) in 5 mL of THF was then added to the cooled reaction mixture. This reaction mixture was allowed to warm slowly to room temperature over 2 hours and then stirred for another hour. A saturated NH₄Cl solution and EtOAc were added, and the organic phase was separated, extracted with brine, dried over Na₂SO₄, filtered and concentrated to give a yellow oil. Purification by column chromatography (SiO₂, 30–40% EtOAc in hexane) provided the alkylated dihydropyrazine (37-3) as a pale yellow oil (417 mg, 65% yield). $^1$HNMR is consistent with the desired product as a 4:1 ratio of trans:cis diastereomers.

The dihydropyrazine 37-3 (1.07 g, 3.02 mmol) was dissolved in 30 mL of THF, and 60 mL of 0.1 N HCl solution were added. This reaction mixture was stirred at room temperature for 5 hours and then diluted with Et₂O. The aqueous phase was extracted twice with Et₂O, saturated with NaCl, brought to pH 10 with conc. NH₄OH, and extracted twice with EtOAc. The two EtOAc extracts were combined and dried over Na₂SO₄, filtered, and concentrated. This oil was resuspended in toluene and concentrated to give 760 mg of the amino ester 37-4 as a yellow oil. $^1$H NMR spectrum is consistent with the desired amino ester.

The amino ester 37-4 (170 mg, 0.656 mmol) was dissolved in 6 mL of CH₂Cl₂ and 0.103 mL of 2,6-lutidine. This solution was cooled to –78° C., and a solution of triflate 37-5 (211 mg, 0.656 mmol) in 2 mL of CH₂Cl₂ was added dropwise. The triflate was prepared in a manner analogous to that described for the trifluoromethane sulfonate of leucic acid methyl ester. The resulting solution was stirred at –78° C. for 1 hour and then warmed to room temperature and stirred overnight. The reaction mixture was diluted with EtOAC and extracted with saturated NH₄Cl solution, H₂O, and brine, dried over Na₂SO₄, filtered and concentrated to give a yellow oil. Purification by column chromatography (SiO₂, 20% EtOAc in hexane) provided the desired 2-[2-(1-benzylpyrazol-3-yl)-1-methoxycarbonyl-ethylamino]-4-methylpentanoic acid benzyl ester as a colorless oil (154 mg, 56% yield).

2-[2-(1-Benzylpyrazol-3-yl)-1-methoxycarbonyl-ethylamino]-4-methylpentanoic acid benzyl ester (150 mg, 0.324 mmol) was dissolved in 3 mL of MeOH and a 1.0 M solution of NaOH (3.24 mL, 3.24 mmol) was added. The reaction mixture was stirred for 14 h at room temperature and then concentrated to give a white solid. Purification by HPLC chromatography provided the desired diacids as white powders. $^1$H NMR spectrum of each of these compounds is consistent with that expected.

Example 10

Synthesis of Phenylthiazolyl Compounds

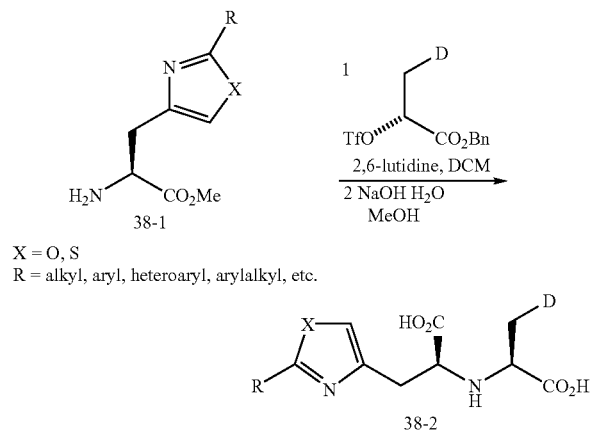

Scheme 38

X = O, S
R = alkyl, aryl, heteroaryl, arylalkyl, etc.

In this example, the compound wherein R is phenyl, X is sulfur and D is isobutyl was synthesized. Racemic leucic acid (10 g, 75.75 mmol) was dissolved in 100 mL of toluene and 15 mL of hexane, and this solution was cooled to 0° C. A solution of TMSCHN₂ in hexane (37.9 mL, 113.6 mmol, 2.0 M) was added dropwise. This solution was stirred at room temperature for 3 hours, carefully concentrated, suspended in EtOAc, extracted twice with saturated NaHCO$_3$ solution, dried over MgSO$_4$, filtered and concentrated to give the desired ester as a yellow oil (8.7 g, 79% yield). $^1$H NMR spectrum is consistent with.

2-Hydroxy-4-methyl pentanoic acid methyl ester (800 mg, 5.47 mmol) was dissolved in 50 mL of CH$_2$Cl$_2$ and the resulting solution was cooled to −78° C. 2,6-Lutidine (0.698 mL, 6.02 mmol) and trifluoromethanesulfonic anhydride (0.968 mL, 5.75 mmol) were added sequentially, and the solution was stirred at −78° C. for 30 min and at room temperature for 30 min. The reaction mixture was then diluted with CH$_2$Cl$_2$, washed with H$_2$O and brine, dried over MgSO$_4$, filtered through a pad of silica gel, and concentrated to give ca. 900 mg of a pink oil. $^1$H NMR spectrum is consistent with the desired trifluoromethane sulfonate.

To the amino ester (38-1, R=Ph, X=S, D=CH$_2$CH(Me)$_2$, 292 mg, 1.11 mmol) in 10 mL of CH$_2$Cl$_2$ was added 2,6-lutidine (0.142 mL, 1.22 mmol) and then a solution of the triflate prepared above (0.465 mL, 1.66 mmol) in 2 mL of CH$_2$Cl$_2$. The reaction mixture was allowed to warm to room temperature and was stirred overnight. The mixture was then diluted with CH$_2$Cl$_2$ and extracted with water and brine, dried over MgSO$_4$, filtered and concentrated to give a brown oil. Purification by column chromatography (SiO$_2$, 10–40% EtOAc in hexane) provided the desired diester as a colorless oil (355 mg, 82% yield). $^1$H NMR spectrum is consistent with 2-[1-methoxycarbonyl-2-(2-phenylthiazol-4-yl)ethylamino]-4-methyl pentanoic acid benzyl ester.

The diester (355 mg, 0.910 mmol) was dissolved in 10 mL of EtOH and 9.1 mL of 1 M NaOH solution. This solution was stirred overnight and concentrated. The residue was taken up in H$_2$O, acidified with 2 N HCl solution, and concentrated again. This very insoluble material was purified by HPLC to give the desired diacids (38-2, R=Ph, X=S, D=CH$_2$CH(Me)$_2$ early running diastereomer 19 mg as a white solid, later running diastereomer 10 mg as a white solid).

Example 11

ACE-2 Competitive Substrate Assay (ACS Assay)

A stock solution of ACE-2 in 10 mM HEPES (Sigma), 15 nM NaCl (Sigma) was stored as aliquots at −70° C.

Mass spectroscopy determined ACE-2 to be a carboxypeptidase that accepts a variety of P1' amino acids with a free carboxylic acid group. Mass spectroscopy data for the ACE-2 hydrolysis of Angiotensin I (1-10) to Angiotensin I (1-9) shows that in a sample with out ACE-2, Angiotensin I is not hydrolyzed. When treated with ACE-2, mass spectroscopy data shows that Angiotensin I (1-10) is converted to Angiotensin I (1-9). Similarly, it has been shown using mass spectroscopy that ACE-2 hydrolyzes Neurotensin (1-13) to Neurotensin (1-12). The mass spectroscopy data for des-Arg bradykinin (1-8) to des-Arg bradykinin (1-7) confirms that ACE-2 can hydrolyze des-Arg bradykinin.

ACE-2 enzymatic activity was assayed in microtitre plates by the following procedure. The ACE-2 assay buffer used contained 50 mM MES (Boehringer-Mannheim), 300 mM NaCl (Sigma) and 0.01% Brij-35 (Pierce Chemical Co.) at pH 6.5.

A 50 µL reaction mixture was prepared containing 25 µL of 1 nM ACE-2 in assay buffer, 20 µL of 125 µM substrate (see below) in assay buffer and 5 µl control solvent or test compound. Reactions were mixed and incubated at 25° C. Enzymatic cleavage of the substrate is marked by a fluorescence change (excitation at 328 nm, emission at 393 nm). Determination of ACE-2 enzymatic activity was found to be possible when fluorescent readings of the reactions were measured at excitation 320 nm and emission 405 nm using a BMG LabTechnologies PolarStar Plate Reader. Caspase 1 substrate (Bachem M-2195, Mca-Tyr-Val-Ala-Asp-Ala-Pro-(Dnp)Lys-OH) (SEQ ID NO:4) was tested as a synthetic substrate for ACE-2. Mass spectroscopy data analysis also showed that ACE-2 hydrolysed this substance between the P1 proline and P1' (DNP)Lys. Substrate optimization was achieved by the custom synthesis of Mca-Ala-Pro-(Dnp)Lys-OH (AnaSpec MIPH1). The results from the substrate optimization are shown in Table 1.

TABLE 1

| Substrate | $K_m$ (µM) | $k_{cat}/K_m$ (M$^{-1}$s$^{-1}$) | Fluorescence Units/mol |
|---|---|---|---|
| Bachem, M-2195 | 130 | 42,000 | 600 |
| AnaSpec MIPH-1 | 340 | 230,000 | 2880 |

ACE (Sigma, A2580) enzymatic activity was assayed in microtiter plates using the following protocol. ACE assay buffer was made from 50 mM HEPES (Sigma), 300 mM sodium chloride (Sigma), and 0.01% Brij-35 (Pierce Chemical Co) at pH 7.5.

A 50 µl reaction mixture was prepared containing 25 µl of 2 nM ACE in ACE assay buffer, 20 µl of 125 µM substrate, Abz-Gly-paranitroPhe-Pro-OH (Bachem M1100) in ACE assay buffer, and 5 µl control solvent or the test compound. Reactions were mixed and incubated at 25° C. Enzymatic cleavage of the substrate is marked by a fluorescence change (excitation 330 nm, emission 415 nm). Determination of ACE enzymatic activity was found to be possible when fluorescent readings of the reactions were measured at excitation 320 nm and emission at 405 nm using a BMG LabTechnologies PolarStar Plate Reader (Germany).

Carboxypeptidase A activity was measured using a literature assay (Holmquist and Riordan, "Carboxypeptidase A," *Methods of Enzymatic Analysis* (1984) p. 44–60). The assay was adapted to a 96 well format by adjusting to a 300 µL assay volume and using ultra-thin bottom plates (Costar/Corning) read at 328 nm. The assay was stopped using EDTA.

The activity of the test compounds was investigated using the procedure outlined above. The compounds were tested in 5% DMSO. Enzyme activity was measured at 12 compound concentrations. The $K_i$ was calculated by using $K_i=K_{iapp}/(1+[S]/K_m)$. The results are tabulated in Table 2.

In Table 2, the following key is used for the $K_i$'s:

| | ACE-2 Activity (Rat and Human) | | ACE Activity | | Carboxypeptidase A Activity |
|---|---|---|---|---|---|
| Some Inhibition | * | >0.5 µM | *** | >50 µM | *** >50 µM |
| Good Inhibition | ** | 0.5–0.1 µM | ** | 10–50 µM | ** 10–50 µM |
| Very Good Inhibition | *** | <0.1 µM | * | <10 µM | * <10 µM |

TABLE 2

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| A | 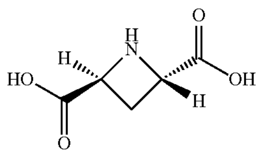 | Azetidine-2,4-dicarboxylic acid | 145.11 | * | | | | | |
| B | 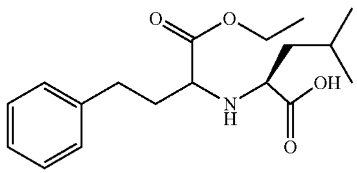 | 2-(1-Ethoxycarbonyl-3-phenyl-propylamino)-4-methyl-pentanoic acid | 321.42 | * | | | | | |
| C | 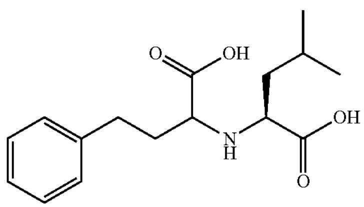 | 2-(1-Carboxy-3-phenyl-propylamino)-4-methyl-pentanoic acid | 293.36 | * | | *** | | | |
| D | 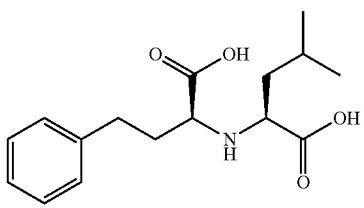 | 2-(1-Carboxy-3-phenyl-propylamino)-4-methyl-pentanoic acid | 293.36 | * | | *** | | % C 65.51, % H 7.90, % N 4.77 | % C 65.56, % H 7.82, % N 4.68 |
| E | 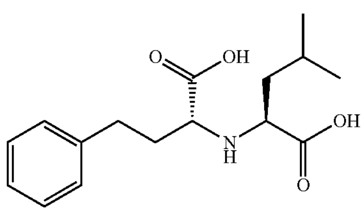 | 2-(1-Carboxy-3-phenyl-propylamino)-4-methyl-pentanoic acid | 293.36 | * | * | * | * | % C 46.44, % H 5.60, % N 3.39 (NaCl) | % C 4.64, % N 5.65, % N 2.94 (NaCl) |

TABLE 2-continued
| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| G | 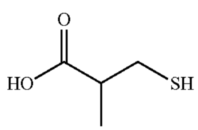 | 3-Mercapto-2-methyl-propionic acid | 120.17 | * | | *** | | | |
| H | 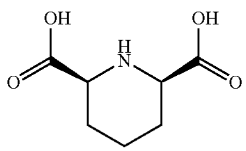 | Pipendine-2,6-dicarboxylic acid | 173.17 | * | | | | | |
| I | 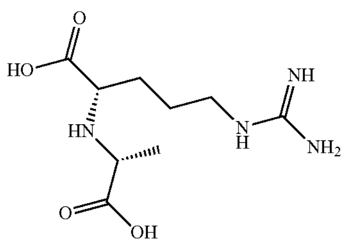 | 2-(1-Carboxy-ethylamino)-5-guanidino-pentanoic acid | 246.27 | * | | | | | |
| J | 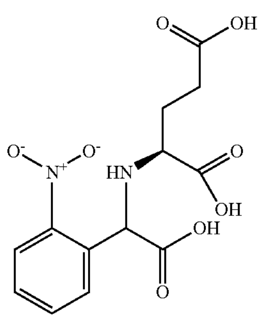 | 2-{[Carboxy-(2-nitro-phenyl)-methyl]-amino}-pentanedioic acid | 326.26 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| K | 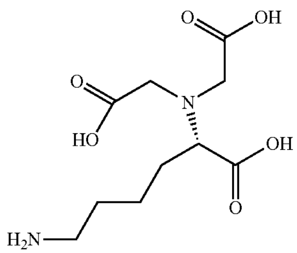 | 6-Amino-2-(bis-carboxymethyl-amino)-hexanoic acid | 262.26 | * | | | | | |
| L | 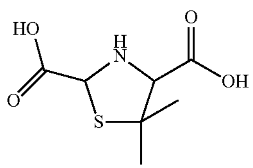 | 5,5-Dimethyl-thiazolidine-2,4-dicarboxylic acid | 205.23 | * | | | | | |
| M | 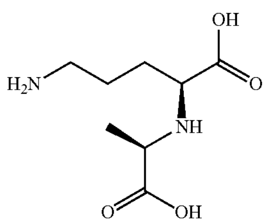 | 5-Amino-2-(1-carboxy-ethylamino)-pentanoic acid | 204.23 | * | | | | | |
| N | 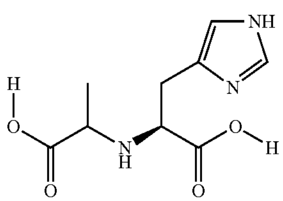 | 2-(1-Carboxy-ethylamino)-3-(1H-imidazol-4-yl)-propionic acid | 227.22 | * | | * | * | % C 44.74, % H 6.09, % N 17.39 (0.8 H2O) | % C 44.96, % H 5.71, % N 17.69 (0.8 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| O | 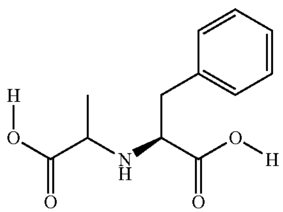 | 2-(1-Carboxy-ethylamino)-3-phenyl-propionic acid | 237.26 | * | | | | % C 58.96, % H 6.51, % N 5.73 (0.4 H2O) | % C 59.16, % H 6.37, % N 5.28 (0.4 H2O) |
| P | 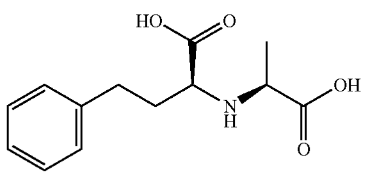 | 2-(1-Carboxy-ethylamino)-4-phenyl-butyric acid | 251.28 | * | | * | * | | |
| Q | 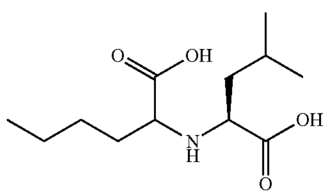 | 2-(1-Carboxy-3-methyl-butylamino)-hexanoic acid | 245.32 | * | | * | * | | |
| R | 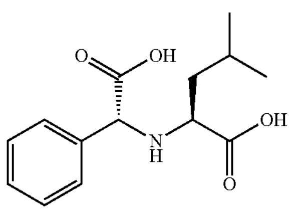 | 2-[(Carboxy-phenyl-methyl)-amino]-4-methyl-pentanoic acid | * | * | * | * | | | |
| T | 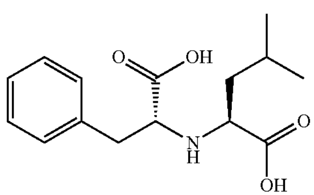 | 2-(1-Carboxy-2-phenyl-ethylamino)-4-methyl-pentanoic acid | 279.34 | * | | * |  | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| U | 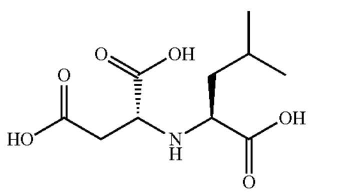 | 2-(1-Carboxy-3-methyl-butylamino)-succinic acid | 247.25 | * | * | * | * | | |
| V | 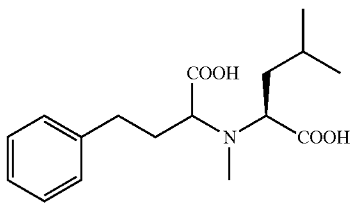 | 2-[(1-Carboxy-3-phenyl-propyl)-methyl-amino]-4-methyl-pentanoic acid | 307.39 | * | * | * | *** | % C 66.43, % H 8.20, % N 4.56 | % C 66.36, % H 8.17, % N 4.37 |
| W | 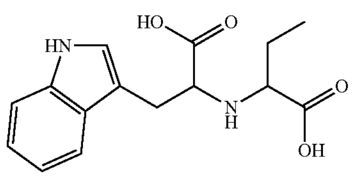 | 2-[1-Carboxy-2-(1H-indol-3-yl)-ethylamino]-butyric acid | 290.32 | * | * | * | *** | % C 59.80, % H 6.12, % N 9.30 (0.3 H2O) | % C 59.68, % H 5.98, % N 9.26 (0.3 H2O) |
| X | 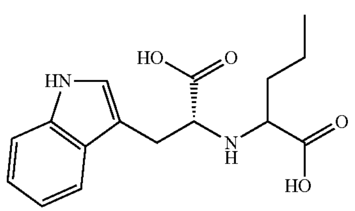 | 2-[1-Carboxy-2-(1H-indol-3-yl)-ethylamino]-pentanoic acid | 340.81 | * | * | * | *** | % C 56.09, % H 6.24, % N 8.18 (1 HCl, 0.1 H2O) | % C 55.99, % H 5.89, % N 7.79 (1 HCl, 0.1 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| Y | 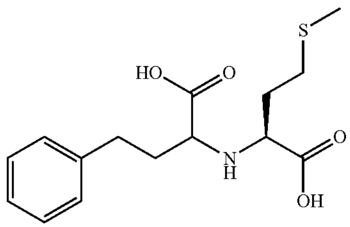 | 2-(1-Carboxy-3-methylsulfanyl-propylamino)-4-phenyl-butyric acid | * | | * | * | % C 54.66, % H 6.57, % N 4.25 (0.5 HCl) | % C 54.95, % H 6.54, % N 4.12 (0.5 HCl) | |
| Z | 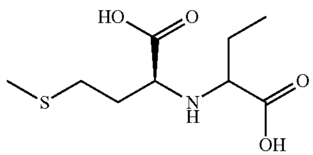 | 2-(1-Carboxy-propylamino)-4-methylsulfanyl-butyric acid | 235.30 | * | | * | * | % C 45.59, % H 7.31, % N 5.91 (0.1 H2O) | % C 45.37, % H 7.09, % N 5.83 (0.1 H2O) |
| AA | 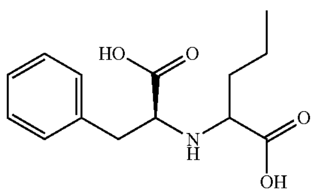 | 2-(1-Carboxy-2-phenyl-ethylamino)-pentanoic acid | 265.31 | * | | * | * | % C 62.53, % H 7.27, % N 5.21 (0.2 H2O) | % C 62.91, % H 6.99, % N 5.24 (0.2 H2O) |
| AB | 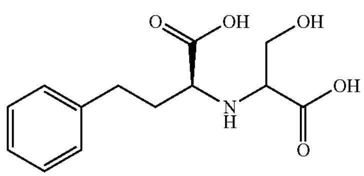 | 2-(1-Carboxy-2-hydroxy-ethylamino)-4-phenyl-butyric acid | 267.28 | * | | * | * | | |
| AC | 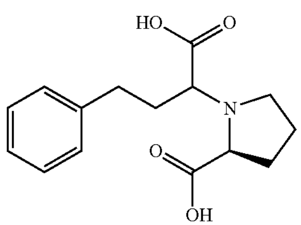 | 1-(1-Carboxy-3-phenyl-propyl)-pyrrolidine-2-carboxylic acid | 277.32 | * | | * | * | % C 60.96, % H 6.65, % N 4.74 (0.5 HCl) | % C 60.80, % H 6.77, % N 4.30 (0.5 HCl) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| AD | 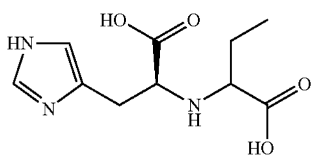 | 2-(1-Carboxy-ethylamino)-3-(1H-imidazol-4-yl)-propionic acid | 241.25 | * | | * | * | % C 43.33, % H 6.18, % N 17.18 (0.8 HCl, 0.4 NH3) | % C 43.54, % H 5.55, % N 16.78 (0.8 HCl, 0.4 NH3) |
| AE | 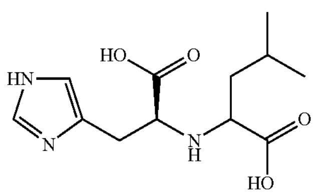 | 2-[1-Carboxy-2-(1H-imidazol-4-yl)-ethylamino] 4-methyl-pentanoic acid | 269.30 | * | | * | * | | |
| AF | 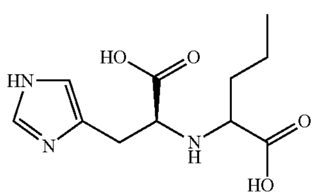 | 2-[1-Carboxy-2-(1H-imidazol-4-yl)-ethylamino] pentanoic acid | 291.73 | * | | * | * | % C 45.29, % H 6.22, % N 14.40 (1 HCl) | % C 45.12, % H 6.01, % N 14.04 (1 HCl) |
| AG | 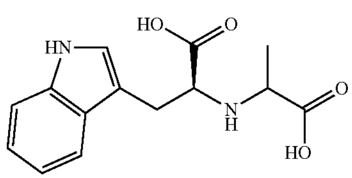 | 2-(1-Carboxy-ethylamino)-3-(1H-indol-3-yl)-propionic acid | 276.29 | * | | * | * | % C 59.31, % H 5.97, % N 9.88 (0.4 H2O) | % C 58.97, % H 5.59, % N 9.66 (0.4 H2O) |
| AH | 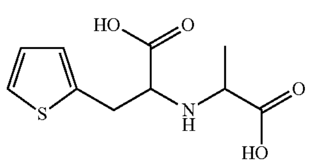 | 2-(1-Carboxy-ethylamino)-3-thiophen-2-yl-propionic acid | 243.28 | * | | * | * | % C 48.65, % H 5.47, % N 5.67 (0.2 H2O) | % C 48.27, % H 5.22, % N 5.32 (0.2 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| AI | 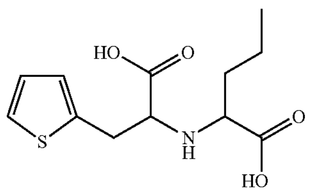 | 2-(1-Carboxy-2-thiophen-2-yl-ethylamino)-pentanoic acid | 271.34 | * | | * | * | % C 53.12, % H 6.32, % N 5.16 | % C 53.23, % H 6.15, % N 5.10 |
| AJ | 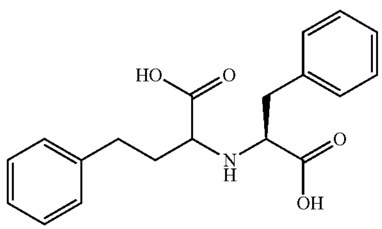 | 2-(1-Carboxy-2-phenyl-ethylamino)-4-phenyl-butynic acid | 327.38 | * | | * |  | % C 68.94, % H 6.42, % N 4.23 (0.1 HCl) | % C 68.88, % H 6.46, % N 3.95 (0.1 HCl) |
| AK | 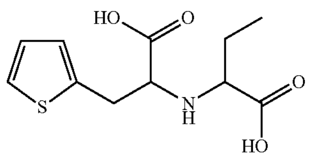 | 2-(1-Carboxy-2-thiophen-2-yl-ethylamino)-butynic acid | 257.31 | * | | * | * | | |
| AL | 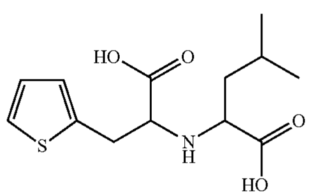 | 2-(1-Carobxy-2-thiophen-2-yl-ethylamino)-4-methyl-pentanoic acid | 321.82 | * | | * | * | % C 50.23, % H 6.39, % N 4.51 (0.7 HCl) | % C 50.56, % H 6.26, % N 4.55 (0.7 HCl) |
| AM | 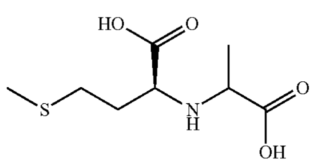 | 2-(1-Carboxy-ethylamino)-4-methylsulfanyl-butynic acid | 221.28 | * | | * | * | % C 39.24, % H 6.55, % N 6.29 (0.6 HCl, 0.1 NH3) | % C 39.41, % H 6.35, % N 6.22 (0.6 HCl, 0.1 NH3) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| AN | 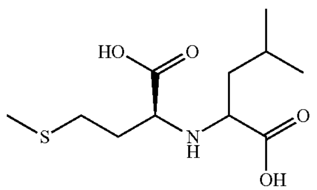 | 2-(1-Carboxy-3-methylsulfanyl-propylamino)-4-methyl-pentanoic acid | 280.39 | * | | * |  | % C 47.41, % H 8.57, % N 9.55 (0.9 NH3) | % C 47.57, % H 8.66, % N 9.37 (0.9 NH3) |
| AO | 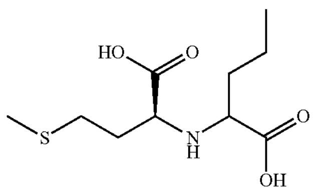 | 2-(1-Carboxy-3-methylsulfanyl-propylamino)-pentanoic acid | 285.79 | * | | * | * | % C 43.70, % H 7.22, % N 5.10 (0.7 HCl) | % C 43.78, % H 6.81, % N 5.30 (0.7 HCl) |
| AP | 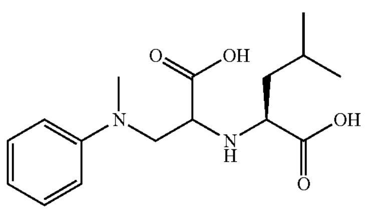 | 2-[1-Carboxy-2-(methyl-phenyl-amino)-ethylamino]-4-methyl-pentanoic acid | 308.38 | * |  | * | ** | % C 59.0, % N 12.4, % H 8.3 (as NH4 salt) M + 1 309, M − 1 307 | % C 58.7, % N 11.9, % H 8.3 M + 1 309, M 1 307 |
| AQ | 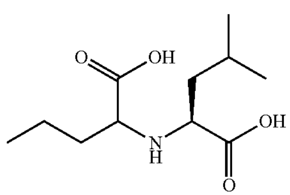 | 2-(1-Carboxy-butylamino)-4-methyl-pentanoic acid | 231.29 | * | | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| AR | 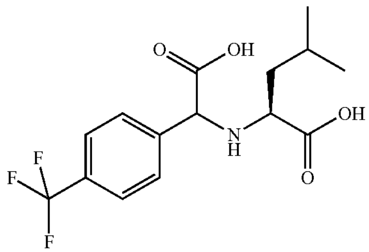 | 2-{[Carboxy-(4-trifluoromethyl-phenyl)-methyl]-amino}-4-methyl-pentanoic acid | 333.31 | * | | * | * | | |
| AS | 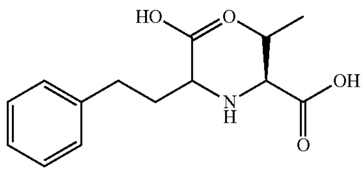 | 2-(1-Carboxy-3-phenyl-propylamino)-3-methyl-butynic acid | 279.34 | * | * | * | * | % C 64.50, % H 7.58, % N 5.01 | % C 64.02, % H 7.23, % N 4.60 |
| AT | 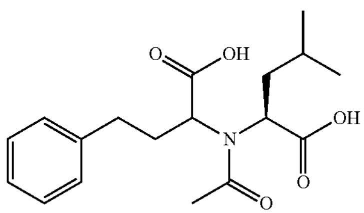 | 2-[Acetyl-(1-carboxy-3-phenyl-propyl)-amino]-4-methyl-pentanoic acid, Isomer A | 335.40 | * | | * | * | | ND |
| AU | 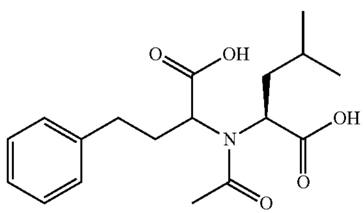 | 2-[Acetyl-(1-carboxy-3-phenyl-propyl)-amino]-4-methyl-pentanoic acid, Isomer B | 335.40 | * | | * | * | | ND |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| AV | 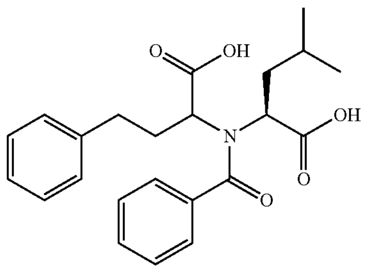 | 2-[Benzoyl-(1-carboxy-3-phenyl-propyl)-amino]-4-methyl-pentanoic acid | 397.47 | * | * | * |  | | |
| AW | 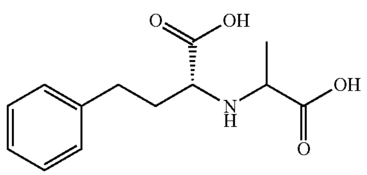 | 2-(1-Carboxy-ethylamino)-4-phenyl-butyric acid | 268.31 | * | | * | * | % C 58.52, % H 7.37, % N 8.92 (0.2 H2O, 0.7 NH3) | % C 58.71, % H 7.56, % N 8.86 (0.2 H2O, 0.7 NH3) |
| AX | 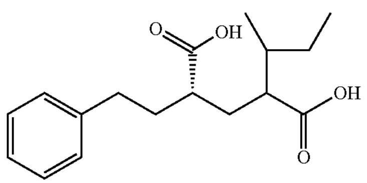 | 2-(1-Carboxy-3-phenyl-propylamino)-3-methyl-pentanoic acid | 293.36 | * | | * | * | % C 63.92, % H 7.78, % N 4.66 (0.2 HCl) | % C 63.85, % H 7.56, % N 5.01 (0.2 HCl) |
| AZ | 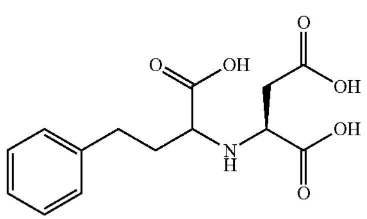 | 2-(1-Carboxy-3-phenyl-propylamino)-succinic acid | 295.29 | * | * | * | * | % C 54.26, % H 5.66, % N 4.52 (0.4 HCl) | % C 54.24, % H 5.74, % N 4.45 (0.4 HCl) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| BA | 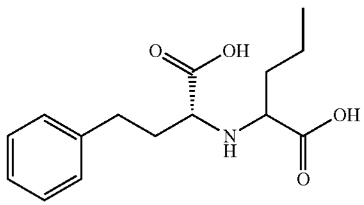 | 2-(1-Carboxy-3-phenyl-propylamino)-pentanoic acid | 279.34 | * | * | * | * | | |
| BB | 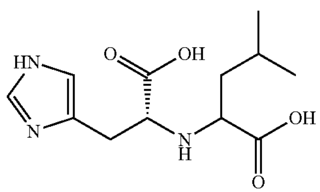 | 2-[1-Carboxy-2-(1H-imidazol-4-yl)-ethylamino]-4-methyl-pentanoic acid | 269.30 | * | * | * | *** | | |
| BC | 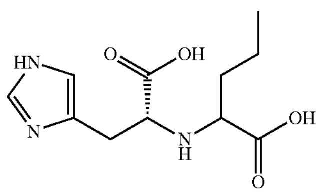 | 2-[1-Carboxy-2-(1H-imidazol-4-yl)-ethylamino]-pentanoic-acid | 255.27 | * | * |  | * | % C 50.05, % H 6.99, % N 17.51 (0.2 H2O, 0.3 NH3) | % C 49.97, % H 7.18, % N 17.70 (0.2 H2O, 0.3 NH3) |
| BD | 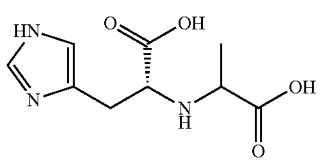 | 2-(1-Carboxy-ethylamino)-3-(1H-imidazol-4-yl)-propionic acid | 227.22 | * | * | * | * | % C 45.76, % H 5.97, % N 17.79 (0.5 H2O) | % C 46.10, % H 5.71, % N 17.38 (0.5 H2O) |
| BE | 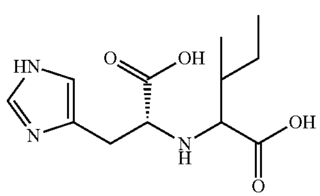 | 2-[1-Carboxy-2-(1H-imidazol-4-yl)-ethylamino]-3-methyl-pentanoic acid | 269.30 | * | * |  | * | % C 52.04, % H 7.41, % N 17.45 (0.5 NH3) | % C 51.71, % H 7.33, % N 17.22 (0.5 NH3) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| BF | 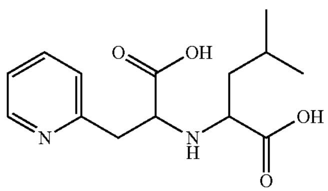 | 2-(1-Carboxy-2-pyridin-2-yl-ethylamino)-4-methyl-pentanoic acid | 280.32 | * |  | * | *** | | |
| BG | 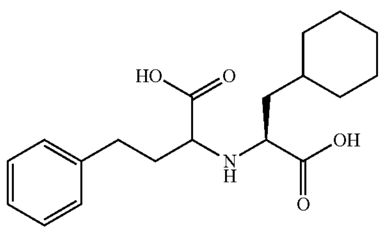 | 2-(1-Carboxy-2-cyclohexy ethylamino)-4-phenyl-butync acid | 369.89 | * | | * | * | | |
| BH | 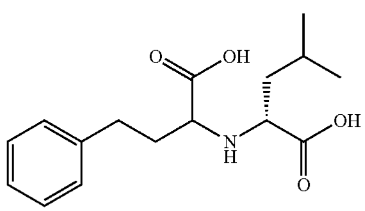 | 2-(1-Carboxy-3-phenyl-propylamino)-4-methyl-pentanoic acid | 293.36 | * | * | * | *** | % C 64.70, % H 7.84, % N 4.72 (0.1 HCl) | % C 64.56, % H 7.28, % N 4.45 (0.1 HCl) |
| BI | 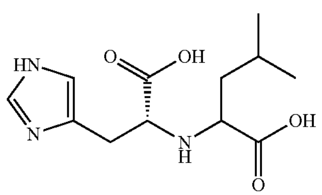 | 2-[1-Carboxy-2-(1H-imidazol-4-yl)-ethylamino] 4-methyl-pentanoic acid, Isomer A | 269.30 | * | * | * | * | % C 50.96, % H 6.93, % N 14.38 (0.3 HCl, 0.2 MeCOOH) | % C 51.39, % H 6.40, % N 13.98 (0.3 HCl, 0.2 MeCOOH) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| BJ | 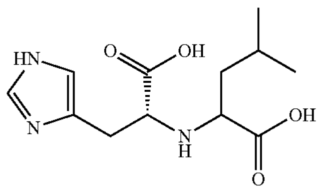 | 2-[1-Carboxy-2-(1H-imidazol-4-yl)-ethylamino] 4-methyl-pentanoic acid, Isomer B | 269.30 | * | * |  | * | % C 50.90, % H 6.90, % N 14.84 (0.4 HCl) | % C 51.39, % H 6.40, % N 14.96 (0.4 HCl) |
| BK | 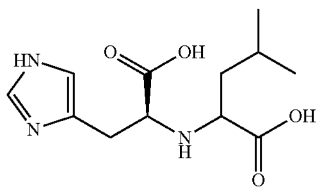 | 2-[1-Carboxy-2-(1H-imidazol-4-yl)-ethylamino] 4-methyl-pentanoic acid, Isomer A | 269.30 | * |  | * | *** | % C 52.94, % H 7.09, % N 14.94 (0.2 MeCOOH) | % C 52.63, % H 6.76, % N 14.56 (0.2 MeCOOH) |
| BL | 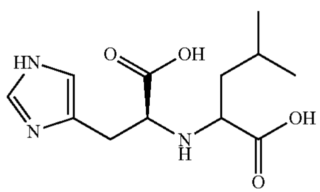 | 2-[1-Carboxy-2-(1H-imidazol-4-yl)-ethylamino] 4-methyl-pentanoic acid, Isomer B | 269.30 | * | * |  | * | % C 52.27, % H 7.04, % N 14.75 (0.2 MeCOOH, 0.1 HCl) | % C 53.39, % H 6.63, % N 14.39 (0.2 MeCOOH, 0.1 HCl) |
| BN | 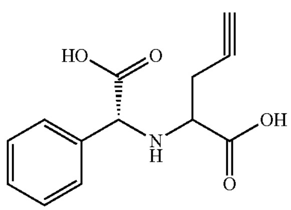 | 2-[(Carboxy-phenyl-methyl)-amino]-pent-4-ylnoic acid | 291.23 | * | | * | * | % C 48.79, % H 4.47, % N 4.38 (DISODIUM SALT, 1.6 H2O) | % C 48.47, % H 4.03, % N 4.08 (DISODIUM SALT 1.6 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| BO | 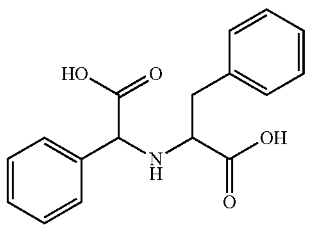 | 2-[(Carboxy-phenyl-methyl)-amino]-3-phenyl-propionic acid | 343.31 | * | | * |  | % C 53.32, % H 5.11, % N 3.66 (DISODIUM SALT, 2.2 H2O) | % C 53.10, % H 4.83, % N 3.38 (DISODIUM SALT, 2.2 H2O) |
| BP | 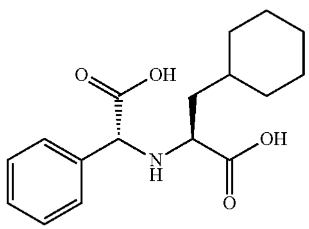 | 2-[(Carboxy-phenyl-methyl)-amino]-3-cyclohexyl-propionic acid | 305.37 | * | | * | * | % C 59.73, % H 7.08, % N 4.10 (HCl salt) | % C 59.70, % H 7.58, % N 4.0 |
| BQ | 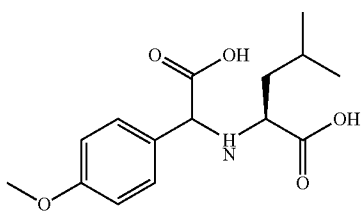 | 2-[(Carboxy-(4-methoxy-phenyl)-methyl]-amino]-4-methyl-pentanoic acid | 295.34 | * | * | * | * | | |
| BR | 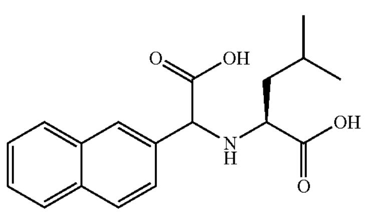 | 2-[(Carboxy-naphthalen-2-yl-methyl)-amino]-4-methyl-pentanoic acid | 315.37 | * | * | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| BS | 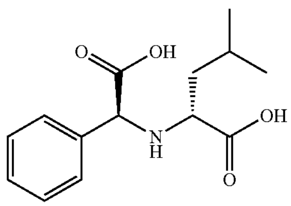 | 2-[(Carboxy-phenyl-methyl)-amino]-4-methyl-pentanoic acid | 265.31 | * | * | * | * | % C 59.3, % N 4.9, % H 6.9 (as 0.5 HCl salt) M + 1 266, M − 1 264 | % C 58.7, % N 4.2, % H 6.8 (as 0.5 HCl salt) M + 1 266, M − 1 264 |
| BT | 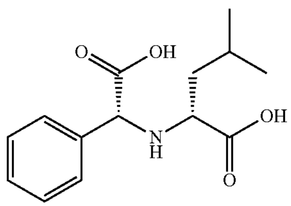 | 2-[(Carboxy-phenyl-methyl)-amino]-4-methyl-pentanoic acid | 265.31 | * | * | * | * | % C 59.3, % N 4.9, % H 6.9 (as 0.5 HCl salt) M + 1 266, M − 1 264 | % C 58.5, % N 4.2, % H 6.8 (as 0.5 HCl salt) M + 1 266, M − 1 264 |
| BU | 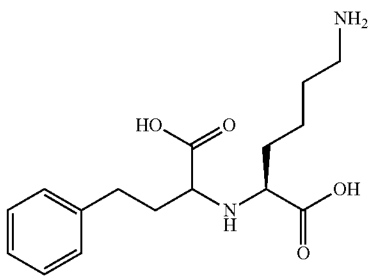 | 6-Amino-2-(1-carboxy-3-phenyl-propylamino)-hexanoic acid | 308.38 | * | * | * | * | % C 58.88, % H 8.03, % N 8.58 | % C 58.76, % H 7.94, % N 8.40 |
| BV | 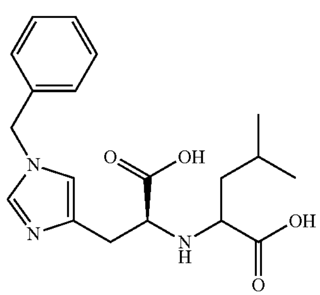 | 2-[2-(1-Benzyl-1H-imidazol-4-yl)-1-carboxy-ethylamino]-4-methyl-pentanoic acid | 359.43 | * | * | ** | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| BW | 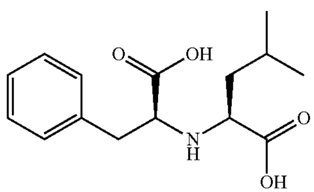 | 2-(1-Carboxy-2-phenyl-ethylamino)-4-methyl-pentanoic acid | 279.34 | * |  | * | ** | | |
| BX | 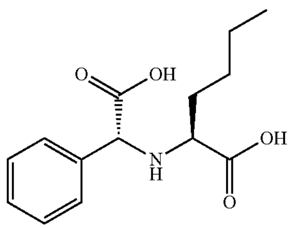 | 2-[(Carboxy-phenyl-methyl)-amino]-hexanoic acid | 265.31 | * | | * | * | | |
| BY | 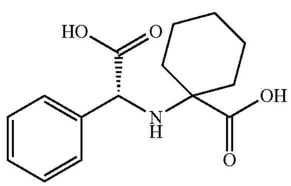 | 1-[(Carboxy-phenyl-methyl)-amino]-cyclohexanecarboxylic acid | 277.32 | * | | * | * | | |
| BZ | 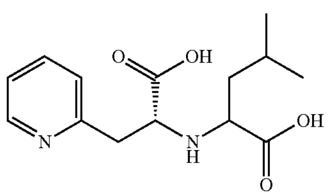 | 2-(1-Carboxy-2-pyridin-2-yl-ethylamino)-4-methyl-pentanoic acid | 280.32 | * | * | * | * | % C 58.18, % H 7.43, % N 11.15 (0.2 H2O, 0.3 NH3) | % C 58.01, % H 7.03, % N 10.95 (0.2 H2O, 0.3 NH3) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| CA | 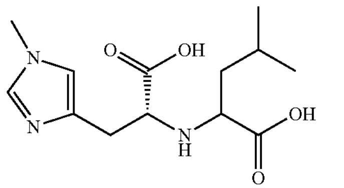 | 2-[-Carboxy-2-(1-methyl-1H-imidazol-4-yl)-ethylamino]-4-methyl-pentanoic acid | 283.33 | * | * | * | * | % C 52.41, % H 7.24, % N 14.10 (0.4 HCl) | % C 52.57, % H 6.87, % N 13.93 (0.4 HCl) |
| CB | 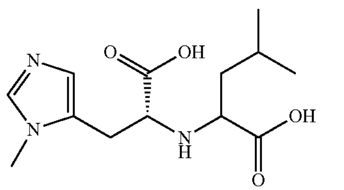 | 2-[1-Carboxy-2-(3-methyl-3H-imidazol-4-yl)-ethylamino]-4-methyl-pentanoic acid | 283.33 | * | * | * | * | % C 52.80, % H 7.53, % N 15.63 (0.2 HCl, 0.3 NH3) | % C 52.49, % H 7.50, % N 15.58 (0.2 HCl, 0.3 NH3) |
| CC | 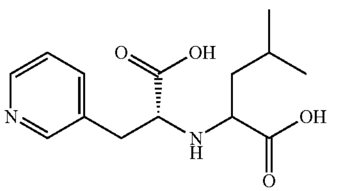 | 2-(1-Carboxy-2-pyridin-3-yl-ethylamino)-4-methyl-pentanoic acid | 280.32 | * | * | * | * | % C 57.44, % H 7.27, % N 11.01 (0.2 HCl, 0.3 NH3) | % C 57.20, % H 7.02, % N 10.83 (0.2 HCl, 0.3 NH3) |
| CD | 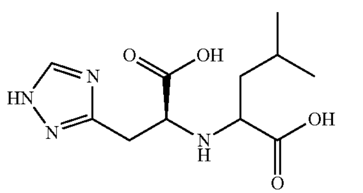 | 2-[1-Caboxy-2-(1H-[1,2,4]triazol-3-yl)-ethylamino]-4-methyl-pentanoic acid | 270.29 | * |  | * | *** | % C 46.98, % H 6.56, % N 19.92 (0.3 HCl) | % C 47.22, % H 6.43, % N 19.87 (0.3 HCl) |
| CE | 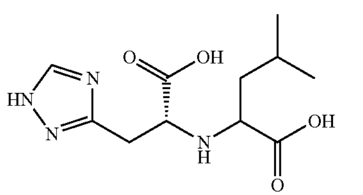 | 2-[1-Carboxy-2-(1H-[1,2,4]triazol-3-yl)-ethylamino]-4-methyl-pentanoic acid | 270.29 | * | * | * | * | % C 45.91, % H 7.00, % N 22.39 (0.2 HCl, 0.6 NH3) | % C 45.85, % H 6.62, % N 22.65 (0.2 HCl, 0.6 NH3) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| CF | 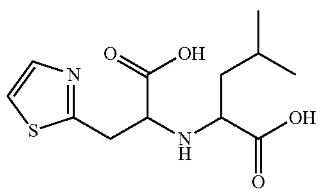 | 2-(1-Carboxy-2-thiazol-2-yl-ethylamino)-4-methyl-pentanoic acid | 286.35 | * |  | * | *** | % C 47.74, % H 6.74, % N 12.53 (0.1 HCl, 0.7 NH3) | % C 47.57, % H 6.49, % N 12.41 (0.1 HCl, 0.7 NH3) |
| CG | 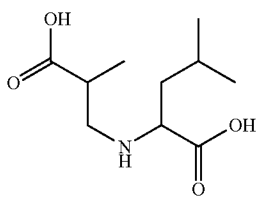 | 2-(2-Carboxy-propylamino)-4-methyl-pentanoic acid | 217.27 | * | | * | * | % C 53.14, % H 8.92, % N 8.06 (0.1 HCl, 0.3 NH3) | % C 53.03, % H 8.75, % N 7.77 (0.1 HCl, 0.3 NH3) |
| CH | 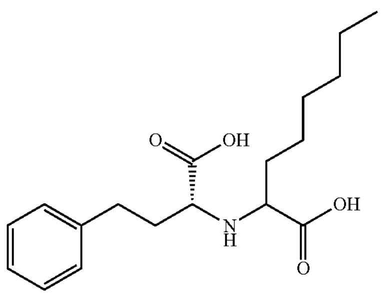 | 2-(1-Carboxy-3-phenyl-propylamino)-octanoic acid | 321.42 | * | | * | * | % C 60.53, % H 7.90, % N 3.92 (1 HCl) | % C 60.88, % H 7.66, % N 3.76 (1 HCl) |
| CI | 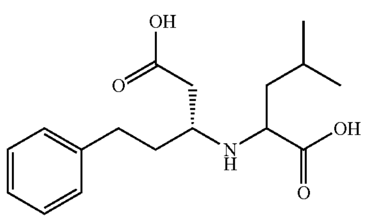 | 2-(1-Carboxymethyl-3-phenyl-propylamino)-4-methyl-pentanoic acid | 307.39 | * | | * | * | % C 65.28, % H 8.25, % N 4.48 (0.3 H2O) | % C 65.17, % H 8.16, % N 4.70 (0.3 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| CJ | 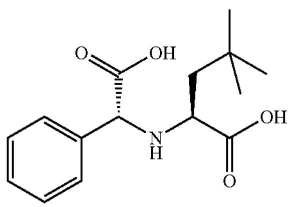 | 2-[(Carboxy-phenyl-methyl)-amino]-4,4-dimethyl-pentanoic acid | 315.80 | * | * | * | * | % C 60.55, % H 7.28, % N 4.71 (0.5 HCl) | % C 60.25, % H 7.68, % N 4.49 (0.5 HCl) |
| CK | 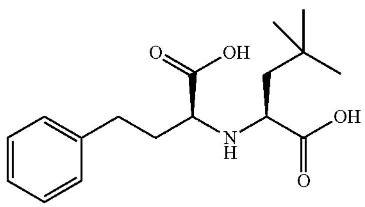 | 2-(1-Carboxy-3-phenyl-propylamino)-4,4-dimethyl pentanoic acid | 307.39 | * |  | * | *** | % C 66.04, % H 8.22, % N 4.53 (0.1 H2O) LOT 1), % C 66.43, % H 8.20, % N 4.56 | % C 65.63, % H 8.28, % N 4.36 (0.1 H2O) (LOT 1), % C 66.40, % H 8.32, % N 4.57 |
| CL | 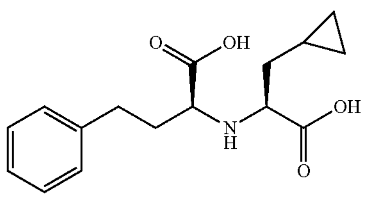 | 2-(1-Carboxy-2-cyclopropyl-ethylamino)-4-phenyl-butynic acid | 291.35 | * |  | * | *** | % C 62.82, % H 7.05, % N 4.58 (0.4 HCl) | % C 63.07, % H 6.88, % N 4.51 (0.4 HCl) |
| CM | 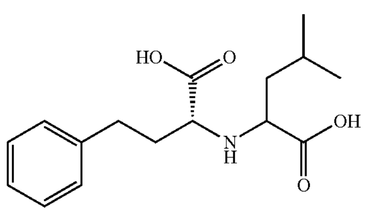 | 2-(1-Carboxy-3-phenyl-propylamino)-4-methyl-pentanoic acid | | * | | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| CN | 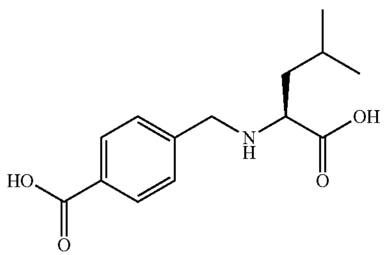 | 4-[(1-Carboxy-3-methyl-butylamino)-methyl]-benzoic acid | 265.31 | * | | * | * | % C 61.3, % N 5.1, % H 7.4 (as monohydrate) | % C 61.9, % N 5.0, % H 7.4 (as monohydrate) |
| CO | 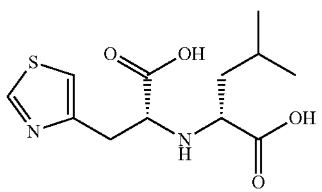 | 2-(1-Carboxy-2-thiazol-4-yl-ethylamino)-4-methyl-pentanoic acid | 303.38 | * | | * | * | % C 43.96, % H 7.24, % N 12.18 (2 MeCOOH, 1.8 NH3) | % C 44.02, % H 6.99, % N 12.11 (2 MeCOOH, 1.8 NH3) |
| CP | 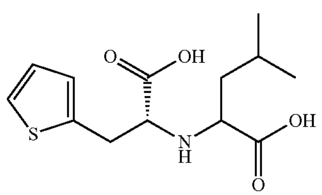 | 2-(1-Carboxy-2-thiophen-2-yl-ethylamino)-4-methyl-pentanoic acid | 285.36 | * | * | * |  | % C 52.70, % H 6.79, % N 5.39, % Cl 1.56, % S 10.82 (0.21 H2O, 0.13 HCl, 0.14 NH3) | % C 52.31, % H 6.63, % N 5.23, % Cl 1.76, % S 11.27 (0.21 H2O, 0.13 HCl, 0.14 NH3) |
| CQ | 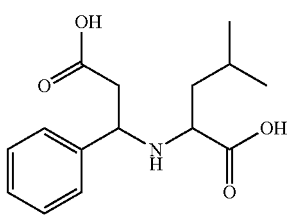 | 2-(2-Carboxy-1-phenyl-ethylamino)-4-methyl-pentanoic acid | 279.34 | * | | * | * | % C 59.91, % H 7.57, % N 6.52 (0.4 HCl, 0.4 NH3) | % C 59.75, % H 7.25, % N 6.77 (0.4 HCl, 0.4 NH3) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| CR | 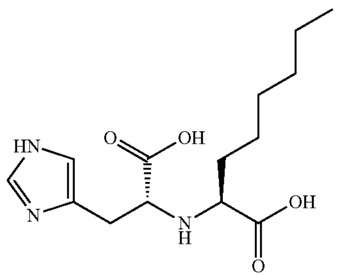 | 2-[1-Carboxy-2-(1H-imidazol-4-yl)-ethylamino) octanoic acid | 297.35 | * | * | * | * | % C 54.95, % H 7.81, % N 13.35 (0.3 H2O, 0.2 MeCOOH) | % C 55.08, % H 7.70, % N 12.97 (0.3 H2O, 0.2 MeCOOH) |
| CS | 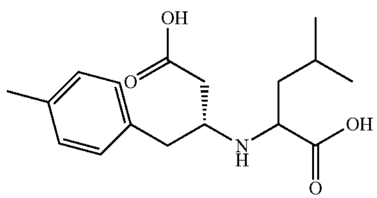 | 2-[2-Carboxy-1-(4-methyl-benzyl)-ethylamino]-4-methyl-pentanoic acid | 343.85 | * | * | * | * | % C 55.87, % H 7.83, % N 3.83 (1.2 H2O, 1 HCl) | % C 55.66, % H 7.64, % N 3.76 (1.2 H2O, 1 HCl) |
| CT | 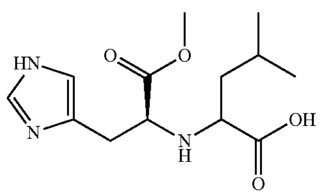 | 2-[2-(1H-Imidazol-4-yl)-1-methoxycarbonyl-ethylamino]-4-methyl-pentanoic acid, Isomer A | 283.33 | * |  | * | *** | % C 48.87, % H 7.64, % N 12.21 (1 H2O, 1.2 MeCOOH, 0.3 NH3) | % C 48.71, % H 7.78, % N 12.12 (1 H2O, 1.2 MeCOOH, 0.3 NH3) |
| CU | 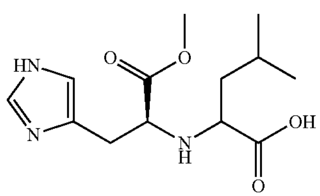 | 2-[2-(1H-Imidazol-4-yl)-1-methoxycarbonyl-ethylamino]-4-methyl-pentanoic acid, Isomer B | 283.33 | * | * | * | *** | % C 52.41, % H 7.46, % N 11.18 (1.1 MeCOOH, 0.3 EtOAc) | % C 52.26, % H 7.69, % N 11.52 (1.1 MeCOOH, 0.3 EtOAc) |

TABLE 2-continued

| Ref. No. | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|
| CV | 2-(1-Carboxy-2-thiazol-4-yl-ethylamino)-4-methyl-pentanoic acid | 303.38 | * | * | *** | *** | % C 47.98, % H 7.22, % N 12.34, % S 9.42 (0.1 H2O, 1 NH3, 0.4 EtOAc) | % C 47.69, % H 6.92, % N 11.70, % S 9.66 (0.1 H2O, 1 NH3, 0.4 EtOAc) |
| CW | 2-[2-(1-Benzyl-1H-imidazol-4-yl)-1-carboxy-ethylamino]-4-methyl-pentanoic acid | 359.43 | * | * | *** | *** | | |
| CX | 2-[2-(1-Benzyl-1H-imidazol-4-yl)-1-carboxy-ethylamino]-4-methyl-pentanoic acid | 395.89 | * | * | ** | *** | % C 56.18, % H 6.76, % N 11.03 (1 HCl, 0.3 NH3, 0.3 MeCOOH) | % C 56.25, % H 6.97, % N 11.19 (1 HCl, 0.3 NH3, 0.3 MeCOOH) |
| CY | 4-Methyl-2-(3-phenyl-propylamino)-pentanoic acid | 249.35 | * | * | *** | *** | % C 72.2, % N 5.6, % H 9.2 | % C 72.2, % N 5.6, % H 9.2 |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| CZ | 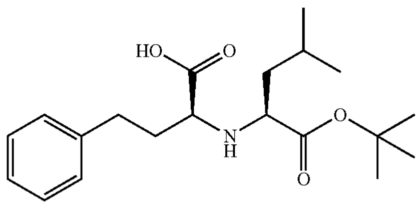 | 2-(1-Carboxy-3-phenyl-propylamino)-4-methyl-pentanoic acid tert-butyl ester | 349.47 | * | | * | * | C, 68.74, H, 8.94; N, 4.01 | C, 68.20, H, 8.90; N, 3.93 |
| DA | 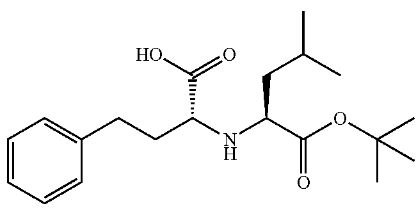 | 2-(1-Carboxy-3-phenyl-propylamino)-4-methyl-pentanoic acid tert-butyl ester | 349.47 | * | | * | * | C, 68.74; H, 8.94 N, 4.01 | C, 68.23; H, 8.85: N, 3.99 |
| DB | 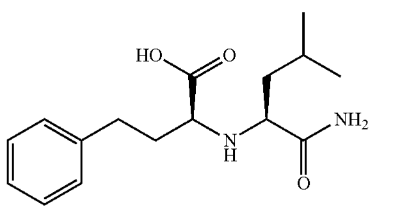 | 2-(1-Carbamoyl-3-methyl-butylamino)-4-phenyl-butanoic acid | 292.38 | * | | * | * | | |
| DC | 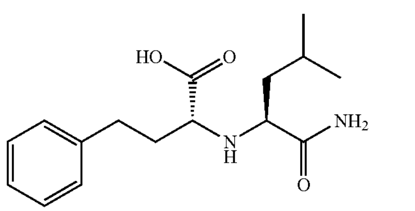 | 2-(1-Carbamoyl-3-methyl-butylamino)-4-phenyl-butynic acid | 322.45 | * | | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| DD | 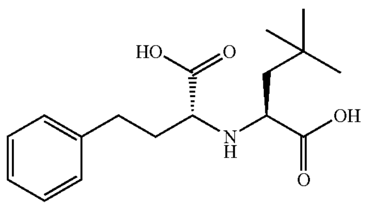 | 2-(1-Carboxy-3-phenyl-propylamino)-4,4-dimethyl pentanoic acid | 307.39 | * | * | * | * | % C 56.70, % H 8.51, % N 6.96 (3 H2O, MeCN) | % C 56.92, % H 8.13, % N 7.23 % Cl 0.0 (3H2O, MeCN) |
| DE | 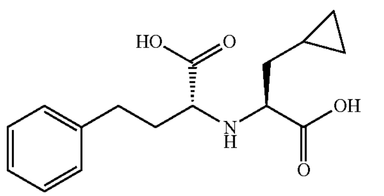 | 2-(1-Carboxy-2-cyclopropyl-ethylamino)-4-phenyl-butyric acid | 291.35 | * | * | * | * | % C 62.82, % H 7.05, % N 4.58 (0.4 HCl) | % C 63.09, % H 7.09, % N 4.49 (0.4 HCl) |
| DF | 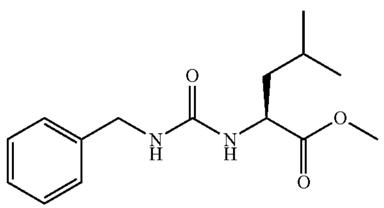 | 2-(3-Benzyl-ureido)-4-methyl-pentanoic acid methyl ester | 278.35 | * | * | * | * | % C 64.73, % H, 7.97, % N 10.06 | % C 64.75, % H 7.867, % N 9.95 |
| DG | 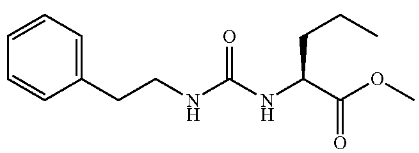 | 4-Methyl-2-(3-phenethyl-ureido)-pentanoic acid methyl ester | 292.38 | * | * | * | * | | |
| DH | 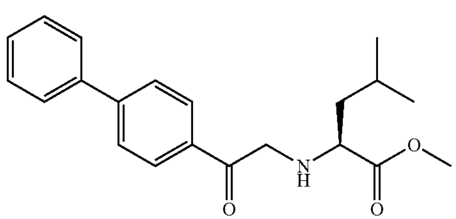 | 2-(2-Biphenyl-4-yl-2-oxo-ethylamino)-4-methyl-pentanoic acid methyl ester | 339.43 | * | * | * | * | | |

TABLE 2-continued

| Ref. No. | Chemical Name | Structure | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| DI | 2-(3-Benzyloxycarbonylamino-2-oxo-4-phenyl-butylamino)-4-methyl-pentanoic acid methyl ester | 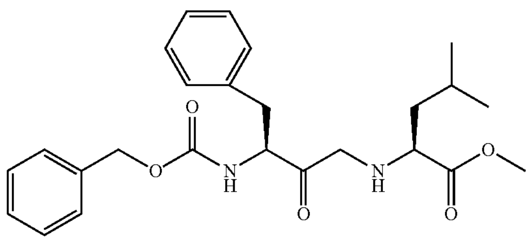 | 440.54 | * | * | * |  | % C 68.16, % H 7.32, % N 6.36 | % C 68.19, % H 7.16, % N 6.31 |
| DJ | 2-[1-Carboxy-2-(1H-imidazol-4-yl)-ethylamino)pentanoic acid, Isomer A | 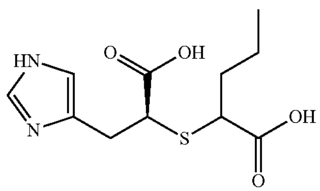 | 315.32 | * |  | * | *** | % C 46.97, % H 6.96, % N 12.84 (1 H2O, 0.9 MeCOOH) | % C 46.60, % H 7.29, % N 13.06 (1 H2O, 0.9 MeCOOH) |
| DK | 2-[1-Carboxy-2-(1H-imidazol-4-yl)-ethylamino)pentanoic acid, Isomer B | 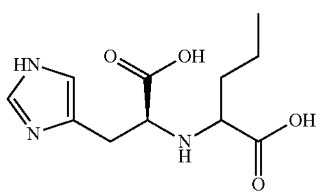 | 255.27 | * | * |  | * | % C 49.35, % H 6.86, % N 14.89 (0.5 H2O, 0.3 MeCOOH) | % C 49.23, % H 6.72, % N 14.63 (0.5 H2O, 0.3 MeCOOH) |
| DL | 2-[2-(1-Benzyl-1H-imidazol-4-yl)-1-carboxy-ethylamino]-4-methyl-pentanoic acid, Isomer A | 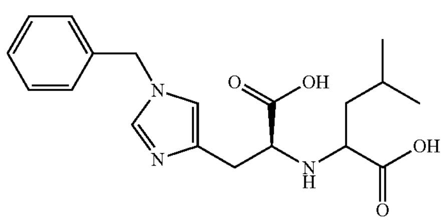 | 359.43 | * | * | * | * | % C 59.05, % H 7.30, % N 10.87 (1.5 H2O) | % C 59.02, % H 7.03, % N 11.08 (1.5 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| DM | 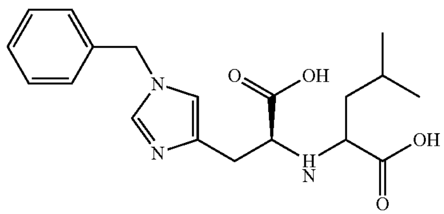 | 2-[2-(1-Benzyl-1H-imidazol-4-yl)-1-carboxy-ethylamino]-4-methyl-pentanoic acid, Isomer B | 359.43 | * | * | * | * | % C 58.77, % H 7.32, % N 11.54 (1 H2O, 0.3 MeCOOH, 0.3 NH3) | % C 58.60, % H 6.96, % N 11.28 (1 H2O, 0.3 MeCOOH, 0.3 NH3) |
| DN | 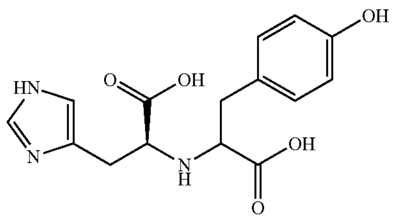 | 2-[1-Carboxy-2-(4-hydroxy-phenyl)-ethylamino]-3-(1H-imidazol-4-yl)-propionic acid, Isomer A | 319.32 | * | * | * | * | | |
| DO | 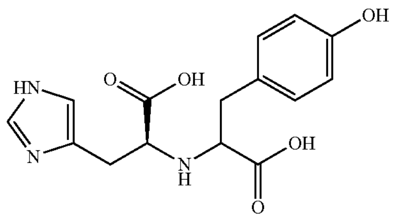 | 2-[1-Carboxy-2-(4-hydroxy-phenyl)-ethylamino]-3-(1H-imidazol-4-yl)-propionic acid, Isomer B | 319.32 | * |  |  | *** | % C 49.39, % H 5.25, % N 11.25 (0.5 H2O, 1 HCl) | % C 49.21, % H 5.55, % N 11.55 (0.5 H2O, 1 HCl) |
| DP | 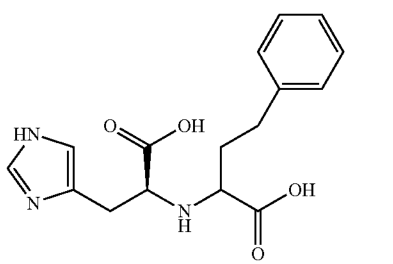 | 2-[1-Carboxy-2-(1H-imidazol-4-yl)-ethylamino]-4-phenyl-butyric acid | 317.34 | * |  |  | *** | % C 59.88, % H 6.09, % N 13.09 (0.2 H2O) | % C 59.97, % H 6.04, % N 13.07 (0.2 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| DQ | 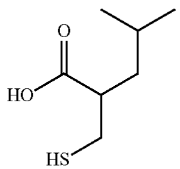 | 2-Mercaptomethyl-4-methyl-pentanoic acid | 162.25 | * |  | * | *** | | |
| DR | 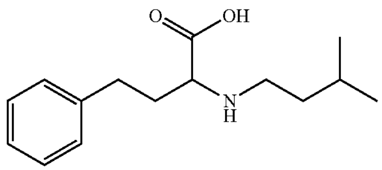 | 2-(3-Methyl-butylamino)-4-phenyl-butynic acid | 249.35 | * |  | * | ** | | |
| DS | 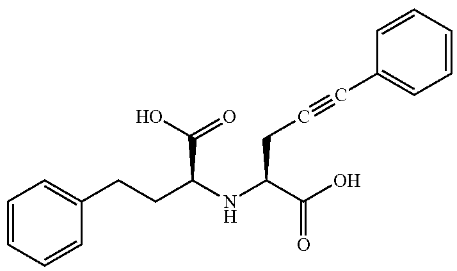 | 2-(1-Carboxy-3-phenyl-propylamino)-5-phenyl-pent-4-ynoic acid | 351.40 | * | * | * | ** | | |
| DT | 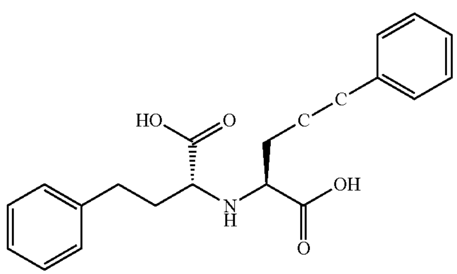 | 2-(1-Carboxy-3-phenyl-propylamino)-5-phenyl-pent-4-ynoic acid | 351.40 | * | * | * | ** | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| DU | 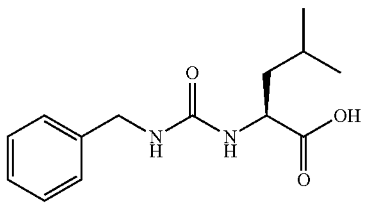 | 2-(3-Benzyl-ureido)-4-methyl-pentanoic acid | 264.32 | * | | * |  | | |
| DV | 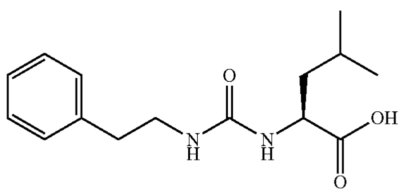 | 4-Methyl-2-(3-phenethyl-ureido)-pentanoic acid | 278.35 | * | | *** | * | | |
| DW | 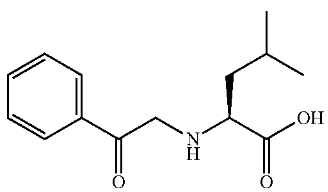 | 4-Methyl-2-(2-oxo-2-phenyl-ethylamino)-pentanoic acid | 285.77 | * | | *** | * | | |
| DX | 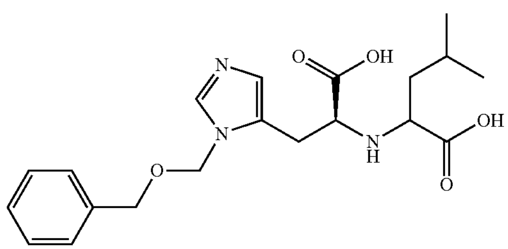 | 2-[2-(3-Benzyloxymethyl-3H-imidazol-4-yl)-1-carboxy-ethylamino]-4-methyl-pentanoic acid | 433.43 |  |  | * | * | % C 53.21, % H 6.47, % N 9.31 (1 H2O, 2Na) | % C 53.60, % H 6.47, % N 9.20 (1 H2O, 2Na) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| DY | 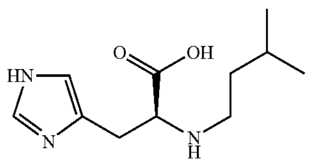 | 3-(1H-Imidazol-4-yl)-2-(3-methyl-butylamino)-propionic acid | 285.34 | * | | * | * | % C 47.01, % H 8.65, % N 15.27 (1.5 H2O, 1.5 MeCOOH, 0.9 NH3) | % C 47.26, % H 8.24, % N 15.30 (1.5 H2O, 1.5 MeCOOH, 0.9 NH3) |
| DZ | 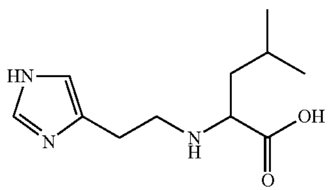 | 2-[2-(1H-imidazol-4-yl)-ethylamino]-4-methyl-pentanoic acid | 225.29 | * |  | * | *** | % C 52.31, % H 8.56, % N 15.51 (1.2 H2O, 0.4 MeCOOH) | % C 52.02, % H 8.25, % N 15.92 (1.2 H2O, 0.4 MeCOOH) |
| EA | 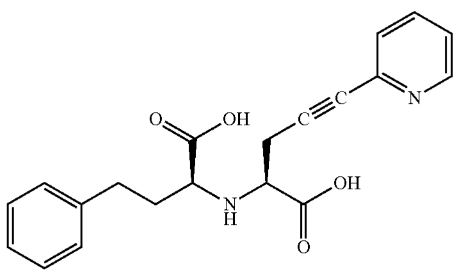 | 2-(1-Carboxy-3-phenyl-propylamino)-5-pyridin-2-yl-pent-4-ynoic acid | 352.39 | * |  | * | * | | |
| EB | 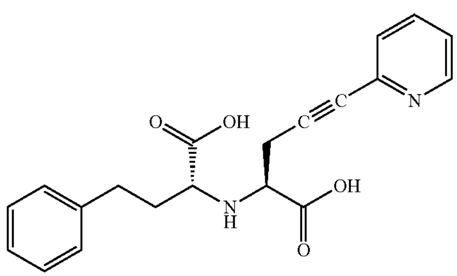 | 2-(1-Carboxy-3-phenyl-propylamino)-5-pyridin-2-yl-pent-4-ynoic acid | 352.39 | * | * | * |  | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| EC | 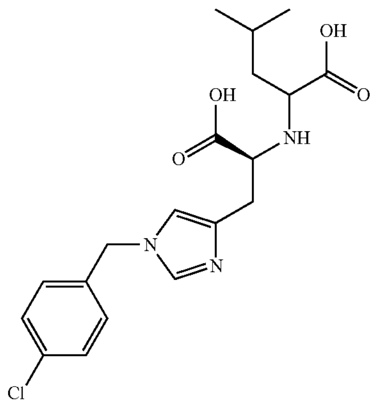 | 2-[1-Carboxy-2-[1-(4-chloro-benzyl)-1H-imidazol-4-yl]-ethylamino)-4-methyl-pentanoic acid | 410.90 | * | * | ** | * | % C 51.48, % H 6.96, % N 12.64 (1.8 H2O, 1 NH3) | % C 51.56, % H 6.94, % N 12.29 (1.8 H2O, 1 NH3) |
| ED | 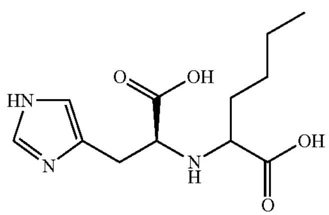 | 2-[1-Carboxy-2-(1H-imidazol-4-yl)-ethylamino] hexanoic acid, Isomer A | 269.30 | * |  | * | *** | % C 47.21, % H 7.59, % N 13.76 (2 H2O) | % C 47.06, % H 7.66, % N 13.94 (2 H2O) |
| EF | 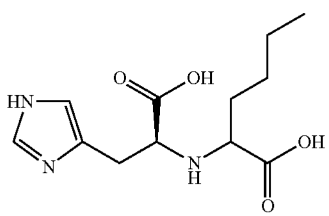 | 2-[1-Carboxy-2-(1H-imidazol-4-yl)-ethylamino] hexanoic acid, Isomer B | 299.39 | * | * |  | * | % C 47.92, % H 7.58, % N 15.04 (1 H2O, 0.5 MeCOOH, 0.5 NH3) | % C 47.76, % H 7.43, % N 14.72 (1 H2O, 0.5 MeCOOH, 0.5 NH3) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| EG | 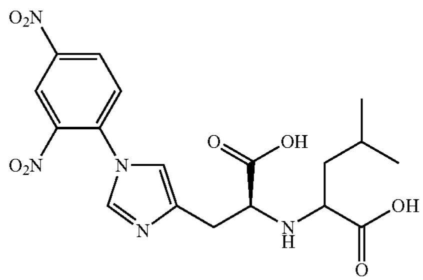 | 2-[1-Carboxy-2-[1-(2,4-dinitro-phenyl)-1H-imidazol-4-yl]-ethylamino)-4-methyl-pentanoic acid | 452.42 | * | * |  | * | % C 43.30<br>% H 6.02,<br>% N 17.28<br>(2 H2O,<br>0.5 MeCOOH,<br>1.5 NH3) | % C 43.06<br>% H 6.34,<br>% N 17.07<br>(2 H2O,<br>0.5 MeCOOH,<br>1.5 NH3) |
| EH | 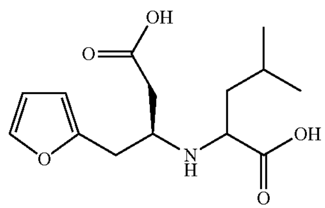 | 2-(1-Carboxymethyl-2-furan-2-yl-ethylamino)-4-methyl-pentanoic acid | 327.30 | * | * | * | * | % C 48.84<br>% H 6.29,<br>% N 4.48<br>(0.1 H2O,<br>0.1 NH3,<br>1 NaCl) | % C 48.69<br>% H 6.26,<br>% N 4.85<br>(0.1 H2O,<br>0.1 NH3,<br>1 NaCl) |
| EI | 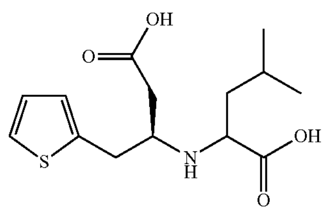 | 2-(1-Carboxymethyl-2-thiophen-2-yl-ethylamino)-4-methyl-pentanoic acid | 343.37 | * | | * | * | % C 47.62<br>% H 5.79,<br>% N 3.97<br>(0.7 H2O,<br>2 Na) | % C 47.23<br>% H 6.10,<br>% N 4.37<br>(0.7 H2O,<br>2 Na) |
| EJ | 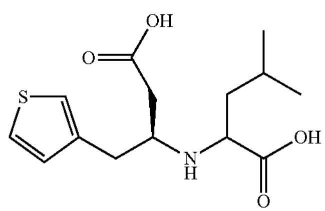 | 2-(1-Carboxymethyl-2-thiophen-3-yl-ethylamino)-4-methyl-pentanoic acid | 343.37 | * | | * | * | % C 50.59<br>% H 6.37,<br>% N 4.21<br>(2 Na) | % C 50.53<br>% H 6.22,<br>% N 4.57<br>(2 Na) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| EK | 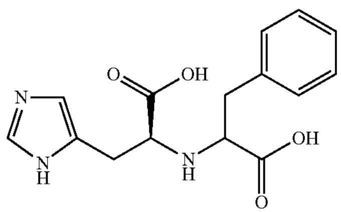 | 2-(1-Carboxy-2-phenyl-ethylamino)-3-(3H-imidazol-4-yl)-propionic acid | 303.32 | * | |  |  | | |
| EL | 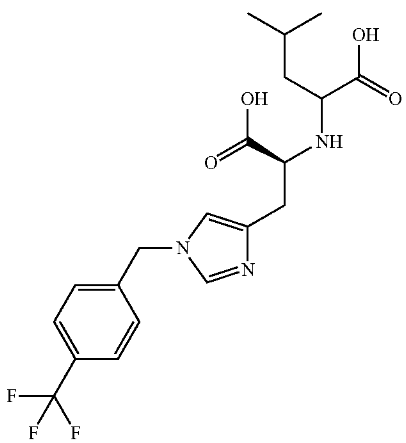 | 2-{1-Carboxy-2-[1-(4-trifluoromethyl-benzyl)-1H-imidazol-4-yl]-ethylamino} 4-methyl-pentanoic acid | 427.42 | * |  | * | ** | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| EM | 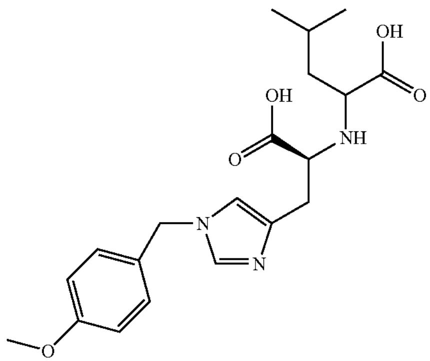 | 2-[1-Carboxy-2-[1-(4-methoxy-benzyl)-1H-imidazol-4-yl]-ethylamino)-4-methyl-pentanoic acid | 389.45 | * | * | * | * | | |
| EN | 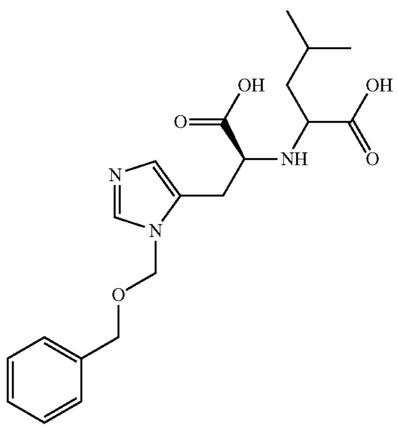 | 2-[2-(3-Benzyloxymethyl-3H-imidazol-4-yl)-1-carboxy-ethylamino]-4-methyl-pentanoic acid, Isomer A | 389.45 |  |  | * | * | % C 54.83, % H 7.45, % N 9.59 (2.7 H2O) | % C 54.87, % H 7.65, % N 9.57 (2.7 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| EO | 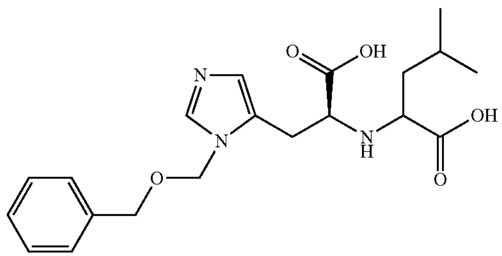 | 2-[2-(3-Benzyloxymethyl-3H-imidazol-4-yl)-1-carboxy-ethylamino]-4-methyl-pentanoic acid, Isomer B | 389.45 | * | * | * | * | % C 56.94, % H 7.31, % N 9.96 (1.8 H2O) | % C 57.09, % H 7.61, % N 10.33 (1.8 H2O) |
| EQ | 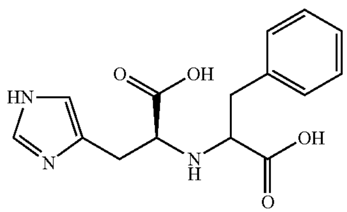 | 2-(1-Carboxy-2-phenyl-ethylamino)-3-(1H-imidazol-4-yl)-propionic acid | 303.32 | * |  | * | ** | % C 53.75, % H 6.07, % N 11.19 (1 H2O, 0.9 MeCOOH) | % C 53.25, % H 5.69, % N 11.59 (1 H2O, 0.9 MeCOOH) |
| ER | 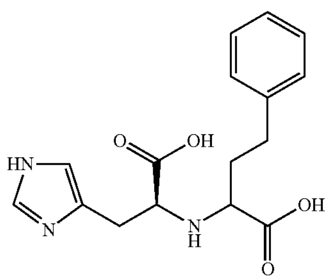 | 2-[1-Carboxy-2-(1H-imidazol-4-yl)-ethylamino]-4-phenyl-butyryic acid | 317.34 | * |  | * | *** | % C 58.56, % H 6.20, % N 12.81 (0.6 H2O) | % C 58.44, % H 5.96, % N 12.68 (0.6 H2O) |
| ES | 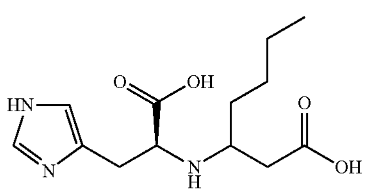 | 3-[1-Carboxy-2-(1H-imidazol-4-yl)-ethylamino]-heptanoic acid, Isomer A | 283.33 | * | * | * | *** | % C 53.47, % H 7.55, % N 14.17 (0.4 H2O, 0.1 MeCOOH) | % C 53.80, % H 7.34, % N 13.82 (0.4 H2O, 0.1 MeCOOH) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| ET | 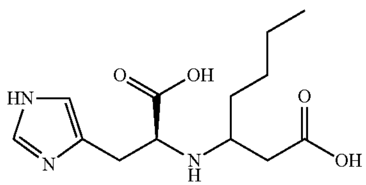 | 3-[1-Carboxy-2-(1H-imidazol-4-yl)-ethylamino] heptanoic acid, Isomer B | 283.33 | * | | * | * | | |
| EU | 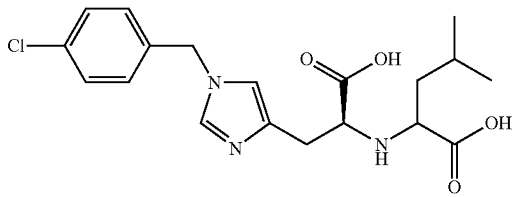 | 2-[1-Carboxy-2-[1-(4-chloro-benzyl)-1H-imidazol-4-yl]-ethylamino) 4-methyl-pentanoic acid | 393.87 | * | * | * |  | | |
| EV | 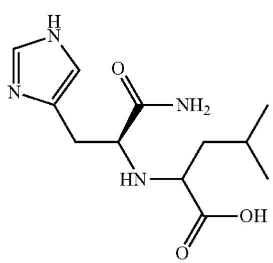 | 2-[1-Carbamoyl-2-(1H-imidazol-4-yl)-ethylamino] 4-methyl-pentanoic acid, Isomer A | 268.316 | * | * | * | * | % C 52.29, % H 7.51, % N 19.53 (0.4 MeCOOH, 0.1 NH3) | % C 52.36, % H 7.32, % N 19.42 (0.4 MeCOOH, 0.1 NH3) |
| EW | 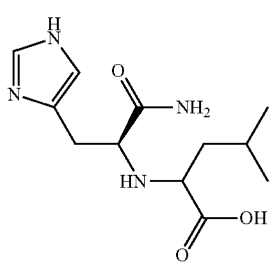 | 2-[1-Carbamoyl-2-(1H-imidazol-4-yl)-ethylamino] 4-methyl-pentanoic acid, Isomer B | 268.316 | * | * | * | * | % C 43.24, % H 7.83, % N 14.90 (5 MeCOOH, 2.5 NH3) | % C 43.01, % H 7.71, 14.68 (5 MeCOOH, 2.5 NH3) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| EX | 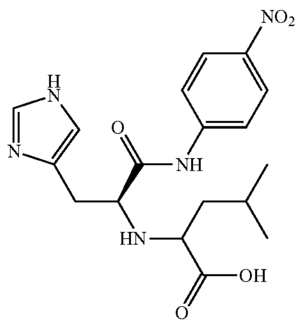 | 2-[2-(1H-Imidazol-4-yl)-1-(4-nitro-phenylcarbamoyl) ethylamino]-4-methyl-pentanoic acid, Isomer A | 389.411 | * | * | * | * | % C 50.18, % H 6.51, % N 15.96 (2 MeCOOH, 1 NH3) | % C 50.01, % H 6.39, % N 15.74 (2 MeCOOH, 1 NH3) |
| EY | 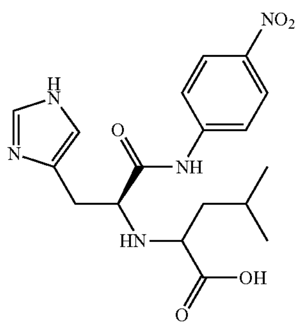 | 2-[2-(1H-Imidazol-4-yl)-1-(4-nitro-phenylcarbamoyl) ethylamino]-4-methyl-pentanoic acid, Isomer B | 389.411 | * | * | * | * | % C 52.20, % H 6.21, % N 15.51 (1.4 MeCOOH, 0.3 NH3) | % C 52.08, % H 6.33, % N 15.61 (1.4 MeCOOH, 0.3 NH3) |
| EZ | 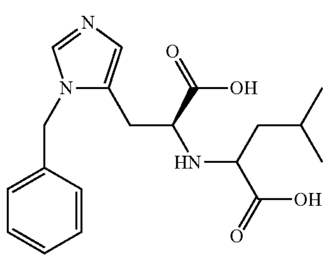 | 2-[2-(3-Benzyl-3H-imidazol-4-yl)-1-carboxy-ethylamino]-4-methyl-pentanoic acid, Isomer A | 359.425 | * | * | * | *** | % C 58.66, % H 7.14, % N 10.06 (0.9 H2O, 0.7 MeCOOH) | % C 58.86, % H 7.54, % N 9.71 (0.9 H2O, 0.7 MeCOOH) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FA | 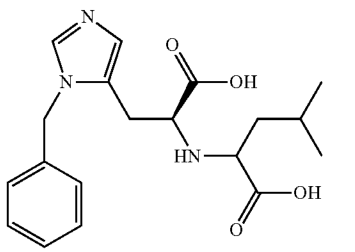 | 2-[2-(3-Benzyl-3H-imidazol-4-yl)-1-carboxy-ethylamino]-4-methyl-pentanoic acid, Isomer B | 359.425 | * | | * | * | % C 56.43, % H 7.34, % N 11.86 (1.6 MeCOOH, 1 NH3) | % C 56.42, % H 7.41, % N 11.99 (1.6 MeCOOH, 1 NH3) |
| FB | 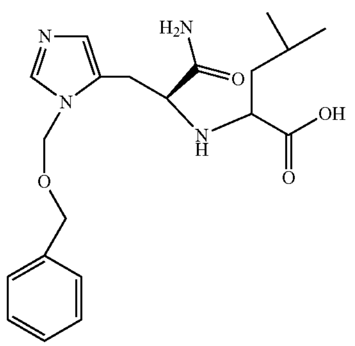 | 2-[2-(3-Benzyloxymethyl-3H-imidazol-4-yl)-1-carbamoyl-ethylamino]-4-methyl-pentanoic acid, Isomer A | 388.47 | * | * | * | * | % C 58.06, % H 6.94, % N 8.99 (1.3 MeCOOH) | % C 58.46, % H 7.06, % N 8.70 (1.3 MeCOOH) |
| FC | 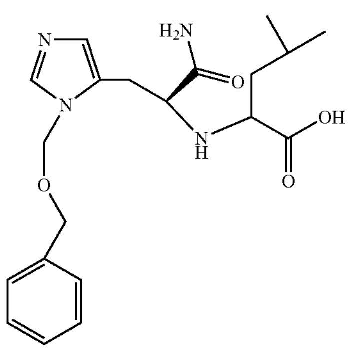 | 2-[2-(3-Benzyloxymethyl-3H-imidazol-4-yl)-1-carbamoyl-ethylamino]-4-methyl-pentanoic acid, Isomer B | 388.47 | * | | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FD | 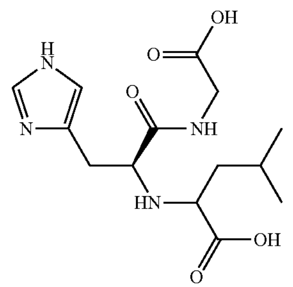 | 2-[1-(Carboxymethyl-carbamoyl)-2-(1H-imidazol-4-yl)-ethylamino] 4-methyl-pentanoic acid | 326.35 | * | * | * | *** | | |
| FE | 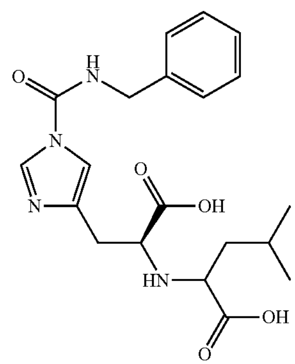 | 2-[1-(Carboxymethyl-carbamoyl)-2-(1H-imidazol-4-yl)-ethylamino] 4-methyl-pentanoic acid | 402.45 | * | * |  | * | | |
| FG | 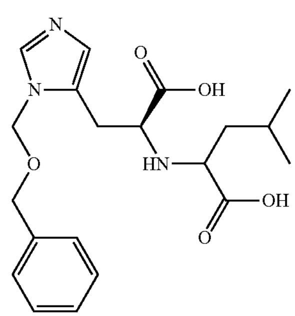 | 2-[2-(3-Benzyloxymethyl-3H-imidazol-4-yl)-1-carboxy-ethylamino]-4-methyl-pentanoic acid, Isomer A | 389.45 | * | * | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FH | 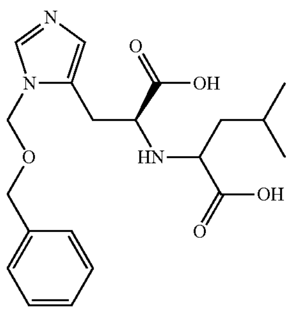 | 2-[2-(3-Benzyloxymethyl-3H-imidazol-4-yl)-1-carboxy-ethylamino]-4-methyl-pentanoic acid, Isomer B | 389.45 | * | * | * | * | | |
| FI | 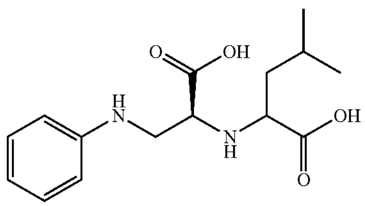 | 2-(1-Carboxy-2-phenylamino-ethylamino)-4-methyl-pentanoic acid, Isomer A | 294.35 | * | | * | * | | |
| FJ | 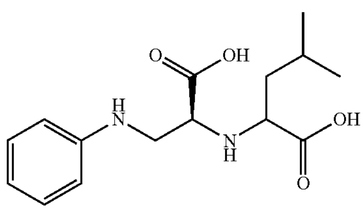 | 2-(1-Carboxy-2-phenylamino-ethylamino)-4-methyl-pentanoic acid, Isomer B | 294.35 | * | | * | * | | |

TABLE 2-continued

| Ref. No. | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|
| FK | 2-{2-(3H-Imidazol-4-yl)-1-[2-(4-methoxy-phenyl)-ethylcarbamoyl]-ethylamino}-4-methyl-pentanoic acid, Isomer A | 402.49 | * | * | *** | *** | % C 61.54<br>% H 7.56<br>% N 12.94<br>(0.2 H2O,<br>0.2 HCO2H) | % C 61.31<br>% H 7.48<br>% N 13.49 |
| FL | 2-{2-(3H-Imidazol-4-yl)-1-[2-(4-methoxy-phenyl)-ethylcarbamoyl]-ethylamino}4-methyl-pentanoic acid, Isomer B | 402.49 | * | * | *** | *** | % C 61.43<br>% H 7.61<br>% N 12.93<br>(0.3 H2O,<br>0.2 HCO2H) | % C 61.05<br>% H 7.49<br>% N 13.43 |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FM | 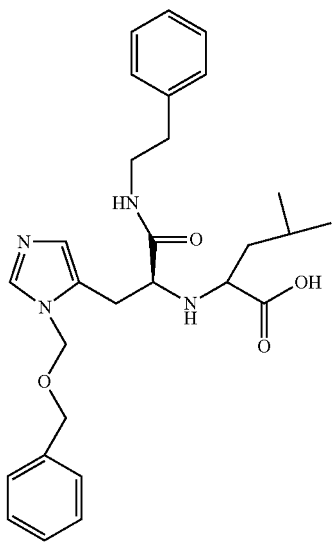 | 2-[2-(3-Benzyloxymethyl-3H-imidazol-4-yl)-1-phenethylcarbamoyl-ethylamino]-4-methyl-pentanoic acid, Isomer A | 492.62 | * | | * | * | % C 61.54<br>% H 7.25<br>% N 10.79<br>(0.2 H2O<br>0.3 HCO2H) | % C 66.65<br>% H 7.31<br>% N 10.99 |
| FN | 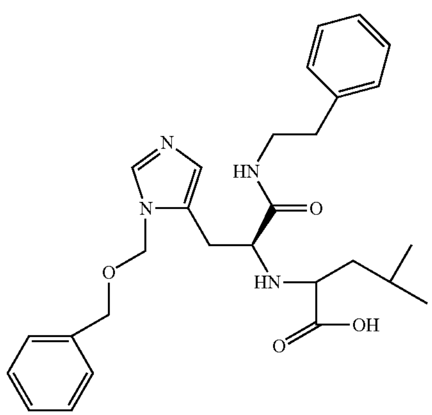 | 2-[2-(3-Benzyloxymethyl-3H-imidazol-4-yl)-1-phenethylcarbamoyl-ethylamino]-4-methyl-pentanoic acid, Isomer B | 492.62 | * | | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FO | 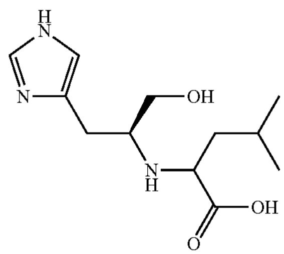 | 2-[1-Hydroxymethyl-2-(1H-imidazol-4-yl)-ethylamino] 4-methyl-pentanoic acid, Isomer A | 255.32 | * | * | * | * | | |
| FP | 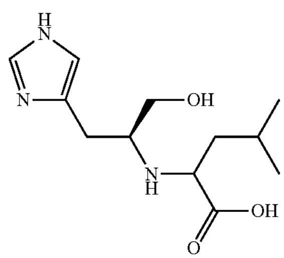 | 2-[1-Hydroxymethyl-2-(1H-imidazol-4-yl)-ethylamino] 4-methyl-pentanoic acid, Isomer B | 255.32 | * | * | * | *** | | |
| FQ | 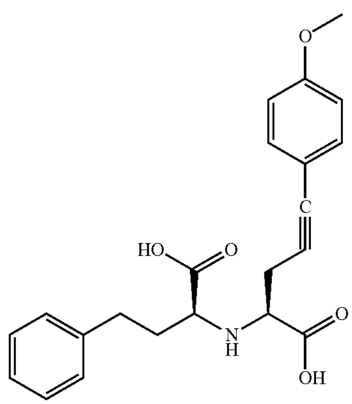 | 2-(1-Carboxy-2-phenyl-propylamino)-5-(4-methoxy-phenyl)-pent-4-ynoic acid | 417.89 | * | * | * | ** | % C 63.19 % H 5.80 % N 3.65 (0.1 MeCN) | % C 62.88 % H 5.90 % N 3.85 |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FR | 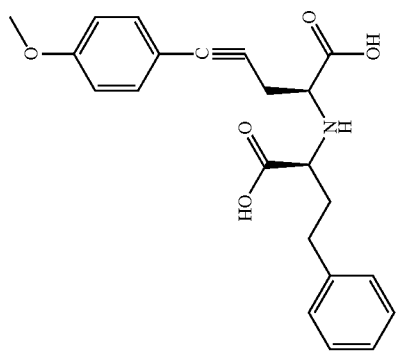 | 2-(1-Carboxy-3-phenyl-propylamino)-5-(4-methoxy-phenyl)-pent-4-ynoic acid | 417.89 | * | | * | * | % C 63.14<br>% H 5.82<br>% N 3.94<br>(0.2 MeCN) | % C 63.53<br>% H 5.95<br>% N 4.20 |
| FS | 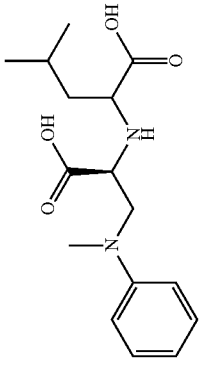 | 2-[1-Carboxy-2-(methyl-phenyl-amino)-ethylamino]-4-methyl-pentanoic acid | 308.38 | * | * | * | ** | | |
| FT | 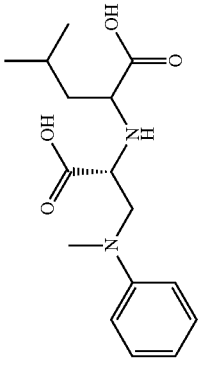 | 2-[1-Carboxy-2-(methyl-phenyl-amino)-ethylamino]-4-methyl-pentanoic acid | 308.38 | * | * | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FU | 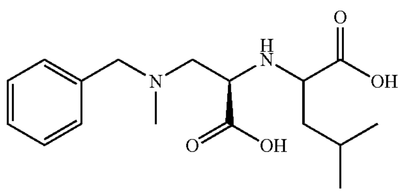 | 2-[2-(Benzyl-methyl-amino)-1-carboxy-ethylamino]-4-methyl-pentanoic acid | 322.40 | * | * | * | * | | |
| FV | 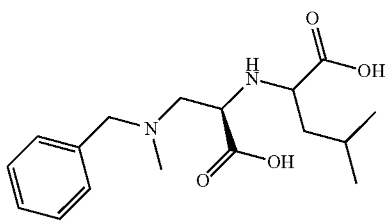 | 2-[2-(Benzyl-methyl-amino)-1-carboxy-ethylamino]-4-methyl-pentanoic acid | 322.40 | * | * | * | * | | |
| FW | 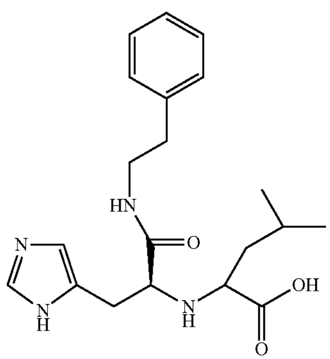 | 2-[2-(3H-Imidazol-4-yl)-1-phenethylcarbamoyl-ethylamino]-4-methyl-pentanoic acid, Isomer A | 372.47 | * | * | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FX | 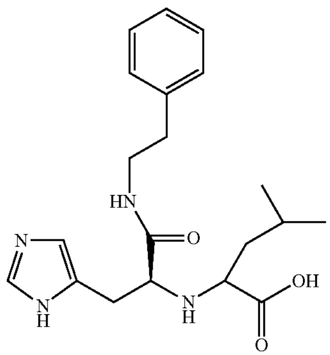 | 2-[2-(3H-Imidazol-4-yl)-1-phenethylcarbamoyl-ethylamino]-4-methyl-pentanoic acid, Isomer B | 372.47 | * | * | * | * | | |
| FY | 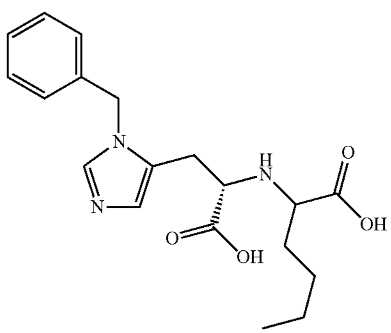 | 2-[2-(3H-Benzyl-3-imidazol-4-yl)-1-carboxy-ethylamino]-hexanoic acid, Isomer A | 359.43 | * | * | * | *** | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| FZ | 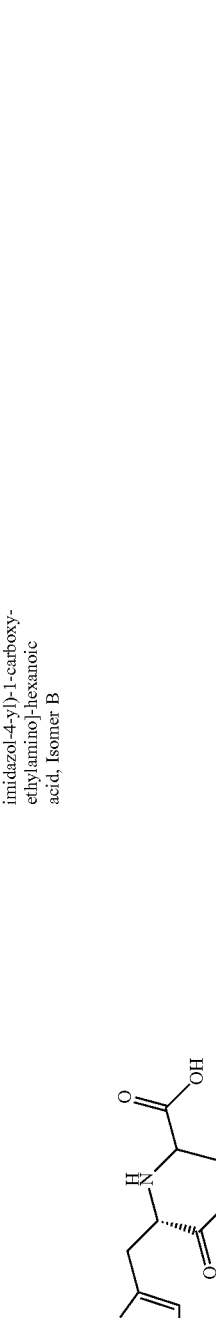 | 2-[2-(3-Benzyl-3H-imidazol-4-yl)-1-carboxy-ethylamino]-hexanoic acid, Isomer B | 359.43 | * | * | * | * | | |
| GA | 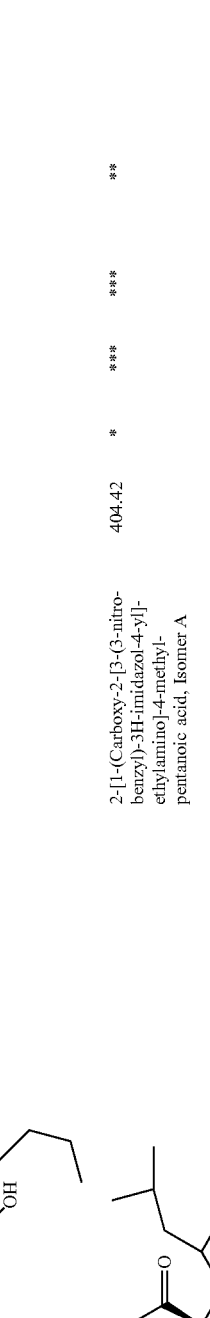 | 2-[1-(Carboxy-2-[3-(3-nitro-benzyl)-3H-imidazol-4-yl]-ethylamino]-4-methyl-pentanoic acid, Isomer A | 404.42 | * | * | * | ** | | |
| GB | 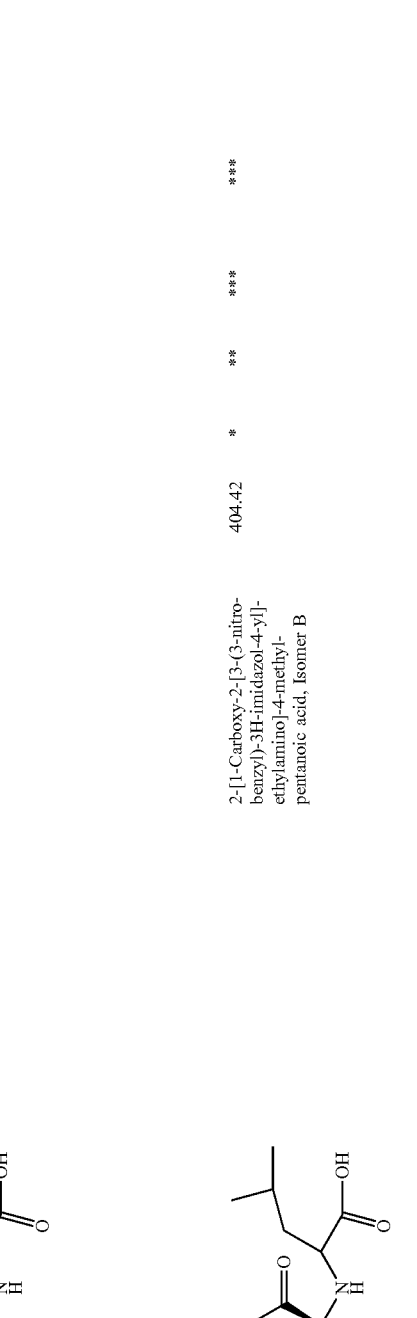 | 2-[1-Carboxy-2-[3-(3-nitro-benzyl)-3H-imidazol-4-yl]-ethylamino]-4-methyl-pentanoic acid, Isomer B | 404.42 | * |  | * | *** | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GC | 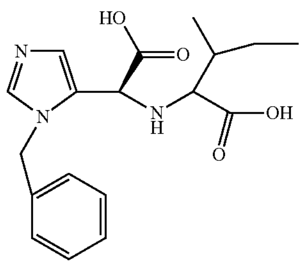 | 2-[2-(3-Benzyl-3H-imidazol-4-yl)-1-carboxy-ethylamino]-3-methyl-pentanoic acid, Isomer A | 359.42 | * |  | * | ** | | |
| GD | 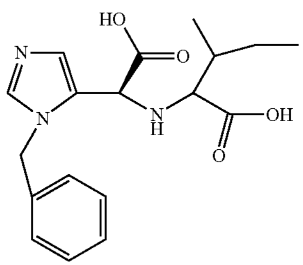 | 2-[2-(3-Benzyl-3H-imidazol-4-yl)-1-carboxy-ethylamino]-3-methyl-pentanoic acid, Isomer B | 359.42 | * | * | * | * | | |
| GE | 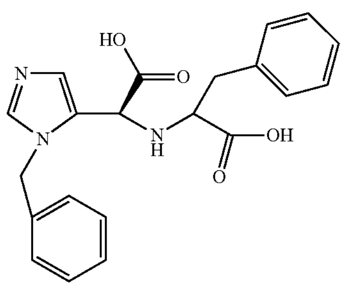 | 3-(3-Benzyl-3H-imidazol-4-yl)-2-(1-carboxy-2-phenyl-ethylamino)-propronic acid, Isomer A | 393.44 | * | * | * | * | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GF | 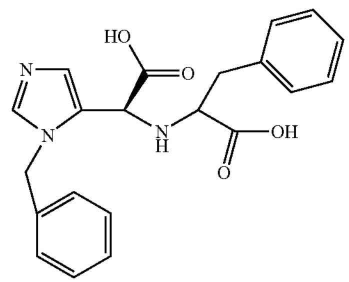 | 3-(3-Benzyl-3H-imidazol-4-yl)-2-(1-carboxy-2-phenyl-ethylamino)-propionic acid, Isomer B | 393.44 | * |  | * | * | | |
| GG | 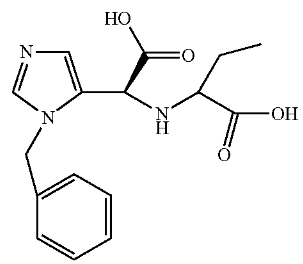 | 2-[2-(3-Benzyl-3H-imidazol-4-yl)-1-carboxy-ethylamino]-butyne acid, Isomer A | 331.37 | * | * | * | *** | | |
| GH | 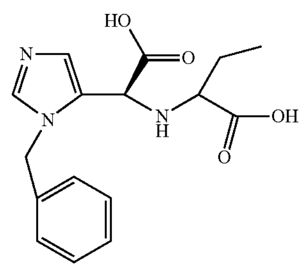 | 2-[2-(3-Benzyl-3H-imidazol-4-yl)-1-carboxy-ethylamino]-butyne acid, Isomer B | 331.37 | * |  | * | *** | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GI | 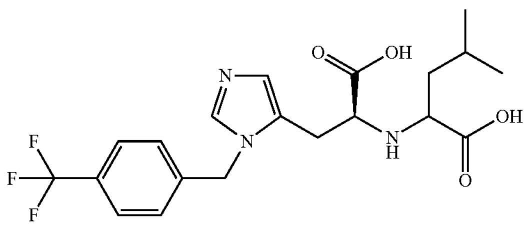 | 2-[1-Carboxy-2-[3-(4-trifluoromethyl-benzyl)-imidazol-4-yl]-ethylamino]-4-methyl-pentanoic acid | 427.17 | * | * | * |  | % C 51.21, % H 6.16, % N 8.60 (2.0 H2O, 0.2 MeCOOH) | % C 51.53, % H 6.11, % N 8.84 (2.0 H2O, 0.2 MeCOOH) |
| GJ | 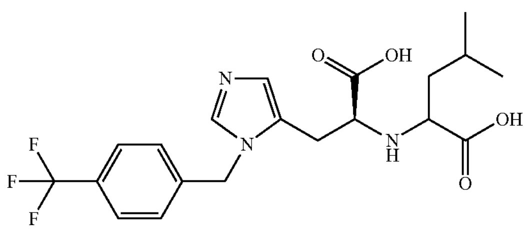 | 2-[1-Carboxy-2-[3-(4-trifluoromethyl-benzyl)-3H-imidazol-4-yl]-ethylamino]-4-methyl-pentanoic acid | 427.424 | * | * |  |  | % C 51.71, % H 5.55, % N 9.32 (1.0 HCl) | % C 51.78, % H 5.43, % N 9.06 (1.0 HCl) |
| GK | 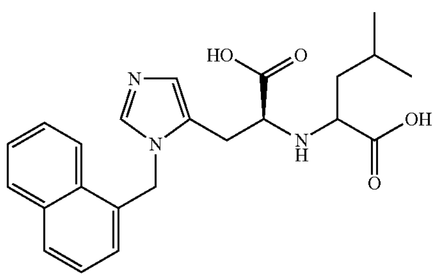 | 2-[1-Carboxy-2-(3-naphthalen-1-ylmethyl-3H-imidazol-4-yl)-ethylamino]-4-methyl-pentanoic acid, Isomer A | 409.48 | * | * | * |  | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GL | 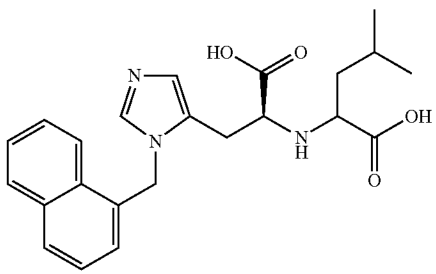 | 2-[1-Carboxy-2-(3-naphthalen-1-ylmethyl-3H imidazol-4-yl)-ethylamino] 4-methyl-pentanoic acid, Isomer B | 409.48 | * | * |  |  | | |
| GM | 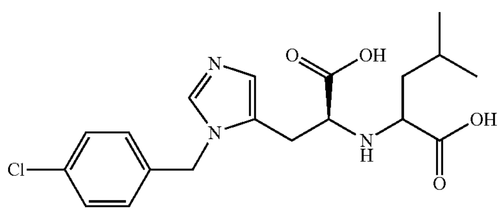 | 2-[1-Carboxy-2-[3-(4-chloro-benzyl)-3H-imidazol-4-yl]-ethylamino] 4-methyl-pentanoic acid, Isomer A | 393.87 | * | * | * |  | % C 54.03, % H 6.35, % N 9.01 (1.3 H2O) | % C 54.12, % H 6.47, % N 9.37 (1.3 H2O) |
| GN | 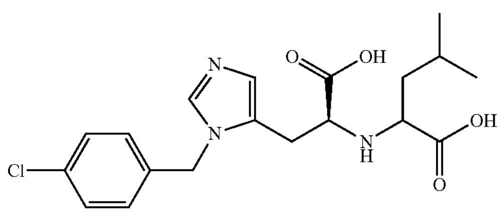 | 2-[1-Carboxy-2-[3-(4-chloro-benzyl)-3H-imidazol-4-yl]-ethylamino] 4-methyl-pentanoic acid, Isomer B | 393.87 | * | * | * | * | % C 54.91, % H 6.13, % N 9.66 (0.5 H2O, 0.5 HCOOH, 0.7 MeOH) | % C 54.69, % H 6.43, % N 10.07 (0.5 H2O, 0.5 HCOOH, 0.7 MeOH) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GO | 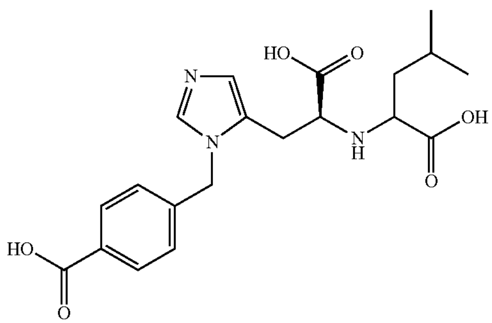 | 4-[5-[2-Carboxy-2-(1-carboxy-3-methyl-butylamino)-ethyl]-imidazol-1-ylmethyl]-benzoic acid, Isomer A | 403.435 | * | | * | * | | |
| GP | 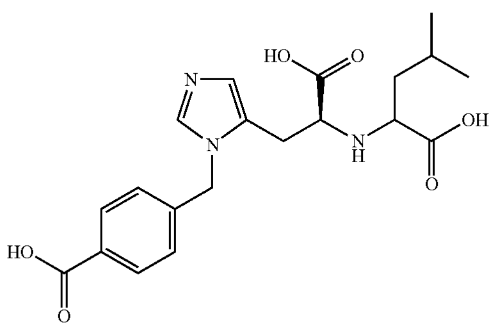 | 4-[5-[2-Carboxy-2-(1-carboxy-3-methyl-butylamino)-ethyl]-imidazol-1-ylmethyl]-benzoic acid, Isomer A | 403.435 | * | | * | * | | |
| GQ | 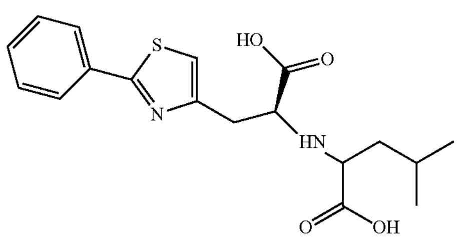 | 2-[1-Carboxy-2-[2-phenyl-thiazol-4-yl)-ethylamino]-4-methyl-pentanoic acid | 362.45 | * | | | | % C 57.47, % H 5.78, % N 7.57 (0.4 HCl) | % C 57.34, % H 5.99, % N 7.43 (0.4 HCl) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GR | 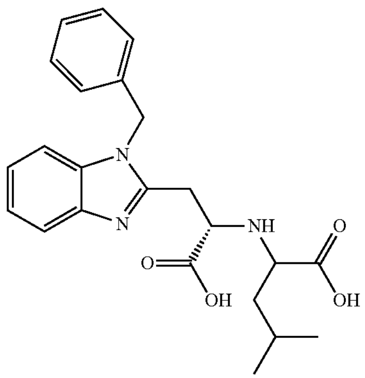 | 2-[2-(1-Benzyl-1H-benzoimidazol-2-yl)-1-carboxy-ethylamino]-4-methyl-pentanoic acid, Isomer A | 409.48 | * | | | | | |
| GS | 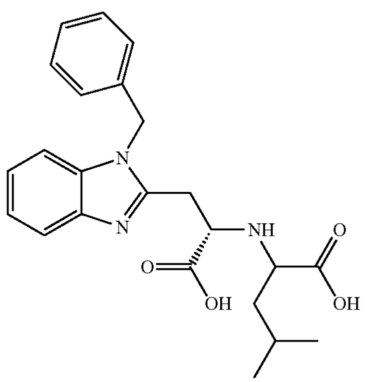 | 2-[2-(1-Benzyl-1H-benzoimidazol-2-yl)-1-carboxy-ethylamino]-4-methyl-pentanoic acid, Isomer B | 409.48 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GT | 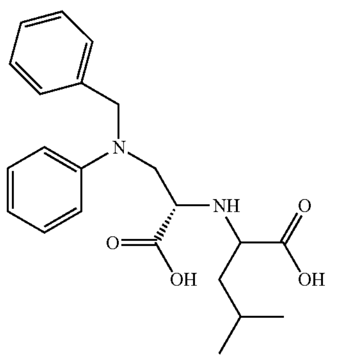 | 2-[2-(Benzyl-phenyl-amino)-1-carboxy-ethylamino]-4-methyl-pentanoic acid | 384.475 | * | | | | | |
| GU | 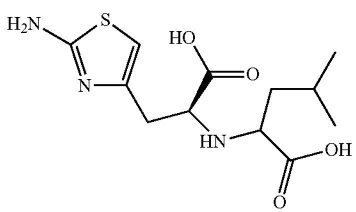 | 2-[2-(2-Amino-thiazol-4-yl)-1-carboxy-ethylamino]-4-methyl-pentanoic acid, Isomer A | 337.82 | * | | | | C, 43.7%; H, 6.15%; N, 12.34% (0.8 HCl) | C12H19N3O4S 0.8 HCl requires. C, 43.61%; H, 6.04%, N, 12.71% |
| GV | 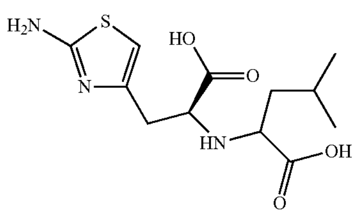 | 2-[2-(2-Amino-thiazol-4-yl)-1-carboxy-ethylamino]-4-methyl-pentanoic acid, Isomer B | 301.37 | * | | | | C, 44.45%; H, 6.34%; N, 12.87% | C12H19N3O4S. 0.6 HCl requires C, 44.59%; H, 6.11%, N, 13.00% |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GW | 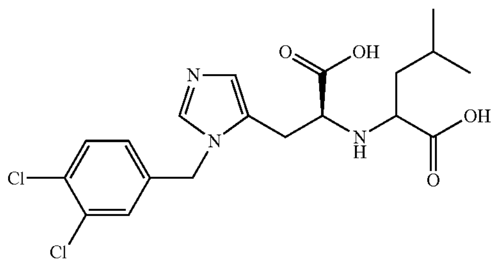 | 2-[1-(Carboxy-2-[3-(3,4-dichloro-benzyl)-3H-imidazol-4-yl]-ethylamino) 4-methyl-pentanoic acid, Isomer A | 428.31 | * | * |  |  | % C 52.32, % H 6.34, % N 10.72 (0.6 NH3, 0.5 EtOAc) | % C 52.27, % H 6.02, % N 10.45 (0.6 NH3, 0.5 EtOAc) |
| GX | 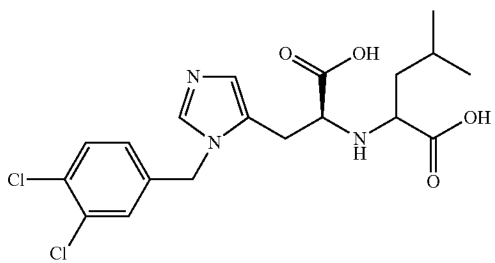 | 2-[1-(Carboxy-2-[3-(3,4-dichloro-benzyl)-3H-imidazol-4-yl]-ethylamino] 4-methyl-pentanoic acid, Isomer B | 428.31 | * | | | | % C 51.74, % H 5.55, % N 8.96, % Cl 14.01 (0.9 H2O, 0.1 EtOAc) does not match | % C 51.40, % H 5.69, % N 9.27, % Cl 15.04 (0.9 H2O, 0.1 EtOAc) |
| GY | 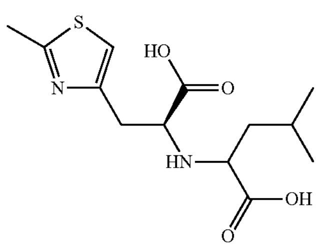 | 2-[1-Carboxy-2-(2-methyl-thiazol-4-yl)-ethylamino]-4-methyl-pentanoic acid; Isomer A | 300.38 | * | | | | C, 51.98%; H, 6.74%; N, 9.23% | % C, 51.98, % H 6.71, % N 9.33% |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| GZ | 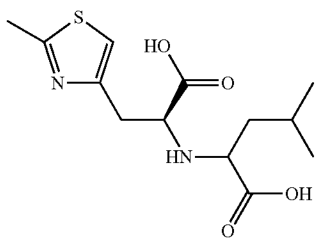 | 2-[1-Carboxy-2-(2-methyl-thiazol-4-yl)-ethylamino]-4-methyl-pentanoic acid, Isomer B | 300.38 | * | | | | C, 52.02%, H, 6.70%, N, 9.24% | C, 51.98%, H, 6.71%, N, 9.33% |
| HA | 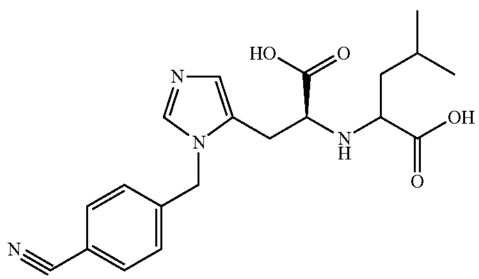 | 2-[1-Carboxy-2-[3-(4-cyano-benzyl)-3H-imidazol-4-yl]-ethylamino)4-methyl-pentanoic acid, Isomer A | 384.435 | * | |  | ** | | |
| HB | 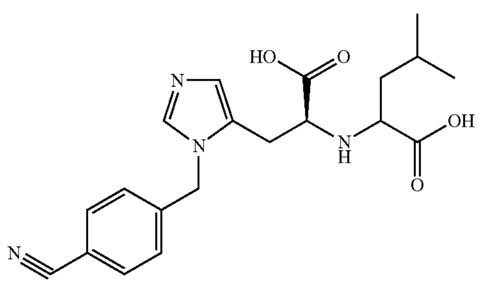 | 2-[1-Carboxy-2-[3-(4-cyano-benzyl)-3H-imidazol-4-yl]-ethylamino)4-methyl-pentanoic acid; Isomer B | 384.43 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| HC | 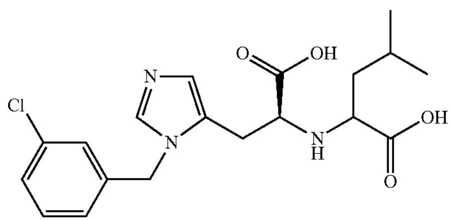 | 2-[1-Carboxy-2-[3-(3-chloro-benzyl)-3H-imidazol-4-yl]-ethylamino]-4-methyl-pentanoic acid, Isomer A | 393.87 | * | * |  |  | % C 54.67, % H 5.91, % N 10.22 (0.7 H2O, 0.3 HCOOH) | % C 54.92, % H 6.26, % N 9.96 (0.7 H2O, 0.3 HCOOH) |
| HD | 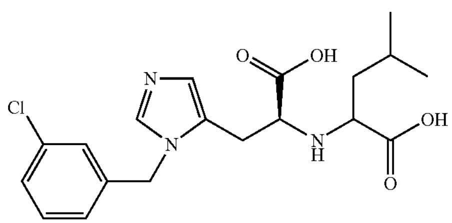 | 2-[1-Carboxy-2-[3-(3-chloro-benzyl)-3H-imidazol-4-yl]-ethylamino]-4-methyl-pentanoic acid, Isomer B | 393.87 | * | | | | % C 56.25, % H 6.00, % N 10.08 (0.5 H2O) | % C 56.64, % H 6.25, % N 10.43 (0.5 H2O) |
| HE | 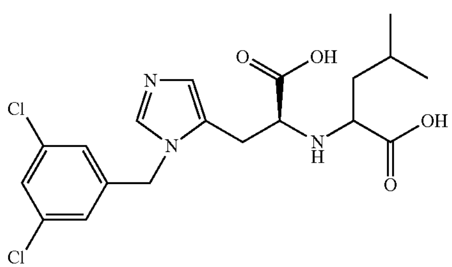 | 2-[1-Carboxy-2-[3-(3,5-dichloro-benzyl)-3H-imidazol-4-yl]-ethylamino]-4-methyl-pentanoic acid, Isomer A | 428.31 | * | * |  |  | % C 51.30, % H 5.44, % N 9.24 (1.0 H2O) | % C 51.13, % H 5.65, % N 9.41 (1.0 H2O) |
| HF | 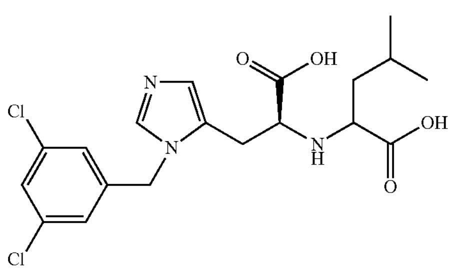 | 2-[1-Carboxy-2-[3-(3,5-dichloro-benzyl)-3H-imidazol-4-yl]-ethylamino]-4-methyl-pentanoic acid, Isomer B | 428.31 | ** | | | | % C 51.29, % H 5.43, % N 9.37 (1.0 H2O) | % C 51.13, % H 5.65, % N 9.41 (1.0 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| HG | 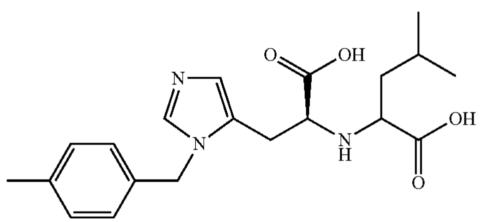 | 2-[1-Carboxy-2-[3-(4-methyl-benzyl)-3H-imidazol-4-yl]-ethylamino) 4-methyl-pentanoic acid, Isomer A | 373.45 | * | * |  |  | % C 60.03, % H 7.08, % N 10.44 (1.0 H2O, 0.3 HCOOH) | % C 61.16, % H 7.36, % N 10.37 (1.0 H2O, 0.3 HCOOH) |
| HH | 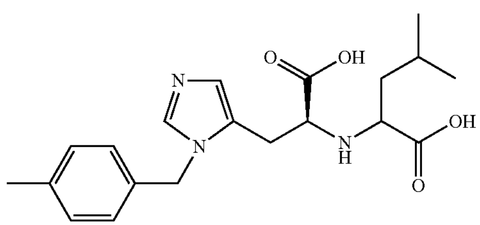 | 2-[1-Carboxy-2-[3-(4-methyl-benzyl)-3H-imidazol-4-yl]-ethylamino) 4-methyl-pentanoic acid, Isomer B | 373.45 | ** | | | | % C 60.93, % H 7.15, % N 10.52 (0.8 H2O, 0.2 HCOOH) | % C 61.10, % H 7.36, % N 10.58 (0.8 H2O, 0.2 HCOOH) |
| HI | 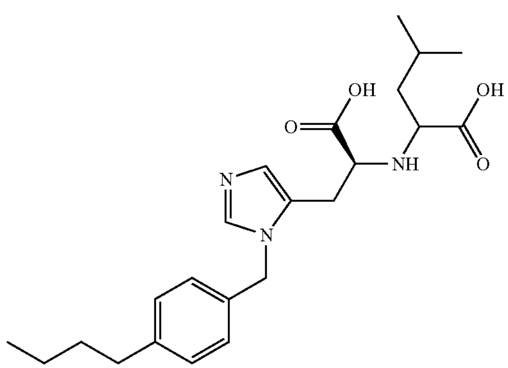 | 2-[2-[3-(4-Butyl-benzyl)-3H-imidazol-4-yl]-1-carboxy-ethylamino]-4-methyl-pentanoic acid, Isomer A | 415.53 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| HJ | 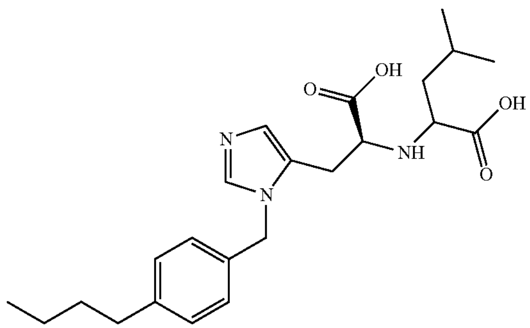 | 2-[2-[3-(4-Butyl-benzyl)-3H-imidazol-4-yl]-1-carboxy-ethylamino]-4-methyl-pentanoic acid, Isomer B | 415.53 | * | | | | | |
| HK | 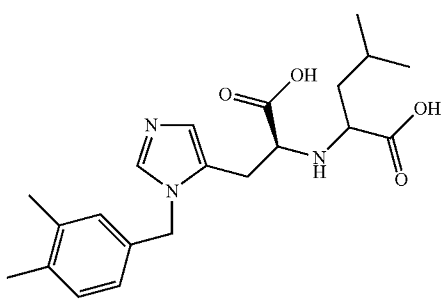 | 2-[1-Carboxy-2-[3-(3,4-dimethyl-benzyl)-3H-imidazol-4-yl]-ethylamino)-4-methyl-pentanoic acid, Isomer A | 387.48 | * | * |  |  | % C 60.31, % H 7.24, % N 9.43 (1.0 H2O, 0.5 HCOOH) | % C 60.26, % H 7.53, % N 9.81 (1.0 H2O, 0.5 HCOOH) |
| HL | 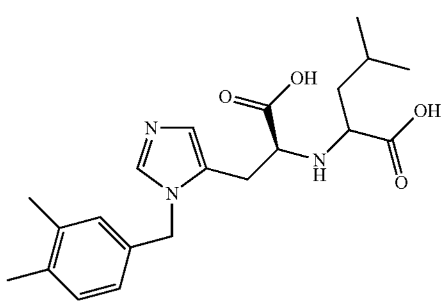 | 2-[1-Carboxy-2-[3-(3,4-dimethyl-benzyl)-3H-imidazol-4-yl]-ethylamino]-4-methyl-pentanoic acid, Isomer B | 387.48 | * | | | | % C 62.06, % H 7.42, % N 10.16 (1.0 H2O) | % C 62.20, % H 7.71, % N 10.36 (1.0 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| HM | 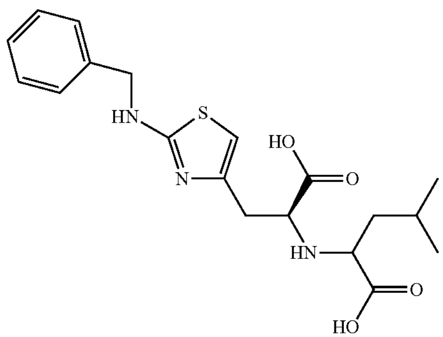 | 2-[2-(2-Benzylamino-thiazol-4-yl)-1-carboxy-ethylamino]-4-methyl-pentanoic acid, Isomer A | 391.49 | * | | | | | |
| HN | 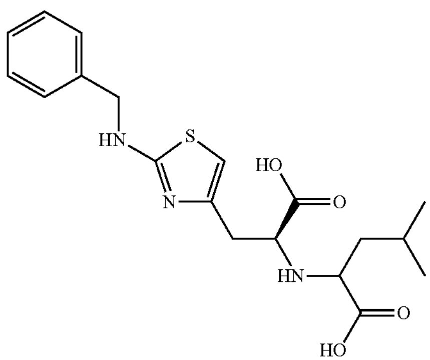 | 2-[2-(2-Benzylamino-thiazol-4-yl)-1-carboxy-ethylamino]-4-methyl-pentanoic acid, Isomer B | 391.49 | * | | | | | |
| HO | 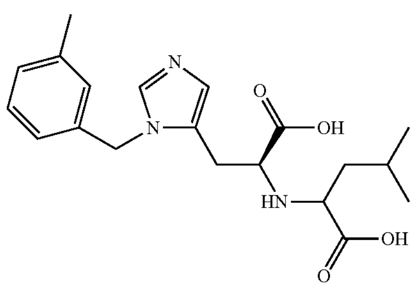 | 2-[1-Carboxy-2-[3-(3-methyl-benzyl)-3H-imidazol-4-yl]-ethylamino]-4-methyl-pentanoic acid, Isomer A | 373.45 | * | * |  |  | % C 60.87, % H 7.11, % N 10.54 (1.1 H2O) | % C 61.08, % H 7.48, % N 10.68 (1.1 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| HP | 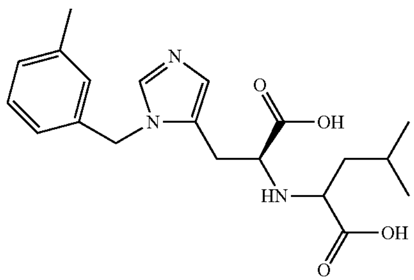 | 2-[1-Carboxy-2-[3-(3-methyl-benzyl)-3H-imidazol-4-yl]-ethylamino] 4-methyl-pentanoic acid, Isomer B | 373.45 | * | | | | | |
| HQ | 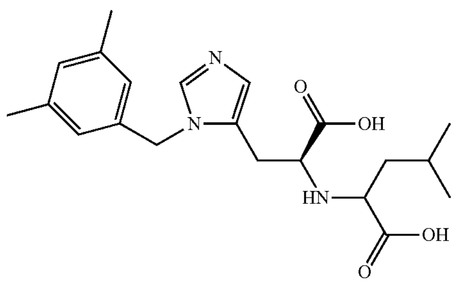 | 2-[1-Carboxy-2-[3-(3,5-dimethyl-benzyl)-3H-imidazol-4-yl]-ethylamino] 4-methyl-pantanoic acid, Isomer A | 387.48 | * | * |  |  | % C 61.71, % H 7.41, % N 10.24 (1.0 H2O, 0.3 HCOOH) | % C 61.01, % H 7.60, % N 10.02 (1.0 H2O, 0.3 HCOOH) |
| HR | 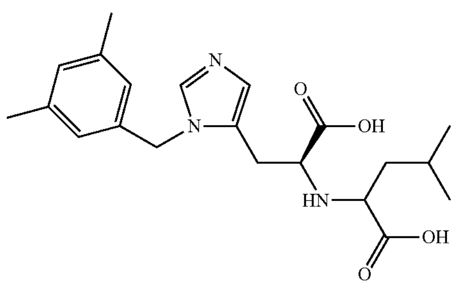 | 2-[1-Carboxy-2-[3-(3,5-dimethyl-benzyl)-3H-imidazol-4-yl]-ethylamino) 4-methyl-pentanoic acid, Isomer B | 387.48 | * | | | | % C 62.50, % H 7.40, % N 10.35 (1.0 H2O) | % C 62.20, % H 7.71, % N 10.36 (1.0 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| HS | 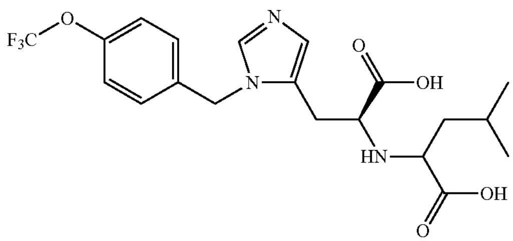 | 2-[1-Carboxy-2-[3-(4-trifluoromethoxy-benzyl)-3H-imidazol-4-yl]-ethylamino]-4-methyl-pentanoic acid, Isomer A | 443.42 | * |  |  |  | | |
| HT | 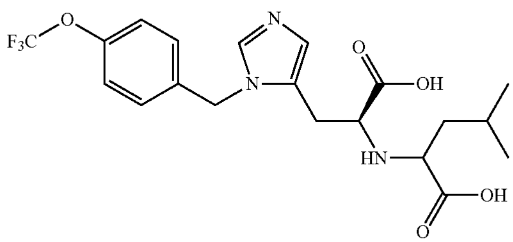 | 2-[1-Carboxy-2-[3-(4-trifluoromethoxy-benzyl)-3H-imidazol-4-yl]-ethylamino]-4-methyl-pentanoic acid, Isomer B | 443.42 | * | | | | % C 53.20, % H 5.46, % N 9.04 (0.5 H2O) | % C 53.10, % H 5.57, % N 9.26 (0.5 H2O) |
| HU | 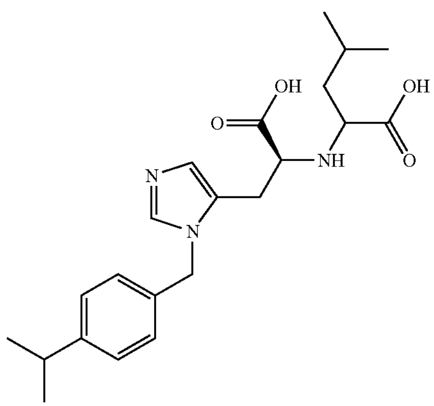 | 2-[1-Carboxy-2-[3-(4-isopropyl-benzyl)-3H-imidazol-4-yl]-ethylamino)-4-methyl-pentanoic acid, Isomer A | 401.51 | * |  | * | * | % C 61.12, % H 7.55, % N 9.72 (1.0 H2O, 0.4 HCOOH) | % C 61.44, % H 7.78, % N 9.60 (1.0 H2O, 0.4 HCOOH) |

TABLE 2-continued

| Ref. No. | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|
| HV | 2-[1-Carboxy-2-[3-(4-isopropyl-benzyl)-3H-imidazol-4-yl]-ethylamino)-4-methyl-pentanoic acid, Isomer B | 401.51 | * | | | | % C 62.87, % H 7.57, % N 9.84 (1.0 H2O) | % C 62.99, % H 7.93, % N 10.02 (1.0 H2O) |
| HW | 2-[1-Carboxy-2-[3-(2-methyl-benzyl)-3H-imidazol-4-yl]-ethylamino]-4-methyl-pentanoic acid, Isomer A | 373.45 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| HX | 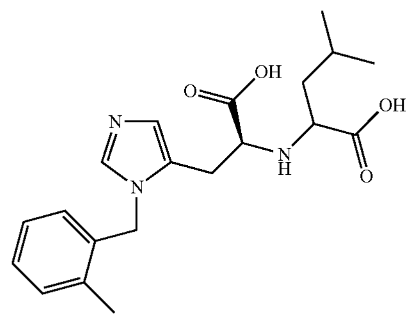 | 2-[1-Carboxy-2-[3-(2-methyl-benzyl)-3H-imidazol-4-yl]-ethylamino]-4-methyl-pentanoic acid, Isomer B | 373.45 | * | | | | % C 60.53, % H 7.08, % N 10.73 (1.0 H2O, 0.2 HCOOH) | % C 60.55, % H 7.40, % N 10.49 (1.0 H2O, 0.2 HCOOH) |
| HY | 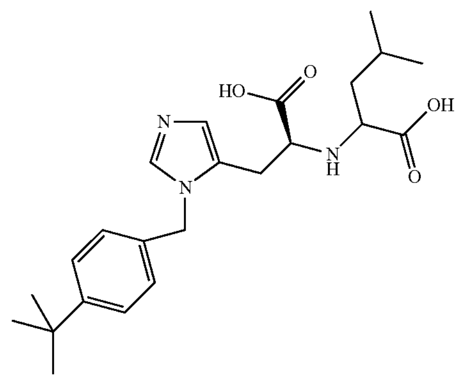 | 2-[2-[3-(4-tert-Butyl-benzyl)-3H-imidazol-4-yl]-1-carboxy-ethylamino)-4-methyl-pentanoic acid, Isomer A | 415.53 | *** | | * | * | % C 60.86, % H 8.00, % N 9.06 (1.4 H2O, 0.5 HCOOH) | % C 60.72, % H 7.96, % N 9.3 (1.4 H2O, 0.5 HCOOH) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| HZ | 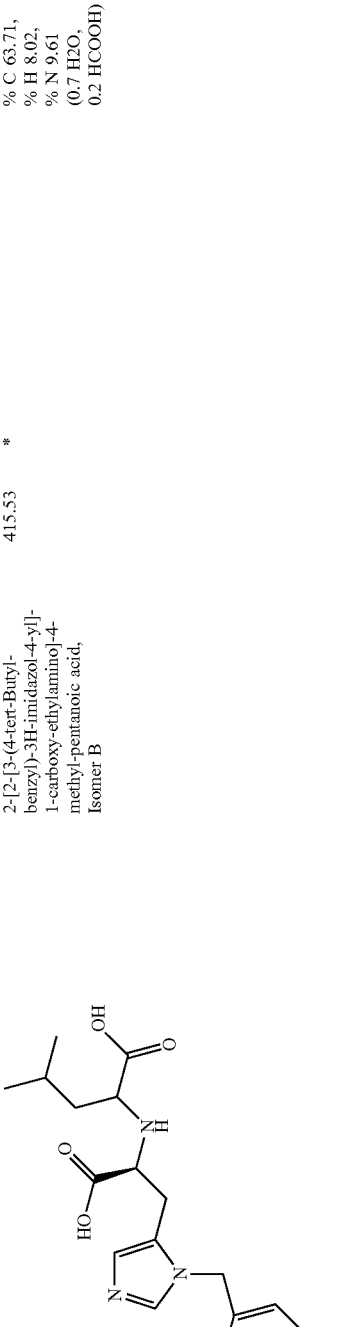 | 2-[2-[3-(4-tert-Butyl-benzyl)-3H-imidazol-4-yl]-1-carboxy-ethylamino]-4-methyl-pentanoic acid, Isomer B | 415.53 | * | | | | % C 63.71, % H 8.02, % N 9.61 (0.7 H2O, 0.2 HCOOH) | % C 63.62, % H 7.86, % N 9.64 (0.7 H2O, 0.2 HCOOH) |
| IA | 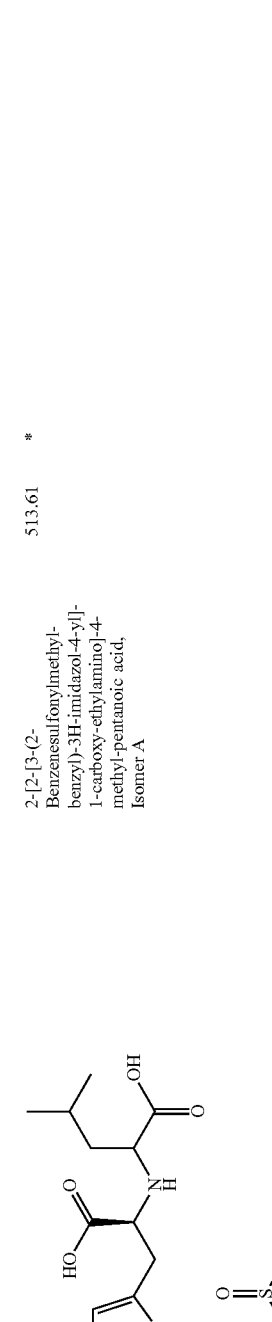 | 2-[2-[3-(2-Benzenesulfonylmethyl-benzyl)-3H-imidazol-4-yl]-1-carboxy-ethylamino]-4-methyl-pentanoic acid, Isomer A | 513.61 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IB | 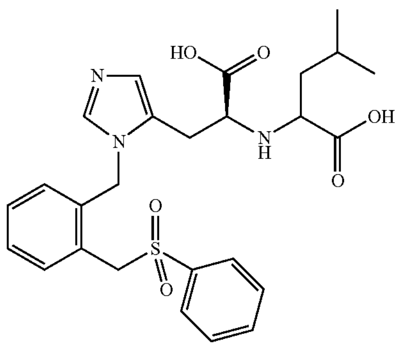 | 2-[2-[3-(2-Benzenesulfonylmethyl-benzyl)-3H-imidazol-4-yl]-1-carboxy-ethylamino]-4-methyl-pentanoic acid, Isomer B | 513.61 | * | | | | % C 57.24, % H 6.12, % N 7.50 (0.8 H2O, 0.7 HCOOH) | % C 57.1, % H 6.13, % N 7.49 (0.8 H2O, 0.7 HCOOH) |
| IC | 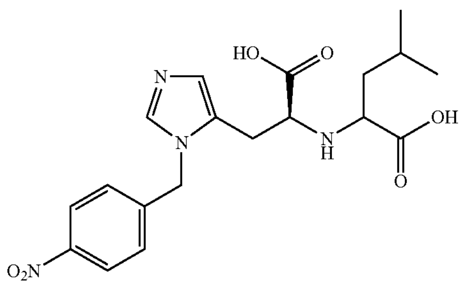 | 2-[1-Carboxy-2-[3-(4-nitro-benzyl)-3H-imidazol-4-yl]-ethylamino]-4-methyl-pentanoic acid, Isomer A | 404.42 | *** | | | | % C 48.61, % H 6.03, % N 10.95 (1.6 H2O, 1.7 HCOOH) | % C 48.5, % H 5.79, % N 10.94 (1.6 H2O, 1.7 HCOOH) |
| ID | 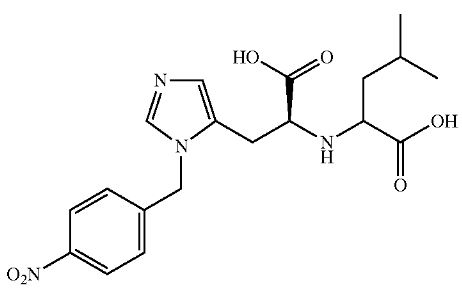 | 2-[1-Carboxy-2-[3-(4-nitro-benzyl)-3H-imidazol-4-yl]-ethylamino]-4-methyl-pentanoic acid, Isomer B | 404.42 | * | | | | % C 53.58, % H 6.10, % N 12.95 does not match | % C 53.80, % H 7.28, % N 7.00 |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IE | 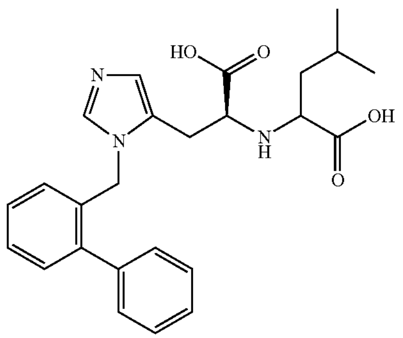 | 2-[2-(3-Biphenyl-2-ylmethyl-3H-imidazol-4-yl]-1-carboxy-ethylamino]-4-methyl-pentanoic acid, Isomer A | 435.52 | * | | | | % C 60.89, % H 6.64, % N 8.10 (1.3 H2O, 1.3 HCOOH) | % C 60.80, % H 6.13, % N 8.11 (1.3 H2O, 1.3 HCOOH) |
| IF | 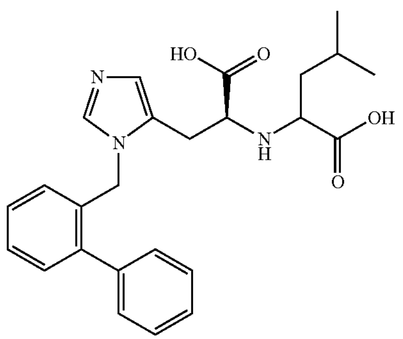 | 2-[2-(3-Biphenyl-2-ylmethyl-3H-imidazol-4-yl]-1-carboxy-ethylamino]-4-methyl-pentanoic acid, Isomer B | 435.52 | * | | | | | |
| IG | 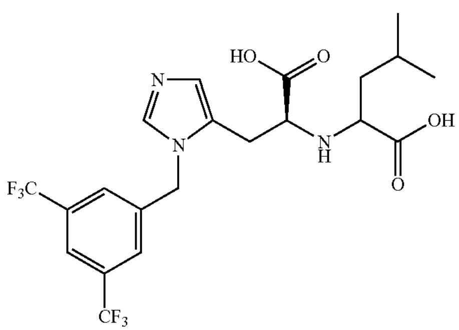 | 2-[2-[3-(3,5-Bis-trifluoromethyl-benzyl)-3H-imidazol-4-yl]-1-carboxy-ethylamino]-4-methyl-pentanoic acid, Isomer A | 495.42 | * | | | | % C 47.69, % H 4.80, % N 7.58 (0.7 H2O, 1.0 HCOOH) | % C 47.42, % H 4.40, % N 7.75 (0.7 H2O, 1.0 HCOOH) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IH | 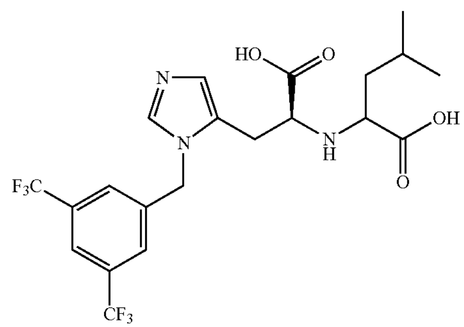 | 2-[2-[3-(3,5-Bis-trifluoromethyl-benzyl)-3H-imidazol-4-yl]-1-carboxy-ethylamino]-4-methyl-pentanoic acid, Isomer B | 495.42 | * | | | | % C 48.76, % H 4.77, % N 7.90, (0.5 H2O, 0.6 HCOOH) | % C 48.73, % H 4.58, % N 8.06, (0.5 H2O, 0.6 HCOOH) |
| II | 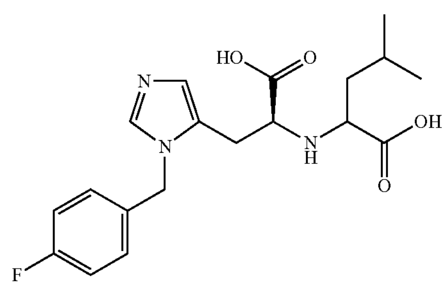 | 2-[1-Carboxy-2-[3-(4-fluoro-benzyl)-3H-imidazol-4-yl]-ethylamino]-4-methyl-pentanoic acid, Isomer A | 377.42 | * | * | | | % C 52.81, % H 6.31, % N 9.01, (1.1 H2O, 1.5 HCOOH) | % C 52.40, % H 5.95, % N 9.61, (1.1 H2O, 1.5 HCOOH) |
| IJ | 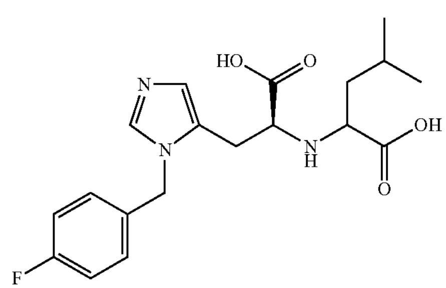 | 2-[1-Carboxy-2-[3-(4-fluoro-benzyl)-3H-imidazol-4-yl]-ethylamino]-4-methyl-pentanoic acid, Isomer B | 377.42 | * | | | | % C 56.43, % H 6.73, % N 10.39 (does not match) | % C 56.45, % H 7.32, % N 6.20 |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IK | 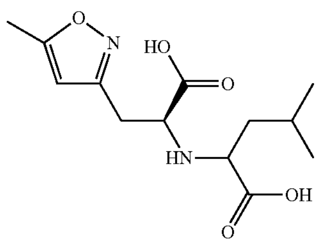 | 2-[1-Carboxy-2-[3-(4-fluoro-benzyl)-3H-imidazol-4-yl]-ethylamino] 4-methyl-pentanoic acid, | 284.31 | * | | | | insufficient sample available | |
| IL | 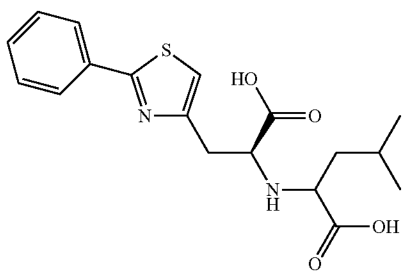 | 2-[1-Carboxy-2-(2-phenyl-thiazol-4-yl)-ethylamino]-4-methyl-pentanoic acid | 362.45 |  | * | | | % C 58.59, % H 6.02, % N 7.52 (0.2 HCl) | % C 58.47, % H 6.05, % N 7.58 (0.2 HCl) |
| IM | 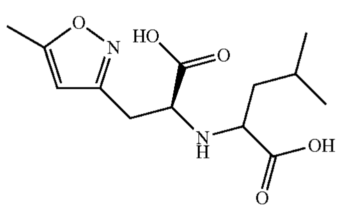 | 2-[1-Carboxy-2-(5-methyl-isoxazol-3-yl)-ethylamino]-4-methyl-pentanoic acid | 284.31 | * | | | | insufficient material available | |

TABLE 2-continued
| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IN | 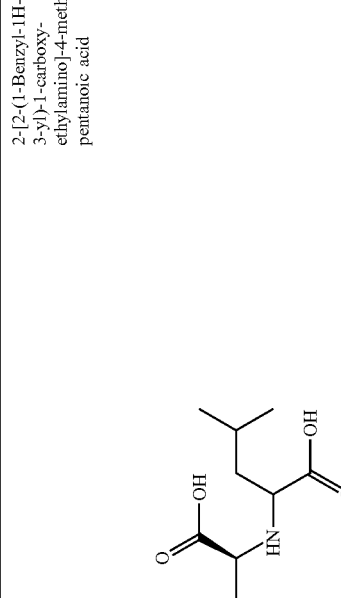 | 2-[2-(1-Benzyl-1H-pyrazo 3-yl)-1-carboxy-ethylamino]-4-methyl-pentanoic acid | 377.42 |  | * | | | % C 60.11, % H 7.02, % N 10.73 (1.0 H2O) | % C 60.46, % H 7.21, % N 11.13 (1.0 H2O) |
| IO | 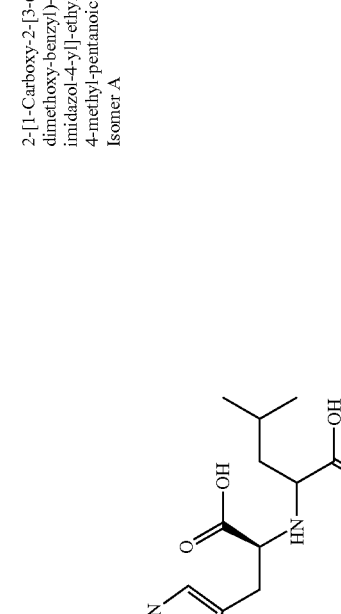 | 2-[1-Carboxy-2-[3-(2,3-dimethoxy-benzyl)-3H-imidazol-4-yl]-ethylamino) 4-methyl-pentanoic acid, Isomer A | 419.48 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IP | 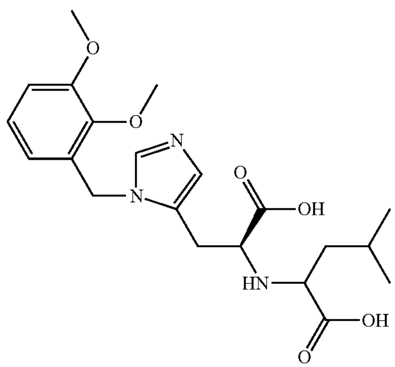 | 2-[1-Carboxy-2-[3-(2,3-dimethoxy-benzyl)-3H-imidazol-4-yl]-ethylamino)-4-methyl-pentanoic acid, Isomer B | 419.48 | * | | | | | |
| IQ | 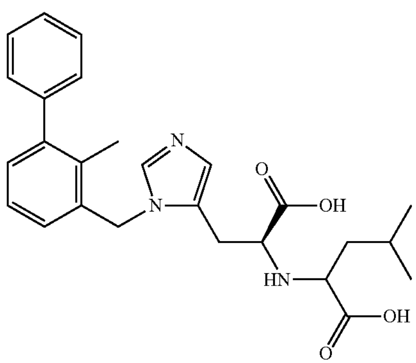 | 2-[1-Carboxy-2-[3-(2-methyl-biphenyl-3-ylmethyl)-3H-imidazol-4-yl]-ethylamino]-4-methyl-pentanoic acid, Isomer A | 449.55 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IR | 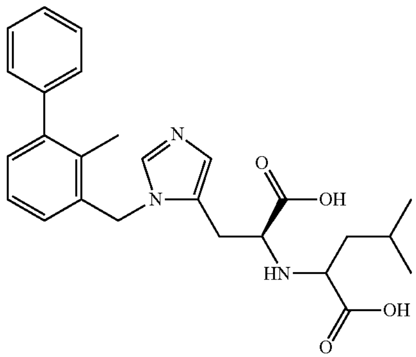 | 2-[1-Carboxy-2-[3-(2-methyl-biphenyl-3-ylmethyl)-3H-imidazol-4-yl]-ethylamino]-4-methyl-pentanoic acid, Isomer B | 449.55 | * | | | | % C 66.35, % H 6.77, % N 8.63 (1.1 H2O) | % C 66.53, % H 7.13, % N 8.95 (1.1 H2O) |
| IS | 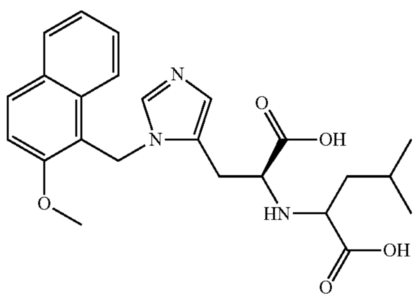 | 2-[1-Carboxy-2-[3-(2-methoxy-naphthalen-1-ylmethyl)-3H-imidazol-4-yl]-ethylamino]-4-methyl-pentanoic acid, Isomer A | 439.51 | * | | | | % C 53.82, % H 5.96, % N 7.23 (0.7 H2O, 1.5 NaCl) does not match | % C 53.55, % H 5.69, % N 7.81 (0.7 H2O, 1.5 NaCl) |
| IT | 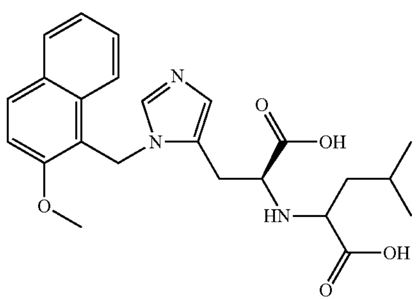 | 2-[1-Carboxy-2-[3-(2-methoxy-naphthalen-1-ylmethyl)-3H-imidazol-4-yl]-ethylamino]-4-methyl-pentanoic acid, Isomer B | 439.51 | * | | | | % C 59.53, % H 6.14, % N 8.33 (1.3 H2O, 1.0 NaCl) | % C 59.57, % H 6.37, % N 8.68 (1.3 H2O, 1.0 NaCl) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IU | 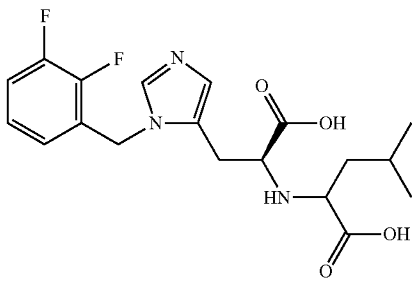 | 2-[1-Carboxy-2-[3-(2,3-difluoro-benzyl)-3H-imidazol-4-yl]-ethylamino]-4-methyl-pentanoic acid, Isomer A | 395.41 | *** | | | | % C 54.07, % H 5.87, % N 9.79 (1.4 H2O) | % C 54.25, % H 6.18, % N 9.99 (1.4 H2O) |
| IV | 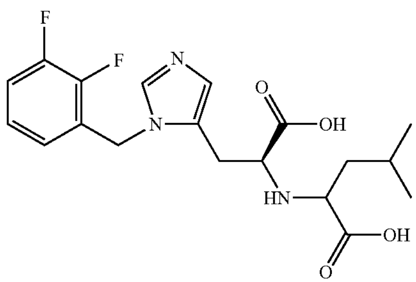 | 2-[1-Carboxy-2-[3-(2,3-difluoro-benzyl)-3H-imidazol-4-yl]-ethylamino]-4-methyl-pentanoic acid, Isomer A | 395.41 | * | | | | % C 55.77, % H 5.67, % N 10.16 (0.7 H2O) | % C 55.93, % H 6.03, % N 10.30 (0.7 H2O) |
| IW | 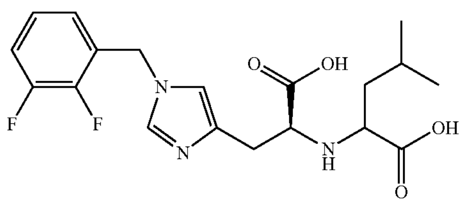 | 2-[1-Carboxy-2-[1-(2,3-difluoro-benzyl)-1H-imidazol-4-yl]-ethylamino]-4-methyl-pentanoic acid | 395.41 | * | | | | % C 54.96, % H 5.74, % N 9.92 (1.0 H2O) | % C 55.20, % H 6.10, % N 10.16 (1.0 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| IX | 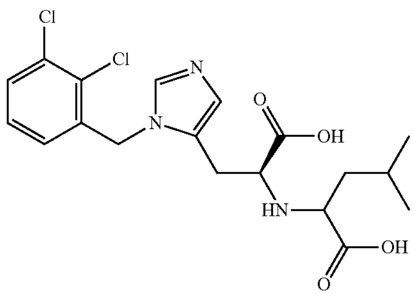 | 2-[1-Carboxy-2-[3-(2,3-dichloro-benzyl)-3H-imidazol-4-yl]-ethylamino 4-methyl-pentanoic acid, Isomer A | 428.31 | * | *** | | | % C 50.02, % H 5.24, % N 9.00 (1.0 H2O, 0.3 HCOOH) | % C 50.38, % H 5.61, % N 9.13 (1.0 H2O, 0.3 HCOOH) |
| IY | 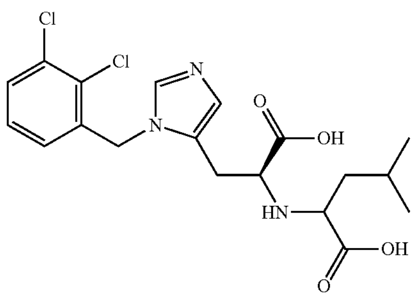 | 2-[1-Carboxy-2-[3-(2,3-dichloro-benzyl)-3H-imidazol-4-yl]-ethylamino 4-methyl-pentanoic acid, Isomer B | 428.31 | *** | | | | % C 50.74, % H 5.37, % N 9.06 | % C 51.13, % H 5.65, % N 9.41 |
| IZ | 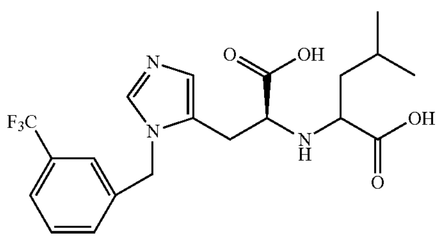 | 2-[1-Carboxy-2-[3-(3-trifluoromethyl-benzyl)-3H-imidazol-4-yl]-ethylamino 4-methyl-pentanoic acid, Isomer A | 427.42 | * | * | | | % C 52.25, % H 5.76, % N 8.83 (0.9 H2O, 0.7 HCOOH) | % C 52.37, % H 5.56, % N 8.78 (0.9 H2O, 0.7 HCOOH) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| JA | 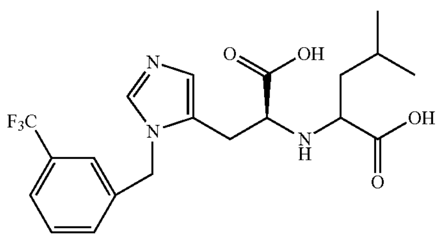 | 2-[1-Carboxy-2-[3-(3-trifluoromethyl-benzyl)-3H-imidazol-4-yl]-ethylamino] 4-methyl-pentanoic acid, Isomer B | 427.42 | * | | | | % C 54.44, % H 5.74, % N 9.43 (0.5 H2O, 0.2 HCOOH) | % C 54.09, % H 5.63, % N 9.42 (0.5 H2O, 0.2 HCOOH) |
| JB | 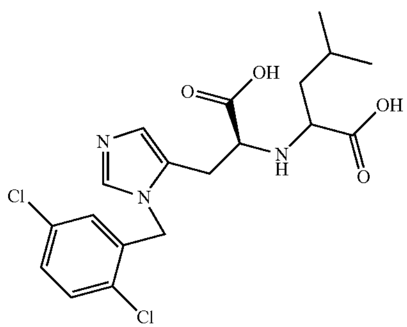 | 2-[1-Carboxy-2-[3-(2,5-dichloro-benzyl)-3H-imidazol-4-yl]-ethylamino] 4-methyl-pentanoic acid, Isomer A | 428.31 | * | * | | | % C 45.33, % H 5.62, % N 7.55 (2.0 H2O, 2.0 HCOOH) | % C 45.15, % H 5.14, % N 7.68 (2.0 H2O, 2.0 HCOOH) |
| JD | 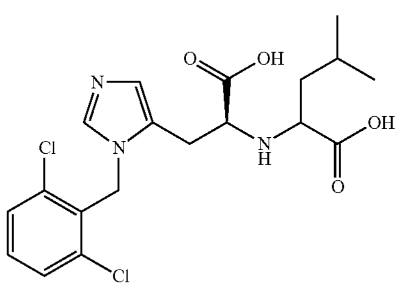 | 2-[1-Carboxy-2-[3-(2,6-dichloro-benzyl)-3H-imidazol-4-yl]-ethylamino] 4-methyl-pentanoic acid, Isomer A | 428.31 | * | | | | % C 48.44, % H 5.57, % N 8.47 (close match) | % C 48.91, % H 6.07, % N 7.15 (close match) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| JE | 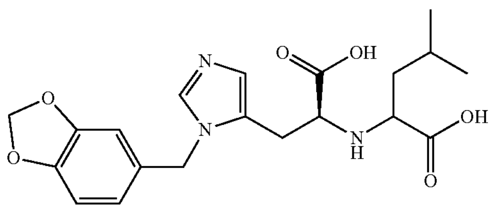 | 2-[2-(3-Benzo[1,3]dioxol-5-ylmethyl-3H-imidazol-4-yl)-1-carboxy-ethyl amino 4-methyl-pentanoic acid, Isomer A | 403.44 | * | * | | | % C 53.58, % H 6.15, % N 9.39 (1.0 H2O, 1.0 HCOOH) | % C 53.96, % H 6.25, % N 8.99 (1.0 H2O, 1.0 HCOOH) |
| JF | 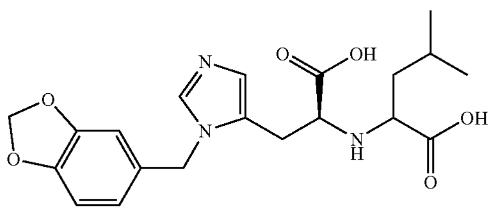 | 2-[2-(3-Benzo[1,3]dioxol-5-ylmethyl-3H-imidazol-4-yl)-1-carboxy-ethyl amino 4-methyl-pentanoic acid, Isomer B | 403.44 | * | | | | % C 54.31, % H 6.11, % N 9.59 (1.0 H2O, 0.8 HCOOH) | % C 54.52, % H 6.29, % N 9.17 (1.0 H2O, 0.8 HCOOH) |
| JG | 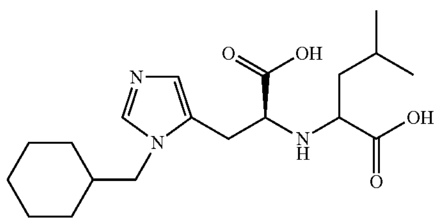 | 2-[1-Carboxy-2-(3-cyclohexylmethyl-3H-imidazol-4-yl)-ethylamino] 4-methyl-pentanoic acid Isomer A | 365.47 | * | | | | % C 56.34, % H 8.11, % N 10.79 (1.5 H2O, 0.4 HCOOH) | % C 56.71, % H 8.54, % N 10.23 (1.5 H2O, 0.4 HCOOH) |
| JH | 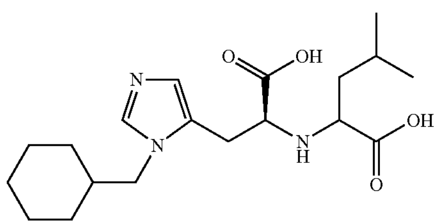 | 2-[1-Carboxy-2-(3-cyclohexylmethyl-3H-imidazol-4-yl)-ethylamino] 4-methyl-pentanoic acid Isomer B | 365.47 | * | | | | % C 58.64, % H 8.45, % N 11.25 (1.2 H2O) | % C 58.95, % H 8.70, % N 10.86 (1.2 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| JI | 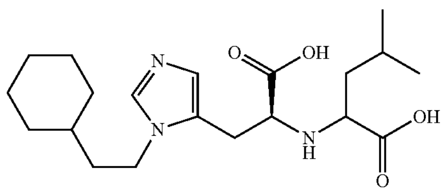 | 2-[1-Carboxy-2-[3-(2-cyclohexyl-ethyl)-3H-imidazol-4-yl]-ethylamino]-4-methyl-pentanoic acid Isomer A | 379.50 | * | * | | | % C 55.53, % H 8.05, % N 9.83 (1.7 H2O, 0.8 HCOOH) | % C 55.90, % H 8.57, % N 9.40 (1.7 H2O, 0.8 HCOOH) |
| JJ | 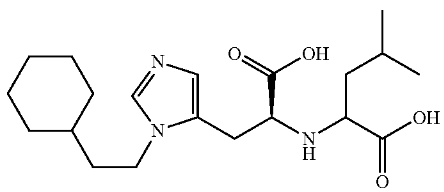 | 2-[1-Carboxy-2-[3-(2-cyclohexyl-ethyl)-3H-imidazol-4-yl]-ethylamino]-4-methyl-pentanoic acid Isomer B | 379.50 | * | | | | % C 62.56, % H 8.83, % N 11.00 (0.2 H2O) | % C 62.70, % H 8.79, % N 10.97 (0.2 H2O) |
| JK | 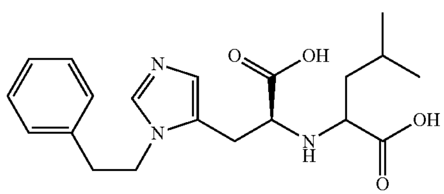 | 2-[1-Carboxy-2-[3-phenethyl-3H-imidazol-4-yl)-ethylamino]-4-methyl-pentanoic acid Isomer A | 373.45 | * | * | | | % C 60.39, % H 7.25, % N 11.20 (0.5 HCOOH, 0.5 H2O, 0.2 NH3) | % C 60.22, % H 7.30, % N 10.96 (0.5 HCOOH, 0.5 H2O, 0.2 NH3) |
| JL | 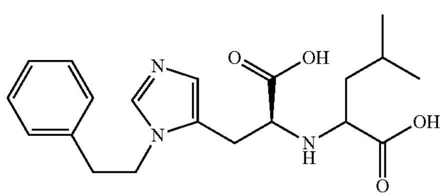 | 2-[1-Carboxy-2-[3-phenethyl-3H-imidazol-4-yl)-ethylamino]-4-methyl-pentanoic acid Isomer B | 373.45 | * | | | | % C 61.61, % H 7.33, % N 10.98 (0.8 H2O) | % C 61.93, % H 7.43, % N 10.83 (0.8 H2O) |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| JM | 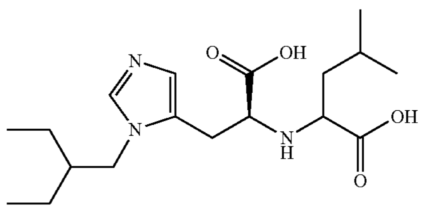 | 2-[1-Carboxy-2-[3-(2-ethyl butyl)-3H-imidazol-4-yl]-ethylamino]-4-methyl-pentanoic acid, Isomer A | 353.46 | *** | | | | % C 56.66, % H 8.59, % N 11.45 (0.6 H2O, 0.5 HCOOH, 0.2 NH3) | % C 56.87, % H 8.72, % N 11.47 (0.6 H2O, 0.5 HCOOH, 0.2 NH3) |
| JN | 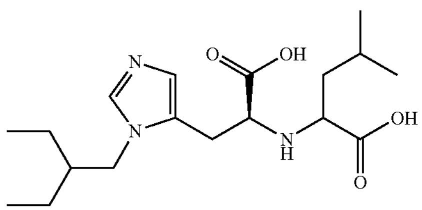 | 2-[1-Carboxy-2-[3-(2-ethyl butyl)-3H-imidazol-4-yl]-ethylamino]-4-methyl-pentanoic acid, Isomer B | 353.46 | * | | | | | |
| JO | 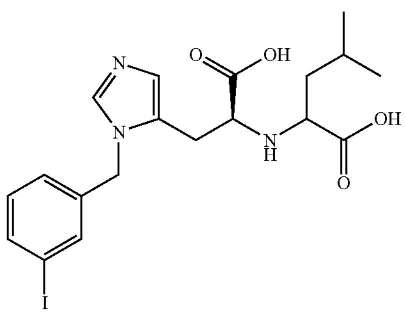 | 2-[1-Carboxy-2-[3-(3-iodo benzyl)-3H-imidazol-4-yl]-ethylamino]-4-methyl-pentanoic acid, Isomer A | 531.35 | * | * | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| JP | 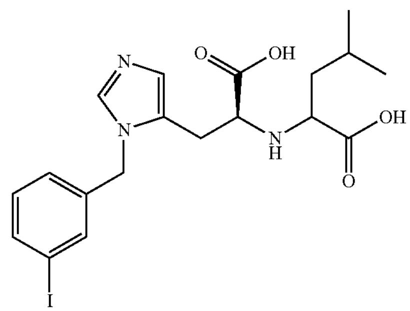 | 2-[1-Carboxy-2-[3-(3-iodo benzyl)-3H-imidazol-4-yl]-ethylamino]-4-methyl-pentanoic acid, Isomer B | 531.35 | * | * | | | | |
| JQ | 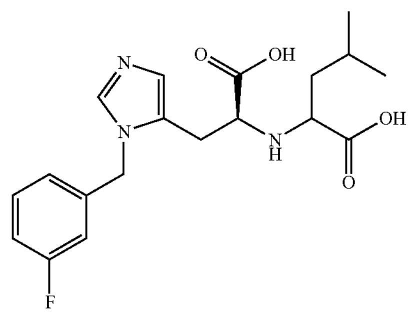 | 2-[1-Carboxy-2-[3-(3-fluoro-benzyl)-3H-imidazol-4-yl]-ethylamino] 4-methyl-pentanoic acid Isomer A | 423.45 | * | * | | | | |
| JR | 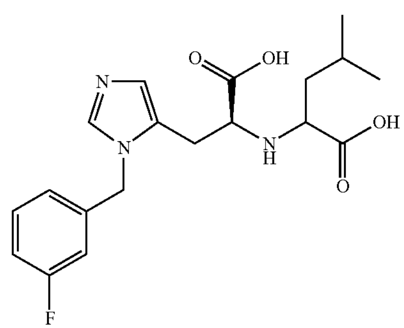 | 2-[1-Carboxy-2-[3-(3-fluoro-benzyl)-3H-imidazol-4-yl]-ethylamino] 4-methyl-pentanoic acid Isomer B | 423.45 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| JZ | 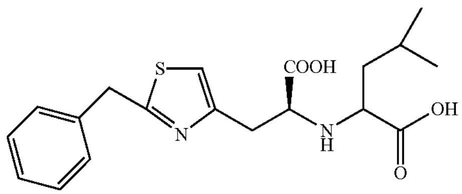 | 2-[2-(2-Benzyl-thiazol-4-yl)-1-carboxy-ethylamino]-4-methyl-pentanoic acid, Isomer A | | * | | | | | |
| KA | 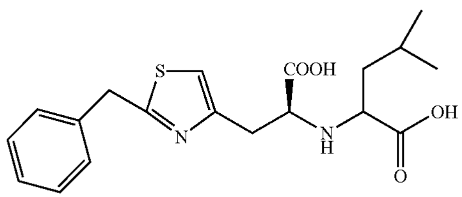 | 2-[2-(2-Benzyl-thiazol-4-yl)-1-carboxy-ethylamino]-4-methyl-pentanoic acid, Isomer B | | * | | | | | |
| KB | 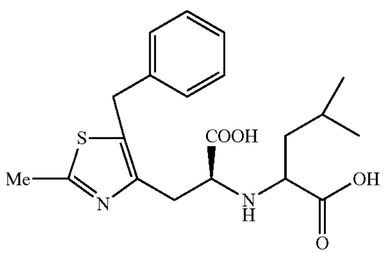 | 2-[2-(5-Benzyl-2-methyl-thiazol-4-yl)-1-carboxy-ethylamino]-4-methyl-pentanoic acid, Isomer A | | ** | | | | | |
| KC | 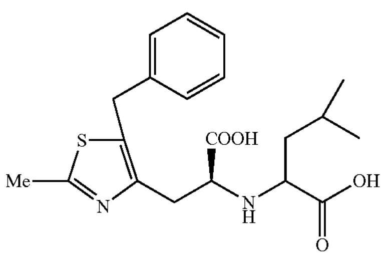 | 2-[2-(5-Benzyl-2-methyl-thiazol-4-yl)-1-carboxy-ethylamino]-4-methyl-pentanoic acid, Isomer B | | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| KD | 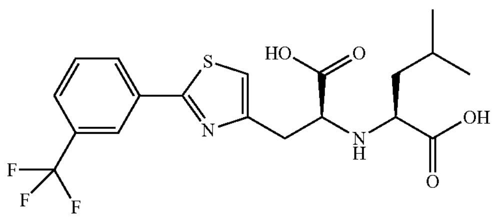 | 2-[1-Carboxy-2-[2-(3-trifluoromethyl-phenyl)-thiazol-4-yl]-ethylamino]-4-methyl-pentanoic acid | 430 | * | | | | | |
| KE | 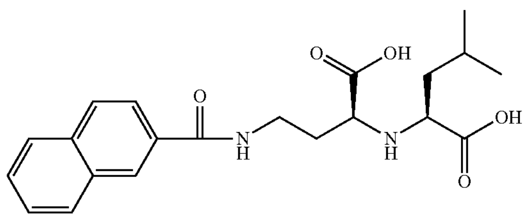 | 2-[1-Carboxy-3-[(naphthalene-2-carbonyl amino]-propylamino)-4-methyl-pentanoic acid | 386 | * | | | | | |
| KF | 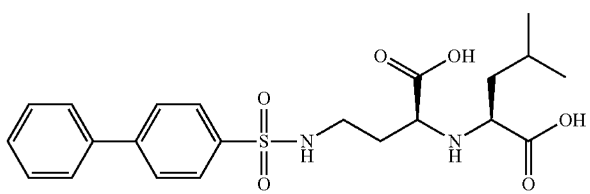 | 2-[3-(Biphenyl-4-sulfonylamino)-1-carboxy-propylamino]-4-methyl-pentanoic acid | 448 | ** | | | | | |
| KG | 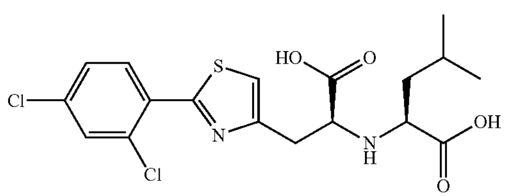 | 2-[1-Carboxy-2-[2-(2,4-dichloro-phenyl)-thiazol-4-yl]-ethylamino]-4-methyl-pentanoic acid | 431 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| KH | 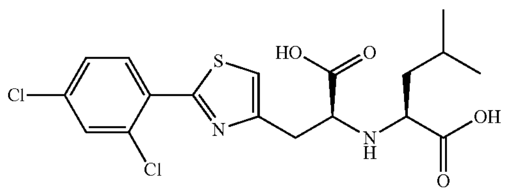 | 2-[1-Carboxy-2-[2-(2,4-dichloro-phenyl)-thiazol-4-yl]-ethylamino]-4-methyl-pentanoic acid | 431 | *** | | | | | |
| KI | 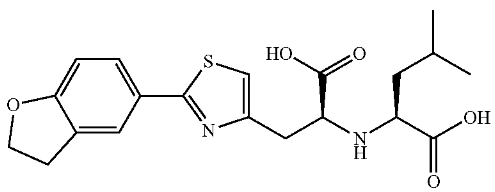 | 2-[1-Carboxy-2-[2-(2,3-dihydro-benzofuran-5-yl)-thiazol-4-yl]-ethylamino]-4-methyl-pentanoic acid | 404 | *** | | | | | |
| KJ | 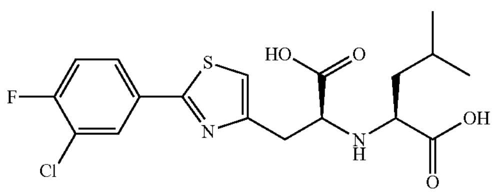 | 2-[1-Carboxy-2-[2-(3-chloro-4-fluoro-phenyl)-thiazol-4-yl]-ethylamino]-4-methyl-pentanoic acid | 415 | *** | | | | | |
| KK | 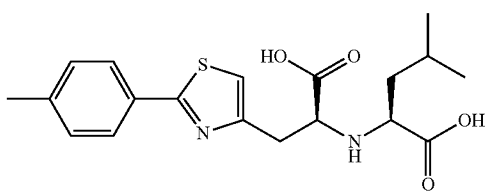 | 2-[1-Carboxy-2-(2-p-tolyl-thiazol-4-yl)-ethylamino]-4-methyl-pentanoic acid | 376 | *** | | | | | |
| KL | 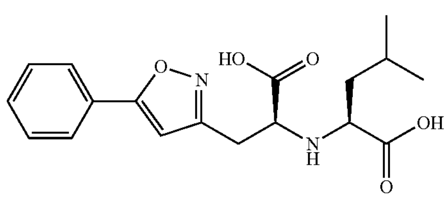 | 2-[1-Carboxy-2-(5-phenyl-isoxazol-3-yl)-ethylamino]-4-methyl-pentanoic acid | 346 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| KM | 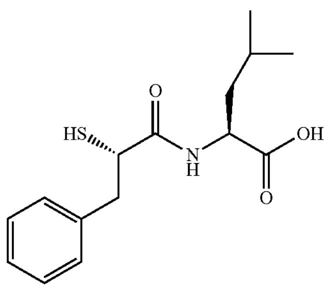 | 2-(2-Mercapto-3-phenyl-propionylamino)-4-methyl-pentanoic acid | 295 | * | | | | | |
| KN | 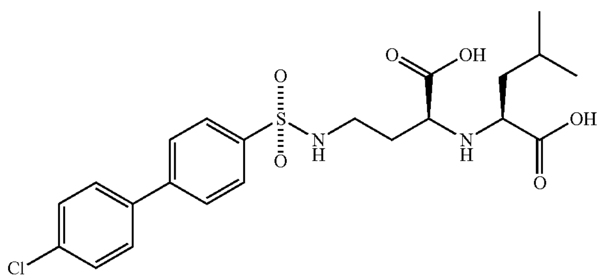 | 2-[1-(Carboxy-3-(4'-chloro-biphenyl-4-sulfonylamino)-propylamino]-4-methyl-pentanoic acid | 483 | * | | | | | |
| KO | 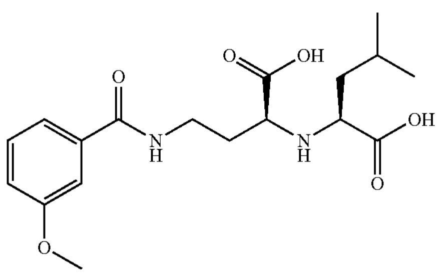 | 2-[1-Carboxy-3-(3-methoxy-benzoylamino)-propylamino]-4-methyl-pentanoic acid | 366 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| KP | 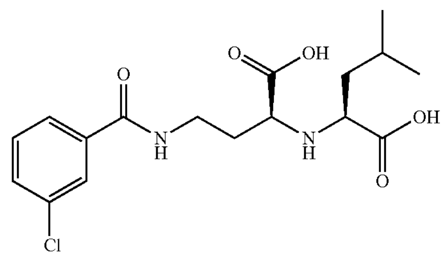 | 2-[1-Carboxy-3-(3-chloro-benzoylamino)-propylamino]-4-methyl-pentanoic acid | 371 | * | | | | | |
| KQ | 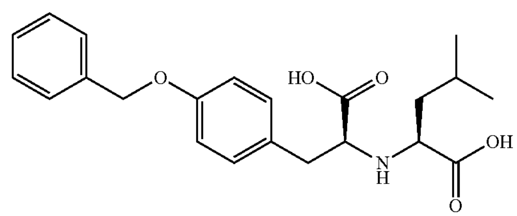 | 2-[2-(4-Benzyloxy-phenyl)-1-carboxy-ethylamino]-4-methyl-pentanoic acid | 386 | ** | | | | | |
| KR | 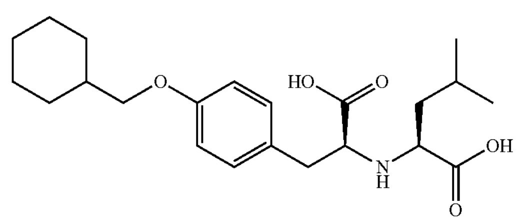 | 2-[1-Carboxy-2-(4-cyclohexylmethoxy-phenyl)-ethylamino]-4-methyl-pentanoic acid | 392 | ** | | | | | |
| KS | 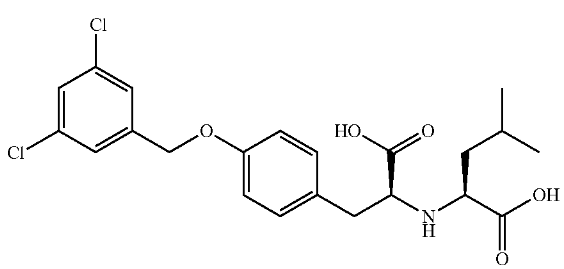 | 2-[1-Carboxy-2-[4-(3,5-dichloro-benzyloxy)-phenyl]-ethylamino]-4-methyl-pentanoic acid | 454 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| KT | 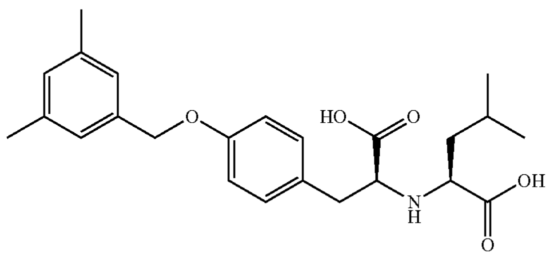 | 2-[1-Carboxy-2-[4-(3,5-dimethyl-benzyloxy)-phenyl]-ethylamino]-4-methyl-pentanoic acid | 414 | ** | | | | | |
| KU | 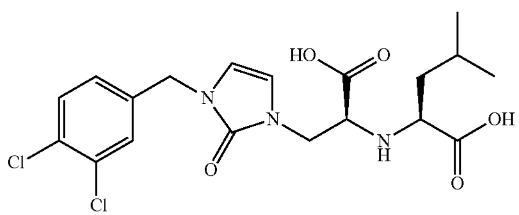 | 2-[1-Carboxy-2-[3-(3,4-dichloro-benzyl)-2-oxo-2,3-dihydro-imidazol-1-yl]-ethylamino]-4-methyl-pentanoic acid | 444 | *** | | | | | |
| KV | 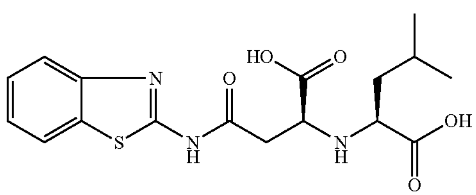 | 2-[2-(Benzothiazol-2-ylcarbamoyl)-1-carboxy-ethylamino]-4-methyl-pentanoic acid | 379 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| KW | 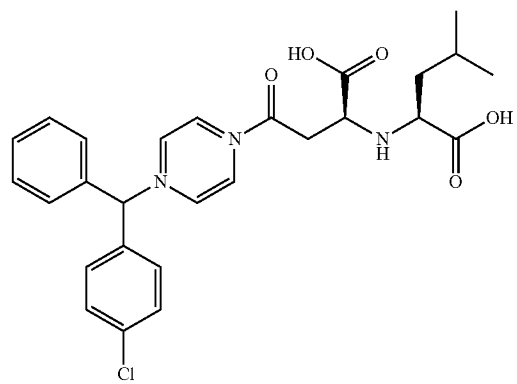 | 2-(1-Carboxy-3-[4-[(4-chloro-phenyl)-phenyl-methyl]-piperazin-1-yl]-3-oxo-propylamino)-4-methyl-pentanoic acid | 516 | * | | | | | |
| KX | 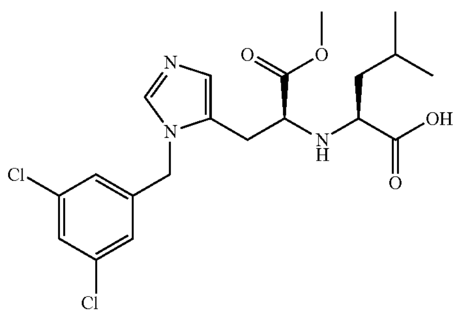 | 2-[2-[3-(3,5-Dichloro-benzyl)-3H-imidazol-4-yl]-1-methoxycarbonyl-ethylamino]-4-methyl-pentanoic acid | 442 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| KY | 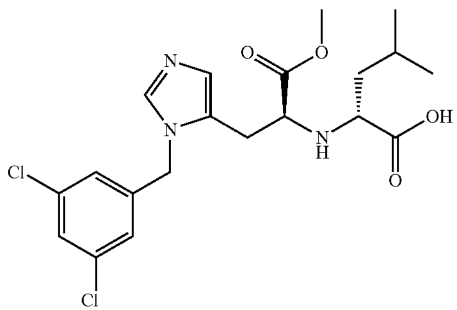 | 2-[2-[3-(3,5-Dichloro-benzyl)-3H-imidazol-4-yl]-1-methoxycarbonyl-ethylamino]-4-methyl-pentanoic acid | 442 | ** | | | | | |
| KZ | 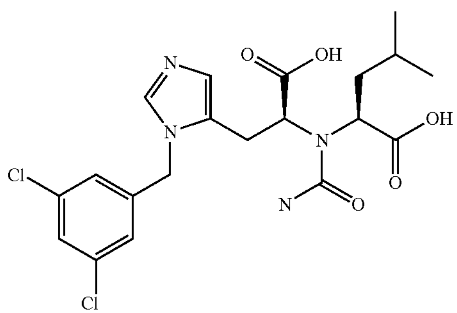 | 2-({1-Carboxy-2-[3-(3,5-dichloro-benzyl)-3H-imidazol-4-yl]-ethyl]-formyl-amino)-4-methyl-pentanoic acid | 456 | *** | | | | | |
| LA | 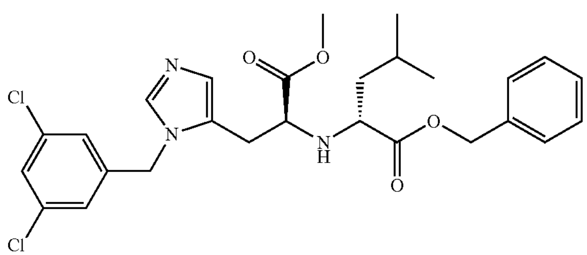 | 2-[2-[3-(3,5-Dichloro-benzyl)-3H-imidazol-4-yl]-1-methoxycarbonyl-ethylamino]-4-methyl-pentanoic acid benzyl ester | 532 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| LB | 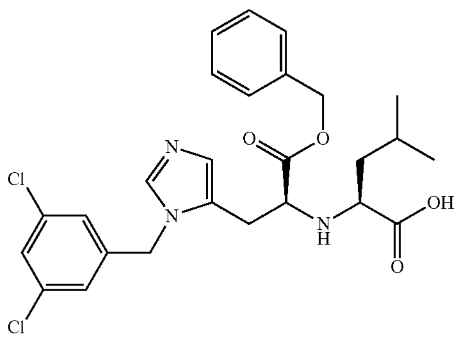 | 2-{1-Benzyloxycarbonyl-2-[3-(3,5-dichloro-benzyl)-3H-imidazol-4-yl]-ethylamino}-4-methyl-pentanoic acid | 518 | * | | | | | |
| LC | 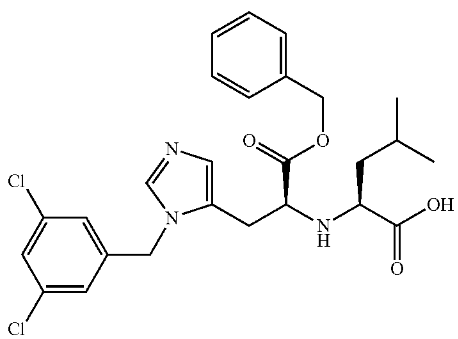 | 2-(1-Benzyloxycarbonyl-2-[3-(3,5-dichloro-benzyl)-3H-imidazol-4-yl]-ethylamino}-4-methyl-pentanoic acid | 518 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| LD | 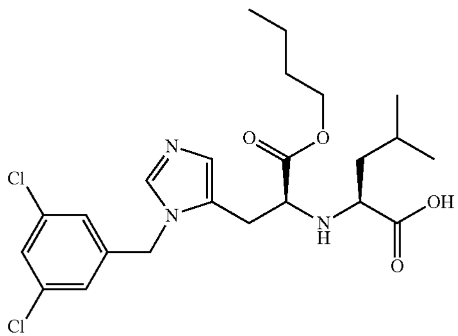 | 2-[1-Butoxycarbonyl-2-[3-(3,5-dichloro-benzyl)-3H-imidazol-4-yl]-ethylamino]-4-methyl-pentanoic acid | 484 | *** | | | | | |
| LE | 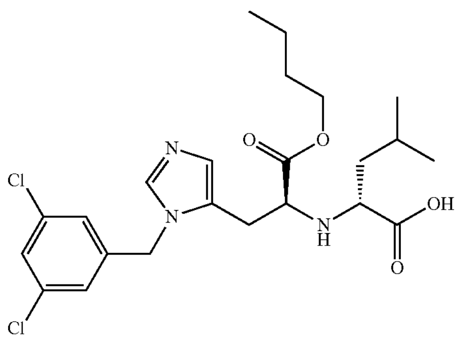 | 2-[1-Butoxycarbonyl-2-[3-(3,5-dichloro-benzyl)-3H-imidazol-4-yl]-ethylamino]-4-methyl-pentanoic acid | 484 | * | | | | | |
| LF | 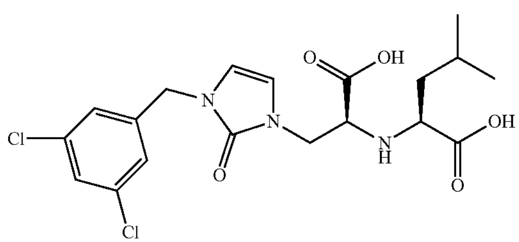 | 2-[1-Carboxy-2-[3-(3,5-dichloro-benzyl)-2-oxo-2,3-dihydro-imidazol-1-yl]-ethylamino]-4-methyl-pentanoic acid | 444 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| LG | 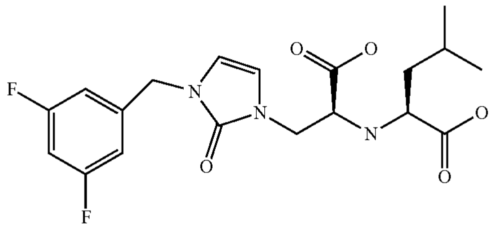 | 2-[1-Carboxy-2-[3-(3,5-difluoro-benzyl)-2-oxo-2,3-dihydro-imidazol-1-yl]-ethylamino]-4-methyl-pentanoic acid | 411 | *** | | | | | |
| LH | 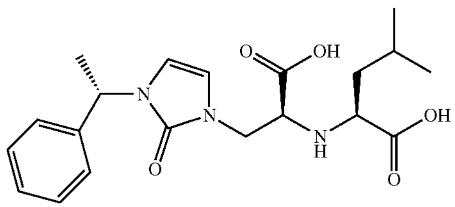 | 2-[1-Carboxy-2-[2-oxo-3-(1-phenyl-ethyl)-2,3-dihydro-imidazol-1-yl]-ethylamino]-4-methyl-pentanoic acid | 390 | ** | | | | | |
| LI | 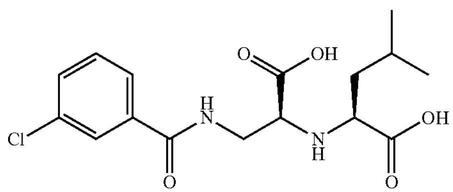 | 2-[1-Carboxy-2-(3-chloro-benzoylamino)-ethylamino]-4-methyl-pentanoic acid | 357 | * | | | | | |
| LJ | 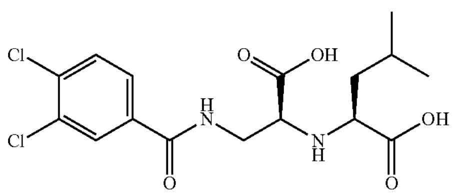 | 2-[1-Carboxy-2-(3,4-dichloro-benzoylamino)-ethylamino]-4-methyl-pentanoic acid | 391 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| LK | 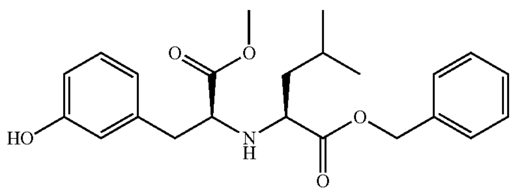 | 2-[2-(3-Hydroxy-phenyl)-1-methoxycarbonyl-ethylamino]-4-methyl-pentanoic acid benzyl ester | 400 | * | | | | | |
| LL | 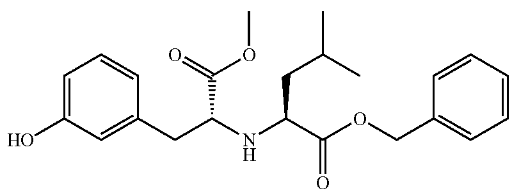 | 2-[2-(3-Hydroxy-phenyl)-1-methoxycarbonyl-ethylamino]-4-methyl-pentanoic acid benzyl ester | 400 | * | | | | | |
| LM | 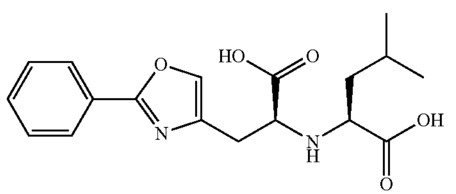 | 2-[1-Carboxy-2-(2-phenyl-oxazol-4-yl)-ethylamino]-4-methyl-pentanoic acid | 346 | * | | | | | |
| LN | 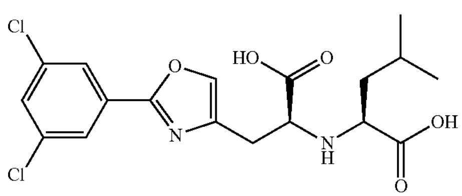 | 2-{1-Carboxy-2-[2-(3,5-dichloro-phenyl)-oxazol-4-yl]-ethylamino}-4-methyl-pentanoic acid | 415 | *** | | | | | |
| LO | 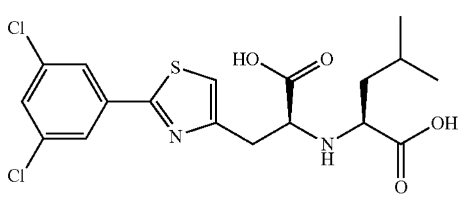 | 2-{1-Carboxy-2-[2-(3,5-dichloro-phenyl)-thiazol-4-yl]-ethylamino}-4-methyl-pentanoic acid | 431 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| LP | 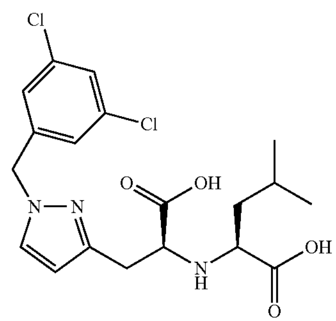 | 2-[1-Carboxy-2-[1-(3,5-dichloro-benzyl)-1H-pyrazol-3-yl]-ethylamino]-4-methyl-pentanoic acid | 428 | *** | | | | | |
| LQ | 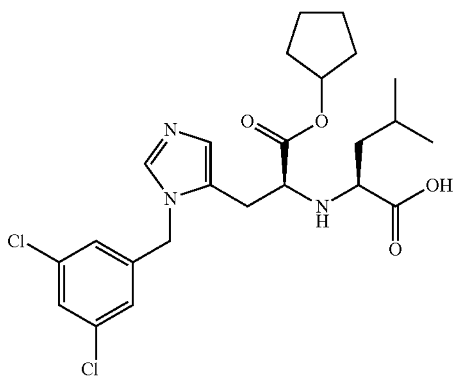 | 2-[1-Cyclopentyloxycarbonyl-2-[3-(3,5-dichloro-benzyl)-3H-imidazol-4-yl]-ethylamino]-4-methyl-pentanoic acid | 496 | * | | | | | |
| LR | 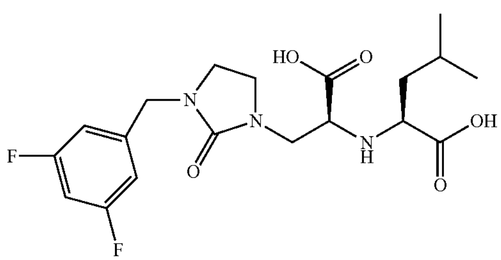 | 2-[1-Carboxy-2-[3-(3,5-difluoro-benzyl)-2-oxo-imidazolidin-1-yl]-ethylamino]-4-methyl-pentanoic acid | 413 | ** | | | | | |

TABLE 2-continued

| Ref, No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| LS | 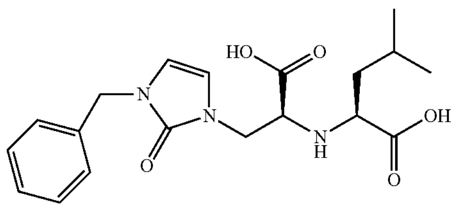 | 2-[2-(3-Benzyl-2-oxo-2,3-dihydro-imidazol-1-yl)-1-carboxy-ethylamino]-4-methyl-pentanoic acid | 375 | ** | | | | | |
| LT | 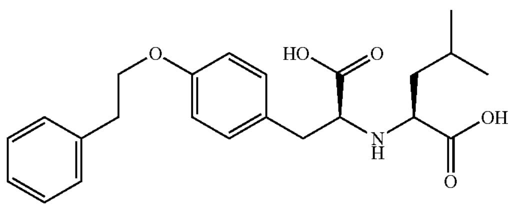 | 2-[1-Carboxy-2-(4-phenethyloxy-phenyl)-ethylamino]-4-methyl-pentanoic acid | 400 | ** | | | | | |
| LU | 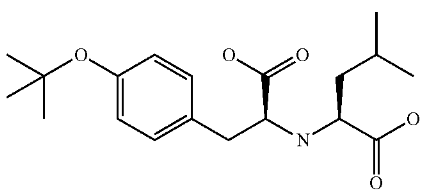 | 2-[2-(4-tert-Butoxy-phenyl)-1-carboxy-ethylamino]-4-methyl-pentanoic acid | 351 | * | | | | | |
| LV | 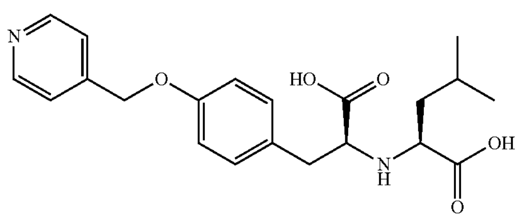 | 2-[1-Carboxy-2-[4-(pyridin 4-ylmethoxy)-phenyl]-ethylamino]-4-methyl-pentanoic acid | 386 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| LW | 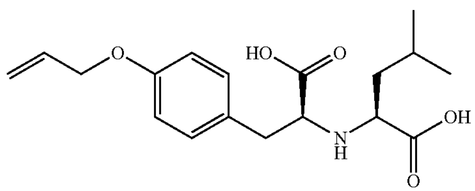 | 2-[2-(4-Allyloxy-phenyl)-1-carboxy-ethylamino]-4-methyl-pentanoic acid | 335 | *** | | | | | |
| LX | 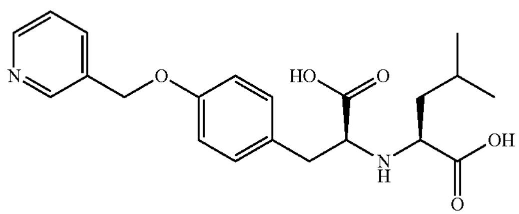 | 2-[1-Carboxy-2-[4-(pyridin 3-ylmethoxy)-phenyl]-ethylamino]-4-methyl-pentanoic acid | 386 | ** | | | | | |
| LY | 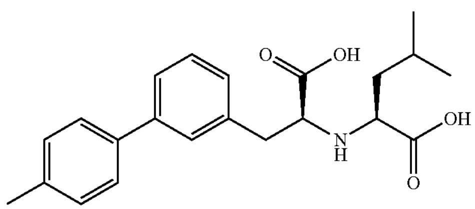 | 2-[1-Carboxy-2-(4'-methyl biphenyl-3-yl)-ethylamino 4-methyl-pentanoic acid | 370 | * | | | | | |
| LZ | 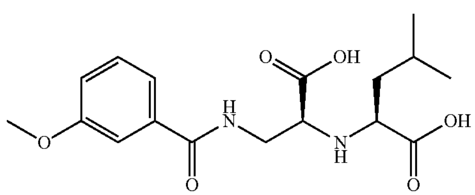 | 2-[1-Carboxy-2-(3-methoxy-benzoylamino)-ethylamino]-4-methyl-pentanoic acid | 352 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| MA | 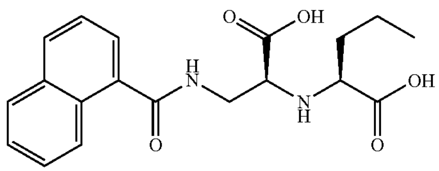 | 2-[1-Carboxy-2-[(naphthalene-1-carbonyl)amino]-ethylamino]-4-methyl-pentanoic acid | 372 | * | | | | | |
| MB | 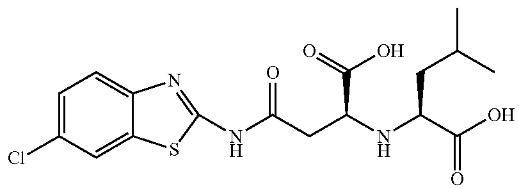 | 2-[1-Carboxy-2-(6-chloro-benzothiazol-2-ylcarbamoyl)-ethylamino]-4-methyl-pentanoic acid | 414 | *** | | | | | |
| MC | 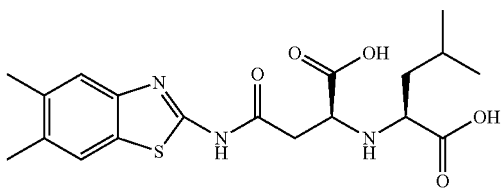 | 2-[1-Carboxy-2-(5,6-dimethyl-benzothiazol-2-ylcarbamoyl)-ethylamino]-4-methyl-pentanoic acid | 408 | * | | | | | |
| MD | 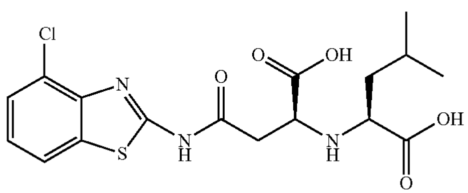 | 2-[1-Carboxy-2-(4-chloro-benzothiazol-2-ylcarbamoyl)-ethylamino]-4-methyl-pentanoic acid | 414 | *** | | | | | |
| ME | 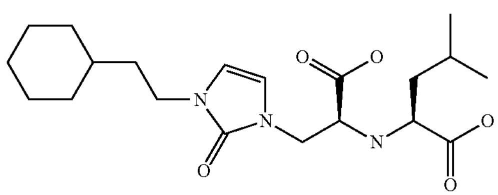 | 2-[1-Carboxy-2-[3-(2-cyclohexyl-ethyl)-2-oxo-2,3-dihydro-imidazol-1-yl]-ethylamino]-4-methyl-pentanoic acid | 396 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| MF | 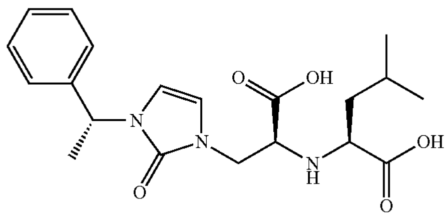 | 2-[1-Carboxy-2-[2-oxo-3-(1-phenyl-ethyl)-2,3-dihydro-imidazol-1-yl]-ethylamino]-4-methyl-pentanoic acid | 390 | * | | | | | |
| MG | 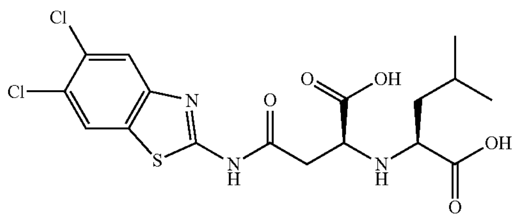 | 2-[1-Carboxy-2-(5,6-dichloro-benzothiazol-2-ylcarbamoyl)-ethylamino]-4-methyl-pentanoic acid | 448 | ** | | | | | |
| MH | 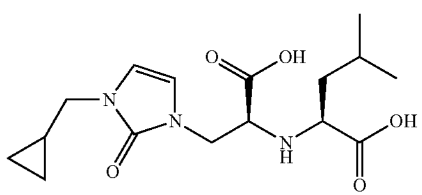 | 2-[1-Carboxy-2-(3-cyclopropyl methyl-2-oxo-2,3-dihydro-imidazol-1-yl)-ethylamino]-4-methyl-pentanoic acid | 339 | ** | | | | | |
| MI | 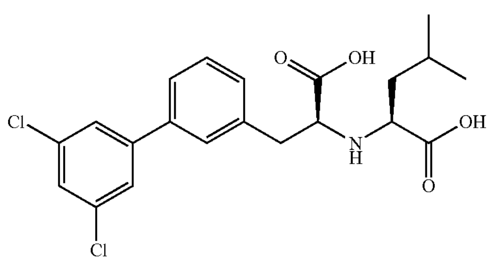 | 2-[1-Carboxy-2-(3',5'-dichloro-biphenyl-3-yl)-ethylamino]-4-methyl-pentanoic acid | 424 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| MJ | 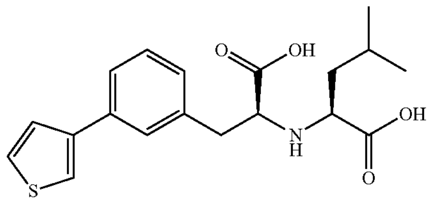 | 2-[1-Carboxy-2-(3-thiophen-3-yl-phenyl)-ethylamino]-4-methyl-pentanoic acid | 362 | * | | | | | |
| MK | 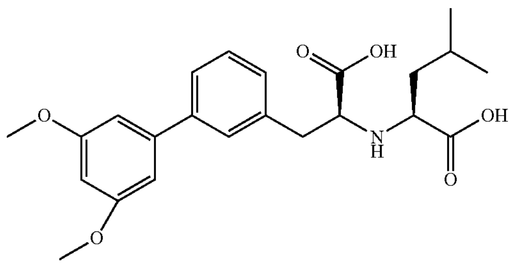 | 2-[1-Carboxy-2-(3',5'-dimethoxy-biphenyl-3-yl)-ethylamino]-4-methyl-pentanoic acid | 416 | * | | | | | |
| ML | 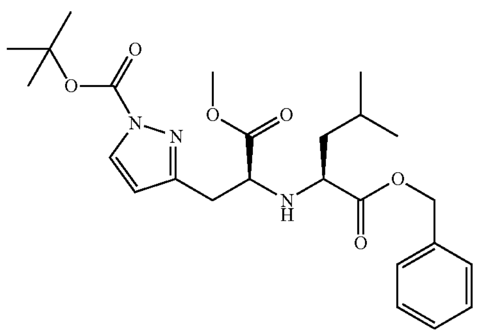 | 3-[2-(1-Benzyloxycarbonyl-3-methyl-butylamino)-2-methoxycarbonyl-ethyl]-pyrazole-1-carboxylic acid tert-butyl ester | 474 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| MM | 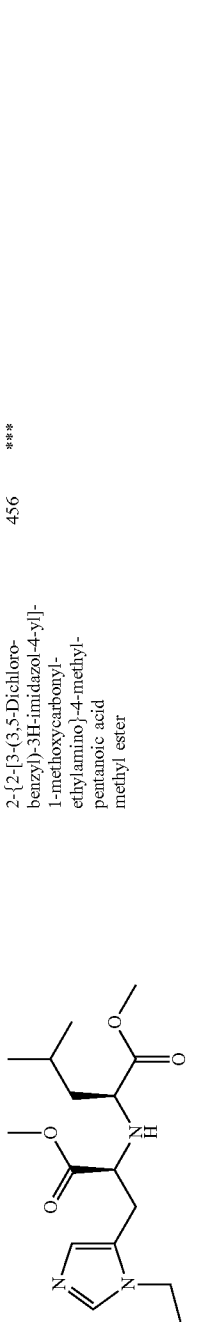 | 2-{2-[3-(3,5-Dichloro-benzyl)-3H-imidazol-4-yl]-1-methoxycarbonyl-ethylamino}-4-methyl-pentanoic acid methyl ester | 456 | *** | | | | | |
| MN | 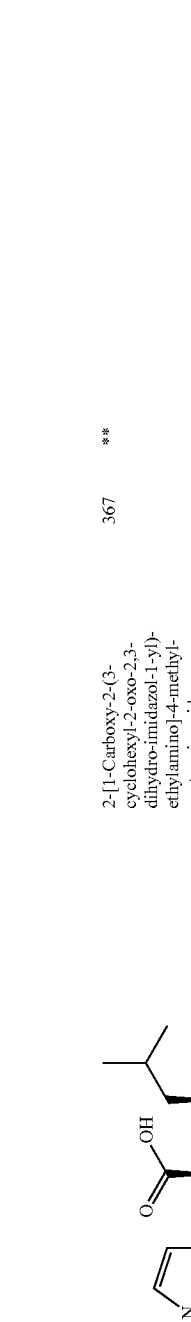 | 2-[1-Carboxy-2-(3-cyclohexyl-2-oxo-2,3-dihydro-imidazol-1-yl)-ethylamino]-4-methyl-pentanoic acid | 367 | ** | | | | | |
| MO | 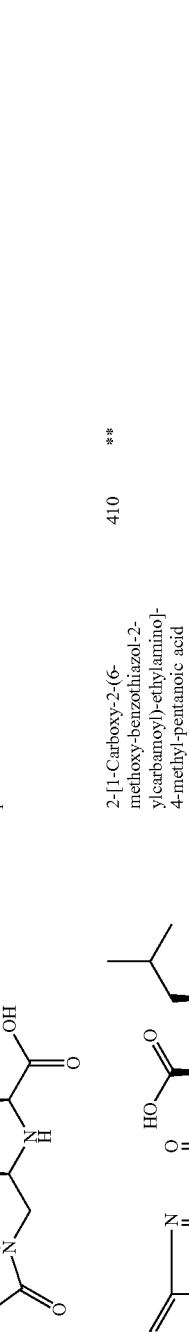 | 2-[1-Carboxy-2-(6-methoxy-benzothiazol-2-ylcarbamoyl)-ethylamino]-4-methyl-pentanoic acid | 410 | ** | | | | | |
| MP | 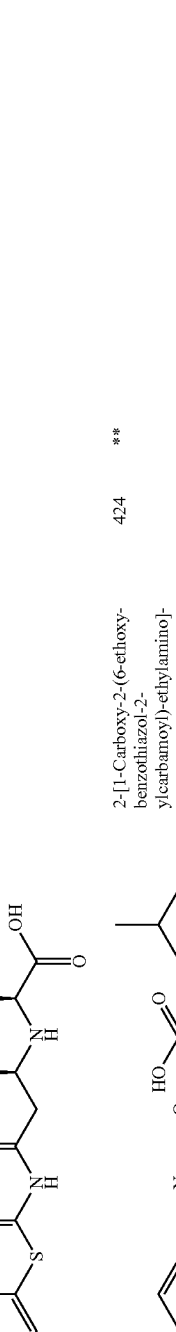 | 2-[1-Carboxy-2-(6-ethoxy-benzothiazol-2-ylcarbamoyl)-ethylamino]-4-methyl-pentanoic acid | 424 | ** | | | | | |

TABLE 2-continued

| Ref, No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| MQ | 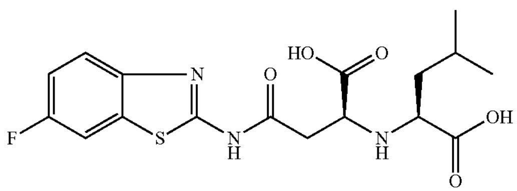 | 2-[1-Carboxy-2-(6-fluoro-benzothiazol-2-ylcarbamoyl)-ethylamino]-4-methyl-pentanoic acid | 397 | *** | | | | | |
| MR | 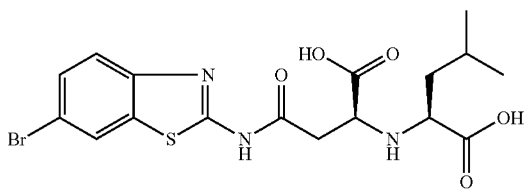 | 2-[2-(6-Bromo-benzothiazol-2-ylcarbamoyl]-1-carboxy-ethylamino]-4-methyl-pentanoic acid | 458 | *** | | | | | |
| MS | 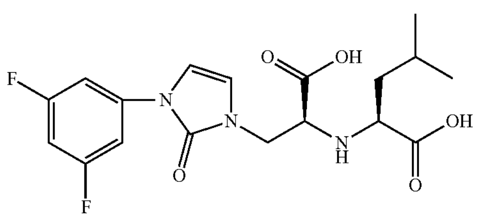 | 2-{1-Carboxy-2-[3-(3,5-difluoro-phenyl)-2-oxo-2,3-dihydro-imidazol-1-yl]-ethylamino}-4-methyl-pentanoic acid | 397 | ** | | | | | |
| MT | 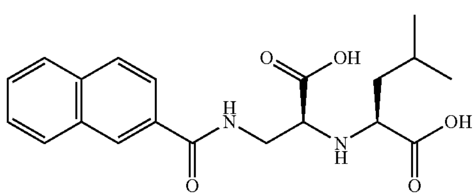 | 2-(1-Carboxy-2-[(naphthalene-2-carbonyl)amino]-ethylamino)-4-methyl-pentanoic acid | 372 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| MU | 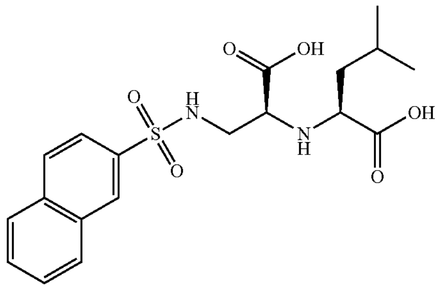 | 2-[1-Carboxy-2-(naphthalene-2-sulfonylamino)-ethylamino]-4-methyl-pentanoic acid | 408 | * | | | | | |
| MV | 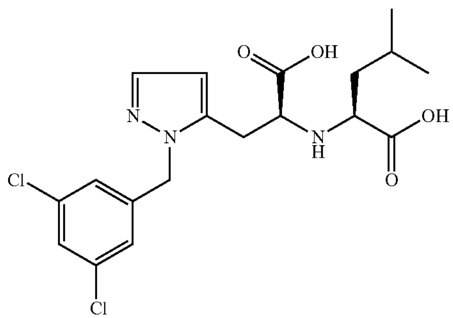 | 2-[1-Carboxy-2-]2-(3,5-dichloro-benzyl)-2H-pyrazol-3-yl]-ethylamino]-4-methyl-pentanoic acid | 428 | *** | | | | | |
| MX | 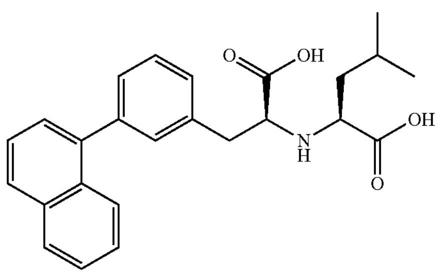 | 2-[1-Carboxy-2-(3-naphthalen-1-yl-phenyl)-ethylamino]-4-methyl-pentanoic acid | 406 | * | | | | | |

TABLE 2-continued

| Ref. No. | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|
| MY | 2-[2-[3-(3,5-Dichloro-benzyl)-3H-imidazol-4-yl]-1-ethoxycarbonyl-ethylamino]-4-methyl-pentanoic acid | 456 | ** | | | | | |
| MZ | 2-[1-Carboxy-2-[3-(3,5-dichloro-benzyl)-3H-imidazol-4-yl]-ethylamino)-4-methyl-pentanoic acid | 428 | ** | | | | | |
| NA | 2-[1-Carboxy-2-[3-(3,5-difluoro-benzyloxy)-phenyl]-ethylamino]-4-methyl-pentanoic acid | 421 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| NB | 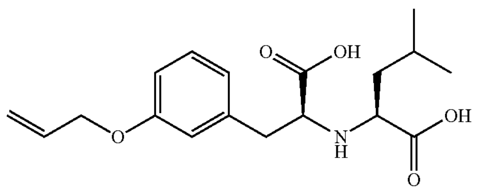 | 2-[2-(3-Allyloxy-phenyl)-1-carboxy-ethylamino]-4-methyl-pentanoic acid | 335 | ** | | | | | |
| NC | 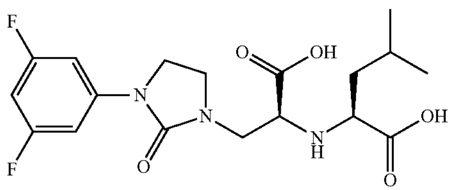 | 2-{1-Carboxy-2-[3-(3,5-difluoro-phenyl)-2-oxo-imidazolidin-1-yl]-ethylamino}-4-methyl-pentanoic acid | 399 | * | | | | | |
| ND | 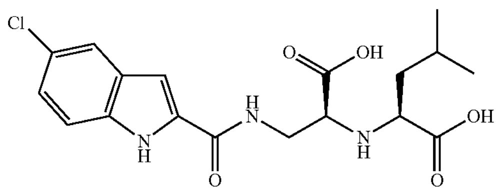 | 2-{1-Carboxy-2-[(5-chloro-1H-indole-2-carbonyl)-amino]-ethylamino}-4-methyl-pentanoic acid | 396 | * | | | | | |
| NE | 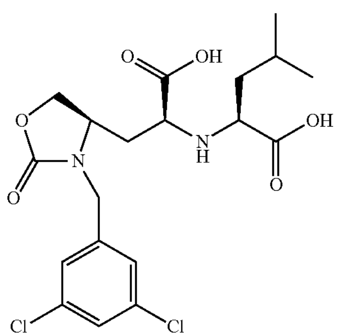 | 2-[1-Carboxy-2-[3-(3,5-dichloro-benoyl)-2-oxo-oxazolidin-4-yl]-ethylamino)-4-methyl-pentanoic acid | 447 | *** | | | | | |

TABLE 2-continued

| Ref, No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| NF | 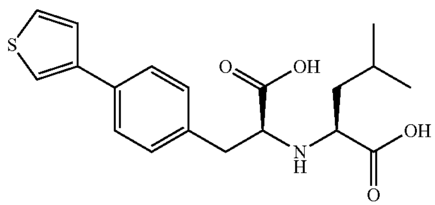 | 2-[1-Carboxy-2-(4-thiophen-3-yl-phenyl)-ethylamino]-4-methyl-pentanoic acid | 362 | *** | | | | | |
| NG | 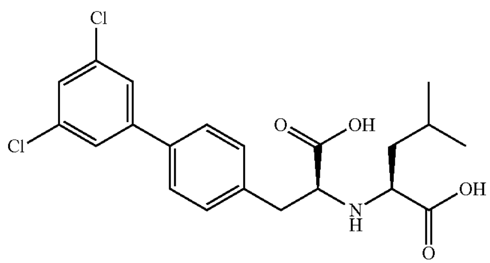 | 2-[1-Carboxy-2-(3',5'-dichloro-biphenyl-4-yl)-ethylamino]-4-methyl-pentanoic acid | 424 | *** | | | | | |
| NH | 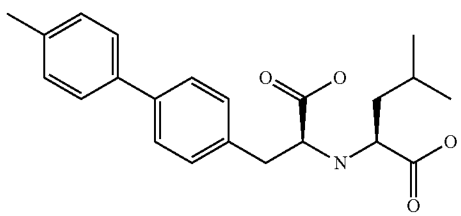 | 2-[1-Carboxy-2-(4'-methyl-biphenyl-4-yl)-ethylamino]-4-methyl-pentanoic acid | 370 | *** | | | | | |
| NI | 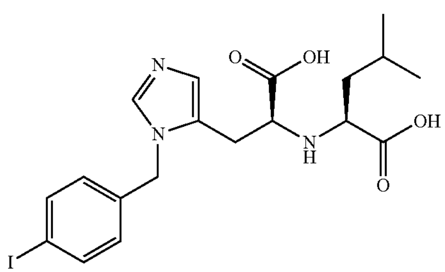 | 2-[1-Carboxy-2-[3-(4-iodo-benzyl)-3H-imidazol-4-yl]-ethylamino]-4-methyl-pentanoic acid | 485 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| NJ | 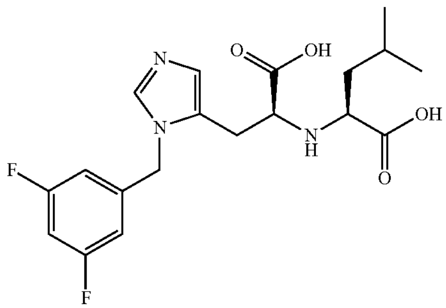 | 2-{1-Carboxy-2-[3-(3,5-difluoro-benzyl)-3H-imidazol-4-yl]-ethylamino} 4-methyl-pentanoic acid | 395 | *** | | | | | |
| NK | 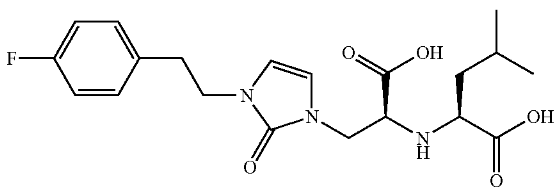 | 2-(1-Carboxy-2-[3-[2-(4-fluoro-phenyl)-ethyl]-2-oxo 2,3-dihydro-imidazol-1-yl)-ethylamino]-4-methyl-pentanoic acid | 407 | ** | | | | | |
| NL | 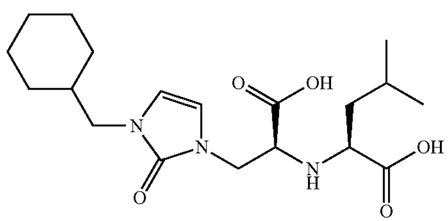 | 2-[1-Carboxy-2-(3-cyclohexylmethyl-2-oxo-2,3-dihydro-imidazol-1-yl)-ethylamino]-4-methyl-pentanoic acid | 382 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| NM | 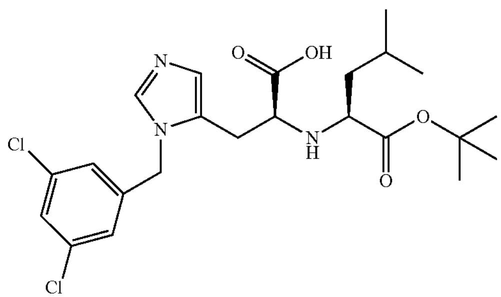 | 2-[1-Carboxy-2-[3-(3,5-dichloro-benzyl)-3H-imidazol-4-yl]-ethylamino)-4-methyl-pentanoic acid tert-butyl ester | 484 | *** | | | | | |
| NN | 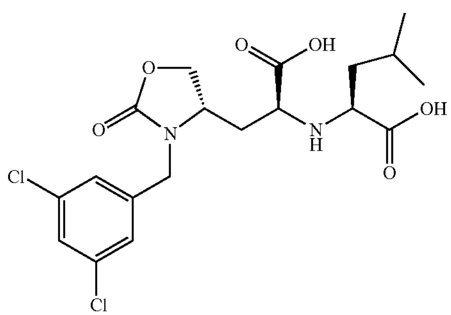 | 2-[1-Carboxy-2-[3-(3,5-dichloro-benzyl)-2-oxo-oxazolidin-4-yl]-ethylamino]-4-methyl-pentanoic acid | 447 | ** | | | | | |
| NO | 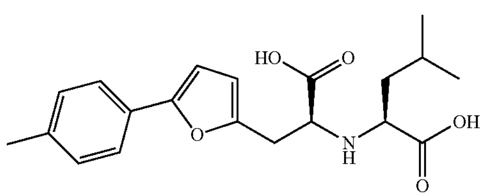 | 2-[1-Carboxy-2-(5-p-tolyl-furan-2-yl)-ethylamino]-4-methyl-pentanoic acid | 359 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| NP | 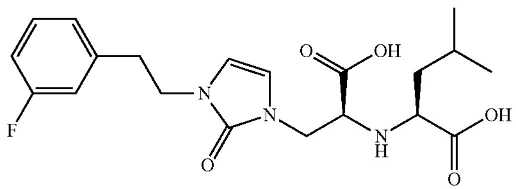 | 2-(1-Carboxy-2-{3-[2-(3-fluoro-phenyl)-ethyl]-2-oxo-2,3-dihydro-imidazol-1-yl]-ethylamino}-4-methyl-pentanoic acid | 407 | ** | | | | | |
| NQ | 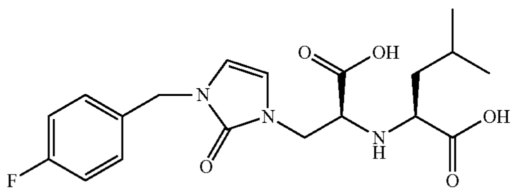 | 2-{1-Carboxy-2-[3-(4-fluoro-benzyl)-2-oxo-2,3-dihydro-imidazol-1-yl]-ethylamino}-4-methyl-pentanoic acid | 393 | ** | | | | | |
| NR | 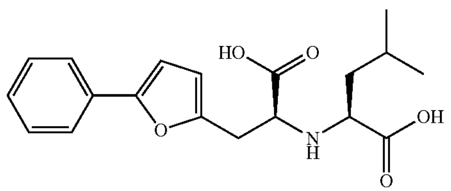 | 2-[1-Carboxy-2-(5-phenyl-furan-2-yl)-ethylamino]-4-methyl-pentanoic acid | 345 | ** | | | | | |
| NS | 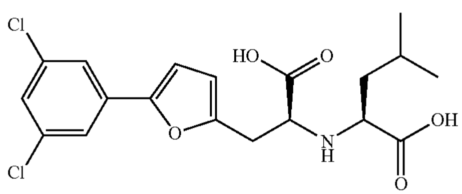 | 2-{1-Carboxy-2-[5-(3,5-dichloro-phenyl)-furan-2-yl]-ethylamino}-4-methyl-pentanoic acid | 414 | ** | | | | | |
| NT | 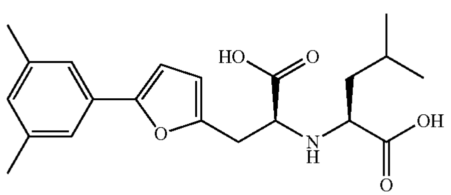 | 2-[1-Carboxy-2-[5-(3,5-dimethyl-phenyl)-furan-2-yl]-ethylamino]-4-methyl-pentanoic acid | 373 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| NU | 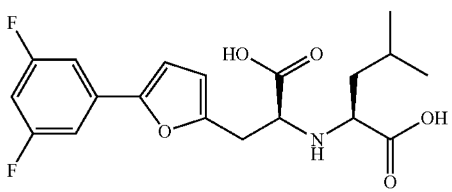 | 2-[1-Carboxy-2-[5-(3,5-difluoro-phenyl)-furan-2-yl ethylamino]-4-methyl-pentanoic acid | 381 | * | | | | | |
| NV | 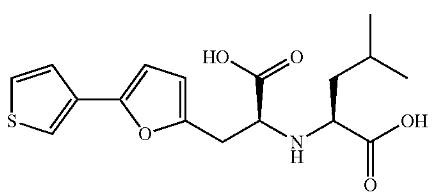 | 2-[1-Carboxy-2-(5-thiophen-3-yl-furan-2-yl)-ethylamino]-4-methyl-pentanoic acid | 351 | * | | | | | |
| NW | 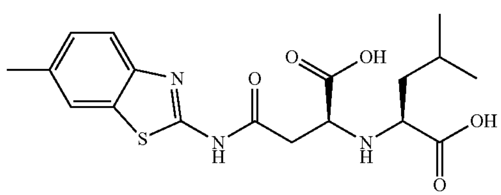 | 2-[1-Carboxy-2-(6-methyl-benzothiazol-2-ylcarbamoyl)-ethylamino]-4-methyl-pentanoic acid | 396 | ** | | | | | |
| NX | 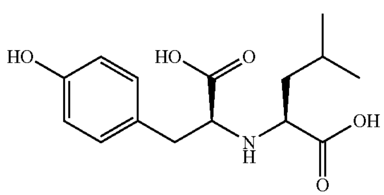 | 2-[1-Carboxy-2-(4-hydroxy-phenyl)-ethylamino]-4-methyl-pentanoic acid | 295 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| NY | 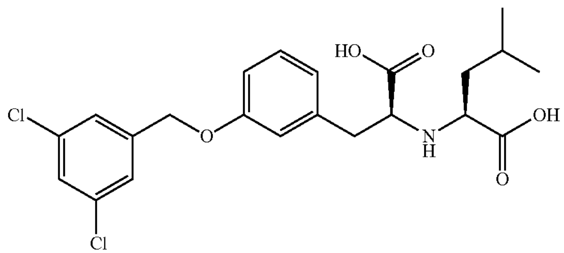 | 2-[1-Carboxy-2-[3-(3,5-dichloro-benzyloxy)-phenyl]-ethylamino]-4-methyl-pentanoic acid | 454 | *** | | | | | |
| NZ | 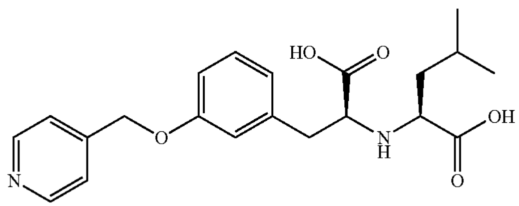 | 2-[1-Carboxy-2-[3-(pyridin-4-ylmethoxy)-phenyl]-ethylamino]-4-methyl-pentanoic acid | 386 | * | | | | | |
| OA | 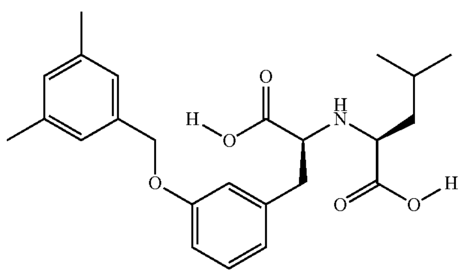 | 2-[1-Carboxy-2-[3-(3,5-dimethyl-benzyloxy)-phenyl]-ethylamino]-4-methyl-pentanoic acid | 414 | * | | | | | |
| OB | 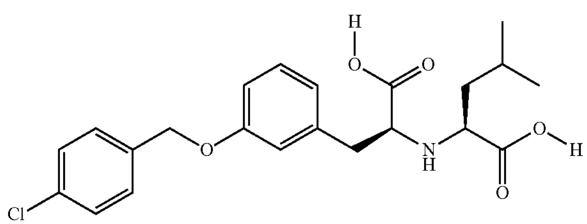 | 2-[1-Carboxy-2-[3-(4-chloro-benzyloxy)-phenyl]-ethylamino]-4-methyl-pentanoic acid | 420 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| OC | 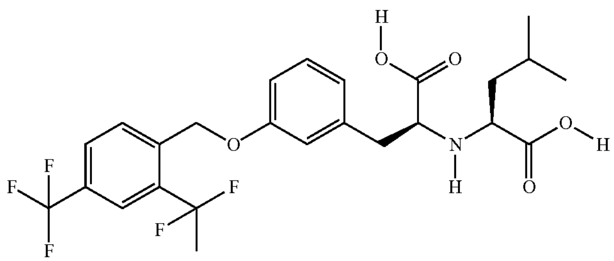 | 2-{2-[3-(2,4-Bis-trifluoromethyl-benzyloxy)-phenyl]-1-carboxy-ethylamino}-4-methyl-pentanoic acid | 522 | * | | | | | |
| OD | 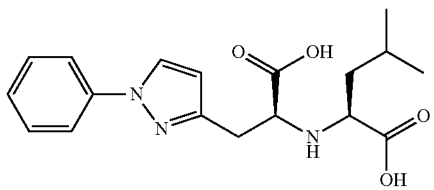 | 2-[1-Carboxy-2-(1-phenyl-1H-pyrazol-3-yl)-ethylamino]-4-methyl-pentanoic acid | 345 | ** | | | | | |
| OE | 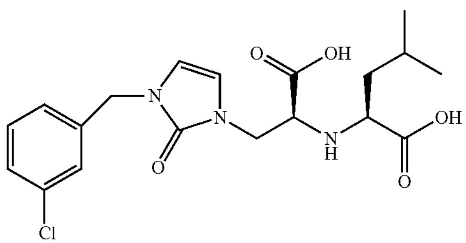 | 2-[1-Carboxy-2-[3-(3-chloro-benzyl)-2-oxo-2,3-dihydro-imidazol-1-yl]-ethylamino]-4-methyl-pentanoic acid | 410 | *** | | | | | |
| OF | 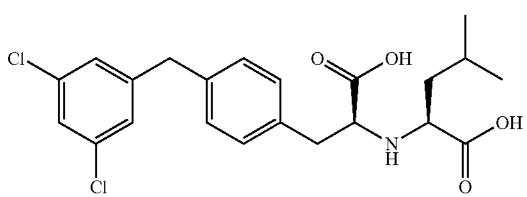 | 2-{1-Carboxy-2-[4-(3,5-dichloro-benzyl)-phenyl]-ethylamino}-4-methyl-pentanoic acid | 438 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| OG | 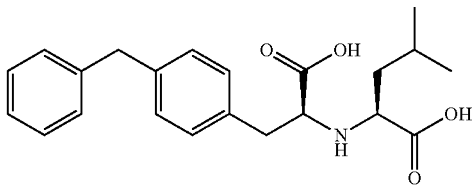 | 2-[2-(4-Benzyl-phenyl)-1-carboxy-ethylamino]-4-methyl-pentanoic acid | 370 | *** | | | | | |
| OH | 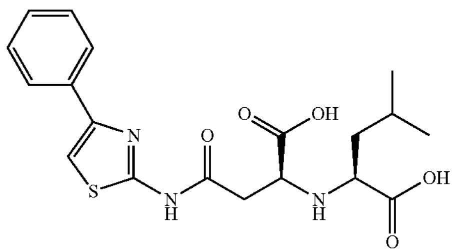 | 2-[1-Carboxy-2-(4-phenyl-thiazol-2-ylcarbamoyl)-ethylamino]-4-methyl-pentanoic acid | 406 | * | | | | | |
| OI | 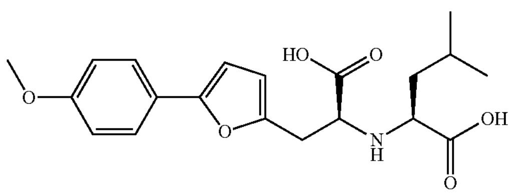 | 2-{1-Carboxy-2-[5-(4-methoxy-phenyl)-furan-2-yl]-ethylamino}-4-methyl-pentanoic acid | 375 | ** | | | | | |
| OJ | 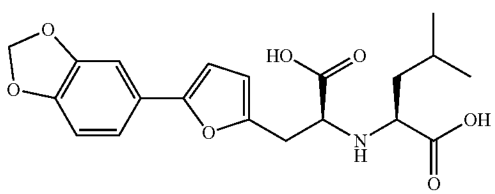 | 2-[2-(5-Benzo[1,3]dioxo-5-yl-furan-2-yl)-1-carboxy-ethylamino]-4-methyl-pentanoic acid | 389 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| OK | 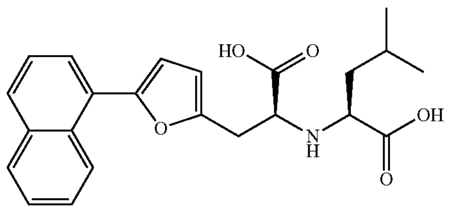 | 2-[1-Carboxy-2-(5-naphthalen-1-yl-furan-2-yl)-ethylamino]-4-methyl-pentanoic acid | 396 | ** | | | | | |
| OL | 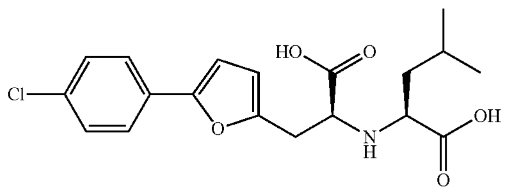 | 2-{1-Carboxy-2-[5-(4-chloro-phenyl)-furan-2-yl]-ethylamino}-4-methyl-pentanoic acid | 380 | * | | | | | |
| OM | 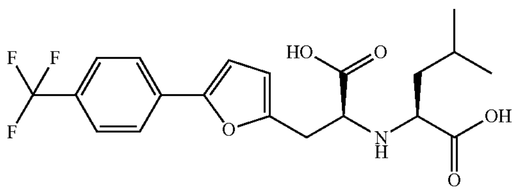 | 2-{1-Carboxy-2-[5-(4-trifluoromethyl-phenyl)-furan-2-yl]-ethylamino}-4-methyl-pentanoic acid | 413 | * | | | | | |
| ON | 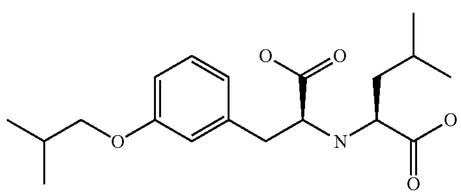 | 2-[1-Carboxy-2-(3-isobutoxy-phenyl)-ethylamino]-4-methyl-pentanoic acid | 351 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| OO | 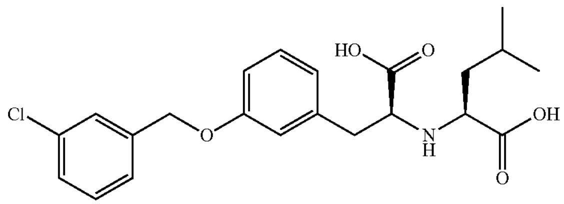 | 2-[1-Carboxy-2-[3-(3-chloro-benzyloxy)-phenyl]-ethylamino]-4-methyl-pentanoic acid | 420 | *** | | | | | |
| OP | 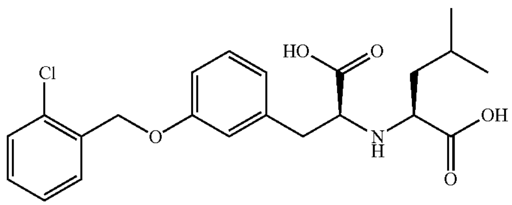 | 2-[1-Carboxy-2-[3-(2-chloro-benzyloxy)-phenyl]-ethylamino]-4-methyl-pentanoic acid | 420 | * | | | | | |
| OQ | 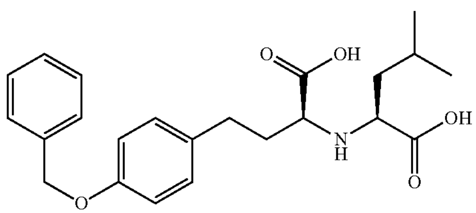 | 2-[3-(4-Benzyloxy-phenyl) 1-carboxy-propylamino]-4-methyl-pentanoic acid | 400 | ** | | | | | |
| OR | 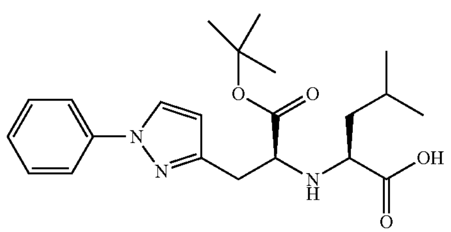 | 2-[1-tert-Butoxycarbonyl-2-(1-phenyl-1H-pyrazol-3-yl ethylamino]-4-methyl-pentanoic acid | 402 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| OS | 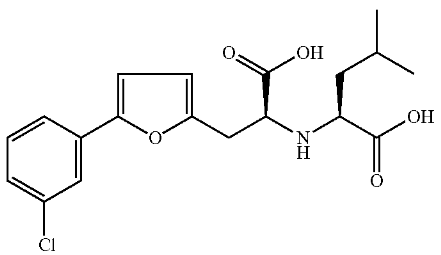 | 2-[1-Carboxy-2-[5-(3-chloro-phenyl)-furan-2-yl]-ethylamino]-4-methyl-pentanoic acid | 380 | * | | | | | |
| OT | 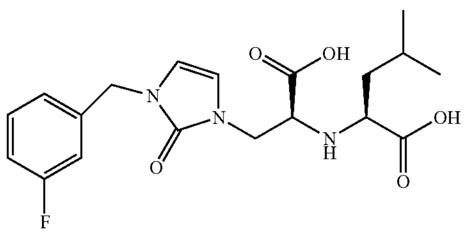 | 2-[1-Carboxy-2-[3-(3-fluoro-benzyl)-2-oxo-2,3-dihydro-imidazol-1-yl]-ethylamino]-4-methyl-pentanoic acid | 393 | *** | | | | | |
| OU | 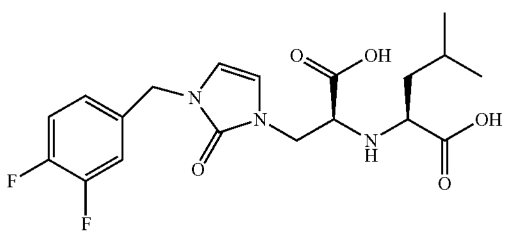 | 2-[1-Carboxy-2-[3-(3,4-difluoro-benzyl)-2-oxo-2,3-dihydro-imidazol-1-yl]-ethylamino]-4-methyl-pentanoic acid | 411 | ** | | | | | |
| OV | 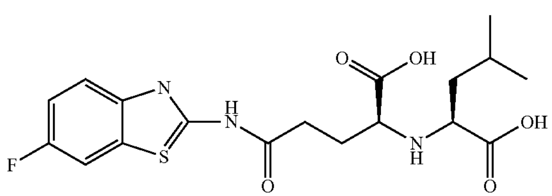 | 2-[1-Carboxy-3-(6-fluoro-benzothiazol-2-ylcarbamoyl)-propylamino]-4-methyl-pentanoic acid | 412 | * | | | | | |

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| OW | 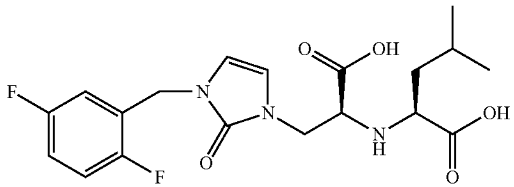 | 2-[1-Carboxy-2-[3-(2,5-difluoro-benzyl)-2-oxo-2,3-dihydro-imidazol-1-yl]-ethylamino]-4-methyl-pentanoic acid | 411 | *** | | | | | |
| OX | 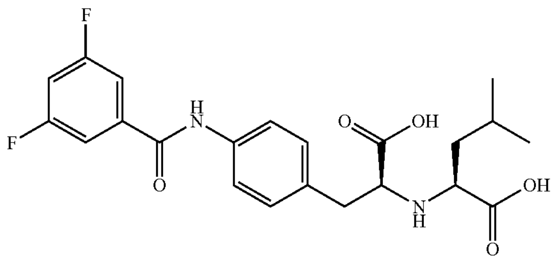 | 2-[1-Carboxy-2-[4-(3,5-difluoro-benzoylamino)-phenyl]-ethylamino]-4-methyl-pentanoic acid | 434 | *** | | | | | |
| OY | 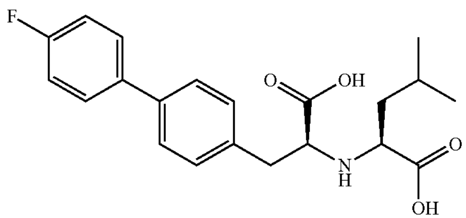 | 2-[1-Carboxy-2-(4'-fluoro-biphenyl-4-yl)-ethylamino]-4-methyl-pentanoic acid | 373 | *** | | | | | |
| OZ | 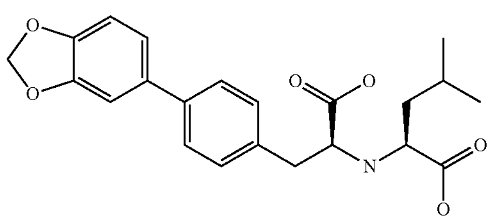 | 2-[2-(4-Benzo[1,3]dioxol-5-yl-phenyl)-1-carboxy-ethylamino]-4-methyl-pentanoic acid | 399 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| PA | 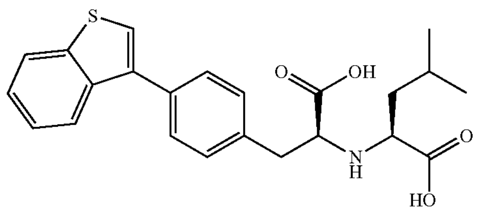 | 2-[2-(4-Benzo[b]thiophen-3-yl-phenyl)-1-carboxy-ethylamino]-4-methyl-pentanoic acid | 412 | *** | | | | | |
| PB | 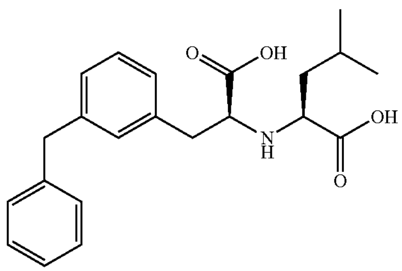 | 2-[2-(3-Benzyl-phenyl)-1-carboxy-ethylamino]-4-methyl-pentanoic acid | 370 | * | | | | | |
| PC | 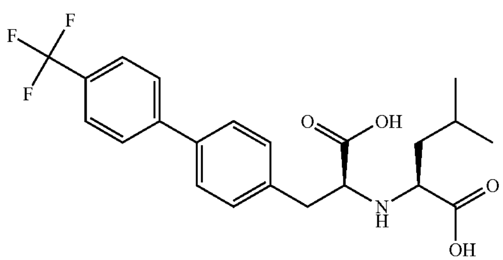 | 2-[1-Carboxy-2-(4-trifluoromethyl-biphenyl-4-yl)-ethylamino]-4-methyl-pentanoic acid | 423 | *** | | | | | |
| PD | 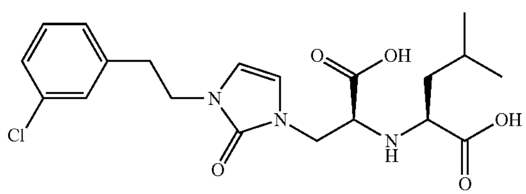 | 2-(1-Carboxy-2-{3-[2-(3-chloro-phenyl)-ethyl]-2-oxo-2,3-dihydro-imidazol-1-yl}-ethylamino)-4-methyl-pentanoic acid | 424 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| PD | 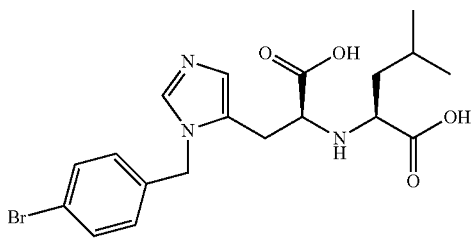 | 2-[2-[3-(4-Bromo-benzyl)-3H-imidazol-4-yl]-1-carboxy-ethylamino]-4-methyl-pentanoic acid | 438 | *** | | | | | |
| PE | 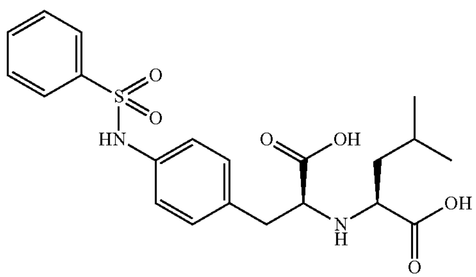 | 2-[2-(4-Benzenesulfonylamino-phenyl)-1-carboxy-ethylamino]-4-methyl-pentanoic acid | 434 | * | | | | | |
| PF | 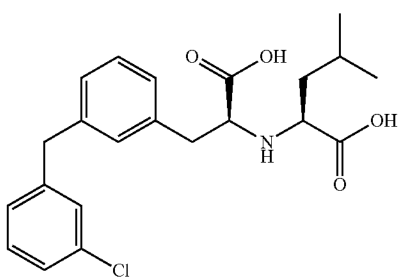 | 2-[1-Carboxy-2-[3-(3-chloro-benzyl)-phenyl]-ethylamino]-4-methyl-pentanoic acid | 404 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| PG | 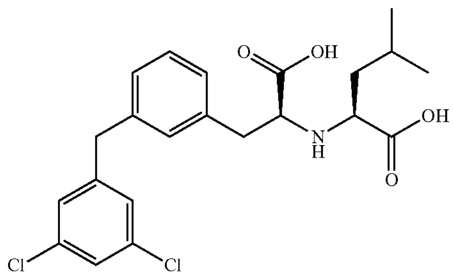 | 2-[1-Carboxy-2-[3-(3,5-dichloro-benzyl)-phenyl]-ethylamino]-4-methyl-pentanoic acid | 438 | ** | | | | | |
| PH | 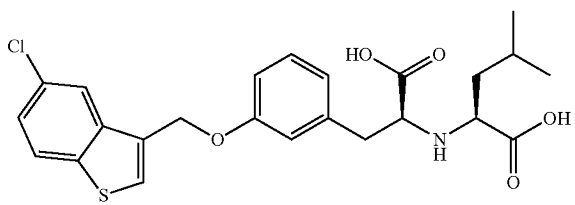 | 2-[1-Carboxy-2-[3-(5-chloro-benzo[b]thiophen-3-ylmethoxy)-phenyl]-ethylamino]-4-methyl-pentanoic acid | 476 | *** | | | | | |
| PI | 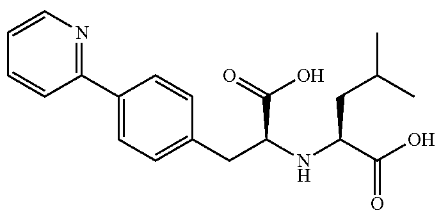 | 2-[1-Carboxy-2-(4-pyridin-2-yl-phenyl)-ethylamino]-4-methyl-pentanoic acid | 356 | *** | | | | | |
| PJ | 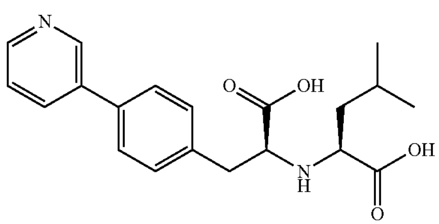 | 2-[1-Carboxy-2-(4-pyridin-3-yl-phenyl)-ethylamino]-4-methyl-pentanoic acid | 356 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| PK | 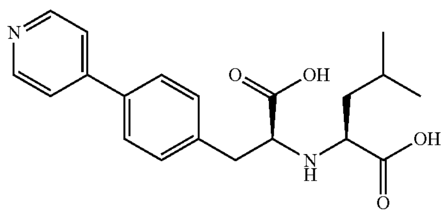 | 2-[1-Carboxy-2-(4-pyridin-4-yl-phenyl)-ethylamino]-4-methyl-pentanoic acid | 356 | ** | | | | | |
| PL | 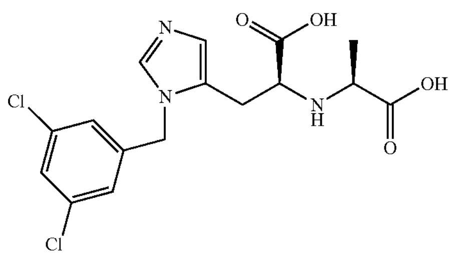 | 2-(1-Carboxy-ethylamino)-3-[3-(3,5-dichloro-benzyl)-3H-imidazol-4-yl]-propionic acid | 386 | *** | | | | | |
| PM | 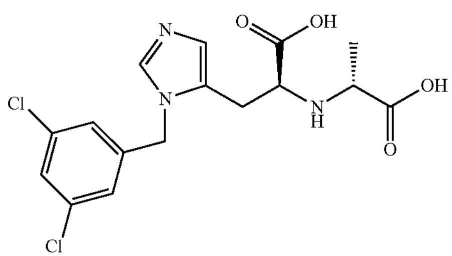 | 2-(1-Carboxy-ethylamino)-3-[3-(3,5-dichloro-benzyl)-3H-imidazol-4-yl]-propionic acid | 386 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| PN | 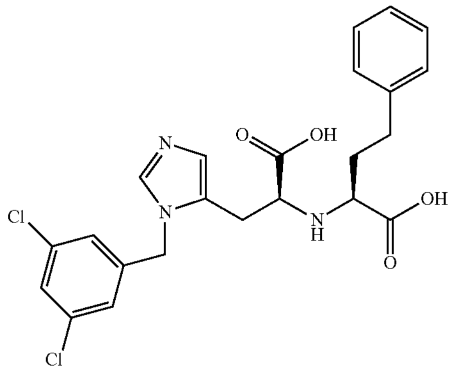 | 2-(1-Carboxy-2-[3-(3,5-dichloro-benzyl)-3H-imidazol-4-yl]-ethylamino) 4-phenyl-butync acid | 476 | *** | | | | | |
| PQ | 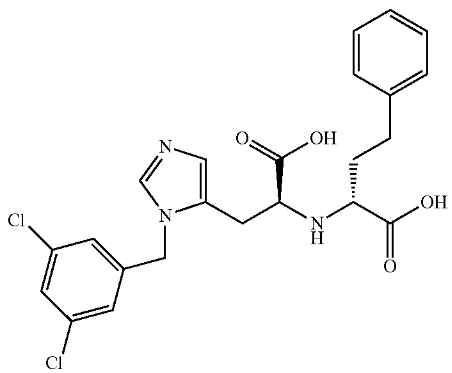 | 2-(1-Carboxy-2-[3-(3,5-dichloro-benzyl)-3H-imidazol-4-yl]-ethylamino) 4-phenyl-butync acid | 476 | ** | | | | | |
| PP | 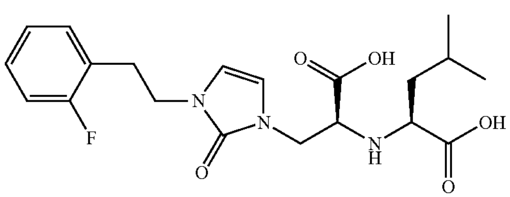 | 2-(1-Carboxy-2-[3-[2-(2-fluoro-phenyl)-ethyl]-2-oxo 2,3-dihydro-imidazol-1-yl]-ethylamino)-4-methyl-pentanoic acid | 407 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| PO | 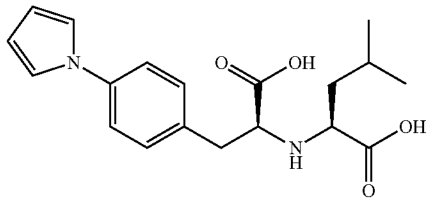 | 2-[1-Carboxy-2-(4-pyrrol-1-yl-phenyl)-ethylamino]-4-methyl-pentanoic acid | 344 | * | | | | | |
| PR | 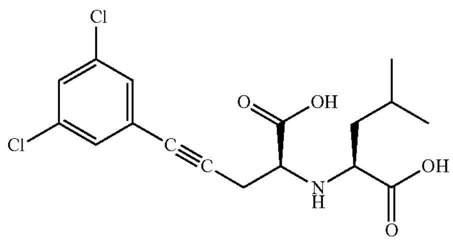 | 2-(1-Carboxy-3-methyl-butylamino)-5-(3,5-dichloro-phenyl)-pent-4-ynoic acid | 372 | * | | | | | |
| PS | 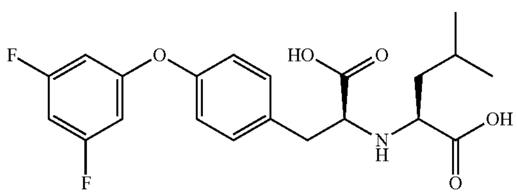 | 2-[1-Carboxy-2-[4-(3,5-difluoro-phenoxy)-phenyl]-ethylamino]-4-methyl-pentanoic acid | 407 | * | | | | | |
| PT | 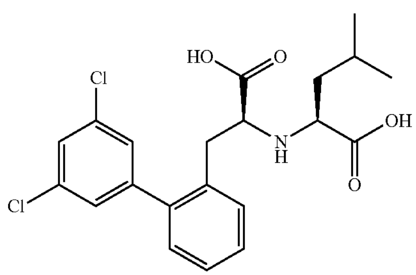 | 2-[1-Carboxy-2-(3',5'-dichloro-biphenyl-2-yl)-ethylamino]-4-methyl-pentanoic acid | 424 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| PU | 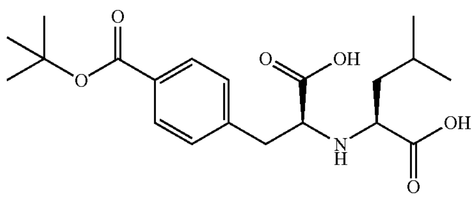 | 4-[2-Carboxy-2-(1-carboxy-3-methyl-butylamino)-ethyl]-benzoic acid tert-butyl ester | 380 | *** | | | | | |
| PV | 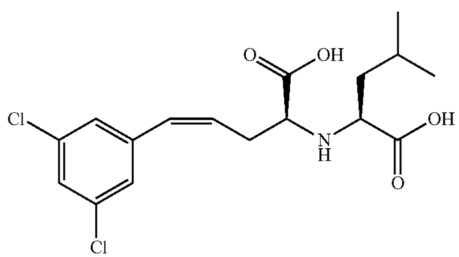 | 2-(1-Carboxy-3-methyl-butylamino)-5-(3,5-dichloro-phenyl)-pent-4-enoic acid | 374 | *** | | | | | |
| PW | 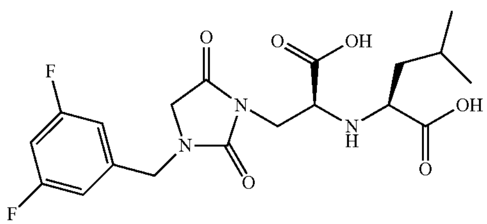 | 2-[1-Carboxy-2-[3-(3,5-difluoro-benzyl)-2,5-dioxo-imidazolidin-1-yl]-ethylamino]-4-methyl-pentanoic acid | 427 | *** | | | | | |
| PX | 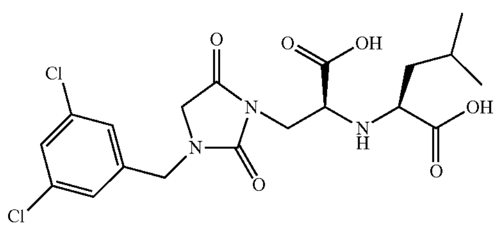 | 2-[1-Carboxy-2-[3-(3,5-dichloro-benzyl)-2,5-dioxo-imidazolidin-1-yl]-ethylamino]-4-methyl-pentanoic acid | 460 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| PY | 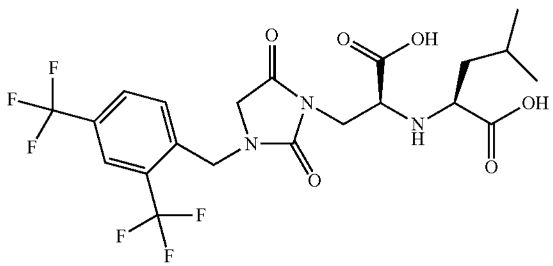 | 2-[2-[3-(2,4-Bis-trifluoromethyl-benzyl)-2,5-dioxo-imidazolidin-1-yl]-1-carboxy-ethylamino]-4-methyl-pentanoic acid | 527 | * | | | | | |
| PZ | 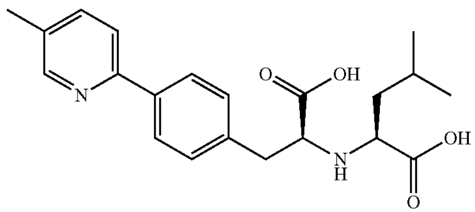 | 2-[1-Carboxy-2-[4-(5-methyl-pyridin-2-yl)-phenyl]-ethylamino]-4-methyl-pentanoic acid | 370 | *** | | | | | |
| QA | 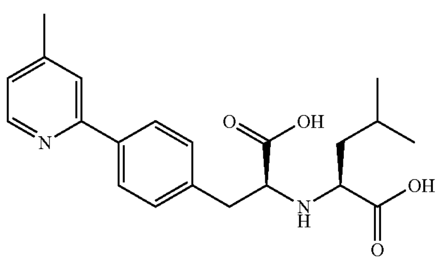 | 2-[1-Carboxy-2-[4-(4-methyl-pyridin-2-yl)-phenyl]-ethylamino]-4-methyl-pentanoic acid | 370 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| QB | 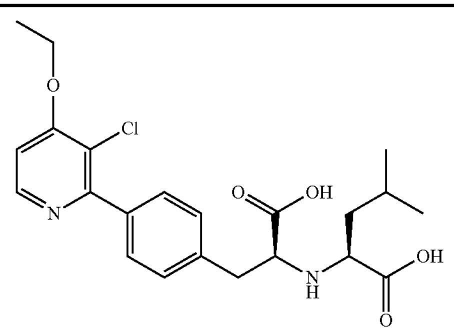 | 2-[1-Carboxy-2-[4-(3-chloro-4-ethoxy-pyridin-2-yl)-phenyl]-ethylamino]-4-methyl-pentanoic acid | 435 | *** | | | | | |
| QC | 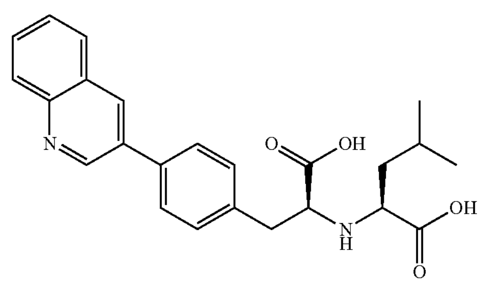 | 2-[1-Carboxy-2-(4-quinolin 3-yl-phenyl)-ethylamino]-4-methyl-pentanoic acid | 406 | *** | | | | | |
| QD | 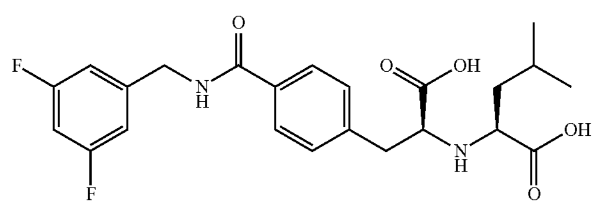 | 2-[1-Carboxy-2-[4-(3,5-difluoro-benzyl(carbamoyl) phenyl]-ethylamino]-4-methyl-pentanoic acid | 448 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| QE | 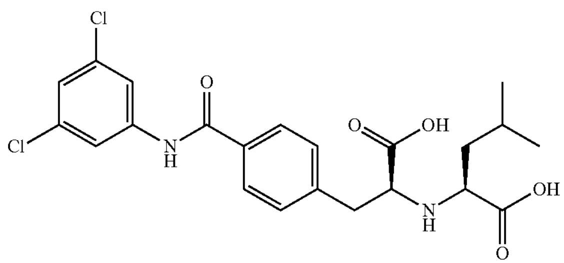 | 2-[1-Carboxy-2-[4-(3,5-dichloro-phenylcarbamoyl)-phenyl]-ethylamino]-4-methyl-pentanoic acid | 467 | *** | | | | | |
| QF | 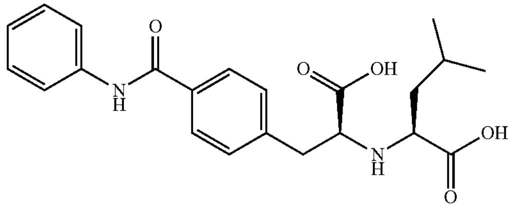 | 2-[1-Carboxy-2-(4-phenylcarbamoyl-phenyl)-ethylamino]-4-methyl-pentanoic acid | 398 | ** | | | | | |
| QG | 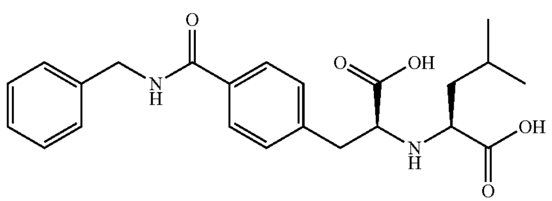 | 2-[2-(4-Benzylcarbamoyl-phenyl)-1-carboxy-ethylamino]-4-methyl-pentanoic acid | 412 | * | | | | | |
| QH | 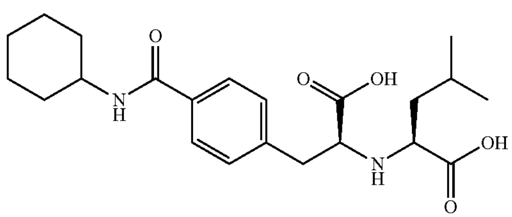 | 2-[1-Carboxy-2-(4-cyclohexylcarbamoyl-phenyl)-ethylamino]-4-methyl-pentanoic acid | 404 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| QI | 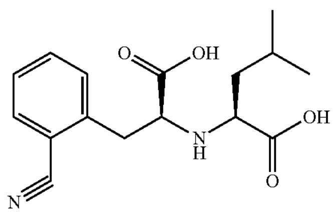 | 2-[1-Carboxy-2-(2-cyano-phenyl)-ethylamino]-4-methyl-pentanoic acid | 304 | ** | | | | | |
| QJ | 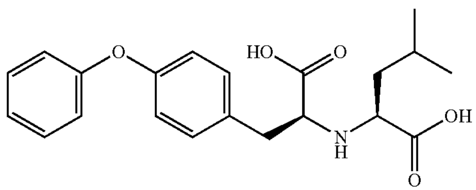 | 2-[1-Carboxy-2-(4-phenoxy-phenyl)-ethylamino]-4-methyl-pentanoic acid | 371 | ** | | | | | |
| QK | 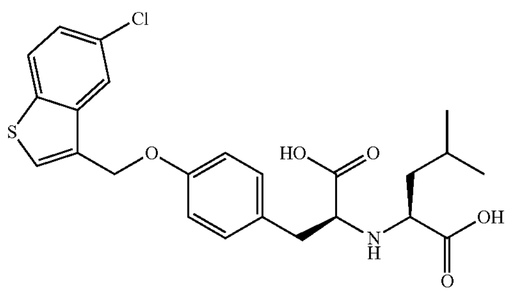 | 2-[1-Carboxy-2-[4-(5-chloro-benzo[b]thiophen-3-ylmethoxy)-phenyl]-ethylamino]-4-methyl-pentanoic acid | 476 | *** | | | | | |
| QL | 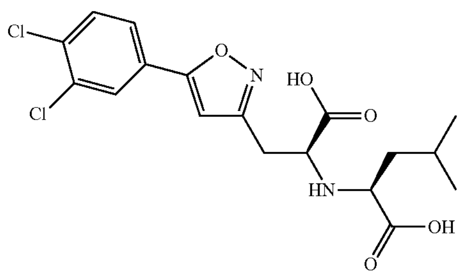 | 2-[1-Carboxy-2-[5-(3,4-dichloro-phenyl)-isoxazol-3-yl]-ethylamino)-4-methyl-pentanoic acid | 415 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| QM | 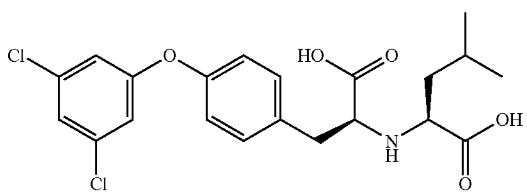 | 2-(1-Carboxy-2-[4-(3,5-dichloro-phenoxy)-phenyl ethylamino]-4-methyl-pentanoic acid | 440 | ** | | | | | |
| QN | 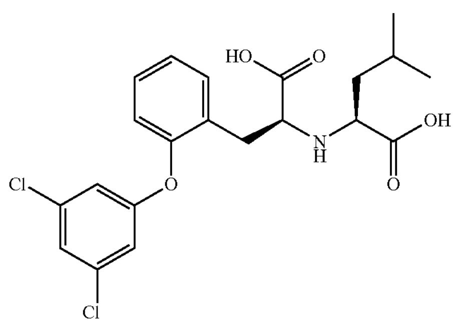 | 2-[1-Carboxy-2-[2-(3,5-dichloro-phenoxy)-phenyl ethylamino]-4-methyl-pentanoic acid | 440 | *** | | | | | |
| QO | 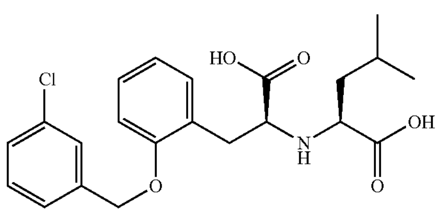 | 2-[1-Carboxy-2-[2-(3-chloro-benzyloxy)-phenyl]-ethylamino]-4-methyl-pentanoic acid | 420 | * | | | | | |
| QP | 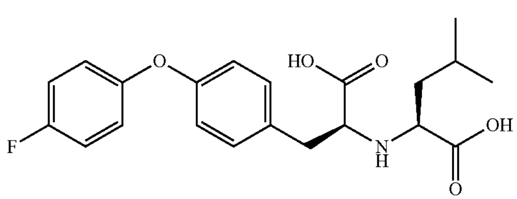 | 2-[1-Carboxy-2-[4-(4-fluoro-phenoxy)-phenyl]-ethylamino]-4-methyl-pentanoic acid | 389 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| QQ | 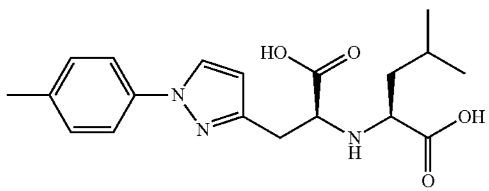 | 2-[1-Carboxy-2-(1-p-tolyl-1H-pyrazol-3-yl)-ethylamino]-4-methyl-pentanoic acid | 359 | *** | | | | | |
| QR | 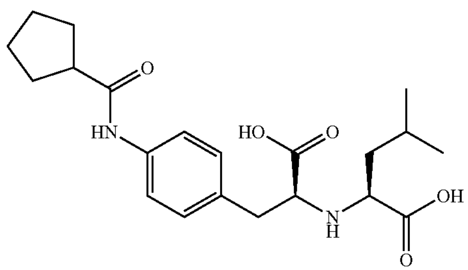 | 2-[1-Carboxy-2-[4-(cyclopentanecarbonyl-amino)-phenyl]-ethylamino]-4-methyl-pentanoic acid | 390 | ** | | | | | |
| QS | 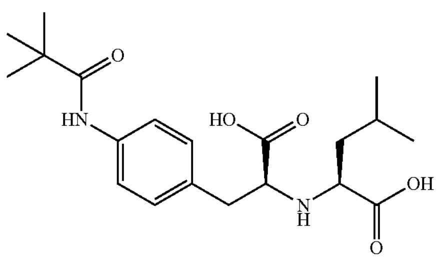 | 2-{1-Carboxy-2-[4-(2,2-dimethyl-propionylamino)-phenyl]-ethylamino}-4-methyl-pentanoic acid | 378 | ** | | | | | |
| QT | 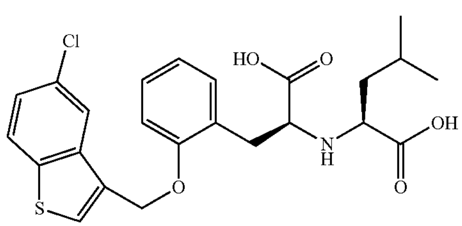 | 2-{1-Carboxy-2-[2-(5-chloro-benzo[b]thiophen-3-ylmethoxy)-phenyl]-ethylamino}-4-methyl-pentanoic acid | 476 | * | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| QU | 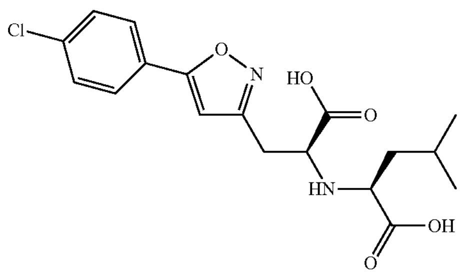 | 2-(1-Carboxy-2-[5-(4-chloro-phenyl)-isoxazol-3-yl]-ethylamino)-4-methyl-pentanoic acid | 381 | *** | | | | | |
| QV | 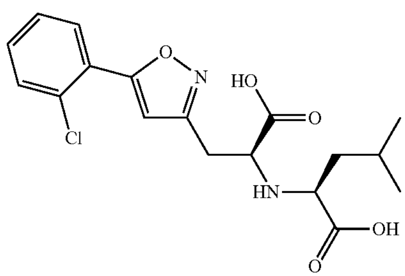 | 2-[1-Carboxy-2-[5-(2-chloro-phenyl)-isoxazol-3-yl]-ethylamino]-4-methyl-pentanoic acid | 381 | *** | | | | | |
| QW | 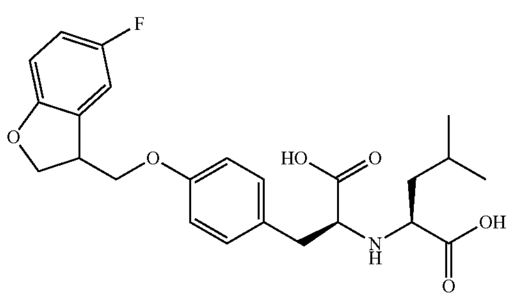 | 2-[1-Carboxy-2-[4-(5-fluoro-2,3-dihydro-benzofuran-3-ylmethoxy)-phenyl]-ethylamino]-4-methyl-pentanoic acid | 446 | *** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| QX | 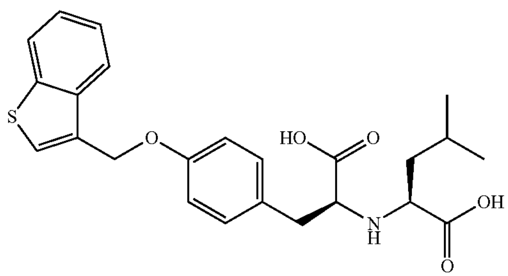 | 2-{2-[4-(Benzo[b]thiophen-3-ylmethoxy)-phenyl]-1-carboxy-ethylamino]-4-methyl-pentanoic acid | 442 | *** | | | | | |
| QY | 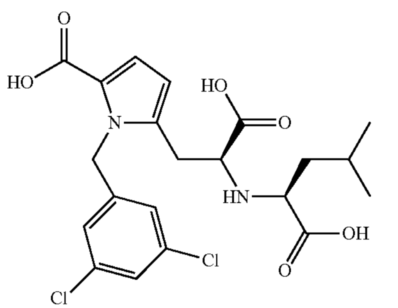 | 5-[2-Carboxy-2-(1-carboxy-3-methyl-butylamino)-ethyl]-1-(3,5-dichloro-benzyl)-1H-pyrrole-2-carboxylic acid | 471 | *** | | | | | |
| QZ | 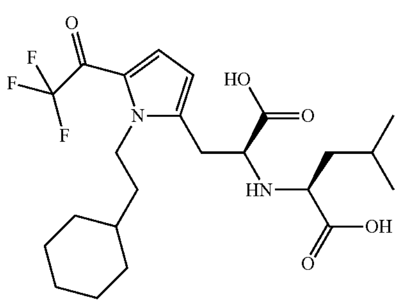 | 2-[1-Carboxy-2-[1-(2-cyclohexyl-ethyl)-5-(2,2,2-trifluoro-acetyl)-1H-pyrrol-2-yl]-ethylamino]-4-methyl-pentanoic acid | 474 | *** | | | | | |

TABLE 2-continued

| Ref. No. | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|
| RA | 2-[1-Carboxy-2-(4-nitro-phenyl)-ethylamino]-4-methyl-pentanoic acid | 324 | ** | | | | | |
| RB | 2-[1-Carboxy-2-[4-(2-methoxy-benzoylamino)-phenyl]-ethylamino]-4-methyl-pentanoic acid | 428 | *** | | | | | |
| RC | 2-[1-Carboxy-2-(2-trifluoromethyl-phenyl)-ethylamino]-4-methyl-pentanoic acid | 347 | *** | | | | | |
| RD | 2-(2-(4-[Bis-(3,5-difluoro-benzyl)-amino]-phenyl)-1-carboxy-ethylamino)-4-methyl-pentanoic acid | 547 | ** | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| RE | 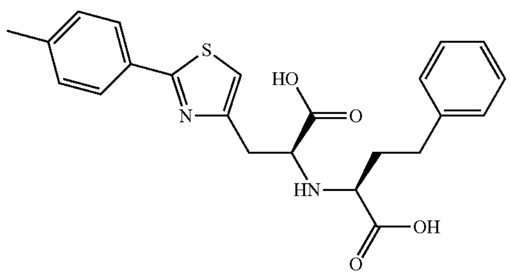 | 2-[1-Carboxy-2-(2-p-tolyl-thiazol-4-yl)-ethylamino]-4-phenyl-butync acid | 424 | | | | | | |
| RF | 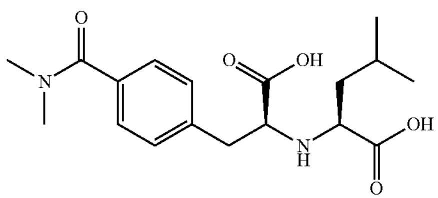 | 2-[1-Carboxy-2-(4-dimethylcarbamoyl-phenyl)-ethylamino]-4-methyl-pentanoic acid | 350 | | | | | | |
| RG | 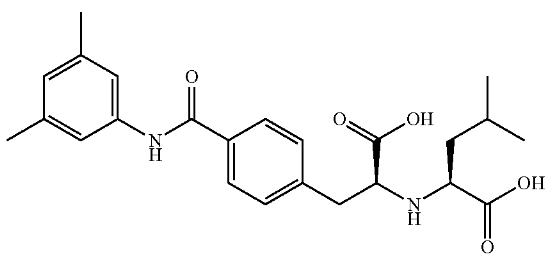 | 2-[1-Carboxy-2-[4-(3,5-dimethyl-phenylcarbamoyl)-phenyl ethylamino]-4-methyl-pentanoic acid | 426 | | | | | | |
| RH | 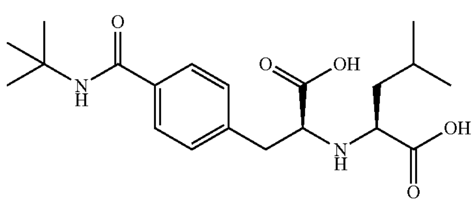 | 2-[2-(4-tert-Butylcarbamoyl-phenyl)-1-carboxy-ethylamino]-4-methyl-pentanoic acid | 378 | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| RJ | | 4-Methyl-2-[[pyrimidin-2-yl (2-p-tolyl-thiazol-4-ylmethyl)-amino]-methyl]-pentanoic acid | 410 | | | | | | |
| RJ | | 2-[1-Carboxy-2-[1-(3,5-dichloro-benzyl)-1H-pyrro 2-yl]-ethylamino}-4-methyl pentanoic acid | 427 | | | | | | |
| RK | 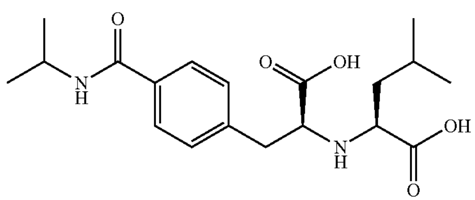 | 2-[1-Carboxy-2-(4-isopropylcarbamoyl-phenyl)-ethylamino]-4-methyl-pentanoic acid | 364 | | | | | | |
| RL | 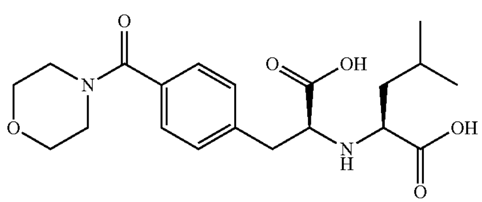 | 2-[1-Carboxy-2-[4-(morpholine-4-carbonyl)-phenyl]-ethylamino]-4-methyl-pentanoic acid | 392 | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| RM | 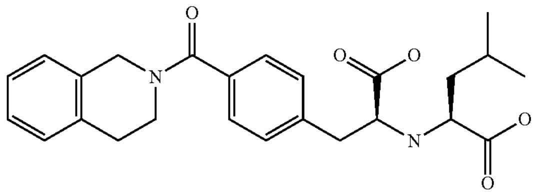 | 2-[1-Carboxy-2-[4-(3,4-dihydro-1H-isoquinoline-2-carbonyl)-phenyl]-ethylamino]-4-methyl-pentanoic acid | 438 | | | | | | |
| RN | 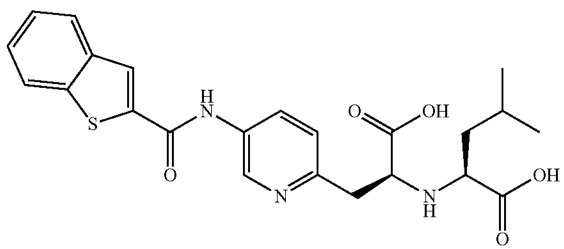 | 2-(2-[5-[(Benzo[b]thiophene-2-carbonyl)-amino]-pyridin-2-yl]-1-carboxy-ethylamino)-4-methyl-pentanoic acid | | | | | | | |
| RO | 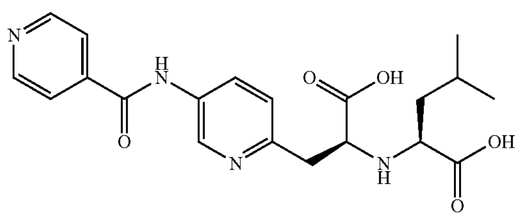 | 2-(1-Carboxy-2-(5-[(pyridine-4-carbonyl)-amino]-pyridin-2-yl)-ethylamino)-4-methyl-pentanoic acid | | | | | | | |
| RP | 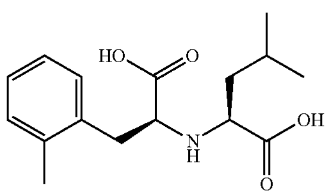 | 2-(1-Carboxy-2-o-tolyl-ethylamino)-4-methyl-pentanoic acid | | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| RQ | 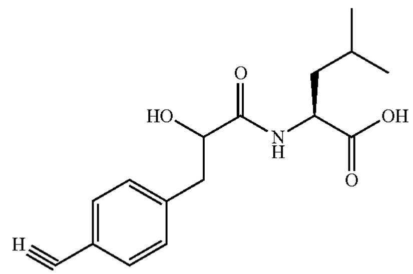 | 2-[3-(4-Cyano-phenyl)-2-mercapto-propionylamino]-4-methyl-pentanoic acid | | | | | | | |
| RS | 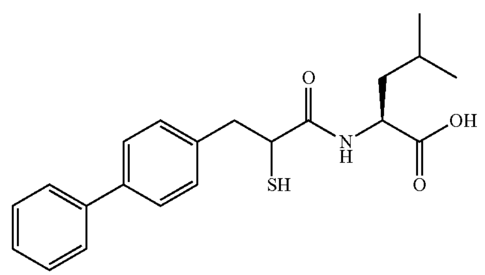 | 2-(3-Biphenyl-4-yl-2-mercapto-propionylamino)-4-methyl-pentanoic acid | | | | | | | |
| RT | 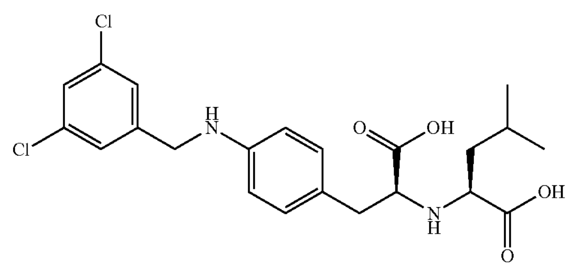 | 2-[1-Carboxy-2-[4-(3,5-dichloro-benzylamino)-phenyl]-ethylamino]-4-methyl-pentanoic acid | | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| RU | 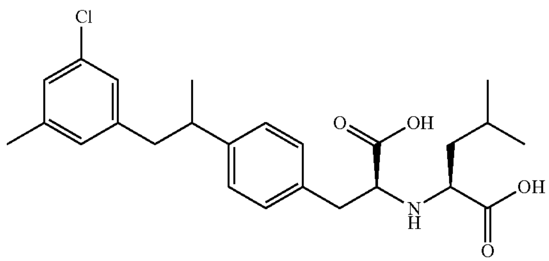 | 2-(1-Carboxy-2-{4-[(3,5-dichloro-benzyl)-methyl-amino]-phenyl}-ethylamino)-4-methyl-pentanoic acid | | | | | | | |
| RV | 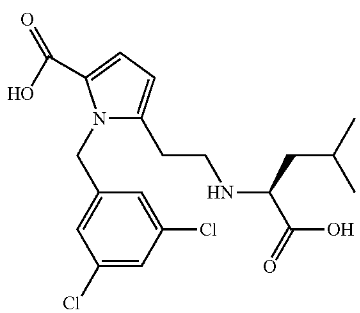 | 5-[2-(1-Carboxy-3-methyl-butylamino)-ethyl]-1-(3,5-dichloro-benzyl)-1H-pyrrole-2-carboxylic acid | | | | | | | |
| RW | 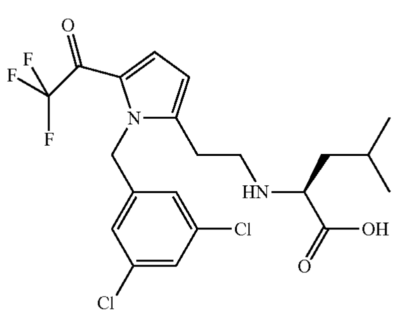 | 2-[2-[1(3,5-Dichloro-benzyl)-5-(2,2,2-trifluoro-acetyl)-1H-pyrrol-2-yl]-ethylamino]-4-methyl-pentanoic acid | | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| RX | 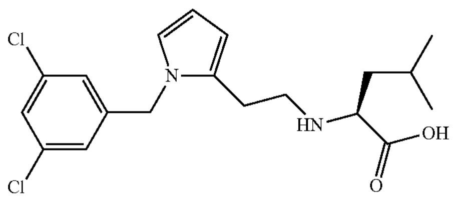 | 2-(2-[1-(3,5-Dichloro-benzyl)-1H-pyrrol-2-yl]-ethylamino]-4-methyl-pentanoic acid | | | | | | | |
| RY | 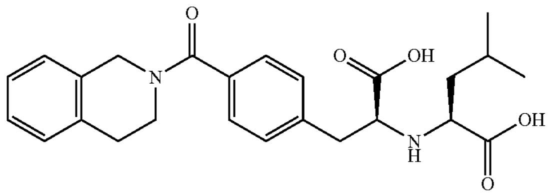 | 2-[1-Carboxy-2-[4-(3,4-dihydro-1H-isoquinoline-2-carbonyl)-phenyl]-ethylamino]-4-methyl-pentanoic acid | | | | | | | |
| RZ | 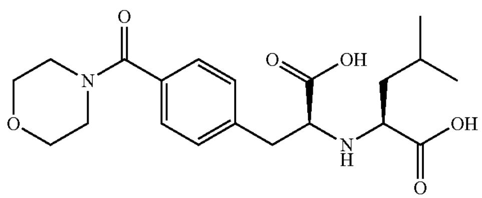 | 2-[1-Carboxy-2-[4-(morpholine-4-carbonyl)-phenyl]-ethylamino]-4-methyl-pentanoic acid | | | | | | | |
| SA | 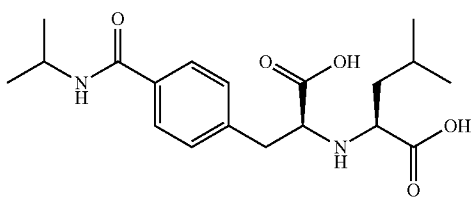 | 2-[1-Carboxy-2-(4-isopropylcarbamoyl-phenyl)-ethylamino]-4-methyl-pentanoic acid | | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| SB | 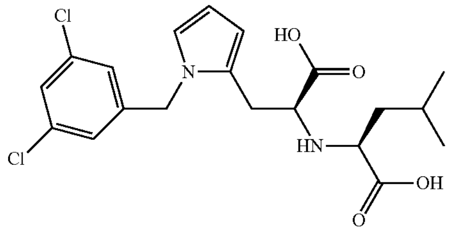 | 2-[1-Carboxy-2-[1-(3,5-dichloro-benzyl)-1H-pyrro-2-yl]-ethylamino]-4-methyl pentanoic acid | | | | | | | |
| SC | 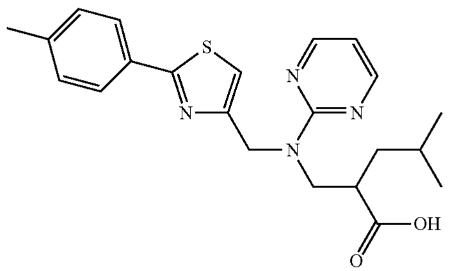 | 4-Methyl-2-[[pyrimidin-2-yl (2-p-tolyl-thiazol-4-ylmethyl)-amino]-methyl)-pentanoic acid | | | | | | | |
| SD | 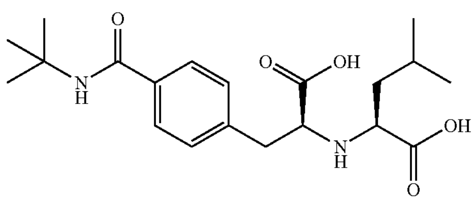 | 2-[2-(4-tert-Butylcarbamoyl-phenyl)-1-carboxy-ethylamino]-4-methyl-pentanoic acid | | | | | | | |
| SE | 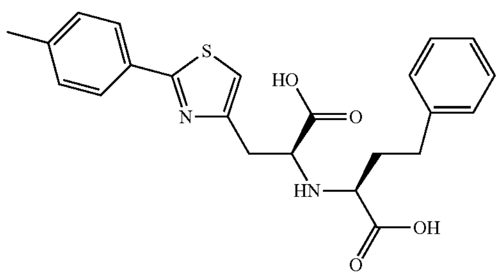 | 2-[1-Carboxy-2-(2-p-tolyl-thiazol-4-yl)-ethylamino]-4-phenyl-butynic acid | | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| SF | 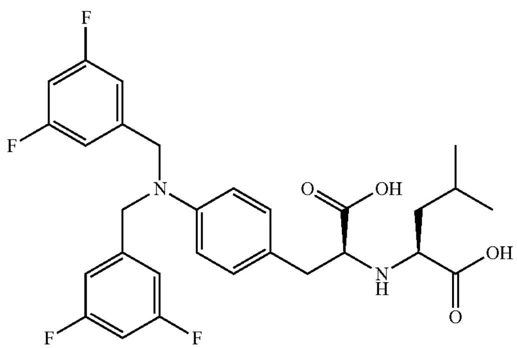 | 2-(2-[4-[Bis-(3,5-difluoro-benzyl)-amino]-phenyl]-1-carboxy-ethylamino)-4-methyl-pentanoic acid | | | | | | | |
| SG | 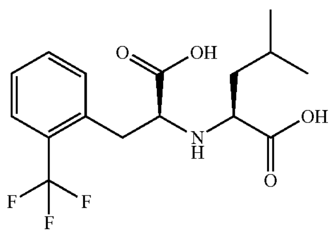 | 2-[1-Carboxy-2-(2-trifluoromethyl-phenyl)-ethylamino]-4-methyl-pentanoic acid | | | | | | | |
| SH | 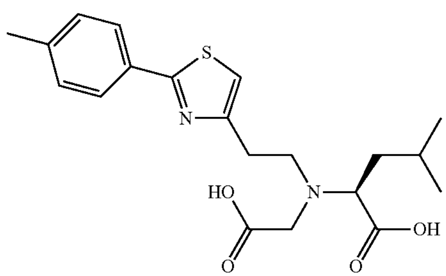 | 2-{Carboxymethyl-[2-(2-p-tolyl-thiazol-4-yl)-ethyl]-amino}-4-methyl-pentanoic acid | | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| SI | 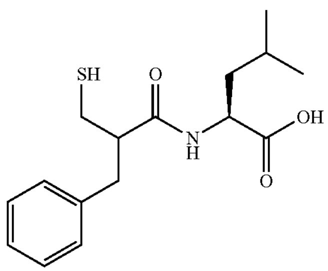 | 2-(2-Benzyl-2-mercapto-propionylamino)-4-methyl-pentanoic acid | | | | | | | |
| SJ | 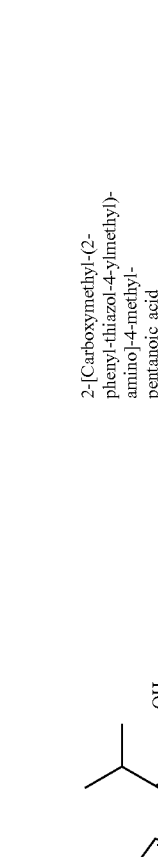 | 2-[(Carboxymethyl-(2-phenyl-thiazol-4-ylmethyl)-amino]-4-methyl-pentanoic acid | | | | | | | |
| SK | 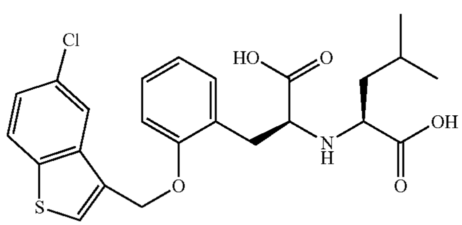 | 2-{1-Carboxy-2-[2-(5-chloro-benzo[b]thiophen-3-ylmethoxy)-phenyl]-ethylamino}-4-methyl-pentanoic acid | | | | | | | |
| SL | 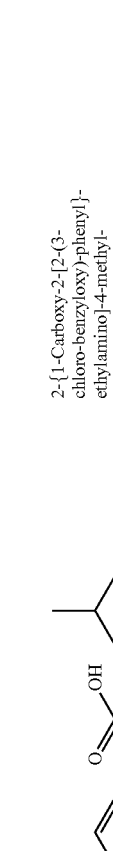 | 2-{1-Carboxy-2-[2-(3-chloro-benzyloxy)-phenyl]-ethylamino}-4-methyl-pentanoic acid | | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| SM | 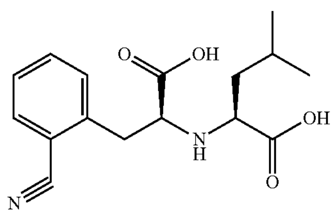 | 2-[1-Carboxy-2-(2-cyano-phenyl)-ethylamino]-4-methyl-pentanoic acid | | | | | | | |
| SN | 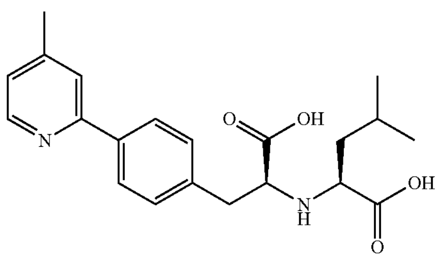 | 2-{1-Carboxy-2-[4-(4-methyl-pyridin-2-yl)-phenyl]-ethylamino}-4-methyl-pentanoic acid | | | | | | | |
| SO | 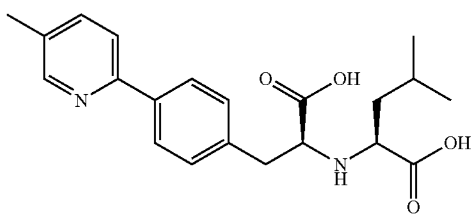 | 2-{1-Carboxy-2-[4-(5-methyl-pyridin-2-yl)-phenyl]-ethylamino}-4-methyl-pentanoic acid | | | | | | | |
| SP | 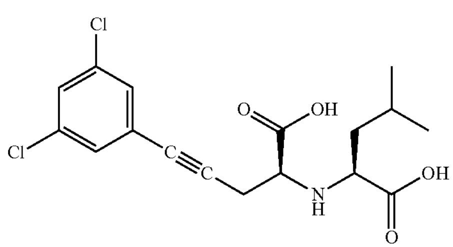 | 2-(1-Carboxy-3-methyl-butylamino)-5-(3,5-dichloro-phenyl)-pent-4-ynoic acid | | | | | | | |

TABLE 2-continued

| Ref. No. | Structure | Chemical Name | M.W. | Human ACE-2 Activity | RAT ACE-2 Activity | ACE Activity | Carboxypeptidase A Activity | CHN Expected | CHN Actual |
|---|---|---|---|---|---|---|---|---|---|
| SQ | 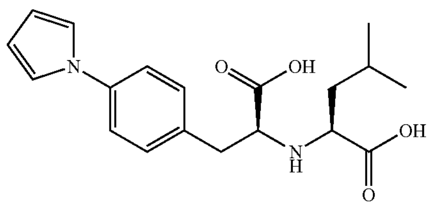 | 2-[1-Carboxy-2-(4-pyrrol-1-yl-phenyl)-ethylamino]-4-methyl-pentanoic acid | | | | | | | |
| SR | 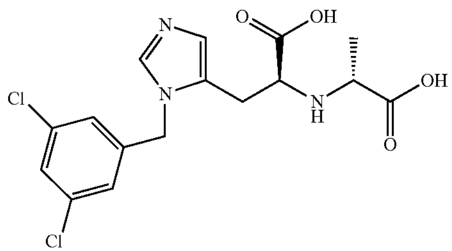 | 2-(1-Carboxy-ethylamino)-3-[3-(3,5-dichloro-benzyl)-3H-imidazol-4-yl]-propionic acid | | | | | | | |
| SS | 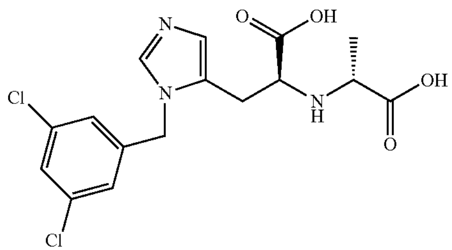 | 2-(1-Carboxy-ethylamino)-3-[3-(3,5-dichloro-benzyl)-3H-imidazol-4-yl]-propionic acid | | | | | | | |

The $K_i$'s for the very good ACE-2 inhibiting compounds are given in Table 3.

TABLE 3

| ACE-2 Activity | Compound ID |
| --- | --- |
| $K_i$ of less than 0.05 µM | OE, OX, OY, PA, PH, PL, PN, PO, PZ, QC, QE, QK, QN, QU, QW, HC, HE, HG, HK, QY, QZ, RB, HO, HQ, IX, JB, IZ, JE, JI, JO, JP, JQ, KK, NJ, NM, NW, KS, KV, KX, KZ, LC, Lp, MB, MD, MM, MQ, MR, MV, NG, NH, NI |
| $K_i$ of between 0.05 µm and 0.1 µM | HA, HS, HU, HY, IC, II, IL, Ql, QP, QQ, IO, IU, KG, KI, KJ, KU, LF, LG, PC, QA, QB, LN, LV, LW, NE, NF, NY, OG, OO, OT, OW, OZ, PI, PJ |

Example 12

Assay for the Identification of ACE-2 Modulating Compounds

The following reagents, equipment, stock solutions, and working solutions are used for the ACE-2 assay.

| Reagents | |
| --- | --- |
| (7-methoxycoumarin-4-yl) acetyl-Tyr-Val-Ala-Asp-Ala-Pro-Lys (2,4-Dinitrophenyl)-OH (Mca-YVADAPK (Dnp)) (SEQ ID NO: 5) | Bachem M-2195 |
| (7-methoxycoumarin-4-yl) acetyl-Ala-Pro-Lys (2,4-Dinitrophenyl)-OH (Mca-APK (Dnp)) | AnaSpec MIPH-1 |
| Mes (4-Morpholine-ethanesulphonic acid) | Boehringer-Mannheim 223 794 |
| Sodium chloride (NaCl) | Sigma S 9888 |
| Brij 35 (10% solution) | Pierce 28316 |
| Ethylenediamineetetraacetic acid (EDTA) | Sigma E 9884 |
| DL-Benzylsuccinnic acid | Sigma B 8011 |
| Dimethylsulphoxide (DMSO) | Sigma 8779 |
| Equipment | |
| Labsystems Multidrop 384 | Labsystems |
| Labsystems Assist | Labsystems |
| FLUOstar plate reader | BMG Labtechnologies |
| 384 well plate | Costar |
| 2-5000 µl Pipetteman | Gilson |
| Stock solutions | |
| ACE-2 in 20 mM HEPES, 15 mM NaCl pH 7.0 (concentration varies by batch - 0.5 uM) | supplied by Protein Group (stored at −80° C.) |
| EDTA (0.5 M, pH 8.0) | Supplied by Media Prep. (stored at room temp.) |
| McaYVADAPK (Dnp) (SEQ ID NO. 5) MW 1145 | 5 mg/m in DMSO (4.37 mM) (stored at −20° C.) |
| McaAPK (Dnp) | 5 mg/ml in DMSO (7.14 mM) (stored at −20° C.) |
| DL-Benzylsuccinnic acid | 20 mM in DMSO (4.2 mg/ml) (stored at −20° C.) |
| Sodium hydroxide (NaOH) | 1 M, 40 g/L (stored at room temp.) |

Working Solutions

The assay buffer is prepared using 50 mM Mes, 300 mM NaCl, and 0.01% Brij 35, pH 6.5. These components are measured and made up to approximately 800 ml with nanopure water. Using 1M NaOH the pH is adjusted to 6.5 and the solution is then made up to the final volume of 1 L using nanopure water. The buffer is filtered through a 0.45 um disposable filter unit and stored at +4° C. until needed.

The working ACE-2 solution (for using with Mca-YVA-DAPK(Dnp)) (SEQ ID NO: 5) is prepared by thawing ACE-2 and diluting it to a concentration of 2 nM using the assay buffer at room temperature. This working solution maintains activity for up to 8 hours at room temperature.

The working ACE-2 solution (for using with Mca-APK (Dnp)) is prepared by thawing ACE-2 and diluting it to a concentration of 1 nM using the assay buffer at room temperature.

The working Mca-YVADAPK (SEQ ID NO:5) and Mca-APK(Dnp) solutions are prepared by thawing the stock Mca-XXXX-(Dnp) and Mca-APK(Dnp) solutions and diluting them to a concentration of 125 µM using the assay buffer at room temperature. These solutions are stable up to 8 hours but can not be frozen-thawed for reuse.

The working DL-Benzylsuccinnic acid solution is prepared by diluting DL-Benzylsuccinnic acid to a final concentration of 2 mM with nanopure water.

The working EDTA solution is prepared by diluting stock EDTA to a final concentration of 50 mM with nanopure water.

Method:

To determine whether a test compound is capable of modulating ACE-2's ability to cleave a substrate the following assay may be used. When using Mca-YVADAPK (Dnp) (SEQ ID NO: 5) as the substrate, the final ACE-2 concentration used is 1 nM and when Mca-APK(Dnp) is used as the substrate, the final ACE-2 concentration used is 0.5 nM.

Multiple well plates are used for this experiment. Each 384 well plate contains 24 control wells containing either 5 µl sample solvent (typically 10% DMSO bal, nanopure water) as the 100% activity control; or 5 µl 2 mM DL-Benzylsuccinnic acid as the 50% inhibition control; or 5 µl 0.5M EDTA as the 100% inhibition control.

Approximately 360 compounds are tested per plate. Five µl per of each test compound is added in each well. Subsequently, using the Labsystems Multidrop 384 and Assist workstation, 25 µl of ACE-2 working solution is added per well and each plate is mixed for 30 seconds. Immediately thereafter, 20 µl of Mca-XXX(Dnp) working solution is added per well and mixed for 30 seconds. The reaction is allowed to progress for approximately 60 minutes.

After approximately 60 minutes, 20 µl of 50 mM EDTA is added per well (reaction is linear up to 90 minutes) and mixed for 30 seconds. At this point the fluorescent signal is stable up to 20 hours at room temperature. The plates are then read on the BMG FLUOstar (excitation 320 nm, emission 405 nm, gain setting 5).

Example 13

Assay for the Identification of ACE Modulating Compounds

The following reagents, stock solutions, and working solutions are used for the ACE assay. The equipment used in this assay are the same as the ones recited above with respect to the ACE-2 assay.

Reagents

| | |
|---|---|
| ACE from porcine kidney | Sigma A-2580 |
| Abz-Gly-para-nitro-PhePro-OH | Bachem M-1100 |
| HEPES | Sigma |
| Sodium chloride (NaCl) | Sigma S 9888 |
| Brij 35 (10% solution) | Pierce 28316 |
| Ethylenediamineetetraacetic acid (EDTA) | Sigma E 9884 |
| Captopril and lisinopril | Sigma |
| Dimethylsulphoxide (DMSO) | Sigma 8779 |

Stock solutions

| | |
|---|---|
| Abz-Gly-para-nitro-Phe-Pro-OH 5 mg/ml in DMSO = 10.34 mM | stored at −20° C. |
| EDTA (0.5 M, pH 8.0) | supplied by Media Prep. (stored at room temp) |
| Sodium hydroxide (NaOH) | 1 M, 40 g/L (stored at room temp) |

Working Solutions

The assay buffer is prepared using 50 mM HEPES, 300 mM NaCl, and 0.01% Brij 35. The stock ACE and substrate solutions are diluted using this assay buffer.

Method

To determine whether a test compound is capable of modulating ACE's ability to cleave a substrate the following assay may be used. The final ACE concentration used in the reaction is 1 nM.

Multiple well plates are used for this experiment. Each 384 well plate contains 24 control wells containing either 5 µl sample solvent (typically 10% DMSO bal, nanopure water) as the 100% activity control; or 5 µl 0.5M EDTA as the 100% inhibition control; or 5 µl captopril/lisinopril as the reference inhibitors.

Approximately 360 compounds are tested per plate. Five µl per of each compound is added in each well. Subsequently, using the Labsystems Multidrop 384 and Assist workstation, 25 µl of 2 nM ACE working solution is added per well and each plate is mixed for 30 seconds. Immediately thereafter, 20 µl of substrate working solution (125 µM) is added per well and mixed for 30 seconds. The reaction is allowed to progress for approximately 30 minutes.

After approximately 30 minutes, 20 µl of 50 mM EDTA is added per well (reaction is linear up to 60 minutes) and mixed for 30 seconds. At this point the fluorescent signal is stable up to 20 hours at room temperature. The plates are then read on the BMG FLUOstar (excitation 320 nm, emission 405 nm, gain setting 5).

Example 14

Assay for the Identification of Compounds Which Modulate Carboxypeptidase A

To determine whether a test compound is capable of modulating carboxypeptidase A's ability to cleave a substrate the method described in Holmquist and Riordan, Carboxypeptidase A, p44–60, Peptidase and Their Inhibitors in Method of Enzymatic Analysis (1984), may be used.

The assay may be adapted to a 96 well format by adjusting to a 300 µl assay volume and using ultrathin bottom plates (Costar/Coming) read at 328 nm with a final assay volume of 300 µl. The assay may be stopped using EDTA.

Example 15

In Situ Analysis of ACE-2 mRNA and Protein

In situ hybridization of a human ACE-2 probe to human and monkey tissues demonstrated the presence of ACE-2 mRNA in some endothelial cells and focally in normal and hypertrophic myocytes in human heart. In human small and large intestine, there is abundant ACE-2 mRNA in luminal, non-differentiating epithelial cells. In monkey kidneys, ACE-2 mRNA was detected in proximal convoluted tubules.

For studying ACE-2 protein, five rabbit polyclonal antipeptide antibodies were generated against human ACE-2: I82283M, which is directed against amino acids 51–69 of SEQ ID NO:2, i.e., NTN ITE ENV QNM NNA GDK W (SEQ ID NO:6); I82284M, which is directed against amino acids 194–214 of SEQ ID NO:2, i.e., NHY EDY GDY WRG DYE VNG VDG (SEQ ID NO:7); K70417K, which is directed against amino acids 489–508 of SEQ ID NO:2, i.e, EPV PHD ETY CDP ASL FHV SN (SEQ ID NO:8); K70418M, which is directed against amino acids 704–723 of SEQ ID NO:2, i.e., IRM SRS RIN DAF RLN DNS LE (SEQ ID NO:9); and K70419M, which is directed against amino acids 785–802 of SEQ ID NO:2, i.e, DIS KGE NNP GFQ NTD DVQ (SEQ ID NO:10). All five antibodies are functional for Western blotting and antibody I82283M is particularly efficient in immunhistochemistry.

ACE-2 protein was evaluated in rat, human and monkey tissues using an antibody generated against a fragment of the human peptide (I82283M). In rat and human heart, ACE-2 protein was abundant in endothelial cells. In normal human kidneys, ACE-2 was limited to endothelial cells (arterial/venous). In addition to endothelial cell expression, ACE-2 was detected in vascular smooth muscle cells of abnormal renal vessels and damaged (sclerotic) glomeruli of hypertensive human kidneys. In clinically healthy monkey kidneys, ACE-2 protein was found in endothelial cells, epithelial cells of Bowman's capsule and proximal tubules. In the human small and large intestine, there is also ACE-2 expression in luminal, non-differentiating epithelium, in smooth muscle cells of the muscularis layer as well as endothelial cells of small penetrating blood vessels and capillaries. In addition, ACE-2 protein is detectable in adipocytes within adipose tissue; there is no mRNA expression detectable in these cells.

Example 16

ACE-2 Knock-out Mice

Mice having one or both ACE-2 genes disrupted were generated by the insertion of a NEO/URA cassette in the site encoding the active site of the enzyme.

Identification of the Murine ACE-2 Gene:

A genomic fragment of the murine ACE-2 gene was obtained by screening an RPCI-22 mouse BAC library with a 1.8 Kb EcoRI fragment of the human ACE-2 cDNA. Of the eight BACs containing the ACE-2 sequence that were identified, the clone designated BAC 145d21 was found to contain the largest ACE-2 genomic fragment. A random sheared library was prepared from BAC145d21 in a nebulizer using $N_2$. The ends were repaired using polynucleotide kinase followed by T4 DNA polymerase. The DNA was size-selected on a 1% agarose gel, ligated to BstXI adaptor linkers and subcloned for sequencing.

Generation of an ACE-2 Targeting Construct:

An XbaI fragment containing the active site exon of ACE-2 was subcloned into pBluescript SK+. The resulting construct, pMD43, was restriction mapped. A 500 bp NciI/SacI fragment of pMD43 was isolated as a 3'flanking probe. Sequence obtained from the sheared library was used to design the following amplification primers to generate a 1.2 Kb 5'flanking probe.

```
                                                  (SEQ ID NO:11)
5'-TTA AGT TCT AGA TTT CTG ATT ATG AGA CAC-3'

(SEQ ID NO:12)
5'-GCT ATA CAT TCT AGA CAT TAA CTC TCA TTG-3'
```

To inactivate ACE-2, a targeting construct was built that replaced the exon encoding the active site of the enzyme with a NEO/URA cassette by homologous recombination.

A 5.2Kb NciI (blunted with Klenow polymerase)/XbaI fragment of pMD43 was subcloned into the SmaI/XbaI sites of the yeast shuttle vector YCplac22 (Storck, et al. (1996) Nuc. Acids Res. 24:4594–6). The resulting plasmid was called pMD44. The following amplification primers were designed with ACE-2 genomic sequence on the 5'end and sequence from the NEO/URA cassette of the pRAY-1 vector on the 3'end (Storck, et al., supra)

```
5'-AAG TAA GAT TCA CTT TAA TCT TGT CCG TTT TTA TGC AGA ATC AAG   (SEQ ID NO:13)
CGA CAA GCT TCT CGA GAT CTG-3'

5'-CAA AAG AAA AAT TAC CGC TAT CTT CTT GAA AAT CGG ATG GCA GAA   (SEQ ID NO:14)
TCG ACC TGC AGC CAA ATA ACT TCG-3'
```

These primers were used to generate by PCR a 3.4 Kb fragment containing the NEO/URA cassette from pRAY-1 flanked by the ACE-2 genomic sequence. The PCR fragment and pMD44 were co-transformed into the yeast strain YPH501 for homologous recombination. The plasmid was rescued from yeast into DH10B E. coli, and the exon encoding the active site of ACE-2 was shown to be replaced with the NEO/URA cassette. The targeting construct thus obtained was named pMD47, and is shown in FIG. 1.

Generation of Targeted ES Cells:

The 129SvEv ES cell line was cultured on SNL76/7mitotically inactive feeder cells as described by Robertson (in *Teratocarcinomas and Embryonic Stem Cells: A Practical Approach*, ed. Roberson, E. J. IRL, Oxford; 1987. Pp 71–112). Electroporation of the cells was performed as described by Huszar, et al (1997; Cell 88:131–141). Briefly, cells were trypsinized and resuspended at a concentration of $1.0 \times 10^7$/ml in PBS ($Ca^{2+}$- and $Mg^{2+}$-free; Gibco). A 0.7 ml aliquot ($7 \times 10^6$ cells) was mixed with 20 µg of the linearized targeting vector and pulsed at 250V, 500 µF (Gio-Rad Gene Pulser). The cells were then diluted in culture medium, plated at $1-2 \times 10^6$ per 100 mm plate containing feeder cells, and placed under selection 24 hr later in G418 sulfate (300 µg/ml solution; Gibco). G418-resistant clones were picked, dissociated with trypsin, and divided into one well each of two 96-well plates. Upon confluence, ES cells were frozen in one of the 96-well plates according to the procedure of Ramirez-Solis, et al (1993; Meth. Enzymol. 225:855–878). DNA was prepared from the other plate for screening by Southern blot hybridization. Positive clones were extended and analyzed by Southern blot hybridization using 5' and 3' flanking probes to confirm recombination.

Generation of Ace-2 Deficient Mice:

ES cell clones that had undergone homologous recombination were injected into blastocysts which were then transferred to pseudopregnant female mice to generate chimeric offspring. Male chimeras were mated with C57B16 females to obtain germline transmission of the NEO/URA disrupted ACE-2 gene. The resulting heterozygotes were interbred to generate mice homozygous or heterozygous for the ACE-2 mutation, along with wild type littermates.

Body Measurements:

Various measurements were taken from eight homozygous ACE-2 knock-out male mice and five wild type mice. Weight gain was regularly measured, beginning at 3–4 weeks of age, using a Sartorius model #14800 P balance. Length, measured by manual immobilization and extension of the mouse to its full length, was determined from the nose to the anus, and recorded in centimeters. Body composition (fat tissue, lean tissue, and total soft tissue) was measured by DEXA (Dual Energy X-rays Absorptiometry) using a Piximus Scanner (Lunar Corporation, WI). The animals were maintained on a chow diet ad libitum. On the day that the measurements were taken, the knock-out and wild type mice ranged in age from about 161 to 188 days, with the average age being approximately 172 ($\pm 4.7$) days, and for the wild type mice, the average age was approximately 167.6 ($\pm 5.1$) days. The average body weight of the knock-out mice was approximately 25 g and ranged from about 17.8 g to about 29.5 g. The average body weight of the wild type mice was approximately 34 g, and ranged from about 29.6 g to about 40.4 g. The average body length of the knock-out mice was approximately 9.8 cm, and ranged from about 8.8 cm to 10.4 cm. The average body length of the wild type mice was approximately 10.3 cm, and ranged from about 9.6 cm to about 10.8 cm. Thus, the knock-out mice and the wild type mice do not differ in length or age, yet the knock-out mice have a lower average body weight than the wild type mice.

Measurement of body composition indicated that the knock-out mice exhibited an average fat mass of approximately 2.4 ($\pm 0.2$) g and a range of about 1.8 g to about 3.2 g, whereas the wild type mice had an average fat mass of approximately 6.4 (±1.0) g and a range of about 4.0 g to about 8.7 g. The average lean mass of the knock-out mice was approximately 20.8 (±1.1) g and ranged from about 14.8 g to about 24.2 g. The average lean mass of the wild type mice was approximately 26.1 (±1.5) g and ranged from about 22.6 g to about 31.4 g. Significantly, the lean-to-fat ratio for the knock-out mice is about 8.7 versus 4.1 for the wild type mice, slightly more than a two-fold difference. The average total soft tissue weight for the knock-out mice was determined to be approximately 23.3 (±1.2) g, with a range of 16.6 g to 27.4 g. The average total soft tissue for the wild type mice was determined to be approximately 32.5 (±2.0) g.

The calculation of the average percentage of body fat indicated that the knock-out mice have an average body fat content of approximately 10.4 (±0.4) percent and a range of 8.8% to 11.6%. In contrast, the wild type mice had an average body fat content of approximately 19.6 (±2.6) percent and a range of 13.8% to 27.1%.

Effect of Diet on ACE-2 Deficient Mice

A second study was undertaken to examine the effects of ACE-2 deficiency on a broader range of metabolic parameters. In the study, ten five-month-old ACE-2 knock-out (KO) mice and ten age-matched wild type (WT) littermates were maintained on a standard mouse diet. Prior to and during the study, body weight, food consumption, water consumption, plasma glucose, and plasma insulin were measured. Body weight and body composition measurements were performed using dual X-ray absorptiometry. A glucose tolerance test (GTT) was performed after overnight fasting in six seven-month old KO mice and six WT littermates. A single intraperitoneal (IP) injection of 2 g/kg of glucose was followed by tail blood glucose measurements at time 0, 15, 30, 60, 120 and 180 minutes post injection. An insulin tolerance test (ITT) was performed in six seven-month-old KO and six WT littermates mice with no access to food. A single IP injection of 0.75 units of insulin was followed by tail blood glucose measurements at time 0, 15, 30, 60 and 120 minutes post-injection. Blood lipid levels in non-fasted animals were assayed in plasma samples using standard colorimetric and immunological assays. Individually housed animals were monitored for activity. The temperature of sub-scapular brown adipose tissue was determined using thermal imaging and infrared photometry.

At five months of age, KO mice had significantly lower total body weights than their WT littermates (28.8±0.54 g vs 30.8±0.75 g, p<0.05). The difference in body weight was due to a reduction in fat tissue mass (4.2±0.18 g vs 5.4±0.30 g, p<0.05) with no statistically significant change in lean tissue mass (24.6±0.42 g vs 25.4±0.50 g). At six months of age the difference in total body weight was statistically significant (KO: 30.8±0.80 g vs WT: 35.3±1.7 g, p<0.05) and can be explained by a difference in fat tissue mass (KO: 3.8±0.20 g vs WT: 7.8±1.1 g, p<0.05) with no statistically significant difference in lean tissue mass (26.0±0.50 g vs 27.6±0.60 g).

As summarized in Table 4, below, neither fasting blood glucose levels nor glucose response during the GTT were significantly different between the KO and WT littermates. However, other experiments have shown that the plasma insulin levels to glucose challenge at 30 and 60 min post-challenge was significantly lower in KO mice than in WT littermate mice.

TABLE 4

| Group | Plasma Glucose (mg/dL ± SEM) | | | | | |
|---|---|---|---|---|---|---|
| | 0 min | 15 min | 30 min | 60 min | 120 min | 180 min |
| KO | 111 ± 14 | 390 ± 50 | 430 ± 44 | 395 ± 48 | 300 ± 57 | 210 ± 30 |
| WT | 120 ± 8.8 | 359 ± 63 | 401 ± 55 | 330 ± 33 | 250 ± 59 | 230 ± 82 |

Example 17

Effect of a Small Molecule ACE-2 Antagonist on Appetite

Male ICR derived mice weighing 20±2 g (10–12 weeks of age), were provided by the animal breeding center of MDS Pharma Services—Taiwan Ltd. The mice were housed in APEC cages (Allentown Caging, Allentown N.J.) and maintained in a hygienic environment under controlled temperature (22° C.–24° C.) and humidity (60%–80%) with 12-hour alternating light/dark cycles for at least one week in the MDS Pharma Services—Taiwan Laboratory prior to the study. During that time, the mice had ad lib access to standard lab chow and tap water.

The effect of Compound HE on appetite was studied essentially as described by Blavet, et al (1982. Gen. Pharmacol. 13:173) Briefly, a food mass was prepared from ground chow, evaporated milk, and sugar, at a ratio of 1 kg:0.75 liter:0.15g. For the study, twelve of the mice described above were divided into three groups of four. The animals were given by oral administration 20 ml/kg vehicle (distilled water), 100 mg/kg Compound HE, or 3 mg/kg amphetamine 30 minutes before being placed in a cage with the food mass. Food consumption was measured at one hour, three hours, and six hours later. For the mice given vehicle, the cumulative food consumption went from about 3.67±0.18 g at one hr, to about 4.92±0.06 g at three hours, and to about 5.91±0.12 g at six hours. For the mice given amphetamine, the cumulative food consumption went from about 0.18±0.05 g at one hour, to about 1.39±0.07 g at three hours, and to about 3.10±0.03 g at six hours. For the mice given Compound HE, the cumulative food consumption went from about 2.22±0.13 g at one hour, to about 4.06±0.27 g at three hour, and to about 5.38±0.41 g at six hour. These results demonstrate that administration of Compound HE reduces food intake about 40% 1 hr and about 18% 3 hr after administration in ICR mice when compared to mice given vehicle.

The effects of Compound HE on body weight and metabolism were studied further in the BBZDR rat, a genetic model of obesity and Type II diabetes (Biomedical Research Models, Inc, Worcester, Mass.). BBZDR rats are a cross between the BBDR/W or strain and the fa/fa rat. In BBZDR rats, diabetes occurs in 98% of obese males at an average age of onset of 68±2 days. Age matched lean male rats do not develop glycosuria or hyperglycemia. The pancreatic islets of the young obese diabetic males are profoundly enlarged with β cell hyperplasia and mild fibrosis. Studies of pancreatic sections immunostained for insulin and the GLUT-2 glucose transporter reveal focal reduction in β cell insulin content and a generalized reduction in GLUT-2 staining of β cell surface membranes. Lymphocytic insulitis is not detected in either lean or obese rats. In the absence of lymphopenia and autoimmunity, the lean BBZDR rats never become diabetic, and their pancreatic islets are normal in all respects.

diabetes as measured by onset of glycosuria was lower in the 100 mg (33% incidence rate) and 300 mg (25% incidence rate) dose groups, compared to placebo controls (83% incidence rate). The plasma levels of insulin, total cholesterol and triglycerides were also lower in both Compound HE-treated groups, compared to placebo controls. Finally, there were no changes in gross abdominal adipose and psoas muscle mass and core body temperature between all three groups.

TABLE 5

| Parameter | Placebo | 100 mg/kg | 300 mg/kg |
|---|---|---|---|
| Incidence of Diabetes | 5/6 (83%) | 2/6 (33%) | 1/4 (25%) |
| Incidence of Glycosuria (Days) | 36/198 (18.2%) | 31/198 (15.7%) | 12/162 (7.4%) |
| Fasted Insulin, Day 34 (ng/mL) | 13.5 ± 10.6 | 8.4 ± 7.0 (62%)[a] | 7.7 ± 4.1 (57%)[a] |
| Fasted Glucose, Day 34 (ng/dL) | 303 ± 26 | 306 ± 24 (100%) | 283 ± 7 (94%) |
| Fasted Leptin, Day 34 (ng/mL) | 110 ± 15 | 99 ± 22 (102.7%) | 92 ± 5.3 (76%) |
| Fasted Total Cholest., Day 34 (mg/dL) | 133 ± 9 | 117 ± 9 (88%) | 104 ± 5 (78%) |
| Total Fasted Triglyc., Day 34 (mg/dL) | 504 ± 20 | 409 ± 6 (82%) | 414 ± 23 (82%) |
| Weight Gain thru Day 34 (g) | 152 ± 9.4 | 123 ± 3.4 (83.9%) | 125 ± 8.3 (82.5%) |
| Water Consumption (mL) | 1468 ± 62.6 | 1388 ± 73.5 (94.6%) | 1271 ± 101.7 (86.7%) |
| Food Consumption (g) | 1359 ± 39.9 | 1283 ± 50.3 (94.4%) | 1249 ± 26.8 (91.9%) |
| Core Temperature (F.) | 98.3 ± 0.11 | 98.4 ± 0.13 (100%) | 98.4 ± 0.20 (100%) |
| Psoas Mass (g) | 1.15 ± 0.12 | 1.30 ± 0.09 (113%) | 1.21 ± 0.10 (105%) |
| Adipose Mass (g) | 51.38 ± 1.52 | 48.03 ± 1.86 (94%) | 48.43 ± 0.55 (94%) |

[a]For values which are not incidence rates, parentheses contain percent of placebo response.

Compound HE was administered to male BBZDR rats (48–60 days of age) via oral gavage for a period of 34 days. There were three treatment groups, each with 6 rats/group: a) placebo (1% carboxy methyl cellulose [CMC]), b) Compound HE at 100 mg/kg/day in 1% CMC, and c) Compound HE at 300 mg/kg/day in 1% CMC. The rats were gavaged twice daily for the entire period of the study. Body weight, food intake, fluid intake, and core body temperature were monitored on a daily basis. In addition, the rats were observed twice daily for any gross behavioral/phenotypic changes. Early in the study, two animals in the 300 mg/kg/day-dose group died from trauma secondary to oral gavage (confirmed during necropsy) and were excluded from all analyses.

To determine the pharmacokinetic profile of Compound HE, plasma samples were taken at 0, 0.5, 1, 2, 4, 8, 12, and 24 hours after dosing in both Compound HE dose groups. The results indicated that animals in the two Compound HE treatment groups were exposed to relatively low systemic levels of Compound HE.

On Day 21, after an overnight fast, whole blood, serum and plasma samples were collected from anesthetized animals. Prior to the termination of the study, tissue and plasma samples were collected from overnight-fasted animals for histological and biochemical analyses. No gross or histomorphological adverse effects were observed during the 34 consecutive days of oral dosing with Compound HE.

Shown below in Table 5 is a summary of the results of the metabolic parameters measured in each of the Compound HE treatment and placebo groups. Body weight gain over the 34 days was approximately 18% less in both Compound HE-treated groups compared to placebo-treated rats; no dose dependence was apparent in this effect. Similarly, food intake was less in both Compound HE treated groups than in placebo-treated rats (5% and 8% less than placebo in 100 mg- and 300 mg-treated groups). A similar pattern was seen for fluid intake: 5% and 15% less in Compound HE-treated groups than in placebo controls. In addition, the incidence of Oral administration for 34 days of Compound HE to BBZDR obese, diabetic rats, resulted in decreased body weight gain, decreased food and water intake, and decreased plasma levels of insulin, cholesterol and triglycerides compared to placebo-treated rats. In addition, the incidence of diabetes was lower in the Compound HE-treated rats than in placebo controls. Although these changes were not statistically significant, the data demonstrate that pharmacological inhibition of ACE-2 activity has a downregulatory effect on metabolic parameters associated with obesity.

Example 18

Hydrolysis of Biologically Active Peptides by Soluble Human ACE-2

The proteolytic activity of ACE-2 was characterized against a panel of peptides using a soluble truncated form of the protein. The soluble truncated form of human ACE2 corresponds to amino acid residues 1–739 of the 805-amino acid full length sequence (SEQ ID NO.: 2). This truncation deletes a transmembrane domain. Approximately 130 biologically active peptides were screened as potential substrates for ACE-2. Detection of proteolytic activity and identification of the peptide product was performed using the following LC/MS (liquid chromatography/mass spectroscopy) procedure. To each tube was added 45 µl of buffer (50 mM MES, 300 mM NaCl, 10 µM $ZnCl_2$, 0.01% Brij-35 pH 6.5), 50 µl of 100 nM ACE-2 (50 nM final) or buffer control, and 5 µl of 1 mM peptide (50 µM final) for a reaction volume of 100 µl. Reactions were performed at room temperature for 2 hours and quenched with 20 µl of 0.5M EDTA. Samples were then analyzed by matrix-assisted laser desorption/ionization time of flight mass spectrometry (MALDI-TOF). MALDI-TOF analysis provided data on the extent of hydrolysis and the peptide product of the hydrolysis. Samples exhibiting hydrolysis were re-assayed and analyzed in the presence of a potent specific inhibitor of ACE-2 activity to confirm specific cleavage by ACE-2.

Ten of the peptides were hydrolyzed by ACE-2, and in every case resulted in removal of the C-terminal residue only, demonstrating that the proteolytic activity of ACE-2 is carboxypeptidase-like. In addition to its ability to hydrolyze angiotensin I (1-10) and angiotensin II (1-8) and (Des-Arg$^9$) bradykinin and Lys-(Des-Arg$^9$) bradykinin, ACE-2 demonstrated complete hydrolysis of apelin-13 and apelin-36, β-casomorphin, dynorphin A 1-13, ghrelin, and neurotensin. ACE-2 did not hydrolyze either bradykinin or angiotensin (1-9).

Some of the results from the peptide screen are shown below in Table 6.

μM ZnCl$_2$, 0.01% Brij-35 pH 6.5), 50 μl of ACE-2, and 5 ul of peptide. Reactions were performed at room temperature for 0, 15, 22.5 or 30 min. and quenched with 5 μl of 0.5M EDTA. Substrate concentrations ranged from 0.8 to 2.0 μM. Enzyme concentrations ranged from 25 pM to 700 pM and were selected to ensure that the assays were conducted under initial velocity conditions (<15% hydrolysis of substrate). Peptides were resolved on a ODS-A 1.0×50 mm 120A 5 um column using a gradient of 10–45%B (A: water/0.1% TFA (v/v); B: acetonitrile/0.1% trifluoroacetic acid (v/v)). Peptides were detected by absorbance at 215 nm. Injection volumes ranged from 20 to 0.5 μl, dependent upon detection limits. Product and substrate peaks were quantified and product peak areas were converted to mol of product by

TABLE 6

| Substrate | Sequence | Hydrolysis |
|---|---|---|
| Angiotensin I(1–10) | DRVYIHPFH↓L (SEQ ID NO. 15) | P |
| Angiotensin 1–9 | DRVYIHPFH (SEQ ID NO. 16) | N |
| Angiotensin II(1–8) | DRVYIHP↓F (SEQ ID NO. 17) | C |
| Apelin-13 | QRPRLSHKGPMP↓F (SEQ ID NO. 18) | C |
| Apelin-36 (C-terminus shown) | QRPRLSHKGPMP↓F (SEQ ID NO. 19) | C |
| Bradykinin | RPPGFSPFR (SEQ ID NO. 20) | N |
| (Des-Arg$^9$) Bradykinin | RPPGFSP↓F (SEQ ID NO. 21) | C |
| Lys-(Des-Arg$^9$) Bradykinin | KRPPGFSP↓F (SEQ ID NO. 22) | P |
| β-Casomorphin | YPFVEP↓I (SEQ ID NO. 23) | C |
| Dynorphin A 1–13 | YGGFLRRIRPKL↓K (SEQ ID NO. 24) | C |
| Ghrelin (C-terminus shown) | . . . ESKKPPAKLQP↓R (SEQ ID NO. 25) | P |
| Neurotensin 1–8 | pE-LYENKP↓R (SEQ ID NO. 26) | P |

(pE: pyroglutamyl, C: complete hydrolysis, P: partial hydrolysis, N: no hydrolysis)

The kinetic constants for ACE-2 hydrolysis of eight of the peptides were determined by reversed phase liquid chromatography (LC) using an Agilent capillary LC pump, UV detector, and software (Agilent Technologies, Palo Alto Calif.). Reactions were performed in 100 μl. To each well was added 45 μl of buffer (50 mM MES, 300 mM NaCl, 10 determining the percent product formed (100*[area of product peak/area of product peak+area of substrate peak]). $K_M$ and $k_{cat}$ values were determined from analysis of initial velocity vs. substrate concentration plots.

The ACE-2 kinetic data is summarized below in Table 7.

TABLE 7

| Substrate | Sequence | $K_M$, μM | $k_{cat}$, sec$^{-1}$ | $k_{cat}/K_M$, M$^{-1}$sec$^{-1}$ | n |
|---|---|---|---|---|---|
| Angiotensin I | DRVYIHPFH↓L (SEQ ID NO. 27) | 6.9 | 0.035 | 5.1 × 10$^3$ | 2 |
| Angiotensin II | DRVYIHP↓F (SEQ ID NO. 28) | 1.7 | 4.6 | 2.7 × 10$^6$ | 2 |
| Apelin-13 | QRPRLSHKGPMP↓F (SEQ ID NO. 29) | 8.0 | 14 | 1.8 × 10$^6$ | 1 |
| β-Casomorphin | YPFVEP↓I (SEQ ID NO. 30) | 31 | 7.0 | 2.2 × 10$^5$ | 2 |
| (Des-Arg$^9$) Bradykinin | RPPGFSP↓F (SEQ ID NO. 31) | 570 | 64 | 1.1 × 10$^5$ | 2 |
| Lys-(Des-Arg$^9$) | KRPPGFSP↓F (SEQ ID NO. 32) | 260 | 27 | 1.0 × 10$^5$ | 2 |
| Dynorphin A 1–13 | YGGFLRRIRPKL↓K (SEQ ID NO. 33) | 5.5 | 16 | 3.1 × 10$^6$ | 2 |
| Neurotensin 1–8 | pE-LYENKP↓R (SEQ ID NO. 34) | 300 | 57 | 1.9 × 10$^5$ | 2 |

(pE: pyroglutamyl)

The peptides angiotensin II, apelin 13, and dynorphin A 1-13 were identified as preferred ACE-2 substrates, all with $k_{cat}/K_m > 1 \times 10^6$ M$^{-1}$sec$^{-1}$. The $k_{cat}/K_m$ value for angiotensin II (1-8) was found to be 500-fold higher than for angiotensin I (1-10). ACE-2 also hydrolyzes (des-Arg$^9$)-bradykinin and lys-(des-Arg$^9$)-bradykinin approximately equally well with a $k_{cat}/K_m$ of $1.1 \times 10^5$ M$^{-1}$sec$^{-1}$ and $1.0 \times 10^5$ M$^{-1}$sec$^{-1}$, respectively.

Example 19

Procedure for the Synthesis of the Oxazolidinones

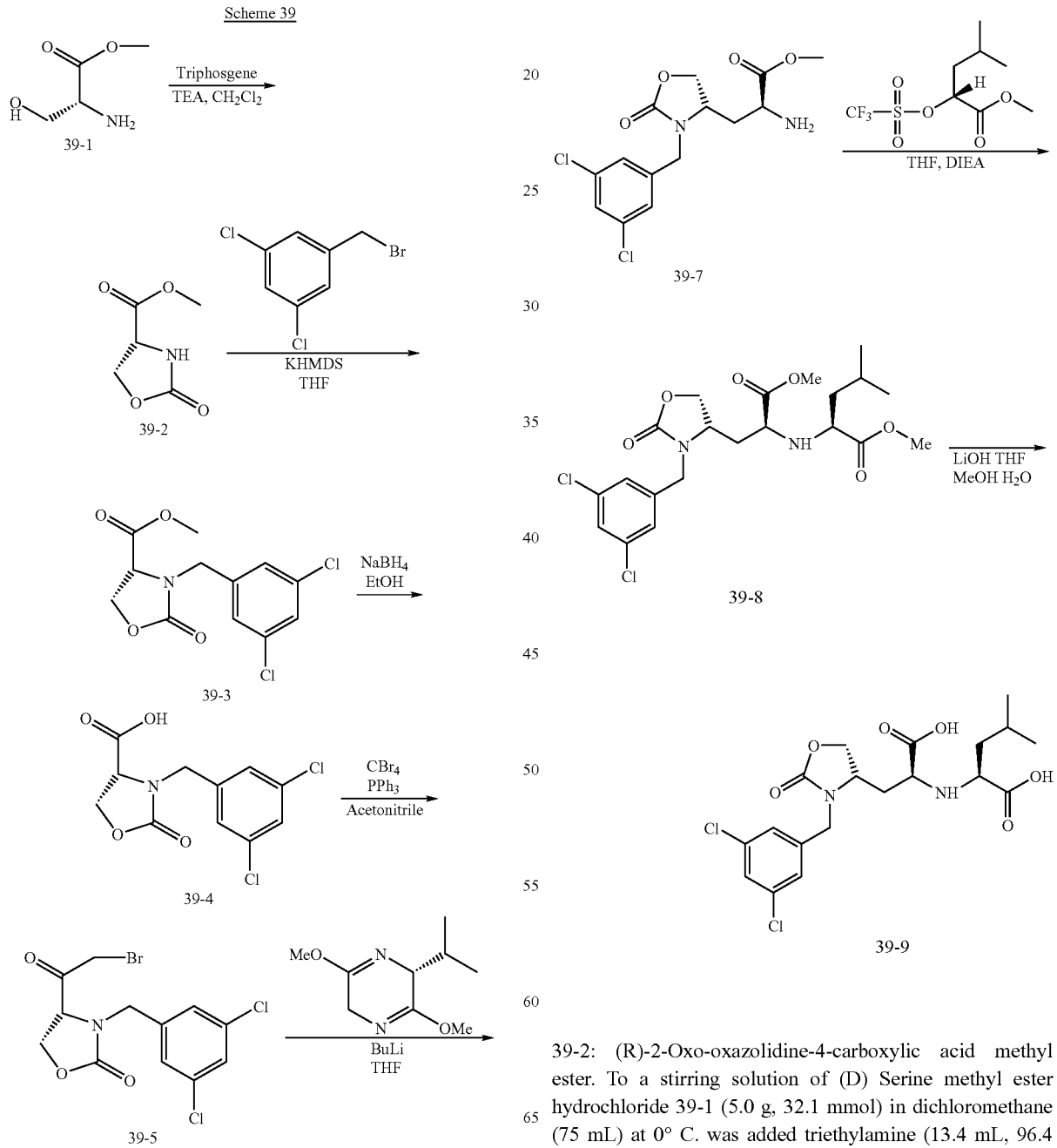

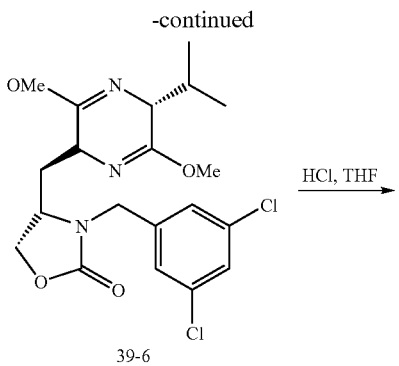

39-2: (R)-2-Oxo-oxazolidine-4-carboxylic acid methyl ester. To a stirring solution of (D) Serine methyl ester hydrochloride 39-1 (5.0 g, 32.1 mmol) in dichloromethane (75 mL) at 0° C. was added triethylamine (13.4 mL, 96.4 mmol). The reaction was stirred at 0° C. for 20 minutes, then a solution of triphosgene (3.24 g, 10.9 mmol) in dichloromethane (50 mL) was added via addition funnel over 2hours. The reaction was stirred an additional 3 hours at 0° C.,then diethyl ether (75 mL) was added and the solution was cooled to −70° C. The white precipitate was filtered off, then the solvent was evaporated. Purification by silica gel chromatography (100% ethyl acetate) gave 3.35 g of the desired product. Rt=0.48, MH+=146.

39-3: (R)-3-(3,5-Dichloro-benzyl)-2-oxo-oxazolidine-4-carboxylic acid methyl ester. To a solution of 39-2 (3.3 g, 22.7 mmol) in tetrahydrofuran (40 mL) at 0° C. was added potassium bis(trimethylsilyl) amide (0.5M in Toluene, 45.5 mL, 22.7 mmol). The reaction was stirred at 0° C. for 30 minutes, then a solution of 3,5-dichlorobenzyl bromide (6.0 g, 25.0 mmol) in tetrahydrofuran (40 mL) was added. The reaction was stirred at 0° C. for 40 minutes, then at 40° C. for 16 hours. The solution was cooled to room temperature, then quenched with ammonium chloride/ammonium hydroxide pH 8.5 buffer. The solution was diluted with ethyl acetate, the layers were separated and the aqueous phase was extracted with ethyl acetate. The combined organics were dried with $Na_2SO_4$, filtered, and concentrated in vacuo. Purification by silica gel chromatography (10–20% ethyl acetate/hexanes) gave 4.85 g of the desired product. Rt=2.44, MH+=304.

39-4: (S)-3-(3,5-Dichloro-benzyl)-4-hydroxymethyl-oxazolidin-2-one. To a stirring solution of 39-3 (4.85 g, 15.9 mmol) in ethyl alcohol (45 mL) at 0° C. was added sodium borohydride (0.664 g, 17.5 mmol). The reaction was allowed to warm to room temperature over 3 hours. The reaction was quenched with saturated aqueous ammonium chloride, then the solvent was evaporated. The residue was diluted with ethyl acetate and water. The layers were separated, and the aqueous phase was extracted with ethyl acetate. The combined organics were dried over $Na_2SO_4$, filtered, and concentrated in vacuo. Purification by silica gel chromatography gave 3.93 g of the desired compound. Rt=1.91, MH+=276.

39-5: (R)-4-Bromomethyl-3-(3,5-dichloro-benzyl)-oxazolidin-2-one. To a stirring solution of 39-4 (3.93 g, 14.2 mmol) in acetonitrile (50 mL) at room temperature was added triphenylphosphine (7.47 g, 28.5 mmol) followed by carbon tetrabromide (9.44 g, 28.5 mmol). The solution was stirred for 16 hours at room temperature, then basified with 15% aqueous sodium hydroxide. The layers were separated, and the aqueous phase was extracted with diethyl ether 3 times. The combined organics were then dried over $Na_2SO_4$, filtered, and concentrated in vacuo. Purification by silica gel chromatography (10–30% ethyl acetate/hexanes) gave 2.83 g of the desired compound. Rt=2.54, MH+=340.

39-6: 3-(3,5-Dichloro-benzyl)-4-(5-isopropyl-3,6-dimethoxy-2,5-dihydro-pyrazin-2-ylmethyl)-oxazolidin-2-one. To a stirring solution of (3R)-3-isopropyl-2,5-diethoxy-3,6-dihydropyrazine (1.5 mL, 8.35 mmol) in tetrahydrofuran (45 mL) at −70° C. was added n-butyllithium (1.6 M in hexanes, 5.75 mL, 9.18 mmol). The solution was stirred at −70° C. for 30 minutes, then added a solution of A-5 in tetrahydrofuran (30 mL). The solution was stirred for 90 minutes at −70° C. then 90 minutes at room temperature. The solution was quenched with saturated aqueous ammonium chloride, then the solvent was evaporated. The residue was diluted with ethyl acetate, then extracted with water, then saturated aqueous sodium bicarbonate, then brine. The organic layer was dried over $Na_2SO_4$, filtered, and concentrated in vacuo. Purification by silica gel chromatography (10–30% ethyl acetate/hexanes) gave 1.77 g of the desired compound. Rt=3.40, MH+=442.

39-7: 2-Amino-3-[3-(3,5-dichloro-benzyl)-2-oxo-oxazolidin-4-yl]-propionic acid methyl ester. To a stirring solution of 39-6 (1.77 g, 4.0 mmol) in tetrahydrofuran (40 mL) was added hydrochloric acid (0.1N, 80 mL, 8.0 mmol). The solution was stirred at room temperature for 3 hours. The solution was extracted with diethyl ether. The aqueous phase was brought to pH 9 with concentrated aqueous ammonium hydroxide, then extracted four times with diethyl ether. The combined organics were dried over $Na_2SO_4$, filtered, and concentrated in vacuo which gave 1.08 g of the desired compound. Rt=1.22, MH+=347.

39-8: 2-{2-[3-(3,5-Dichloro-benzyl)-2-oxo-oxazolidin-4-yl]-1-methoxycarbonyl-ethylamino}-4-methyl-pentanoic acid methyl ester. To a solution of (R)-4-Methyl-2-trifluoromethanesulfonyloxy-pentanoic acid methyl ester (1.04 g, 3.75 mmol) in dichloromethane (15 mL) at −70° C. was added N,N-diisopropylethylamine (0.82 mL, 4.69 mmol) followed by a solution of 39-7 (1.08 g, 3.12 mmol) in dichloromethane (15 mL) dropwise. The solution was allowed to slowly warm to room temperature, and stirred for 16 hours. The solvent was evaporated, and the residue was diluted with ethyl acetate. The solution was washed with saturated aqueous sodium bicarbonate twice, followed by brine. The organic layer was then dried over $Na_2SO_4$, filtered, and concentrated in vacuo. Purification by silica gel chromatography (10–30% ethyl acetate/hexanes) gave 0.645 g of the desired compound. Rt=2.94, MH+=476.

39-9: (S,S,S)-2-{1-Carboxy-2-[3-(3,5-dichloro-benzyl)-2-oxo-oxazolidin-4-yl]-ethylamino}-4-methyl-pentanoic acid (Compound NE). To a solution of 39-8 (0.093 g, 0.196 mmol) in tetrahydrofuran (3.6 mL), methanol (1.2 mL), and water (1.2 mL) at 0° C. was added lithium hydroxide monohydrate (0.049 g, 1.17 mmol). The solution was stirred at 0° C. for 6 hours. After evaporation of the organics in vacuo, the solution was acidified with 1N HCl until a white precipitate formed which was filtered off. The aqueous layer was stored at room temperature for 16 hours. A crystalline solid formed which was filtered off and dried in vacuo to give 0.010 g of the desired compound. Rt=1.64, MH+=447. $^1$H NMR is consistent with the assigned structure.

Compounds synthesized using the same general procedure.

(R,S,S)-2-{1-Carboxy-2-[3-(3,5-dichloro-benzyl)-2-oxo-oxazolidin-4-yl]-ethylamino}-4-methyl-pentanoic acid (Compound NN) Rt=1.87, MH+=447.

(R,S,S)-2-{1-Carboxy-2-[3-(3,5-difluoro-benzyl)-2-oxo-oxazolidin-4-yl]-ethylamino}-4-methyl-pentanoic acid. Rt=1.53, MH+=415.

Example 20

Synthesis of Indole Analogs

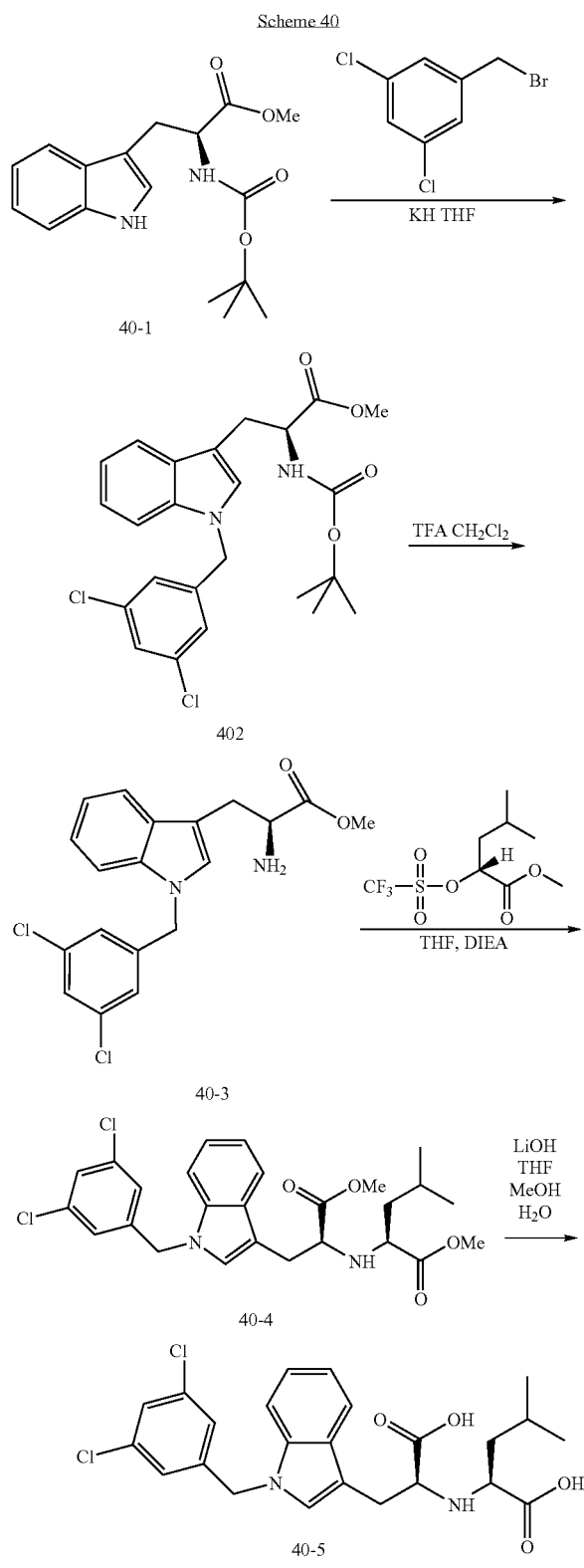

40-2: (S)-2-tert-Butoxycarbonylamino-3-[1-(3,5-dichlorobenzyl)-1H-indol-3-yl]-propionic acid methyl ester. To a stirring suspension of potassium hydride (0.46 g, 30 wt % in mineral oil, 3.45 mmol) in tetrahydrofuran (4 mL) at −50° C. was added a solution of (S)-2-tert-Butoxycarbonylamino-3-(1H-indol-3-yl)-propionic acid methyl ester (1.0 g, 3.14 mmol) in tetrahydrofuran (6 mL). The solution was stirred for 30 minutes at −50° C., then 3,5-dichlorobenzyl bromide (0.829 g, 3.45 mmol) was added. The reaction was allowed to warm to room temperature, then stirred for 16 hours. The reaction was then quenched by the addition of water and diluted with ethyl acetate. The organic phase was separated and dried over $Na_2SO_4$, filtered and concentrated in vacuo. Purification by silica gel chromatography (30% ethyl acetate/hexanes) gave 1.2 g of the desired compound. Rt=3.46, MH+=478.

40-3: (S)-2-Amino-3-[1-(3,5-dichloro-benzyl)-1H-indol-3-yl]-propionic acid methyl ester. To a stirring solution of 40-2 (1.2 g, 2.50 mmol) in dichloromethane (8 mL) at room temperature was added trifluoroacetic acid (2 mL). The reaction was stirred at room temperature for 2 hours, then quenched with saturated aqueous sodium bicarbonate solution, and diluted with dicholoromethane. The organic phase was washed with saturated aqueous sodium bicarbonate solution twice, then dried over $Na_2SO_4$, filtered, and concentrated in vacuo to give 0.919 g of the desired compound. Rt=1.73, MH+=378.

40-4: (S,S)-2-{2-[1-(3,5-Dichloro-benzyl)-1H-indol-3-yl]-1-methoxycarbonyl-ethylamino}-4-methyl-pentanoic acid methyl ester. To a solution of (R)-4-Methyl-2-trifluoromethanesulfonyloxy-pentanoic acid methyl ester (0.746 g, 2.68 mmol) in dichloromethane (8 mL) at −70° C. was added N,N-diisopropylethylamine (0.47 mL, 2.68 mmol), followed by a solution of 40-3 (0.919 g, 2.43 mmol) in dichloromethane (8 mL) dropwise. The solution was allowed to slowly warm to room temperature, and stirred for 16 hours. The solvent was evaporated, and the residue was diluted with ethyl acetate. The solution was washed with saturated aqueous sodium bicarbonate twice, followed by brine. The organic layer was then dried over $Na_2SO_4$, filtered, and concentrated in vacuo. Purification by silica gel chromatography (10–30% ethyl acetate/hexanes) gave 0.71 g of the desired compound. Rt=3.51, MH+=506.

40-5: (S,S)-2-{1-Carboxy-2-[1-(3,5-dichloro-benzyl)-1H-indol-3-yl]-ethylamino}-4-methyl-pentanoic acid. To a stirring solution of 40-4 (0.710 g, 1.40 mmol) in tetrahydrofuran (16 mL), methanol (5.5 mL), and water (5.5 mL) at 0° C. was added lithium hydroxide monohydrate (0.236 g, 5.62 mmol). The solution was allowed to warm to room temperature and stirred for 16 hours. After concentrating the organics in vacuo, the aqueous layer was acidified with 1N HCl until a white precipitate formed which was filtered and dried to give 0.438 g of the desired compound. Rt=2.44, MH+=477. $^1$H NMR consistent with the assigned structure.

Compounds synthesized using the same general procedure:

(S,S)-2-[2-(1-Benzyl-1H-indol-3-yl)-1-carboxy-ethylamino]-4-methyl-pentanoic acid. Rt=1.93, MH+=409.

(R,S)-2-[2-(1-Benzyl-1H-indol-3-yl)-1-carboxy-ethylamino]-4-methyl-pentanoic acid. Rt=2.04, MH+=409.

Example 21

Synthesis of Glutamic Acid 2-aminobenzothiazole Analog

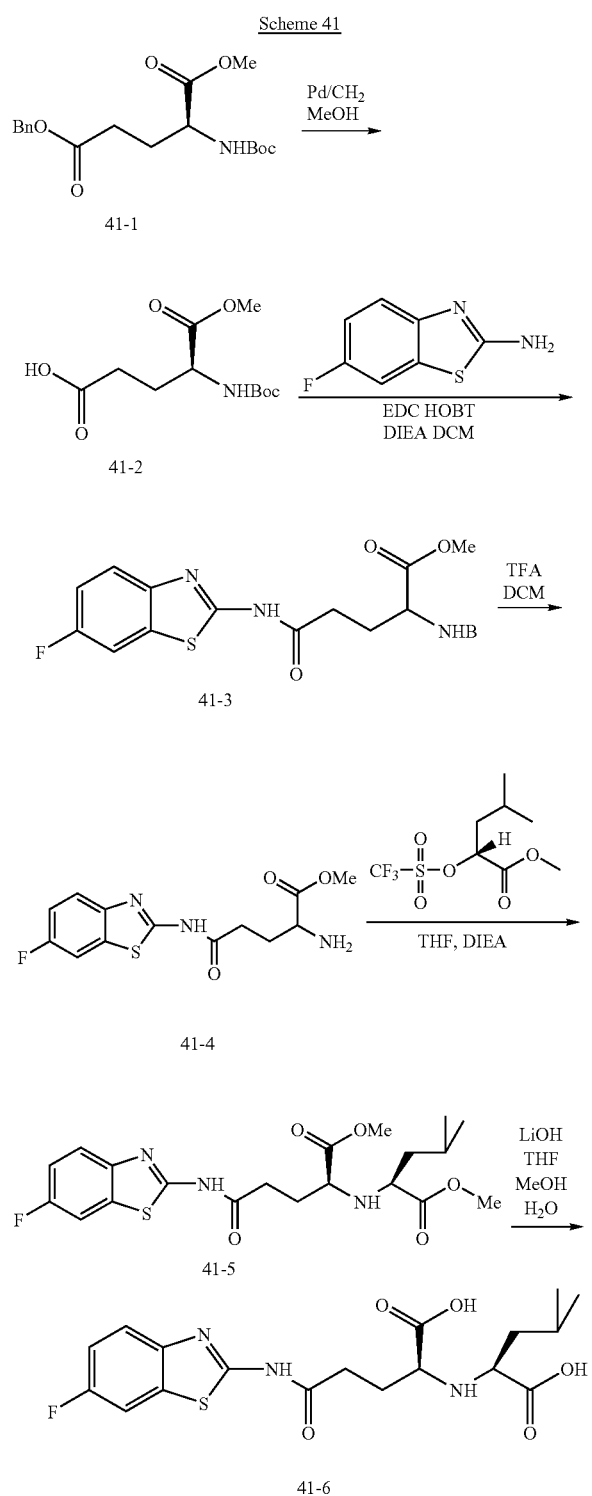

41-2: (S)-2-tert-Butoxycarbonylamino-pentanedioic acid 1-methyl ester. A solution of (S)-2-tert-Butoxycarbonylamino-pentanedioic acid 5-benzyl ester 1-methyl ester 41-1 (4.32 g, 12.3 mmol) and palladium on carbon (10%, 0.432 g) in methanol (45 mL) were stirred under 1 atmosphere of hydrogen for 4 hours. The solution was then filtered through a pad of celite and concentrated in vacuo to give 2.86 g of the desired product. Rt=1.61, MH+=262.

41-3: (S)-2-tert-Butoxycarbonylamino-4-(6-fluoro-benzothiazol-2-ylcarbamoyl)-butyric acid methyl ester. To a stirring solution of 41-2 (0.50 g, 1.91 mmol), N,N-diisopropylethylamine (1.0 mL, 5.74 mmol), 6-Fluoro-benzothiazol-2-ylamine (0.293 g, 1.74 mmol) and benzotriazol-1-ol (0.259 g, 1.91 mmol) in dichloromethane (10 mL) at 0° C. was added 1-(3-Dimethylaminopropyl)-3-ethylcarbodiimide hydrochloride (0.367 g, 1.91 mmol). The solution was allowed to warm to room temperature and stirred overnight. The solution was then concentrated in vacuo, and the residue was diluted with ethyl acetate and washed with 1N HCl twice, saturated aqueous sodium bicarbonate twice, then brine. The organic layer was dried over $Na_2SO_4$, filtered, and concentrated in vacuo. Purification by silica gel chromatography (30% ethyl acetate/hexanes) gave 0.234 g of the desired product. Rt=2.46, MH+=412.

41-4: (S)-2-Amino-4-(6-fluoro-benzothiazol-2-ylcarbamoyl)-butyric acid methyl ester. To a stirring solution of 41-3 (0.234 g, 0.569 mmol) in dichloromethane (7 mL) was added trifluoroacetic acid (3 mL). The reaction was stirred at room temperature for 3 hours, then concentrated in vacuo. The residue was diluted with ethyl acetate then washed with saturated aqueous sodium bicarbonate solution twice, then dried over $Na_2SO_4$, filtered, and concentrated in vacuo to give 0.161 g of the desired product. Rt=1.03, MH+=312.

41-5: (S,S)-2-[3-(6-Fluoro-benzothiazol-2-ylcarbamoyl)-1-methoxycarbonyl-propylamino]-4-methyl-pentanoic acid methyl ester. To a solution of (R)-4-Methyl-2-trifluoromethanesulfonyloxy-pentanoic acid methyl ester (0.187 g, 0.672 mmol) in dichloromethane (4 mL) at −70° C. was added N,N-diisopropylethylamine (0.18 mL, 1.03 mmol) followed by a solution of 41-4 (0.161 g, 0.517 mmol) in dichloromethane (3 mL) dropwise. The solution was allowed to slowly warm to room temperature, and stirred for 16 hours. The solvent was evaporated, and the residue was diluted with ethyl acetate. The solution was washed with saturated aqueous sodium bicarbonate twice, followed by brine. The organic layer was then dried over $Na_2SO_4$, filtered, and concentrated in vacuo. Purification by silica gel chromatography (10–30% ethyl acetate/hexanes) gave 0.075 g of the desired product. Rt=2.34, MH+=440.

41-6: (S,S)-2-[1-Carboxy-3-(6-fluoro-benzothiazol-2-ylcarbamoyl)-propylamino]-4-methyl-pentanoic acid (Compound OV). To a stirring solution of 41-5 (0.075 g, 0.171 mmol) in tetrahydrofuran (2.1 mL), methanol (0.7 mL), and water (0.7 mL) at 0° C. was added lithium hydroxide monohydrate (0.029 g, 0.682 mmol). The solution was allowed to warm to room temperature and stirred for 16 hours. After concentrating the organics in vacuo, the aqueous layer was acidified with 1N HCl until a white precipitate formed which was filtered and dried to give 0.043 g of the desired compound. Rt=1.62, MH+=412. NMR consistent with the assigned structure.

Example 22

Synthesis of Imidazolones

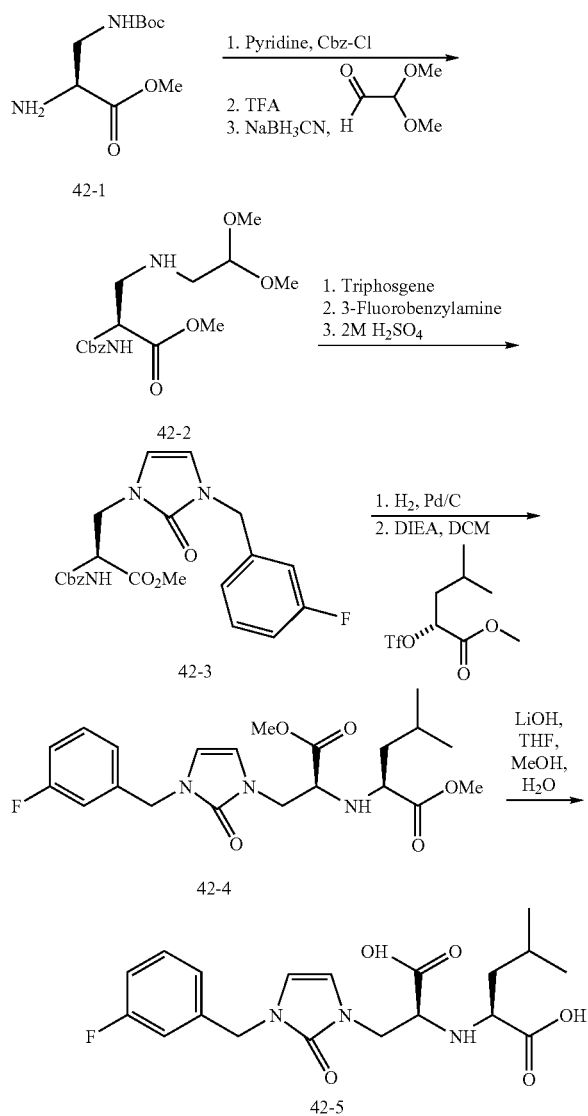

42-2: (S)-2-Benzyloxycarbonylamino-3-(2,2-dimethoxyethylamino)-propionic acid methyl ester. To a solution of H-DAP(Boc)-OMe 42-1 (5 g, 19.6 mmol) in acetonitrile at 0° C. (100 ml) was added pyridine (3.17 ml, 39.2 mmol) followed by Cbz-Cl (3.08 ml, 21.6 mmol) dropwise. The reaction was stirred overnight warming to room temperature. The reaction was concentrated in vacuo and the residue diluted in ethyl acetate. After washing 1×1N HCl, 1× satd. NaHCO$_3$, and 1×H$_2$O, the organic phase was dried with Na$_2$SO$_4$, filtered, and conc in vacuo. The residue was taken up in DCM (20 ml) under Argon, and TFA (20 ml) was added dropwise. The reaction was stirrred for 4 h at RT and then conc in vacuo from toluene several times to give 6.46 g of the desired product. Rt=0.84, MH+=253 which was used directly in the next reaction. To a solution of Cbz-DAP-OMe TFA salt (6.46 g, 17.6 mmol) in MeOH (100 ml) at 0° C., was added glyoxal dimethyl acetal (5.4 ml of 45% wt in MTBE, 21.2 mmol), followed by NaBH$_3$CN (20 ml of a 1M THF, 19.4 mmol) dropwise over 0.5 h. The reaction was stirred 5 h and 50 ml of satd. NaHCO$_3$ was added. After removing most of the methanol under reduced pressure, the residue was diluted with H$_2$O and extracted 3×ethyl acetate. The organics were combined, dried with Na$_2$SO$_4$, filtered and conc in vacuo. Purification by silica gel chromatography (90–100% ethyl acetate/hexane) gave 4.29 g of the desired product. Rt=1.21, MH+=341.

42-3: (S)-2-Benzyloxycarbonylamino-3-[3-(3-fluoro-benzyl)-2-oxo-2,3-dihydro-imidazol-1-yl]-propionic acid methyl ester. To a solution of 42-2 (0.84 g, 2.45 mmol) in THF (25 ml) at 0° C. was added triethylamine (0.79 ml, 5.6 mmol), followed by triphosgene (0.28 mg, 0.93 mmol) in one portion. The reaction was stirred for 0.5 h at 0° C. and 0.5 h at RT. After purging the excess phosgene with a balloon of argon, 3-fluorobenzylamine (0.31 ml, 2.7 mmol) was added and the reaction was stirred overnight at RT. 2M H$_2$SO$_4$ (4 ml) was added and the reaction was stirred an additional 24 h. The reaction was diluted with ethyl acetate and washed once with H$_2$O. The aqueous phase was extracted twice with ethyl acetate. The organics were combined, dried with Na$_2$SO$_4$, filtered, and conc in vacuo. Purification by silica gel chromatography (70–80% ethyl acetate/hexane) gave 0.69 g of the desired product. Rt=2.27, MH+=428.

42-4: (S,S)-2-{2-[3-(3-Fluoro-benzyl)-2-oxo-2,3-dihydro-imidazol-1-yl]-1-methoxycarbonyl-ethylamino}-4-methyl-pentanoic acid methyl ester. A solution of 42-3 (0.67 g) and 10% Pd/C (0.05 g) in MeOH (2.5 ml) was stirred under 1 atmosphere of hydrogen for 1 h, filtered through a pad of celite and concentrated in vacuo to give a residue which was used in the next reaction. A solution of leucic acid triflate (0.56 g, 2.03 mmol) in DCM (3 ml) was cooled to −78° C. Diisopropylethylamine (0.41 ml, 2.3 mmol) was added to the reaction followed by a solution of the above free amine (1.56 mmol) in DCM (3 ml) dropwise. The reaction was stirred overnight warming to room temperature and concentrated in vacuo. Purification by silica gel chromatography (80–90% ethyl acetate/hexane) gave 0.36 g of the desired product. Rt=2.34, MH+=422.

42-5: (S,S) 2-{1-Carboxy-2-[3-(3-fluoro-benzyl)-2-oxo-2,3-dihydro-imidazol-1-yl]-ethylamino}-4-methyl-pentanoic acid. To a solution of 42-4 (0.36 g, 0.87 mmol) in methanol (0.5 ml), THF (2.0 ml), and H$_2$O (0.5 ml) was added LiOH—H$_2$O (0.15 g, 3.46 mmol). The reaction was stirred overnight at RT. After concentrating the organics in vacuo, the aqueous layer was acidified with 1N HCl until a white precipitate formed which was filtered and dried to give 0.19 g of the desired product. Rt=1.51, MH+=394, NMR consistent with assigned structure.

Compounds synthesized using the same general procedure:

(S,S) 2-{1-Carboxy-2-[3-(3,4-dichloro-benzyl)-2-oxo-2,3-dihydro-imidazol-1-yl]ethylamino}-4-methyl-pentanoic acid (Compound KU): Rt=1.86, MH+=444.

(S,S) 2-{1-Carboxy-2-[3-(3,5-dichloro-benzyl)-2-oxo-2,3-dihydro-imidazol-1-yl]-ethylamino}-4-methyl-pentanoic acid (Compound LF): Rt=1.94, MH+=444.

C 2-{1-Carboxy-2-[3-(3,5-difluoro-benzyl)-2-oxo-2,3-dihydro-imidazol-1-yl]-ethylamino}-4-methyl-pentanoic acid: Rt=1.64, MH+=412.

(S,S)-2-{1-Carboxy-2-[2-oxo-3-(1-phenyl-ethyl)-2,3-dihydro-imidazol-1-yl]-ethylamino}-4-methyl-pentanoic acid (Compound LH): Rt=1.61, MH+=390.

(S,S)-2-[2-(3-Benzyl-2-oxo-2,3-dihydro-imidazol-1-yl)-1-carboxy-ethylamino]-4-methyl-pentanoic acid: Rt=1.38, MH+=376.

(S,S)-2-{1-Carboxy-2-[3-(2-cyclohexyl-ethyl)-2-oxo-2,3-dihydro-imidazol-1-yl]-ethylamino}-4-methyl-pentanoic acid (Compound ME): Rt=1.94, MH+=396.

(S,S)-2-[1-Carboxy-2-(3-cyclopropylmethyl-2-oxo-2,3-dihydro-imidazol-1-yl)-ethylamino]-4-methyl-pentanoic acid: Rt=1.11, MH+=340.

(S,S)-2-[1-Carboxy-2-(3-cyclohexyl-2-oxo-2,3-dihydro-imidazol-1-yl)-ethylamino]-4-methyl-pentanoic acid: Rt=1.5, MH+=368.

(S,S)-2-{1-Carboxy-2-[3-(3,5-difluoro-phenyl)-2-oxo-2,3-dihydro-imidazol-1-yl]-ethylamino}-4-methyl-pentanoic acid: Rt=1.64, MH+=398.

(S,S)-2-(1-Carboxy-2-{3-[2-(4-fluoro-phenyl)-ethyl]-2-oxo-2,3-dihydro-imidazol-1-yl}-ethylamino)-4-methyl-pentanoic acid: Rt=1.6, MH+=408.

(S,S)-2-[1-Carboxy-2-(3-cyclohexylmethyl-2-oxo-2,3-dihydro-imidazol-1-yl)-ethylamino]-4-methyl-pentanoic acid: Rt=1.62, MH+=382.

(S,S)-2-(1-Carboxy-2-{3-[2-(3-fluoro-phenyl)-ethyl]-2-oxo-2,3-dihydro-imidazol-1-yl}-ethylamino)-4-methyl-pentanoic acid: Rt=1.58, MH+=408.

(S,S)-2-{1-Carboxy-2-[3-(4-fluoro-benzyl)-2-oxo-2,3-dihydro-imidazol-1-yl]-ethylamino}-4-methyl-pentanoic acid: Rt=1.45, MH+=394.

(S,S)-2-{1-Carboxy-2-[3-(3-chloro-benzyl)-2-oxo-2,3-dihydro-imidazol-1-yl]-ethylamino}-4-methyl-pentanoic acid (Compound OE): Rt=1.63, MH+=410.

(S,S)-2-{1-Carboxy-2-[3-(3-fluoro-benzyl)-2-oxo-2,3-dihydro-imidazol-1-yl]-ethylamino}-4-methyl-pentanoic acid: Rt=1.51, MH+=394.

(S,S)-2-{1-Carboxy-2-[3-(3,4-difluoro-benzyl)-2-oxo-2,3-dihydro-imidazol-1-yl]-ethylamino}-4-methyl-pentanoic acid: Rt=1.53, MH+=412.

(S,S)-2-{1-Carboxy-2-[3-(2,5-difluoro-benzyl)-2-oxo-2,3-dihydro-imidazol-1-yl]ethylamino}-4-methyl-pentanoic acid: Rt=1.48, MH+=412.

(S,S)-2-(1-Carboxy-2-{3-[2-(3-chloro-phenyl)-ethyl]-2-oxo-2,3-dihydro-imidazol-1-yl}-ethylamino)-4-methyl-pentanoic acid (Compound PD): Rt=1.78, MH+=424.

(S,S)-2-(1-Carboxy-2-{3-[2-(2-fluoro-phenyl)-ethyl]-2-oxo-2,3-dihydro-imidazol-1-yl}-ethylamino)-4-methyl-pentanoic acid: Rt=1.63, MH+=408.

Example 23

Synthesis of Cyclic Ureas from Imidazolones

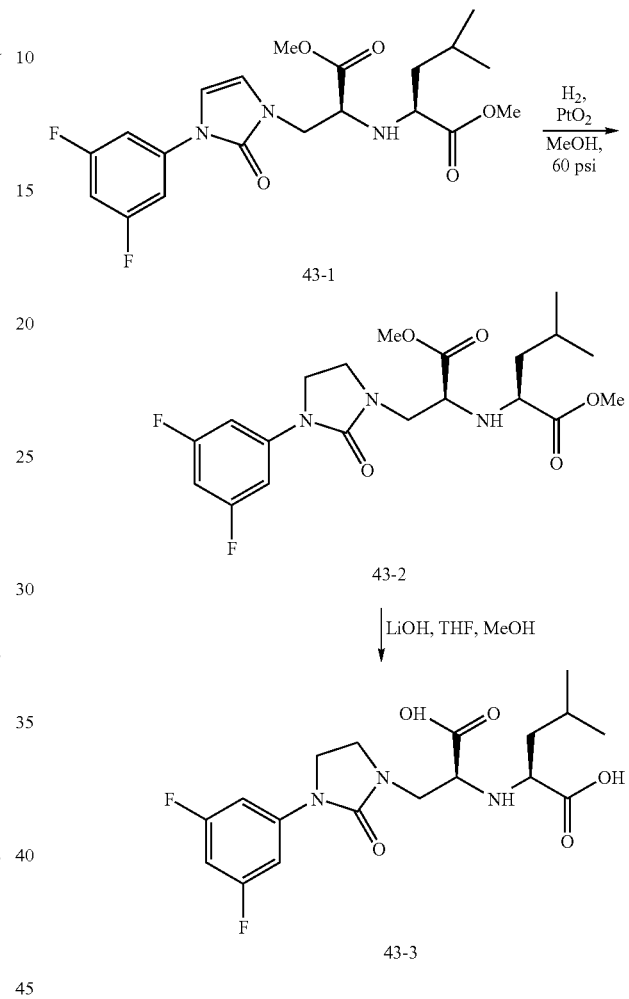

43-2: (S,S)-2-{2-[3-(3,5-Difluoro-phenyl)-2-oxo-imidazolidin-1-yl]-1-methoxycarbonyl-ethylamino}-4-methyl-pentanoic acid methyl ester. A solution of 2-{2-[3-(3,5-Difluoro-phenyl)-2-oxo-2,3-dihydro-imidazol-1-yl]-1-methoxycarbonyl-ethylamino}-4-methyl-pentanoic acid methyl ester (0.3 g) and $PtO_2$ (45 mg) in MeOH (25 ml) was shaken under 60 psi $H_2$ for 24 hours and then filtered through celite and concentrated in vacuo. The residue was purified by silica gel chromatography (50% ethyl acetate/hexane) to give 0.28 g of the desired product. Rt=2.66, MH+=428.

43-3: (S,S)-2-{1-Carboxy-2-[3-(3,5-difluoro-phenyl)-2-oxo-imidazolidin-1-yl]-ethylamino}-4-methyl-pentanoic acid. To a solution of 43-2 (0.28 g, 0.66 mmol) in methanol (1.0 ml), THF (3.0 ml), and $H_2O$ (1.0 ml) was added LiOH—$H_2O$ (0.11 g, 2.62 mmol). The reaction was stirred overnight at RT. After concentrating the organics in vacuo, the aqueous layer was acidified with 1N HCl until a white precipitate formed which was filtered and dried to give 0.21 g of the desired product. Rt=1.74, MH+=400, NMR consistent with assigned structure.

Compounds synthesized using the same general procedure:

(S,S)-2-{1-Carboxy-2-[3-(3,5-difluoro-benzyl)-2-oxo-imidazolidin-1-yl]-ethylamino}-4-methyl-pentanoic acid: Rt=1.76, MH+=414

Example 24

Synthesis of Thiols (see *Biorg. Med. Chem. Lett.* 2000, 10, 2037.)

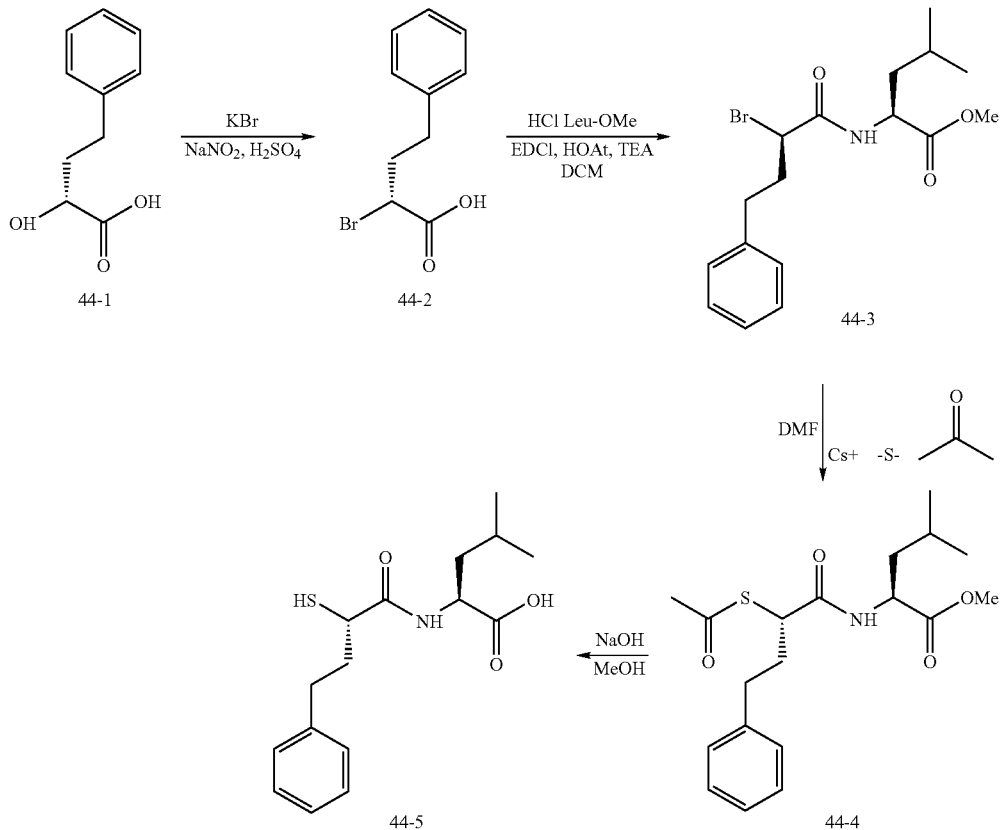

Scheme 44

44-2: (R)-2-Bromo-4-phenyl-butyric acid (prepared according to *Bull. Chem. Soc. Jpn.*, 1952, 52, 265.) NaNO$_2$ (0.54 g, 7.8 mmol) was added over 15 min to a solution of (S)-2-Hydroxy-4-phenyl-butyric acid 44-1 (1 g, 5.58 mmol) and KBr (2.19 g, 18.4 mmol) in 3 N H$_2$SO$_4$ (9 ml) at 0° C. The reaction was stirred at 0° C. for 1 h then at room temperature overnight. The reaction was extracted 3×ether, the organics were combined and dried with MgSO$_4$, filtered, and conc in vacuo to give 0.98 g of a 3:1 mix of the desired product and starting material. Rt=2.34, MH+=243.

44-3: (R,S) 2-(2-Bromo-4-phenyl-butyrylamino)-4-methyl-pentanoic acid methyl ester.

To a solution of 44-2 in dichloromethane (DCM) at 0° C. was added triethylamine (TEA), HCl (L)-H-Leu-OMe, HOAt and EDCl. The reaction was stirred from 0° C. to room temperature overnight. The reaction was diluted with ethyl acetate, washed with 1 N HCl, satd. NaHCO$_3$, brine, dried with Na$_2$SO$_4$, filltered, and conc in vacuo. The residue was purified by silica gel chromatography (10–30% ethyl acetate/hexane to give 0.95 g of product. Rt=2.87, MH+=370.

44-4: (S,S)-2-(2-Acetylsulfanyl-4-phenyl-butyrylamino)-4-methyl-pentanoic acid methyl ester. Cs$_2$CO$_3$ (0.88 g) was added to a solution of thiolacetic acid (0.21 ml) in methanol (10 ml). The methanol was concentrated under reduced pressure followed by concentration of acetone under reduced pressure twice. The residue was put on the high vacuum pump for 15 minutes and then dissolved in DMF (10 ml) at 0° C. A solution of 44-3 in DMF was then added and the reaction was stirred at 0° C. for 1 h and then room temperature for 12 h. The reaction was diluted with H$_2$O and extracted 3× ethyl acetate. The organics were combined, dried with Na$_2$SO$_4$, filtered and conc. in vacuo. The residue was purified with silica gel chromatography (10–30% ethyl acetate/hexane) to give 0.75 g of the desired product. Rt=2.81, MH+=366.

44-5: (S,S)-(2-Mercapto-4-phenyl-butyrylamino)-4-methyl-pentanoic acid. A solution of 44-4 (0.75 g, 2.0 mmol) in methanol (14 ml) was degassed with Argon and cooled to 0° C. A degassed 1 N NaOH solution (8.14 ml) was added dropwise to the reaction which was stirred overnight warming to room temperature. The mixture was acidified with 1N KHSO$_4$ (degassed with argon) and the white slurry was diluted with ethyl acetate and H$_2$O. The water was extracted twice with ethyl acetate, the organics were combined, dried with Na$_2$SO$_4$, filtered and concentrated in vacuo to give 0.6 g of product. Rt=2.38, MH+=310. NMR consistent with assigned structure.

Compounds synthesized with same general procedure:

(S,S)-2-(2-Mercapto-3-phenyl-propionylamino)-4-methyl-pentanoic acid (R,S)-2-(2-Mercapto-3-phenyl-propionylamino)-4-methyl-pentanoic acid

Example 25

Synthesis of Methyl Thiols mmol, prepared according to *J. Med. Chem.* 1994, 37, 2461–2476.) in DCM (1.8 ml) was treated with thiolacetic acid (3.5 ml, 49 mmol) and stirred for 48 h at room temperature. The reaction was concentrated 3× from toluene to give the desired product which was used crude in the next reaction. Rt=2.12, MH−=237.

45-3: (S,S) and (R-S)-2-(2-Acetylsulfanylmethyl-3-phenyl-propionylamino)-4-methyl-pentanoic acid methyl ester. To a solution of 45-2, HCl H-Leu-OMe (0.53 g, 2.9 mmol), HOBt (0.39 g, 2.9 mmol), and TEA (0.41 ul, 2.9 mmol) in DCM (13 ml) at 0° C. was added EDCI (0.59 g, 2.9 mmol). The reaction was stirred overnight warming to room temperature. The solution was diluted with ethyl acetate, washed

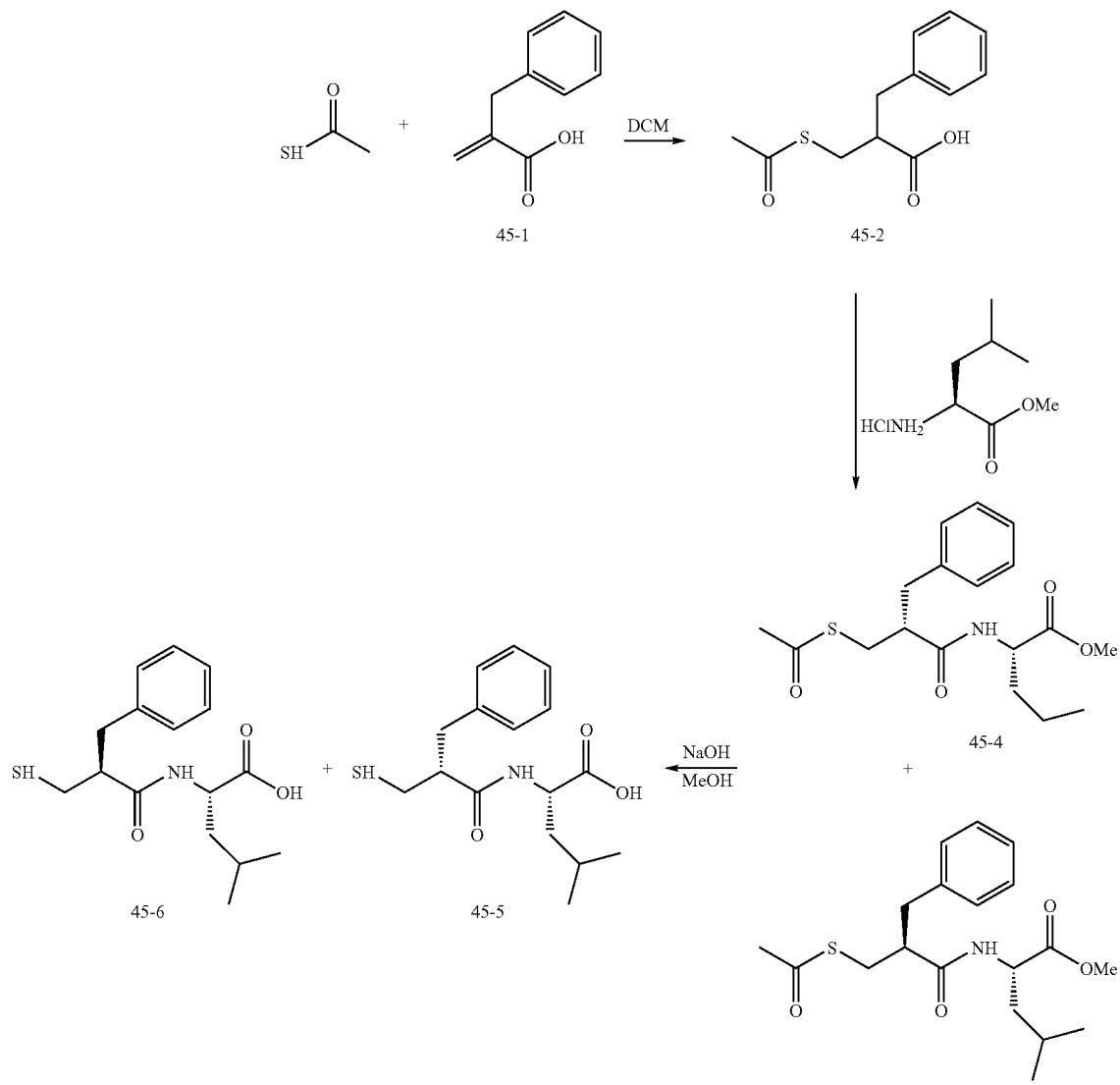

Synthesis of (S,S) and (R,S)-2-(2-Benzyl-3-mercapto-propionylamino)-4-methyl-pentanoic acid 45-2: 2-Acetylsulfanylmethyl-3-phenyl-propionic acid. A solution of 2-benzyl-acrylic acid acid 45-1 (1.17 g, 7.2

1×NaHCO$_3$, 1×1N HCl, 1×brine and concentrated in vacuo. The residue was purified by silica gel chromatography (10–30% ethyl acetate/hexane) to give 0.1 g of the top isomer, and 0.076 g of the bottom isomer. Top isomer: Rt=2.58, MH+=366. Bottom isomer: Rt=2.60, MH+=366.

45-4: 2-(2-Mercaptomethyl-3-phenyl-propionylamino)-4-methyl-pentanoic acid. A solution of 45-3 (top isomer, 0.1 g, 0.29 mmol) in methanol (6 ml) was degassed with argon and cooled to 0° C. A degassed 1 N NaOH solution (0.87 ml, 0.87 mmol) was added dropwise to the reaction which was stirred overnight warming to room temperature. The mixture was acidified with 1N HCl (degassed with argon) and the white slurry was diluted with ethyl acetate and H$_2$O. The water was extracted twice with ethyl acetate, the organics were combined, dried with Na$_2$SO$_4$, filtered and concentrated in vacuo to provide the desired product as a mixture of disulfide and monomer. Monomer: Rt=Disulfide: Rt=2.57, MH+=617. NMR consistent with assigned structure.

Additional compounds synthesized with same general procedure:

(S,S)-2-(2-Mercaptomethyl-3-phenyl-propionylamino)-4-methyl-pentanoic acid (R,S)-2-(2-Mercaptomethyl-3-phenyl-propionylamino)-4-methyl-pentanoic acid Example 26

Synthesis of Alkynes

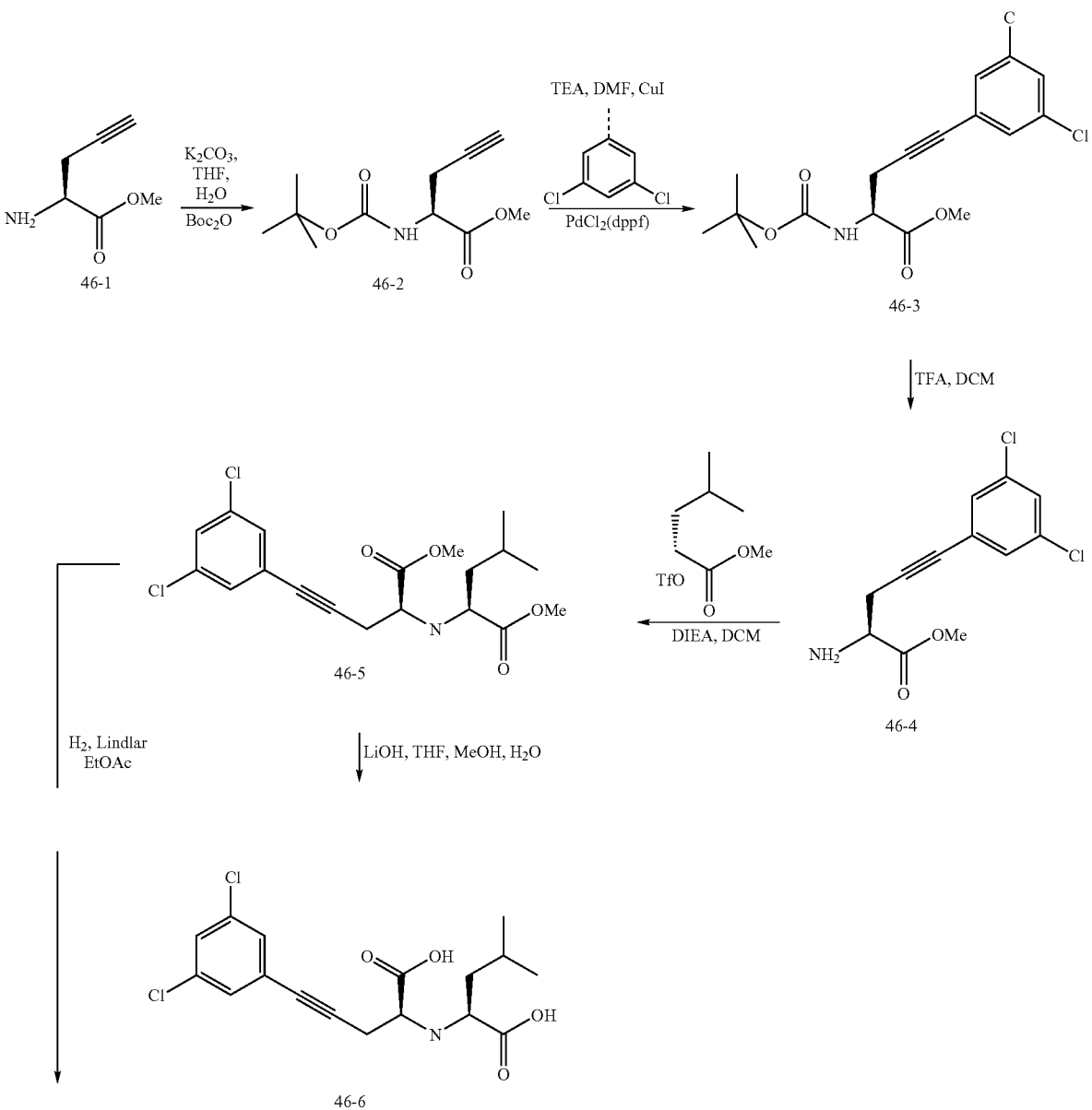

Scheme 46

-continued

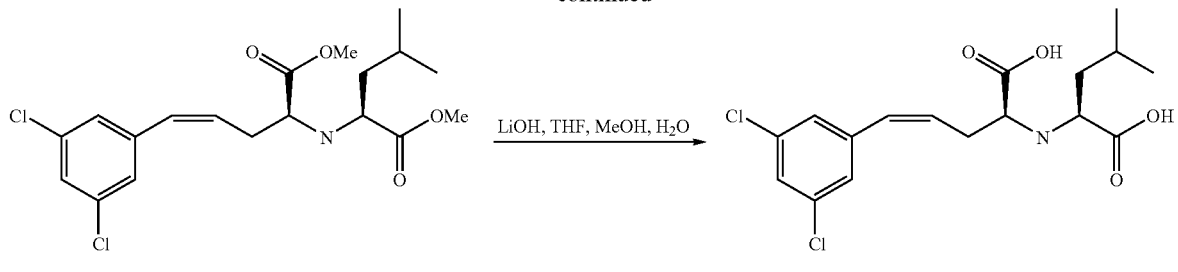

46-7 → 46-8

46-2: (S)-2-tert-Butoxycarbonylamino-pent-4-ynoic acid methyl ester. To a solution of (S)-2-amino-pent-4-ynoic acid methyl ester 46-1 (1 g, 6.1 mmol) in THF/H$_2$O (2:1 30 ml) was added K$_2$CO$_3$ (1.86 g, 13.4 mmol) and Boc$_2$O (1.47 g, 6.74 mmol). The reaction was stirred at room temperature for 12 hours and then partitioned between ethyl acetate and H$_2$O. The aqueous layer was extracted an additional two times with ethyl acetate, the organics were combined, dried with Na$_2$SO$_4$, filtered and concentrated in vacuo. The resulting residue was taken directly on to the next reaction.

46-3: (S)-2-tert-Butoxycarbonylamino-5-(3,5-dichloro-phenyl)-pent-4-ynoic acid methyl ester. (Prepared according to *J. Med. Chem.* 1998, 41, 1513–1523.) To a solution of 46-2 (1.35 g, 5.9 mmol) in DMF (30 ml) was added PdCl$_2$ (dppf) (0.243 g, 0.3 mmol), followed by 1,3 dichloro-5-iodobenzene (1.79 g, 0.66 mmol). The mixture was degassed under house vacuum and stirred 0.5 h. The reaction was diluted with H$_2$O and extracted three times with ethyl acetate, the organics were combined, dried with Na$_2$SO$_4$, filtered, and concentrated in vacuo. The residue was first filtered through a pad of silica gel (5% ethyl acetate/hexane) and then purified by silica gel chromatography (5–10% ethyl acetate/hexane) to give 1.59 g of the desired product. Rt=3.4, MH+=372.

46-4: (S)-2-Amino-5-(3,5-dichloro-phenyl)-pent-4-ynoic acid methyl ester. A solution of 46-3 (1.59 g, 4.3 mmol) in 4N HCl/dioxane (10 ml) was stirred at room temperature for 1 h and then concentrated in vacuo. The residue was partitioned between ethyl acetate and 1N NaHCO$_3$. The aqueous layer was extracted twice with ethyl acetate, the organics were combined, dried with Na$_2$SO$_4$, filtered and concentrated in vacuo to give 1.13 g of the desired product. Rt=1.37, MH+=272.

46-5: (S,S)-5-(3,5-Dichloro-phenyl)-2-(1-methoxycarbonyl-3-methyl-butylamino)-pent-4-ynoic acid methyl ester. A solution of leucic acid triflate (1.39 g, 5.0 mmol) in DCM (5 ml) was cooled to −78° C. Diisopropylethylamine (1.08 ml, 6.26 mmol) was added to the reaction followed by dropwise addition of a solution 46-4 (1.56 mmol) in DCM (5 ml). The reaction was stirred overnight warming to room temperature and then concentrated in vacuo. Purification by silica gel chromatography (80–90% ethyl acetate/hexane) gave 1.07 g of the desired product. Rt=3.58, MH+=400.

46-6: (S,S)-2-(1-Carboxy-3-methyl-butylamino)-5-(3,5-dichloro-phenyl)-pent-4-ynoic acid. To a solution of 46-5 (0.35 g, 0.87 mmol) in methanol (0.5 ml), THF (2.0 ml), and H$_2$O (0.5 ml) was added LiOH—H$_2$O (0.15 g, 3.46 mmol). The reaction was stirred overnight at RT. After concentrating the organics in vacuo, the aqueous layer was acidified with 1N HCl until a white precipitate formed which was filtered and dried to give 0.21 g of the desired product. Rt=2.07, MH+=372, $^1$H NMR consistent with assigned structure.

46-7: 5-(3,5-Dichloro-phenyl)-2-(1-methoxycarbonyl-3-methyl-butylamino)-pent-4-enoic acid methyl ester. A solution of 46-5 (0.23 g) and Lindlar's catalyst (0.05 g) in ethyl acetate (5 ml) were stirred under 1 atmosphere of hydrogen for 18 hours. The mixture was filtered through celite and concentrated in vacuo. The residue was purified by silica gel chromatography (20–30% ethyl acetate/hexane) to give 0.12 mg of the desired product.

46-8: 2-(1-Carboxy-3-methyl-butylamino)-5-(3,5-dichloro-phenyl)-pent-4-enoic acid (Compound PV). To a solution of 46-7 (0.12 g, 0.29 mmol) in methanol (0.5 ml), THF (2.0 ml), and H$_2$O (0.5 ml) was added LiOH—H$_2$O (0.05 g, 1.16 mmol). The reaction was stirred overnight at room temperature. After concentrating the organics in vacuo, the aqueous layer was acidified with 1N HCl until a white precipitate formed which was filtered and dried to give 0.07 g of the desired product. Rt=1.88, MH+=374, $^1$H NMR consistent with assigned structure.

Example 27

Synthesis of Diaminobutyric Acid Analogs

Scheme 47

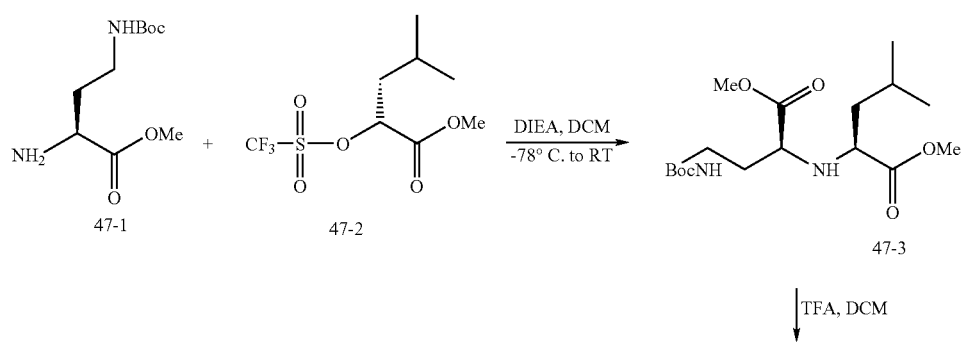

TFA, DCM

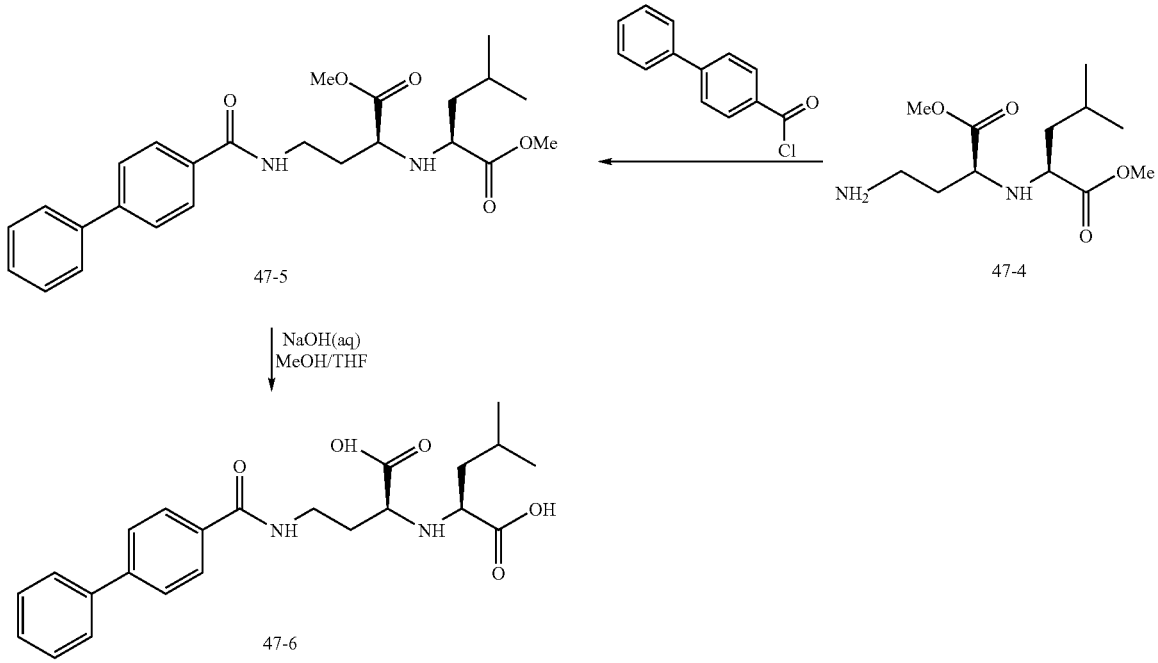

47-3: (S)-2-(3-tert-Butoxycarbonylamino-1-methoxycarbonyl-propylamino)-4-methyl-pentanoic acid methyl ester. A solution of the leucic methyl ester triflate (1.46 g, 5.3 mmol) was dissolved in dichloromethane (20 ml) and cooled to −78° C. under argon. DIEA (0.91 ml, 5.3 mmol) was then added to the mixture. To this mixture was added a solution of H-DAB-OMe (1.1 g, 4.77 mmol) in DCM (15 ml) dropwise over 15 minutes. The solution was stirred overnight warming to room temperature. The reaction was concentrated in vacuo and purified by silica gel chromatography (10–20% ethyl acetate/hexane) to give 0.82 g (55%) of the desired product. Rt=2.67, MH+ 361.

47-4: (S)-2-(3-Amino-1-methoxycarbonyl-propylamino)-4-methyl-pentanoic acid methyl ester. To a solution of 47-3 (0.82 g) in DCM (5 ml) was added TFA (5 ml) dropwise. The reaction was stirred for 2 h at RT and then concentrated in vacuo. The residue was concentrated from ether several times and then from toluene several times. The residue was partitioned between ethyl acetate and saturated NaHCO₃. The layers were separated and the aqueous layer was extracted an additional two times with ethyl acetate. The combined organics were dried with MgSO₄, filtered, and concentrated in vacuo. Rt=1.53, MH+=261

47-5: (S,S)-2-{3-[(Biphenyl-4-carbonyl)-amino]-1-methoxycarbonyl-propylamino}-4-methyl-pentanoic acid methyl ester. To a solution of 47-4 (65 mg, 0.25 mmol) in DCM (2 ml) at RT was added TEA (0.039 ml, 0.28 mmol), followed by biphenyl-4-carbonyl chloride (60 mg, 0.28 mmol). The reaction was stirred overnight at room temperature and then concentrated in vacuo. The resulting residue was purified by ion-exchange chromatography and silica gel chromatography (40% ethyl acetate/hexane) to give 40 mg of product. Rt=2.9, MH+=441.

47-6: (S,S)-2-{3-[(Biphenyl-4-carbonyl)-amino]-1-carboxy-propylamino}-4-methyl-pentanoic acid. To a solution of 47-5 (40 mg) in methanol (0.5 ml) and THF (1.5 ml) was added NaOH (aq) (300 uL of a 1N solution). The reaction was stirred overnight at RT. After concentrating the organics in vacuo, the aqueous layer was acidified with 1N HCl until a white precipitate formed which was filtered and dried. Rt=1.83, MH+=413, ¹H NMR consistent with assigned structure.

Compounds synthesized using the same general procedure:

(S,S)-2-[3-(3,5-Bis-trifluoromethyl-benzoylamino)-1-carboxy-propylamino]-4-methyl-pentanoic acid: Rt=1.96, MH+=473.

(S,S)-2-{1-Carboxy-3-[(naphthalene-2-carbonyl)-amino]-propylamino}-4-methyl-pentanoic acid: Rt=1.59, MH+=387.

(S,S)-2-(1-Carboxy-3-diphenylacetylamino-propylamino)-4-methyl-pentanoic acid: Rt=1.78, MH+=427.

(S,S)-2-{1-Carboxy-3-[(9-oxo-9H-fluorene-4-carbonyl)-amino]-propylamino}-4-methyl-pentanoic acid: Rt=1.49, MH+=439.

(S,S)-2-[1-Carboxy-3-(3-phenyl-propionylamino)-propylamino]-4-methyl-pentanoic acid: Rt=1.42, MH+=365.

(S,S)-2-[1-Carboxy-3-(4-methoxy-benzenesulfonylamino)-propylamino]-4-methyl-pentanoic acid: Rt=1.34, MH+=403.

(S,S)-2-[1-Carboxy-3-(naphthalene-2-sulfonylamino)-propylamino]-4-methyl-pentanoic acid: Rt=1.67, MH+=423.

(S,S)-2-[1-Carboxy-3-(4-ethyl-benzoylamino)-propylamino]-4-methyl-pentanoic acid: Rt=1.54, MH+=365.

(S,S)-2-[1-Carboxy-3-(3-methoxy-benzoylamino)-propylamino]-4-methyl-pentanoic acid: Rt=1.3, MH+=367.

(S,S)-2-[3-(4-tert-Butyl-benzoylamino)-1-carboxy-propylamino]-4-methyl-pentanoic acid: Rt=1.92, MH+=393.

(S,S)-2-[1-Carboxy-3-(3-chloro-benzenesulfonylamino)-propylamino]-4-methyl-pentanoic acid: Rt=1.48, MH+=407.

(S,S)-2-[1-Carboxy-3-(2-naphthalen-1-yl-ethanesulfonylamino)-propylamino]-4-methyl-pentanoic acid: Rt=1.9, MH+=451.

(S,S)-2-{1-Carboxy-3-[(2-ethoxy-naphthalene-1-carbonyl)-amino]-propylamino}-4-methyl-pentanoic acid: Rt=1.57, MH+=431.

(S,S)-2-[3-(3',5'-Bis-trifluoromethyl-biphenyl-4-sulfonylamino)-1-carboxy-propylamino]-4-methyl-pentanoic acid: Rt=2.6, MH+=585.

(S,S)-2-[1-Carboxy-3-(4'-methyl-biphenyl-4-sulfonylamino)-propylamino]-4-methyl-pentanoic acid: Rt=2.08, MH+=463

(S,S)-2-[1-Carboxy-3-(3',4'-dichloro-biphenyl-4-sulfonylamino)-propylamino]-4-methyl-pentanoic acid: Rt=2.36, MH+=517.

(S,S)-2-[1-Carboxy-3-(4'-chloro-biphenyl-4-sulfonylamino)-propylamino]-4-methyl-pentanoic acid (Compound KN): Rt=2.16, MH+=483.

(S,S)-2-[1-Carboxy-3-(4'-fluoro-biphenyl-4-sulfonylamino)-propylamino]-4-methyl-pentanoic acid: Rt=1.96, MH+=467.

(S,S)-2-[3-(Biphenyl-4-sulfonylamino)-1-carboxy-propylamino]-4-methyl-pentanoic acid: Rt=1.88, MH+=449.

(S,S)-2-(3-Benzyloxycarbonylamino-1-carboxy-propylamino)-4-methyl-pentanoic acid: Rt=1.35, MH+=367.

(S,S)-2-[1-Carboxy-3-(3-chloro-benzoylamino)-propylamino]-4-methyl-pentanoic acid (Compound KP): Rt=1.36, MH+=371.

(S,S)-2-[1-Carboxy-3-(3,4-dichloro-benzoylamino)-propylamino]-4-methyl-pentanoic acid: Rt=1.57, MH+=405.

(S,S)-2-[1-Carboxy-3-(2,5-dichloro-benzoylamino)-propylamino]-4-methyl-pentanoic acid: Rt=1.11, MH+=405.

(S,S)-2-{1-Carboxy-3-[(naphthalene-1-carbonyl)-amino]-propylamino}-4-methyl-pentanoic acid: Rt=1.38, MH+=387.

Example 28

Synthesis of Diaminopropionic Acid Analogs

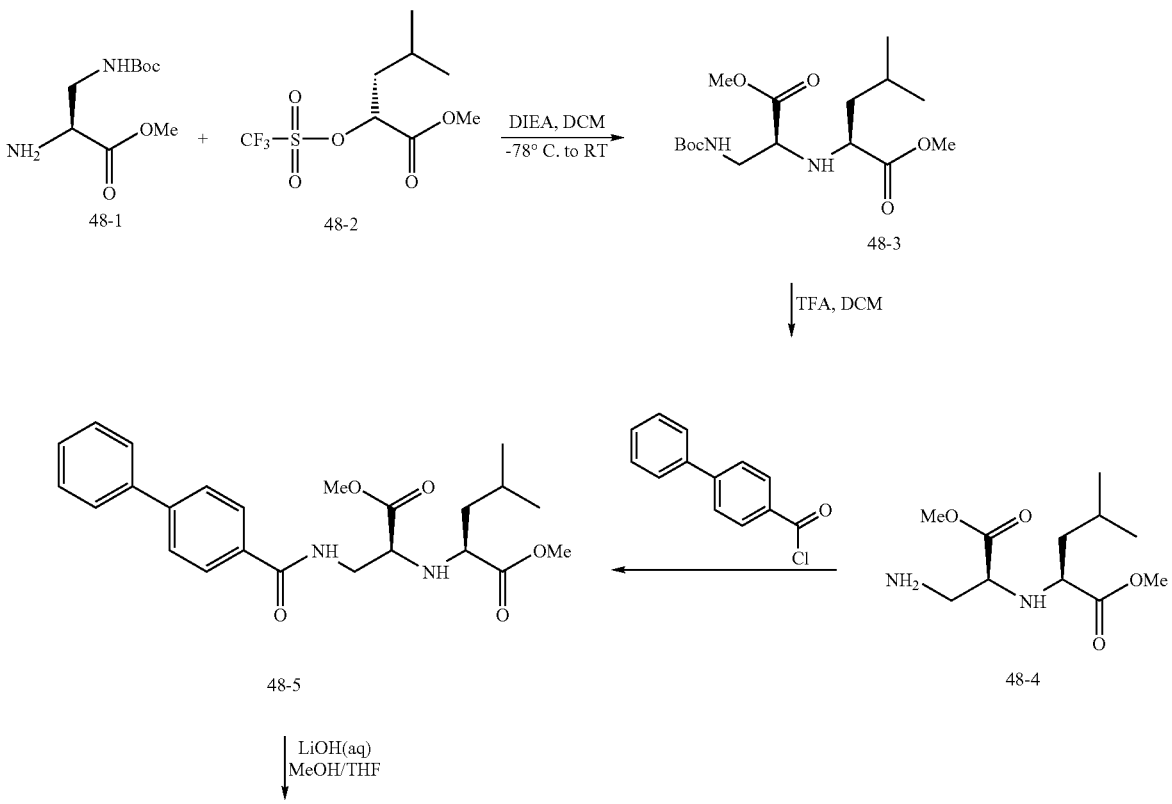

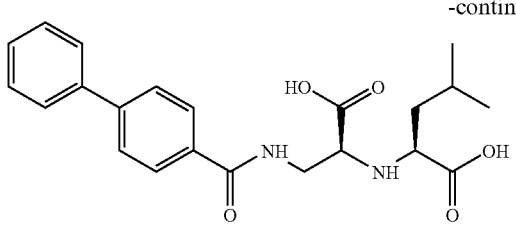

48-6

48-3: 2-(2-tert-Butoxycarbonylamino-1-methoxycarbonyl-ethylamino)-4-methyl-pentanoic acid methyl ester. A solution of the leucic methyl ester triflate (4.54 g, 16.3 mmol) was dissolved in dichloromethane (100 ml) and cooled to −78° C. under argon. DIEA (2.84 ml, 16.3 mmol) was then added to the mixture. To this mixture, was added a solution of H-DAP-OMe (3.24 g, 14.8 mmol) in dichloromethane (40 ml) dropwise over 30 minutes. The solution was stirred overnight warming to room temperature. The reaction was concentrated in vacuo and purified by silica gel chromatography (20–30% ethyl acetate/hexane) to give 3.9 g of the desired product. Rt=2.29, MH+ 347.

48-4: 2-(2-Amino-1-methoxycarbonyl-ethylamino)-4-methyl-pentanoic acid methyl ester. To a solution of 48-4 (3.9 g) in dichloromethane (20 ml) was added TFA (20 ml) dropwise. The reaction was stirred for 3 hours at room temperature and then concentrated in vacuo. The residue was concentrated from ether several times and then from toluene several times. Rt=0.99, MH+=247.

48-5: 2-{2-[(Biphenyl-4-carbonyl)-amino]-1-methoxycarbonyl-ethylamino}-4-methyl-pentanoic acid methyl ester. To a solution of 48-4 (160 mg, 0.35 mmol) in DCM (2.5 ml) at RT was added TEA (0.140 ml, 1.0 mmol), followed by biphenyl-4-carbonyl chloride (80 mg, 0.37 mmol). The reaction was stirred overnight at room temperature and then concentrated in vacuo. The resulting residue was purified by silica gel chromatography (20–30% ethyl acetate/hexane) to give 0.084 g of product. Rt=2.67, MH+=427.

48-6: 2-{2-[(Biphenyl-4-carbonyl)-amino]-1-carboxy-ethylamino}-4-methyl-pentanoic acid. To a solution of 48-5 (84 mg) in methanol (0.5 ml), THF (1.5 ml), and H$_2$O (0.3 ml) was added LiOH—H$_2$O (33 mg, 0.79 mmol). The reaction was stirred overnight at RT. After concentrating the organics in vacuo, the aqueous layer was acidified with 1N HCl until a white precipitate formed which was filtered and dried. Rt=2.02, MH+=399, NMR consistent with assigned structure.

Compounds synthesized using the same general procedure:

(S,S)-2-[1-Carboxy-2-(3-chloro-benzoylamino)-ethylamino]-4-methyl-pentanoic acid (Compound LI): Rt=1.36, MH+=357.

(S,S)-2-[1-Carboxy-2-(3,4-dichloro-benzoylamino)-ethylamino]-4-methyl-pentanoic acid (Compound LJ): Rt=1.6, MH+=391.

(S,S)-2-(1-Carboxy-2-diphenylacetylamino-ethylamino)-4-methyl-pentanoic acid: Rt=1.73, MH+=413.

(S,S)-2-[1-Carboxy-2-(3-methoxy-benzoylamino)-ethylamino]-4-methyl-pentanoic acid: Rt=1.35, MH+=353.

(S,S)-2-{1-Carboxy-2-[(naphthalene-1-carbonyl)-amino]-ethylamino}-4-methyl-pentanoic acid: Rt=1.59, MH+=373.

(S,S)-2-{1-Carboxy-2-[(naphthalene-2-carbonyl)-amino]-ethylamino}-4-methyl-pentanoic acid: Rt=1.62, MH+=373.

(S,S)-2-[1-Carboxy-2-(naphthalene-2-sulfonylamino)-ethylamino]-4-methyl-pentanoic acid: Rt=1.69, MH+=409.

(S,S)-2-[2-(Biphenyl-4-sulfonylamino)-1-carboxy-ethylamino]-4-methyl-pentanoic acid: Rt=1.95, MH+=435.

(S,S)-2-[1-Carboxy-2-(3',5'-dichloro-biphenyl-4-sulfonylamino)-ethylamino]-4-methyl-pentanoic acid: Rt=2.42, MH+=503.

Example 29

Procedure for Synthesis of Benzothiazole Analogs

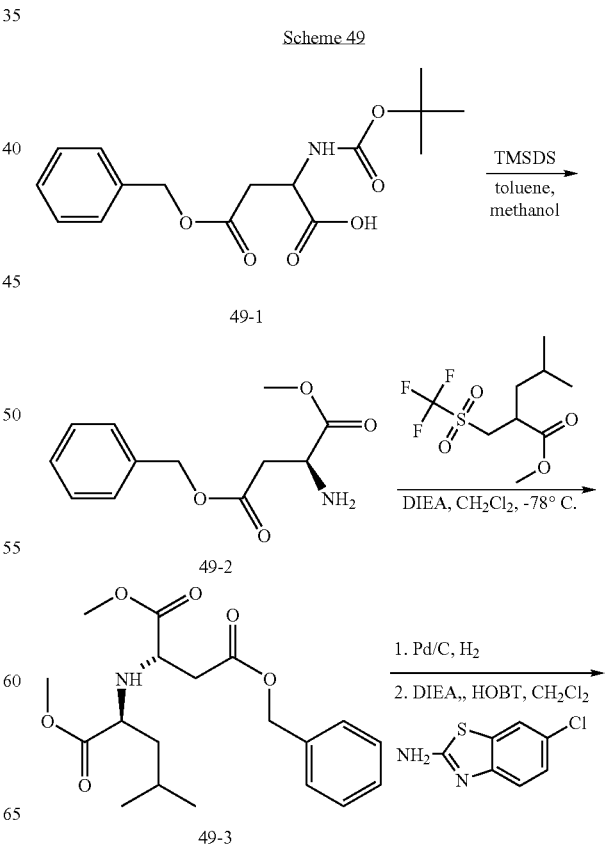

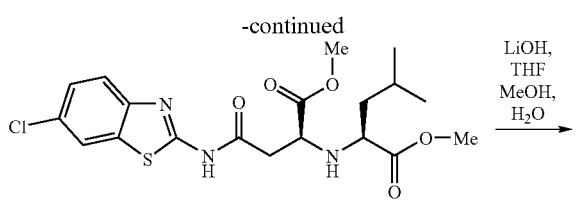

49-4

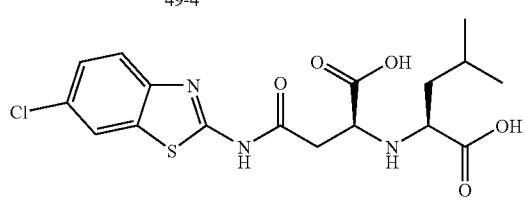

49-5

49-2: (S)-2-Amino-succinic acid 4-benzyl ester 1-methyl ester. To a solution of 2-tert-butoxycarbonylamino-succinic acid 4-benzyl ester (25 g, 77.31 mmol) in 2:1 mixture of toluene and methanol (200 ml, 100 ml) at 0° C. was added trimethylsilyldiazomethane (58 ml, 116 mmol) dropwise until a yellow color persisted. After stirring for ten minutes, the reaction was concentrated in vacuo. Purification by silica gel chromatography (10–30% ethyl acetate/hexane) gave 21.2 g of 2-tert-butoxycarbonylamino-succinic acid 4-benzyl ester 1-methyl ester. Rt=2.68, MH+=238. This product was then stirred for one hour at room temperature in 4N HCl in dioxane (157 ml, 565 mmol) and concentrated in vacuo. The solid was dissolved in ethyl acetate and washed three times with NaHCO$_3$, once with brine, dried over Na$_2$SO$_4$, filtered, and concentrated in vacuo to give 15.79 g of the desired product. Rt=0.84, MH+=238.

49-3: (S,S)-2-(1-Methoxycarbonyl-3-methyl-butylamino)-succinic acid 4-benzyl ester 1-methyl ester. To a solution of 4-methyl-2-trifluoromethanesulfonylmethyl-pentanoic acid methyl ester (6.69 g, 25 mmol) and N,N-diisopropylethylamine (5.04 ml, 28.92 mmol) in methylene chloride at −78° C. was added 49-2 (4.57 g, 19.28 mmol) and the reaction was stirred overnight. The reaction was concentrated to dryness, then redissolved in ethyl acetate and washed twice with NaHCO$_3$, once with brine, dried over Na$_2$SO$_4$, filtered, and concentrated in vacuo. Purification by silica gel chromatography gave 5.84 g of the desired product. Rt=2.85, MH+=366.

49-4: (S,S)-2-[2-(6-Chloro-benzothiazol-2-ylcarbamoyl)-1-methoxycarbonyl-ethylamino]-4-methyl-pentanoic acid methyl ester. A mixture of 49-3 (5.84 g) and Pd/C (0.200 g) in MeOH (100 ml) was stirred under 1 atmosphere of hydrogen for 1 h, filtered through a pad of celite and concentrated in vacuo to give 3.75 g of 2-(1-methoxycarbonyl-3-methyl-butylamino)-succinic acid 1-methyl ester. Rt=1.48, MH+=276. To a mixture of this product (3.75 g, 13.63 mmol), N,N-diisopropylethylamine (8.73 ml, 37.19 mmol), 6-chloro-benzothiazol-2-ylamine (2.28 g, 13.63 mmol), and benzotriazol-1-ol (1.84 g, 13.63 mmol) in methylene chloride at 0° C., was added 1-(3-dimethylaminopropyl)-3-ethylcarbodiimide hydrochloride (2.605 g, 13.63 mmol) and stirred at room temperature overnight. The reaction mixture was concentrated in vacuo, dissolved in ethyl acetate and washed twice with NaHCO$_3$, twice with 1N HCl, once with brine, dried over Na$_2$SO$_4$, filtered and concentrated in vacuo. Purification by silica gel chromatography gave 1.77 g of the desired product. Rt=2.89, MH+=442.

49-5: (S,S)-2-[1-Carboxy-2-(6-chloro-benzothiazol-2-ylcarbamoyl)-ethylamino]-4-methyl-pentanoic acid (Compound MB). To a solution of 49-4 (1.77 g, 4.013 mmol) in THF (15 ml), methanol (5 ml), and water (5 ml) was added LiOH—H$_2$O (0.674 g, 16 mmol). The reaction stirred overnight at room temperature. After concentrating the organics in vacuo, the aqueous layer was acidified with 1N HCl until a white precipitate formed which was filtered and dried. The solid was dissolved in 4N HCl in dioxane and concentrated in vacuo to give 1.7 g of the HCl salt of the desired product. Rt=1.89, MH+=414, $^1$H NMR consistent with the assigned structure.

Compounds synthesized using the same general procedure:

(S,S)-2-[2-(Benzothiazol-2-ylcarbamoyl)-1-carboxy-ethylamino]-4-methyl-pentanoic acid: Rt=1.53, MH+=380.

(S,S)-2-[1-Carboxy-2-(5,6-dichloro-benzothiazol-2-ylcarbamoyl)-ethylamino]-4-methyl-pentanoic acid (Compound MG): Rt=2.25, MH+=448.

(S,S)-2-[1-Carboxy-2-(6-fluoro-benzothiazol-2-ylcarbamoyl)-ethylamino]-4-methyl-pentanoic acid: Rt=1.713, MH+=398.

(S,S)-2-[2-(6-Bromo-benzothiazol-2-ylcarbamoyl)-1-carboxy-ethylamino]-4-methyl-pentanoic acid: Rt=1.95, MH+=460.

(S,S)-2-[1-Carboxy-2-(6-methoxy-benzothiazol-2-ylcarbamoyl)-ethylamino]-4-methyl-pentanoic acid (Compound MO): Rt=1.62, MH+=410.

(S,S)-2-[1-Carboxy-2-(6-ethoxy-benzothiazol-2-ylcarbamoyl)-ethylamino]-4-methyl-pentanoic acid (Compound MP): Rt=1.79, MH+=424.

(S,S)-2-[1-Carboxy-2-(6-methyl-benzothiazol-2-ylcarbamoyl)-ethylamino]-4-methyl-pentanoic acid: Rt=1.75, MH+=394.

(S,S)-2-[1-Carboxy-2-(4-phenyl-thiazol-2-ylcarbamoyl)-ethylamino]-4-methyl-pentanoic acid (Compound OH): Rt=1.81, MH+=406.

(S,S)-2-[1-Carboxy-2-(5,6-dimethyl-benzothiazol-2-ylcarbamoyl)-ethylamino]-4-methyl-pentanoic acid (Compound MC): Rt=1.89, MH+=408.

(S,S)-2-[1-Carboxy-2-(4-chloro-benzothiazol-2-ylcarbamoyl)-ethylamino]-4-methyl-pentanoic acid (Compound MD): Rt=1.89, MH+=414.

(S,S)-2-{1-Carboxy-2-[(5-chloro-1H-indole-2-carbonyl)-amino]-ethylamino}-4-methyl-pentanoic acid: Rt=1.51, MH+=392.

(S,S)-2-{1-Carboxy-2-[(5-methoxy-1H-indole-2-carbonyl)-amino]-ethylamino}-4-methyl-pentanoic acid: Rt=1.86, MH+=396.

Example 30

Synthesis of Thiazole and Oxazole Compounds

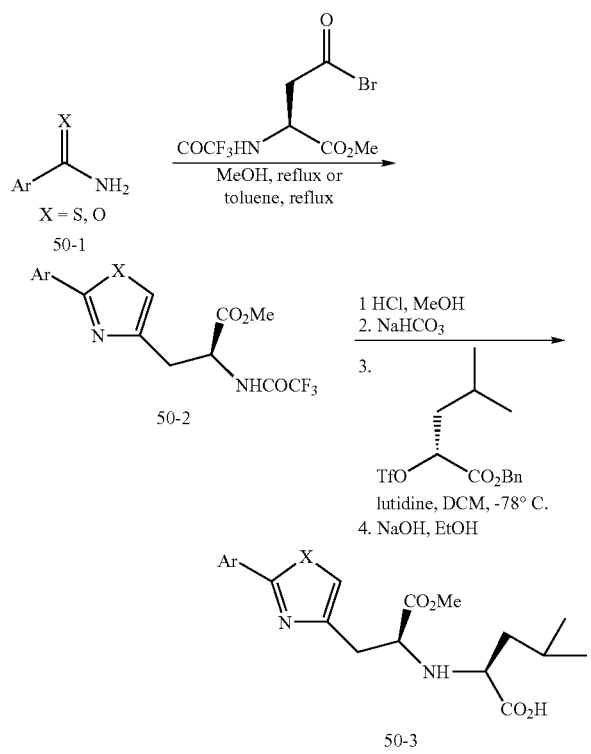

To a solution of N-trifluoromethyl-5-bromo-4-oxonorvaline methyl ester (prepared as described by Svete et al. J. Heterocyclic Chem., 31, 1259 (1994)) in methanol was added the appropriate thiobenzamide. The solution was heated at 55° C. for 2 hours. The reaction was cooled to room temperature and the solvent was evaporated in vacuo. The residue was taken up in dichloromethane and washed with saturated sodium bicarbonate solution. The organics were dried over sodium sulfate and the solvent was evaporated in vacuo. The residue was triturated in ethyl acetate/hexane to give the desired compounds as white solids.

The oxazoles were prepared in a similar manner, using the appropriate benzamide, refluxing in toluene for 18 hrs.

50-1a: (S)-2-(2,2,2-Trifluoro-acetylamino)-3-[2-(3-trifluoromethyl-phenyl)-thiazol-4-yl]-propionic acid methyl ester. $MH^+$=427, $MH^-$=425.

50-1b: (S)-2-(2,2,2-Trifluoro-acetylamino)-3-[2-(2,4-dichloro-phenyl)-thiazol-4-yl]-propionic acid methyl ester. $MH^+$=427, $MH^-$=425.

50-1c: (S)-3-[2-(2,3-dihydro-benzofuran-5-yl)-thiazol-4-yl]-2-(2,2,2,-trifluoro-acetylamino)-propionic acid methyl ester. $MH^+$=401, $MH^-$=399.

50-1d: (S)-2-(2,2,2-Trifluoro-acetylamino)-3-[2-(3-chloro-4-fluoro-phenyl)-thiazol-4-yl]-propionic acid methyl ester. $MH^+$=411, $MH^-$=409.

50-1e: (S)-2-(2,2,2-Trifluoro-acetylamino)-3-[2-p-tolyl-thiazol-4-yl]-propionic acid methyl ester. $MH^+$=373, $MH^-$=371.

50-1f: (S)-2-(2,2,2-Trifluoro-acetylamino)-3-[2-(3,5-dichloro-phenyl)-thiazol-4-yl]-propionic acid methyl ester. $MH^+$=427, $MH^-$=425.

50-1g: (S)-3-(Phenyl-oxazol-4-yl)-2-(2,2,2,-trifluoro-acetylamino)-propionic acid methyl ester. $MH^+$=343, $MH^-$=341.

50-1h: (S)-3-[2-(3,5-Dichloro-phenyl)-oxazol-4-yl]-2-(2,2,2,-trifluoro-acetylamino)-propionic acid methyl ester. $MH^-$=409.

The N-trifluoroacetyl amino esters (50-1) were dissolved in dry methanol, and hydrogen chloride gas was bubbled through the solution for 10 minutes. The reaction was heated under reflux for four hours. The solvents were evaporated in vacuo. Saturated sodium bicarbonate solution was added until the pH was between 8–9, and then the mixture was extracted with ethyl acetate three times. The combined organic phases were dried over sodium sulfate and evaporated in vacuo to give the desired methyl esters as oils. LC/MS data was consistent with the desired amino esters. These amino esters were immediately reacted with the trifluoromethane sulfonate of D-leucic acid benzyl ester in an analogous manner to that described in Example 5. The resulting diester was dissolved in EtOH and 1 M aqueous NaOH solution. The solution was stirred overnight and concentrated. The residue was taken up in $H_2O$, acidified with 2 N HCl solution, and concentrated again. The very insoluble material was purified by HPLC to give the desired diacids.

50-2a: (S,S)-2-{1-Carboxy-2-[2-(3-trifluoromethyl-phenyl)-thiazol-4-yl-]-ethylamino}-4-methyl-pentanoic acid (Compound KD). $^1$H NMR (300 MHz, $d_6$DMSO) δ (8.21, s);, 8.21–8.14 (1H, m); 7.85–7.71 (2H, m); 7.57 (1H, s); 3.53 (1H, t, J=7.3 Hz); 3.22–2.99 (3H, m);, 1.79–1.69 (1H, m);, 1.40 (2H, t, J=6.9 Hz); 0.83 (6H, d, J=6.5 Hz). Analysis: found: C, 51.21%; H, 4.78%; N, 6.21%. $C_{19}H_{21}F_3N_2O_4S.0.8H_2O$ requires: C, 51.30%; H, 5.12%; N, 6.30%.

50-2b: (S,S)-2-{1-Carboxy-2-[2-(2,4-dichloro-phenyl)-thiazol-4-yl-]-ethylamino}-4-methyl-pentanoic acid (Compound KG).: $^1$H NMR (300 MHz, $d_6$DMSO) δ 8.25 (1H, d, J=8.9 Hz); 7.82 (1H, d, J=2.0 Hz);, 7.67 (1H, s); 7.57 (1H, dd, J=2.0 Hz, 8.5 Hz); 3.55 (1H, t, J=5.7 Hz); 3.22–3.02 (3H, m); 1.74 (1H, quintet, J=6.5 Hz); 1.39 (2H, t, J=6.9 Hz); 0.83 (6H, d, J=6.5 Hz). Analysis: found: C, 48.47%; H, 4.57%; N, 6.29%. $C_{18}H_{20}Cl_2N_2O_4S.H_2O$ requires: C, 48.11%; H 4.93%; N, 6.23%.

50-2c: (S,S)-2-{1-Carboxy-2-[2(2,3-dihydro-benzofaran-5-yl]-thiazol-4-yl]-ethylamino}-4-methyl pentanoic acid (Compound KI). $MH^+$ 405, $MH^-$ 403. Analysis: found: C, 55.92%; H, 5.83%; N, 6.51%. $C_{20}H_{24}N_2O_5S.H_2O.0.2HCO_2H$ requires: C, 56.20%; H, 6.16%; N, 6.49%.

50-2d: (S,S)-2-{1-Carboxy-2-[2-(3-chloro-4-fluoro-phenyl)-thiazol-4-yl-]-ethylamino}-4-methyl-pentanoic acid (Compound KJ). $MH^+$ 415, $MH^-$ 413. Analysis: found: C, 47.17%; H, 4.67%; N, 5.61%. $C_{18}H_{20}ClFN_2O_4S.2HCO_2H$ requires: C, 47.39%; H, 4.77%; N, 5.53%.

50-2e: (S,S)-2-[1-Carboxy-2-(2-p-tolyl-thiazol-4-yl)-ethylamino]-4-methyl-pentanoic acid (Compound KK). $MH^+$ 377, MH⁻ 375. Analysis: found: C, 60.34%; H, 6.38%; N, 7.34%. $C_{19}H_{24}N_2O_4S$ requires: C, 60.62%; H, 6.43%; N, 7.44%.

50-2f: (S,S)-2-{1-Carboxy-2-[2-(3,5-dichlorophenyl)-thiazol-4-yl]-ethylamino}-4-methyl-pentanoic acid (Compound LO). MH⁺ 431, MH⁻ 429. Analysis: found: C, 43.08%; H, 4.33%; N, 5.50%. $C_{18}H_{18}Cl_2N_2O_5S\cdot Na_2\cdot 1.5H_2O$ requires: C, 43.04%; H, 4.21%; N, 5.58%.

50-2g: (S,S)-2-[1-Carboxy-2-(2-phenyl-oxazol-4-yl)ethylamino]-4-methyl-pentanoic acid (Compound LM). MH⁺ 347, MH⁻ 345. Analysis: found: C, 52.79%; H, 5.54%; N, 6.81%. $C_{18}H_{20}N_2O_5\cdot Na_2\cdot H_2O$ requires: C, 52.94%; H, 5.43%; N, 6.86%.

50-2h: (S,S)-2-{1-Carboxy-2-[2-(3,5-dichlorophenyl)-oxazol-4-yl]ethylamino}-4-methyl-pentanoic acid (Compound LN). MH⁺ 415, MH⁻ 413. Analysis: found: C, 45.40%; H, 4.21%; N, 5.66%. $C_{18}H_{18}Cl_2N_2O_5\cdot Na_2\cdot H_2O$ requires: C, 45.30%; H, 4.22%; N, 5.87%.

Oxazoles: (S,S)-2-[Carboxy-2-(5-phenyl-isoxazol-3-yl)-ethylamino]-4-methyl-pentanoic acid S-2-Amino-3-(5-phenylisoxazol-3-yl)-propionic acid methyl ester was prepared from (2R)-(-)-2,5-dihydro-3,6-dimethoxy-2-isopropylpyrazine and 3-chloromethyl-5-phenylisoxazole as described in Example 30. The title compound was prepared from this amino ester and trifluoromethane sulfonate of D-leucic acid benzyl ester as described in Scheme N. MH⁺ 347, MH⁻ 345. ¹H NMR (300 MHz, CD₃OD) δ 7.83–7.80 (2H, m), 7.50–7.44 (3H, m), 3.92 (1H, t, J=5.3 Hz), 3.76 (1H, t, J=6.9 Hz), 3.39–3.36 (2H, m), 1.94 (1H, ddd, J=6.5, 6.9 Hz), 1.75 (2H, dd, J=6.5, 6.9 Hz) 0.99 (6H, d, J=6.5 Hz).

Example 31

Synthesis of Furanyl Compounds

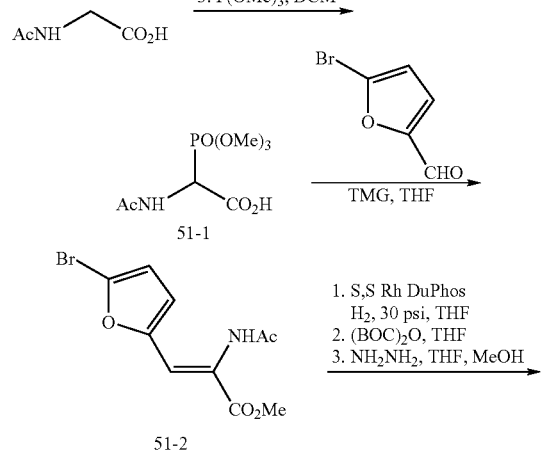

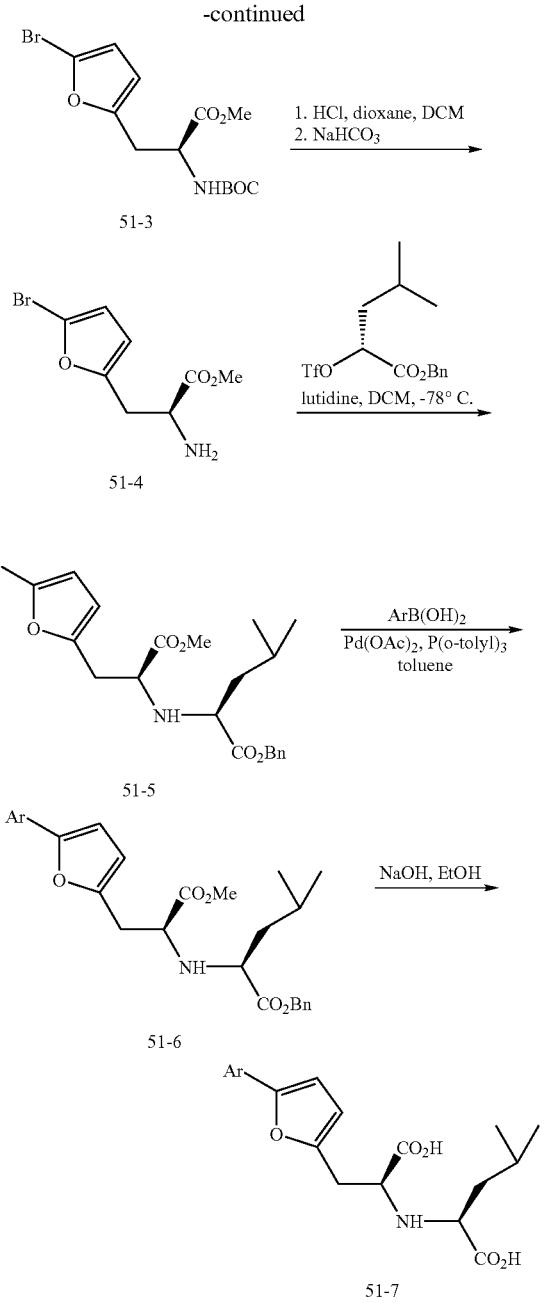

51-1: Methyl N-acetyl-2-(dimethoxyphosphoryl)glycinate. To a solution of methyl 2-acetamidoacetate (prepared as described by Nishiyama et. al. J. Chem. Soc. Perkin Trans. 1 1995, 1603–1609) (16.3 g, 124 mmol) in carbon tetrachloride (1250 mL) at room temperature under nitrogen, was added freshly recrystallized N-bromosuccinamide (22.1 g, 124 mmol). The mixture was heated under reflux with UV irradiation for 30 minutes. The reaction was cooled to room temperature and the solvents were evaporated to give the crude bromide as an orange oil. The title compound was prepared from this bromide and trimethylphosphite as described by Nishiyama et. al. J. Chem. Soc. Perkin Trans. 1 1995, 1603–1609. ¹H NMR was consistent with the literature.

51-2: 2-Acetylamino-3-(5-bromo-furan-2-yl)-acrylic acid methyl ester. To a solution of methyl N-acetyl-2-(dimethoxyphosphoryl)glycinate (62 mmol) in tetrahydrofuran (500 mL) at −78° C. under nitrogen, was added tetramethyl guanidine (7.45 mL, 59 mmol) dropwise. The reaction was stirred for 15 minutes at −78° C., then a solution of 5-bromo-2-furaldehyde (9.9 g, 57 mmol) in tetrahydrofuran (10 mL) was added dropwise. The reaction was stirred for 45 minutes at −78° C. then allowed to warm to room temperature and stirred for 48 hrs. The solvents were evaporated in vacuo, and the residue was dissolved in ethyl acetate, washed with water (3×), then 1N sulfuric acid (1×). The organics were dried over sodium sulfate and evaporated in vacuo. The residue was purified by chromatography on silica eluting with 70% ethyl acetate/hexane to give the title compound as a white solid (7.4 g, 40%). $^1$H NMR (300 MHz, CDCl$_3$) δ 7.04 (1H, s), 6.52 (1H, s), 6.42 (1H, d, J=3.6 Hz), 3.83 (3H, s), 2.18 (1H, s).

51-3: (S)-3-(5-Bromo-furan-2-yl)-tert butoxycarbonylamino-propionic acid methyl ester. 2-Acetylamino-3-(5-bromo-furan-2-yl)-acrylic acid methyl ester was reduced as described by Burk et. al. J. Am. Chem. Soc., 1994, 116, 10847–10848. $^1$H NMR and optical rotation were consistent with literature. The tert-butoxycarbamate group was installed as described by Burk et. al. (J. Org. Chem., 1997, 62, 7054–7057) to give compound 51-3. $^1$H NMR (300 MHz, CDCl$_3$) δ 6.19 (1H, d, J=3.3 Hz), 6.08 (1H, d, J=3.3 Hz), 5.12 (1H, d, J=7.7 Hz), 4.54 (1H, dd, J=5.3, 7.7 Hz), 3.76 (3H, s), 5.12 (2H, d, J=5.3 Hz), 1.44 (9H, s).

51-4: (S)-2-Amino-3-(5-bromo-furan-2-yl)-propionic acid methyl ester. (S)-3-(5-Bromo-furan-2-yl)-tert-butoxycarbonylamino-propionic acid methyl ester (8.5 g, 24 mmol) was dissolved in dichloromethane (120 mL) and a solution of HCl (61 mL, 4.0 N solution in dioxane, 240 mmol) was added dropwise. The reaction was stirred at room temperature for 1.5 hrs. The solvents were evaporated in vacuo to give a white solid. $^1$H NMR (300 MHz, CDCl$_3$) δ 8.83 (2H, br s), 6.40 (1H, d, J=3.0 Hz), 6.23 (1H, d, J=3.0 Hz), 4.45 (1H, t, J=6.0 Hz), 3.81 (3H, s), 3.49 (2H, d, J=6.0 Hz).

Saturated sodium bicarbonate solution was added until the pH was between 8–9 and then the mixture was extracted with ethyl acetate (3×). The combined organic phases were dried over sodium sulfate and evaporated in vacuo to give the desired compound as an oil which was immediately used.

51-5: (S,S)-2-[2-(5-bromo-furan-2-yl)-1-methoxycarbonyl-ethylamino]-4-methyl-pentanoic acid benzyl ester. The title compound was prepared from (S)-2-amino-3-(5-bromo-furan-2-yl)-propionic acid methyl ester and trifluoromethane sulfonate of D-leucic acid benzyl ester as described in Example 5. $^1$H NMR (300 MHz, CDCl$_3$) δ 7.40–7.40 (5H, m), 6.18 (1H, d, J=3.3 Hz), 6.09 (1H, d, J=3.3 Hz), 5.13 (2H, d, J=3.3 Hz), 3.68 (3H, s), 3.58 (1H, dd, J=7.3, 6.1 Hz), 3.39 (1H, dd, J=7.7, 6.5 Hz), 3.04–2.89 (2H, m), 1.73–1.64 (1H, m), 1.50–1.42 (2H, m), 0.90–0.89 (6H, m).

General Procedure for Suzuki Couplings of (S,S)-2-[2-(5-bromo-furan-2-yl)-1-methoxycarbonyl-ethylamino]-4-methyl-pentanoic acid benzyl ester with boronic acids.

To a degassed solution of (S),(S)-2-[2-(5-bromo-furan-2-yl)-1-methoxycarbonyl-ethylamino]-4-methyl-pentanoic acid benzyl ester (51-5, 1.0 eq), 2M aqueous sodium carbonate solution (2.0 eq) and the appropriate phenyl boronic acid (2.0 eq) in dry toluene (0.16 M) at room temperature, was added tri-o-tolylphosphine (0.4 eq) and palladium (II) acetate (0.2 eq). The mixture was heated at 80° C. for 4–18 hrs. The reaction mixture was cooled to room temperature, diluted with ethyl acetate, and then filtered through a short column of solid sodium carbonate on top of silica, eluting with ethyl acetate. The filtrate was evaporated and the residue purified by chromatography on silica eluting with ethyl acetate/hexane.

51-6a: (S,S)-2-[1-Methoxycarbonyl-2-(5-p-tolyl-furan-2-yl)-ethylamino]-4-methyl-pentanoic acid benzyl ester. MH$^+$=464.

51-6b: (S,S)-2-[1-Methoxycarbonyl-2-(5-phenyl-furan-2-yl)-ethylamino]-4-methyl-pentanoic acid benzyl ester. MH$^+$=450.

51-6c: (S,S)-2-{2-[5-(3,5-Dichloro-phenyl)-furan-2-yl]-1-methoxycarbonyl-ethylamino}-4-methyl-pentanoic acid benzyl ester. MH$^+$=518.

51-6d: (S,S)-2-{2-[5-(3,5-Dimethyl-phenyl)-furan-2-yl]-1-methoxycarbonyl-ethylamino}-4-methyl-pentanoic acid benzyl ester. MH$^+$=478.

51-6e: (S,S)-2-{2-[5-(3,5-Difluoro-phenyl)-furan-2-yl]-1-methoxycarbonyl-ethylamino}-4-methyl-pentanoic acid benzyl ester. MH$^+$=486.

51-6f: (S,S)-2-[1-Methoxycarbonyl-2-(5-thiophen-3-yl-furan-2-yl)-ethylamino]-4-methyl-pentanoic acid benzyl ester. MH$^+$=456.

51-6g: (S,S)-2-{1-Methoxycarbonyl-2-[5-(4-methoxy-phenyl)-furan-2-yl]-ethylamino}-4-methyl-pentanoic acid benzyl ester. MH$^+$=480.

51-6h: (S,S)-2-[2-(5-Benzo{1,3}dioxol-5-yl-furan-2-yl)-1-methoxycarbonyl-ethylamino]-4-methyl-pentanoic acid benzyl ester. MH$^+$=494.

51-6i: (S,S)-2-[1-Methoxycarbonyl-2-(5-napthalen-1-yl-furan-2-yl)-ethylamino]-4-methyl-pentanoic acid benzyl ester. MH$^+$=500.

51-6j: (S,S)-2-{2-[5-(4-Chloro-phenyl)-furan-2-yl]-1-methoxycarbonyl-ethylamino}-4-methyl-pentanoic acid benzyl ester. MH$^+$=484.

51-6k: (S,S)-2-{1-Methoxycarbonyl-2-[5-(4-trifluoromethyl-phenyl)-furan-2-yl)-ethylamino}-4-methyl-pentanoic acid benzyl ester. MH$^+$=518.

51-6l: (S,S)-2-{2-[5-(3-Chloro-phenyl)-furan-2-yl]-1-methoxycarbonyl-ethylamino}-4-methyl-pentanoic acid benzyl ester. MH$^+$=484.

The diesters were hydrolysed as described previously to give the desired diacids.

51-7a: (S,S)-2[1-Carboxy-2-(5-p-tolyl-furan-2-yl)-ethylamino]-4-methyl-pentanoic acid (Compound NO). MH$^+$=360, MH$^-$=358. Analysis: found: C, 67.13%; H, 7.06%; N, 3.85%. C$_{20}$H$_{25}$NO$_5$ requires: C, 66.84%; H, 7.01%; N, 3.90%.

51-7b: (S,S)-2-[1-Carboxy-2-(5-phenyl-furan-2-yl)-ethylamino]-4-methyl-pentanoic acid (Compound NR). MH$^+$ 346, MH$^-$ 344. Analysis: found: C, 65.79%; H, 6.68%; N, 4.00%. C$_{19}$H$_{23}$NO$_5$ requires: C, 66.07%; H, 6.71%; N, 4.06%.

51-7c: (S,S)-2-{1-Carboxy-2-[5-(3,5-dichlorophenyl)-furan-2-yl]-ethylamino}-4-methyl-pentanoic acid (Compound NS). MH$^+$=414, MH$^-$=412. Analysis: found: C, 55.16%; H, 5.21%; N, 3.36%; Cl, 16.43% C$_{19}$H$_{21}$Cl$_2$NO$_5$.0.2CH$_3$OH requires: C, 54.82%; H, 5.22%; N, 3.33%; Cl, 16.85%.

51-7d: (S,S)-2-{1-Carboxy-2-[5-(3,5-dimethyl-phenyl)-furan-2-yl]-ethylamino}-4-methyl-pentanoic acid (Compound NT). MH$^+$=374, MH$^-$=372. Analysis: found: C, 67.01%; H, 7.20%; N, 3.78% $C_{21}H_{27}NO_5$·0.1$H_2O$ requires: C, 67.22%; H, 7.31%; N, 3.73%.

51-7e: (S,S)-2-{1-Carboxy-2-[5-(3,5-difluoro-phenyl)-furan-2-yl]-ethylamino}-4-methyl-pentanoic acid (Compound NU). MH$^+$=382, MH$^-$=380. Analysis: found: C, 59.76%; H, 5.71%; N, 3.68% $C_{19}H_{21}F_2NO_5$ requires: C, 59.84%; H, 5.55%; N, 3.67%.

51-7f: (S,S)-2-[1-Carboxy-2-(5-thiophen-3-yl-furan-2-yl)-ethylamino]-4-methyl-pentanoic acid (Compound NV). MH$^+$=352, MH$^-$=350 (M−1). Analysis: found: C, 58.00%; H, 6.03%; N, 4.01% $C_{17}H_{21}NO_5S$ requires: C, 58.10%; H, 6.02%; N, 3.99%.

51-7g: (S,S)-2-{1-Carboxy-2-[5-(4-methoxy-phenyl)-furan-2-yl]-ethylamino}-4-methyl-pentanoic acid (Compound OI). MH$^+$=376, MH$^-$=374. Analysis: found: C, 64.08%; H, 6.70%; N, 3.70% $C_{20}H_{25}NO_6$ requires: C, 63.99%; H, 6.71%; N, 3.73%.

51-7h: (S,S)-2-[2-(5-Benzo[1,3]dioxol-5-yl-furan-2-yl)-1-carboxy-ethylamino]-4-methyl-pentanoic acid (Compound OJ). MH$^+$=390, MH$^-$=388 (M−1). Analysis: found: C, 61.64%; H, 6.05%; N, 3.56% $C_{20}H_{23}NO_7$ requires: C, 61.69%; H, 5.95%; N, 3.60%.

51-7i: (S,S)-2-[1-Carboxy-2-(5-napthalen-1-yl-furan-2-yl)-ethylamino]-4-methyl-pentanoic acid (Compound OK). MH$^+$=396, MH$^-$=394 (M−1). Analysis: found: C, 69.82%; H, 6.51%; N, 3.54% $C_{23}H_{25}NO_5$ requires: C, 69.86%; H, 6.37%; N, 3.54%.

51-7j: (S,S)-2-{1-Carboxy-2-[5-(4-chloro-phenyl)-furan-2-yl]-ethylamino}-4-methyl-pentanoic acid (Compound OL). MH$^+$=380, MH$^-$=378 (M−1). Analysis: found: C, 59.89%; H, 5.95%; N, 3.64%; Cl, 9.26% $C_{19}H_{22}ClNO_5$ requires: C, 60.08%; H, 5.84%; N, 3.69%; Cl, 9.33%.

51-7k: (S,S)-2-{1-Carboxy-2-[5-(4-trifluoromethyl-phenyl)-furan-2-yl]-ethylamino}-4-methyl-pentanoic acid (Compound OM). MH$^+$=414, MH$^-$=412 (M−1). Analysis: found: C, 57.95%; H, 5.42%; N, 3.39% $C_{20}H_{22}F_3NO_5$ requires: C, 58.11%; H, 5.36%; N, 3.39%.

51-7l: (S), (S)-2-{1-Carboxy-2-[5-(3-chloro-phenyl)-furan-2-yl]-ethylamino}-4-methyl-pentanoic acid (Compound OS). MH$^+$=380, MH$^-$=378 (M−1). Analysis: found: C, 60.47%; H, 5.94%; N, 3.57%; Cl, 9.24% $C_{19}H_{22}ClNO_5$ requires: C, 60.08%; H, 5.84%; N, 3.69%; Cl, 9.33%.

Example 32

Synthesis of Benzyl Pyrazole Compounds

Scheme 52

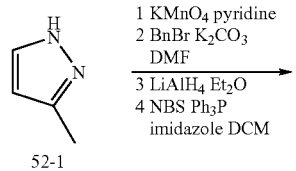

1 KMnO$_4$ pyridine
2 BnBr K$_2$CO$_3$
DMF
3 LiAlH$_4$ Et$_2$O
4 NBS Ph$_3$P
imidazole DCM

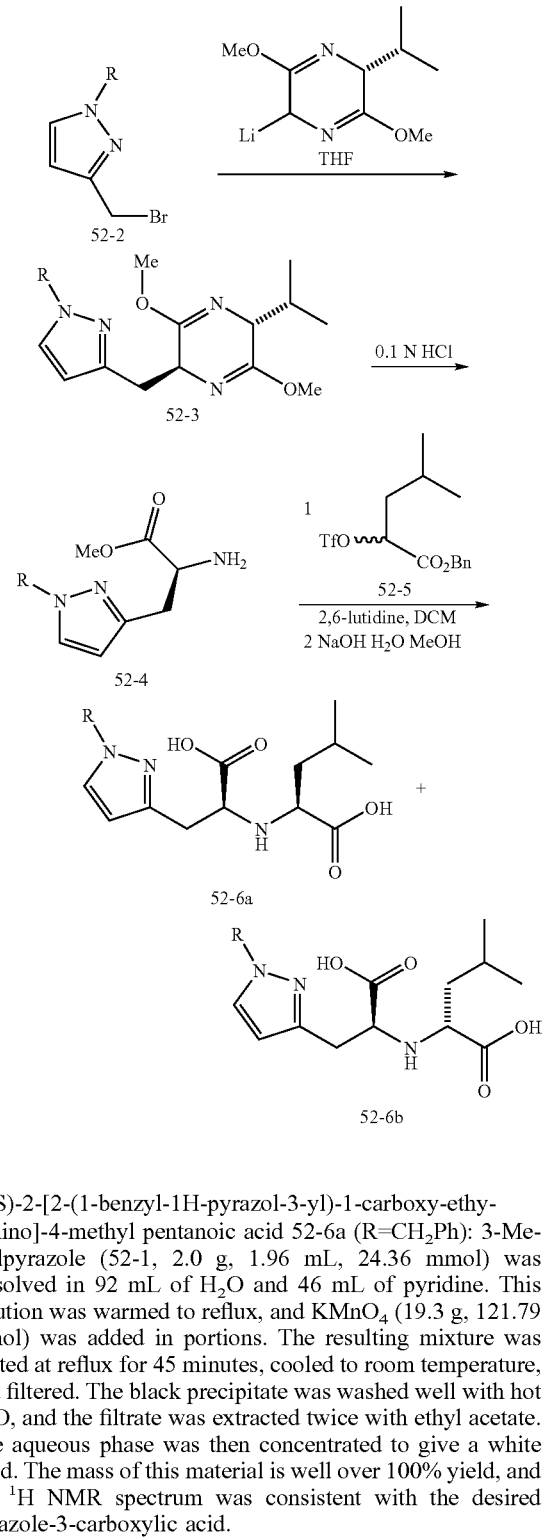

(S,S)-2-[2-(1-benzyl-1H-pyrazol-3-yl)-1-carboxy-ethylamino]-4-methyl pentanoic acid 52-6a (R=CH$_2$Ph): 3-Methylpyrazole (52-1, 2.0 g, 1.96 mL, 24.36 mmol) was dissolved in 92 mL of H$_2$O and 46 mL of pyridine. This solution was warmed to reflux, and KMnO$_4$ (19.3 g, 121.79 mmol) was added in portions. The resulting mixture was heated at reflux for 45 minutes, cooled to room temperature, and filtered. The black precipitate was washed well with hot H$_2$O, and the filtrate was extracted twice with ethyl acetate. The aqueous phase was then concentrated to give a white solid. The mass of this material is well over 100% yield, and the $^1$H NMR spectrum was consistent with the desired pyrazole-3-carboxylic acid.

A portion of this white solid (3.18 g, estimated to be 1.13 g or 10.1 mmol of desired acid) was suspended in 100 mL of DMF. K$_2$CO$_3$ (6.98 g, 50.5 mmol) and benzyl bromide (2.34 mL, 20.2 mmol) were added. The reaction mixture was stirred overnight, and then diluted with H$_2$O and ethyl acetate. The aqueous phase was extracted with ethyl acetate. The combined organic phases were washed with H$_2$O and brine, dried over Na$_2$SO$_4$, filtered, and concentrated to give a pale yellow oil. Purification by column chromatography (SiO$_2$, elution with 20% ethyl acetate in hexane) provided 1.06 g of the desired ester as a yellow oil that contains a small amount of DMF. $^1$H NMR spectrum was consistent with desired 1-benzylpyrazole-3-carboxylic acid benzyl ester.

1-Benzylpyrazole-3-carboxylic acid benzyl ester (1.06 g, 3.63 mmol) was then dissolved in 50 mL of Et$_2$O, and LiAlH$_4$ (334 mg, 9.06 mmol) was added in portions. This slurry was warmed to reflux, stirred overnight, and then cooled to room temperature. H$_2$O and MeOH were added carefully, and the resulting mixture was saturated with CO$_2$ gas. The slurry was then filtered, and the precipitate was washed well with MeOH. The filtrate was concentrated and purified by column chromatography (SiO$_2$, elution with 50% ethyl acetate in hexane) to give 475 mg of the desired alcohol as a colorless oil (69% yield). $^1$H NMR spectrum was consistent with the desired (1-benzylpyrazol-3-yl)methanol.

This alcohol (1.0 g, 5.31 mmol) was dissolved in CH$_2$Cl$_2$ and 0.515 mL of pyridine. This solution was cooled to 0° C., and Ph$_3$P (3.90 g, 14.87 mmol) and NBS (2.84 g, 15.94 mmol) were added sequentially. The resulting brown mixture was stirred at 0° C. for 90 minutes, then diluted with ethyl acetate, and extracted with H$_2$O. The aqueous phase was extracted with ethyl acetate, and the combined organic phases were washed with brine, dried over Na$_2$SO$_4$, filtered, and concentrated to give a light brown solid. Purification by column chromatography (SiO$_2$, elution with 5–10% ethyl acetate in hexane) provided the desired bromide (52-2) as a colorless oil (1.26 g, 95% yield). $^1$H NMR spectrum was consistent with the desired 1-benzyl-3-bromomethylpyrazole.

2-Isopropyl-3,6-dimethoxy-2,5-dihydropyrazine (0.324 mL, 1.81 mmol) was dissolved in 20 mL of THF, and the resulting solution was cooled to −78° C. A solution of n-BuLi (0.869 mL, 2.17 mmol, 2.5 M solution in hexane) was added dropwise via syringe, and the yellow solution was stirred for 30 minutes. A solution of the bromide (52-2, 500 mg, 1.99 mmol) in 5 mL of THF was then added to the cooled reaction mixture. This reaction mixture was allowed to warm slowly to room temperature over 2 hours and then stirred for another hour. A saturated NH$_4$Cl solution and ethyl acetate were added, and the organic phase was separated, extracted with brine, dried over Na$_2$SO$_4$, filtered, and concentrated to give a yellow oil. Purification by column chromatography (SiO$_2$, elution with 30–40% ethyl acetate in hexane) provided the alkylated dihyropyrazine (52-3) as a pale yellow oil (417 mg, 65% yield). $^1$HNMR was consistent with the desired product as a 4:1 ratio of trans:cis diastereomers.

The dihydropyrazine 52-3 (1.07 g, 3.02 mmol) was dissolved in 30 mL of THF, and 60 mL of 0.1 N HCl solution were added. This reaction mixture was stirred at room temperature for 5 hours and then diluted with Et$_2$O. The aqueous phase was extracted twice with Et$_2$O, saturated with NaCl, brought to pH 10 with concentrated NH$_4$OH, and extracted twice with ethyl acetate. The two ethyl acetate extracts were combined and dried over Na$_2$SO$_4$, filtered, and concentrated. This oil was resuspended in toluene and concentrated to give 760 mg of the amino ester 52-4 as a yellow oil. $^1$H NMR spectrum is consistent with the desired amino ester.

The amino ester 52-4 (170 mg, 0.656 mmol) was dissolved in 6 mL of CH$_2$Cl$_2$ and 0.103 mL of 2,6-lutidine. This solution was cooled to −78° C., and a solution of racemic triflate 52-5[1] (211 mg, 0.656 mmol) in 2 mL of CH$_2$Cl$_2$ was added dropwise. The resulting solution was stirred at −78° C. for 1 hour and then warmed to room temperature and stirred overnight. The reaction mixture was diluted with ethyl acetate and extracted with saturated NH$_4$Cl solution, H$_2$O, and brine, dried over Na$_2$SO$_4$, filtered and concentrated to give a yellow oil. Purification by column chromatography (SiO$_2$, 20% ethyl acetate in hexane) provided the desired 2-[2-(1-benzylpyrazol-3-yl)-1-methoxycarbonyl-ethylamino]-4-methylpentanoic acid benzyl ester as a colorless oil (154 mg, 56% yield).

[1] Racemic triflate is prepared from racemic leucic acid benzyl ester in a manner analogous to that described for the trifluoromethane sulfonate of leucic acid methyl ester. Enanitopure triflate can be prepared in an analogous manner. D-Leucine is converted to R-leucic acid and R-leucic acid is converted to benzyl ester by treatment with BnBr in DMF and CsCO$_3$ 2-[2-(1-Benzylpyrazol-3-yl)-1-methoxycarbonyl-ethylamino]-4-methylpentanoic acid benzyl ester (150 mg, 0.324 mmol) was dissolved in 3 mL of MeOH and a 1.0 M solution of NaOH (3.24 mL, 3.24 mmol) was added. The reaction mixture was stirred for 14 h at room temperature and then concentrated to give a white solid. Purification by reverse-phase HPLC chromatography provided (S,S)-2-[2-(1-benzyl-1H-pyrazol-3-yl)-1-carboxy-ethylamino]-4-methyl pentanoic acid (less polar fractions, 52-6a, R=CH$_2$Ph) and (S,R)-2-[2-(1-benzyl-1H-pyrazol-3-yl)-1-carboxy-ethylamino]-4-methyl pentanoic acid (more polar fractions, 52-6b, R=CH$_2$Ph) as white powders.

(S,S)-2-[2-(1-benzyl-1H-pyrazol-3-yl)-1-carboxy-ethylamino]-4-methyl pentanoic acid (Compound IN): $^1$H NMR (300 MHz, CD$_3$OD) δ 7.60 (d, 1H, J=2.3 Hz); 7.22–7.35 (m, 5H); 6.23 (d, 1H, J=2.4 Hz); 5.31 (s, 2H); 3.86 (dd, 1H, J$_1$=4.7 Hz, J$_2$'7.9 Hz); 3.78 (dd, 1H, J$_1$=J$_2$=6.7 Hz); 3.27–3.30 (m, 1H); 3.17 (dd, 1H, J$_1$=8.1 Hz, J$_2$=15.8 Hz); 1.82–1.91 (m, 1H); 1.68–1.74 (m, 2H); 0.98 (d, 3H, J=4.5 Hz); 0.96 (d, 3H, J=4.5 Hz). Anal. Calc'd. for C$_{19}$H$_{25}$N$_3$O$_4$.2/3H$_2$O: % C, 61.44; % H, 7.15; % N, 11.31. Found: % C, 61.00; % H, 6.75; and % N, 11.17.

(S,R)-2-[2-(1-benzyl-1H-pyrazol-3-yl)-1-carboxy-ethylamino]-4-methyl pentanoic acid: $^1$H NMR (300 MHz, CD$_3$OD) δ 7.64 (d, 1H, J=2.4 Hz); 7.22–7.37 (m, 5H); 6.23 (d, 1H, J=2.3 Hz); 5.31 (s, 2H); 3.96–4.00 (m, 1H); 3.77–3.82 (m, 1H); 3.28–3.30 (m, 2H); 1.55–1.80 (m, 3H); 0.86 (d, 3H, J=6.6 Hz); 0.84 (d, 3H, J=6.4 Hz).

52-6a: (R=3,5-diCl-PhCH$_2$) (S,S)-2-{1-carboxy-2-[1-(3,5-dichlorobenzyl)-1H-pyrazol-3-yl]-ethylamino}-4-methyl pentanoic acid. Crude pyrazole 3-carboxylic acid was treated with 3,5-dichlorobenzyl bromide in a manner analogous to the treatment of pyrazole 3-carboxylic acid with benzyl bromide. The same procedures were used to carry the material through to 2-[1-(3,5-dichlorobenzyl)-1H-pyrazol-3ylmethyl]-5-isopropyl-3,6-dimethyoxy-2,5-dihydropyrazine, which was isolated as a single isomer. Hydrolysis with HCl, preparation of the methyl ester, and alkylation of the amine proceeded as described above. 2-{2-[1-[1-(3,5-dichlorobenzyl)-1H-pyrazol-3-yl]-1-methoxycarbonyl-ethylamino}-4-methyl pentanoic acid benzyl ester was treated with NaOH as described above. Purification of the resulting diacid was accomplished by column chromatography (ISCO purification system, C-18 bondisil, H$_2$O to MeOH over 30 min) to give a white powder. This material was dissolved in 1N NaOH solution (aqueous) and then treated with 1 N HCl (aqueous) until pH of 1 was obtained. The resulting precipitate was isolated by filtration to give a white solid (Compound LP). $^1$H NMR (300 MHz, CD$_3$OD) δ 7.71 (d, 1H, J=2.0 Hz); 7.37 (s, 1H); 7.21 (s, 2H); 6.28 (d, 2H, J=2.4 Hz); 5.30 (s, 2H); 4.05 (dd, 1H, J$_1$=4.9 Hz, J$_2$=7.7 Hz); 3.93 (dd, 1H, J$_1$=J$_2$=6.9 Hz); 3.34 (dd, 1H, J$_1$=4.5 Hz, J$_2$=15.9 Hz); 3.21 (dd, 1H, J$_1$=7.7 Hz, J$_2$=15.9 Hz); 1.85–1.70 (m, 3H); 0.99 (d, 3H, J=2.8 Hz); 0.97 (d, 3H, J=2.4 Hz). Anal. Calc'd for C$_{19}$H$_{23}$Cl$_2$N$_3$O$_4$·H$_2$O: % C, 51.13; % H, 5.65; % Cl, 15.89; % N, 9.41. Found: % C, 51.41; % H, 5.24; % Cl, 16.24; and % N, 9.42.

Example 33

Alternate Synthesis of Benzyl Pyrazolyl Compounds

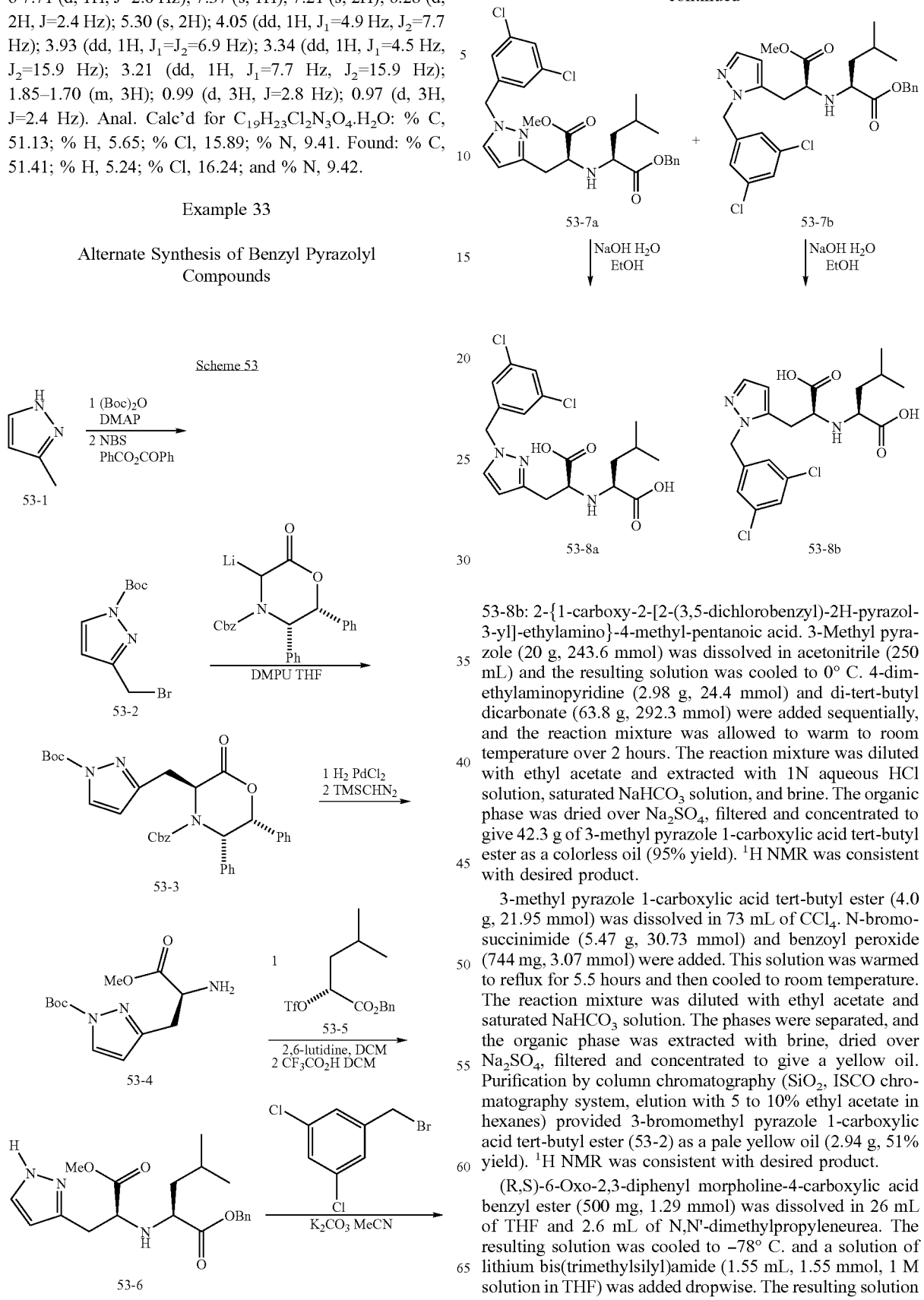

53-8b: 2-{1-carboxy-2-[2-(3,5-dichlorobenzyl)-2H-pyrazol-3-yl]-ethylamino}-4-methyl-pentanoic acid. 3-Methyl pyrazole (20 g, 243.6 mmol) was dissolved in acetonitrile (250 mL) and the resulting solution was cooled to 0° C. 4-dimethylaminopyridine (2.98 g, 24.4 mmol) and di-tert-butyl dicarbonate (63.8 g, 292.3 mmol) were added sequentially, and the reaction mixture was allowed to warm to room temperature over 2 hours. The reaction mixture was diluted with ethyl acetate and extracted with 1N aqueous HCl solution, saturated NaHCO$_3$ solution, and brine. The organic phase was dried over Na$_2$SO$_4$, filtered and concentrated to give 42.3 g of 3-methyl pyrazole 1-carboxylic acid tert-butyl ester as a colorless oil (95% yield). $^1$H NMR was consistent with desired product.

3-methyl pyrazole 1-carboxylic acid tert-butyl ester (4.0 g, 21.95 mmol) was dissolved in 73 mL of CCl$_4$. N-bromosuccinimide (5.47 g, 30.73 mmol) and benzoyl peroxide (744 mg, 3.07 mmol) were added. This solution was warmed to reflux for 5.5 hours and then cooled to room temperature. The reaction mixture was diluted with ethyl acetate and saturated NaHCO$_3$ solution. The phases were separated, and the organic phase was extracted with brine, dried over Na$_2$SO$_4$, filtered and concentrated to give a yellow oil. Purification by column chromatography (SiO$_2$, ISCO chromatography system, elution with 5 to 10% ethyl acetate in hexanes) provided 3-bromomethyl pyrazole 1-carboxylic acid tert-butyl ester (53-2) as a pale yellow oil (2.94 g, 51% yield). $^1$H NMR was consistent with desired product.

(R,S)-6-Oxo-2,3-diphenyl morpholine-4-carboxylic acid benzyl ester (500 mg, 1.29 mmol) was dissolved in 26 mL of THF and 2.6 mL of N,N'-dimethylpropyleneurea. The resulting solution was cooled to −78° C. and a solution of lithium bis(trimethylsilyl)amide (1.55 mL, 1.55 mmol, 1 M solution in THF) was added dropwise. The resulting solution was stirred at −78° C. for 30 minutes and then a solution of 3-bromomethyl pyrazole 1-carboxylic acid tert-butyl ester (53-2, 440 mg, 1.68 mmol) in 5 mL of THF was added. The reaction mixture was stirred at −78° C. for 2 hours and then warmed to room temperature and stirred overnight. Saturated NH$_4$Cl solution and ethyl acetate were added. The aqueous phase was extracted with ethyl acetate. Combined organic phases were extracted with water and brine, dried over Na$_2$SO$_4$, filtered, and concentrated to give a colorless oil. Purification by column chromatography (ISCO chromatography system, SiO$_2$, elution with 20% ethyl acetate in hexane) provided (S,S,R)-3-(1-tert-bytoxycarbonyl-1H-pyrazol-3-ylmethyl)-2-oxo-5,6-diphenyl morpholine-4-carboxylic acid benzyl ester (53-3) as a white solid (516 mg, 69% yield). $^1$H NMR was consistent with desired product (single isomer).

Pyrazole 53-3 (4.33 g, 7.63 mmol) was dissolved in EtOH (37 mL) and THF (42 mL) in a high-pressure hydrogenation flask. PdCl$_2$ (400 mg, 2.26 mmol) was added, and the reaction flask was pressurized to 50 psi H$_2$ gas. The reaction mixture was shaken for 16 hours and then depressurized and filtered through a pad of celite. The filtrate was concentrated to give an off-white solid. This solid was triturated with diethyl ether. The resulting solid (1.96 g, 7.68 mmol, and 100% yield) was then dissolved in methanol (40 mL) and toluene (40 mL). A solution of trimethylsilyldiazomethane (9.76 mL, 19.52 mmol) was added (a yellow color persisted). The reaction mixture was then concentrated to a brown oil. $^1$H NMR was consistent with 3-(2-amino-2-methyoxycarbonyl-ethyl)-pyrazole-1-carboxylic acid tert-butyl ester (53-4). This amino ester was then alkylated with triflate (53-5) as described above to give 3-[2-(1-benzyloxycarbonyl-3-methyl-butylamino)-2-methoxycarbonyl-ethyl]-pyrazole-1-carboxylic acid tert-butyl ester.

This diester (1.03 g, 2.19 mmol) was dissolved in 10 mL of dichloromethane. The solution was cooled to 0° C. and trifluoromethyl acetic acid (10 mL) was added dropwise. The reaction mixture was stirred at 0° C. for 20 minutes and then warmed to room temperature and stirred for 40 minutes. The reaction mixture was then concentrated. The resulting oil was dissolved in dichloromethane, and the solution was extracted with saturated NaHCO$_3$ solution. The organic phase was dried over Na$_2$SO$_4$, filtered, and concentrated to give a pale yellow oil (773 mg, 94% yield). $^1$H NMR was consistent with 2-[1-methoxycarbonyl-2-(1H-pyrazol-3-yl)-ethylamino]-4-methyl pentanoic acid benzyl ester (53-6).

The pyrazole 53-6 (300 mg, 0.803 mmol) was dissolved in acetonitrile (8 mL). K$_2$CO$_3$ (212 mg, 1.61 mmol) and 3,5-dichlorobenzyl bromide (231 mg, 0.964 mmol) were added, and the resulting mixture was warmed to 50° C. and stirred overnight. The reaction mixture was cooled to room temperature and diluted with ethyl acetate and water. The aqueous phase was extracted with ethyl acetate. Combined organic phases were washed with water and brine, dried over Na$_2$SO$_4$, filtered, and concentrated to give a yellow oil. Purification by column chromatography (ISCO chromatography system, SiO$_2$, elution with 10 to 20% ethyl acetate in hexane) provided two sets of fractions. A pale yellow oil (152 mg, Rf=0.5, 40% ethyl acetate in hexane) provided a $^1$H NMR consistent with the previously isolated 53-7a. Another yellow oil (38 mg, mixture of spots by TLC) provided a $^1$H NMR consistent with a mixture of compounds. Further purification of this material by column chromatography (ISCO chromatography system, SiO$_2$, elution with 10 to 20% ethyl acetate in hexane) provided a colorless oil (23 mg, Rf=0.58, 40% ethyl acetate in hexane) consistent with 2-{2-[2-(3,5 dichloro-benzyl)-2H-pyrazol-3-yl]-1-methoxycarbonyl-ethylamino}-4-methyl-pentanoic acid benzyl ester 53-7b. The proposed structure was supported by 2D NMR methods (NOESY, HMBC and HMQC).

2-{2-[2-(3,5 dichloro-benzyl)-2H-pyrazol-3-yl]-1-methoxycarbonyl-ethylamino}-4-methyl-pentanoic acid benzyl ester 53-7b was converted to 2-{1-carboxy-2-[2-(3,5-dichlorobenzyl)-2H-pyrazol-3-yl]-ethylamino}-4-methyl-pentanoic acid 53-8b (Compound MV) as described above. $^1$H NMR (300 MHz, CD$_3$OD) δ 7.55 (d, 1H, J=2.0 Hz); 7.37–7.38 (m, 1H); 7.04–7.05 (m, 2H); 6.45 (d, 2H, J=2.0 Hz); 5.40 (s, 2H); 4.18 (dd, 1H, J$_1$=6.1 Hz, J$_2$=7.3 Hz); 3.96 (dd, 1H, J$_1$=6.5 Hz, J$_2$=6.9 Hz); 3.19–3.30 (m, 2H); 1.89–1.98 (m, 1H); 1.66–1.86 (m, 2H); 1.00 (s, 3H); 0.98 (s, 3H). MH+=428 and MH−=426.

Example 34

Synthesis of Phenyl Pyrazolyl Compounds

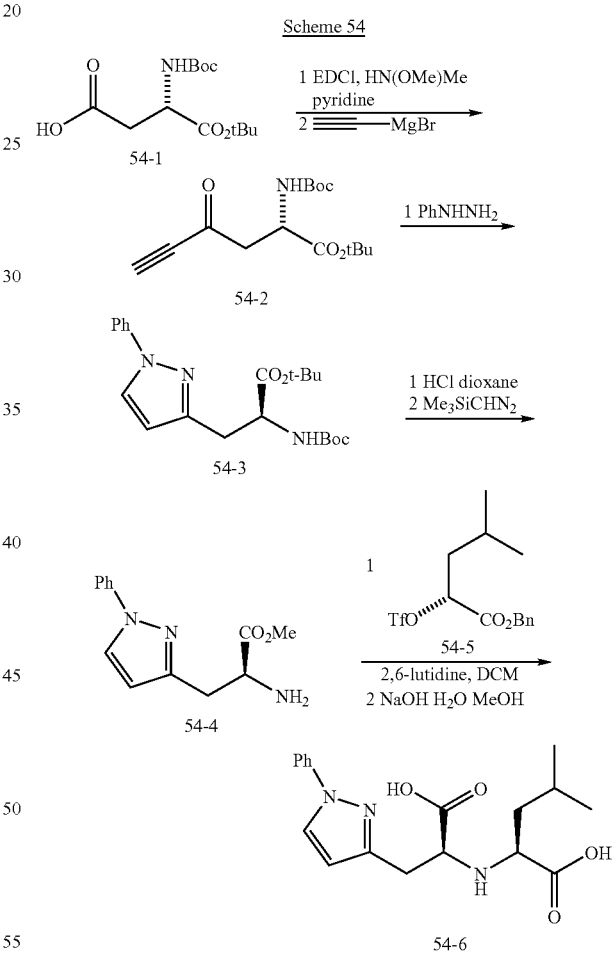

54-6: 2-[1-carboxy-2-(1phenyl-1H-pyrazol-3-yl)-ethylamino]-4-methyl-pentanoic acid Phenyl pyrazole 54-3 was prepared as described by R. M. Adlington et al. from 54-1 (*J. Chem. Soc. Perkin Trans I* 2000, 2311–2316). This reaction with phenyl hydrazine provided a single isomer whose structure was confirmed with 2D NMR methods (NOESY, HMBC, and HMQC). Phenyl pyrazole 54-3 (380 mg, 0.98 mmol) was dissolved in dichloromethane (4 mL) and a solution of HCl (2.45 mL, 9.80 mmol, 4 N in dioxane) was added dropwise. The resulting mixture was stirred for 2 hours at room temperature, and a precipitate formed. The reaction mixture was concentrated to give a brown oil (290 mg, 100% yield). $^1$H NMR was consistent with the desired amino acid (with some tert-butyl ester). This oil was dissolved in methanol (5 mL) and toluene (5 mL) and a solution of trimethylsilyldiazomethane (2 mL, 3.92 mmol, 2 M in hexane) was added (gas evolution and precipitate formation). After 2 hours, the reaction mixture was concentrated to a brown oil. This oil was redissolved in ethyl acetate and the solution was extracted with saturated NaHCO$_3$ solution, dried over Na$_2$SO$_4$, filtered and concentrated to give 2-amino-3-(1-phenyl-1H-pyrazol-3-yl)-propionic acid methyl ester (54-4) as a brown oil (262 mg, >100% yield, contaminated with some tert-butyl ester). This ester was alkylated with triflate 54-5 as described above. The resulting diester was hydrolyzed to 2-[1-carboxy-2-(1phenyl-1H-pyrazol-3-yl)-ethylamino]-4-methyl-pentanoic acid 54-6 (Compound OD) as described above. $^1$H NMR (300 MHz, CD$_3$OD) δ 8.17 (d, 1H, J=2.4 Hz); 7.76 (d, 2H, J=7.7 Hz); 7.46 (dd, 2H, J$_1$=7.7 Hz, J$_2$=8.1 Hz); 7.30 (t, 1H, J=7.3 Hz); 6.45 (d, 1H, J=2.4 Hz); 4.08 (dd, 1H, J$_1$=4.5 Hz, J$_2$=7.3 Hz); 3.97 (dd, 1H, J$_1$=J$_2$=6.9 Hz); 3.43 (dd, 1H, J$_1$=4.7 Hz, J$_2$=16.1 Hz); 3.34 (dd, 1H, J$_1$=7.3 Hz, J$_2$=16.3 Hz); 1.90–1.98 (m, 1H); 1.78–1.84 (m, 2H); 1.01 (d, 3H, J=5.3 Hz); 0.99 (d, 3H, J=5.7 Hz). Anal. Calc'd. for C$_{18}$H$_{23}$N$_3$O$_4$·H$_2$O: % C, 59.49; % H 6.93; % N, 11.56. Found: % C, 59.85; % H, 6.96; and % N, 11.46.

Example 35

Synthesis of Biphenyl Compounds

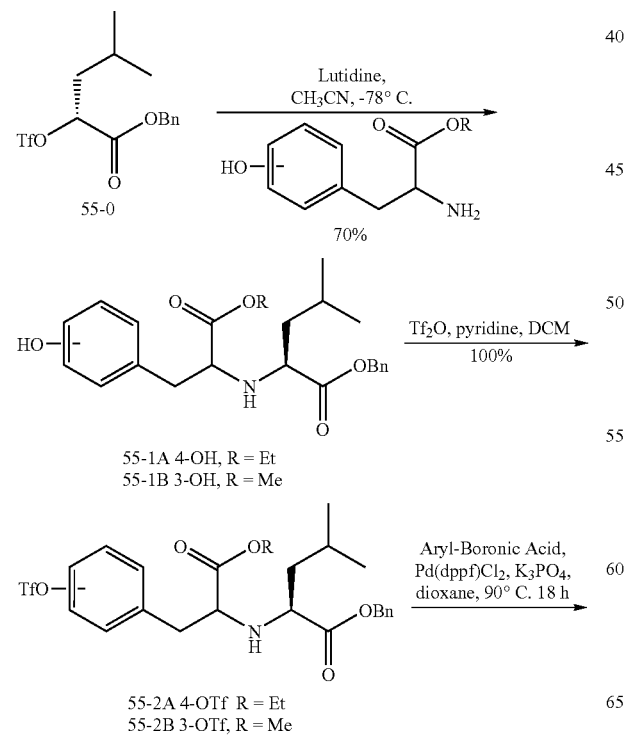

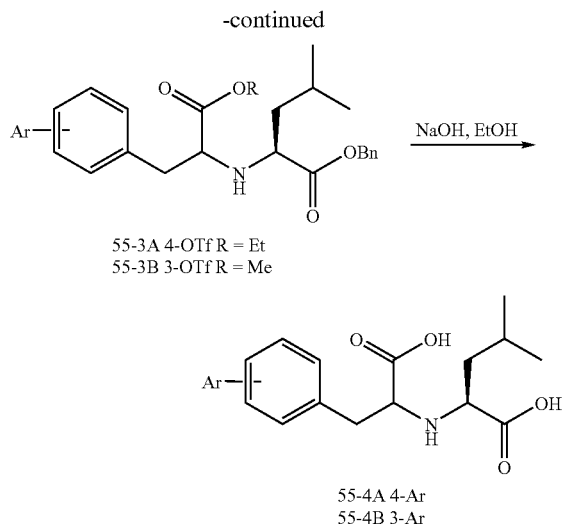

TABLE 8

3- and 4-Substituted Biphenyl Analogs

| Ar | ID |
|---|---|
| thiophen-3-yl | a |
| 3,5-dichlorophenyl | b |
| 4-methylphenyl | c |
| 4-fluorophenyl | d |
| 4-trifluoromethylphenyl | e |
| benzo[1,3]dioxol-5-yl | f |

TABLE 8-continued

3- and 4-Substituted Biphenyl Analogs

| Ar | ID |
|---|---|
| (benzothiophene-3-yl structure) | g |
| (naphthalen-1-yl structure) | h |
| (3,5-dimethoxyphenyl structure, MeO, OMe) | i |

(S)-2-Amino-3-(4-hydroxy-phenyl)-propionic acid ethyl ester: The free base was obtained by neutralizing commercially available material with sodium bicarbonate and extracting with ethyl acetate (250 mL EtOAc per 1 g amino ester).

(R,S)-2-Amino-3-(3-hydroxy-phenyl)-propionic acid methyl ester: The methyl ester was prepared from commercially available D,L-meta-tyrosine (10 g, 55 mmole) with thionyl chloride (8 mL, 110 mmole) in 276 mL MeOH (100%). The free base was obtained by neutralizing with sodium bicarbonate and extracting with ethyl acetate (250 mL EtOAc per 1 g amino ester (100% recovery). LC-MS: Rt=0.94 min (gradient: 5–100% $CH_3CN$ in 10 mM $NH_4OAc$ Buffer), MH+=196.

Procedure for N-alkylation of Tyrosine (S,S)-2-[1-Ethoxycarbonyl-2-(4-hydroxy-phenyl)-ethylamino]-4-methyl-pentanoic acid benzyl ester (55-1A). D-Benzyl protected leucic acid triflate (55-0) (23.3 mmole) was added to a cooled solution (−78° C.) of L-tyrosine methyl ester (3.2 g, 15.5 mmole), 2,6 lutidine (2.0 mL, 17.1 mmole) and acetonitrile (155 mL). The solution was stirred overnight and slowly warmed to room temperature. Water was added and the product was extracted with ethyl acetate, washed with brine and dried over $NaSO_4$. The product was purified by silica gel flash chromatography (ISCO-combi-flash system; gradient—0–50% ethyl acetate in hexanes). A yellow oil was isolated (4.54 g, 70%). LC-MS Rt=2.82 min: (gradient: 5–100% $CH_3CN$ in 10 mM $NH_4OAc$ Buffer) MH+=414.

55-1B: (S,S)-2-[1-Methoxycarbonyl-2-(3-hydroxy-phenyl)-ethylamino]-4-methyl-pentanoic acid benzyl ester.

55-1B diastereomer: (S,R)-2-[1-Methoxycarbonyl-2-(3-hydroxy-phenyl)-ethylamino]-4-methyl-pentanoic acid benzyl ester. Racemic meta-tyrosine was used for the alkylation. The resulting diastereomeric mixture was separated via reverse phase gravity chromatography (C18, 30/70 MeOH/$H_2O$). The early fractions yielded the (S,S) diastereomer $^1H$ NMR (300 MHz, $CDCl_3$) δ 7.34 (m, 5H), 7.14 (t, 1H, J=7.7 Hz, 6.9 (m, 3H,), 5.09 (dd, 2H, J=12.2, 17.8 Hz), 3.64 (s, 3H), 3.54 (t, 1H, J=7.1 Hz), 3.35 (t, 1H, J=7.1 Hz), 2.89 (ddd, 2H, J=6.5, 13.8, 38.6 Hz), 1.67 (m, 1H), 1.42 (t, 2H, J=7.1 Hz), 0.86 (t, 6H, J=6.9 Hz). LC-MS Rt=2.62, 2.76 min (gradient: 5–100% $CH_3CN$ in 0.1% Formic Acid Aqueous Solution), Molecular ion ES+=401. The later fractions yielded the (R,S) diastereomer. $^1H$ NMR (300 MHz, $CDCl_3$) δ 7.34 (m, 5H), 7.12 (t, 1H, J=7.5 Hz), 6.74 (d, 1H, J=7.3 Hz), 6.68 (m, 2H), 5.09 (s, 2H), 3.59 (s, 3H), 3.44 (t, 1H, J=7.1 Hz), 3.20 (t, 1H, J=6.71 Hz), 2.89 (ddd, 2H, J=6.1, 13.4, 33.6 Hz), 1.63 (1H, m), 1.42 (2H, J=7.1 Hz), 0.79 (dd, 6H, J=6.5, 22.0 Hz); LC-MS Rt=2.71 min (gradient 5–100% $CH_3CN$ in 1.0% formic acid buffer); MH+=401.

Procedure for Tyrosine Phenyl Triflate 55-2A: (S,S) 2-[1-Ethoxycarbonyl-2-(4-trifluoromethanesulfonyloxy-phenyl)-ethylamino]-4-methyl-pentanoic acid benzyl ester. A solution of phenol (6.1 g, 14.6 mmole), dichloromethane (146 mL) and pyridine (8.24 mL, 102.5 mmole) was cooled to 0° C. Triflic anhydride (3.0 mL, 17.6 mmole) was added dropwise to the stirring solution. After 3 hours, the reaction mixture was treated with 1N HCl, extracted with dichloromethane, washed with brine, dried over $MgSO_4$, filtered and concentrated. A yellow oil was obtained and used without further purification (8.0 g, 100%). $^1H$ NMR (300 MHz, $CDCl_3$) δ 7.34 (m, 5H), 7.23 (m, 2H), 7.15 (m, 2H), 5.12 (2H, m), 4.06 (2H, t, 7.53 Hz), 3.52 (1H, t, J=7.1 Hz), 3.37 (1H, t, J=7.1 Hz), 2.94 (2H, q, 5.6 Hz), 1.8 (1H, br s), 1.66 (1H, m), 1.46 (m, 2H), 1.14 (3H, t, J=7.1 Hz), 0.88 (6H, t, J=6.5 Hz). LC-MS Rt=3.64 min (gradient 5–100% $CH_3CN$ in 10 mM $NH_4OAc$ Buffer); MH+=546.

55-2B: (S,S)-2-[1-Methoxycarbonyl-2-(3-trifluoromethanesulfonyloxy-phenyl)-ethylamino]-4-methyl-pentanoic acid benzyl ester. TLC (1/1 hexane/ethyl acetate $R_f$=0.4); LC-MS: Rt=3.51 min (gradient: 5–100% $CH_3CN$ in 1.0% formic acid buffer); MH+=532.

Procedure for Palladium Catalyzed 3- and 4-Substituted Biphenyl Couplings 55-3A-a: (S,S)-2-[1-Ethoxycarbonyl-2-(4-thiophen-3-yl-phenyl)-ethylamino]-4-methyl-pentanoic acid benzyl ester. Triflate 55-2, (249 mg, 0.47 mmole), potassium phosphate tribasic (193 mg, 0.91 mmole), thiophen-3-yl boronic acid (116 mg, 0.91 mmole), and dioxane (2.4 mL) were added to screw cap vial. $N_2$(g) was bubbled through the solution for 60 sec. Pd(dppf)$Cl_2$ (10 mg, 0.01 mmole) was added and the solution was again flushed with $N_{2(g)}$. The vial was capped and the solution was heated to 90° C. for 18 h. The reaction mixture was cooled to room temperature, filtered through celite, and purified by silica gel flash chromatography (isco combi-flash system; gradient—10–30% ethyl acetate in hexanes). A pale yellow oil was isolated (167 mg, 73%). LC-MS: Rt=3.60 min (gradient: 5–100% $CH_3CN$ in 10 mM $NH_4Ac$ Buffer); MH+ 480.

55-3B-b: (S,S)-2-[2-(3',5'-Dichloro-biphenyl-4-yl)-1-ethoxycarbonyl-ethylamino]-4-methyl-pentanoic acid benzyl ester. LC-MS Rt=4.02 min (gradient: 5–100% $CH_3CN$ in 10 mM $NH_4OAc$ Buffer); MH+ 452.

55-3A-c: (S,S)-2-[1-Ethoxycarbonyl-2-(4'-methyl-biphenyl-4-yl)-ethylamino]-4-methyl-pentanoic acid benzyl ester. LC-MS Rt=3.79 min (gradient: 5–100% $CH_3CN$ in 10 mM $NH_4OAc$ Buffer); MH+=488.

55-3A-d: (S,S)-2-[1-Ethoxycarbonyl-2-(4'-fluoro-biphenyl-4-yl)-ethylamino]-4-methyl-pentanoic acid benzyl ester. LC-MS Rt=3.60 min (gradient: 5–100% $CH_3CN$ in 10 mM $NH_4OAc$ Buffer); MH+=492.

55-3A-e: (S,S)-2-[1-Ethoxycarbonyl-2-(4-trifluoromethyl-biphenyl-4-yl)-ethylamino]-4-methyl-pentanoic acid ester benzyl. LC-MS Rt=3.73 min (gradient: 5–100% $CH_3CN$ in 10 mM $NH_4OAc$ Buffer r); MH+=542.

55-3A-f: (S,S)-2-[2-(4-Benzo[1,3]dioxol-2-yl-phenyl)-1-ethoxycarbonyl-ethylamino]-4-methyl-pentanoic acid benzyl ester. LC-MS Rt=3.49 min (gradient: 5–100% $CH_3CN$ in 10 mM $NH_4OAc$ Buffer); MH+=518.

55-3A-g: (S,S)-2-[2-(4-Benzo[b]thiophen-3-yl-phenyl)-1-ethoxycarbonyl-ethylamino]-4-methyl-pentanoic acid benzyl ester. LC-MS Rt=3.77 min (gradient: 5–100% $CH_3CN$ in 10 mM $NH_4OAc$ Buffer); MH+=530.

55-3B-a: (S,S)-2-[1-Methoxycarbonyl-2-(3-thiophen-3-yl-phenyl)-ethylamino]-4-methyl-pentanoic acid benzyl ester. LC-MS Rt=3.52 min (gradient: 5–100% $CH_3CN$ in 10 mM $NH_4OAc$ Buffer); MH+=466.

55-3B-b: (S,S)-2-[2-(3',5'-Dichloro-biphenyl-3-yl)-1-methoxycarbonyl-ethylamino]-4-methyl-pentanoic acid benzyl ester. LC-MS Rt=3.89 min (gradient: 5–100% $CH_3CN$ in 10 mM $NH_4OAc$ Buffer); MH+=528.

55-3B-c: (S,S)-2-[1-Methoxycarbonyl-2-(4'-methyl-biphenyl-3-yl)-ethylamino]-4-methyl-pentanoic acid benzyl ester. LC-MS Rt=3.67 min (gradient: 5–100% $CH_3CN$ in 10 mM $NH_4OAc$ Buffer); MH=474.

55-3B-h: (S,S)-2-[2-(3'5'-Dimethoxy-biphenyl-3-yl)-1-methoxycarbonyl-ethylamino]-4-methyl-pentanoic acid benzyl ester. LC-MS Rt=3.38 min (gradient: 5–100% $CH_3CN$ in 10 mM $NH_4OAc$ Buffer); MH+=520.

55-3B-i: (S,S)-2-[1-Methoxycarbonyl-2-(3-naphthalen-1-yl-phenyl)-ethylamino]-4-methyl-pentanoic acid benzyl ester. LC-MS Rt=3.81 min (gradient: 5–100% $CH_3CN$ in 10 mM $NH_4OAc$ Buffer); MH+=510.

Procedure for Ester Hydrolysis 55-4A-a: (S,S)-2-[1-Carboxy-2-(4-thiophen-3-yl-phenyl)-ethylamino]-4-methyl-pentanoic acid (Compound NF). Ethanol (3.4 mL) and a solution of 1N NaOH (3.4 mL) was added to the diester, 55-3A-a, (167 mg, 0.34 mmole). The solution stirred overnight at room temperature. The solution was concentrated then desalted using a HP20 column (0 to 100% $MeOH/H_2O$) to yield 97.5 mg of a white solid (79%). LC-MS Rt=1.35 min (gradient: 5–100% $CH_3CN$ in 10 mM $NH_4OAc$ Buffer); MH+=362. Anal Cald for $C_{19}H_{22}NO_4Na_{1.5}S \times H_2O$: C, 55.26; H, 5.86; N, 3.39. Found: C, 55.66; H, 5.93; N, 3.42.

55-4A-b: (S,S)-2-[1-Carboxy-2-(3',5'-dichloro-biphenyl-4-yl)-ethylamino]-4-methyl-pentanoic acid (Compound NG). LC-MS Rt=1.75 min (gradient 5–100% $CH_3CN$ in 10 mM $NH_4Ac$ Buffer); MH+=424. Anal Cald for $C_{21}H_{22}NO_4Cl_2Na_{1.5} \times 1.3H_2O$: C, 52.41; H, 5.15; N, 2.91. Found: C, 52.58; H, 5.16; N, 2.99.

55-4A-c: (S,S)-2-[1-Carboxy-2-(4'-methyl-biphenyl-4-yl)-ethylamino]-4-methyl-pentanoic acid (Compound NH). LC-MS Rt=1.54 min (gradient 5–100% $CH_3CN$ in 10 mM $NH_4Ac$ Buffer); MH+=370. Anal Calcd for $C_{22}H_{26}NO_4Cl_2Na_2$: C, 61.1; H, 6.53; N, 3.24. Found: C, 61.34; H, 6.45; N, 3.40.

55-4A-d: (S,S)-[1-Carboxy-2-(4'-fluoro-biphenyl-4-yl)-ethylamino]-4-methyl-pentanoic acid (Compound OY). LC-MS Rt=1.39 min (gradient 5–100% $CH_3CN$ in 10 mM $NH_4Ac$ Buffer); MH+=374 Anal. Calcd. for $C_{21}H_{24}NO_4FNa_2 \times 0.7H_2O$: C, 58.88; H, 5.93; N, 3.24. Found: C, 58.56; H, 5.85; N, 3.34.

55-4A-e: (S,S)-2-[1-Carboxy-2-(4'-trifluoromethyl-biphenyl-4-yl)-ethylamino]-4-methyl-pentanoic acid (Compound PC). LC-MS Rt=1.72 min (gradient 5–100% $CH_3CN$ in 10 mM $NH_4Ac$ Buffer); MH+=424. Anal. Calcd. for $C_{22}H_{22}NO_4FNa_{1.5} \times H_2O$ C, 55.76; H, 5.10; N, 2.6. Found: C, 57.66; H, 5.39; N, 2.97.

55-4A-f: (S,S)-2-[2-(4-Benzo[1,3]dioxol-2-yl-phenyl)-1-carboxy-ethylamino]-4-methyl-pentanoic acid. LC-MS Rt=1.36 min (gradient 5–100% $CH_3CN/H_2O$ with 10 mM $NH_4Ac$ Buffer); MH+=400. Anal. Calcd. for $C_{21}H_{24}NO_4FNa_2$: C, 54.52; H, 6.27; N, 3.03. Found: C, 54.45; H, 5.29; N, 2.88.

55-4A-g: 2-[2-(4-Benzo[b]thiophen-3-yl-phenyl)-1-carboxy-ethylamino]-4-methyl-pentanoic acid (Compound PA). LC-MS Rt=1.60 min (gradient 5–100% $CH_3CN$ in 10 mM $NH_4Ac$ Buffer); MH+=412. Anal. Calcd. for $C_{23}H_{25}NO_4FSNa_2$: C, 60.38; H, 5.51; N, 3.06. Found: C, 60.00; H, 5.46, N, 2.87.

55-4B-a: (S,S)-2-[1-Carboxy-2-(3-thiophen-3-yl-phenyl)-ethylamino]-4-methyl-pentanoic acid (Compound MJ). LC-MS Rt=1.36 min (gradient 5–100% $CH_3CN$ in 10 mM $NH_4Ac$ Buffer); MH+=360. Anal. Calcd. for $C_{19}H_{23}NO_4FS.0.25H_2O$: C, 62.36; H, 6.47; N, 3.83. Found: C, 62.54; H, 6.31, N, 3.80.

55-4B-b: (S,S)-2-[1-Carboxy-2-(3,5'-dichloro-biphenyl-3-yl)-ethylamino]-4-methyl-pentanoic acid (Compound MI). $^1$HNMR (300 MHz, DMSO) δ 7.71 (m, 2H), 7.63 (br s, 1H), 7.56 (m, 2H) 7.31 (m, 2H) 3.43 (t, 1H, J=6.3 Hz), 3.39 (br s, 1H), 3.08 (t, 1H, J=6.3 Hz), 3.0 (ddd, 2H, J=7.3, 20.7, 33.9 Hz), 1.71 (m, 1H), 1.37 (t, 2H, J=6.7 Hz), 0.79 (d, 6H, J=6.5 Hz), LC-MS Rt=2.22 min (gradient 5–100% $CH_3CN$ in 10 mM $NH_4Ac$ Buffer); MH+=424.

55-4B-c: (S,S)-2-[1-Carboxy-2-(4'-methyl-biphenyl-3-yl)-ethylamino]-4-methyl-pentanoic acid (Compound LY). LC-MS Rt=1.33 min (gradient 5–100% $CH_3CN$ in 10 mM $NH_4Ac$ Buffer); MH+=416.

55-4B-h: (S,S)-2-[1-Carboxy-2-(3-naphthalen-1-yl-phenyl)-ethylamino]-4-methyl-pentanoic acid (Compound MX). LC-MS Rt=1.59 min (gradient 5–100% $CH_3CN$ in 10 mM NH$_4$Ac Buffer); MH+=406. Anal. Calcd. for C$_{25}$H$_{27}$NO$_4$Na.0.80H$_2$O: C, 67.80; H, 6.51; N, 3.16. Found: C, 67.97; H, 6.39; N, 3.19.

55-4B-i: (S,S)-2-[1-Carboxy-2-(3',5'-dimethoxy-biphenyl-3-yl)-ethylamino]-4-methyl-pentanoic acid (Compound MK). LC-MS Rt=1.86 min (gradient 5–100% CH$_3$CN in 10 mM NH$_4$Ac Buffer); MH+370. Anal. Calcd. for C$_{22}$H$_{27}$NO$_4$Cl: C, 65.26; H, 6.72; N, 3.46. Found: C, 64.98; H, 7.04; N, 3.44.

Example 36

Benzyl Substituted Phenyl Compounds

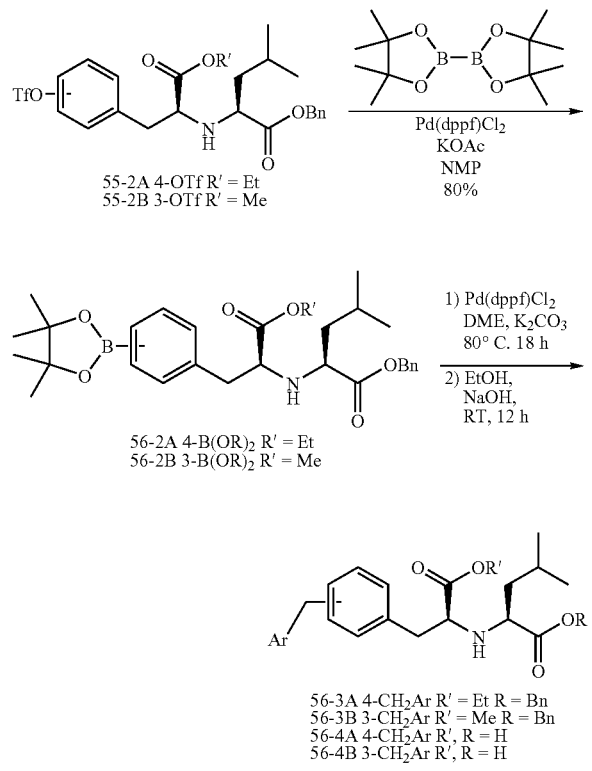

General Boronic Ester Formation Procedure 56-2A: (S,S)-2-{1-Ethoxycarbonyl-2-[4-(4,4,5,5-tetramethyl-[1,3,2]-dioxaborolan-2-yl)-phenyl]-ethylamino}-4-methyl-pentanoic acid benzyl ester. Triflate 55-2A (2.07 g, 3.8 mmole), potassium acetate (1.5 g, 15.2 mmole) diborane (1.1 g, 4.2 mmole) and N-methyl pyrollidinone (19 mL) were added together in a sealed tube. The solution was degassed with nitrogen. Pd(dppf)Cl$_2$ (78 mg, 0.095 mmole) was added. The reactions mixture was degassed again with nitrogen, sealed and heated to 100° C. for 15 hours. The reaction mixture was cooled to room temperature and concentrated. Water was added, and the mixture was extracted with ethyl acetate. The organic phase was dried over NaSO$_4$, filtered and concentrated. Purification was carried out via silica gel chromatography (isco-combi flash system-gradient 10–20%: ethyl acetate in hexanes 0–20 min). A pale yellow oil was isolated (1.64 g, 79%). $^1$H NMR (300 MHz, CDCl$_3$) δ 7.71 (m, 2H), 7.34 (m, 5H), 7.16 (d, 2H, J=7.7 Hz), 5.08 (t,2H, J=12,2, 22.0 Hz), 4.08 (q, 2H, J=7.3 Hz), 3.54 (1H, t, J=7.1 Hz), 3.36 (t, 1H, J=7.1 Hz), 2.95 (ddd, 2H, J=6.9, 13.4, 32.5 Hz), 1.77 (br.s, 1H,), 1.65 (m, 1H), 1.44 (m, 2H), 1.34 (s, 12H), 1.15(t, 3H, J=7.1 Hz), 0.85 (t, 6H, J=6.7 Hz). LC-MS Rt=3.82 min (gradient 5–100% CH$_3$CN in 10 mM NH$_4$OAc Buffer); MH+ 524.

56-2B: (S,S)-2-{-Methoxycarbonyl-2-[3-(4,4,5,5-tetramethyl-[1,3,2]dioxaborolan-2-yl)-phenyl]-ethylamino}-4-methyl-pentanoic acid benzyl ester $^1$H NMR (300 MHz, CDCl$_3$) δ 7.66 (m, 2H), 7.31 (m, 7H0, 5.07 (dd, 2H, J=12.2, 23.0 Hz), 3.60 (s, 3H), 3.58 (t, 1H, J=7.1 Hz), 3.37 (t, 1H, J=7.1 Hz), 2.93 (ddd, 2H, J=6.5, 13.8, 35.4 Hz), 1.64 (q, 1H, J 6.5 Hz), 1.43 (t, 2H, J=6.9 Hz), 1.33 (s, 12H), 0.85 (t, 6H, J=6.7 Hz). LC-MS Rt=3.43 min (gradient 5–100% CH$_3$CN in 10 mM NH$_4$Ac Buffer); MH+ 510.

TABLE 9

3- and 4-Substituted Benzyl Analogs

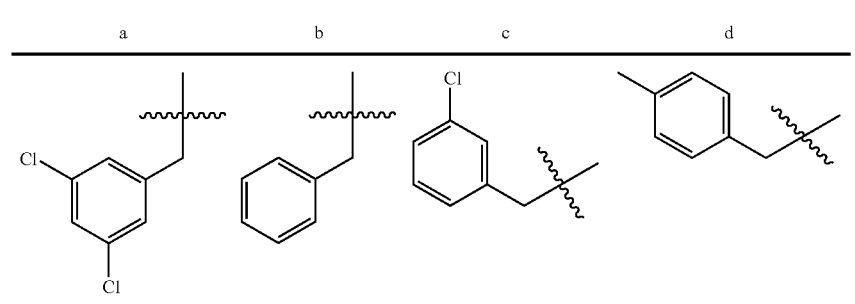

| a | b | c | d |

General Procedure for 3- and 4-Substituted Phenylalanine Boronic Ester Couplings with Benzyl Bromides 56-3A-a: (S,S)-2-{2-[4-(3,5-Dichloro-benzyl)-phenyl]-1-ethoxycarbonyl-ethylamino}-4-methyl-pentanoic acid benzyl ester. Borate, 56-2A (233 mg, 0.46 mmole), potassium carbonate (308 mg, 2.25 mmole), 3,5-dichloro-benzyl bromide (128.12 mg, 0.53 mmole), and Pd(dppf)Cl$_2$ (36 mg) were added together in a sealed tube. Dimethyl ethylene glycol (4.4 mL) was added to the reaction vessel. The reaction mixture was flushed with nitrogen, sealed and heated to 80° C. for 18 h. The solution was cooled and water was added. The product was extracted with ethyl acetate, dried over NaSO$_4$, filtered and concentrated. Silica gel chromatography (ISCO-combi flash 10% ethyl acetate in hexanes) yielded a pale yellow oil (197.9 mg, 80%). LC-MS Rt=3.74 min (gradient 5–100% CH$_3$CN in 10 mM NH$_4$OAc Buffer); MH+=502.

56-3A-b: (S,S)-2-[2-(4-Benzyl-phenyl)-1-ethoxycarbonyl-ethylamino]-4-methyl-pentanoic acid benzyl ester. LC-MS Rt=3.90 min (gradient 5–100% CH$_3$CN in 10 mM NH$_4$OAc Buffer); MH+=556.

56-3B-a: (S,S)-2-{2-[3-(3,5-Dichloro-benzyl)-phenyl]-1-methoxycarbonyl-ethylamino}-4-methyl-pentanoic acid benzyl ester. LC-MS Rt=3.82 min (gradient 5–100% CH$_3$CN in 10 mM NH$_4$OAc Buffer); MH+=542.

56-3B-b: (S,S)-2-[2-(3-Benzyl-phenyl)-1-methoxycarbonyl-ethylamino]-4-methyl-pentanoic acid benzyl ester. LC-MS Rt=3.67 min (gradient 5–100% CH$_3$CN in 10 mM NH$_4$OAc Buffer); MH+=488.

56-3B-c: (S,S)-2-{2-[3-(3-Chloro-benzyl)-phenyl]-1-methoxycarbonyl-ethylamino}-4-methyl-pentanoic acid benzyl ester. LC-MS Rt=3.66 min (gradient 5–100% CH$_3$CN in 10 mM NH$_4$OAc Buffer); MH+=508.

56-3B-c: (S,S)-2-{1-Methoxycarbonyl-2-[3-(4-methyl-benzyl)-phenyl]-ethylamino}-4-methyl-pentanoic acid benzyl ester. LC-MS Rt=3.64 min (gradient 5–100% CH$_3$CN in 10 mM NH$_4$OAc Buffer); MH+=474.

Ester Hydrolysis 56-4A-a: (S,S)-2-{1-Carboxy-2-[4-(3,5-dichloro-benzyl)-phenyl]-ethylamino}-4-methyl-pentanoic acid (Compound OF). See general ester hydrolysis procedure given in Example 29. LC-MS Rt=1.78 min (gradient 5–100% CH$_3$CN in 10 mM NH$_4$OAc Buffer); Molecular ion ES+=438. Anal. Calcd. for C$_{22}$H$_{25}$NO$_4$Cl$_2$Na$_3$1.5H$_2$O: C, 49.45; H, 5.28; N, 2.62. Found: C, 49.70; H, 4.91; N, 2.51.

56-4A-b: (S,S)-2-[2-(4-Benzyl-phenyl)-1-carboxy-ethylamino]-4-methyl-pentanoic acid (Compound OG). LC-MS Rt=1.82 min (gradient 5–100% CH$_3$CN in 10 mM NH$_4$OAc Buffer); MH+=370.

56-4B-a: (S,S)-2-{1-Carboxy-2-[3-(3,5-dichloro-benzyl)-phenyl]-ethylamino}-4-methyl-pentanoic acid (Compound PG). LC-MS Rt=1.73 min (gradient 5–100% CH$_3$CN in 10 mM NH$_4$Ac Buffer); MH+=438.

56-4B-b: (S,S)-2-[2-(3-Benzyl-phenyl)-1-carboxy-ethylamino]-4-methyl-pentanoic acid (Compound PB). LC-MS Rt=1.59 min (gradient 5–100% CH$_3$CN in 10 mM NH$_4$OAc Buffer); MH+=370.

56-4B-c: (S,S)-2-{1-Carboxy-2-[3-(3-chloro-benzyl)-phenyl]-ethylamino}-pentanoic acid. LC-MS Rt=1.59 min (gradient 5–100% CH$_3$CN in 10 mM NH$_4$OAc Buffer); MH+=404

56-4B-d: (S,S)-2-{1-Carboxy-2-[3-(4-methyl-benzyl)-phenyl]-ethylamino}-4-methyl-pentanoic acid. LC-MS Rt=2.35 min (gradient 5–100% CH$_3$CN in 10 mM NH$_4$OAc Buffer); MH+=384.

Example 37

Synthesis of Pyridyl Substituted Phenyl Compounds

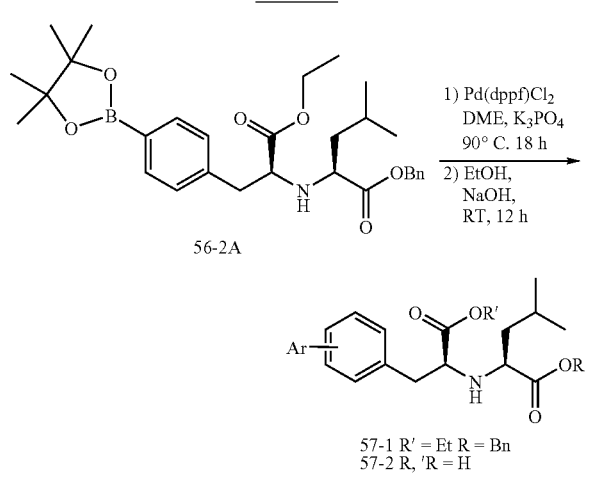

Scheme 57

TABLE 10

3-Pyridyl biphenyl analogs

| Ar | ID |
|---|---|
| 2-pyridyl | a |
| 3-pyridyl | b |
| 4-pyridyl | c |

TABLE 10-continued

3-Pyridyl biphenyl analogs

| Ar | ID |
|---|---|
| 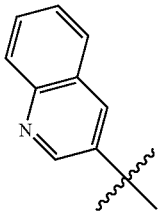 | d |
| 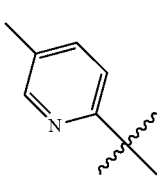 | e |
| 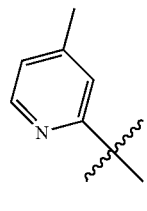 | f |
| 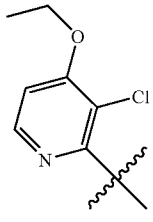 | g |

General Pd Catalyzed Couplings with Bromo Pyridines 57-1a: (S,S)-2-[1-Ethoxycarbonyl-2-(4-pyridin-2-yl-phenyl)-ethylamino]-4-methyl-pentanoic acid benzyl ester. Boronic ester 56-2-A (1 equiv), $K_3PO_4$ (5 equiv), amino pyridine (1.2 equiv) were added to a sealed tube. DME was added to bring the concentration of borate to 0.1 M. The reaction mixture was degassed with $N_2(g)$. Pd(dppf)Cl$_2$ was added to the solution which was again degassed with $N_2(g)$. The solution was heated at 90° C. for 18 h. The reaction mixture was filtered through celite and concentrated. Silica gel chromatography using the Biotage Quad™ system (gradient of 0–100% ethyl acetate in hexanes) yielded a white solid (30%). LC-MS Rt=3.40 min (gradient 5–100% CH$_3$CN in 10 mM NH$_4$OAc Buffer); MH+=475.

57-1b: (S,S)-2-[1-Ethoxycarbonyl-2-(4-pyridin-3-yl-phenyl)-ethylamino]-4-methyl-pentanoic acid benzyl ester. LC-MS Rt=3.21 min (gradient 5–100% CH$_3$CN in 10 mM NH$_4$OAc Buffer); MH+=475.

57-1c: (S,S)-2-[1-Ethoxycarbonyl-2-(4-pyridin-4-yl-phenyl)-ethylamino]-4-methyl-pentanoic acid benzyl ester. LC-MS Rt=3.21 min (gradient 5–100% CH$_3$CN in 10 mM NH$_4$OAc Buffer); MH+=475.

57-1d: (S,S)-2-[1-Ethoxycarbonyl-2-(4-quinolin-3-yl-phenyl)-ethylamino]-4-methyl-pentanoic acid benzyl ester. LC-MS Rt=3.56 min (gradient 5–100% CH$_3$CN in 10 mM NH$_4$OAc Buffer); MH+=525.

57-1e: (S,S)-2-{1-Ethoxycarbonyl-2-[4-(5-methyl-pyridin-2-yl)-phenyl]-ethylamino}-4-methyl-pentanoic acid benzyl ester LC-MS Rt=3.52 min (gradient 5–100% CH$_3$CN in 10 mM NH$_4$OAc Buffer); MH+=489.

57-1f: (S,S)-2-{1-Ethoxycarbonyl-2-[4-(4-methyl-pyridin-2-yl)-phenyl]-ethylamino}-4-methyl-pentanoic acid benzyl ester. LC-MS Rt=3.49 min (gradient 5–100% CH$_3$CN in 10 mM NH$_4$OAc Buffer); MH+=489.

57-1g: 2-{2-[4-(3-Chloro-4-ethoxy-pyridin-2-yl)-phenyl]-1-ethoxycarbonyl-ethylamino}-4-methyl-pentanoic acid benzyl ester. LC-MS Rt=3.53 min (gradient 5–100% CH$_3$CN in 10 mM NH$_4$OAc Buffer); MH+=453.

Ester Hydrolysis 57-2a: (S,S)-2-[1-Carboxy-2-(4-pyridin-2-yl-phenyl)-ethylamino]-4-methyl-pentanoic acid (Compound PI). See general ester hydrolysis procedure given in Example 29. LC-MS Rt=1.08 min (gradient 5–100% CH$_3$CN in 10 mM NH$_4$OAc Buffer); MH+=357.

57-2b: (S,S)-2-[1-Carboxy-2-(4-pyridin-3-yl-phenyl)-ethylamino]-4-methyl-pentanoic acid (Compound PJ). LC-MS Rt=0.98 min (gradient 5–100% CH$_3$CN in 10 mM NH$_4$OAc Buffer); MH+=357.

57-2c: (S,S)-2-[1-Carboxy-2-(4-pyridin-4-yl-phenyl)-ethylamino]-4-methyl-pentanoic acid (Compound PK). LC-MS Rt=0.95 min (gradient 5–100% CH$_3$CN in 10 mM NH$_4$OAc Buffer); MH+=357.

57-2d: (S,S)-2-[1-Carboxy-2-(4-quinolin-3-yl-phenyl)-ethylamino]-4-methyl-pentanoic acid (Compound QC). LC-MS Rt=1.33 min (gradient 5–100% CH$_3$CN in 10 mM NH$_4$OAc Buffer); MH+=407.

57-2e: (S,S)-2-{1-Carboxy-2-[4-(5-methyl-pyridin-2-yl)-phenyl]-ethylamino}-4-methyl-pentanoic acid (Compound PZ). LC-MS Rt=1.21 min (gradient 5–100% CH$_3$CN in 10 mM NH$_4$OAc Buffer); MH+=377.

57-2f: (S,S)-2-{1-Carboxy-2-[4-(4-methyl-pyridin-2-yl)-phenyl]-ethylamino}-4-methyl-pentanoic acid (Compound QA). LC-MS Rt=1.20 min (gradient 5–100% CH$_3$CN in 10 mM NH$_4$OAc Buffer); MH+=371.

57-2g: (S,S)-2-{1-Carboxy-2-[4-(3-chloro-4-ethoxy-pyridin-2-yl)-phenyl]-ethylamino}-4-methyl pentanoic acid (Compound QB). LC-MS Rt=1.38 min (gradient 5–100% CH$_3$CN in 10 mM NH$_4$OAc Buffer); MH+=435.

Example 38

Synthesis of Substituted Phenoxy Compounds

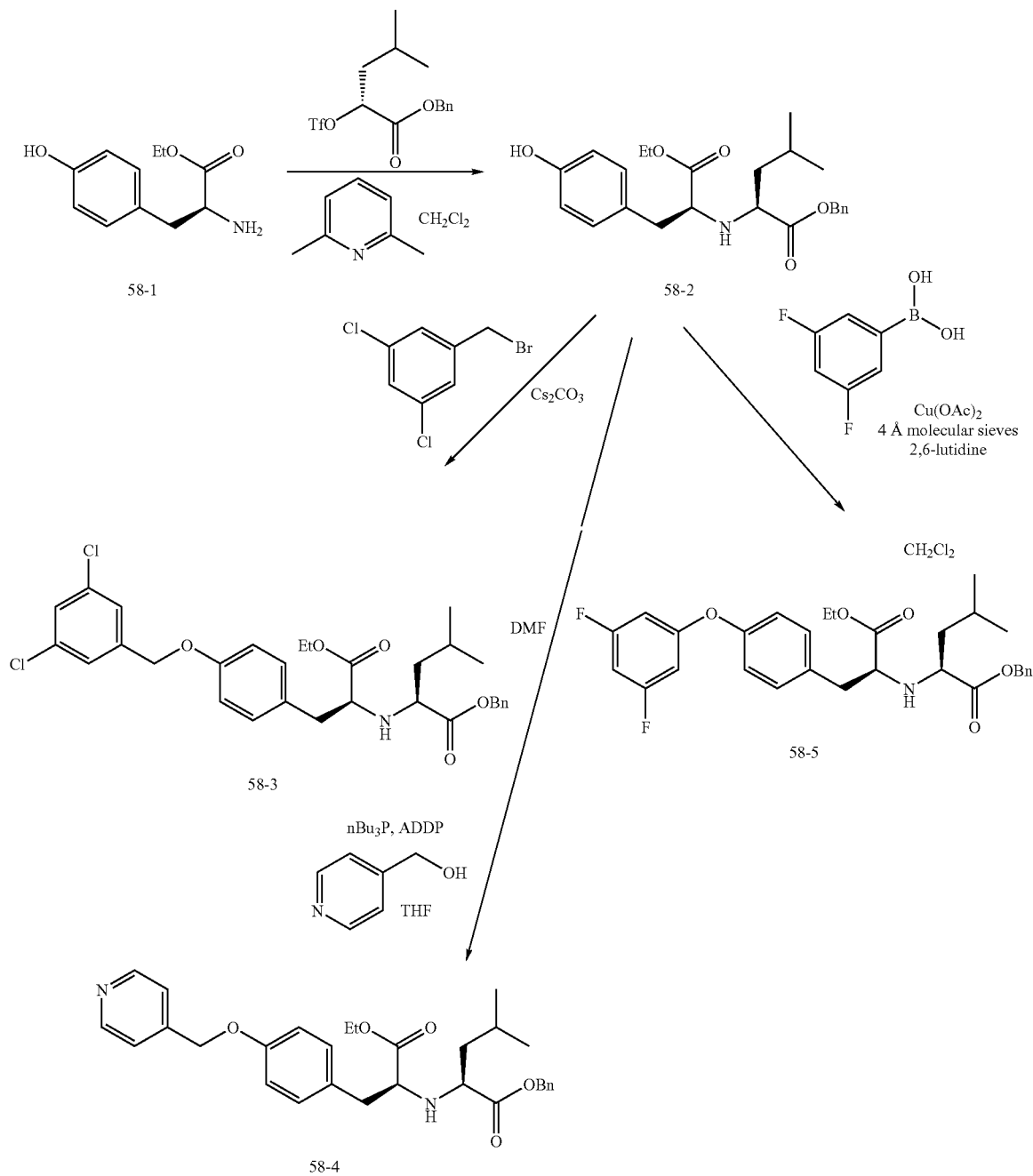

58-2: S,S-2-[1-Ethoxycarbonyl-2-(4-hydroxy-phenyl)-ethylamino]-4-methyl-pentanoic acid benzyl ester. Triflate (36.6 mmol, prepared as previously described in Example 9) in 100 mL CH$_2$Cl$_2$ was added to a solution of ethyl tyrosine (5.5 g, 26.2 mmol) and 2,6-lutidine (6 mL, 52.36 mmol) in CH$_2$Cl$_2$ (200 mL). This mixture was stirred at room temperature overnight. The reaction was concentrated with the aid of toluene three times to give a brown oil. Hexanes were added and the mixture was sonicated for 30 minutes to give a tan solid which consisted of a roughly 1:1 mixture of desired product and 2,6-lutidine. This was recrystallized from 10% ethyl acetate in Hexanes to give the desired product (8.8 g, 81%) as a single diastereomer. $^1$HNMR (300 MHz, CDCl$_3$) δ 7.41 (m, 5H), 7.0 (d, 2H, J=8.5 Hz), 6.67 (d, 2H, J=8.5 Hz), 5.11 (dd, 2H, J=3.8, 12.2 Hz), 4.09 (q, 2H, J=7.2 Hz), 3.53 (t, 1H, J=6.8 Hz), 3.40 (t, 1H, J=7.2 Hz), 2.86 (dddd, 2H, J=6.6, 7.2, 13.5, 14.8 Hz), 1.67 (m, 1H Hz), 1.50 (t, 2H, J=6.8 Hz), 1.17 (t, 3H, J=7.2 Hz), 0.86 (t, 6H, J=6.7 Hz). LCMS: Method FA RT=2.72 min, MH$^+$=414.

58-3: S,S-2-{1-Ethoxycabonyl-2-[4-(3,5-dichlorobenzyloxy)-phenyl]-ethylamino}-4-methyl pentanoic benzyl ester. Phenol 58-2 (200 mg, 0.483 mmol) and cesium carbonate (315 mg, 0.966 mmol) were stirred in DMF for 30 minutes to give a tan cloudy solution. 3,5-Dichlorobenzyl bromide (159 mg, 0.531 mmol) was added and this was allowed to stir at 60° C. overnight. The carbonate was removed by filtration and the solvents were removed in vacuo with the aid of toluene to give tan oil, which was purified by silica gel chromatography (10% ethyl acetate in Hexanes eluant) to give the desired product (58-3, 213 mg, 83%) as a colorless oil.

58-4: S,S-2-{1-Ethoxycarbonyl-2[4-(pyridin-4-ylmethoxy)-phenyl]-ethylamino}-4-methyl pentanoic benzyl ester. Tributyl phosphine (265 mL, 1.06 mmol) was added to a solution of 1,1'-(azodicarbonyl)dipiperidine (267 mg, 1.06 mmol) in THF at 0° C. This was stirred for 15 minutes before adding to a solution of 4-hydroxymethylpyridine (58 mg, 0.531 mmol) and phenol 58-2 (200 mg, 0.483 mmol) in THF at room temperature. The reaction was allowed to stir overnight before concentrating and adding diethyl ether to give a white precipitate, which was removed by filtration. The resulting orange solution was concentrated and purified by silica chromatography (10% ethyl acetate in hexanes eluant) to give the desired product (58-4, 245 mg, 98%) as a colorless oil.

58-5: S,S-2-{2-[4-(3,5-Difluoro-phenoxy)-phenyl]-1-ethoxycarbonyl-ethylamino}-4-methyl-pentanoic acid benzyl ester. A solution of copper(II) acetate (22 mg, 0.121 mmol), 3,5-difluorophenyl boronic acid (57 mg, 0.363 mmol), leucyl tyrosine 58-2 (50 mg, 0.121 mmol) and 2,6-lutidine (70 mL, 0.605 mmol) in CH$_2$Cl$_2$ in the presence of 4 Å beaded molecular sieves was stirred overnight under ambient atmosphere. The resulting blue-green solution was diluted with ethyl acetate, filtered to remove the solids and concentrated to give a green oil which was purified by silica chromatography (10% ethyl acetate in hexanes eluant) to give the desired product (58-5, 59 mg, 91%).

LCMS Conditions:

Spectra were run on a Phenominex Luna 5μ C18 50×4.6 mm column on a Hewlett-Packard HP1100 at 3.5 ml/min for a 4 minute run using the following gradients:

Method Polar Formic Acid (PFA): Acetonitrile containing zero to 50 percent 0.1% formic acid in water.

Method Formic Acid (FA): Acetonitrile containing zero to 100 percent 0.1% formic acid in water.

Method Nonpolar Formic Acid (NFA): Acetonitrile containing 70 to 100 percent 0.1% formic acid in water.

Method Polar Ammonium Acetate (PAA): Acetonitrile containing zero to 50 percent 10 mM ammonium acetate in water.

Method Ammonium Acetate (AA): Acetonitrile containing zero to 100 percent 10 mM ammonium acetate in water.

Method Nonpolar Ammonium Acetate (NAA): Acetonitrile containing 70 to 100 percent 10 mM ammonium acetate in water.

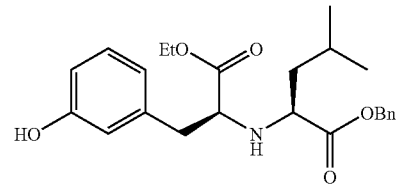

S,S-2-[1-Ethoxycarbonyl-2-(3-hydroxy-phenyl)-ethylamino]-4-methyl-pentanoic acid benzyl ester (58-6). The title compound was prepared from the reaction of L-orthotyrosine with O-trifluoromethanesulfonyl-2-hydroxyisocaproic acid benzyl ester as described above to give the title compound, which following flash chromatography (silica prepacked ISCO™ cartridge, hexanes: ethyl acetate eluant) provided the title compound as a colorless oil.

$^1$HNMR (300 MHz, CDCl$_3$) δ 7.39 (m, 5H), 7.11 (t, 1H, J=7.7 Hz), 6.67 (m, 3H,), 5.1 (dd, 2H, J=6.1, 12.4 Hz), 4.10 (q, 2H, J=7.1 Hz), 3.54 (t, 1H, J=7.2 Hz), 3.38 (t, 1H, J=6.9 Hz), 2.89 (dddd, 2H, J=6.9, 7.7, 13.5, 15.8 Hz), 1.67 (m, 1H), 1.46 (t, 2H, J=6.9 Hz), 1.16 (t, 2H, J=7.2 Hz), 0.86 (t, 6H, J=7.1 Hz). LCMS: Method FA Rt=2.74 min, MH$^+$=414.

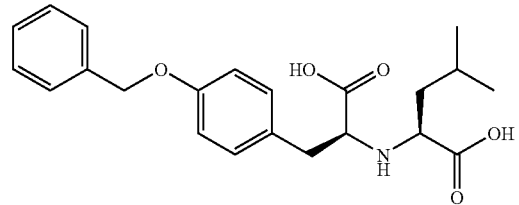

Compound KQ

S,S-2-[2-(4-Benzyloxy-phenyl)-1-carboxy-ethylamino-]4-methyl-pentanoic acid (Compound KQ). The title compound was prepared from the reaction of O-benzyl-tyrosine with O-trifluoromethanesulfonyl-2-hydroxyisocaproic acid benzyl ester as described above, followed by lithium hydroxide mediated hydrolysis. NMR data was consistent with the desired product. LCMS: Method AA Rt=1.42 min, MH$^+$=386.

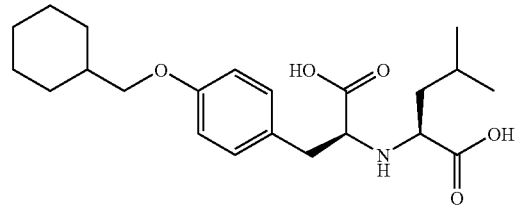

Compound KR

S,S-2-[1-Carboxy-2-(4-cyclohexylmethoxy-phenyl)-ethylamino]-4-methyl pentanoic acid (Compound KR). The title compound was prepared from the reaction of benzyl ester 58-2 with bromomethyl cyclohexane as described above, followed by lithium hydroxide mediated hydrolysis. NMR data was consistent with the desired product. LCMS: Method AA Rt=1.66 min, MH⁺=392.

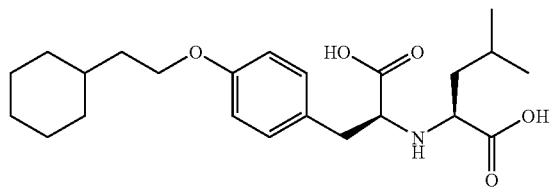

S,S-2-{1-Carboxy-2-[4-(2-cyclohexyl-ethoxy)-phenyl]-ethylamino}-4-4methyl pentanoic acid. The title compound was prepared from the reaction of benzyl ester 58-2 with bromoethyl cyclohexane as described above, followed by lithium hydroxide mediated hydrolysis. NMR data was consistent with the desired product. LCMS: Method AA Rt=1.78 min, MH⁺=406.

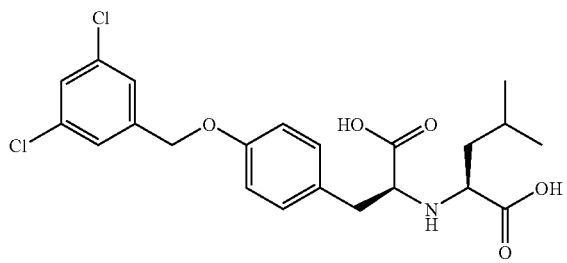

S,S-2-{1-Carboxy-2-[4-(3,5-dichlorobenzyloxy)-phenyl]-ethylamino}-4-methyl pentanoic acid. The title compound was prepared from the reaction of benzyl ester 58-2 with 3,5 dichlorobenzyl bromide as described above, followed by lithium hydroxide mediated hydrolysis. NMR data was consistent with the desired product. LCMS: Method AA Rt=1.75 min, MH⁺=454.

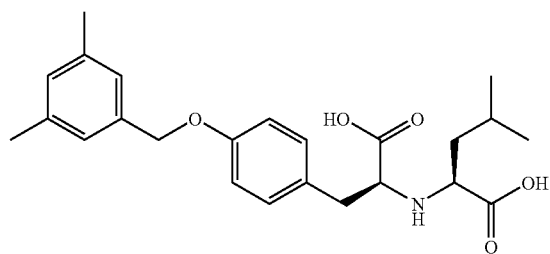

S,S-2-{1-Carboxy-2-[4-(3.5-dimethylbenzyloxy)-phenyl]-ethylamino}-4-methyl pentanoic acid. The title compound was prepared from the reaction of benzyl ester 58-2 with 3,5 dimethylbenzyl bromide as described above, followed by lithium hydroxide mediated hydrolysis. NMR data was consistent with the desired product. LCMS: Method AA Rt=1.70 min, MH⁺=414.

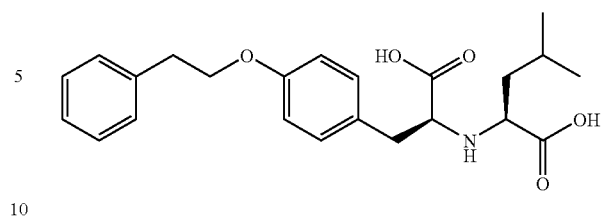

S,S-2-[1-Carboxy-2-(4-phenethyloxyphenyl)-ethylamino]-4-methyl pentanoic acid. The title compound was prepared from the reaction of benzyl ester 58-2 with bromoethyl benzene as described above, followed by lithium hydroxide mediated hydrolysis. NMR data was consistent with the desired product. LCMS: Method AA Rt=1.62 min, MH⁺=400.

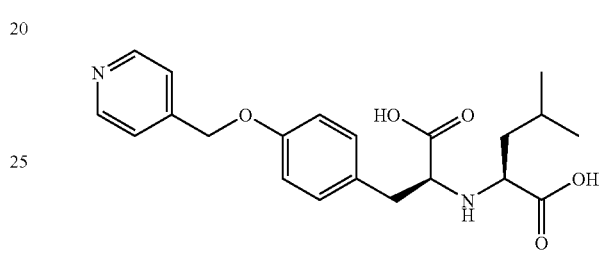

S,S-2-{1-Carboxy-2[4-(pyridin-4-ylmethoxy)-phenyl]-ethylamino}-4-methyl pentanoic acid. The title compound was prepared from the reaction of benzyl ester 58-2 with 4-hydroxymethylpyridine as described above, followed by lithium hydroxide mediated hydrolysis. NMR data was consistent with the desired product. LCMS: Method AA Rt=1.04 min, MH⁺=387.

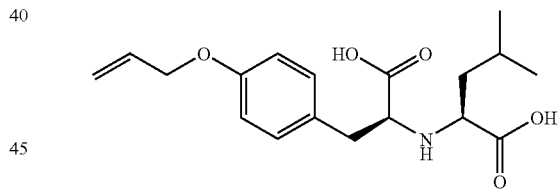

S,S-2-[2-(4-Allyloxy-phenyl)-1-1carboxy-ethylamino]-4-methyl pentanoic acid. The title compound was prepared from the reaction of O-allyl-tyrosine with O-trifluoromethanesulfonyl-2-hydroxyisocaproic acid benzyl ester as described above, followed by lithium hydroxide mediated hydrolysis. NMR data was consistent with the desired product. LCMS: Method AA Rt=1.10 min, MH⁺=336.

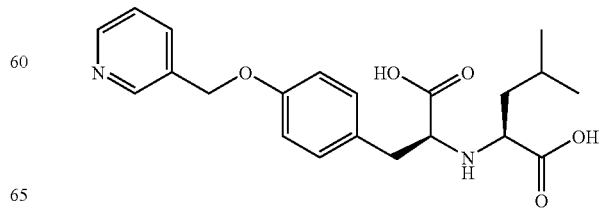

Compound LX

S,S-2-{1-Carboxy-2-[4-(pyridin-3-ylmethoxy)-phenyl]-ethylamino}-4-methyl pentanoic acid (Compound LX). The title compound was prepared from the reaction of benzyl ester 58-2 with 3-hydroxymethylpyridine as described above, followed by lithium hydroxide mediated hydrolysis. NMR data was consistent with the desired product. LCMS: Method AA Rt=1.04 min, MH$^+$=387

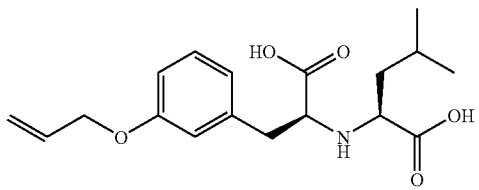

Compound NB

S,S-2-[2-(3-Allyloxy-phenyl)-1-carboxy-ethylamino]-4-methyl pentanoic acid (Compound NB). The title compound was prepared from the reaction of benzyl ester 58-6 with allyl bromide as described above, followed by lithium hydroxide mediated hydrolysis. NMR data was consistent with the desired product. LCMS: Method FA Rt=1.61 min, MH$^+$=336.

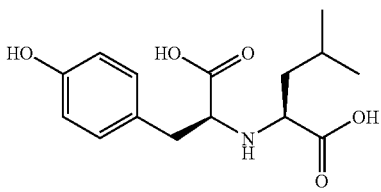

S,S-2-[1-Carboxy-2-(4-hydroxy-phenyl)-ethylamino]-4-methyl pentanoic acid. The title compound was prepared from the lithium hydroxide mediated hydrolysis of benzyl ester 58-2. NMR data was consistent with the desired product. LCMS: Method FA Rt=0.86 min, MH$^+$=296.

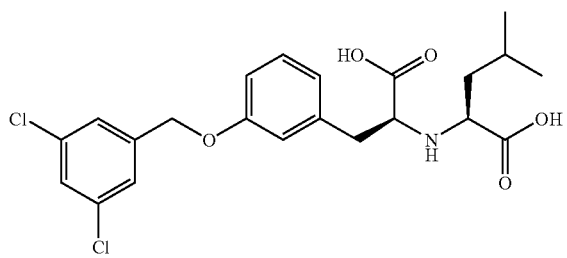

S,S-2-{1-Carboxy-2-[3,5-dichloro-benzyloxy)-phenyl]-ethylamino}-4-methyl pentanoic acid. The title compound was prepared from the reaction of benzyl ester 58-6 with 3,5 dichlorobenzyl bromide as described above, followed by lithium hydroxide mediated hydrolysis. NMR data was consistent with the desired product. LCMS: Method FA Rt=2.33 min, MH$^+$=454.

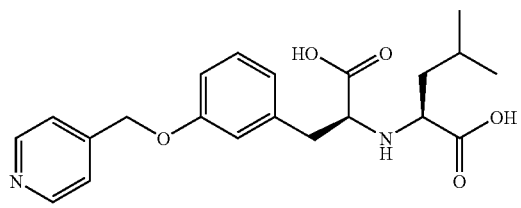

Compound NZ

S,S-2-{1-Carboxy-2-[3-(pyridin-4-ylmethoxy)-phenyl]-ethylamino}-4-methyl pentanoic acid (Compound NZ). The title compound was prepared from the reaction of benzyl ester 58-6 with 4-hydroxymethylpyridine as described above, followed by lithium hydroxide mediated hydrolysis. NMR data was consistent with the desired product. LCMS: Method FA Rt=0.77 min, MH$^+$=387. Anal. Calcd. Expected for $C_{22}H_{23}F_2NO_5Li_2$: C, 58.01, H, 5.80, N, 6.44, found C, 58.21, H, 5.9 6.22.

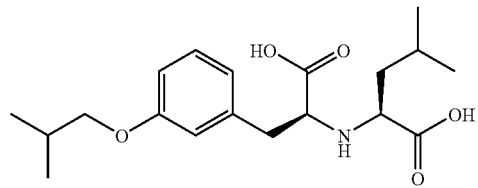

S,S-2-[1-Carboxy-2-(3-isobutoxy-phenyl)-ethylamino]-4-methyl pentanoic acid. The title compound was prepared from the reaction of benzyl ester 58-6 with isobutyl bromide as described above, followed by lithium hydroxide mediated hydrolysis. NMR data was consistent with the desired product. LCMS: Method FA Rt=1.76 min, MH$^+$= 352. Anal. Calcd. For $C_{19}H_{29}Li_2NO_5·H_2O$ expected C, 59.85; H, 7.67, N, 3.67. Found: C, 58.55; H, 7.40; N, 3.61.

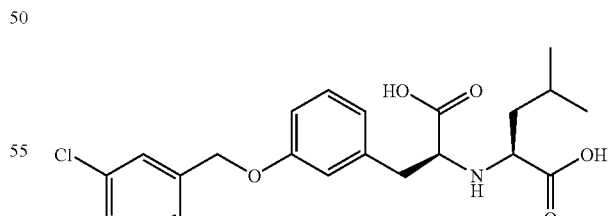

Compound OO

S,S-2-{1-Carboxy-2-[3-(3-chloro-benzyloxy)-phenyl]-ethylamino}-4-methyl-pentanoic acid (Compound OO). The title compound was prepared from the reaction of benzyl ester 58-6 with 3-chlorobenzyl bromide as described above, followed by lithium hydroxide mediated hydrolysis. NMR data was consistent with the desired product. LCMS: Method FA Rt=2.05 min, MH$^+$=420. Anal. Calcd. For C$_{22}$H$_{34}$Li$_2$NO$_5$ expected C, 61.2; H, 5.60, N, 3.24. Found: C, 60.87; H, 5.91; N, 3.24.

benzyl ester 58-2 and 3,5-difluorophenyl boronic acid as described above, followed by lithium hydroxide mediated hydrolysis. NMR data was consistent with the desired product. LCMS: Method FA Rt=2.00 min, MH$^+$=408.

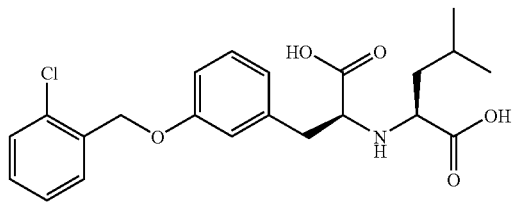

Compound OP

S,S-2-{1-Carboxy-2-[3-(2-chloro-benzyloxy)-phenyl]-ethylamino}-4-methyl-pentanoic acid (Compound OP). The title compound was prepared from the reaction of benzyl ester 58-6 with 2-chlorobenzyl bromide as described above, followed by lithium hydroxide mediated hydrolysis. NMR data was consistent with the desired product. LCMS: Method FA Rt=2.06 min, MH$^+$=420. For C$_{22}$H$_{34}$Li$_2$NO$_5$·1.5H$_2$O expected C, 61.61; H, 6.34, N, 3.27. Found: C, 61.8; H, 6.22; N, 3.7.

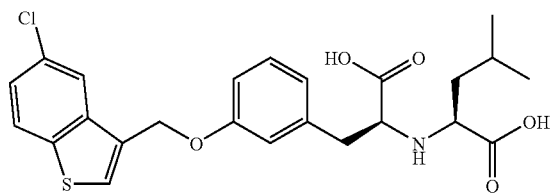

Compound PH

S,S-2-{1-Carboxy-2-[3-(5-chloro-benzo[b]thiophen-3-yl-methoxy)-phenyl]-ethylamino}-4-methyl-pentanoic acid (Compound PH). The title compound was prepared from the reaction of benzyl ester 58-6 with 3-chlorobenzyl bromide as described above, followed by lithium hydroxide mediated hydrolysis. NMR data was consistent with the desired product. LCMS: Method FA Rt=2.34 min, MH$^+$=476.

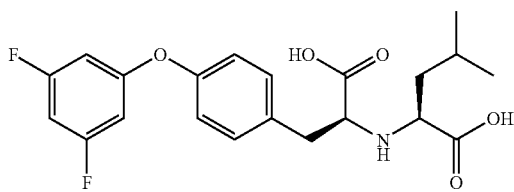

S,S-2-{2-[4-(3,5-Difluoro-phenoxy)-phenyl]-1-ethoxycarbonyl-ethylamino}-4-methyl-pentanoic acid benzyl ester. The title compound was prepared from the reaction of

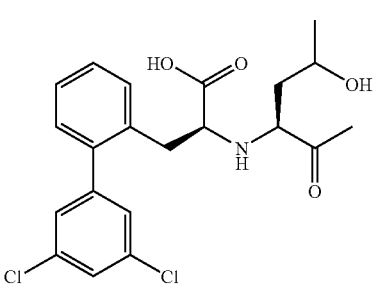

Compound PT

S,S-2-[1-Carboxy-2-(3',5'dichloro-biphenyl-2-yl)-ethylamino]-4-methyl-pentanoic acid (Compound PT). The title compound was prepared from the reaction of 2-bromoalanine methyl ester with 3,5-dichloroboronic acid as described in method above, followed by lithium hydroxide mediated hydrolysis. NMR data was consistent with the desired product. LCMS: Method FARt=2.18 min, MH$^+$=425.

Example 39

Synthesis of Ester Prodrugs

Synthesis of Mono Methyl Esters

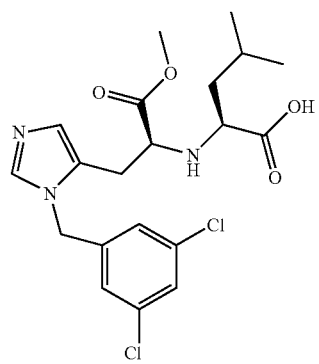

Compound KX (S,S) 2-{2-[3-(3,5-Dichloro-benzyl)-3H-imidazol-4-yl]-1-methoxycarbonyl-ethylamino}-4-methyl-pentanoic acid (Compound KX) Compound KX is synthesized as described above in Scheme 25. NMR data for the final product was consistent with the depicted structure. LCMS MH+=, 442 Rt=1.48 min.

Synthesis of Methyl and Benzyl Diesters

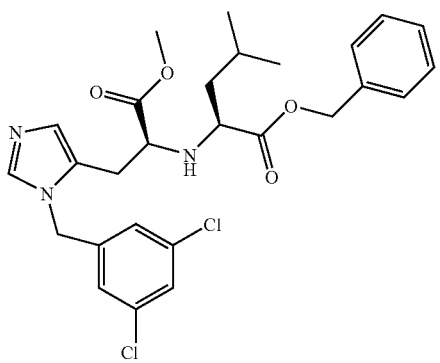

(S,S) 2-{2-[3-(3,5-Dichloro-benzyl)-3H-imidazol-4-yl]-1-methoxycarbonyl-ethylamino}-4-methyl-pentanoic acid benzyl ester. The compound is synthesized as described above in Scheme 25. NMR data for the title compound was consistent with the structure. LCMS MH+=532, Rt=3.29 min.

Alternate Synthesis of Mono Ester Prodrugs:

Scheme 59

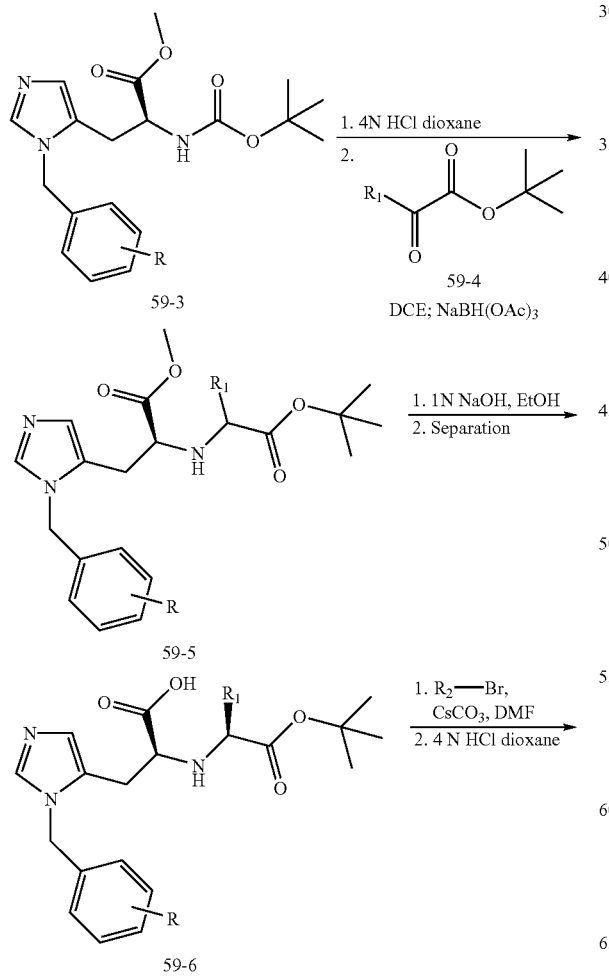

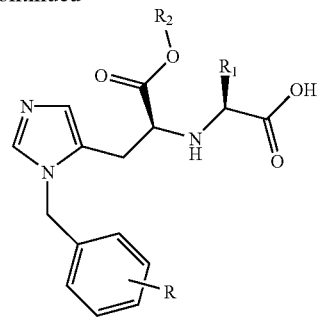

Mono esters prodrugs were synthesized via the general procedure outlined in Scheme 59. N-Boc cleavage of the protected histidine derivative (59-3) using 4 N HCl in dioxane (15–20 eq) followed by reductive amination with a t-butyl keto ester (as described earlier; 2 eq keto ester, 2 eq NaBH(OAc)$_3$, 0.1 M DCE) provided the differentially protected diester (59-5) as an inseparable mixture of diastereomers. Hydrolysis of the methyl ester using 1N aqueous NaOH (3 eq) in EtOH (equimolar with the aqueous NaOH) provided the mono t-butyl ester, 59-6. At this point, the diastereomers were separated using HP-20 chromatography. The S,S mono t-butyl ester (59-6) (1 eq, mmol) was then alkylated using CsCO$_3$ (>2 eq) and an alkyl or benzyl bromide (1 eq) in DMF (0.1 M) to provide the desired diester precursor to the mono ester prodrug. Cleavage of the t-butyl ester using 4N HCl in dioxane (>10 eq; the reaction mixture was resubjected as necessary to achieve complete conversion to the acid) followed by purification (recrystallization or HPLC) provided the desired mono ester 59-7 in >99% purity.

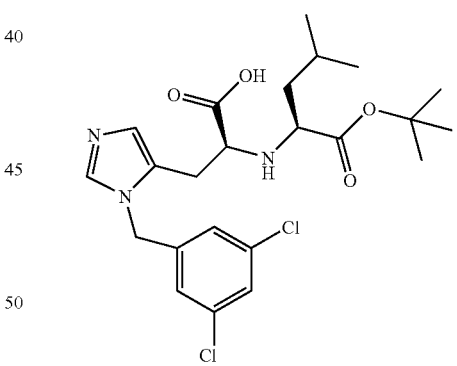

59-6: (S,S) 2-{1-Carboxy-2-[3-(3,5-dichloro-benzyl)-3H-imidazol-4-yl]-ethylamino}-4-methyl-pentanoic acid tert-butyl ester. The title compound was prepared as described in Scheme 59. The protected histidine derivative (59-3, 10 g, 22 mmol) was treated with 4N HCl in dioxane (100 mL, 400 mmol, 18 eq) for 1 hour. The resulting slurry was concentrated and the residue was resuspended in ether and concentrated (two times) to give the dihydrochloride product as a white powder (8.6 g, 97%). The dihydrochloride salt of N-3-(3,5-dichlorobenzyl)-histidine methyl ester (8.6 g, 21.5 mmol) was suspended in dichloroethane (200 mL, 0.1 M) and 4-methyl-2-oxo-pentanoic acid t-butyl ester (8.0 g, 43 mmol) was added slowly. This mixture was stirred for 1 hour, then NaBH(OAc)$_3$ (9.1 g, 43 mmol) was added portion-wise over 10 minutes. After two hours, the reaction mixture became clear and the reaction was about half way done by LCMS. After 16 hours, the reaction was complete and saturated NaHCO$_3$ was added to bring the mixture to pH 7–8. The mixture was stirred for 1 hour then the layers were separated. The aqueous layer was further extracted with CH$_2$Cl$_2$ twice. The combined organic layers washed with brine once, dried with MgSO$_4$, and fitered. Concentration in vacuo provided the crude diester as a yellow oil. Chromotography (ISCO (0–10% MeOH in CH$_2$Cl$_2$)) provided 9.3 g of the diester (87%). The diester (59-5, 9.3 g, 18.8 mmol) was dissolved in EtOH (60 mL) and 1N NaOH (60 mL) was added. After 12 hours the reaction mixture was concentrated completely. Purification and separation of diastereomers was accomplished with HP-20 (water-methanol gradient) and 4.2 g (46%) of the desired S,S diastereomer (59-6) was recovered. LCMS MH+=484, Rt=1.71 min.

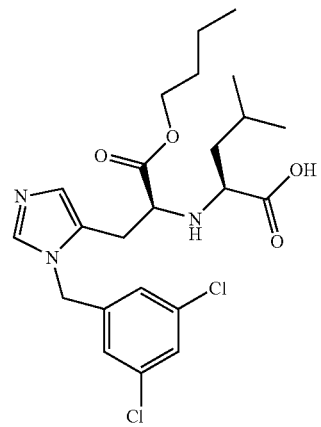

Compound LD

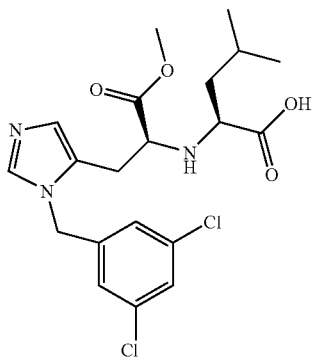

Compound MY (S,S) 2-{2-[3-(3,5-Dichloro-benzyl)-3H-imidazol-4-yl]-1-ethoxycarbonyl-ethylamino}-4-methyl-pentanoic acid (Compound MY). The title compound was prepared as described in Scheme 59. The mono acid (59-6 200 mg, 0.41 mmol) was dissolved in DMF (4 mL, 0.1 M) and Cs$_2$CO$_3$ (325 mg, 1 mmol) was added. The mixture was stirred for 1 hour, then ethyl bromide was added (30 uL, 0.41 mmol). After 18 hours the reaction mixture was diluted with EtOAc and H$_2$O. The layers were separated and the organic layer was further washed with H$_2$O twice, then brine, then dried over MgSO$_4$. Concentration in vacuo provided the diester as a yellow oil which was purified using the ISCO chromatography system (1–10% MeOH in CH$_2$Cl$_2$) to yield 150 mg of the diester (71%). The diester (150 mg, 0.29 mmol) was dissolved in 4N HCl (5 mL) and the t-butyl ester cleavage was monitored by LCMS. After 48 hours, the reaction mixture was concentrated completely, then resubjected to 4N HCl (5 mL). After 24 hours the reaction was complete and the reaction mixture was concentrated completely and purified (ISCO chromatography (1–10% MeOH in CH$_2$Cl$_2$)) to give 75 mg (55%) of the desired mono ester 59-7 (R-Et, Compound MY). NMR data for the final product as well as the intermediates was consistent with the depicted structure. LCMS MH+=456, Rt=1.93 min.

(S,S) 2-{1-Butoxycarbonyl-2-[3-(3,5-dichloro-benzyl)-3H-imidazol-4-yl]-ethylamino}-4-methyl-pentanoic acid (Compound LD). Prepared according to Scheme 59 and the procedure above. The mono acid (59-6, 59-8, 200 mg, 0.41 mmol) was dissolved in DMF (4 mL, 0.1 M) and CsCO$_3$ (325 mg, 1 mmol) was added. The mixture was stirred for 1 hour then butyl bromide was added (44 uL, 0.41 mmol). After 18 hours the reaction mixture was diluted with EtOAc and H$_2$O. The layers were separated and the organic layer was further washed with H$_2$O twice, then brine, then dried over MgSO$_4$. Concentration in vacuo provided the diester as a yellow oil which was purified using the ISCO (1–10% MeOH in CH$_2$Cl$_2$) to yield 165 mgs of the diester (74%). The diester (165 mg, 0.34 mmol) was dissolved in 4N HCl (5 mL) and the t-butyl ester cleavage was monitored by LCMS. After 48 hours, the reaction mixture was concentrated completely, then resubjected to 4N HCl (5 mL). After 24 hours the reaction was complete and the reaction mixture was concentrated completely and purified by ISCO chromatography (1–10% MeOH in CH$_2$Cl$_2$) to give 72 mg of the mono ester (43%). NMR data for the final product as well as the intermediates was consistent with the depicted structure. LCMS MH+=484, Rt=2.15 min.

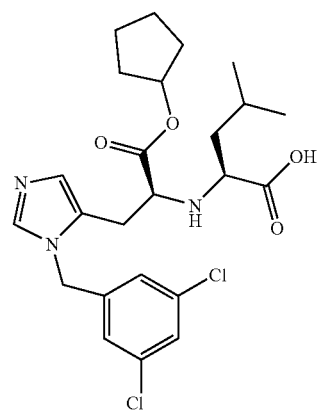

Compound LQ (S,S) 2-{1-Cyclopentyloxycarbonyl-2-[3-(3,5-dichloro-benzyl)-3H-imidazol-4-yl]-ethylamino}-4-methyl-pentanoic acid (Compound LQ). Prepared according to Scheme 59 and the procedure above. The mono acid (59-6, 59-8, 190 mg, 0.37 mmol) was dissolved in DMF (4 mL, 0.1 M) and $Cs_2CO_3$ (325 mg, 1 mmol) was added. The mixture was stirred for 1 hour then cyclopentyl bromide was added (39 uL, 0.37 mmol). After 18 hours the reaction mixture was diluted with EtOAc and $H_2O$. The layers were separated and the organic layer was further washed with $H_2O$ twice, then brine, then dried over $MgSO_4$ and filtered. Concentration in vacuo provided the diester as a yellow oil which was purified (ISCO (1–10% MeOH in $CH_2Cl_2$)) to yield 122 mgs of the diester (60%). The diester (122 mg, 0.22 mmol) was dissolved in 4N HCl (5 mL) and the t-butyl ester cleavage was monitored by LCMS. After 48 hours, the reaction mixture was concentrated completely, then resubjected to 4N HCl (5 mL). After 24 hours the reaction was complete and the reaction mixture was concentrated completely by HPLC to give 65 mg of the mono ester (60%). NMR data for the final product, as well as the intermediates, was consistent with the depicted structure. LCMS MH+=496, Rt=1.78 min.

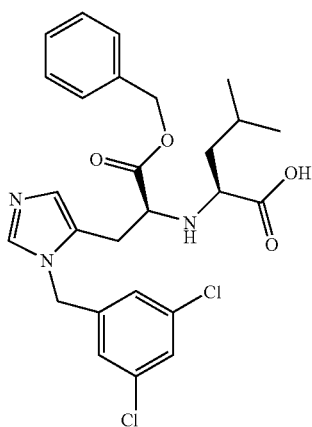

Compound LB (S,S) 2-{1-Benzyloxycarbonyl-2-[3-(3,5-dichloro-benzyl)-3H-imidazol-4-yl]-ethylamino}-4-methyl-pentanoic acid (Compound LB). Prepared according to Scheme 59 and the procedure above. The mono acid (59-6, 500 mg, 1.0 mmol) was dissolved in DMF (10 mL, 0.1 M) and $CsCO_3$ (700 mg, 2.2 mmol) was added. The mixture was stirred for 1 hour then benzyl bromide was added (118 uL, 1.0 mmol). After 18 hours the reaction mixture was diluted with EtOAc and $H_2O$. The layers were separated and the organic layer was further washed with $H_2O$ twice, then brine, then dried over $MgSO_4$. Concentration in vacuo provided the diester as a yellow oil which was purified using the ISCO chromatography system (1–10% MeOH in $CH_2Cl_2$) to yield 400 mg of the diester (70%). The diester (400 mg, 0.70 mmol) was dissolved in 4N HCl in dioxane (10 mL) and the t-butyl ester cleavage was monitored by LCMS. After 36 hours, the reaction mixture was concentrated completely, then resubjected to 4N HCl in dioxane (5 mL). After 24 hours the reaction was complete and the reaction mixture was concentrated completely and purified HPLC to give 205 mg of the mono ester (56%). NMR data for the final product as well as the intermediates was consistent with the depicted structure. LCMS EI+ 518, Rt=1.85 min.

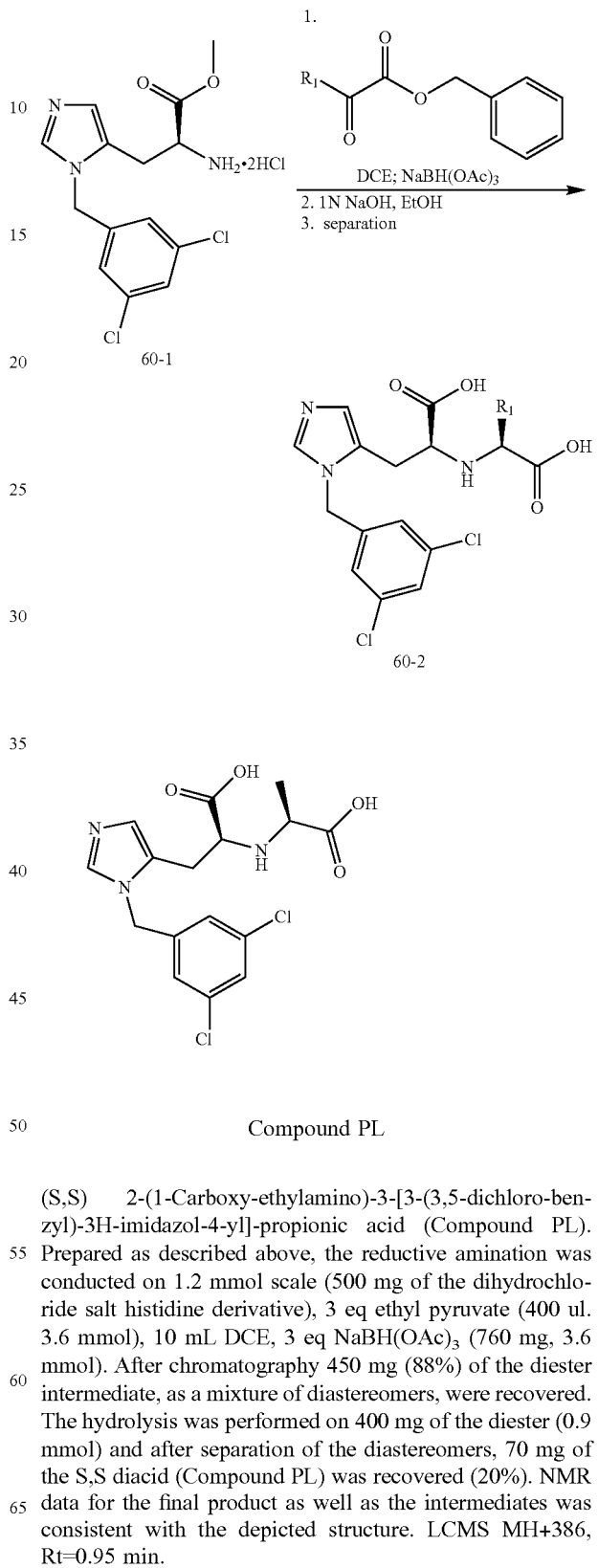

(S,S) 2-(1-Carboxy-ethylamino)-3-[3-(3,5-dichloro-benzyl)-3H-imidazol-4-yl]-propionic acid (Compound PL). Prepared as described above, the reductive amination was conducted on 1.2 mmol scale (500 mg of the dihydrochloride salt histidine derivative), 3 eq ethyl pyruvate (400 ul. 3.6 mmol), 10 mL DCE, 3 eq $NaBH(OAc)_3$ (760 mg, 3.6 mmol). After chromatography 450 mg (88%) of the diester intermediate, as a mixture of diastereomers, were recovered. The hydrolysis was performed on 400 mg of the diester (0.9 mmol) and after separation of the diastereomers, 70 mg of the S,S diacid (Compound PL) was recovered (20%). NMR data for the final product as well as the intermediates was consistent with the depicted structure. LCMS MH+386, Rt=0.95 min.

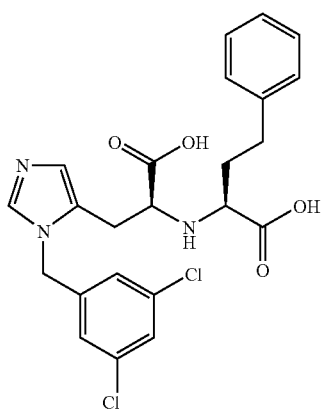

Compound PN (S,S) 2-{1-Carboxy-2-[3-(3,5-dichloro-benzyl)-3H-imidazol-4-yl]-ethylamino}-4-phenyl-butyric acid (Compound PN). Prepared as described above, the reductive amination was conducted on 1.2 mmol scale (500 mg of the dihydrochloride salt histidine derivative), 3 eq 2-oxo-4-phenyl-butyric acid ethyl ester (680 ul. 3.6 mmol), 10 mL DCE, 3 eq NaBH(OAc)$_3$ (760 mg, 3.6 mmol). After chromatography 490 mgs (79%) of the diester intermediate (as a mixture of diastereomers) was recovered. The hydrolysis was performed on 490 mg of the diester (0.95 mmol) and after separation of the diastereomers, 135 mg of the S,S diacid (Compound PN) was recovered (30%). NMR data for the final product as well as the intermediates was consistent with the depicted structure. LCMS EI+ 476, Rt=1.46 min (S,R diacid LCMS EI+ 476, Rt=1.56).

Imidazole Derivatives:

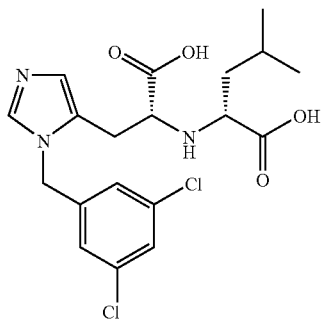

Compound MZ (R,R)-2-{1-Carboxy-2-[3-(3,5-dichloro-benzyl)-3H-imidazol-4-yl]-ethylamino}-4-methyl-pentanoic acid (Compound MZ). Prepared as described previously. NMR data for the final product as well as the intermediates was consistent with the depicted structure. LCMS MH+ 428, Rt=1.18 min (R,S diacid LCMS MH+=428, Rt=1.31 min) (Method FA).

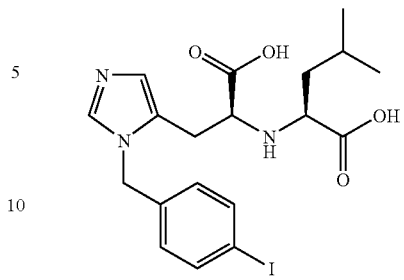

(S,S) 2-{1-Carboxy-2-[3-(4-iodo-benzyl)-3H-imidazol-4-yl]-ethylamino}-4-methyl-pentanoic acid. Prepared as described above. NMR data for the final product as well as the intermediates was consistent with the depicted structure. LCMS MH+, Rt=min (S,R diacid LCMSMH+, Rt=) (Method FA).

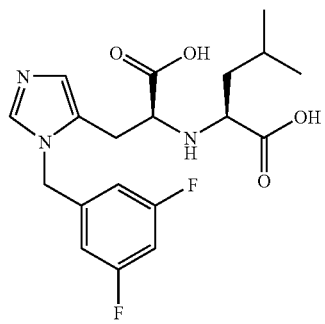

Compound NJ (S,S) 2-{1-Carboxy-2-[3-(3,5-difluoro-benzyl)-3H-imidazol-4-yl]-ethylamino}-4-methyl-pentanoic acid (Compound NJ). NMR data for the final product as well as the intermediates was consistent with the depicted structure. LCMS MH+ 396, Rt=0.88 min (S,R diacid LCMS MH+ 396, Rt=1.05) (Method FA).

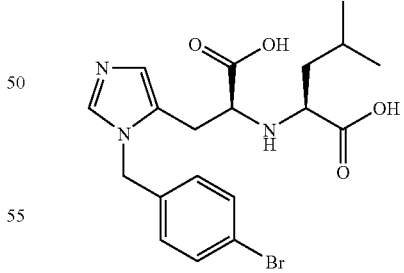

Compound PD (S,S) 2-{2-[3-(4-Bromo-benzyl)-3H-imidazol-4-yl]-1-carboxy-ethylamino}-4-methyl-pentanoic acid (Compound PD). Prepared as described above. NMR data for the final product as well as the intermediates was consistent with the depicted structure. LCMS MH+, 438, 440 Rt=1.05 min (S,R diacid LCMS MH+ 438, 440, Rt=1.18) (Method FA).

Scheme 61

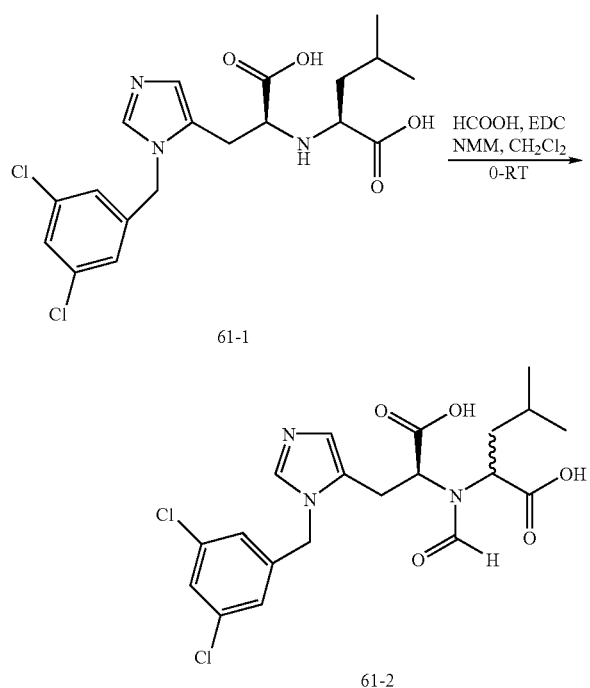

(S,S) 2-({1-Carboxy-2-[3-(3,5-dichloro-benzyl)-3H-imidazol-4-yl]-ethyl}-formyl-amino)-4-methyl-pentanoic acid. EDC (138 mg, 0.72 mmol) was dissolved in CH$_2$Cl$_2$ (2 mL, 0.15 M), formic acid (56 uL, 1.5 mmol) was added and the reaction mixture was cooled to 0 C. After 10 minutes, the diacid (61-1, 150 mg, 0.3 mmol) was added followed by N-methyl morpholine (160 uL, 1.5 mmol). The reaction mixture was allowed to warm to RT overnight. After 18 hours, the reaction was not complete. Additional formic acid and EDC (premixed, 11 uL formic acid, 29 mg EDC, 0.5 mL CH$_2$Cl$_2$) were added (1 additional equivalent). After 24 hours, the reaction had gone to completion. The reaction mixture was diluted with water and the layers were separated. The product partitioned into the aqueous layer. Ion exchange chromatography provided the product as a 2:1 mixture of epimers. NMR data for the title compound was consistent with the depicted structure. LCMS MH+, 456 Rt=1.71 min (Method FA).

Scheme 62

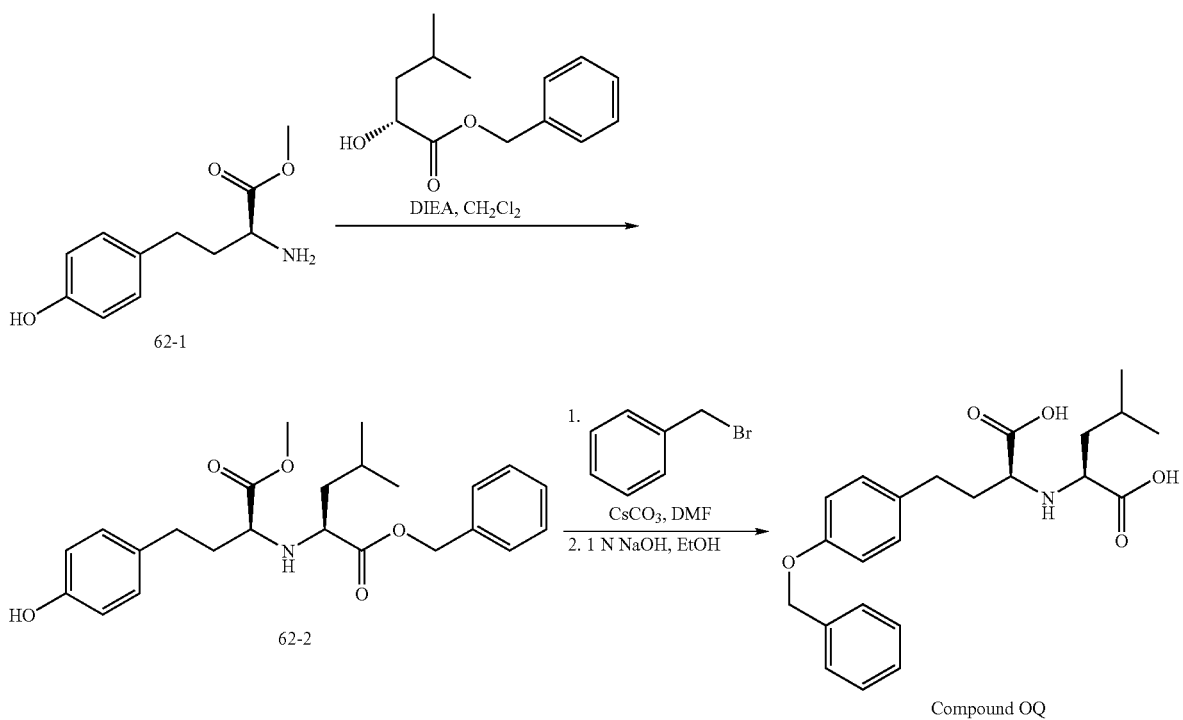

(S,S) 2-[3-(4-Benzyloxy-phenyl)-1-carboxy-propylamino]-4-methyl-pentanoic acid (Compound OQ). The title compound was synthesized via Scheme 62. NMR data for the title compound was consistent with the depicted structure. LCMS MH+, 400 Rt=1.98 min (Method FA).

4-Amino-Phenylalanine Derivatives

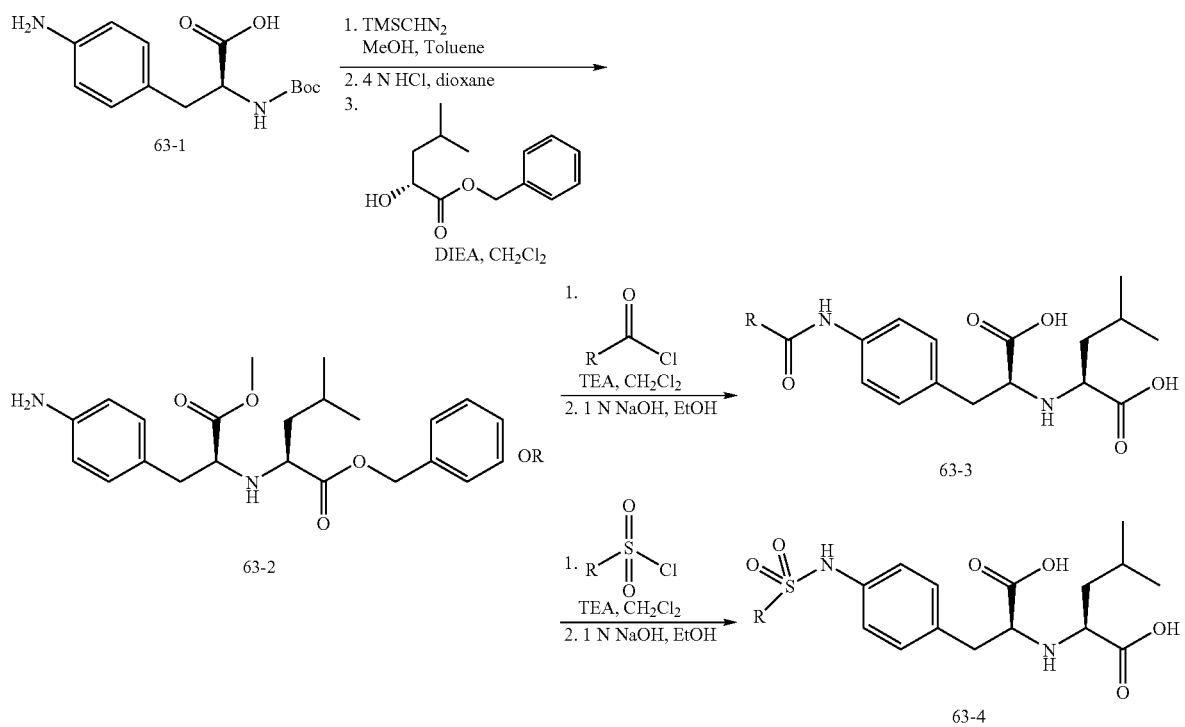

4-Amino phenylalanine derivatives were prepared according to Scheme 63. Boc protected 4-amino phenylalanine (63-1, 5.0 g, 17.8 mmol) was dissolved in methanol (30 mL, 0.6 M) and toluene (60 mL, 0.3 M) then TMSCHN$_2$ (2 M solution in hexanes, 10 mL, 20 mmol) was added slowly. After 2 hours the reaction mixture was concentrated completely and purified using the ISCO chromatography system. The resulting pale yellow oil was dissolved in 4N HCl in dioxane (100 mL). After 2 hours, the reaction mixture was concentrated completely and resuspended in ether and concentrated twice. The resulting primary amine (HCl salt) was coupled with the leucinyl triflate as described earlier to provide the diester 63-2. The aniline nitrogen was then coupled with either an acid chloride or a sulfonyl chloride to provide 63-3 or 63-4 following hydrolysis.

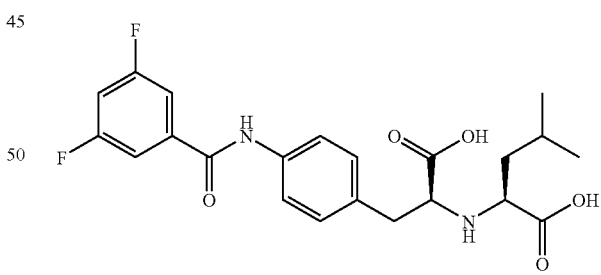

Compound OX (S,S) 2-{1-Carboxy-2-[4-(3,5-difluoro-benzoylamino)-phenyl]-ethylamino}-4-methyl-pentanoic acid (Compound OX). The diester aniline (140 mg, 0.35 mmol) was dissolved in CH$_2$Cl$_2$ (4 mL, 0.1 M) and TEA (55 uL, 0.39 mmol) then 3,5-difluorobenzoyl chloride (42 uL, 0.35 mmol) was added slowly. After 4 hours, the reaction mixture was diluted with EtOAc and washed with saturated NaHCO$_3$, water and brine, then dried over MgSO$_4$. The crude product was purified using the ISCO (5–25% EtOAc in hexane) to provide 154 mgs of the coupled product (82%). This diester was then dissolved in EtOH (2 mL) and NaOH (1N, 2 mL) to provide the diacid. After 18 hours, the reaction mixture was concentrated completely and redissolved in a small amount of water. 6N HCl was then added to precipitate the diacid product. The precipitate was filtered and washed with a small amount of water then ether to give Compound OX as a white solid (50 mg, 41%). NMR data for the title compound was consistent with the depicted structure. LCMS MH+, 435 Rt=1.75 min (Method FA).

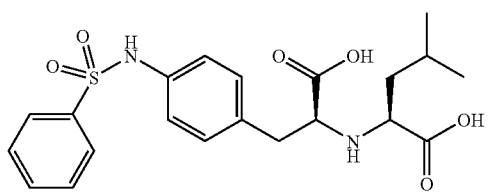

Compound PE (S,S) 2-[2-(4-Benzenesulfonylamino-phenyl)-1-carboxy-ethylamino]-4-methyl-pentanoic acid (Compound PE). The diester aniline (300 mg, 0.75 mmol) was dissolved in CH$_2$Cl$_2$ (10 mL) and TEA (153 uL, 1.1 mmol) then benzenesulfonyl chloride (95 uL, 0.75 mmol) was added slowly. After 6 hours, the reaction mixture was diluted with EtOAc and washed with saturated NaHCO$_3$, water and brine, then dried over MgSO$_4$. The crude product was purified using the ISCO (5–25% EtOAc in hexane) to provide 347 mgs of the coupled product (86%). This diester was then dissolved in EtOH (5 mL) and NaOH (1N, 5 mL) to provide the diacid. After 18 hours, the reaction mixture was concentrated completely and redissolved in a small amount of water. 6N HCl was then added to precipitate the diacid product. The precipitate was filtered and washed with a small amount of water then ether to give Compound PE as a white solid (136 mg, 48%). NMR data for the title compound was consistent with the depicted structure. LCMS MH+, 435 Rt=1.55 min (Method FA).

(S,S) 2-[1-Carboxy-2-(4-pyrrol-1-yl-phenyl)-ethylamino]-4-methyl-pentanoic acid (Compound PQ). The title compound was prepared according the methods described above. NMR data for the title compound was consistent with the depicted structure. LCMS MH+, 345 Rt=1.65 min (Method FA).

Scheme 64

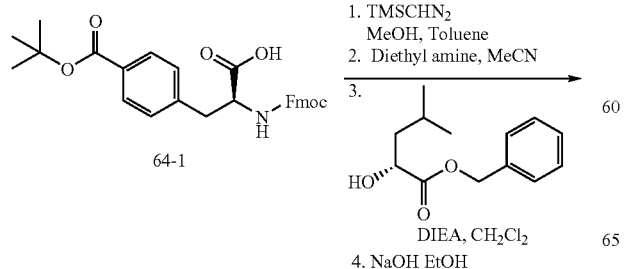

-continued

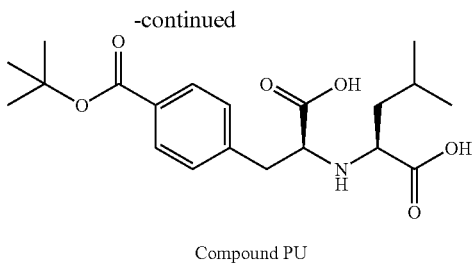

Compound PU (S,S) 4-[2-Carboxy-2-(1-carboxy-3-methyl-butylamino)-ethyl]-benzoic acid tert-butyl ester (Compound PU). The title compound was synthesized according to Scheme 64 and methods described above. Fmoc-p(CO$_2$-tBu)-Phe-OH (64-1, 1.0 g, 2.0 mmol) was dissolved in MeOH (3 mL) and toluene (10 mL) then TMSCHN$_2$ (2M in hexanes, 1.1 mL, 2.2 mmol) was added. After 6 hours, the reaction mixture was concentrated and the crude material was used without further purification. This crude material was dissolved in MeCN (5 mL) and diethylamine (5 mL). After 1 hour the reaction mixture was concentrated, redissolved in MeCN (3×) and reconcentrated then, the crude material was coupled directly with the leucyl triflate (as described previously). The crude amine was dissolved in CH$_2$Cl$_2$ (10 mL) and DIEA (0.53 mL, 3 mmol), then the triflate (700 mg, 2.0 mmol) was added. After 14 hours, the reaction mixture was diluted with EtOAc and washed with NaHCO$_3$, water and brine. The crude material was purified using the ISCO (5–30% EtOAc in hexane) to give 100 mg of the diester. The diester was dissolved in EtOH (3 mL), THF (3 mL) and NaOH (1N, 3 mL). After 16 hours, the reaction mixture was concentrated completely and redissolved in a small amount of H$_2$O. 6N HCl was carefully added to precipitate the product diacid, Compound PU. NMR data for the title compound was consistent with the depicted structure. LCMS MH+, 380 Rt=1.91 min (Method FA).

Example 40

Unnatural Amino Acid Derivatives

Scheme 65

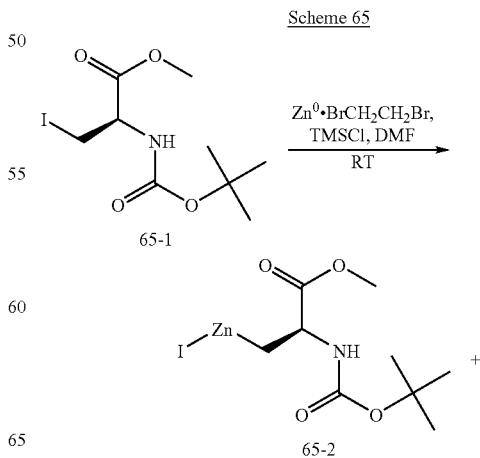

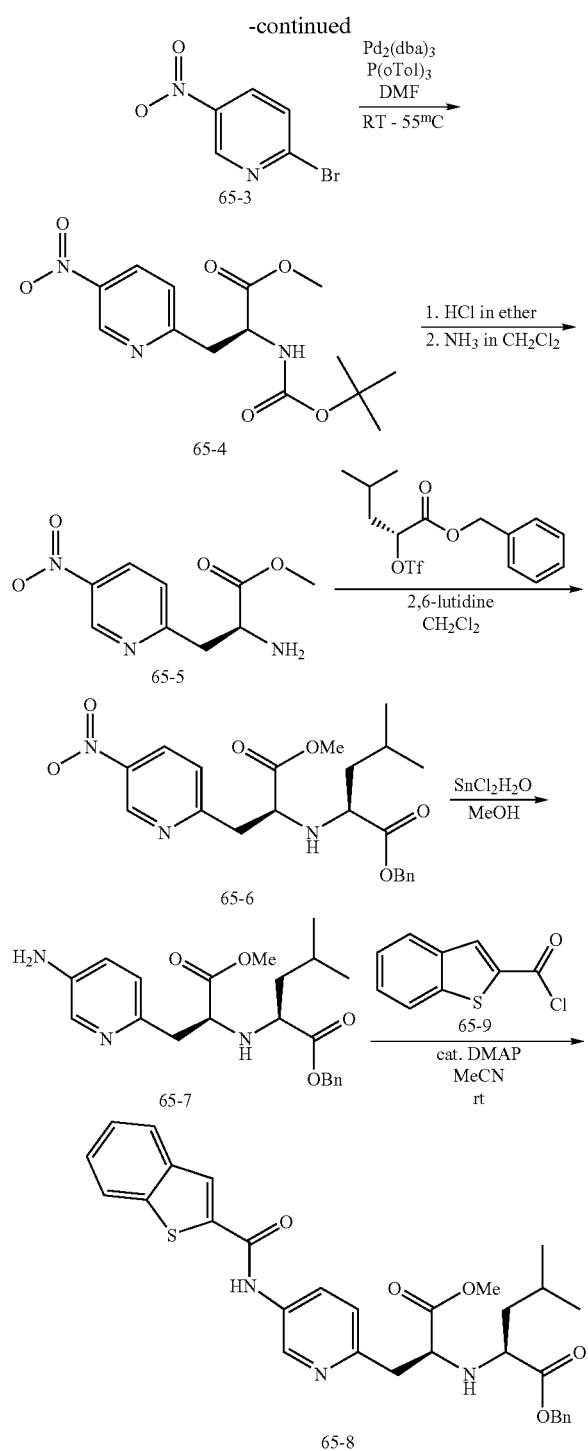

65-2: S-3-[2-tert-Butoxycarbonylamino-propionic acid methyl ester]iodozincate: Zinc powder (1.11 g, 18.2 mmol) was annealed in a round bottom flask under nitrogen and allowed to cool. To this was added dry DMF (3 mL) and dibromoethane (79 mL, 0.912 mmol). This mixture was stirred for 15 minutes during which time it was heated to reflux and allowed to cool three times. TMSCl (23 mL, 0.18 mmol) was then added and the mixture stirred for 30 minutes, after which time a solution of iodide 65-1 in DMF (1 mL) was added. This was stirred at room temperature until TLC indicated complete conversion of the iodide. The iodozincate was used without further purification.

65-4: 2-tert-Butoxycarbonylamino-3-(5-nitro-pyridin-2-yl)-propionic acid methyl ester: A solution of freshly prepared zincate 65-2 in DMF was thoroughly degassed while adding aryl bromide 65-3 (617 mg, 3.04 mmol) in DMF (3 mL) followed by solid triorthotolylphospine (278 mg, 0.912 mmol) then $Pd_2(dba)_3$ (61 mg, 0.06 mmol). After further degassing, the reaction was allowed to stir under nitrogen at RT overnight. Excess zinc was removed via filtration and the reaction was quenched with water (50 mL). This mixture was extracted with EtOAc (3×30 mL) and the organic layers were combined, dried, and concentrated to give a dark brown oil which was purified by flash chromatography (35 g prepacked ISCO™ cartridge, hexanes eluant gradient to 50% ethyl acetate) to give the title compound (540 mg, 55%) as a yellow oil. $^1$HNMR (300 MHz, $CDCl_3$) δ 9.32 (d, 1H, J=2.4 Hz), 8.38 (dd, 1H, J=8.5, 2.8 Hz), 7.35 (d, 1H, J=8.5 Hz), 5.60 (d, 2H, J=7.3 Hz), 4.74 (dd, 1H, J=7.7, 5.3 Hz), 3.71 (3H, s), 3.44 (d, 2H, J=4.9 Hz), 1.4 (s, 9H). LCMS: Method AA Rt=2.24 min, MH$^+$=326.

65-6: 2-[1-Methoxycarbonyl-2-(5-nitro-pyridin-2-yl)-ethylamino]-4-methyl-pentanoic acid benzyl ester: Amine 65-4 (540 mg, 1.67 mmol) was suspended in 1.0 N HCl in $Et_2O$ (15 mL) and stirred overnight. The ether was removed in vacuo and the resulting tan solid was suspended in $NH_3$ saturated in methylene chloride. This was stirred for 2 h at RT and the precipitated ammonium chloride was removed via filtration and rinsed with acetonitrile. Excess ammonia was removed in vacuo and 2,6-lutidine (590 mL, 5.01 mmol) and a solution of freshly prepared triflate (710 mg, 2.0 mmol) in methylene chloride were added. The reaction was allowed to stir overnight at room temperature before concentrating in vacuo to give a dark brown oil which could be purified by flash chromatography (10 g prepacked ISCO™ cartridge, Hexanes/EtOAc eluant) to give the title compound as a tan oil (424 mg, 59% for 2 steps). $^1$HNMR (300 MHz, $CDCl_3$) δ 9.26 (d, 1H, J=2.8 Hz), 8.30 (dd, 1H, J=8.5, 2.9 Hz), 7.4–7.2 (m, 6H), 5.061 (s, 2H), 3.80 (dd, 1H, J=7.7, 5.8 Hz), 3.7 (s, 3H), 3.44 (dd, 1H, J=8.1, 6.1 Hz), 3.22 (dddd, 2H, J=5.3, 5.6, 7.7, 7.6, 14.3 Hz), 1.71–1.59 (m, 1H), 1.55–1.38 (m, 2H), 0.87 (dd, 6H, J=6.5, 3.3 Hz). LCMS: Method AA Rt=3.10 min, EI$^+$=430.

65-7: 2-[2-(5-Amino-pyridin-2-yl)-1-methoxycarbonyl-ethylamino]-4-methyl-pentanoic acid benzyl ester Nitropyridine 65-6 and tin(II) chloride dihydrate were stirred in EtOH at 60° C. for 2 h, at which point LCMS indicated complete formation of the hydroxylamine. More tin(II) chloride was added and this was stirred at 60° C. for an additional 2 h. Aqueous ammonium hydroxide (25 mL) and ethyl acetate (25 mL) were added and the reaction was stirred for 1 h to break up the resulting emulsion. The aqueous layer was extracted with ethyl acetate (3×25 mL) and the combined organic layers were dried and concentrated to give the title compound as a yellow oil (201 mg, 62%). The aqueous layer was found to contain a small amount (10%) of the mono methyl ester mono acid hydrolysis product. LCMS of title compound: Method AA Rt=2.44 min, MH$^+$=400.

65-8: 2-(2-{5-[(Benzo[b]thiophene-2-carbonyl)-amino]-pyridin-2-yl}-1-methoxycarbonyl-ethylamino)-4-methyl-pentanoic acid benzyl ester: A solution of pyridylamine 65-7 (150 mg, 0.376 mmol), acyl chloride 65-9 (81 mg, 0.414 mmol) and a catalytic amount of DMAP in acetonitrile was stirred at room temperature overnight. The reaction mixture was concentrated in vacuo and the residue was purified by flash chromatography (Biotage prepacked 10 g column, Ethyl Acetate to 20% Methanol eluant) to give a small amount of the undesired pyridyl imide (4 mg) plus the title compound as a tan oil (135 mg, 64%). LCMS: Method AA Rt=3.17 min, MH$^+$=560.

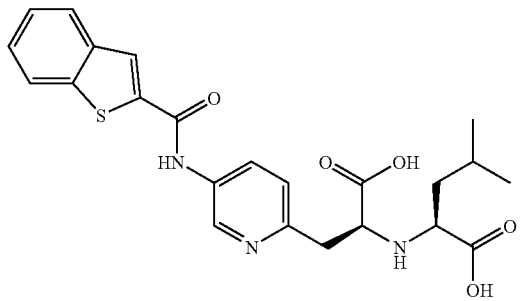

2-(2-{5-[(Benzo[b]thiophene-2-carbonyl)-amino]-pyridin-2-yl}-1-carboxy-ethylamino)-4-methyl-pentanoic acid: The diacid was prepared from diester 65-8 via lithium hydroxide mediated hydrolysis as described above, to give the title compound whose NMR data was consistent with the desired product. LCMS: Method FA Rt=2.33 min, MH$^+$=454.

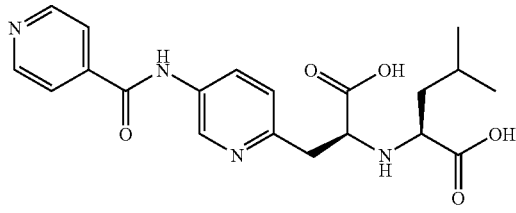

2-(1-Carboxy-2-{5-[(pyridine-4-carbonyl)-amino]-pyridin-2-yl}-ethylamino)-4-methyl-pentanoic acid: The diacid was prepared from the corresponding diester via lithium hydroxide mediated hydrolysis as described above, to give the title compound whose NMR data was consistent with the desired product. LCMS: Method FA Rt=0.83 min, MH$^+$=401.

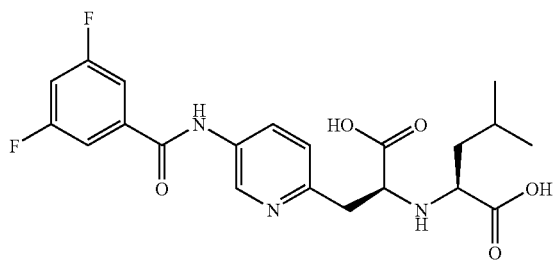

2-{1-Carboxy-2-[5-(3,5-difluoro-benzoylamino)-pyridin-2-yl]-ethylamino}-4-methyl-pentanoic acid: The diacid was prepared from the corresponding diester via lithium hydroxide mediated hydrolysis as described above, to give the title compound whose NMR data was consistent with the desired product. LCMS: Method FA Rt=1.68 min, MH$^+$=436.

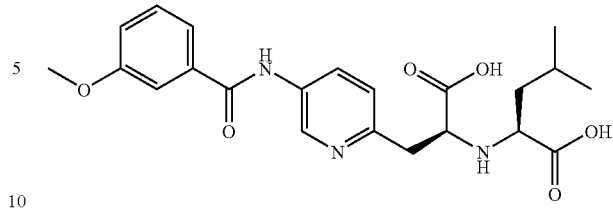

2-{1-Carboxy-2-[5-(3-methoxy-benzoylamino)-pyridin-2-yl]-ethylamino}-4-methyl-pentanoic acid: The diacid was prepared from the corresponding diester via lithium hydroxide mediated hydrolysis as described above, to give the title compound whose NMR data was consistent with the desired product. LCMS: Method FA Rt=1.53 min, MH$^+$=430.

Example 41

Synthesis of 2-{1-carboxy-2-[2-(3,5-dichlorobenzyl)-2H-pyrazol-3-yl]-ethylamino}-4-methyl-pentanoic acid

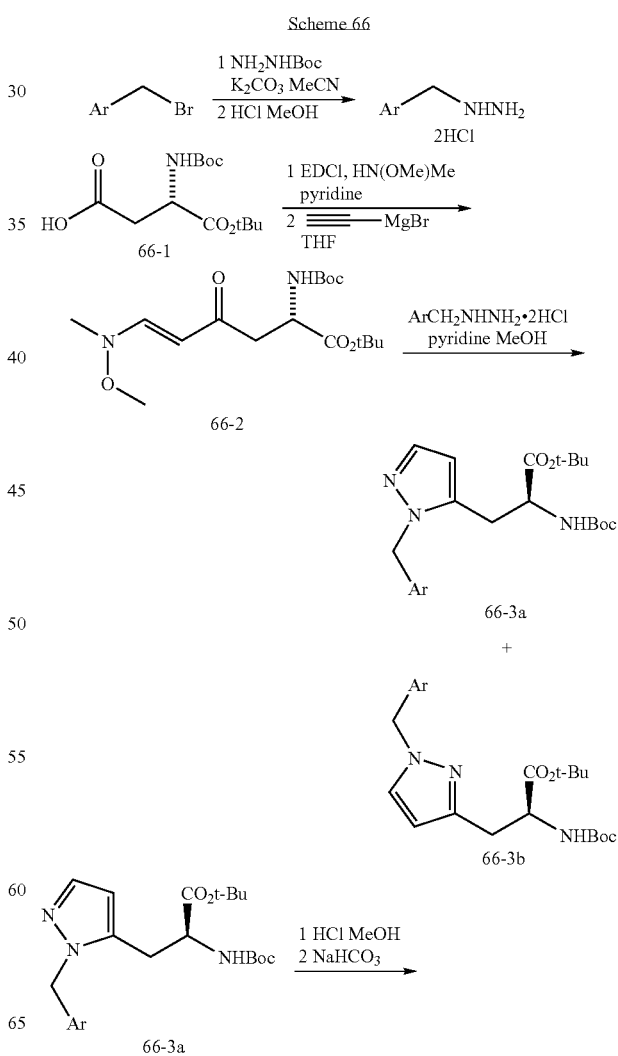

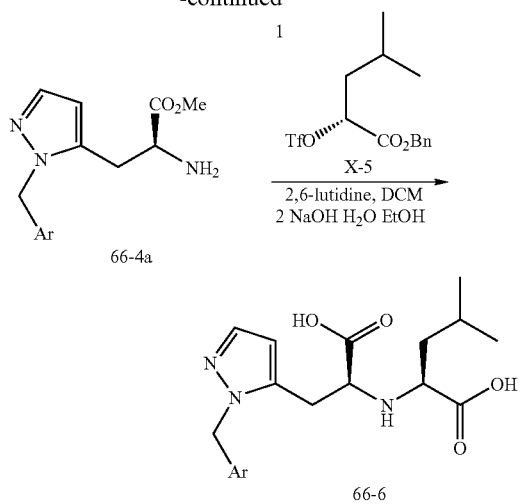

3,5-Dichlorobenzyl hydrazine dihydrochloride: 3,5 Dichlorobenzyl bromide (10 g, 41.7 mmol) was dissolved in 200 mL of acetonitrile and $K_2CO_3$ (11.0 g, 83.36 mmol) and hydrazine carboxylic acid tert-butyl ester (11.0 g, 83.36 mmol) were added. The resulting mixture was warmed to reflux for 3 hours. The reaction mixture was then cooled to room temperature, concentrated in vacuo, and diluted with water and EtOAc. The aqueous phase was extracted with EtOAc, and the combined organic phases were washed with brine, dried over $Na_2SO_4$, filtered and concentrated to give a yellow oil. Purification by column chromatography ($SiO_2$, 5–10% EtOAc/Hex eluent) provided 6.4 g of N-(3,5 dichlorobenzyl)hydrazine carboxylic acid tert-butyl ester as a white solid (53% yield). $^1H$ NMR data is consistent with desired product. This material was dissolved in 200 mL of MeOH and $SOCl_2$ (12.8 mL, 176.1 mmol) was added slowly. The resulting solution was stirred at room temperature for 5 hours and concentrated to give 5.8 g of 3,5-dichlorobenzyl hydrazine dihydrochloride salt as a pale yellow solid (100% yield).

66-2: E-2-tert-Butoxycarbonylamino-6-(methoxy-methylamino)-4-oxo-hex-5-enoic acid tert-butyl ester: Diprotected aspartic acid 66-1 (25 g, 86.41 mmol) and N,N-methoxymethylamine hydrochloride (8.85 g, 90.73 mmol) were dissolved in 180 mL of pyridine and this solution was cooled to 0° C. 1-[3-Dimethylamino)propyl]-3-ethylcarbodiimide hydrochloride (EDCI, 18.2 g, 95.05 mmol) was added in one portion and the resulting mixture was stirred at 0° C. for 90 minutes. The reaction mixture was then warmed to room temperature and stirred for another 90 minutes. The reaction mixture was diluted with EtOAC and 1N (aq) HCl solution. The organic phase was extracted with 1N (aq) HCl solution (3 times), concentrated, redissolved in EtOAc. This solution was extracted with 1N (aq) HCl solution (3 times) and once with brine, dried over $Na_2SO_4$, filtered and concentrated to give a yellow oil (28.81 g, >100% yield). $^1H$ NMR is consistent with desired amide. A solution of ethynyl magnesium chloride (0.5 N in THF, 864 mL, 432 mmol) was cooled to −78° C. The amide prepared above was dissolved in 45 mL of THF and this solution was added via cannula to the cooled Grignard solution. The reaction mixture was then allowed to warm to room temperature and stirred overnight. The reaction mixture was then recooled to 0° C. and 1N (aq) HCl solution was added. The mixture was stirred at 0° C. for 30 minutes and then warmed to room temperature and stirred for 1 hour. EtOAc was then added and the organic phase was extracted with 1N (aq) HCl solution, water, and brine; dried over $Na_2SO_4$; filtered; and concentrated to give a brown oil. Purification by column chromatography ($SiO_2$, 10–60% EtOAc in hexanes) provided about 10 g of a brown oil that solidified upon standing (ca. 33% yield). $^1H$ NMR and LC/MS data are consistent with the desired product (66-2). 2D NMR techniques (HMQC, HMBC, and nOeSY) confirmed the structure as the E alkene.

66-3a: 2-tert-Butoxycarbonylamino-3-[2-(3,5-dichlorobenzyl)-2-H-pyrazol-3-yl]propionic acid tert-butyl ester: E-2-tert-Butoxycarbonylamino-6-(methoxy-methylamino)-4-oxo-hex-5-enoic acid tert-butyl ester (66-2, 3.54 g, 9.89 mmol) and pyridine (1.76 mL, 21.76 mmol) were combined in 100 mL of methanol. 3,5-Dichlorobenzyl hydrazine dihydrochloride (2.74 g, 10.38 mmol) was added and the resulting solution was stirred overnight at room temperature. The reaction mixture was concentrated to a brown oil. Purification by column chromatography ($SiO_2$, 20% EtOAc in hexane as eluent) provided 2.25 g of a yellow oil (48% yield). $^1H$ NMR spectrum is consistent with the desired product as the desired isomer (<10% of the 1,3 disubstituted pyrazole is present in this material). Another 140 mg of material was also isolated. This material corresponds to a 1:1 mixture of pyrazoles 66-3a : 66-3b as determined by $^1H$ NMR.

66-4a: 2-Amino-3-[2-(3,5-dichlorobenzyl)-2-H-pyrazol-3-yl]propionic acid methyl ester (R=3,5 diClPh): 2-tert-Butoxycarbonylamino-3-[2-(3,5-dichlorobenzyl)-2-H-pyrazol-3-yl]propionic acid tert-butyl ester (66-3a, 2.25 g, 4.78 mmol) was dissolved in 50 mL of methanol and $SOCl_2$ (2.8 mL, 38.26 mmol) was added slowly. The resulting solution was warmed to reflux for 18 hours, cooled to room temperature, and concentrated. The resulting brown foam was partitioned between EtOAc and saturated $NaHCO_3$ solution. The aqueous phase was extracted with EtOAc. Combined organic phases were dried with $Na_2SO_4$, filtered and concentrated to give a brown oil (1.49 g, 95% yield). $^1H$ NMR spectra is consistent with desired compound.

2-Amino-3-[2-(3,5-dichlorobenzyl)-2-H-pyrazol-3-yl]propionic acid methyl ester (66-4a, R=3,5 diClPh) was then alkylated with the triflate of leucic acid benzyl ester and the resulting diester was treated with aqueous NaOH solution in EtOH as previously described to proved the diacid 66-6 (R=3,5 diClPh).

Equivalents

Those skilled in the art will recognize, or be able to ascertain using no more than routine experimentation, many equivalents to the specific embodiments and methods described herein. Such equivalents are intended to be encompassed by the scope of the following claims.

This application is related to U.S. patent application Ser. No. 09/407,427, entitled "Angiotensin Converting Enzyme Homolog and Therapeutic and Diagnostic Uses Therefor," filed on Sep. 29, 1999; U.S. patent application Ser. No. 09/163,648 entitled "Angiotensin Converting Enzyme Homolog and Therapeutic and Diagnostic Uses Therefor," filed on Sep. 30, 1998; and to U.S. Pat. No. 6,194,556, the entire contents of each of which are hereby expressly incorporated herein by reference.

All patents, patent applications, and literature references cited herein are hereby expressly incorporated by reference.

What is claimed is:

1. A method of treating an ACE-2 associated state in a subject, comprising administering to a subject in need of decreasing appetite, decreasing body fat, increasing muscle mass, or treating a body weight disorder, an effective amount of an ACE-2 inhibitor, wherein said ACE-2 inhibitor is of the formula (IV):

(IV)

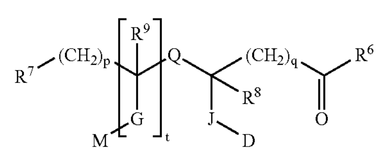

wherein

R⁶ is hydroxyl or a protecting prodrug moiety;

$R^7$ is a hydrogen atom, carboxylic acid, arylaminocarbonyl, aroyl, aryl, alkylaminocarbonyl, aminocarbonyl, alkenylaminocarboxy, hydroxyl, alkoxy, ether, thiol, amino group heterocycle, or a protecting prodrug moiety;

$R^8$ is hydrogen, or alkyl, and optionally linked to D to form a cyclic structure;

$R^9$ is lower alkyl or hydrogen;

Q is a bond, O, S, $CR^3OH$, $CR^3SH$, $CR^3NR^{3a}R^{3b}$, $NR^3$, $(CR^3R^{3a})_n$, $O(CR^3R^{3b})_n$, or $(CR^3R^{3a})_nO(CR^{3b}R^{3c})_n$, wherein n is 0, 1, 2, or 3 and $R^3$, $R^{3a}$, $R^{3b}$, and $R^{3c}$ are each independently hydrogen, substituted or unsubstituted, branched, cyclic, or straight chain $C_1$–$C_6$ alkyl, $C_2$–$C_6$ alkenyl, acyl, arylalkyl, aryloxycarbonyl, arylaminocarbonyl, arylalkylsulfonyl, or aryl;

G is a linking moiety;

M is an anchor moiety;

J is a bond, an alkyl, alkenyl, or alkynyl moiety;

D is hydrogen, alkoxy, amine, alkyl, alkenyl, alkynyl, aryl, or heteroaryl, optionally linked to G, M or Q to form a ring;

t is 0 or 1;

p is 0, 1, 2, 3, 4, or 5;

q is 0, 1, 2, or 3, or an enantiomer, diastereomer, mixture of enantiomers, mixture of diastereomers or pharmaceutically acceptable salt thereof; and wherein said inhibitor is not a naturally occurring amino acid.

2. A method of treating an ACE-2 associated state in a subject, comprising administering to a subject in need of decreasing appetite, decreasing body fat, increasing muscle mass, or treating a body weight disorder, an effective amount of an ACE-2 inhibitor, wherein said ACE-2 inhibitor is of the formula:

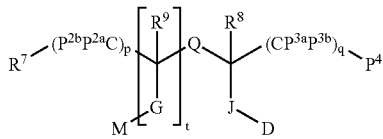

wherein $P^4$ is selected from the group consisting of a carboxylic acid, cleavable prodrug moieties, $COOP^{4'}$, $(CH_2)_{1-4}SP^{4'}$, or $C(O)NP^{4'}P^{4''}$;

$R^7$ is hydrogen, carboxylic acid, unsubstituted or substituted lower alkyl esters, lower alkenyl esters, dilower alkyl amino esters, arylaminocarbonyl, aroyl, aryl, alkylaminocarbonyl, aminocarbonyl, $COOR^{7'}$, $CONR^{7'}R^{7''}$, hydroxy, ether, thio, amino, $(CH_2)_{1-4}SR^{7'}$, a heterocycle, or a cleavable prodrug moiety;

$P^{4'}$, $P^{4''}$, $R^{7'}$ and $R^{7''}$ are each independently hydrogen, $C_1$–$C_6$ alkyl, $C_2$–$C_6$ alkenyl, $C_2$–$C_6$ alkynyl or optionally substituted aryl;

$R^8$ is selected from the group consisting of hydrogen, alkyl and a covalent bond to D;

$R^9$ is lower alkyl or hydrogen;

Q is a bond, O, S, $CR^3OH$, $CR^3SH$, $CR^3NR^{3a}R^{3b}$, $NR^3$, $(CR^3R^{3a})_n$, $O(CR^3R^{3b})_n$, or $(CR^3R^{3a})_nO(CR^{3b}R^{3c})_n$, wherein n is 0, 1, 2, or 3, and $R^3$, $R^{3a}$, $R^{3b}$, and $R^{3c}$ are each independently hydrogen, substituted or unsubstituted $C_1$–$C_6$ branched or straight chain alkyl, $C_2$–$C_6$ branched or straight chain alkenyl, aryloxycarbonyl, arylaminocarbonyl, arylalkylsulfonyl, arylalkyl, substituted or unsubstituted acyl, aryl, or $C_3$–$C_8$ ring, wherein the $C_3$–$C_8$ ring is optionally substituted with up to four heteroatoms;

$P^{2a}$, $P^{2b}$, $P^{3a}$ and $P^{3b}$ are each independently hydrogen, substituted or unsubstituted, branched, straight chain or cyclic $C_1$–$C_5$ alkyl, G is a linking moiety;

M is an anchor moiety;

J is a bond, alkyl, alkenyl, or alkynyl moiety;

D is hydrogen, alkyl, alkenyl, alkynyl, aryl, or optionally linked to G, M, or Q to form a ring;

t is 0 or 1;

p is 0, 1, 2, 3, 4, or 5;

q is 1, 2, or 3; or an enantiomer, diastereomer, mixture of enantiomers, mixture of diastereomers or pharmaceutically acceptable salt thereof; and wherein said inhibitor is not a naturally occurring amino acid.

3. A method of treating an ACE-2 associated state in a subject, comprising administering to a subject in need of decreasing appetite, decreasing body fat, increasing muscle mass, or treating a body weight disorder, an effective amount of an ACE-2 inhibitor, wherein said ACE-2 inhibitor is of the formula:

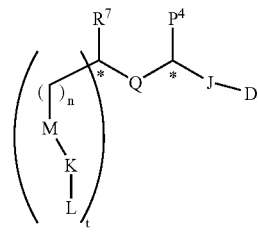

wherein

M is carbocyclic, heterocyclic, or CONR'R" wherein R' and R" are each independently hydrogen, $C_1$–$C_6$ alkyl, $C_2$–$C_6$ alkenyl, $C_2$–$C_6$ alkynyl or optionally substituted aryl;

Q is a bond, O, S, $CR^3OH$, $CR^3SH$, $CR^3NR^{3a}R^{3b}$, $NR^3$, $(CR^3R^{3a})_n$, $O(CR^3R^{3b})_n$, or $(CR^3R^{3a})_nO(CR^{3b}R^{3c})_n$, wherein n is 0, 1, 2, or 3 and $R^3$, $R^{3a}$, $R^{3b}$, and $R^{3c}$ are each independently hydrogen, substituted or unsubstituted, branched, cyclic, or straight chain $C_1$–$C_6$ alkyl, $C_2$–$C_6$ alkenyl, acyl, arylalkyl, aryloxycarbonyl, arylaminocarbonyl, arylalkylsulfonyl, or aryl;

K is an independently selected sublinking moiety for each occurrence;

L is an independently selected subanchor moiety for each occurrence;

$P^4$ is a hydrogen, carboxylic acid, $(CH_2)_{1-4}SP^{4'}$, a cleavable prodrug moiety, carboxylic acid, $COOP^{4'}$, or $CONP^{4'}P^{4''}$;

$R^7$ is hydrogen, carboxylic acid, aroyl, aryl, $COOR^{7'}$, $C(O)NR^{7'}R^{7''}$, hydroxy, ether, thio, $(CH_2)_{1-4}SR^{7'}$, a heterocycle, or a cleavable prodrug moiety;

$P^{4'}$, $P^{4''}$, $R^{7'}$ and $R^{7''}$ independently hydrogen, $C_1$–$C_6$ alkyl, $C_2$–$C_6$ alkenyl, $C_2$–$C_6$ alkynyl or optionally substituted aryl;

n is 0, 1, 2, 3, or 4;

J is a bond, substituted or unsubstituted alkyl, alkenyl, or alkynyl;

D is hydrogen, alkyl, alkoxy, alkenyl, amine, hydroxy, alkynyl, aryl, or heteroaryl;

t is 0 or 1, or an enantiomer, diastereomer, mixture of enantiomers, mixture of diastereomers or pharmaceutically acceptable salt thereof; and wherein said inhibitor is not a naturally occurring amino acid.

4. A method of treating an ACE-2 associated state in a subject, comprising administering to a subject in need of decreasing appetite, decreasing body fat, increasing muscle mass, or treating a body weight disorder, an effective amount of an ACE-2 inhibitor, wherein said ACE-2 inhibitor is of the formula:

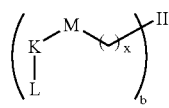

wherein Π is

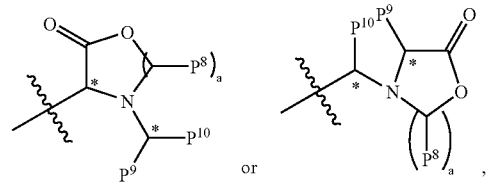

M is carbocyclic, heterocyclic, or CONR'R" wherein R' and R" are each independently hydrogen, $C_1$–$C_6$ alkyl, $C_2$–$C_6$ alkenyl, $C_2$–$C_6$ alkynyl or optionally substituted aryl;

K is an independently selected sublinking moiety for each occurrence;

L is an independently selected subanchor moiety for each occurrence;

$P^8$ is hydrogen or alkyl;

$P^9$ is carboxylic acid, unsubstituted or substituted lower alkyl esters, $(CH_2)_{1-4}SP^{9'}$, lower alkcenyl esters, dilower alkyl amino esters, lower alkyl amides, dilower alkyl amides, lower alkenyl amides, dilower alkenyl amides, lower alkynyl amides, or aryl amides;

$P^{10}$ is carboxylic acid, unsubstituted or substituted lower alkyl esters, $(CH_2)_{1-4}SP^{10'}$, lower alkenyl esters, dilower alkyl amino esters, lower alkyl amides, dilower alkyl amides, lower alkyl amides, lower alkenyl amides, dilower alkenyl amides, lower alkynyl amides, or aryl amides;

$P^{9'}$ and $P^{10'}$ are each independently alkyl, alkenyl, alkynyl, aryl, or hydrogen;

a is 1, 2, or 3;

b is 0 or 1; and x is 0, 1, 2, 3, or 4, or a pharmaceutically acceptable salt thereof.

5. The method of any one of claims 1–4, wherein said subject has a body mass index of greater than about 23 kg/m².

6. The method of claim 5, wherein said subject has a body mass index of greater than about 24.9 kg/m².

7. The method of any one of claims 1–4, wherein said subject is suffering from obesity of grade 1 or greater.

8. The method of any one of claims 1–4, wherein said subject is a human.

9. The method of any one of claims 1–4, wherein said ACE-2 inhibitor interacts with ACE-2 with a $K_i$ of 1 μM or less.

10. The method of claim 9, wherein said ACE-2 inhibitor interacts with ACE-2 with a $K_i$ of 0.1 μM or less.

11. The method of claim 10, wherein said ACE-2 inhibitor interacts with ACE-2 with a $K_i$ of 0.025 μM or less.

12. The method of any one of claims 1–3, wherein said ACE-2 inhibitor is of the formula:

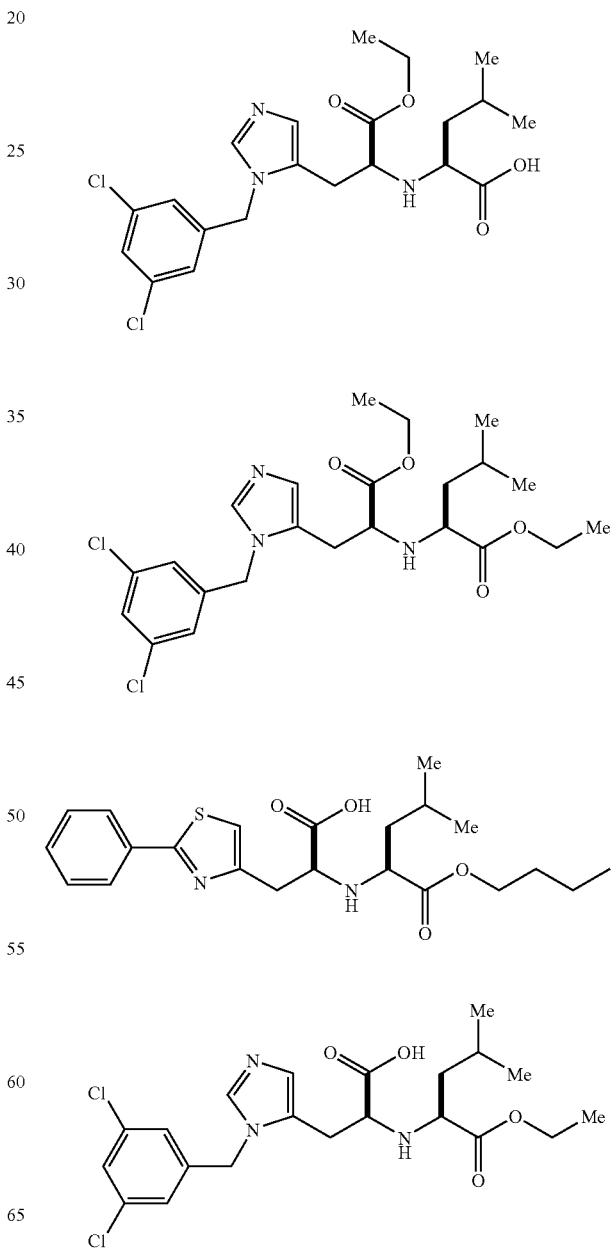

567
-continued
568
-continued
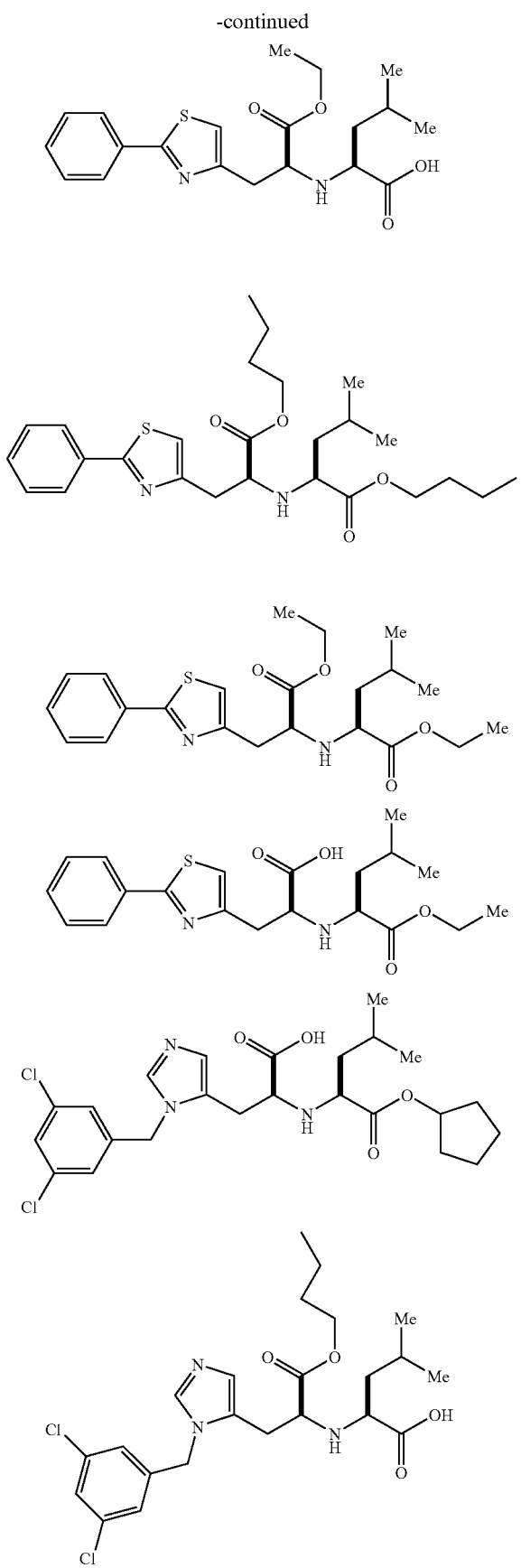
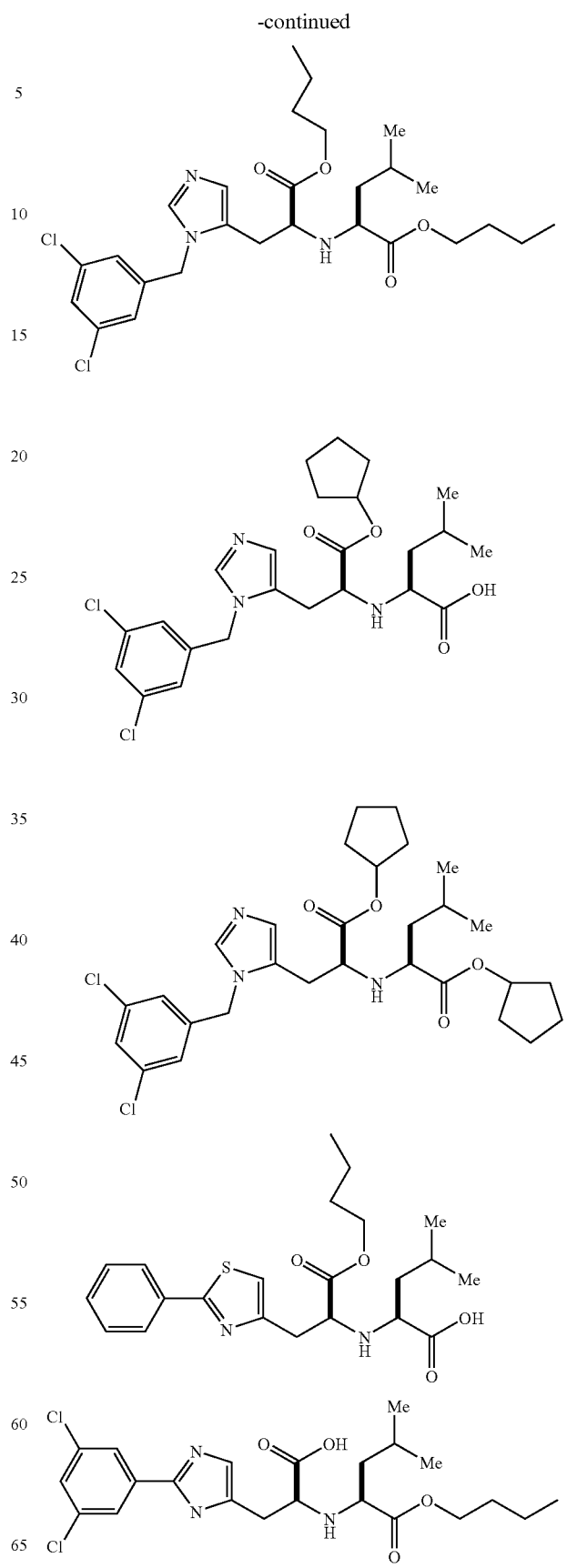

569
-continued
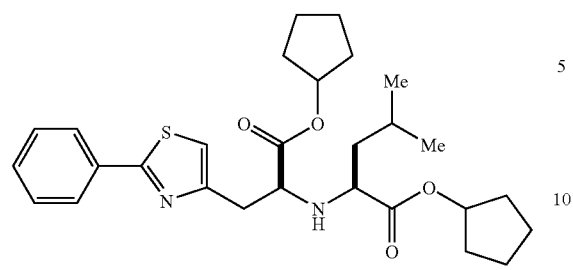
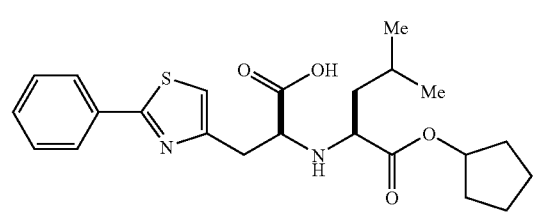
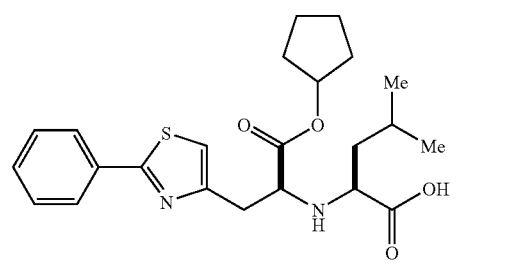
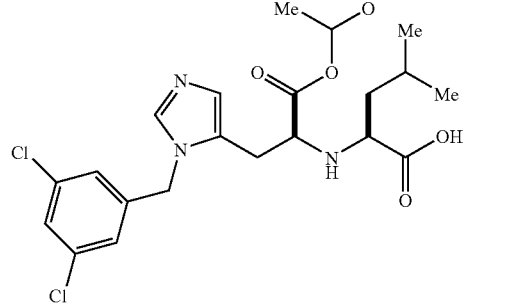
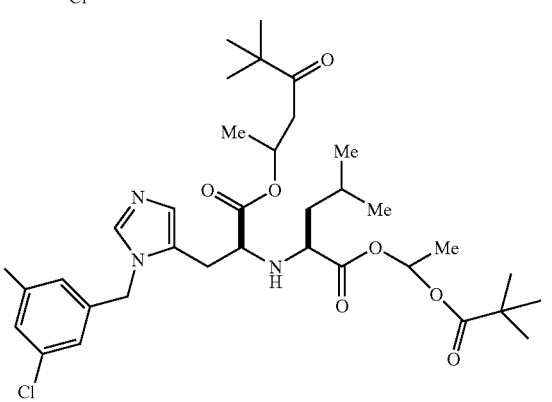
570
-continued
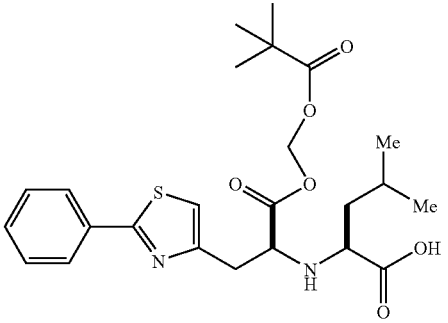
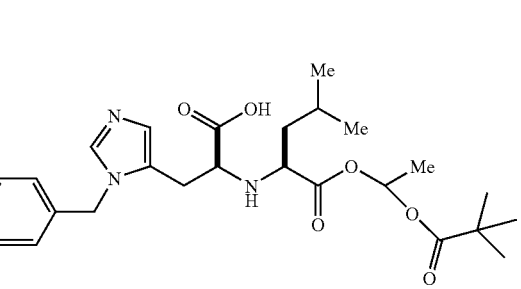
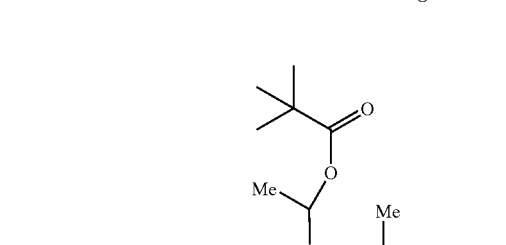
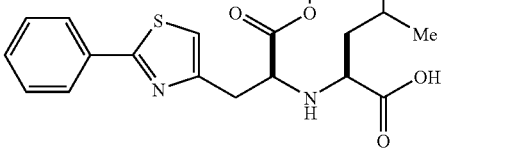
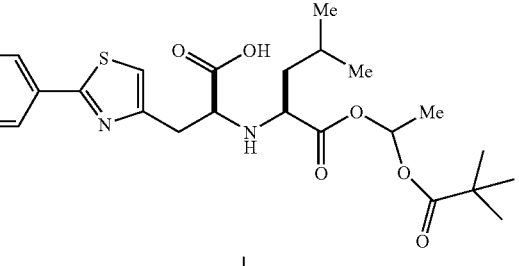
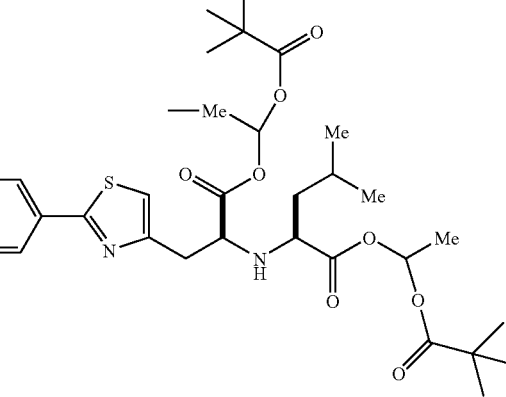

-continued
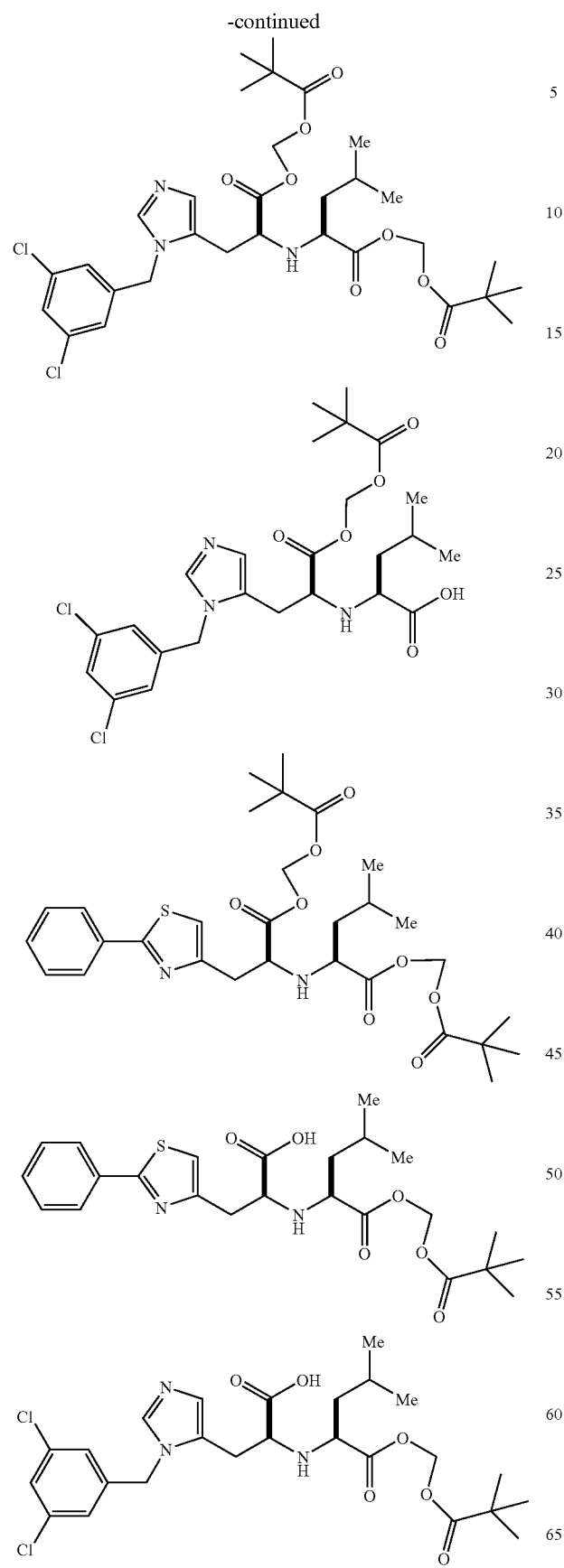
-continued
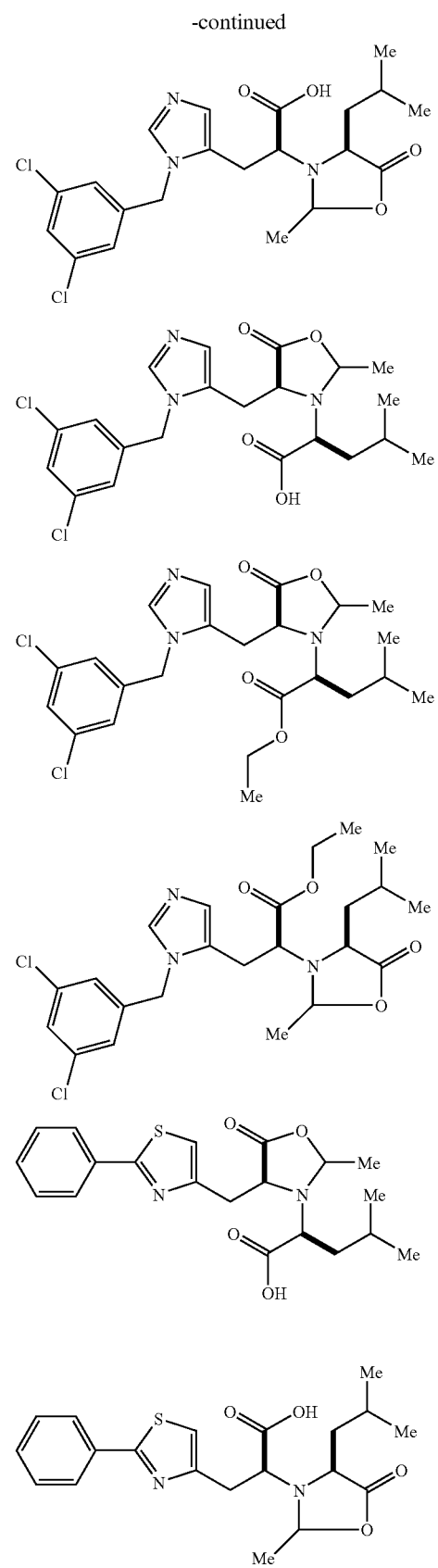

-continued
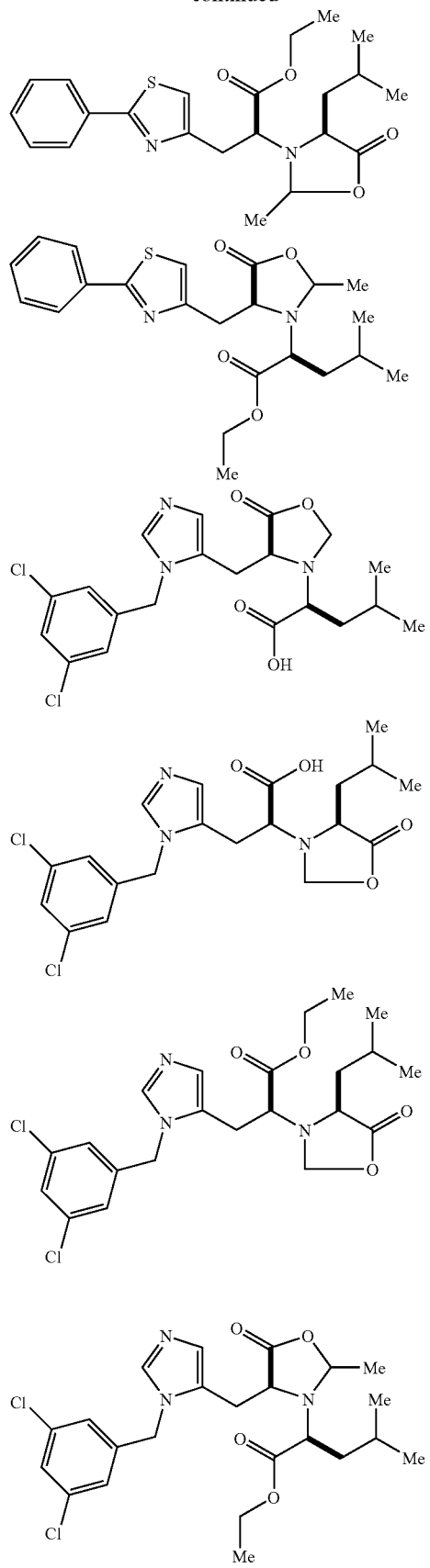
-continued
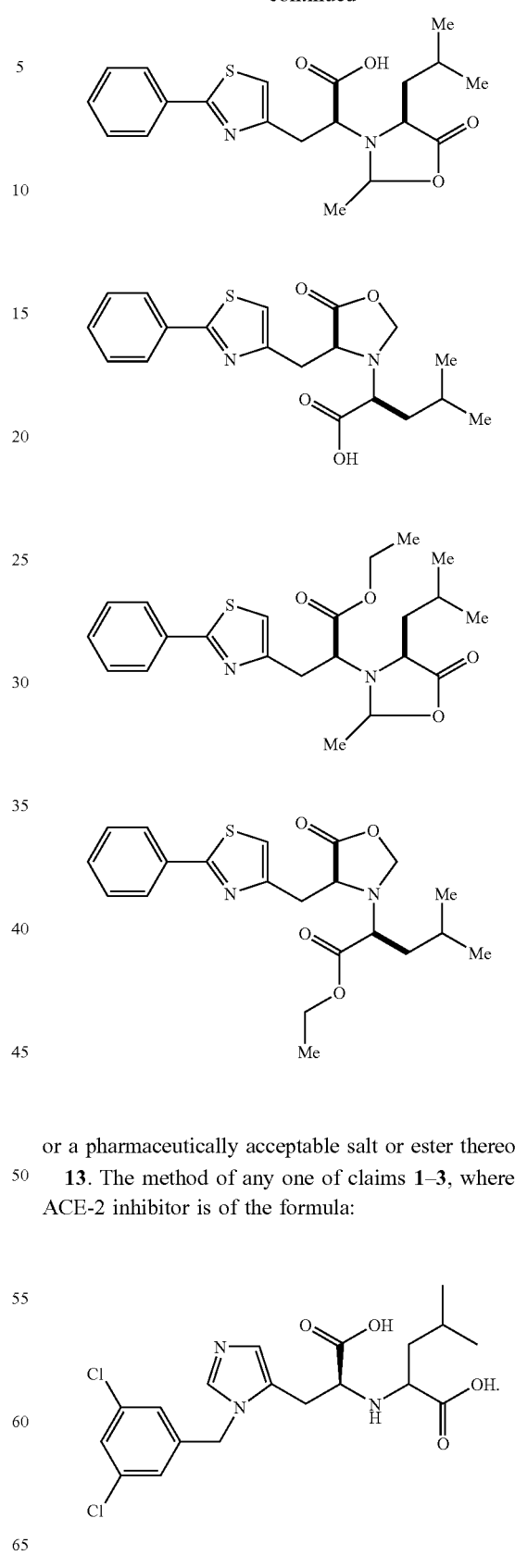
or a pharmaceutically acceptable salt or ester thereof.
13. The method of any one of claims 1–3, wherein said ACE-2 inhibitor is of the formula:
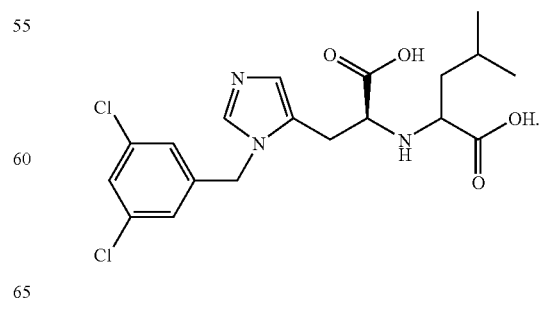

14. The method of any one of claims 1–3, wherein said ACE-2 inhibitor is of the formula:

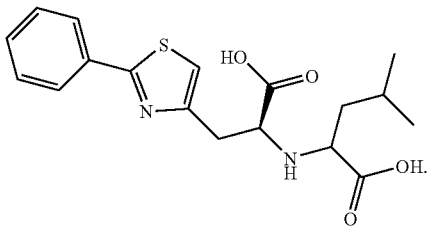

15. The method of any one of claims 1–3, wherein said ACE-2 inhibitor is:

2-{1-Carboxy-2-[3-(3-nitro-benzyl)-3H-imidazol-4-yl]-ethylamino}-4-methyl-pentanoic acid;
2-[2-(3-Benzyl-3H-imidazol-4-yl)-1-carboxy-ethylamino]-hexanoic acid;
2-[2-(3-Benzyl-3H-imidazol-4-yl)-1-carboxy-ethylamino]-4-methyl-pentanoic acid;
2-[1-Carboxy-2-(1H-imidazol-4-yl)-ethylamino]-4-phenyl-butyric acid;
2-[2-(3-Benzyloxymethyl-3H-imidazol-4-yl)-1-carboxy-ethylamino]-4-methyl-pentanoic acid;
2-[1-Carboxy-2-(methyl-phenyl-amino)-ethylamino]-4-methyl-pentanoic acid;
2-[1-Carboxy-2-(1H-imidazol-4-yl)-ethylamino]-4-methyl-pentanoic acid;
2-[2-(1-Benzyl-1H-imidazol-4-yl)-1-carboxy-ethylamino]-4-methyl-pentanoic acid;
2-(1-Carboxy-2-phenyl-ethylamino)-3-(3H-imidazol-4-yl)-propionic acid;
2-[1-Carboxy-2-(1H-imidazol-4-yl)-ethylamino]-4-methyl-pentanoic acid;
2-[1-Carboxy-2-(4-hydroxy-phenyl)-ethylamino]-3-(1H-imidazol-4-yl)-propionic acid;
2-[1-Carboxy-2-(1H-imidazol-4-yl)-ethylamino]-4-phenyl-butyric acid;
2-[1-Carboxy-2-(1H-imidazol-4-yl)-ethylamino]-pentanoic acid;
2-[2-(1H-Imidazol-4-yl)-1-methoxycarbonyl-ethylamino]-4-methyl-pentanoic acid;
2-(1-Carboxy-3-phenyl-propylamino)-5-pyridin-2-yl-pent-4-ynoic acid;
2-{1-Carboxy-2-[1-(4-chloro-benzyl)-1H-imidazol-4-yl]-ethylamino}-4-methyl-pentanoic acid;
2-[2-(1-Benzyl-1H-imidazol-4-yl)-1-carboxy-ethylamino]-4-methyl-pentanoic acid;
2-[1-Carboxy-2-(1H-imidazol-4-yl)-ethylamino]-pentanoic acid;
2-[1-Carboxy-2-(1H-imidazol-4-yl)-ethylamino]-hexanoic acid;
2-(1-Carboxy-2-thiophen-2-yl-ethylamino)-4-methyl-pentanoic acid;
6-Amino-2-(1-carboxy-3-phenyl-propylamino)-hexanoic acid;
2-[1-Carboxy-2-(1H-imidazol-4-yl)-ethylamino]-3-methyl-pentanoic acid;
2-[(Carboxy-phenyl-methyl)-amino]-4-methyl-pentanoic acid;
2-{1-Carboxy-2-[1-(2,4-dinitro-phenyl)-1H-imidazol-4-yl]-ethylamino}-4-methyl-pentanoic acid;
2-(1-Carboxy-2-thiazol-2-yl-ethylamino)-4-methyl-pentanoic acid;
2-(1-Carboxy-2-pyridin-2-yl-ethylamino)-4-methyl-pentanoic acid;
2-(1-Carboxy-ethylamino)-3-(1H-imidazol-4-yl)-propionic acid;
2-(1-Carboxy-3-methylsulfanyl-propylamino)-4-phenyl-butyric acid;
2-(1-Carboxy-3-methyl-butylamino)-succinic acid;
2-(1-Carboxy-3-methyl-butylamino)-hexanoic acid;
2-(1-Carboxy-3-methylsulfanyl-propylamino)-4-methyl-pentanoic acid;
2-[1-Carboxy-2-(3-methyl-3H-imidazol-4-yl)-ethylamino]-4-methyl-pentanoic acid;
2-(1-Carboxy-3-phenyl-propylamino)-4-methyl-pentanoic acid;
2-(1-Carboxy-2-phenyl-ethylamino)-4-methyl-pentanoic acid;
2-(1-Carboxy-2-phenyl-ethylamino)-pentanoic acid;
2-(1-Carboxy-2-phenyl-ethylamino)-4-phenyl-butyric acid;
2-(1-Carboxy-3-phenyl-propylamino)-4,4-dimethyl-pentanoic acid;
2-(1-Carboxy-ethylamino)-3-(1H-imidazol-4-yl)-propionic acid;
2-(1-Carboxy-2-thiophen-2-yl-ethylamino)-pentanoic acid;
2-[1-Carboxy-2-(1H-[1,2,4]triazol-3-yl)-ethylamino]-4-methyl-pentanoic acid;
2-(1-Carboxy-2-cyclopropyl-ethylamino)-4-phenyl-butyric acid;
2-[1-Carboxy-2-(4-hydroxy-phenyl)-ethylamino]-3-(1H-imidazol-4-yl)-propionic acid;
2-[2-(1-Benzyl-1H-imidazol-4-yl)-1-carboxy-ethylamino]-4-methyl-pentanoic acid;
2-(1-Carboxy-2-cyclohexyl-ethylamino)-4-phenyl-butyric acid;
2-(1-Carboxy-3-phenyl-propylamino)-5-phenyl-pent-4-ynoic acid;
2-[2-(1H-Imidazol-4-yl)-1-methoxycarbonyl-ethylamino]-4-methyl-pentanoic acid;
2-{1-Carboxy-2-[1-(4-methoxy-benzyl)-1H-imidazol-4-yl]-ethylamino}-4-methyl-pentanoic acid;
2-{1-Carboxy-2-[1-(4-trifluoromethyl-benzyl)-1H-imidazol-4-yl]-ethylamino}-4-methyl-pentanoic acid;
2-[(Carboxy-phenyl-methyl)-amino]-4-methyl-pentanoic acid;
2-(1-Carboxy-propylamino)-4-methylsulfanyl-butyric acid;
2-(1-Carboxy-2-phenyl-ethylamino)-4-methyl-pentanoic acid;
2-[2-(1H-Imidazol-4-yl)-1-methoxycarbonyl-ethylamino]-4-methyl-pentanoic acid;
2-{1-Carboxy-2-[1-(4-methoxy-benzyl)-1H-imidazol-4-yl]-ethylamino}-4-methyl-pentanoic acid;
2-{1-Carboxy-2-[1-(4-trifluoromethyl-benzyl)-1H-imidazol-4-yl]-ethylamino}-4-methyl-pentanoic acid;
2-[(Carboxy-phenyl-methyl)-amino]-4-methyl-pentanoic acid;
2-(1-Carboxy-propylamino)-4-methylsulfanyl-butyric acid;
2-(1-Carboxy-3-phenyl-propylamino)-5-pyridin-2-yl-pent-4-ynoic acid;
2-{1-Carboxy-2-[3-(4-trifluoromethyl-benzyl)-3H-imidazol-4-yl]-ethylamino}-4-methyl-pentanoic acid;
2-[1-Carboxy-2-(3-naphthalen-1-ylmethyl-3H-imidazol-4-yl)-ethylamino]-4-methyl-pentanoic acid;
2-{1-Carboxy-2-[3-(4-chloro-benzyl)-3H-imidazol-4-yl]-ethylamino}-4-methyl-pentanoic acid;

4-{5-[2-Carboxy-2-(1-carboxy-3-methyl-butylamino)-ethyl]-imidazol-1-ylmethyl}-benzoic acid;
2-[1-Carboxy-2-(2-phenyl-thiazol-4-yl)-ethylamino]-4-methyl-pentanoic acid;
2-[2-(1-Benzyl-1H-benzoimidazol-2-yl)-1-carboxy-ethylamino]-4-methyl-pentanoic acid;
2-[2-(Benzyl-phenyl-amino)-1-carboxy-ethylamino]-4-methyl-pentanoic acid;
2-[2-(2-Amino-thiazol-4-yl)-1-carboxy-ethylamino]-4-methyl-pentanoic acid;
2-{1-Carboxy-2-[3-(3,4-dichloro-benzyl)-3H-imidazol-4-yl]-ethylamino}-4-methyl-pentanoic acid;
2-[1-Carboxy-2-(2-methyl-thiazol-4-yl)-ethylamino]-4-methyl-pentanoic acid;
2-{1-Carboxy-2-[3-(4-cyano-benzyl)-3H-imidazol-4-yl]-ethylamino}-4-methyl-pentanoic acid;
2-{1-Carboxy-2-[3-(3-chloro-benzyl)-3H-imidazol-4-yl]-ethylamino}-4-methyl-pentanoic acid;
'2-{1-Carboxy-2-[3-(3,5-dichloro-benzyl)-3H-imidazol-4-yl]-ethylamino}-4-methyl-pentanoic acid;
2-{1-Carboxy-2-[3-(4-methyl-benzyl)-3H-imidazol-4-yl]-ethylamino}-4-methyl-pentanoic acid;
2-{2-[3-(4-Butyl-benzyl)-3H-imidazol-4-yl]-1-carboxy-ethylamino}-4-methyl-pentanoic acid;
2-{1-Carboxy-2-[3-(3,4-dimethyl-benzyl)-3H-imidazol-4-yl]-ethylamino}-4-methyl-pentanoic acid;
2-[2-(2-Benzylamino-thiazol-4-yl)-1-carboxy-ethylamino]-4-methyl-pentanoic acid;
2-{1-Carboxy-2-[3-(3-methyl-benzyl)-3H-imidazol-4-yl]-ethylamino}-4-methyl-pentanoic acid;
2-{1-Carboxy-2-[3-(3,5-dimethyl-benzyl)-3H-imidazol-4-yl]-ethylamino}-4-methyl-pentanoic acid;
2-{1-Carboxy-2-[3-(4-trifluoromethoxy-benzyl)-3H-imidazol-4-yl]-ethylamino}-4-methyl-pentanoic acid;
2-{1-Carboxy-2-[3-(4-isopropyl-benzyl)-3H-imidazol-4-yl]-ethylamino}-4-methyl-pentanoic acid;
2-{1-Carboxy-2-[3-(2-methyl-benzyl)-3H-imidazol-4-yl]-ethylamino}-4-methyl-pentanoic acid;
2-{2-[3-(4-tert-Butyl-benzyl)-3H-imidazol-4-yl]-1-carboxy-ethylamino}-4-methyl-pentanoic acid;
2-{2-[3-(2-Benzenesulfonylmethyl-benzyl)-3H-imidazol-4-yl]-1-carboxy-ethylamino}-4-methyl-pentanoic acid;
2-{1-Carboxy-2-[3-(4-nitro-benzyl)-3H-imidazol-4-yl]-ethylamino}-4-methyl-pentanoic acid;
2-[2-(3-Biphenyl-2-ylmethyl-3H-imidazol-4-yl)-1-carboxy-ethylamino]-4-methyl-pentanoic acid;
'2-{2-[3-(3,5-Bis-trifluoromethyl-benzyl)-3H-imidazol-4-yl]-1-carboxy-ethylamino}-4-methyl-pentanoic acid;
2-{1-Carboxy-2-[3-(4-fluoro-benzyl)-3H-imidazol-4-yl]-ethylamino}-4-methyl-pentanoic acid;
2-[1-Carboxy-2-(2-phenyl-thiazol-4-yl)-ethylamino]-4-methyl-pentanoic acid;
2-[1-Carboxy-2-(5-methyl-isoxazol-3-yl)-ethylamino]-4-methyl-pentanoic acid;
2-[2-(1-Benzyl-1H-pyrazol-3-yl)-1-carboxy-ethylamino]-4-methyl-pentanoic acid;
2-{1-Carboxy-2-[3-(2,3-dimethoxy-benzyl)-3H-imidazol-4-yl]-ethylamino}-4-methyl-pentanoic acid;
2-{1-Carboxy-2-[3-(2-methyl-biphenyl-3-ylmethyl)-3H-imidazol-4-yl]-ethylamino}-4-methyl-pentanoic acid;
'2-{1-Carboxy-2-[3-(2-methoxy-naphthalen-1-ylmethyl)-3H-imidazol-4-yl]-ethylamino}-4-methyl-pentanoic acid;
2-{1-Carboxy-2-[3-(2,3-difluoro-benzyl)-3H-imidazol-4-yl]-ethylamino}-4-methyl-pentanoic acid;
2-{1-Carboxy-2-[1-(2,3-difluoro-benzyl)-1H-imidazol-4-yl]-ethylamino}-4-methyl-pentanoic acid;
2-{1-Carboxy-2-[3-(2,3-dichloro-benzyl)-3H-imidazol-4-yl]-ethylamino}-4-methyl-pentanoic acid;
'2-{1-Carboxy-2-[3-(3-trifluoromethyl-benzyl)-3H-imidazol-4-yl]-ethylamino}-4-methyl-pentanoic acid;
2-{1-Carboxy-2-[3-(2,5-dichloro-benzyl)-3H-imidazol-4-yl]-ethylamino}-4-methyl-pentanoic acid;
2-{1-Carboxy-2-[3-(2,6-dichloro-benzyl)-3H-imidazol-4-yl]-ethylamino}-4-methyl-pentanoic acid;
4-Methyl-2-[1-methylcarbamoyl-2-(3-phenylamino-3H-imidazol-4-yl)-ethylamino]-pentanoic acid;
2-[2-(4-Benzyl-furan-3-yl)-1-carboxy-ethylamino]-4-methyl-pentanoic acid;
2-[1-Carboxy-2-(3-phenyl-3H-imidazol-4-yl)-ethylamino]-4-methyl-pentanoic acid;
2-[1-Carboxy-2-(3-phenethyl-3H-imidazol-4-yl)-ethylamino]-4-methyl-pentanoic acid;
2-{1-Carboxy-2-[3-(pyridin-3-yloxy)-3H-imidazol-4-yl]-ethylamino}-4-methyl-pentanoic acid;
2-{1-Carboxy-2-[3-(4-nitro-phenoxy)-3H-imidazol-4-yl]-ethylamino}-4-methyl-pentanoic acid;
2-[1-Carboxy-2-(3-phenoxy-3H-imidazol-4-yl)-ethylamino]-4-methyl-pentanoic acid;
2-{1-Carboxy-2-[3-(2-nitro-benzyl)-3H-imidazol-4-yl]-ethylamino}-4-methyl-pentanoic acid;
2-{1-Carboxy-2-[3-(3-nitro-benzyl)-3H-imidazol-4-yl]-ethylamino}-4-methyl-pentanoic acid;
2-{1-Carboxy-2-[3-(2-trifluoromethyl-benzyl)-3H-imidazol-4-yl]-ethylamino}-4-methyl-pentanoic acid;
2-{1-Carboxy-2-[3-(3-trifluoromethyl-benzyl)-3H-imidazol-4-yl]-ethylamino}-4-methyl-pentanoic acid;
2-{1-Carboxy-2-[3-(2-methyl-benzyl)-3H-imidazol-4-yl]-ethylamino}-4-methyl-pentanoic acid;
2-{1-Carboxy-2-[3-(3-methyl-benzyl)-3H-imidazol-4-yl]-ethylamino}-4-methyl-pentanoic acid;
2-{1-Carboxy-2-[3-(2-chloro-benzyl)-3H-imidazol-4-yl]-ethylamino}-4-methyl-pentanoic acid;
2-{1-Carboxy-2-[3-(3-chloro-benzyl)-3H-imidazol-4-yl]-ethylamino}-4-methyl-pentanoic acid;
2-{1-Carboxy-2-[3-(2-hydroxy-benzyl)-3H-imidazol-4-yl]-ethylamino}-4-methyl-pentanoic acid;
2-{1-Carboxy-2-[3-(3-hydroxy-benzyl)-3H-imidazol-4-yl]-ethylamino}-4-methyl-pentanoic acid;
2-{1-Carboxy-2-[3-(2-fluoro-benzyl)-3H-imidazol-4-yl]-ethylamino}-4-methyl-pentanoic acid;
2-[2-(3-Benzyl-3H-imidazol-4-yl)-1-carboxy-ethylamino]-4-methyl-pentanoic acid;
2-[1-Carboxy-2-(3-phenylamino-3H-imidazol-4-yl)-ethylamino]-4-methyl-pentanoic acid;
2-{[2,3-Dioxo-1-(3-phenylamino-3H-imidazol-4-ylmethyl)-butyl]-methyl-amino}-4-methyl-pentanoic acid;
2-{[2,3-Dioxo-1-(4-phenylamino-furan-3-ylmethyl)-butyl]-methyl-amino}-4-methyl-pentanoic acid;
2-[2,3-Dioxo-1-(4-phenylamino-furan-3-ylmethyl)-butylamino]-4-methyl-pentanoic acid;
2-[1-Carboxy-2-(4-phenylamino-furan-3-yl)-ethylamino]-4-methyl-pentanoic acid;
2-[1-Carboxy-2-(2-o-tolyl-2H-isoindol-1-yl)-ethylamino]-4-methyl-pentanoic acid;
2-[2-(2-Benzyl-2H-isoindol-1-yl)-1-carboxy-ethylamino]-4-methyl-pentanoic acid;
2-[1-Carboxy-2-(2-phenyl-2H-isoindol-1-yl)-ethylamino]-4-methyl-pentanoic acid;
2-[1-Carboxy-2-(2-pyridin-2-yl-2H-isoindol-1-yl)-ethylamino]-4-methyl-pentanoic acid;

2-{1-Carboxy-2-[2-(3-nitro-phenyl)-2H-isoindol-1-yl]-ethylamino}-4-methyl-pentanoic acid;
2-{1-Carboxy-2-[2-(4-nitro-phenyl)-2H-isoindol-1-yl]-ethylamino}-4-methyl-pentanoic acid;
2-{1-Carboxy-2-[2-(4-nitro-benzyl)-2H-isoindol-1-yl]-ethylamino}-4-methyl-pentanoic acid;
2-({Carboxy-[3-(4-nitro-phenyl)-naphthalen-1-yl]-methyl}-amino)-4-methyl-pentanoic acid;
2-({Carboxy-[3-(4-nitro-benzyl)-naphthalen-1-yl]-methyl}-amino)-4-methyl-pentanoic acid;
'2-{1-Carboxy-2-[3-(3-trifluoromethyl-benzyl)-3H-imidazol-4-yl]-ethylamino}-4-methyl-pentanoic acid;
2-{1-Carboxy-2-[3-(2,5-dichloro-benzyl)-3H-imidazol-4-yl]-ethylamino}-4-methyl-pentanoic acid;
2-{1-Carboxy-2-[3-(2,6-dichloro-benzyl)-3H-imidazol-4-yl]-ethylamino}-4-methyl-pentanoic acid;
2-[1-Carboxy-2-(3-cyclohexylmethyl-3H-imidazol-4-yl)-ethylamino]-4-methyl-pentanoic acid;
2-[1-Carboxy-2-(3-phenethyl-3H-imidazol-4-yl)-ethylamino]-4-methyl-pentanoic acid;
2-{1-Carboxy-2-[3-(2-ethyl-butyl)-3H-imidazol-4-yl]-ethylamino}-4-methyl-pentanoic acid;
2-{1-Carboxy-2-[3-(3-iodo-benzyl)-3H-imidazol-4-yl]-ethylamino}-4-methyl-pentanoic acid;
2-{1-Carboxy-2-[3-(3-fluoro-benzyl)-3H-imidazol-4-yl]-ethylamino}-4-methyl-pentanoic acid;
2-{1-Carboxy-2-[3-(3-fluoro-benzyl)-3H-imidazol-4-yl]-ethylamino}-4-methyl-pentanoic acid;
2-[1-Carboxy-2-(2-phenylethynyl-1H-imidazol-4-yl)-ethylamino]-4-methyl-pentanoic acid;
2-[1-Carboxy-2-(1-methyl-2-phenylethynyl-1H-imidazol-4-yl)-ethylamino]-4-methyl-pentanoic acid;
2-[1-Carboxy-2-(2-phenethyl-1H-imidazol-4-yl)-ethylamino]-4-methyl-pentanoic acid;
2-[1-Carboxy-3-(3-phenyl-3H-imidazol-4-yl)-propylamino]-4-methyl-pentanoic acid;
2-[1-Carboxy-2-(3-phenyl-3H-imidazol-4-yl)-ethylamino]-4-methyl-pentanoic acid;
2-[2-(3-Benzyl-2,5-dimethyl-3H-imidazol-4-yl)-1-carboxy-ethylamino]-4-methyl-pentanoic acid;
2-[1-Carboxy-4-(3-phenyl-3H-imidazol-4-yl)-butylamino]-4-methyl-pentanoic acid;
2-[2-(2-Benzyl-thiazol-4-yl)-1-carboxy-ethylamino]-4-methyl-pentanoic acid;
2-[1-Carboxy-2-(2-phenyl-oxazol-4-yl)-ethylamino]-4-methyl-pentanoic acid;
2-{1-Carboxy-2-[2-(3,5-dichloro-phenyl)-oxazol-4-yl]-ethylamino}-4-methyl-pentanoic acid;
2-{1-Carboxy-2-[2-(3,5-dimethyl-phenyl)-oxazol-4-yl]-ethylamino}-4-methyl-pentanoic acid;
2-[2-(2-Benzyl-oxazol-4-yl)-1-carboxy-ethylamino]-4-methyl-pentanoic acid;
2-{1-Carboxy-2-[2-(3,5-dichloro-benzyl)-oxazol-4-yl]-ethylamino}-4-methyl-pentanoic acid;
2-{1-Carboxy-2-[2-(3,5-dimethyl-benzyl)-oxazol-4-yl]-ethylamino}-4-methyl-pentanoic acid;
2-{1-Carboxy-2-[2-(2-cyclohexyl-ethyl)-oxazol-4-yl]-ethylamino}-4-methyl-pentanoic acid;
2-[1-Carboxy-2-(4-phenyl-oxazol-2-yl)-ethylamino]-4-methyl-pentanoic acid;
2-{1-Carboxy-2-[4-(3,5-dichloro-phenyl)-oxazol-2-yl]-ethylamino}-4-methyl-pentanoic acid;
2-{1-Carboxy-2-[4-(3,5-dimethyl-phenyl)-oxazol-2-yl]-ethylamino}-4-methyl-pentanoic acid;
2-[2-(4-Benzyl-oxazol-2-yl)-1-carboxy-ethylamino]-4-methyl-pentanoic acid;
2-{1-Carboxy-2-[4-(3,5-dichloro-benzyl)-oxazol-2-yl]-ethylamino}-4-methyl-pentanoic acid;
2-{1-Carboxy-2-[4-(3,5-dimethyl-benzyl)-oxazol-2-yl]-ethylamino}-4-methyl-pentanoic acid;
2-{1-Carboxy-2-[4-(2-cyclohexyl-ethyl)-oxazol-2-yl]-ethylamino}-4-methyl-pentanoic acid;
2-{2-[5-(1H-Benzoimidazol-2-yl)-isoxazol-3-yl]-1-carboxy-ethylamino}-4-methyl-pentanoic acid;
2-{1-Carboxy-2-[1-(3-phenyl-propyl)-1H-[1,2,3]triazol-4-yl]-ethylamino}-4-methyl-pentanoic acid;
2-[1-Carboxy-2-(4-pyridin-4-yl-oxazol-2-yl)-ethylamino]-4-methyl-pentanoic acid;
2-{1-Carboxy-2-[2-(3,5-dichloro-phenyl)-thiazol-4-yl]-ethylamino}-4-methyl-pentanoic acid;
2-{1-Carboxy-2-[2-(3,5-dimethyl-phenyl)-thiazol-4-yl]-ethylamino}-4-methyl-pentanoic acid;
2-[2-(2-Benzyl-thiazol-4-yl)-1-carboxy-ethylamino]-4-methyl-pentanoic acid;
2-{1-Carboxy-2-[2-(3,5-dimethyl-benzyl)-thiazol-4-yl]-ethylamino}-4-methyl-pentanoic acid;
2-{1-Carboxy-2-[2-(3,5-dichloro-benzyl)-thiazol-4-yl]-ethylamino}-4-methyl-pentanoic acid;
2-[1-Carboxy-2-(4-phenyl-thiazol-2-yl)-ethylamino]-4-methyl-pentanoic acid;
2-{1-Carboxy-2-[2-(2-cyclohexyl-ethyl)-thiazol-4-yl]-ethylamino}-4-methyl-pentanoic acid;
2-{1-Carboxy-2-[4-(3,5-dimethyl-phenyl)-thiazol-2-yl]-ethylamino}-4-methyl-pentanoic acid;
2-{1-Carboxy-2-[4-(3,5-dichloro-phenyl)-thiazol-2-yl]-ethylamino}-4-methyl-pentanoic acid;
2-[1-Carboxy-2-(2-pyridin-4-yl-thiazol-4-yl)-ethylamino]-4-methyl-pentanoic acid;
2-[2-(4-Benzyl-thiazol-2-yl)-1-carboxy-ethylamino]-4-methyl-pentanoic acid;
2-{1-Carboxy-2-[4-(3,5-dichloro-benzyl)-thiazol-2-yl]-ethylamino}-4-methyl-pentanoic acid;
2-{1-Carboxy-2-[4-(3,5-dimethyl-benzyl)-thiazol-2-yl]-ethylamino}-4-methyl-pentanoic acid;
2-{1-Carboxy-2-[4-(2-cyclohexyl-ethyl)-thiazol-2-yl]-ethylamino}-4-methyl-pentanoic acid;
2-[1-Carboxy-2-(4-pyridin-4-yl-thiazol-2-yl)-ethylamino]-4-methyl-pentanoic acid;
2-[(3-Benzo[1,3]dioxol-5-yl-propyl)-(2-mercapto-ethyl)-amino]-4-methyl-pentanoic acid;
2-[Cyclohexanecarbonyl-(2-mercapto-ethyl)-amino]-4-methyl-pentanoic acid;
2-[(Benzo[1,2,5]thiadiazol-5-ylmethanesulfonyl)-(2-mercapto-ethyl)-amino]-4-methyl-pentanoic acid;
2-[But-3-enyloxycarbonyl-(2-mercapto-ethyl)-amino]-4-methyl-pentanoic acid;
2-[N'-(1-Benzyl-pyrrolidin-3-yl)-N-(2-mercapto-ethyl)-guanidino]-4-methyl-pentanoic acid;
2-[1-(2-Mercapto-ethyl)-3-(1-phenyl-ethyl)-ureido]-4-methyl-pentanoic acid;
2-[3-Furan-2-ylmethyl-1-(2-mercapto-ethyl)-thioureido]-4-methyl-pentanoic acid;
2-{1-Carboxy-2-[2-(3-trifluoromethyl-phenyl)-thiazol-4-yl]-ethylamino}-4-methyl-pentanoic acid;
2-(1-Carboxy-3-methylamino-propylamino)-4-methyl-pentanoic acid; compound with 3-phenyl-propionaldehyde;
2-{1-Carboxy-3-[2-(4-chloro-phenoxy)-acetylamino]-propylamino}-4-methyl-pentanoic acid;
2-[3-(Biphenyl-4-sulfonylamino)-1-carboxy-propylamino]-4-methyl-pentanoic acid;
2-{3-[(Biphenyl-4-carbonyl)-amino]-1-carboxy-propylamino}-4-methyl-pentanoic acid;

2-{1-Carboxy-3-[(naphthalene-2-carbonyl)-amino]-propylamino}-4-methyl-pentanoic acid;
2-[1-Carboxy-3-(4-methoxy-benzenesulfonylamino)-propylamino]-4-methyl-pentanoic acid;
2-[1-Carboxy-3-(naphthalene-2-sulfonylamino)-propylamino]-4-methyl-pentanoic acid;
2-[3-(3,5-Bis-trifluoromethyl-benzoylamino)-1-carboxy-propylamino]-4-methyl-pentanoic acid;
2-[2-(5-Benzyl-2-methyl-thiazol-4-yl)-1-carboxy-ethylamino]-4-methyl-pentanoic acid;
2-{1-Carboxy-3-[(naphthalene-2-carbonyl)-amino]-propylamino}-4-methyl-pentanoic acid;
2-[3-(Biphenyl-4-sulfonylamino)-1-carboxy-propylamino]-4-methyl-pentanoic acid;
2-{1-Carboxy-2-[2-(2,4-dichloro-phenyl)-thiazol-4-yl]-ethylamino}-4-methyl-pentanoic acid;
2-{1-Carboxy-2-[2-(2,3-dihydro-benzofuran-5-yl)-thiazol-4-yl]-ethylamino}-4-methyl-pentanoic acid;
2-{1-Carboxy-2-[2-(3-chloro-4-fluoro-phenyl)-thiazol-4-yl]-ethylamino}-4-methyl-pentanoic acid;
2-[1-Carboxy-2-(2-p-tolyl-thiazol-4-yl)-ethylamino]-4-methyl-pentanoic acid;
2-[1-Carboxy-2-(5-phenyl-isoxazol-3-yl)-ethylamino]-4-methyl-pentanoic acid;
2-(2-Mercapto-3-phenyl-propionylamino)-4-methyl-pentanoic acid;
2-[1-Carboxy-3-(4'-chloro-biphenyl-4-sulfonylamino)-propylamino]-4-methyl-pentanoic acid;
2-[1-Carboxy-3-(3-methoxy-benzoylamino)-propylamino]-4-methyl-pentanoic acid;
2-[1-Carboxy-3-(3-chloro-benzoylamino)-propylamino]-4-methyl-pentanoic acid;
2-[2-(4-Benzyloxy-phenyl)-1-carboxy-ethylamino]-4-methyl-pentanoic acid;
2-[1-Carboxy-2-(4-cyclohexylmethoxy-phenyl)-ethylamino]-4-methyl-pentanoic acid;
2-{1-Carboxy-2-[4-(3,5-dichloro-benzyloxy)-phenyl]-ethylamino}-4-methyl-pentanoic acid;
2-{1-Carboxy-2-[4-(3,5-dimethyl-benzyloxy)-phenyl]-ethylamino}-4-methyl-pentanoic acid;
2-{1-Carboxy-2-[3-(3,4-dichloro-benzyl)-2-oxo-2,3-dihydro-imidazol-1-yl]-ethylamino}-4-methyl-pentanoic acid;
2-[2-(Benzothiazol-2-ylcarbamoyl)-1-carboxy-ethylamino]-4-methyl-pentanoic acid;
2-(1-Carboxy-3-{4-[(4-chloro-phenyl)-phenyl-methyl]-piperazin-1-yl}-3-oxo-propylamino)-4-methyl-pentanoic acid;
2-{2-[3-(3,5-Dichloro-benzyl)-3H-imidazol-4-yl]-1-methoxycarbonyl-ethylamino}-4-methyl-pentanoic acid;
2-({1-Carboxy-2-[3-(3,5-dichloro-benzyl)-3H-imidazol-4-yl]-ethyl}-formyl-amino)-4-methyl-pentanoic acid;
2-{2-[3-(3,5-Dichloro-benzyl)-3H-imidazol-4-yl]-1-methoxycarbonyl-ethylamino}-4-methyl-pentanoic acid benzyl ester;
2-{1-Benzyloxycarbonyl-2-[3-(3,5-dichloro-benzyl)-3H-imidazol-4-yl]-ethylamino}-4-methyl-pentanoic acid;
2-{1-Butoxycarbonyl-2-[3-(3,5-dichloro-benzyl)-3H-imidazol-4-yl]-ethylamino}-4-methyl-pentanoic acid;
2-{1-Carboxy-2-[3-(3,5-dichloro-benzyl)-2-oxo-2,3-dihydro-imidazol-1-yl]-ethylamino}-4-methyl-pentanoic acid;
2-{1-Carboxy-2-[3-(3,5-difluoro-benzyl)-2-oxo-2,3-dihydro-imidazol-1-yl]-ethylamino}-4-methyl-pentanoic acid;
2-{1-Carboxy-2-[2-oxo-3-(1-phenyl-ethyl)-2,3-dihydro-imidazol-1-yl]-ethylamino}-4-methyl-pentanoic acid;
2-[1-Carboxy-2-(3-chloro-benzoylamino)-ethylamino]-4-methyl-pentanoic acid;
2-[1-Carboxy-2-(3,4-dichloro-benzoylamino)-ethylamino]-4-methyl-pentanoic acid;
2-[2-(3-Hydroxy-phenyl)-1-methoxycarbonyl-ethylamino]-4-methyl-pentanoic acid benzyl ester;
2-[1-Carboxy-2-(2-phenyl-oxazol-4-yl)-ethylamino]-4-methyl-pentanoic acid;
2-{1-Carboxy-2-[2-(3,5-dichloro-phenyl)-oxazol-4-yl]-ethylamino}-4-methyl-pentanoic acid;
2-{1-Carboxy-2-[2-(3,5-dichloro-phenyl)-thiazol-4-yl]-ethylamino}-4-methyl-pentanoic acid;
2-{1-Carboxy-2-[1-(3,5-dichloro-benzyl)-1H-pyrazol-3-yl]-ethylamino}-4-methyl-pentanoic acid;
2-{1-Cyclopentyloxycarbonyl-2-[3-(3,5-dichloro-benzyl)-3H-imidazol-4-yl]-ethylamino}-4-methyl-pentanoic acid;
2-{1-Carboxy-2-[3-(3,5-difluoro-benzyl)-2-oxo-imidazolidin-1-yl]-ethylamino}-4-methyl-pentanoic acid;
2-[2-(3-Benzyl-2-oxo-2,3-dihydro-imidazol-1-yl)-1-carboxy-ethylamino]-4-methyl-pentanoic acid;
2-[1-Carboxy-2-(4-phenethyloxy-phenyl)-ethylamino]-4-methyl-pentanoic acid;
2-[2-(4-tert-Butoxy-phenyl)-1-carboxy-ethylamino]-4-methyl-pentanoic acid;
2-{1-Carboxy-2-[4-(pyridin-4-ylmethoxy)-phenyl]-ethylamino}-4-methyl-pentanoic acid;
2-[2-(4-Allyloxy-phenyl)-1-carboxy-ethylamino]-4-methyl-pentanoic acid;
2-{1-Carboxy-2-[4-(pyridin-3-ylmethoxy)-phenyl]-ethylamino}-4-methyl-pentanoic acid;
2-[1-Carboxy-2-(4'-methyl-biphenyl-3-yl)-ethylamino]-4-methyl-pentanoic acid;
2-[1-Carboxy-2-(3-methoxy-benzoylamino)-ethylamino]-4-methyl-pentanoic acid;
2-{1-Carboxy-2-[(naphthalene-1-carbonyl)-amino]-ethylamino}-4-methyl-pentanoic acid;
2-[1-Carboxy-2-(6-chloro-benzothiazol-2-ylcarbamoyl)-ethylamino]-4-methyl-pentanoic acid;
2-[1-Carboxy-2-(5,6-dimethyl-benzothiazol-2-ylcarbamoyl)-ethylamino]-4-methyl-pentanoic acid;
2-[1-Carboxy-2-(4-chloro-benzothiazol-2-ylcarbamoyl)-ethylamino]-4-methyl-pentanoic acid;
2-{1-Carboxy-2-[3-(2-cyclohexyl-ethyl)-2-oxo-2,3-dihydro-imidazol-1-yl]-ethylamino}-4-methyl-pentanoic acid;
2-{1-Carboxy-2-[2-oxo-3-(1-phenyl-ethyl)-2,3-dihydro-imidazol-1-yl]-ethylamino}-4-methyl-pentanoic acid;
2-[1-Carboxy-2-(5,6-dichloro-benzothiazol-2-ylcarbamoyl)-ethylamino]-4-methyl-pentanoic acid;
2-[1-Carboxy-2-(3-cyclopropylmethyl-2-oxo-2,3-dihydro-imidazol-1-yl)-ethylamino]-4-methyl-pentanoic acid;
2-[1-Carboxy-2-(3',5'-dichloro-biphenyl-3-yl)-ethylamino]-4-methyl-pentanoic acid;
2-[1-Carboxy-2-(3-thiophen-3-yl-phenyl)-ethylamino]-4-methyl-pentanoic acid;
2-[1-Carboxy-2-(3',5'-dimethoxy-biphenyl-3-yl)-ethylamino]-4-methyl-pentanoic acid;
3-[2-(1-Benzyloxycarbonyl-3-methyl-butylamino)-2-methoxycarbonyl-ethyl]-pyrazole-1-carboxylic acid tert-butyl ester;
2-{2-[3-(3,5-Dichloro-benzyl)-3H-imidazol-4-yl]-1-methoxycarbonyl-ethylamino}-4-methyl-pentanoic acid methyl ester;

2-[1-Carboxy-2-(3-cyclohexyl-2-oxo-2,3-dihydro-imidazol-1-yl)-ethylamino]-4-methyl-pentanoic acid;
2-[1-Carboxy-2-(6-methoxy-benzothiazol-2-ylcarbamoyl)-ethylamino]-4-methyl-pentanoic acid;
2-[1-Carboxy-2-(6-ethoxy-benzothiazol-2-ylcarbamoyl)-ethylamino]-4-methyl-pentanoic acid;
2-[1-Carboxy-2-(6-fluoro-benzothiazol-2-ylcarbamoyl)-ethylamino]-4-methyl-pentanoic acid;
2-[2-(6-Bromo-benzothiazol-2-ylcarbamoyl)-1-carboxy-ethylamino]-4-methyl-pentanoic acid;
2-{1-Carboxy-2-[3-(3,5-difluoro-phenyl)-2-oxo-2,3-dihydro-imidazol-1-yl]-ethylamino}-4-methyl-pentanoic acid;
2-{1-Carboxy-2-[(naphthalene-2-carbonyl)-amino]-ethylamino}-4-methyl-pentanoic acid;
2-[1-Carboxy-2-(naphthalene-2-sulfonylamino)-ethylamino]-4-methyl-pentanoic acid;
2-{1-Carboxy-2-[2-(3,5-dichloro-benzyl)-2H-pyrazol-3-yl]-ethylamino}-4-methyl-pentanoic acid;
2-[1-Carboxy-2-(3-naphthalen-1-yl-phenyl)-ethylamino]-4-methyl-pentanoic acid;
2-{1-Carboxy-2-[3-(3,5-dichloro-benzyl)-3H-imidazol-4-yl]-ethylamino}-4-methyl-pentanoic acid;
2-{1-Carboxy-2-[3-(3,5-difluoro-benzyloxy)-phenyl]-ethylamino}-4-methyl-pentanoic acid;
2-[2-(3-Allyloxy-phenyl)-1-carboxy-ethylamino]-4-methyl-pentanoic acid;
2-{1-Carboxy-2-[3-(3,5-difluoro-phenyl)-2-oxo-imidazolidin-1-yl]-ethylamino}-4-methyl-pentanoic acid;
2-{1-Carboxy-2-[(5-chloro-1H-indole-2-carbonyl)-amino]-ethylamino}-4-methyl-pentanoic acid;
2-{1-Carboxy-2-[3-(3,5-dichloro-benzyl)-2-oxo-oxazolidin-4-yl]-ethylamino}-4-methyl-pentanoic acid;
2-[1-Carboxy-2-(4-thiophen-3-yl-phenyl)-ethylamino]-4-methyl-pentanoic acid;
2-[1-Carboxy-2-(3',5'-dichloro-biphenyl-4-yl)-ethylamino]-4-methyl-pentanoic acid;
2-[1-Carboxy-2-(4'-methyl-biphenyl-4-yl)-ethylamino]-4-methyl-pentanoic acid;
2-{1-Carboxy-2-[3-(4-iodo-benzyl)-3H-imidazol-4-yl]-ethylamino}-4-methyl-pentanoic acid;
2-{1-Carboxy-2-[3-(3,5-difluoro-benzyl)-3H-imidazol-4-yl]-ethylamino}-4-pentanoic acid;
2-(1-Carboxy-2-{3-[2-(4-fluoro-phenyl)-ethyl]-2-oxo-2,3-dihydro-imidazol-1-yl}-ethylamino)-4-methyl-pentanoic acid;
2-[1-Carboxy-2-(3-cyclohexylmethyl-2-oxo-2,3-dihydro-imidazol-1-yl)-ethylamino]-4-methyl-pentanoic acid;
2-{1-Carboxy-2-[3-(3,5-dichloro-benzyl)-3H-imidazol-4-yl]-ethylamino}-4-methyl-pentanoic acid tert-butyl ester;
2-{1-Carboxy-2-[3-(3,5-dichloro-benzyl)-2-oxo-oxazolidin-4-yl]-ethylamino}-4-methyl-pentanoic acid;
2-[1-Carboxy-2-(5-p-tolyl-furan-2-yl)-ethylamino]-4-methyl-pentanoic acid;
2-(1-Carboxy-2-{3-[2-(3-fluoro-phenyl)-ethyl]-2-oxo-2,3-dihydro-imidazol-1-yl}-ethylamino)-4-methyl-pentanoic acid;
2-[1-Carboxy-2-(5-phenyl-furan-2-yl)-ethylamino]-4-methyl-pentanoic acid;
2-{1-Carboxy-2-[5-(3,5-dichloro-phenyl)-furan-2-yl]-ethylamino}-4-methyl-pentanoic acid;
2-{1-Carboxy-2-[5-(3,5-dimethyl-phenyl)-furan-2-yl]-ethylamino}-4-methyl-pentanoic acid;
2-{1-Carboxy-2-[5-(3,5-difluoro-phenyl)-furan-2-yl]-ethylamino}-4-methyl-pentanoic acid;
2-[1-Carboxy-2-(5-thiophen-3-yl-furan-2-yl)-ethylamino]-4-methyl-pentanoic acid;
2-[1-Carboxy-2-(6-methyl-benzothiazol-2-ylcarbamoyl)-ethylamino]-4-methyl-pentanoic acid;
2-[1-Carboxy-2-(4-hydroxy-phenyl)-ethylamino]-4-methyl-pentanoic acid;
2-{1-Carboxy-2-[3-(3,5-dichloro-benzyloxy)-phenyl]-ethylamino}-4-methyl-pentanoic acid;
2-{1-Carboxy-2-[3-(pyridin-4-ylmethoxy)-phenyl]-ethylamino}-4-methyl-pentanoic acid;
2-{1-Carboxy-2-[3-(3,5-dimethyl-benzyloxy)-phenyl]-ethylamino}-4-methyl-pentanoic acid;
2-{1-Carboxy-2-[3-(4-chloro-benzyloxy)-phenyl]-ethylamino}-4-methyl-pentanoic acid;
2-{2-[3-(2,4-Bis-trifluoromethyl-benzyloxy)-phenyl]-1-carboxy-ethylamino}-4-methyl-pentanoic acid;
2-[1-Carboxy-2-(1-phenyl-1H-pyrazol-3-yl)-ethylamino]-4-methyl-pentanoic acid;
2-{1-Carboxy-2-[3-(3-chloro-benzyl)-2-oxo-2,3-dihydro-imidazol-1-yl]-ethylamino}-4-methyl-pentanoic acid;
2-{1-Carboxy-2-[4-(3,5-dichloro-benzyl)-phenyl]-ethylamino}-4-methyl-pentanoic acid;
2-[2-(4-Benzyl-phenyl)-1-carboxy-ethylamino]-4-methyl-pentanoic acid;
2-[1-Carboxy-2-(4-phenyl-thiazol-2-ylcarbamoyl)-ethylamino]-4-methyl-pentanoic acid;
2-{1-Carboxy-2-[5-(4-methoxy-phenyl)-furan-2-yl]-ethylamino}-4-methyl-pentanoic acid;
2-[2-(5-Benzo[1,3]dioxol-5-yl-furan-2-yl)-1-carboxy-ethylamino]-4-methyl-pentanoic acid;
2-[1-Carboxy-2-(5-naphthalen-1-yl-furan-2-yl)-ethylamino]-4-methyl-pentanoic acid;
2-{1-Carboxy-2-[5-(4-chloro-phenyl)-furan-2-yl]-ethylamino}-4-methyl-pentanoic acid;
2-{1-Carboxy-2-[5-(4-trifluoromethyl-phenyl)-furan-2-yl]-ethylamino}-4-methyl-pentanoic acid;
2-[1-Carboxy-2-(3-isobutoxy-phenyl)-ethylamino]-4-methyl-pentanoic acid;
2-{1-Carboxy-2-[3-(3-chloro-benzyloxy)-phenyl]-ethylamino}-4-methyl-pentanoic acid;
2-{1-Carboxy-2-[3-(2-chloro-benzyloxy)-phenyl]-ethylamino}-4-methyl-pentanoic acid;
2-[3-(4-Benzyloxy-phenyl)-1-carboxy-propylamino]-4-methyl-pentanoic acid;
2-{1-Carboxy-2-[5-(3-chloro-phenyl)-furan-2-yl]-ethylamino}-4-methyl-pentanoic acid;
2-{1-Carboxy-2-[3-(3-fluoro-benzyl)-2-oxo-2,3-dihydro-imidazol-1-yl]-ethylamino}-4-methyl-pentanoic acid;
2-{1-Carboxy-2-[3-(3,4-difluoro-benzyl)-2-oxo-2,3-dihydro-imidazol-1-yl]-ethylamino}-4-methyl-pentanoic acid;
2-[1-Carboxy-3-(6-fluoro-benzothiazol-2-ylcarbamoyl)-propylamino]-4-methyl-pentanoic acid;
2-{1-Carboxy-2-[3-(2,5-difluoro-benzyl)-2-oxo-2,3-dihydro-imidazol-1-yl]-ethylamino}-4-methyl-pentanoic acid;
2-{1-Carboxy-2-[4-(3,5-difluoro-benzoylamino)-phenyl]-ethylamino}-4-methyl-pentanoic acid;
2-[1-Carboxy-2-(4'-fluoro-biphenyl-4-yl)-ethylamino]-4-methyl-pentanoic acid;
2-[2-(4-Benzo[1,3]dioxol-5-yl-phenyl)-1-carboxy-ethylamino]-4-methyl-pentanoic acid;
2-[2-(4-Benzo[b]thiophen-3-yl-phenyl)-1-carboxy-ethylamino]-4-methyl-pentanoic acid;
2-[2-(3-Benzyl-phenyl)-1-carboxy-ethylamino]-4-methyl-pentanoic acid;

2-[1-Carboxy-2-(4'-trifluoromethyl-biphenyl-4-yl)-ethylamino]-4-methyl-pentanoic acid;
2-(1-Carboxy-2-{3-[2-(3-chloro-phenyl)-ethyl]-2-oxo-2,3-dihydro-imidazol-1-yl}-ethylamino)-4-methylpentanoic acid;
2-{2-[3-(4-Bromo-benzyl)-3H-imidazol-4-yl]-1-carboxy-ethylamino}-4-methyl-pentanoic acid;
2-[2-(4-Benzenesulfonylamino-phenyl)-1-carboxy-ethylamino]-4-methyl-pentanoic acid;
2-{1-Carboxy-2-[3-(3-chloro-benzyl)-phenyl]-ethylamino}-4-methyl-pentanoic acid;
2-{1-Carboxy-2-[3-(3,5-dichloro-benzyl)-phenyl]-ethylamino}-4-methyl-pentanoic acid;
2-{1-Carboxy-2-[3-(5-chloro-benzo[b]thiophen-3-ylmethoxy)-phenyl]-ethylamino}-4-methyl-pentanoic acid;
2-[1-Carboxy-2-(4-pyridin-2-yl-phenyl)-ethylamino]-4-methyl-pentanoic acid;
2-[1-Carboxy-2-(4-pyridin-3-yl-phenyl)-ethylamino]-4-methyl-pentanoic acid;
2-[1-Carboxy-2-(4-pyridin-4-yl-phenyl)-ethylamino]-4-methyl-pentanoic acid;
2-(1-Carboxy-ethylamino)-3-[3-(3,5-dichloro-benzyl)-3H-imidazol-4-yl]-propionic acid;
2-{1-Carboxy-2-[3-(3,5-dichloro-benzyl)-3H-imidazol-4-yl]-ethylamino}-4-phenyl-butyric acid;
2-(1-Carboxy-2-{3-[2-(2-fluoro-phenyl)-ethyl]-2-oxo-2,3-dihydro-imidazol-1-yl}-ethylamino)-4-methyl-pentanoic acid;
2-[1-Carboxy-2-(4-pyrrol-1-yl-phenyl)-ethylamino]-4-methyl-pentanoic acid;
2-(1-Carboxy-3-methyl-butylamino)-5-(3,5-dichloro-phenyl)-pent-4-ynoic acid;
2-{1-Carboxy-2-[4-(3,5-difluoro-phenoxy)-phenyl]-ethylamino}-4-methyl-pentanoic acid;
2-[1-Carboxy-2-(3',5'-dichloro-biphenyl-2-yl)-ethylamino]-4-methyl-pentanoic acid;
4-[2-Carboxy-2-(1-carboxy-3-methyl-butylamino)-ethyl]-benzoic acid tert-butyl ester;
2-(1-Carboxy-3-methyl-butylamino)-5-(3,5-dichloro-phenyl)-pent-4-enoic acid;
2-{1-Carboxy-2-[3-(3,5-difluoro-benzyl)-2,5-dioxo-imidazolidin-1-yl]-ethylamino}-4-methyl-pentanoic acid;
2-{1-Carboxy-2-[3-(3,5-dichloro-benzyl)-2,5-dioxo-imidazolidin-1-yl]-ethylamino}-4-methyl-pentanoic acid;
2-{2-[3-(2,4-Bis-trifluoromethyl-benzyl)-2,5-dioxo-imidazolidin-1-yl]-1-carboxy-ethylamino}-4-methyl-pentanoic acid;
2-{1-Carboxy-2-[4-(5-methyl-pyridin-2-yl)-phenyl]-ethylamino}-4-methyl-pentanoic acid;
2-{1-Carboxy-2-[4-(4-methyl-pyridin-2-yl)-phenyl]-ethylamino}-4-methyl-pentanoic acid;
2-{1-Carboxy-2-[4-(3-chloro-4-ethoxy-pyridin-2-yl)-phenyl]-ethylamino}-4-methyl-pentanoic acid;
2-[1-Carboxy-2-(4-quinolin-3-yl-phenyl)-ethylamino]-4-methyl-pentanoic acid;
2-{1-Carboxy-2-[4-(3,5-difluoro-benzylcarbamoyl)-phenyl]-ethylamino}-4-methyl-pentanoic acid;
2-{1-Carboxy-2-[4-(3,5-dichloro-phenylcarbamoyl)-phenyl]-ethylamino}-4-methyl-pentanoic acid;
2-[1-Carboxy-2-(4-phenylcarbamoyl-phenyl)-ethylamino]-4-methyl-pentanoic acid;
2-[1-Carboxy-2-(4-cyclohexylcarbamoyl-phenyl)-ethylamino]-4-methyl-pentanoic acid;
2-[1-Carboxy-2-(2-cyano-phenyl)-ethylamino]-4-methyl-pentanoic acid;
2-[1-Carboxy-2-(4-phenoxy-phenyl)-ethylamino]-4-methyl-pentanoic acid;
2-{1-Carboxy-2-[4-(5-chloro-benzo[b]thiophen-3-ylmethoxy)-phenyl]-ethylamino}-4-methyl-pentanoic acid;
2-{1-Carboxy-2-[5-(3,4-dichloro-phenyl)-isoxazol-3-yl]-ethylamino}-4-methyl-pentanoic acid;
2-{1-Carboxy-2-[4-(3,5-dichloro-phenoxy)-phenyl]-ethylamino}-4-methyl-pentanoic acid;
2-{1-Carboxy-2-[2-(3,5-dichloro-phenoxy)-phenyl]-ethylamino}-4-methyl-pentanoic acid;
2-{1-Carboxy-2-[2-(3-chloro-benzyloxy)-phenyl]-ethylamino}-4-methyl-pentanoic acid;
2-{1-Carboxy-2-[4-(4-fluoro-phenoxy)-phenyl]-ethylamino}-4-methyl-pentanoic acid;
2-[1-Carboxy-2-(1-p-tolyl-1H-pyrazol-3-yl)-ethylamino]-4-methyl-pentanoic acid;
2-{1-Carboxy-2-[4-(cyclopentanecarbonyl-amino)-phenyl]-ethylamino}-4-methyl-pentanoic acid;
2-{1-Carboxy-2-[4-(2,2-dimethyl-propionylamino)-phenyl]-ethylamino}-4-methyl-pentanoic acid;
2-{1-Carboxy-2-[2-(5-chloro-benzo[b]thiophen-3-ylmethoxy)-phenyl]-ethylamino}-4-methyl-pentanoic acid;
2-{1-Carboxy-2-[5-(4-chloro-phenyl)-isoxazol-3-yl]-ethylamino}-4-methyl-pentanoic acid;
2-{1-Carboxy-2-[5-(2-chloro-phenyl)-isoxazol-3-yl]-ethylamino}-4-methyl-pentanoic acid;
2-{1-Carboxy-2-[4-(5-fluoro-2,3-dihydro-benzofuran-3-ylmethoxy)-phenyl]-ethylamino}-4-methyl-pentanoic acid;
2-{2-[4-(Benzo[b]thiophen-3-ylmethoxy)-phenyl]-1-carboxy-ethylamino}-4-methyl-pentanoic acid;
5-[2-Carboxy-2-(1-carboxy-3-methyl-butylamino)-ethyl]-1-(3,5-dichloro-benzyl)-1H-pyrrole-2-carboxylic acid;
2-{1-Carboxy-2-[1-(2-cyclohexyl-ethyl)-5-(2,2,2-trifluoro-acetyl)-1H-pyrrol-2-yl]-ethylamino}-4-methyl-pentanoic acid;
2-[1-Carboxy-2-(4-nitro-phenyl)-ethylamino]-4-methyl-pentanoic acid;
2-{1-Carboxy-2-[4-(2-methoxy-benzoylamino)-phenyl]-ethylamino}-4-methyl-pentanoic acid;
2-[1-Carboxy-2-(2-trifluoromethyl-phenyl)-ethylamino]-4-methyl-pentanoic acid;
2-(2-{4-[Bis-(3,5-difluoro-benzyl)-amino]-phenyl}-1-carboxy-ethylamino)-4-methyl-pentanoic acid;
2-[1-Carboxy-2-(2-p-tolyl-thiazol-4-yl)-ethylamino]-4-phenyl-butyric acid;
2-[1-Carboxy-2-(4-dimethylcarbamoyl-phenyl)-ethylamino]-4-methyl-pentanoic acid;
2-{1-Carboxy-2-[4-(3,5-dimethyl-phenylcarbamoyl)-phenyl]-ethylamino}-4-methyl-pentanoic acid;
2-[2-(4-tert-Butylcarbamoyl-phenyl)-1-carboxy-ethylamino]-4-methyl-pentanoic acid;
4-Methyl-2-{[pyrimidin-2-yl-(2-p-tolyl-thiazol-4-ylmethyl)-amino]-methyl}-pentanoic acid;
2-{1-Carboxy-2-[1-(3,5-dichloro-benzyl)-1H-pyrrol-2-yl]-ethylamino}-4-methyl-pentanoic acid;
2-[1-Carboxy-2-(4-isopropylcarbamoyl-phenyl)-ethylamino]-4-methyl-pentanoic acid;
2-{1-Carboxy-2-[4-(morpholine-4-carbonyl)-phenyl]-ethylamino}-4-methyl-pentanoic acid;
2-{1-Carboxy-2-[4-(3,4-dihydro-1H-isoquinoline-2-carbonyl)-phenyl]-ethylamino}-4-methyl-pentanoic acid;
or a pharmaceutically acceptable salt or ester thereof.

16. The method of any one of claims 1–3, wherein said ACE-2 inhibitor is of the formula:
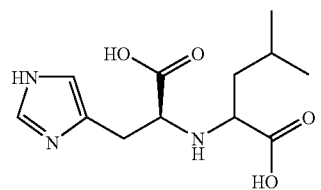
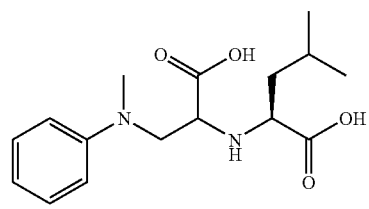
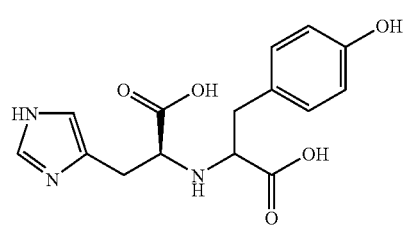
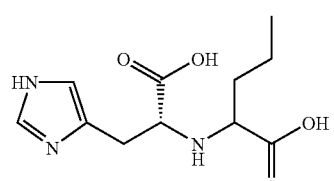
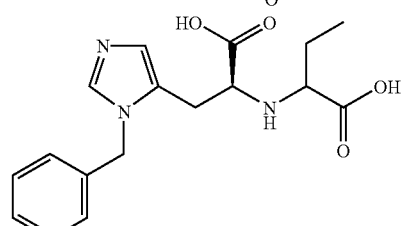
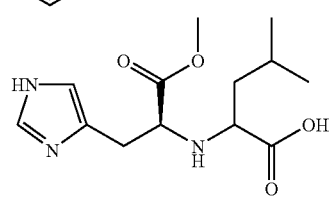
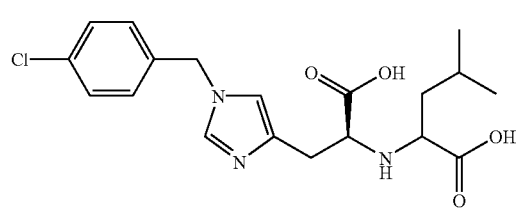
-continued
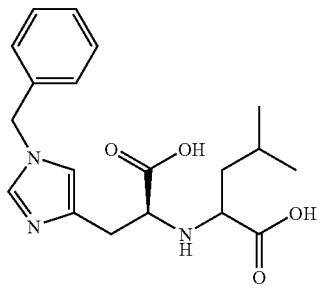
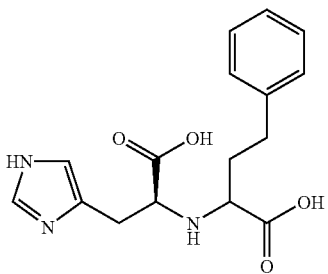
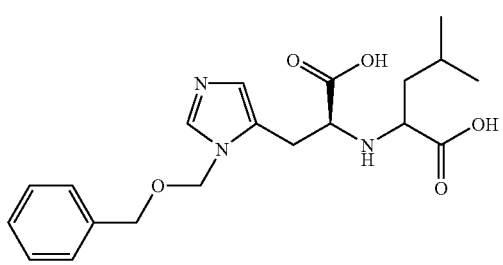
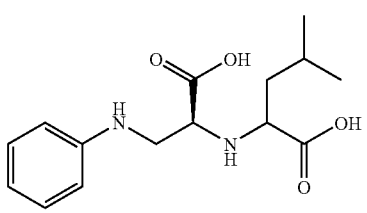
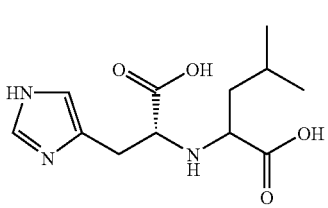
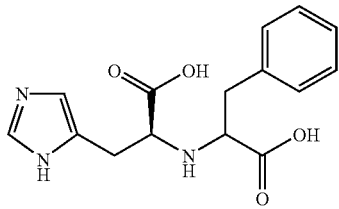

-continued
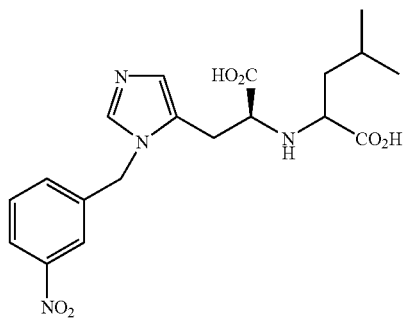
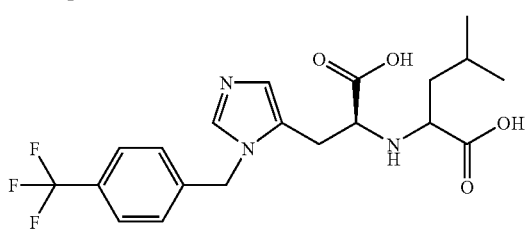
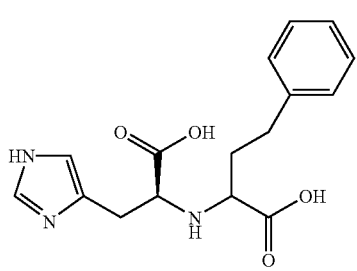
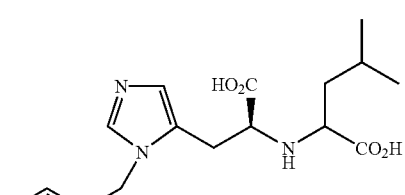
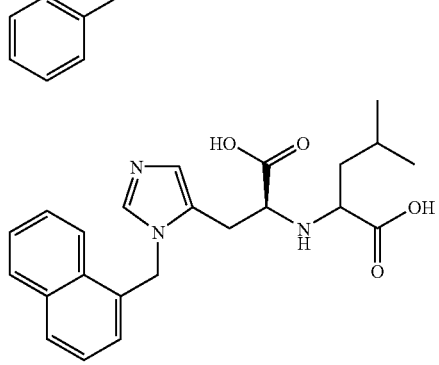
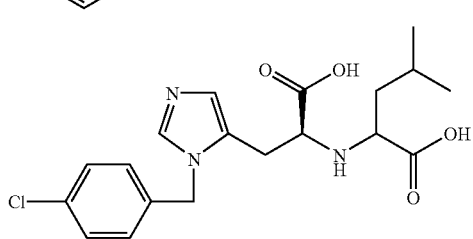
-continued
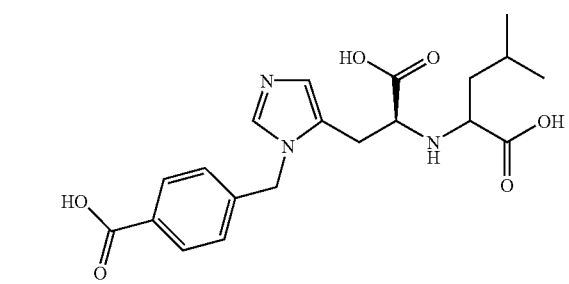
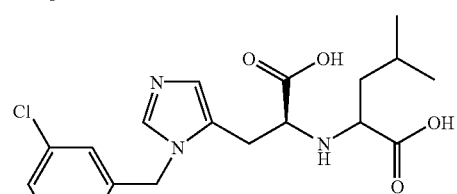
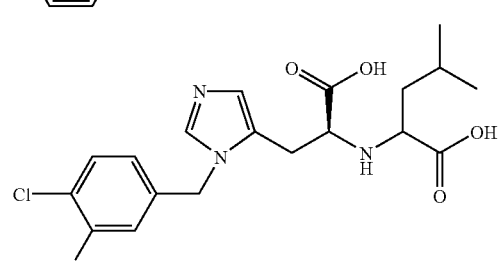
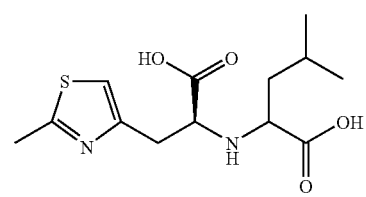
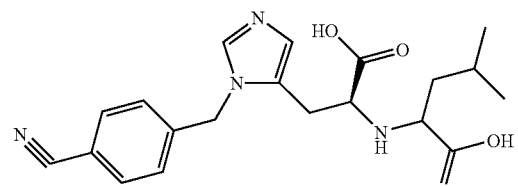
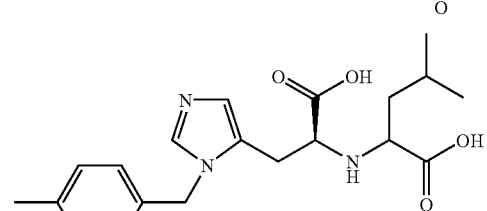
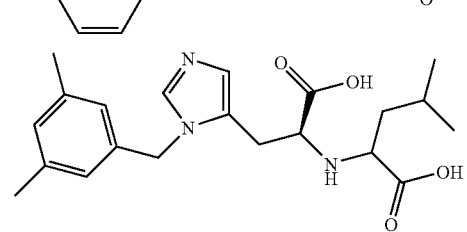

591
-continued
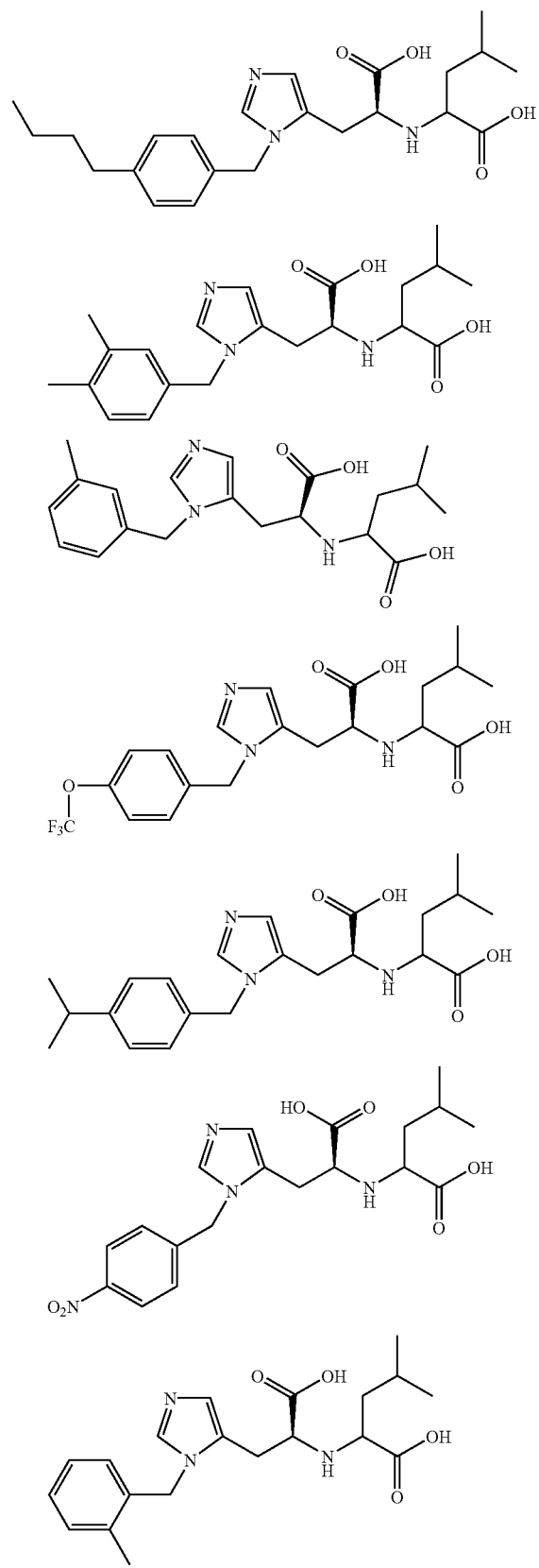
592
-continued
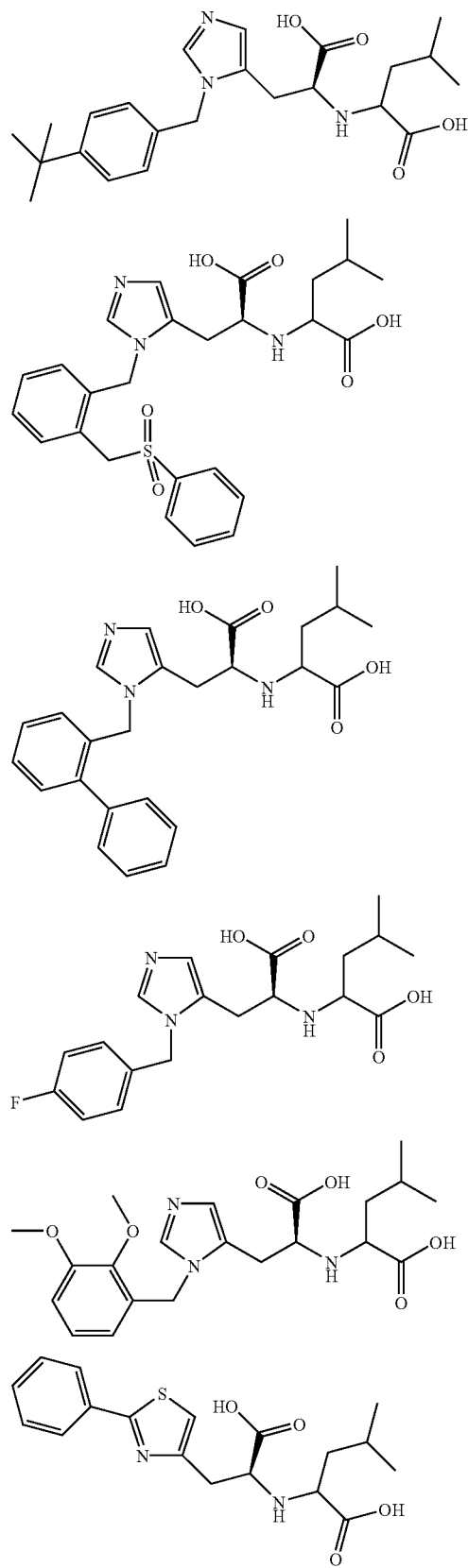

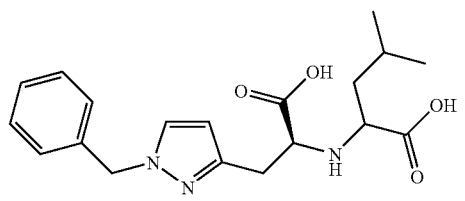
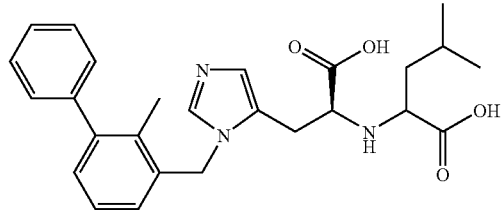
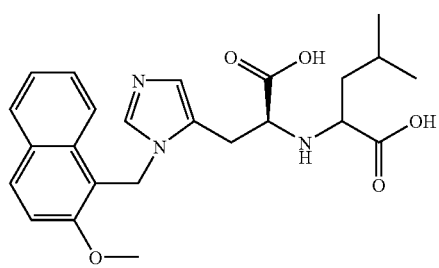
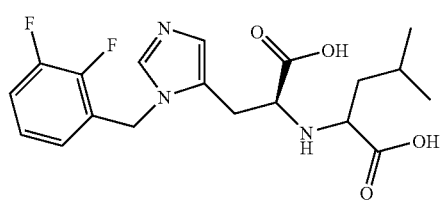
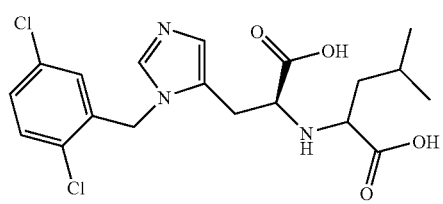
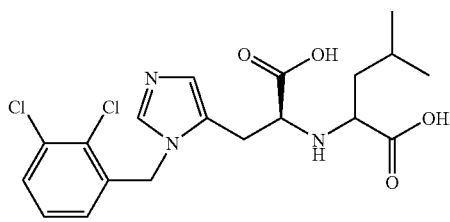
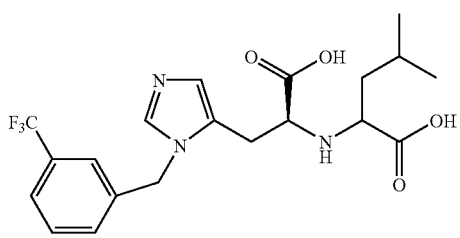
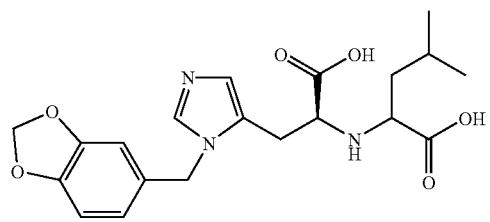
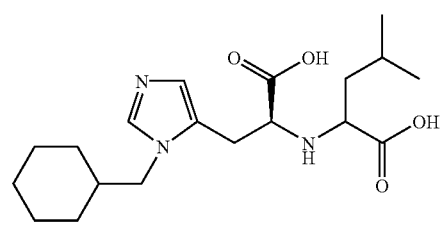
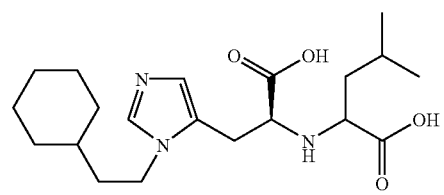
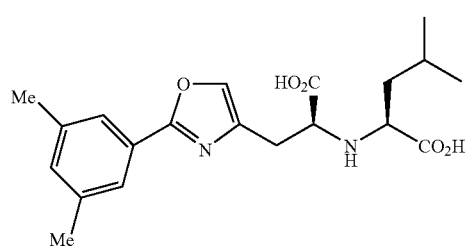
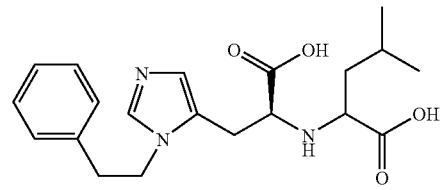
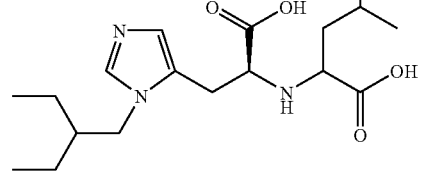
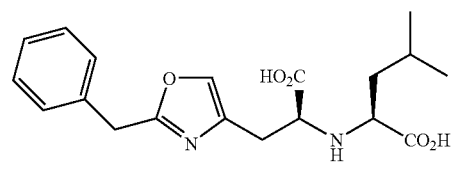

-continued
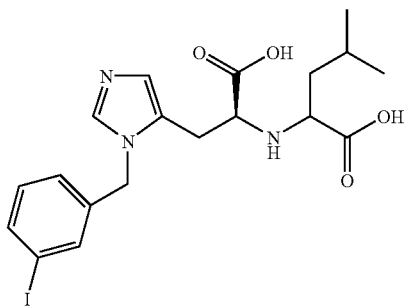
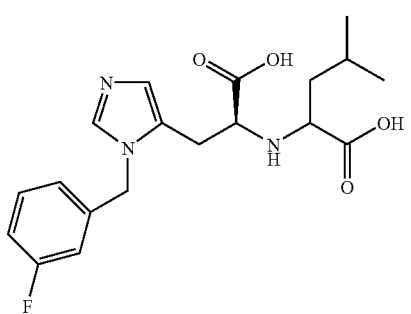
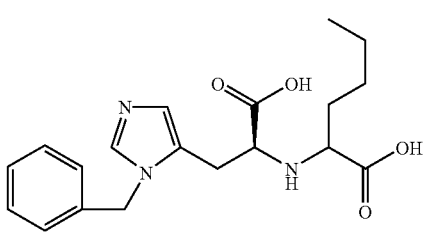
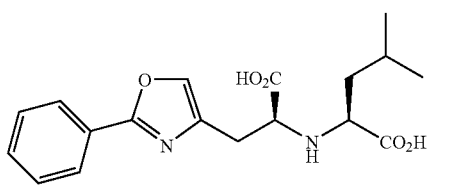
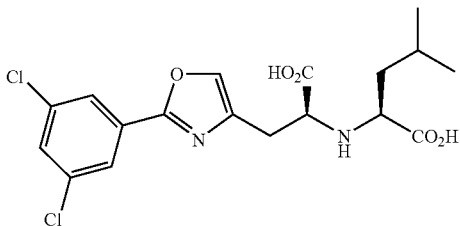
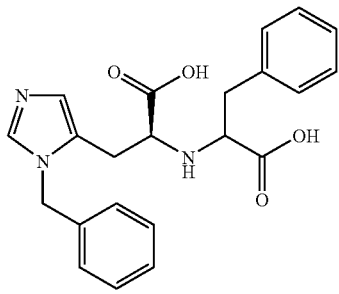
-continued
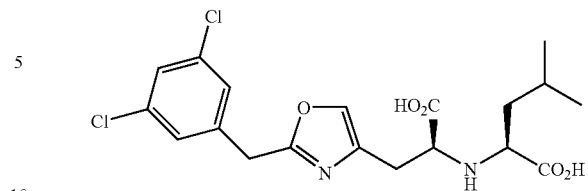
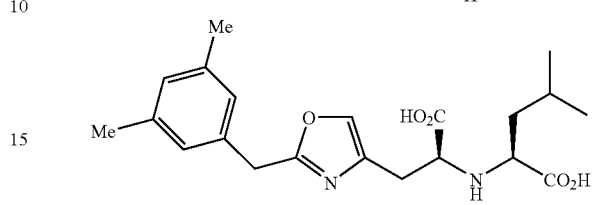
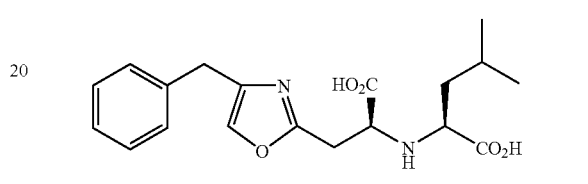
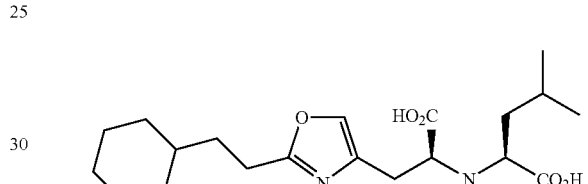
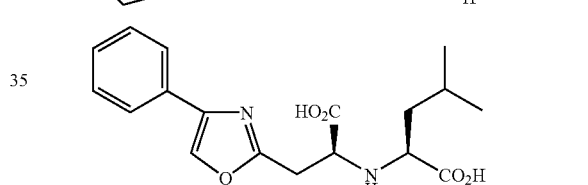
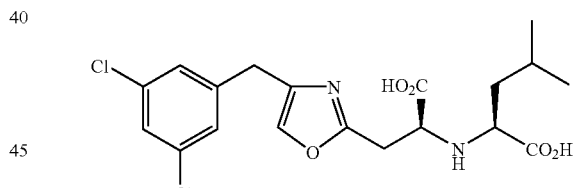
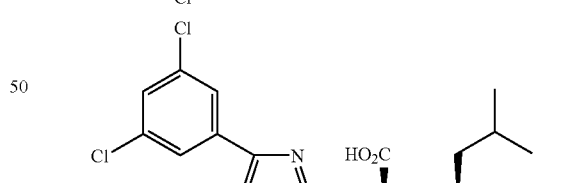
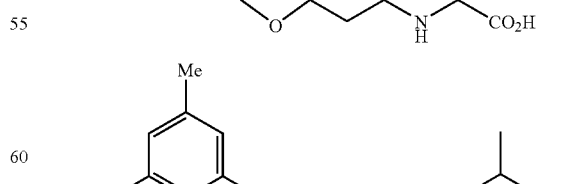
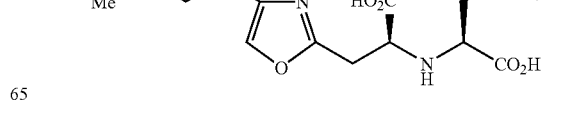

597
-continued
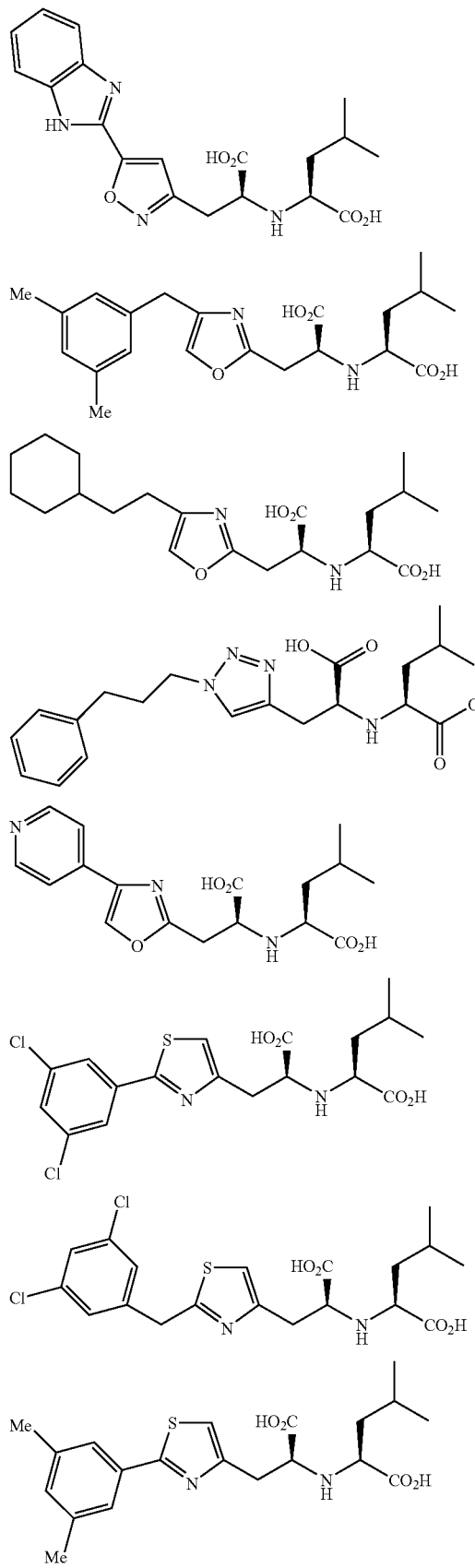
598
-continued
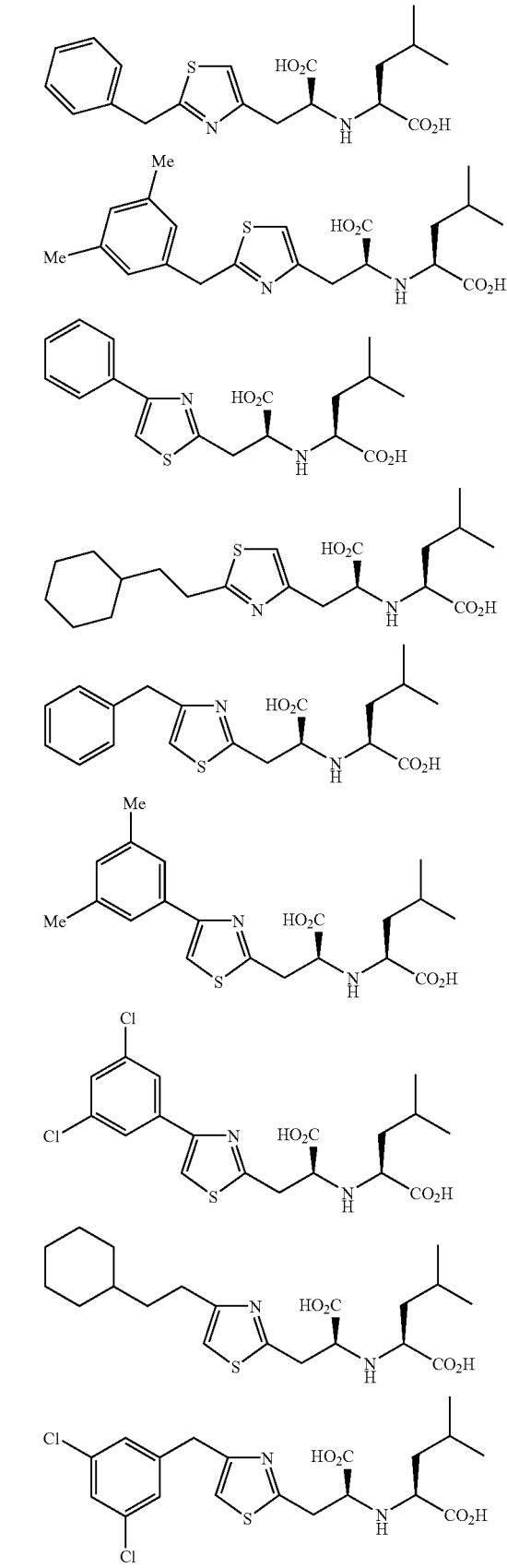

599
-continued
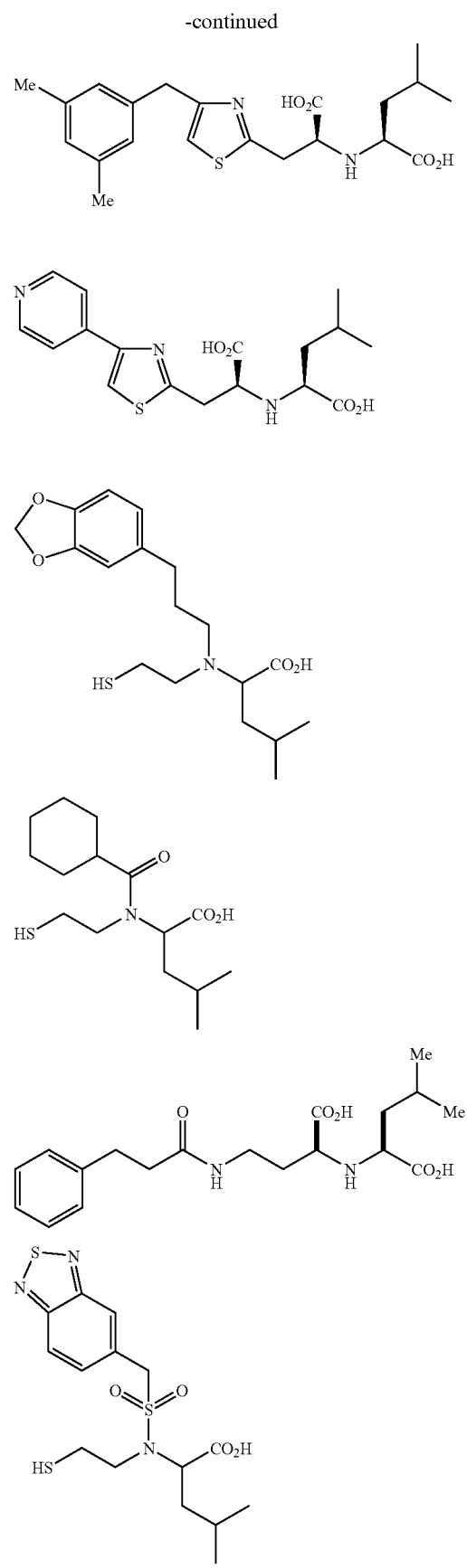
600
-continued
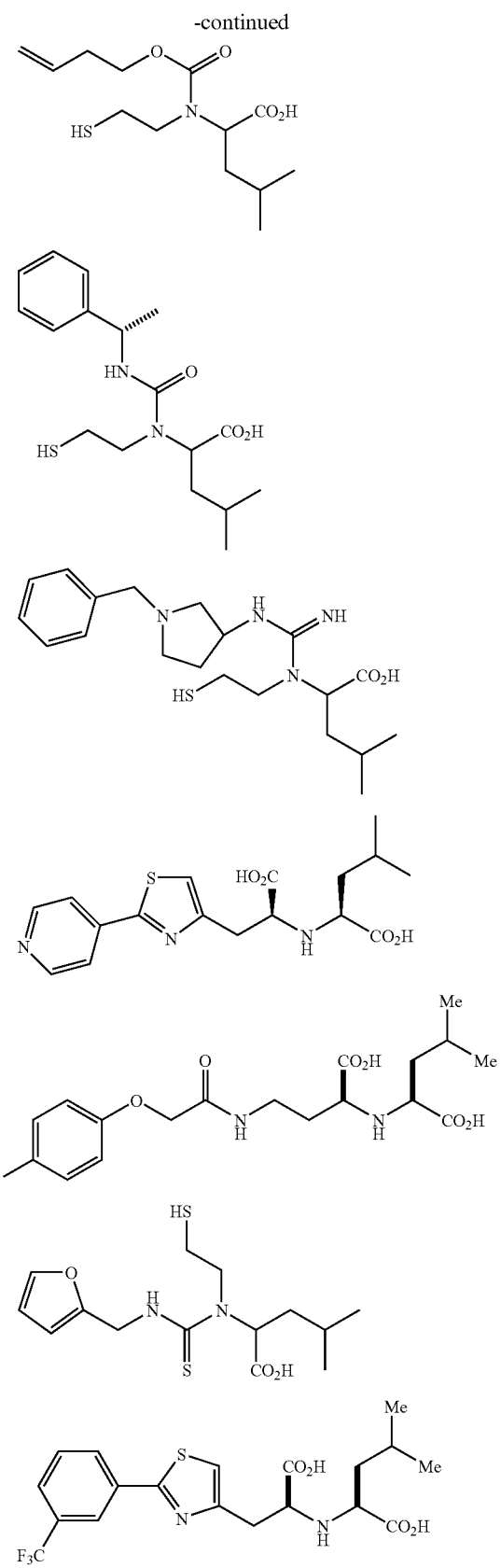

-continued
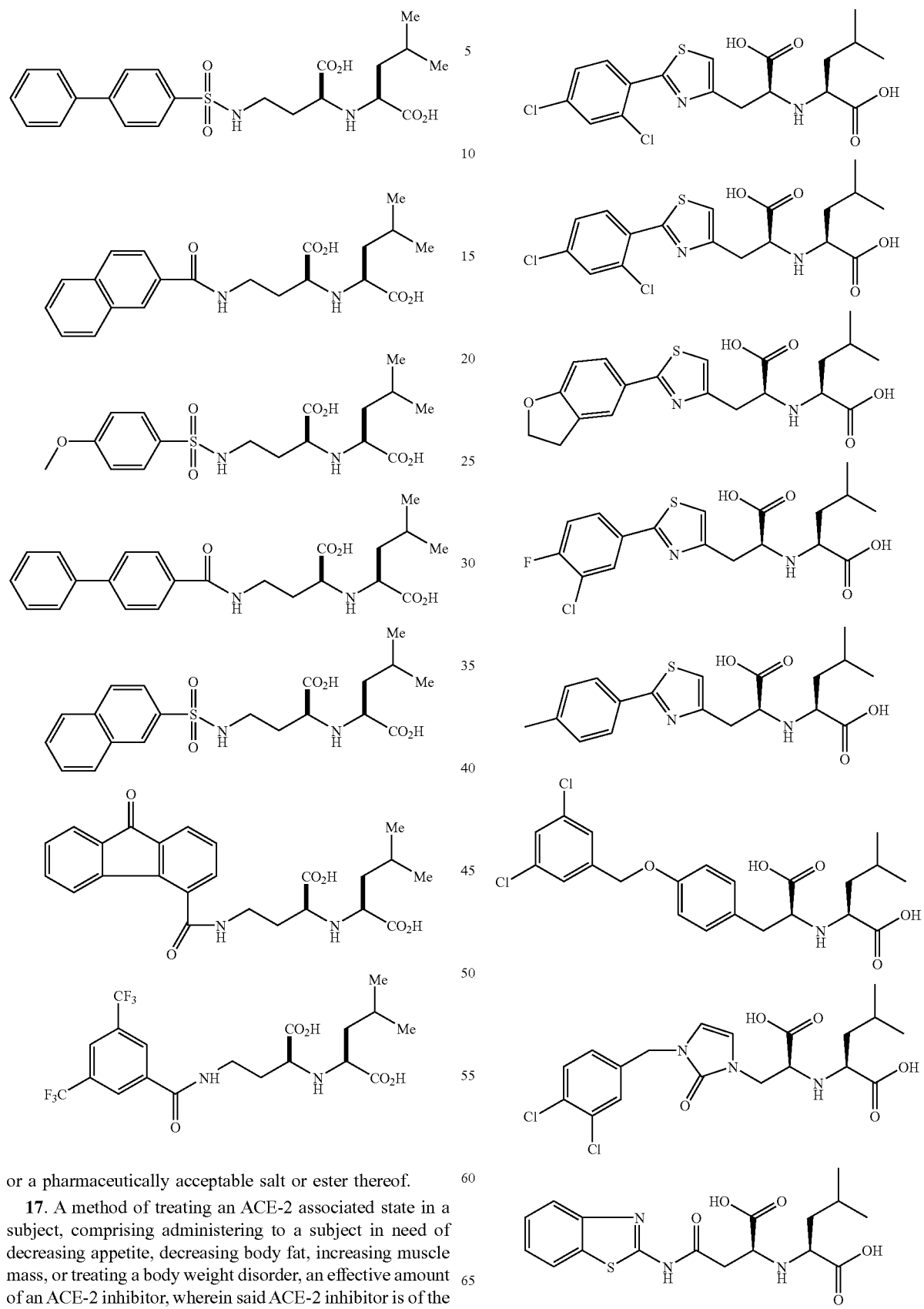
or a pharmaceutically acceptable salt or ester thereof.
17. A method of treating an ACE-2 associated state in a subject, comprising administering to a subject in need of decreasing appetite, decreasing body fat, increasing muscle mass, or treating a body weight disorder, an effective amount of an ACE-2 inhibitor, wherein said ACE-2 inhibitor is of the formula:

603
-continued
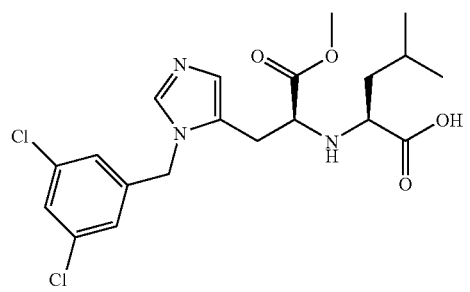
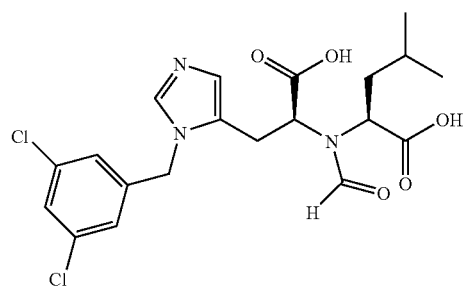
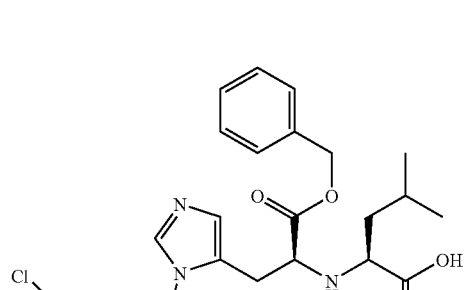
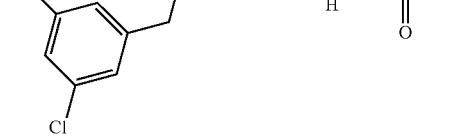
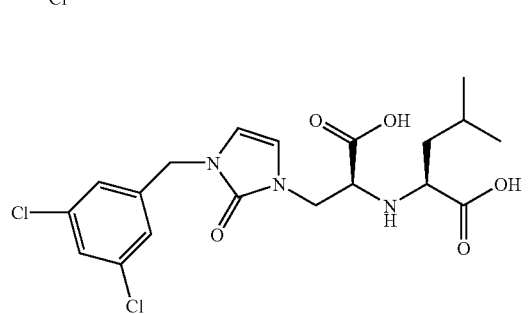
604
-continued
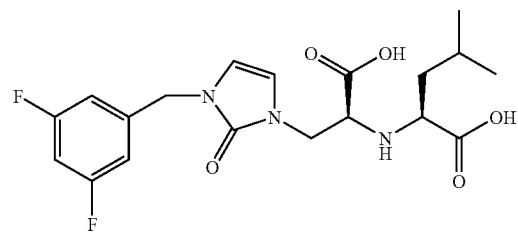
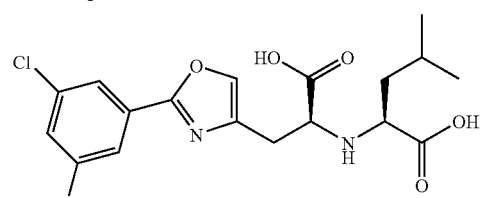
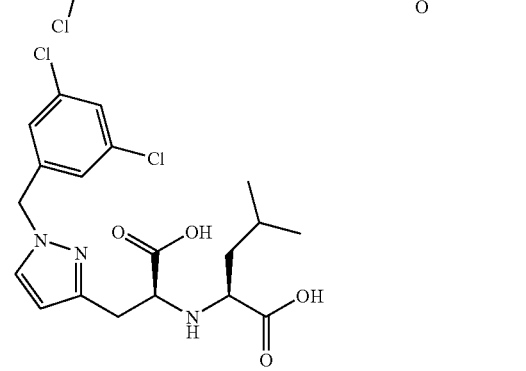
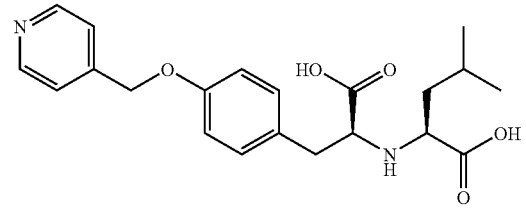
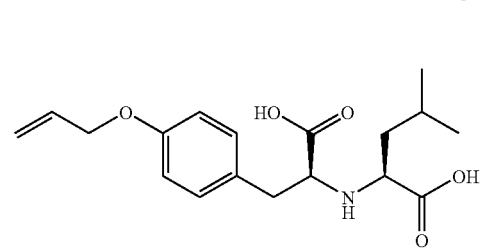
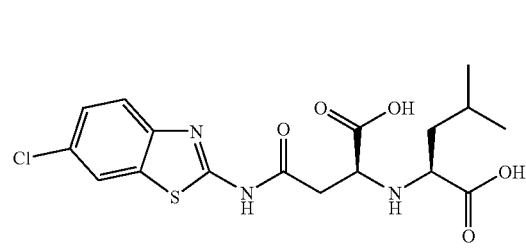
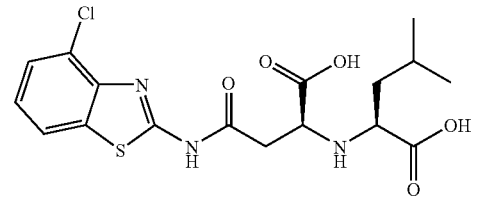

605
-continued
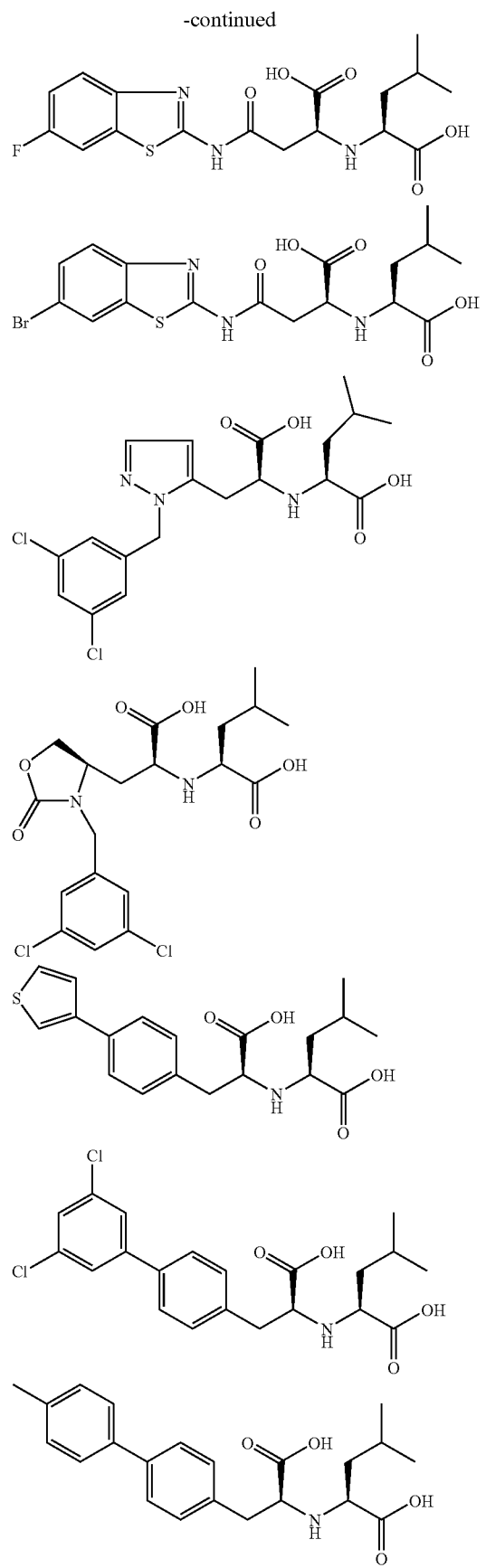
606
-continued
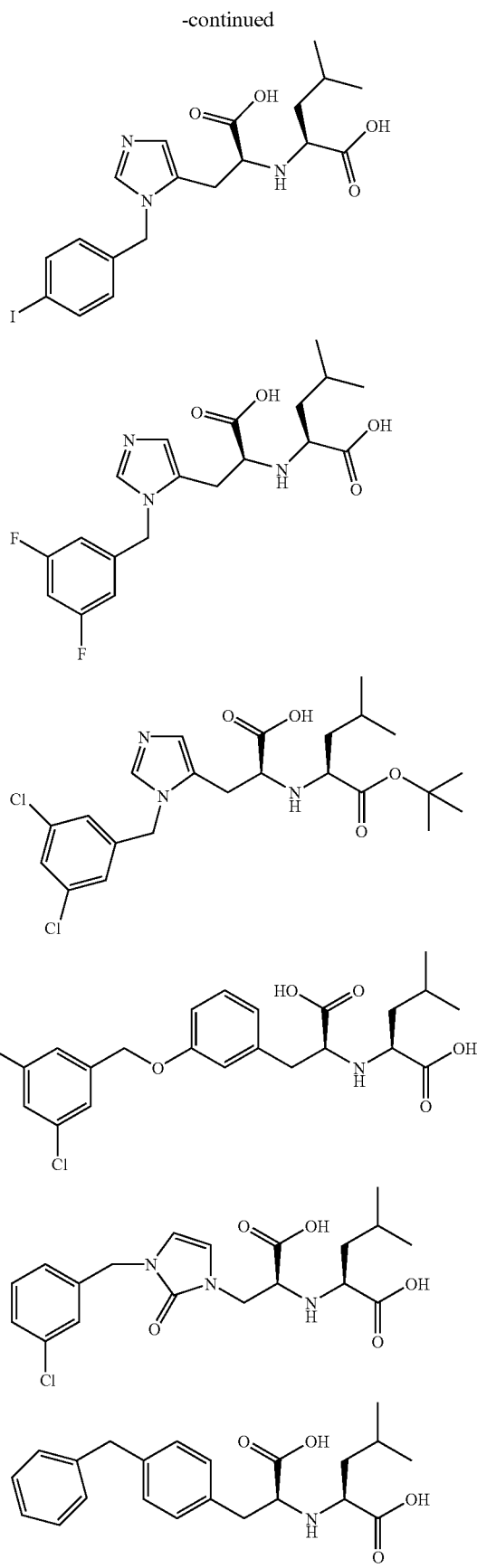

-continued
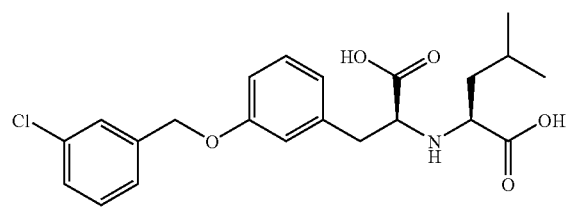
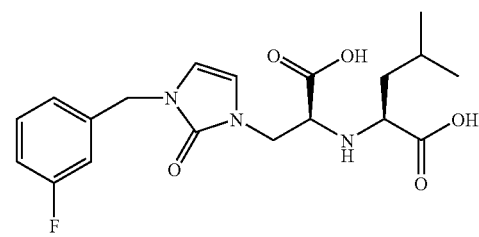
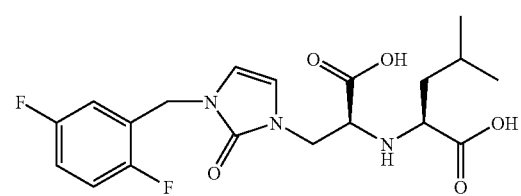
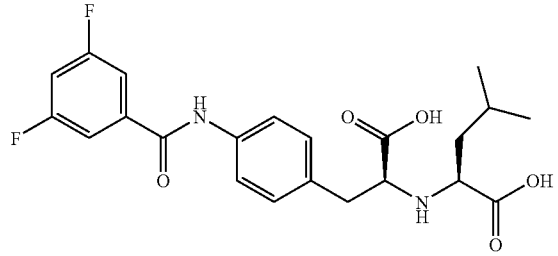
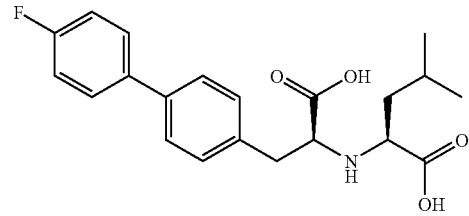
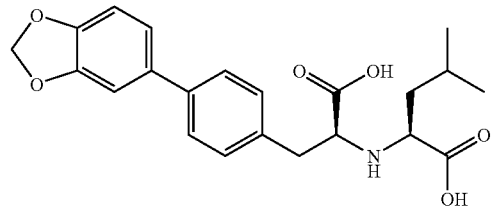
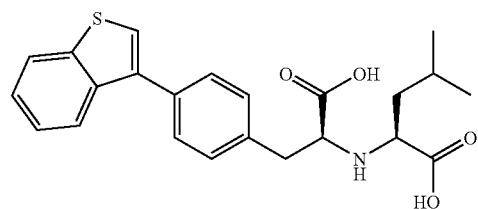
-continued
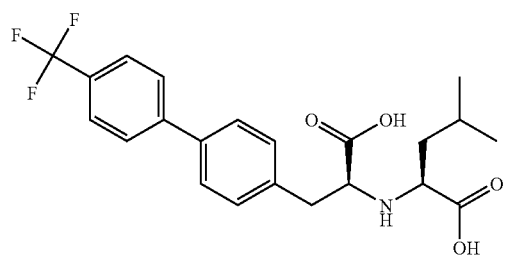
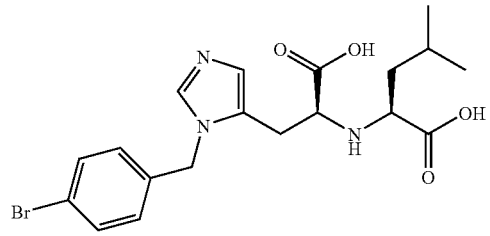
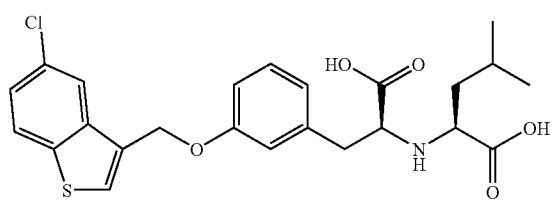
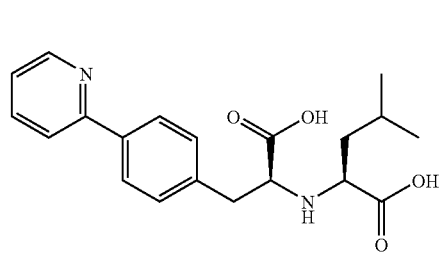
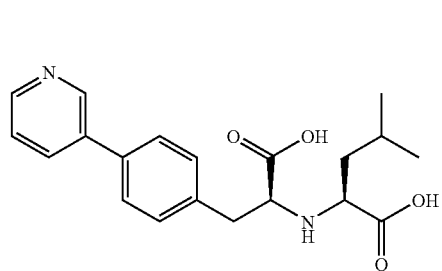
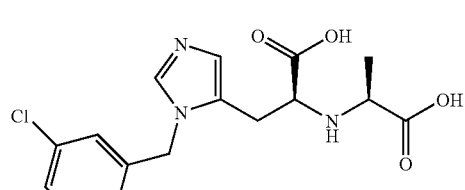

609
-continued
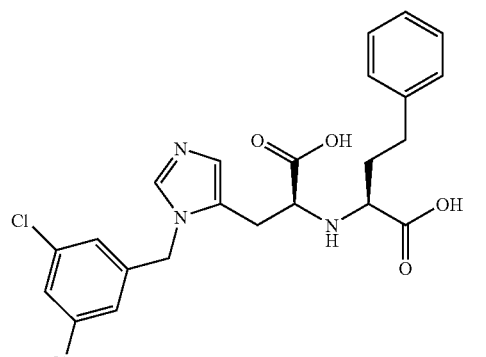
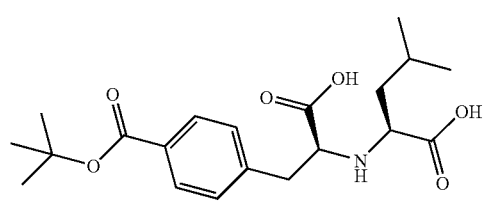
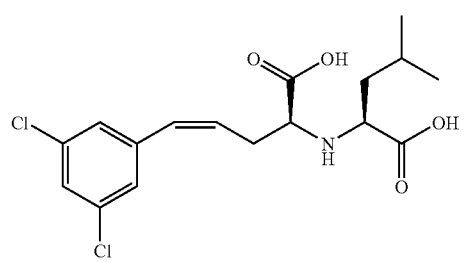
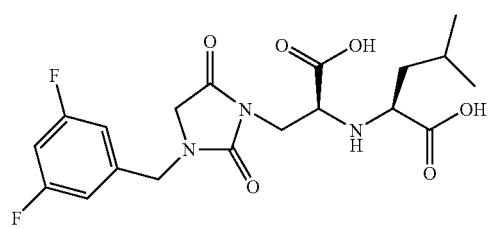
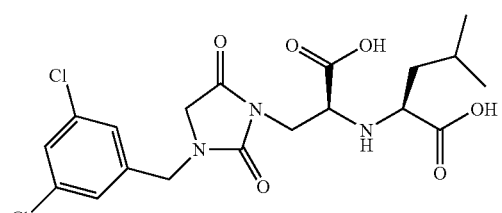
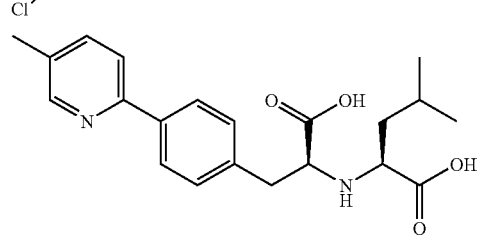
610
-continued
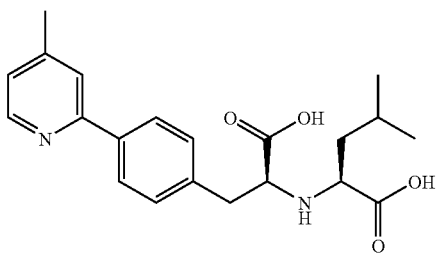
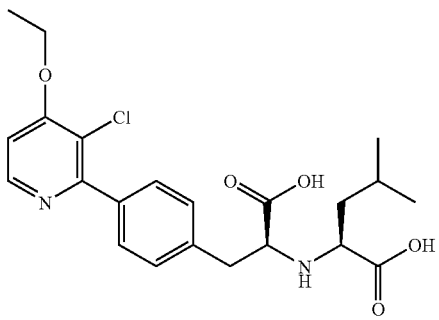
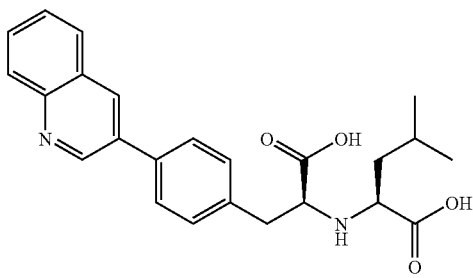
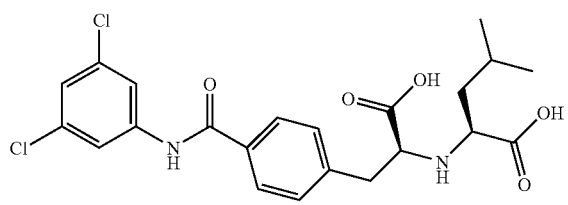
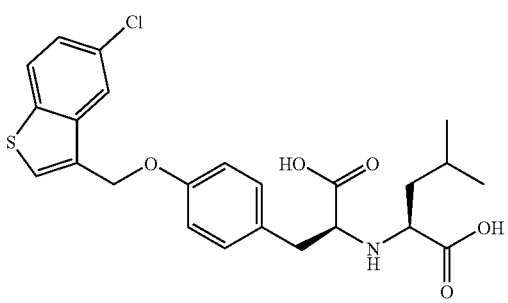
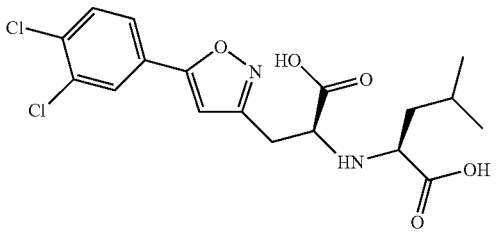

-continued

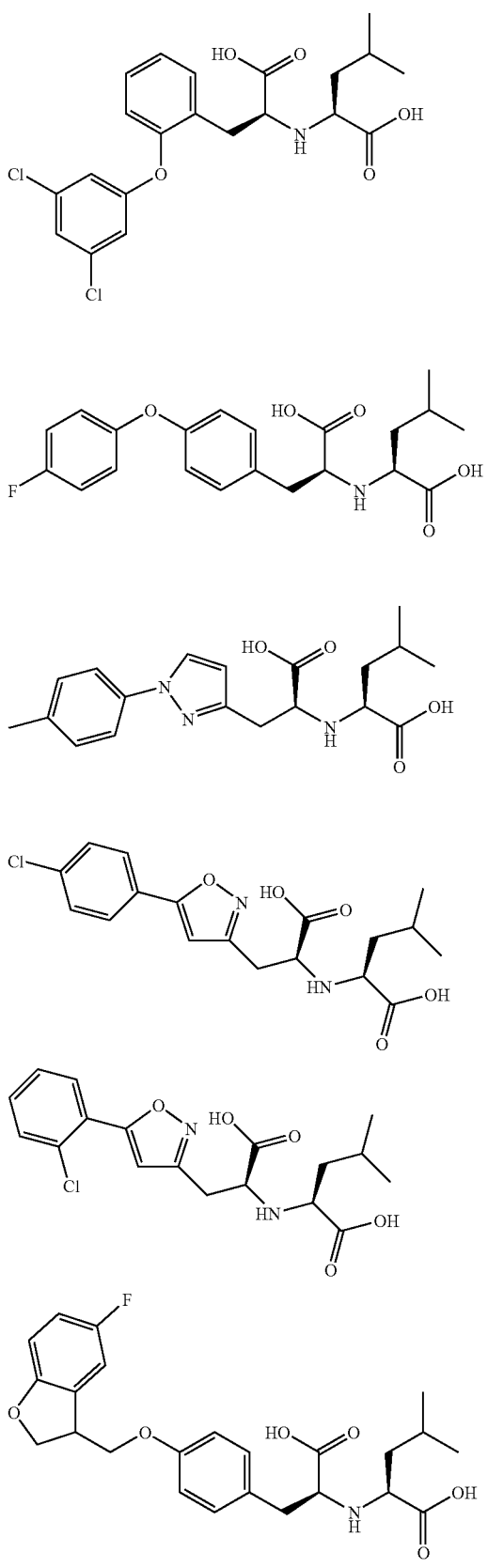

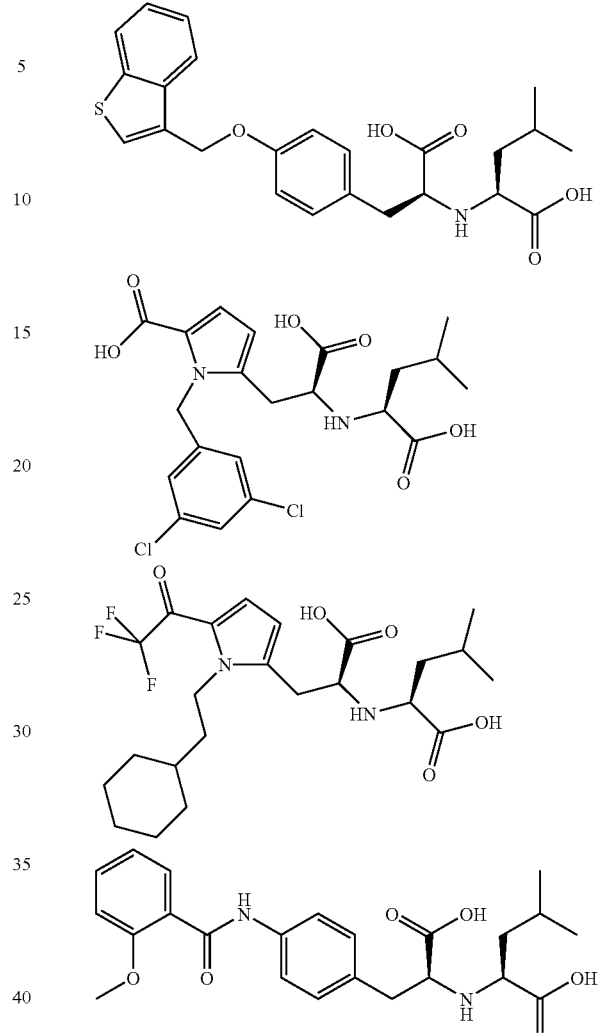

or a pharmaceutically acceptable salt, prodrug, or ester thereof.

18. The method of any one of claims 1–4, wherein said body weight disorder is rapid weight loss, rapid weight gain, obesity, anorexia, cachexia, bulimia, diabetes, generalized partial lipodystrophy, familial partial lipodystrophy, hypercholesterolemia, hyperlipidemia, or an aberrant metabolic rate.

19. The method of any one of claims 1–4, further comprising administering a pharmaceutically acceptable carrier.

20. The method of any one of claims 1–3, wherein said ACE-2 inhibitor is a compound of the formula:

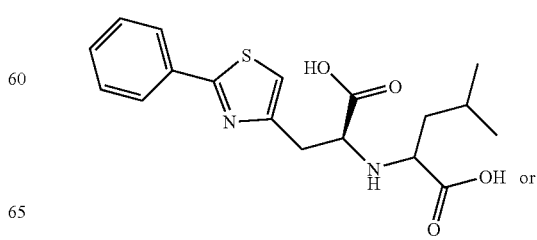

-continued

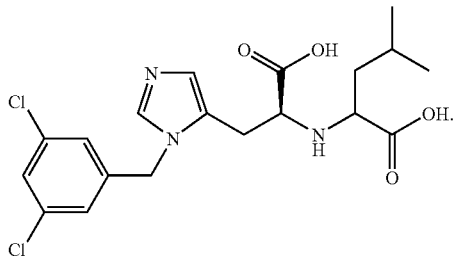

21. A method for treating diabetes or a state associated with aberrant lipid metabolism in a subject, comprising administering to said subject an effective amount of an ACE-2 inhibitor, wherein said ACE-2 inhibitor is a compound of the formula (IV):

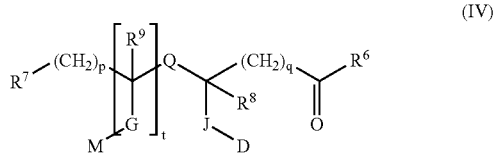

wherein
$R^6$ is hydroxyl or a protecting prodrug moiety;
$R^7$ is a hydrogen atom, carboxylic acid, arylaminocarbonyl, aroyl, aryl, alkylaminocarbonyl, aminocarbonyl, alkenylaminocarboxy, hydroxyl, alkoxy, ether, thiol, amino group heterocycle, or a protecting prodrug moiety;
$R^8$ is hydrogen, or alkyl, and optionally linked to D to form a cyclic structure;
$R^9$ is lower alkyl or hydrogen;
Q is a bond, O, S, $CR^3OH$, $CR^3SH$, $CR^3NR^{3a}R^{3b}$, $NR^3$, $(CR^3R^{3a})_n$, $O(CR^3R^{3b})_n$, or $(CR^3R^{3a})_nO(CR^{3b}R^{3c})_n$, wherein n is 0, 1, 2, or 3 and $R^3$, $R^{3a}$, $R^{3b}$, and $R^{3c}$ are each independently hydrogen, substituted or unsubstituted, branched, cyclic, or straight chain $C_1$–$C_6$ alkyl, $C_2$–$C_6$ alkenyl, acyl, arylalkyl, aryloxycarbonyl, arylaminocarbonyl, arylalkylsulfonyl, or aryl;
G is a linking moiety;
M is an anchor moiety;
J is a bond, an alkyl, alkenyl, or alkynyl moiety;
D is hydrogen, alkoxy, amine, alkyl, alkenyl, alkynyl, aryl, or heteroaryl, optionally linked to G, M or Q to form a ring;
t is 0 or 1;
p is 0, 1, 2, 3, 4, or 5; and
q is 0, 1, 2, or 3, or an enantiomer, diastereomer, mixture of enantiomers, mixture of diastereomers or pharmaceutically acceptable salt thereof; and
wherein said inhibitor is not a naturally occurring amino acid.

22. A method for treating diabetes or a state associated with aberrant lipid metabolism in a subject, comprising administering to said subject an effective amount of an ACE-2 inhibitor, wherein said ACE-2 inhibitor is a compound of the formula:

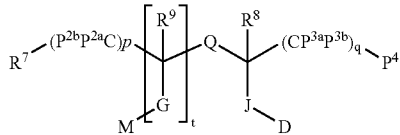

wherein
$P^4$ is selected from the group consisting of a carboxylic acid, cleavable prodrug moieties, $COOP^{4'}$, $(CH_2)_{1-4}SP^{4'}$, or $C(O)NP^{4'}P^{4''}$;
$R^7$ is hydrogen, carboxylic acid, unsubstituted or substituted lower alkyl esters, lower alkenyl esters, dilower alkyl amino esters, arylaminocarbonyl, aroyl, aryl, alkylaminocarbonyl, aminocarbonyl, $COOR^{7'}$, $CONR^{7'}R^{7''}$, hydroxy, ether, thio, amino, $(CH_2)_{1-4}SR^{7'}$, a heterocycle, or a cleavable prodrug moiety;
$P^{4''}$, $P^{4'''}$, $R^{7'}$ and $R^{7''}$ are each independently hydrogen, $C_1$–$C_6$ alkyl, $C_2$–$C_6$ alkenyl, $C_2$–$C_6$ alkynyl or optionally substituted aryl;
$R^8$ is selected from the group consisting of hydrogen, alkyl and a covalent bond to D;
$R^9$ is lower alkyl or hydrogen;
Q is a bond, O, S, $CR^3OH$, $CR^3SH$, $CR^3NR^{3a}R^{3b}$, $NR^3$, $(CR^3R^{3a})_n$, $O(CR^3R^{3b})_n$, or $(CR^3R^{3a})_nO(CR^{3b}R^{3c})_n$, wherein n is 0, 1, 2, or 3, and $R^3$, $R^{3a}$, $R^{3b}$, and $R^{3c}$ are each independently hydrogen, substituted or unsubstituted $C_1$–$C_6$ branched or straight chain alkyl, $C_2$–$C_6$ branched or straight chain alkenyl, aryloxycarbonyl, arylaminocarbonyl, arylalkylsulfonyl, arylalkyl, substituted or unsubstituted acyl, aryl, or $C_3$–$C_8$ ring, said $C_3$–$C_8$ ring being optionally substituted with up to four heteroatoms;
$P^{2a}$, $P^{2b}$, $P^{3a}$ and $P^{3b}$ each independently hydrogen, substituted or unsubstituted, branched, straight chain or cyclic $C_1$–$C_5$ alkyl,
G is a linking moiety;
M is an anchor moiety;
J is a bond, alkyl, alkenyl, or alkynyl moiety;
D is hydrogen, alkyl, alkenyl, alkynyl, aryl, or optionally linked to G, M, or Q to form a ring;
t is 0 or 1;
p is 0, 1, 2, 3, 4, or 5;
q is 1, 2, or 3; or an enantiomer, diastereomer, mixture of enantiomers, mixture of diastereomers or pharmaceutically acceptable salt thereof; and
wherein said inhibitor is not a naturally occurring amino acid.

23. A method for treating diabetes or a state associated with aberrant lipid metabolism in a subject, comprising administering to said subject an effective amount of an ACE-2 inhibitor, wherein said ACE-2 inhibitor is a compound of the formula:

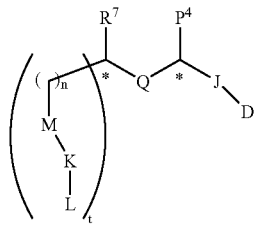

wherein
- M is carbocyclic, heterocyclic, or CONR'R" wherein R' and R" are each independently hydrogen, $C_1$–$C_6$ alkyl, $C_2$–$C_6$ alkenyl, $C_2$–$C_6$ alkynyl or optionally substituted aryl;
- Q is a bond, O, S, $CR^3OH$, $CR^3SH$, $CR^3NR^{3a}R^{3b}$, $NR^3$, $(CR^3R^{3a})_n$, $O(CR^3R^{3b})_n$, or $(CR^3R^{3a})_nO(CR^{3b}R^{3c})_n$, wherein n is 0, 1, 2, or 3, and $R^3$, $R^{3a}$, $R^{3b}$, and $R^{3c}$ are each independently hydrogen, substituted or unsubstituted, branched, cyclic, or straight chain $C_1$–$C_6$ alkyl, $C_2$–$C_6$ alkenyl, acyl, arylalkyl, aryloxycarbonyl, arylaminocarbonyl, arylalkylsulfonyl, or aryl;
- K is an independently selected sublinking moiety for each occurrence;
- L is an independently selected subanchor moiety for each occurrence;
- $P^4$ is a hydrogen, carboxylic acid, $(CH_2)_{1-4}SP^{4'}$, a cleavable prodrug moiety, carboxylic acid, $COOP^{4''}$, or $CONP^{4''}P^{4'''}$;
- $R^7$ is hydrogen, carboxylic acid, aroyl, aryl, $COOR^{7'}$, $C(O)NR^{7'}R^{7''}$, hydroxy, ether, thio, $(CH_2)_{1-4}SR^{7'}$, a heterocycle, or a cleavable prodrug moiety;
- $P^{4'}$, $P^{4''}$, $R^{7'}$ and $R^{7''}$ independently hydrogen, $C_1$–$C_6$ alkyl, $C_2$–$C_6$ alkenyl, $C_2$–$C_6$ alkynyl or optionally substituted aryl;
- n is 0, 1, 2, 3, or 4;
- J is a bond, substituted or unsubstituted alkyl, alkenyl, or alkynyl;
- D is hydrogen, alkyl, alkoxy, alkenyl, amine, hydroxy, alkynyl, aryl, or heteroaryl;
- t is 0 or 1, or an enantiomer, diastereomer, mixture of enantiomers, mixture of diastereomers or pharmaceutically acceptable salt thereof; and
- wherein said inhibitor is not a naturally occurring amino acid.

24. A method for treating diabetes or a state associated with aberrant lipid metabolism in a subject, comprising administering to said subject an effective amount of an ACE-2 inhibitor, wherein said ACE-2 inhibitor is a compound of the formula:

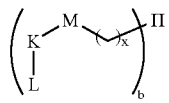

wherein Π is

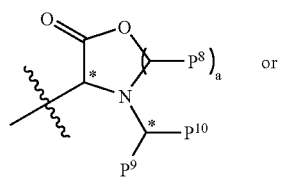 or 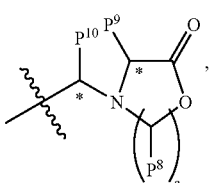

- M is carbocyclic, heterocyclic, or CONR'R" wherein R' and R" are each independently hydrogen, $C_1$–$C_6$ alkyl, $C_2$–$C_6$ alkenyl, $C_2$–$C_6$ alkynyl or optionally substituted aryl;
- K is an independently selected sublinking moiety for each occurrence;
- L is an independently selected subanchor moiety for each occurrence;
- $P^8$ is hydrogen or alkyl;
- $P^9$ is carboxylic acid, unsubstituted or substituted lower alkyl esters, $(CH_2)_{1-4}SP^{9'}$, lower alkenyl esters, dilower alkyl amino esters, lower alkyl amides, dilower alkyl amides, lower alkenyl amides, dilower alkenyl amides, lower alkynyl amides, or aryl amides;
- $P^{10}$ is carboxylic acid, unsubstituted or substituted lower alkyl esters, $(CH_2)_{1-4}SP^{10'}$, lower alkenyl esters, dilower alkyl amino esters, lower alkyl amides, dilower alkyl amides, lower alkyl amides, lower alkenyl amides, dilower alkenyl amides, lower alkynyl amides, or aryl amides;
- $P^{9'}$ and $P^{10'}$ are each independently alkyl, alkenyl, alkynyl, aryl, or hydrogen;
- a is 1, 2, or 3;
- b is 0 or 1; and
- x is 0, 1, 2, 3, or 4, or a pharmaceutically acceptable salt thereof.

25. The method of any one of claims 21–24, wherein said subject is a human.

26. The method of any one of claim 21–24, wherein said ACE-2 inhibitor interacts with ACE-2 with a $K_i$ of 1 μM or less.

27. The method of claim 26, wherein said ACE-2 inhibitor interacts with ACE-2 with a $K_i$ of 0.1 μM or less.

28. The method of claim 27, wherein said ACE-2 inhibitor interacts with ACE-2 with a $K_i$ of 0.025 μM or less.

29. The method of any one of claims 21–23, wherein said ACE-2 inhibitor is of the formula:

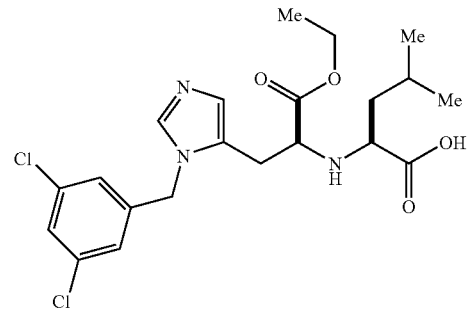

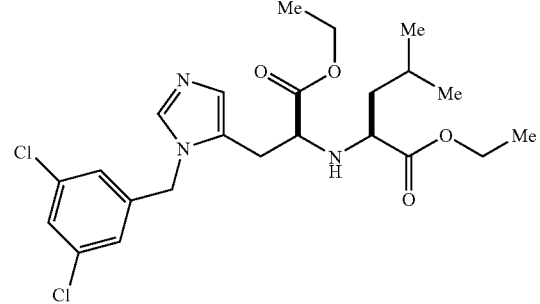

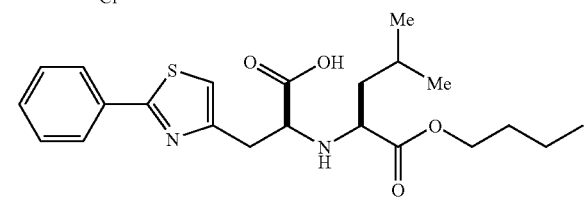

-continued
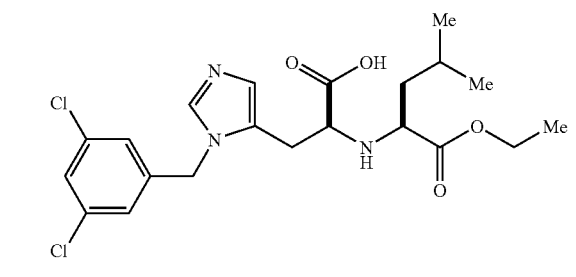
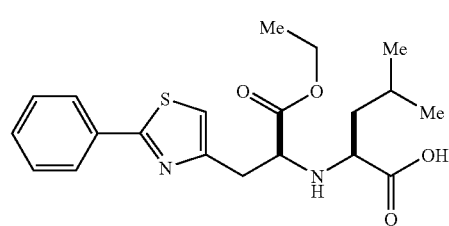
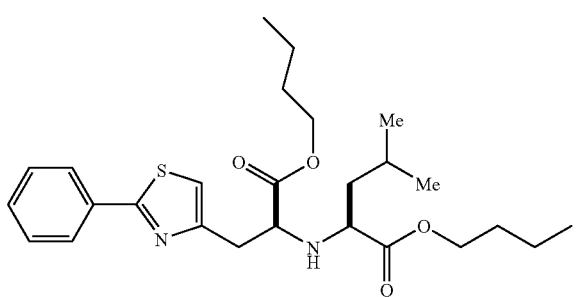
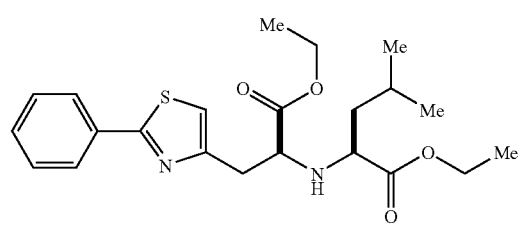
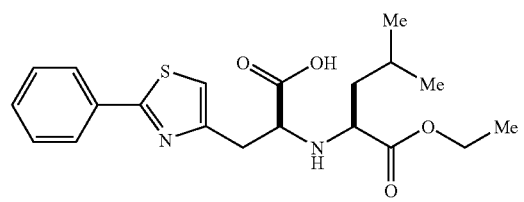
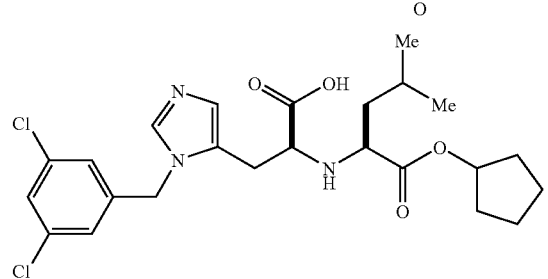
-continued
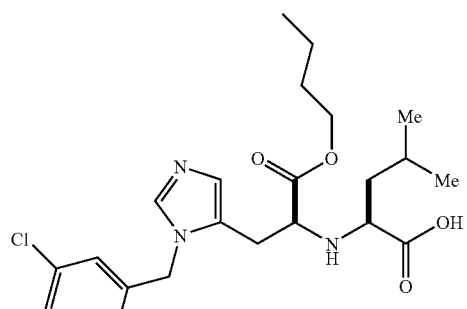
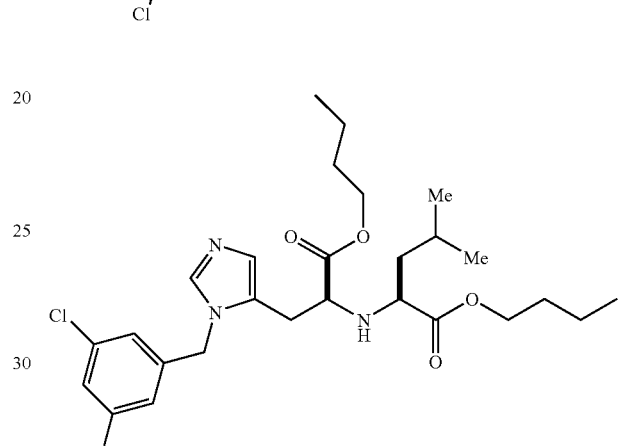
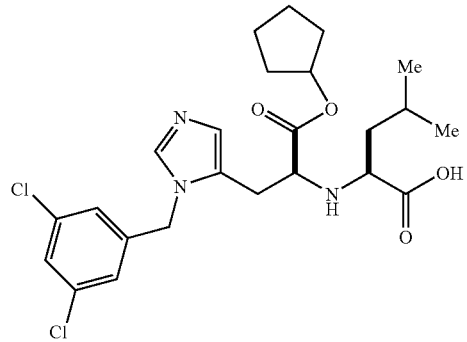
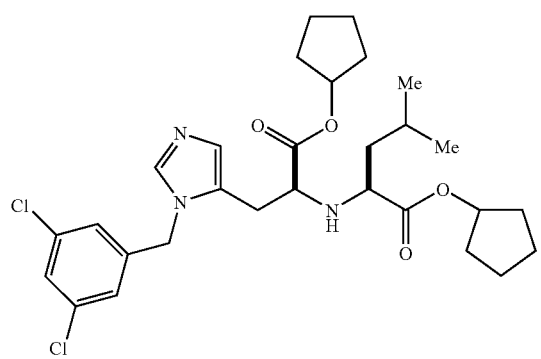

619
-continued
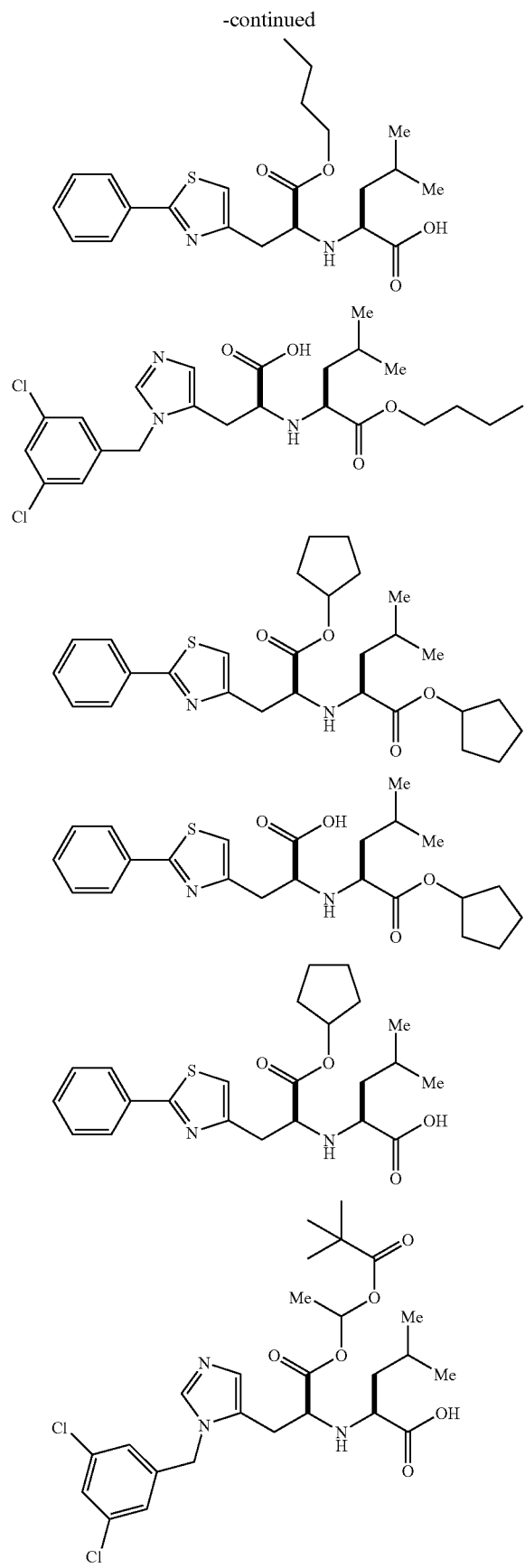
620
-continued
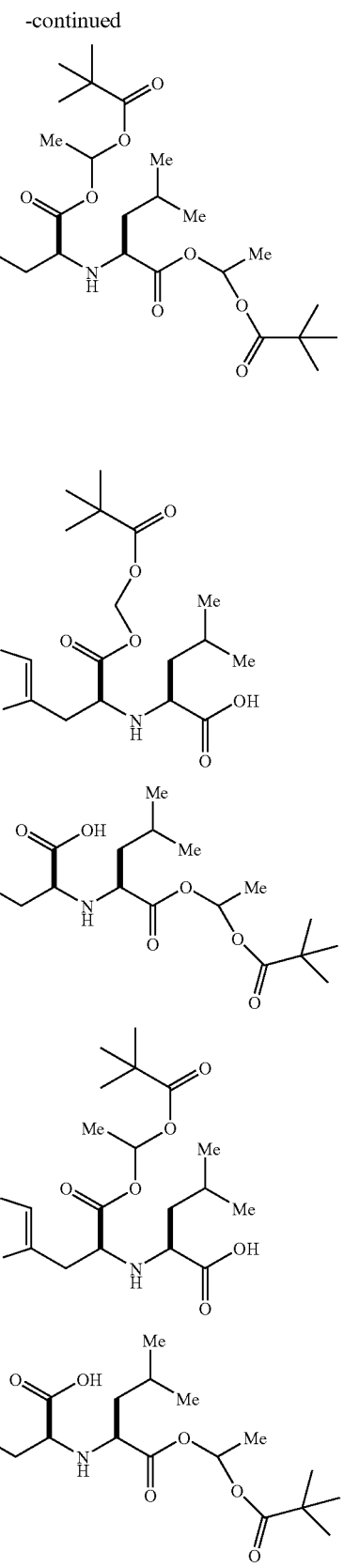

621
-continued
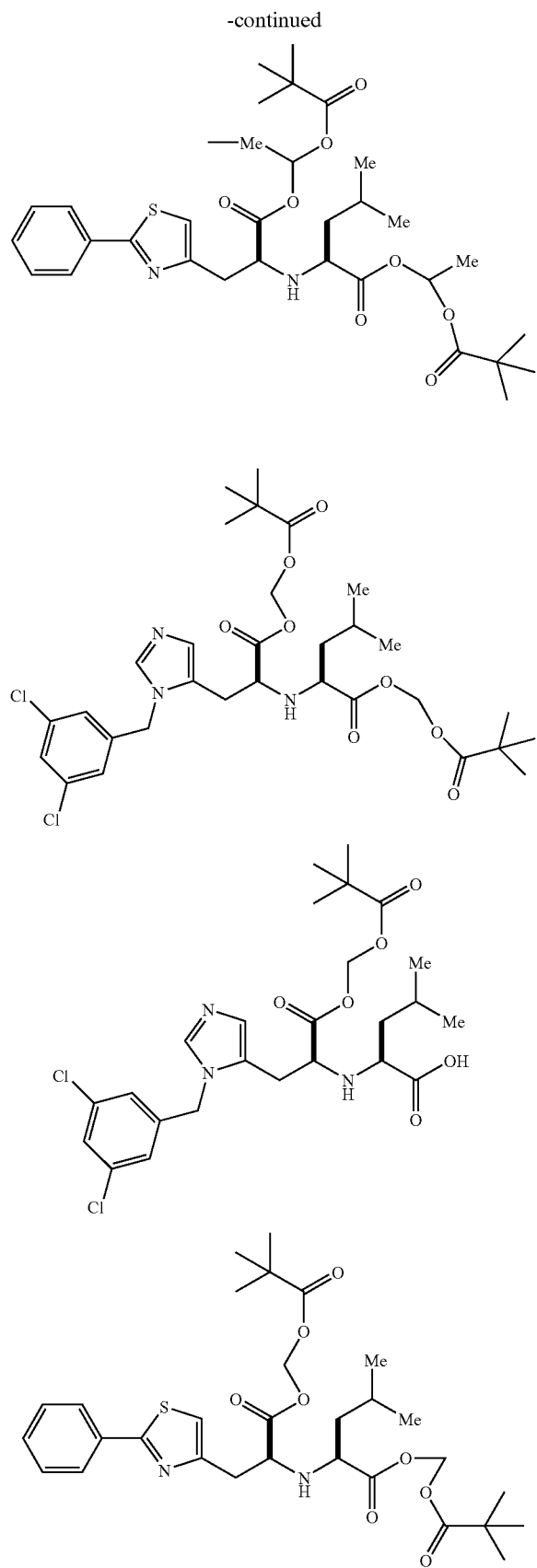
622
-continued
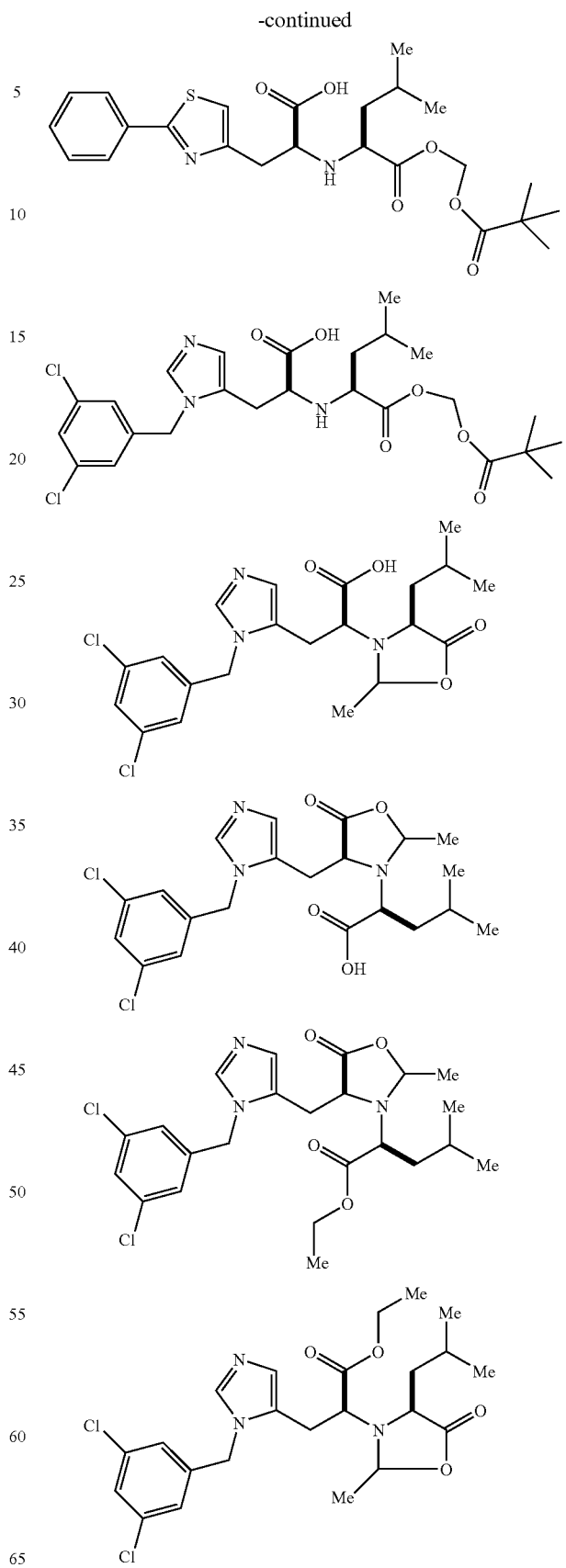

-continued
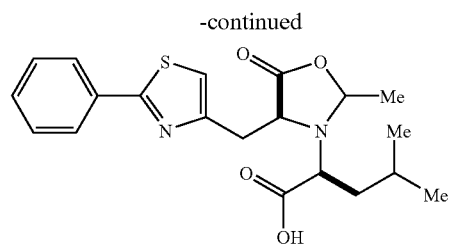
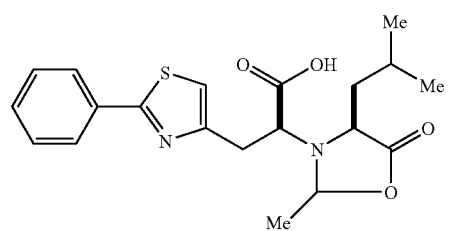
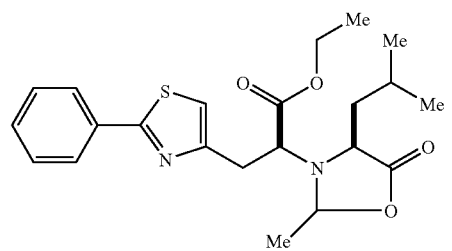
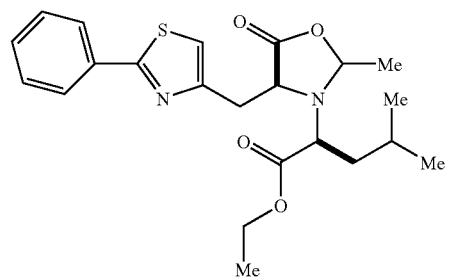
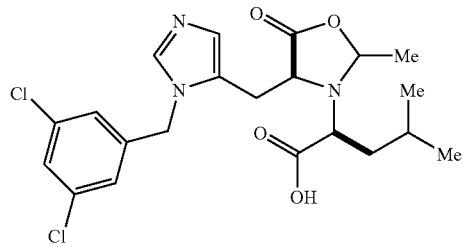
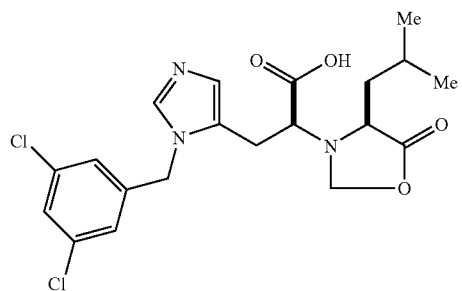
-continued
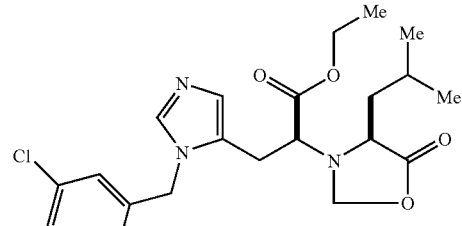
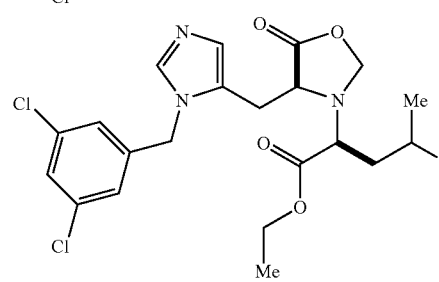
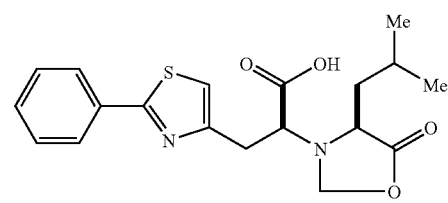
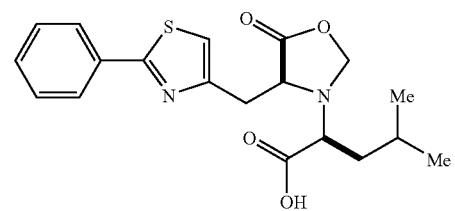
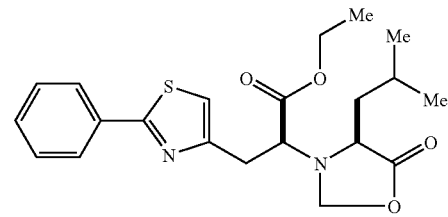
or a pharmaceutically acceptable salt or ester thereof.

30. The method of any one of claims 21–23, wherein said ACE-2 inhibitor is of the formula:

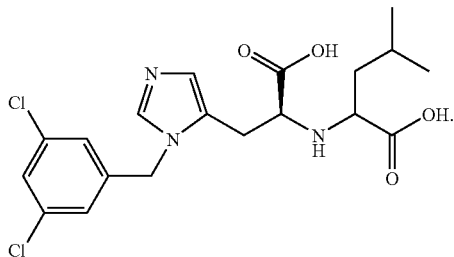

31. The method of any one of claims 21–23, wherein said ACE-2 inhibitor is of the formula:

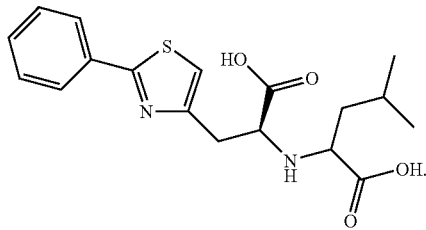

32. The method of any one of claims 21–23, wherein said ACE-2 inhibitor is selected from the group consisting of:
2-{1-Carboxy-2-[3-(3-nitro-benzyl)-3H-imidazol-4-yl]-ethylamino}-4-methyl-pentanoic acid;
2-[2-(3-Benzyl-3H-imidazol-4-yl)-1-carboxy-ethylamino]-hexanoic acid;
2-[2-(3-Benzyl-3H-imidazol-4-yl)-1-carboxy-ethylamino]-4-methyl-pentanoic acid;
2-[1-Carboxy-2-(1H-imidazol-4-yl)-ethylamino]-4-phenyl-butyric acid;
2-[2-(3-Benzyloxymethyl-3H-imidazol-4-yl)-1-carboxy-ethylamino]-4-methyl-pentanoic acid;
2-[1-Carboxy-2-(methyl-phenyl-amino)-ethylamino]-4-methyl-pentanoic acid;
2-[1-Carboxy-2-(1H-imidazol-4-yl)-ethylamino]-4-methyl-pentanoic acid;
2-[2-(1-Benzyl-1H-imidazol-4-yl)-1-carboxy-ethylamino]-4-methyl-pentanoic acid;
2-(1-Carboxy-2-phenyl-ethylamino)-3-(3H-imidazol-4-yl)-propionic acid;
2-[1-Carboxy-2-(1H-imidazol-4-yl)-ethylamino]-4-methyl-pentanoic acid;
2-[1-Carboxy-2-(4-hydroxy-phenyl)-ethylamino]-3-(1H-imidazol-4-yl)-propionic acid;
2-[1-Carboxy-2-(1H-imidazol-4-yl)-ethylamino]-4-phenyl-butyric acid;
2-[1-Carboxy-2-(1H-imidazol-4-yl)-ethylamino]-pentanoic acid;
2-[2-(1H-Imidazol-4-yl)-1-methoxycarbonyl-ethylamino]-4-methyl-pentanoic acid;
2-(1-Carboxy-3-phenyl-propylamino)-5-pyridin-2-yl-pent-4-ynoic acid;
2-{1-Carboxy-2-[1-(4-chloro-benzyl)-1H-imidazol-4-yl]-ethylamino}-4-methyl-pentanoic acid;
2-[2-(1-Benzyl-1H-imidazol-4-yl)-1-carboxy-ethylamino]-4-methyl-pentanoic acid;
2-[1-Carboxy-2-(1H-imidazol-4-yl)-ethylamino]-pentanoic acid;
2-[1-Carboxy-2-(1H-imidazol-4-yl)-ethylamino]-hexanoic acid;
2-(1-Carboxy-2-thiophen-2-yl-ethylamino)-4-methyl-pentanoic acid;
6-Amino-2-(1-carboxy-3-phenyl-propylamino)-hexanoic acid;
2-[1-Carboxy-2-(1H-imidazol-4-yl)-ethylamino]-3-methyl-pentanoic acid;
2-[(Carboxy-phenyl-methyl)-amino]-4-methyl-pentanoic acid;
2-{1-Carboxy-2-[1-(2,4-dinitro-phenyl)-1H-imidazol-4-yl]-ethylamino}-4-methyl-pentanoic acid;
2-(1-Carboxy-2-thiazol-2-yl-ethylamino)-4-methyl-pentanoic acid;
2-(1-Carboxy-2-pyridin-2-yl-ethylamino)-4-methyl-pentanoic acid;
2-(1-Carboxy-ethylamino)-3-(1H-imidazol-4-yl)-propionic acid;
2-(1-Carboxy-3-methylsulfanyl-propylamino)-4-phenyl-butyric acid;
2-(1-Carboxy-3-methyl-butylamino)-succinic acid;
2-(1-Carboxy-3-methyl-butylamino)-hexanoic acid;
2-(1-Carboxy-3-methylsulfanyl-propylamino)-4-methyl-pentanoic acid;
2-[1-Carboxy-2-(3-methyl-3H-imidazol-4-yl)-ethylamino]-4-methyl-pentanoic acid;
2-(1-Carboxy-3-phenyl-propylamino)-4-methyl-pentanoic acid;
2-(1-Carboxy-2-phenyl-ethylamino)-4-methyl-pentanoic acid;
2-(1-Carboxy-2-phenyl-ethylamino)-pentanoic acid;
2-(1-Carboxy-2-phenyl-ethylamino)-4-phenyl-butyric acid;
2-(1-Carboxy-3-phenyl-propylamino)-4,4-dimethyl-pentanoic acid;
2-(1-Carboxy-ethylamino)-3-(1H-imidazol-4-yl)-propionic acid;
2-(1-Carboxy-2-thiophen-2-yl-ethylamino)-pentanoic acid;
2-[1-Carboxy-2-(1H-[1,2,4]triazol-3-yl)-ethylamino]-4-methyl-pentanoic acid;
2-(1-Carboxy-2-cyclopropyl-ethylamino)-4-phenyl-butyric acid;
2-[1-Carboxy-2-(4-hydroxy-phenyl)-ethylamino]-3-(1H-imidazol-4-yl)-propionic acid;
2-[2-(1-Benzyl-1H-imidazol-4-yl)-1-carboxy-ethylamino]-4-methyl-pentanoic acid;
2-(1-Carboxy-2-cyclohexyl-ethylamino)-4-phenyl-butyric acid;
2-(1-Carboxy-3-phenyl-propylamino)-5-phenyl-pent-4-ynoic acid;
2-[2-(1H-Imidazol-4-yl)-1-methoxycarbonyl-ethylamino]-4-methyl-pentanoic acid;
2-{1-Carboxy-2-[1-(4-methoxy-benzyl)-1H-imidazol-4-yl]-ethylamino}-4-methyl-pentanoic acid;
2-{1-Carboxy-2-[1-(4-trifluoromethyl-benzyl)-1H-imidazol-4-yl]-ethylamino}-4-methyl-pentanoic acid;
2-[(Carboxy-phenyl-methyl)-amino]-4-methyl-pentanoic acid;
2-(1-Carboxy-propylamino)-4-methylsulfanyl-butyric acid;
2-(1-Carboxy-2-phenyl-ethylamino)-4-methyl-pentanoic acid;
2-[2-(1H-Imidazol-4-yl)-1-methoxycarbonyl-ethylamino]-4-methyl-pentanoic acid;

2-{1-Carboxy-2-[1-(4-methoxy-benzyl)-1H-imidazol-4-yl]-ethylamino}-4-methyl-pentanoic acid;
2-{1-Carboxy-2-[1-(4-trifluoromethyl-benzyl)-1H-imidazol-4-yl]-ethylamino}-4-methyl-pentanoic acid;
2-[(Carboxy-phenyl-methyl)-amino]-4-methyl-pentanoic acid;
2-(1-Carboxy-propylamino)-4-methylsulfanyl-butyric acid;
2-(1-Carboxy-3-phenyl-propylamino)-5-pyridin-2-yl-pent-4-ynoic acid;
2-{1-Carboxy-2-[3-(4-trifluoromethyl-benzyl)-3H-imidazol-4-yl]-ethylamino}-4-methyl-pentanoic acid;
2-[1-Carboxy-2-(3-naphthalen-1-ylmethyl-3H-imidazol-4-yl)-ethylamino]-4-methyl-pentanoic acid;
2-{1-Carboxy-2-[3-(4-chloro-benzyl)-3H-imidazol-4-yl]-ethylamino}-4-methyl-pentanoic acid;
4-{5-[2-Carboxy-2-(1-carboxy-3-methyl-butylamino)-ethyl]-imidazol-1-ylmethyl}-benzoic acid;
2-[1-Carboxy-2-(2-phenyl-thiazol-4-yl)-ethylamino]-4-methyl-pentanoic acid;
2-[2-(1-Benzyl-1H-benzoimidazol-2-yl)-1-carboxy-ethylamino]-4-methyl-pentanoic acid;
2-[2-(Benzyl-phenyl-amino)-1-carboxy-ethylamino]-4-methyl-pentanoic acid;
2-[2-(2-Amino-thiazol-4-yl)-1-carboxy-ethylamino]-4-methyl-pentanoic acid;
2-{1-Carboxy-2-[3-(3,4-dichloro-benzyl)-3H-imidazol-4-yl]-ethylamino}-4-methyl-pentanoic acid;
2-[1-Carboxy-2-(2-methyl-thiazol-4-yl)-ethylamino]-4-methyl-pentanoic acid;
2-{1-Carboxy-2-[3-(4-cyano-benzyl)-3H-imidazol-4-yl]-ethylamino}-4-methyl-pentanoic acid;
2-{1-Carboxy-2-[3-(3-chloro-benzyl)-3H-imidazol-4-yl]-ethylamino}-4-methyl-pentanoic acid;
'2-{1-Carboxy-2-[3-(3,5-dichloro-benzyl)-3H-imidazol-4-yl]-ethylamino}-4-methyl-pentanoic acid;
2-{1-Carboxy-2-[3-(4-methyl-benzyl)-3H-imidazol-4-yl]-ethylamino}-4-methyl-pentanoic acid;
2-{2-[3-(4-Butyl-benzyl)-3H-imidazol-4-yl]-1-carboxy-ethylamino}-4-methyl-pentanoic acid;
2-{1-Carboxy-2-[3-(3,4-dimethyl-benzyl)-3H-imidazol-4-yl]-ethylamino}-4-methyl-pentanoic acid;
2-[2-(2-Benzylamino-thiazol-4-yl)-1-carboxy-ethylamino]-4-methyl-pentanoic acid;
2-{1-Carboxy-2-[3-(3-methyl-benzyl)-3H-imidazol-4-yl]-ethylamino}-4-methyl-pentanoic acid;
2-{1-Carboxy-2-[3-(3,5-dimethyl-benzyl)-3H-imidazol-4-yl]-ethylamino}-4-methyl-pentanoic acid;
2-{1-Carboxy-2-[3-(4-trifluoromethoxy-benzyl)-3H-imidazol-4-yl]-ethylamino}-4-methyl-pentanoic acid;
2-{1-Carboxy-2-[3-(4-isopropyl-benzyl)-3H-imidazol-4-yl]-ethylamino}-4-methyl-pentanoic acid;
2-{1-Carboxy-2-[3-(2-methyl-benzyl)-3H-imidazol-4-yl]-ethylamino}-4-methyl-pentanoic acid;
2-{2-[3-(4-tert-Butyl-benzyl)-3H-imidazol-4-yl]-1-carboxy-ethylamino}-4-methyl-pentanoic acid;
2-{2-[3-(2-Benzenesulfonylmethyl-benzyl)-3H-imidazol-4-yl]-1-carboxy-ethylamino}-4-methyl-pentanoic acid;
2-{1-Carboxy-2-[3-(4-nitro-benzyl)-3H-imidazol-4-yl]-ethylamino}-4-methyl-pentanoic acid;
2-[2-(3-Biphenyl-2-ylmethyl-3H-imidazol-4-yl)-1-carboxy-ethylamino]-4-methyl-pentanoic acid;
'2-{2-[3-(3,5-Bis-trifluoromethyl-benzyl)-3H-imidazol-4-yl]-1-carboxy-ethylamino}-4-methyl-pentanoic acid;
2-{1-Carboxy-2-[3-(4-fluoro-benzyl)-3H-imidazol-4-yl]-ethylamino}-4-methyl-pentanoic acid;
2-[1-Carboxy-2-(2-phenyl-thiazol-4-yl)-ethylamino]-4-methyl-pentanoic acid;
2-[1-Carboxy-2-(5-methyl-isoxazol-3-yl)-ethylamino]-4-methyl-pentanoic acid;
2-[2-(1-Benzyl-1H-pyrazol-3-yl)-1-carboxy-ethylamino]-4-methyl-pentanoic acid;
2-{1-Carboxy-2-[3-(2,3-dimethoxy-benzyl)-3H-imidazol-4-yl]-ethylamino}-4-methyl-pentanoic acid;
2-{1-Carboxy-2-[3-(2-methyl-biphenyl-3-ylmethyl)-3H-imidazol-4-yl]-ethylamino}-4-methyl-pentanoic acid;
'2-{1-Carboxy-2-[3-(2-methoxy-naphthalen-1-ylmethyl)-3H-imidazol-4-yl]-ethylamino}-4-methyl-pentanoic acid;
2-{1-Carboxy-2-[3-(2,3-difluoro-benzyl)-3H-imidazol-4-yl]-ethylamino}-4-methyl-pentanoic acid;
2-{1-Carboxy-2-[1-(2,3-difluoro-benzyl)-1H-imidazol-4-yl]-ethylamino}-4-methyl-pentanoic acid;
2-{1-Carboxy-2-[3-(2,3-dichloro-benzyl)-3H-imidazol-4-yl]-ethylamino}-4-methyl-pentanoic acid;
'2-{1-Carboxy-2-[3-(3-trifluoromethyl-benzyl)-3H-imidazol-4-yl]-ethylamino}-4-methyl-pentanoic acid;
2-{1-Carboxy-2-[3-(2,5-dichloro-benzyl)-3H-imidazol-4-yl]-ethylamino}-4-methyl-pentanoic acid;
2-{1-Carboxy-2-[3-(2,6-dichloro-benzyl)-3H-imidazol-4-yl]-ethylamino}-4-methyl-pentanoic acid;
4-Methyl-2-[1-methylcarbamoyl-2-(3-phenylamino-3H-imidazol-4-yl)-ethylamino]-pentanoic acid;
2-[2-(4-Benzyl-furan-3-yl)-1-carboxy-ethylamino]-4-methyl-pentanoic acid;
2-[1-Carboxy-2-(3-phenyl-3H-imidazol-4-yl)-ethylamino]-4-methyl-pentanoic acid;
2-[1-Carboxy-2-(3-phenethyl-3H-imidazol-4-yl)-ethylamino]-4-methyl-pentanoic acid;
2-{1-Carboxy-2-[3-(pyridin-3-yloxy)-3H-imidazol-4-yl]-ethylamino}-4-methyl-pentanoic acid;
2-{1-Carboxy-2-[3-(4-nitro-phenoxy)-3H-imidazol-4-yl]-ethylamino}-4-methyl-pentanoic acid;
2-[1-Carboxy-2-(3-phenoxy-3H-imidazol-4-yl)-ethylamino]-4-methyl-pentanoic acid;
2-{1-Carboxy-2-[3-(2-nitro-benzyl)-3H-imidazol-4-yl]-ethylamino}-4-methyl-pentanoic acid;
2-{1-Carboxy-2-[3-(3-nitro-benzyl)-3H-imidazol-4-yl]-ethylamino}-4-methyl-pentanoic acid;
2-{1-Carboxy-2-[3-(2-trifluoromethyl-benzyl)-3H-imidazol-4-yl]-ethylamino}-4-methyl-pentanoic acid;
2-{1-Carboxy-2-[3-(3-trifluoromethyl-benzyl)-3H-imidazol-4-yl]-ethylamino}-4-methyl-pentanoic acid;
2-{1-Carboxy-2-[3-(2-methyl-benzyl)-3H-imidazol-4-yl]-ethylamino}-4-methyl-pentanoic acid;
2-{1-Carboxy-2-[3-(3-methyl-benzyl)-3H-imidazol-4-yl]-ethylamino}-4-methyl-pentanoic acid;
2-{1-Carboxy-2-[3-(2-chloro-benzyl)-3H-imidazol-4-yl]-ethylamino}-4-methyl-pentanoic acid;
2-{1-Carboxy-2-[3-(3-chloro-benzyl)-3H-imidazol-4-yl]-ethylamino}-4-methyl-pentanoic acid;
2-{1-Carboxy-2-[3-(2-hydroxy-benzyl)-3H-imidazol-4-yl]-ethylamino}-4-methyl-pentanoic acid;
2-{1-Carboxy-2-[3-(3-hydroxy-benzyl)-3H-imidazol-4-yl]-ethylamino}-4-methyl-pentanoic acid;
2-{1-Carboxy-2-[3-(2-fluoro-benzyl)-3H-imidazol-4-yl]-ethylamino}-4-methyl-pentanoic acid;
2-[2-(3-Benzyl-3H-imidazol-4-yl)-1-carboxy-ethylamino]-4-methyl-pentanoic acid;
2-[1-Carboxy-2-(3-phenylamino-3H-imidazol-4-yl)-ethylamino]-4-methyl-pentanoic acid;
2-{[2,3-Dioxo-1-(3-phenylamino-3H-imidazol-4-ylmethyl)-butyl]-methyl-amino}-4-methyl-pentanoic acid;

2-{[2,3-Dioxo-1-(4-phenylamino-furan-3-ylmethyl)-butyl]-methyl-amino}-4-methyl-pentanoic acid;
2-[2,3-Dioxo-1-(4-phenylamino-furan-3-ylmethyl)-butylamino]-4-methyl-pentanoic acid;
2-[1-Carboxy-2-(4-phenylamino-furan-3-yl)-ethylamino]-4-methyl-pentanoic acid;
2-[1-Carboxy-2-(2-o-tolyl-2H-isoindol-1-yl)-ethylamino]-4-methyl-pentanoic acid;
2-[2-(2-Benzyl-2H-isoindol-1-yl)-1-carboxy-ethylamino]-4-methyl-pentanoic acid;
2-[1-Carboxy-2-(2-phenyl-2H-isoindol-1-yl)-ethylamino]-4-methyl-pentanoic acid;
2-[1-Carboxy-2-(2-pyridin-2-yl-2H-isoindol-1-yl)-ethylamino]-4-methyl-pentanoic acid;
2-{1-Carboxy-2-[2-(3-nitro-phenyl)-2H-isoindol-1-yl]-ethylamino}-4-methyl-pentanoic acid;
2-{1-Carboxy-2-[2-(4-nitro-phenyl)-2H-isoindol-1-yl]-ethylamino}-4-methyl-pentanoic acid;
2-{1-Carboxy-2-[2-(4-nitro-benzyl)-2H-isoindol-1-yl]-ethylamino}-4-methyl-pentanoic acid;
2-({Carboxy-[3-(4-nitro-phenyl)-naphthalen-1-yl]-methyl}-amino)-4-methyl-pentanoic acid;
2-({Carboxy-[3-(4-nitro-benzyl)-naphthalen-1-yl]-methyl}-amino)-4-methyl-pentanoic acid;
'2-{1-Carboxy-2-[3-(3-trifluoromethyl-benzyl)-3H-imidazol-4-yl]-ethylamino}-4-methyl-pentanoic acid;
2-{1-Carboxy-2-[3-(2,5-dichloro-benzyl)-3H-imidazol-4-yl]-ethylamino}-4-methyl-pentanoic acid;
2-{1-Carboxy-2-[3-(2,6-dichloro-benzyl)-3H-imidazol-4-yl]-ethylamino}-4-methyl-pentanoic acid;
2-[1-Carboxy-2-(3-cyclohexylmethyl-3H-imidazol-4-yl)-ethylamino]-4-methyl-pentanoic acid;
2-[1-Carboxy-2-(3-phenethyl-3H-imidazol-4-yl)-ethylamino]-4-methyl-pentanoic acid;
2-{1-Carboxy-2-[3-(2-ethyl-butyl)-3H-imidazol-4-yl]-ethylamino}-4-methyl-pentanoic acid;
2-{1-Carboxy-2-[3-(3-iodo-benzyl)-3H-imidazol-4-yl]-ethylamino}-4-methyl-pentanoic acid;
2-{1-Carboxy-2-[3-(3-fluoro-benzyl)-3H-imidazol-4-yl]-ethylamino}-4-methyl-pentanoic acid;
2-{1-Carboxy-2-[3-(3-fluoro-benzyl)-3H-imidazol-4-yl]-ethylamino}-4-methyl-pentanoic acid;
2-[1-Carboxy-2-(2-phenylethynyl-1H-imidazol-4-yl)-ethylamino]-4-methyl-pentanoic acid;
2-[1-Carboxy-2-(1-methyl-2-phenylethynyl-1H-imidazol-4-yl)-ethylamino]-4-methyl-pentanoic acid;
2-[1-Carboxy-2-(2-phenethyl-1H-imidazol-4-yl)-ethylamino]-4-methyl-pentanoic acid;
2-[1-Carboxy-3-(3-phenyl-3H-imidazol-4-yl)-propylamino]-4-methyl-pentanoic acid;
2-[1-Carboxy-2-(3-phenyl-3H-imidazol-4-yl)-ethylamino]-4-methyl-pentanoic acid;
2-[2-(3-Benzyl-2,5-dimethyl-3H-imidazol-4-yl)-1-carboxy-ethylamino]-4-methyl-pentanoic acid;
2-[1-Carboxy-4-(3-phenyl-3H-imidazol-4-yl)-butylamino]-4-methyl-pentanoic acid;
2-[2-(2-Benzyl-thiazol-4-yl)-1-carboxy-ethylamino]-4-methyl-pentanoic acid;
2-[1-Carboxy-2-(2-phenyl-oxazol-4-yl)-ethylamino]-4-methyl-pentanoic acid;
2-{1-Carboxy-2-[2-(3,5-dichloro-phenyl)-oxazol-4-yl]-ethylamino}-4-methyl-pentanoic acid;
2-{1-Carboxy-2-[2-(3,5-dimethyl-phenyl)-oxazol-4-yl]-ethylamino}-4-methyl-pentanoic acid;
2-[2-(2-Benzyl-oxazol-4-yl)-1-carboxy-ethylamino]-4-methyl-pentanoic acid;
2-{1-Carboxy-2-[2-(3,5-dichloro-benzyl)-oxazol-4-yl]-ethylamino}-4-methyl-pentanoic acid;
2-{1-Carboxy-2-[2-(3,5-dimethyl-benzyl)-oxazol-4-yl]-ethylamino}-4-methyl-pentanoic acid;
2-{1-Carboxy-2-[2-(2-cyclohexyl-ethyl)-oxazol-4-yl]-ethylamino}-4-methyl-pentanoic acid;
2-[1-Carboxy-2-(4-phenyl-oxazol-2-yl)-ethylamino]-4-methyl-pentanoic acid;
2-{1-Carboxy-2-[4-(3,5-dichloro-phenyl)-oxazol-2-yl]-ethylamino}-4-methyl-pentanoic acid;
2-{1-Carboxy-2-[4-(3,5-dimethyl-phenyl)-oxazol-2-yl]-ethylamino}-4-methyl-pentanoic acid;
2-[2-(4-Benzyl-oxazol-2-yl)-1-carboxy-ethylamino]-4-methyl-pentanoic acid;
2-{1-Carboxy-2-[4-(3,5-dichloro-benzyl)-oxazol-2-yl]-ethylamino}-4-methyl-pentanoic acid;
2-{1-Carboxy-2-[4-(3,5-dimethyl-benzyl)-oxazol-2-yl]-ethylamino}-4-methyl-pentanoic acid;
2-{1-Carboxy-2-[4-(2-cyclohexyl-ethyl)-oxazol-2-yl]-ethylamino}-4-methyl-pentanoic acid;
2-{2-[5-(1H-Benzoimidazol-2-yl)-isoxazol-3-yl]-1-carboxy-ethylamino}-4-methyl-pentanoic acid;
2-{1-Carboxy-2-[1-(3-phenyl-propyl)-1H-[1,2,3]triazol-4-yl]-ethylamino}-4-methyl-pentanoic acid;
2-[1-Carboxy-2-(4-pyridin-4-yl-oxazol-2-yl)-ethylamino]-4-methyl-pentanoic acid;
2-{1-Carboxy-2-[2-(3,5-dichloro-phenyl)-thiazol-4-yl]-ethylamino}-4-methyl-pentanoic acid;
2-{1-Carboxy-2-[2-(3,5-dimethyl-phenyl)-thiazol-4-yl]-ethylamino}-4-methyl-pentanoic acid;
2-[2-(2-Benzyl-thiazol-4-yl)-1-carboxy-ethylamino]-4-methyl-pentanoic acid;
2-{1-Carboxy-2-[2-(3,5-dimethyl-benzyl)-thiazol-4-yl]-ethylamino}-4-methyl-pentanoic acid;
2-{1-Carboxy-2-[2-(3,5-dichloro-benzyl)-thiazol-4-yl]-ethylamino}-4-methyl-pentanoic acid;
2-[1-Carboxy-2-(4-phenyl-thiazol-2-yl)-ethylamino]-4-methyl-pentanoic acid;
2-{1-Carboxy-2-[2-(2-cyclohexyl-ethyl)-thiazol-4-yl]-ethylamino}-4-methyl-pentanoic acid;
2-{1-Carboxy-2-[4-(3,5-dimethyl-phenyl)-thiazol-2-yl]-ethylamino}-4-methyl-pentanoic acid;
2-{1-Carboxy-2-[4-(3,5-dichloro-phenyl)-thiazol-2-yl]-ethylamino}-4-methyl-pentanoic acid;
2-[1-Carboxy-2-(2-pyridin-4-yl-thiazol-4-yl)-ethylamino]-4-methyl-pentanoic acid;
2-[2-(4-Benzyl-thiazol-2-yl)-1-carboxy-ethylamino]-4-methyl-pentanoic acid;
2-{1-Carboxy-2-[4-(3,5-dichloro-benzyl)-thiazol-2-yl]-ethylamino}-4-methyl-pentanoic acid;
2-{1-Carboxy-2-[4-(3,5-dimethyl-benzyl)-thiazol-2-yl]-ethylamino}-4-methyl-pentanoic acid;
2-{1-Carboxy-2-[4-(2-cyclohexyl-ethyl)-thiazol-2-yl]-ethylamino}-4-methyl-pentanoic acid;
2-[1-Carboxy-2-(4-pyridin-4-yl-thiazol-2-yl)-ethylamino]-4-methyl-pentanoic acid;
2-[(3-Benzo[1,3]dioxol-5-yl-propyl)-(2-mercapto-ethyl)-amino]-4-methyl-pentanoic acid;
2-[Cyclohexanecarbonyl-(2-mercapto-ethyl)-amino]-4-methyl-pentanoic acid;
2-[(Benzo[1,2,5]thiadiazol-5-ylmethanesulfonyl)-(2-mercapto-ethyl)-amino]-4-methyl-pentanoic acid;
2-[But-3-enyloxycarbonyl-(2-mercapto-ethyl)-amino]-4-methyl-pentanoic acid;
2-[N'-(1-Benzyl-pyrrolidin-3-yl)-N-(2-mercapto-ethyl)-guanidino]-4-methyl-pentanoic acid;

2-[1-(2-Mercapto-ethyl)-3-(1-phenyl-ethyl)-ureido]-4-methyl-pentanoic acid;
2-[3-Furan-2-ylmethyl-1-(2-mercapto-ethyl)-thioureido]-4-methyl-pentanoic acid;
2-{1-Carboxy-2-[2-(3-trifluoromethyl-phenyl)-thiazol-4-yl]-ethylamino}-4-methyl-pentanoic acid;
2-(1-Carboxy-3-methylamino-propylamino)-4-methyl-pentanoic acid; compound with 3-phenyl-propionaldehyde;
2-{1-Carboxy-3-[2-(4-chloro-phenoxy)-acetylamino]-propylamino}-4-methyl-pentanoic acid;
2-[3-(Biphenyl-4-sulfonylamino)-1-carboxy-propylamino]-4-methyl-pentanoic acid;
2-{3-[(Biphenyl-4-carbonyl)-amino]-1-carboxy-propylamino}-4-methyl-pentanoic acid;
2-{1-Carboxy-3-[(naphthalene-2-carbonyl)-amino]-propylamino}-4-methyl-pentanoic acid;
2-[1-Carboxy-3-(4-methoxy-benzenesulfonylamino)-propylamino]-4-methyl-pentanoic acid;
2-[1-Carboxy-3-(naphthalene-2-sulfonylamino)-propylamino]-4-methyl-pentanoic acid;
2-[3-(3,5-Bis-trifluoromethyl-benzoylamino)-1-carboxy-propylamino]-4-methyl-pentanoic acid;
2-[2-(5-Benzyl-2-methyl-thiazol-4-yl)-1-carboxy-ethylamino]-4-methyl-pentanoic acid;
2-{1-Carboxy-3-[(naphthalene-2-carbonyl)-amino]-propylamino}-4-methyl-pentanoic acid;
2-[3-(Biphenyl-4-sulfonylamino)-1-carboxy-propylamino]-4-methyl-pentanoic acid;
2-{1-Carboxy-2-[2-(2,4-dichloro-phenyl)-thiazol-4-yl]-ethylamino}-4-methyl-pentanoic acid;
2-{1-Carboxy-2-[2-(2,3-dihydro-benzofuran-5-yl)-thiazol-4-yl]-ethylamino}-4-methyl-pentanoic acid;
2-{1-Carboxy-2-[2-(3-chloro-4-fluoro-phenyl)-thiazol-4-yl]-ethylamino}-4-methyl-pentanoic acid;
2-[1-Carboxy-2-(2-p-tolyl-thiazol-4-yl)-ethylamino]-4-methyl-pentanoic acid;
2-[1-Carboxy-2-(5-phenyl-isoxazol-3-yl)-ethylamino]-4-methyl-pentanoic acid;
2-(2-Mercapto-3-phenyl-propionylamino)-4-methyl-pentanoic acid;
2-[1-Carboxy-3-(4'-chloro-biphenyl-4-sulfonylamino)-propylamino]-4-methyl-pentanoic acid;
2-[1-Carboxy-3-(3-methoxy-benzoylamino)-propylamino]-4-methyl-pentanoic acid;
2-[1-Carboxy-3-(3-chloro-benzoylamino)-propylamino]-4-methyl-pentanoic acid;
2-[2-(4-Benzyloxy-phenyl)-1-carboxy-ethylamino]-4-methyl-pentanoic acid;
2-[1-Carboxy-2-(4-cyclohexylmethoxy-phenyl)-ethylamino]-4-methyl-pentanoic acid;
2-{1-Carboxy-2-[4-(3,5-dichloro-benzyloxy)-phenyl]-ethylamino}-4-methyl-pentanoic acid;
2-{1-Carboxy-2-[4-(3,5-dimethyl-benzyloxy)-phenyl]-ethylamino}-4-methyl-pentanoic acid;
2-{1-Carboxy-2-[3-(3,4-dichloro-benzyl)-2-oxo-2,3-dihydro-imidazol-1-yl]-ethylamino}-4-methyl-pentanoic acid;
2-[2-(Benzothiazol-2-ylcarbamoyl)-1-carboxy-ethylamino]-4-methyl-pentanoic acid;
2-(1-Carboxy-3-{4-[(4-chloro-phenyl)-phenyl-methyl]-piperazin-1-yl}-3-oxo-propylamino)-4-methyl-pentanoic acid;
2-{2-[3-(3,5-Dichloro-benzyl)-3H-imidazol-4-yl]-1-methoxycarbonyl-ethylamino}-4-methyl-pentanoic acid;
2-({1-Carboxy-2-[3-(3,5-dichloro-benzyl)-3H-imidazol-4-yl]-ethyl}-formyl-amino)-4-methyl-pentanoic acid;
2-{2-[3-(3,5-Dichloro-benzyl)-3H-imidazol-4-yl]-1-methoxycarbonyl-ethylamino}-4-methyl-pentanoic acid benzyl ester;
2-{1-Benzyloxycarbonyl-2-[3-(3,5-dichloro-benzyl)-3H-imidazol-4-yl]-ethylamino}-4-methyl-pentanoic acid;
2-{1-Butoxycarbonyl-2-[3-(3,5-dichloro-benzyl)-3H-imidazol-4-yl]-ethylamino}-4-methyl-pentanoic acid;
2-{1-Carboxy-2-[3-(3,5-dichloro-benzyl)-2-oxo-2,3-dihydro-imidazol-1-yl]-ethylamino}-4-methyl-pentanoic acid;
2-{1-Carboxy-2-[3-(3,5-difluoro-benzyl)-2-oxo-2,3-dihydro-imidazol-1-yl]-ethylamino}-4-methyl-pentanoic acid;
2-{1-Carboxy-2-[2-oxo-3-(1-phenyl-ethyl)-2,3-dihydro-imidazol-1-yl]-ethylamino}-4-methyl-pentanoic acid;
2-[1-Carboxy-2-(3-chloro-benzoylamino)-ethylamino]-4-methyl-pentanoic acid;
2-[1-Carboxy-2-(3,4-dichloro-benzoylamino)-ethylamino]-4-methyl-pentanoic acid;
2-[2-(3-Hydroxy-phenyl)-1-methoxycarbonyl-ethylamino]-4-methyl-pentanoic acid benzyl ester;
2-[1-Carboxy-2-(2-phenyl-oxazol-4-yl)-ethylamino]-4-methyl-pentanoic acid;
2-{1-Carboxy-2-[2-(3,5-dichloro-phenyl)-oxazol-4-yl]-ethylamino}-4-methyl-pentanoic acid;
2-{1-Carboxy-2-[2-(3,5-dichloro-phenyl)-thiazol-4-yl]-ethylamino}-4-methyl-pentanoic acid;
2-{1-Carboxy-2-[1-(3,5-dichloro-benzyl)-1H-pyrazol-3-yl]-ethylamino}-4-methyl-pentanoic acid;
2-{1-Cyclopentyloxycarbonyl-2-[3-(3,5-dichloro-benzyl)-3H-imidazol-4-yl]-ethylamino}-4-methyl-pentanoic acid;
2-{1-Carboxy-2-[3-(3,5-difluoro-benzyl)-2-oxo-imidazolidin-1-yl]-ethylamino}-4-methyl-pentanoic acid;
2-[2-(3-Benzyl-2-oxo-2,3-dihydro-imidazol-1-yl)-1-carboxy-ethylamino]-4-methyl-pentanoic acid;
2-[1-Carboxy-2-(4-phenethyloxy-phenyl)-ethylamino]-4-methyl-pentanoic acid;
2-[2-(4-tert-Butoxy-phenyl)-1-carboxy-ethylamino]-4-methyl-pentanoic acid;
2-{1-Carboxy-2-[4-(pyridin-4-ylmethoxy)-phenyl]-ethylamino}-4-methyl-pentanoic acid;
2-[2-(4-Allyloxy-phenyl)-1-carboxy-ethylamino]-4-methyl-pentanoic acid;
2-{1-Carboxy-2-[4-(pyridin-3-ylmethoxy)-phenyl]-ethylamino}-4-methyl-pentanoic acid;
2-[1-Carboxy-2-(4'-methyl-biphenyl-3-yl)-ethylamino]-4-methyl-pentanoic acid;
2-[1-Carboxy-2-(3-methoxy-benzoylamino)-ethylamino]-4-methyl-pentanoic acid;
2-{1-Carboxy-2-[(naphthalene-1-carbonyl)-amino]-ethylamino}-4-methyl-pentanoic acid;
2-[1-Carboxy-2-(6-chloro-benzothiazol-2-ylcarbamoyl)-ethylamino]-4-methyl-pentanoic acid;
2-[1-Carboxy-2-(5,6-dimethyl-benzothiazol-2-ylcarbamoyl)-ethylamino]-4-methyl-pentanoic acid;
2-[1-Carboxy-2-(4-chloro-benzothiazol-2-ylcarbamoyl)-ethylamino]-4-methyl-pentanoic acid;
2-{1-Carboxy-2-[3-(2-cyclohexyl-ethyl)-2-oxo-2,3-dihydro-imidazol-1-yl]-ethylamino}-4-methyl-pentanoic acid;
2-{1-Carboxy-2-[2-oxo-3-(1-phenyl-ethyl)-2,3-dihydro-imidazol-1-yl]-ethylamino}-4-methyl-pentanoic acid;
2-[1-Carboxy-2-(5,6-dichloro-benzothiazol-2-ylcarbamoyl)-ethylamino]-4-methyl-pentanoic acid;

2-[1-Carboxy-2-(3-cyclopropylmethyl-2-oxo-2,3-dihydro-imidazol-1-yl)-ethylamino]-4-methyl-pentanoic acid;

2-[1-Carboxy-2-(3',5'-dichloro-biphenyl-3-yl)-ethylamino]-4-methyl-pentanoic acid;

2-[1-Carboxy-2-(3-thiophen-3-yl-phenyl)-ethylamino]-4-methyl-pentanoic acid;

2-[1-Carboxy-2-(3',5'-dimethoxy-biphenyl-3-yl)-ethylamino]-4-methyl-pentanoic acid;

3-[2-(1-Benzyloxycarbonyl-3-methyl-butylamino)-2-methoxycarbonyl-ethyl]-pyrazole-1-carboxylic acid tert-butyl ester;

2-{2-[3-(3,5-Dichloro-benzyl)-3H-imidazol-4-yl]-1-methoxycarbonyl-ethylamino}-4-methyl-pentanoic acid methyl ester;

2-[1-Carboxy-2-(3-cyclohexyl-2-oxo-2,3-dihydro-imidazol-1-yl)-ethylamino]-4-methyl-pentanoic acid;

2-[1-Carboxy-2-(6-methoxy-benzothiazol-2-ylcarbamoyl)-ethylamino]-4-methyl-pentanoic acid;

2-[1-Carboxy-2-(6-ethoxy-benzothiazol-2-ylcarbamoyl)-ethylamino]-4-methyl-pentanoic acid;

2-[1-Carboxy-2-(6-fluoro-benzothiazol-2-ylcarbamoyl)-ethylamino]-4-methyl-pentanoic acid;

2-[2-(6-Bromo-benzothiazol-2-ylcarbamoyl)-1-carboxy-ethylamino]-4-methyl-pentanoic acid;

2-{1-Carboxy-2-[3-(3,5-difluoro-phenyl)-2-oxo-2,3-dihydro-imidazol-1-yl]-ethylamino}-4-methyl-pentanoic acid;

2-{1-Carboxy-2-[(naphthalene-2-carbonyl)-amino]-ethylamino}-4-methyl-pentanoic acid;

2-[1-Carboxy-2-(naphthalene-2-sulfonylamino)-ethylamino]-4-methyl-pentanoic acid;

2-{1-Carboxy-2-[2-(3,5-dichloro-benzyl)-2H-pyrazol-3-yl]-ethylamino}-4-methyl-pentanoic acid;

2-[1-Carboxy-2-(3-naphthalen-1-yl-phenyl)-ethylamino]-4-methyl-pentanoic acid;

2-{1-Carboxy-2-[3-(3,5-dichloro-benzyl)-3H-imidazol-4-yl]-ethylamino}-4-methyl-pentanoic acid;

2-{1-Carboxy-2-[3-(3,5-difluoro-benzyloxy)-phenyl]-ethylamino}-4-methyl-pentanoic acid;

2-[2-(3-Allyloxy-phenyl)-1-carboxy-ethylamino]-4-methyl-pentanoic acid;

2-{1-Carboxy-2-[3-(3,5-difluoro-phenyl)-2-oxo-imidazolidin-1-yl]-ethylamino}-4-methyl-pentanoic acid;

2-{1-Carboxy-2-[(5-chloro-1H-indole-2-carbonyl)-amino]-ethylamino}-4-methyl-pentanoic acid;

2-{1-Carboxy-2-[3-(3,5-dichloro-benzyl)-2-oxo-oxazolidin-4-yl]-ethylamino}-4-methyl-pentanoic acid;

2-[1-Carboxy-2-(4-thiophen-3-yl-phenyl)-ethylamino]-4-methyl-pentanoic acid;

2-[1-Carboxy-2-(3',5'-dichloro-biphenyl-4-yl)-ethylamino]-4-methyl-pentanoic acid;

2-[1-Carboxy-2-(4'-methyl-biphenyl-4-yl)-ethylamino]-4-methyl-pentanoic acid;

2-{1-Carboxy-2-[3-(4-iodo-benzyl)-3H-imidazol-4-yl]-ethylamino}-4-methyl-pentanoic acid;

2-{1-Carboxy-2-[3-(3,5-difluoro-benzyl)-3H-imidazol-4-yl]-ethylamino}-4-pentanoic acid;

2-(1-Carboxy-2-{3-[2-(4-fluoro-phenyl)-ethyl]-2-oxo-2,3-dihydro-imidazol-1-yl}-ethylamino)-4-methyl-pentanoic acid;

2-[1-Carboxy-2-(3-cyclohexylmethyl-2-oxo-2,3-dihydro-imidazol-1-yl)-ethylamino]-4-methyl-pentanoic acid;

2-{1-Carboxy-2-[3-(3,5-dichloro-benzyl)-3H-imidazol-4-yl]-ethylamino}-4-methyl-pentanoic acid tert-butyl ester;

2-{1-Carboxy-2-[3-(3,5-dichloro-benzyl)-2-oxo-oxazolidin-4-yl]-ethylamino}-4-methyl-pentanoic acid;

2-[1-Carboxy-2-(5-p-tolyl-furan-2-yl)-ethylamino]-4-methyl-pentanoic acid;

2-(1-Carboxy-2-{3-[2-(3-fluoro-phenyl)-ethyl]-2-oxo-2,3-dihydro-imidazol-1-yl}-ethylamino)-4-methyl-pentanoic acid;

2-[1-Carboxy-2-(5-phenyl-furan-2-yl)-ethylamino]-4-methyl-pentanoic acid;

2-{1-Carboxy-2-[5-(3,5-dichloro-phenyl)-furan-2-yl]-ethylamino}-4-methyl-pentanoic acid;

2-{1-Carboxy-2-[5-(3,5-dimethyl-phenyl)-furan-2-yl]-ethylamino}-4-methyl-pentanoic acid;

2-{1-Carboxy-2-[5-(3,5-difluoro-phenyl)-furan-2-yl]-ethylamino}-4-methyl-pentanoic acid;

2-[1-Carboxy-2-(5-thiophen-3-yl-furan-2-yl)-ethylamino]-4-methyl-pentanoic acid;

2-[1-Carboxy-2-(6-methyl-benzothiazol-2-ylcarbamoyl)-ethylamino]-4-methyl-pentanoic acid;

2-[1-Carboxy-2-(4-hydroxy-phenyl)-ethylamino]-4-methyl-pentanoic acid;

2-{1-Carboxy-2-[3-(3,5-dichloro-benzyloxy)-phenyl]-ethylamino}-4-methyl-pentanoic acid;

2-{1-Carboxy-2-[3-(pyridin-4-ylmethoxy)-phenyl]-ethylamino}-4-methyl-pentanoic acid;

2-{1-Carboxy-2-[3-(3,5-dimethyl-benzyloxy)-phenyl]-ethylamino}-4-methyl-pentanoic acid;

2-{1-Carboxy-2-[3-(4-chloro-benzyloxy)-phenyl]-ethylamino}-4-methyl-pentanoic acid;

2-{2-[3-(2,4-Bis-trifluoromethyl-benzyloxy)-phenyl]-1-carboxy-ethylamino}-4-methyl-pentanoic acid;

2-[1-Carboxy-2-(1-phenyl-1H-pyrazol-3-yl)-ethylamino]-4-methyl-pentanoic acid;

2-{1-Carboxy-2-[3-(3-chloro-benzyl)-2-oxo-2,3-dihydro-imidazol-1-yl]-ethylamino}-4-methyl-pentanoic acid;

2-{1-Carboxy-2-[4-(3,5-dichloro-benzyl)-phenyl]-ethylamino}-4-methyl-pentanoic acid;

2-[2-(4-Benzyl-phenyl)-1-carboxy-ethylamino]-4-methyl-pentanoic acid;

2-[1-Carboxy-2-(4-phenyl-thiazol-2-ylcarbamoyl)-ethylamino]-4-methyl-pentanoic acid;

2-{1-Carboxy-2-[5-(4-methoxy-phenyl)-furan-2-yl]-ethylamino}-4-methyl-pentanoic acid;

2-[2-(5-Benzo[1,3]dioxol-5-yl-furan-2-yl)-1-carboxy-ethylamino]-4-methyl-pentanoic acid;

2-[1-Carboxy-2-(5-naphthalen-1-yl-furan-2-yl)-ethylamino]-4-methyl-pentanoic acid;

2-{1-Carboxy-2-[5-(4-chloro-phenyl)-furan-2-yl]-ethylamino}-4-methyl-pentanoic acid;

2-{1-Carboxy-2-[5-(4-trifluoromethyl-phenyl)-furan-2-yl]-ethylamino}-4-methyl-pentanoic acid;

2-[1-Carboxy-2-(3-isobutoxy-phenyl)-ethylamino]-4-methyl-pentanoic acid;

2-{1-Carboxy-2-[3-(3-chloro-benzyloxy)-phenyl]-ethylamino}-4-methyl-pentanoic acid;

2-{1-Carboxy-2-[3-(2-chloro-benzyloxy)-phenyl]-ethylamino}-4-methyl-pentanoic acid;

2-[3-(4-Benzyloxy-phenyl)-1-carboxy-propylamino]-4-methyl-pentanoic acid;

2-{1-Carboxy-2-[5-(3-chloro-phenyl)-furan-2-yl]-ethylamino}-4-methyl-pentanoic acid;

2-{1-Carboxy-2-[3-(3-fluoro-benzyl)-2-oxo-2,3-dihydro-imidazol-1-yl]-ethylamino}-4-methyl-pentanoic acid;

2-{1-Carboxy-2-[3-(3,4-difluoro-benzyl)-2-oxo-2,3-dihydro-imidazol-1-yl]-ethylamino}-4-methyl-pentanoic acid;

2-[1-Carboxy-3-(6-fluoro-benzothiazol-2-ylcarbamoyl)-propylamino]-4-methyl-pentanoic acid;
2-{1-Carboxy-2-[3-(2,5-difluoro-benzyl)-2-oxo-2,3-dihydro-imidazol-1-yl]-ethylamino}-4-methyl-pentanoic acid;
2-{1-Carboxy-2-[4-(3,5-difluoro-benzoylamino)-phenyl]-ethylamino}-4-methyl-pentanoic acid;
2-[1-Carboxy-2-(4'-fluoro-biphenyl-4-yl)-ethylamino]-4-methyl-pentanoic acid;
2-[2-(4-Benzo[1,3]dioxol-5-yl-phenyl)-1-carboxy-ethylamino]-4-methyl-pentanoic acid;
2-[2-(4-Benzo[b]thiophen-3-yl-phenyl)-1-carboxy-ethylamino]-4-methyl-pentanoic acid;
2-[2-(3-Benzyl-phenyl)-1-carboxy-ethylamino]-4-methyl-pentanoic acid;
2-[1-Carboxy-2-(4'-trifluoromethyl-biphenyl-4-yl)-ethylamino]-4-methyl-pentanoic acid;
2-(1-Carboxy-2-{3-[2-(3-chloro-phenyl)-ethyl]-2-oxo-2,3-dihydro-imidazol-1-yl}-ethylamino)-4-methylpentanoic acid;
2-{2-[3-(4-Bromo-benzyl)-3H-imidazol-4-yl]-1-carboxy-ethylamino}-4-methyl-pentanoic acid;
2-[2-(4-Benzenesulfonylamino-phenyl)-1-carboxy-ethylamino]-4-methyl-pentanoic acid;
2-{1-Carboxy-2-[3-(3-chloro-benzyl)-phenyl]-ethylamino}-4-methyl-pentanoic acid;
2-{1-Carboxy-2-[3-(3,5-dichloro-benzyl)-phenyl]-ethylamino}-4-methyl-pentanoic acid;
2-{1-Carboxy-2-[3-(5-chloro-benzo[b]thiophen-3-ylmethoxy)-phenyl]-ethylamino}-4-methyl-pentanoic acid;
2-[1-Carboxy-2-(4-pyridin-2-yl-phenyl)-ethylamino]-4-methyl-pentanoic acid;
2-[1-Carboxy-2-(4-pyridin-3-yl-phenyl)-ethylamino]-4-methyl-pentanoic acid;
2-[1-Carboxy-2-(4-pyridin-4-yl-phenyl)-ethylamino]-4-methyl-pentanoic acid;
2-(1-Carboxy-ethylamino)-3-[3-(3,5-dichloro-benzyl)-3H-imidazol-4-yl]-propionic acid;
2-{1-Carboxy-2-[3-(3,5-dichloro-benzyl)-3H-imidazol-4-yl]-ethylamino}-4-phenyl-butyric acid;
2-(1-Carboxy-2-{3-[2-(2-fluoro-phenyl)-ethyl]-2-oxo-2,3-dihydro-imidazol-1-yl}-ethylamino)-4-methyl-pentanoic acid;
2-[1-Carboxy-2-(4-pyrrol-1-yl-phenyl)-ethylamino]-4-methyl-pentanoic acid;
2-(1-Carboxy-3-methyl-butylamino)-5-(3,5-dichloro-phenyl)-pent-4-ynoic acid;
2-{1-Carboxy-2-[4-(3,5-difluoro-phenoxy)-phenyl]-ethylamino}-4-methyl-pentanoic acid;
2-[1-Carboxy-2-(3',5'-dichloro-biphenyl-2-yl)-ethylamino]-4-methyl-pentanoic acid;
4-[2-Carboxy-2-(1-carboxy-3-methyl-butylamino)-ethyl]-benzoic acid tert-butyl ester;
2-(1-Carboxy-3-methyl-butylamino)-5-(3,5-dichloro-phenyl)-pent-4-enoic acid;
2-{1-Carboxy-2-[3-(3,5-difluoro-benzyl)-2,5-dioxo-imidazolidin-1-yl]-ethylamino}-4-methyl-pentanoic acid;
2-{1-Carboxy-2-[3-(3,5-dichloro-benzyl)-2,5-dioxo-imidazolidin-1-yl]-ethylamino}-4-methyl-pentanoic acid;
2-{2-[3-(2,4-Bis-trifluoromethyl-benzyl)-2,5-dioxo-imidazolidin-1-yl]-1-carboxy-ethylamino}-4-methyl-pentanoic acid;
2-{1-Carboxy-2-[4-(5-methyl-pyridin-2-yl)-phenyl]-ethylamino}-4-methyl-pentanoic acid;
2-{1-Carboxy-2-[4-(4-methyl-pyridin-2-yl)-phenyl]-ethylamino}-4-methyl-pentanoic acid;
2-{1-Carboxy-2-[4-(3-chloro-4-ethoxy-pyridin-2-yl)-phenyl]-ethylamino}-4-methyl-pentanoic acid;
2-[1-Carboxy-2-(4-quinolin-3-yl-phenyl)-ethylamino]-4-methyl-pentanoic acid;
2-{1-Carboxy-2-[4-(3,5-difluoro-benzylcarbamoyl)-phenyl]-ethylamino}-4-methyl-pentanoic acid;
2-{1-Carboxy-2-[4-(3,5-dichloro-phenylcarbamoyl)-phenyl]-ethylamino}-4-methyl-pentanoic acid;
2-[1-Carboxy-2-(4-phenylcarbamoyl-phenyl)-ethylamino]-4-methyl-pentanoic acid;
2-[1-Carboxy-2-(4-cyclohexylcarbamoyl-phenyl)-ethylamino]-4-methyl-pentanoic acid;
2-[1-Carboxy-2-(2-cyano-phenyl)-ethylamino]-4-methyl-pentanoic acid;
2-[1-Carboxy-2-(4-phenoxy-phenyl)-ethylamino]-4-methyl-pentanoic acid;
2-{1-Carboxy-2-[4-(5-chloro-benzo[b]thiophen-3-ylmethoxy)-phenyl]-ethylamino}-4-methyl-pentanoic acid;
2-{1-Carboxy-2-[5-(3,4-dichloro-phenyl)-isoxazol-3-yl]-ethylamino}-4-methyl-pentanoic acid;
2-{1-Carboxy-2-[4-(3,5-dichloro-phenoxy)-phenyl]-ethylamino}-4-methyl-pentanoic acid;
2-{1-Carboxy-2-[2-(3,5-dichloro-phenoxy)-phenyl]-ethylamino}-4-methyl-pentanoic acid;
2-{1-Carboxy-2-[2-(3-chloro-benzyloxy)-phenyl]-ethylamino}-4-methyl-pentanoic acid;
2-{1-Carboxy-2-[4-(4-fluoro-phenoxy)-phenyl]-ethylamino}-4-methyl-pentanoic acid;
2-[1-Carboxy-2-(1-p-tolyl-1H-pyrazol-3-yl)-ethylamino]-4-methyl-pentanoic acid;
2-{1-Carboxy-2-[4-(cyclopentanecarbonyl-amino)-phenyl]-ethylamino}-4-methyl-pentanoic acid;
2-{1-Carboxy-2-[4-(2,2-dimethyl-propionylamino)-phenyl]-ethylamino}-4-methyl-pentanoic acid;
2-{1-Carboxy-2-[2-(5-chloro-benzo[b]thiophen-3-ylmethoxy)-phenyl]-ethylamino}-4-methyl-pentanoic acid;
2-{1-Carboxy-2-[5-(4-chloro-phenyl)-isoxazol-3-yl]-ethylamino}-4-methyl-pentanoic acid;
2-{1-Carboxy-2-[5-(2-chloro-phenyl)-isoxazol-3-yl]-ethylamino}-4-methyl-pentanoic acid;
2-{1-Carboxy-2-[4-(5-fluoro-2,3-dihydro-benzofuran-3-ylmethoxy)-phenyl]-ethylamino}-4-methyl-pentanoic acid;
2-{2-[4-(Benzo[b]thiophen-3-ylmethoxy)-phenyl]-1-carboxy-ethylamino}-4-methyl-pentanoic acid;
5-[2-Carboxy-2-(1-carboxy-3-methyl-butylamino)-ethyl]-1-(3,5-dichloro-benzyl)-1H-pyrrole-2-carboxylic acid;
2-{1-Carboxy-2-[1-(2-cyclohexyl-ethyl)-5-(2,2,2-trifluoro-acetyl)-1H-pyrrol-2-yl]-ethylamino}-4-methyl-pentanoic acid;
2-[1-Carboxy-2-(4-nitro-phenyl)-ethylamino]-4-methyl-pentanoic acid;
2-{1-Carboxy-2-[4-(2-methoxy-benzoylamino)-phenyl]-ethylamino}-4-methyl-pentanoic acid;
2-[1-Carboxy-2-(2-trifluoromethyl-phenyl)-ethylamino]-4-methyl-pentanoic acid;
2-(2-{4-[Bis-(3,5-difluoro-benzyl)-amino]-phenyl}-1-carboxy-ethylamino)-4-methyl-pentanoic acid;
2-[1-Carboxy-2-(2-p-tolyl-thiazol-4-yl)-ethylamino]-4-phenyl-butyric acid;
2-[1-Carboxy-2-(4-dimethylcarbamoyl-phenyl)-ethylamino]-4-methyl-pentanoic acid;
2-{1-Carboxy-2-[4-(3,5-dimethyl-phenylcarbamoyl)-phenyl]-ethylamino}-4-methyl-pentanoic acid;

2-[2-(4-tert-Butylcarbamoyl-phenyl)-1-carboxy-ethylamino]-4-methyl-pentanoic acid;

4-Methyl-2-{[pyrimidin-2-yl-(2-p-tolyl-thiazol-4-ylmethyl)-amino]-methyl}-pentanoic acid;

2-{1-Carboxy-2-[1-(3,5-dichloro-benzyl)-1H-pyrrol-2-yl]-ethylamino}-4-methyl-pentanoic acid;

2-[1-Carboxy-2-(4-isopropylcarbamoyl-phenyl)-ethylamino]-4-methyl-pentanoic acid;

2-{1-Carboxy-2-[4-(morpholine-4-carbonyl)-phenyl]-ethylamino}-4-methyl-pentanoic acid; and 2-{1-Carboxy-2-[4-(3,4-dihydro-1H-isoquinoline-2-carbonyl)-phenyl]-ethylamino}-4-methyl-pentanoic acid, or a pharmaceutically acceptable salt or ester thereof.

33. The method of any one of claims 21–23, wherein said ACE-2 inhibitor is of the formula:

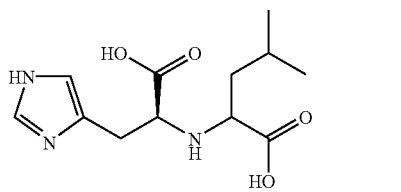

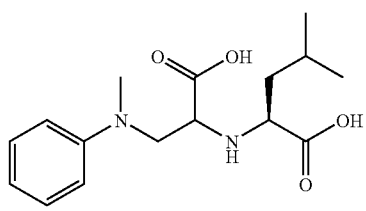

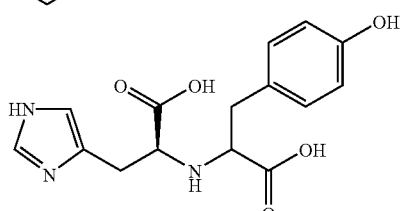

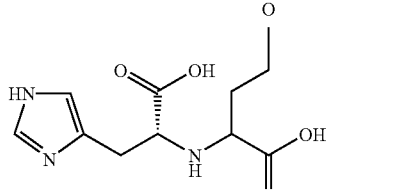

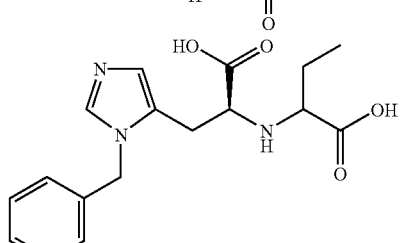

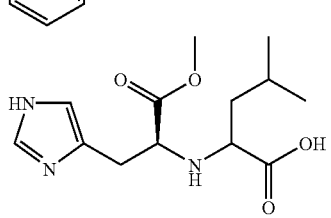

-continued

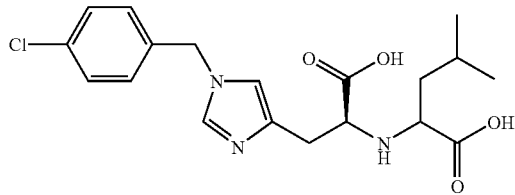

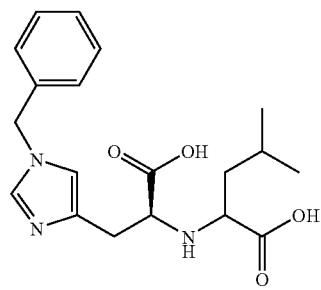

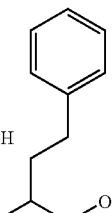

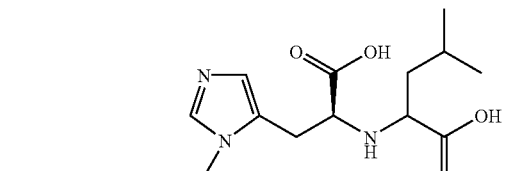

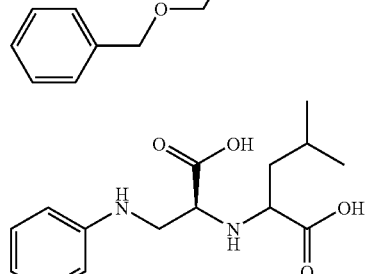

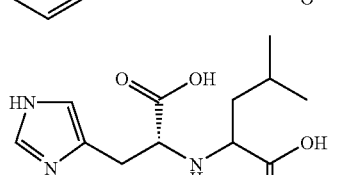

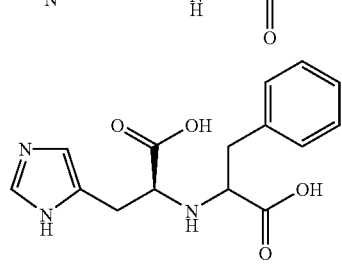

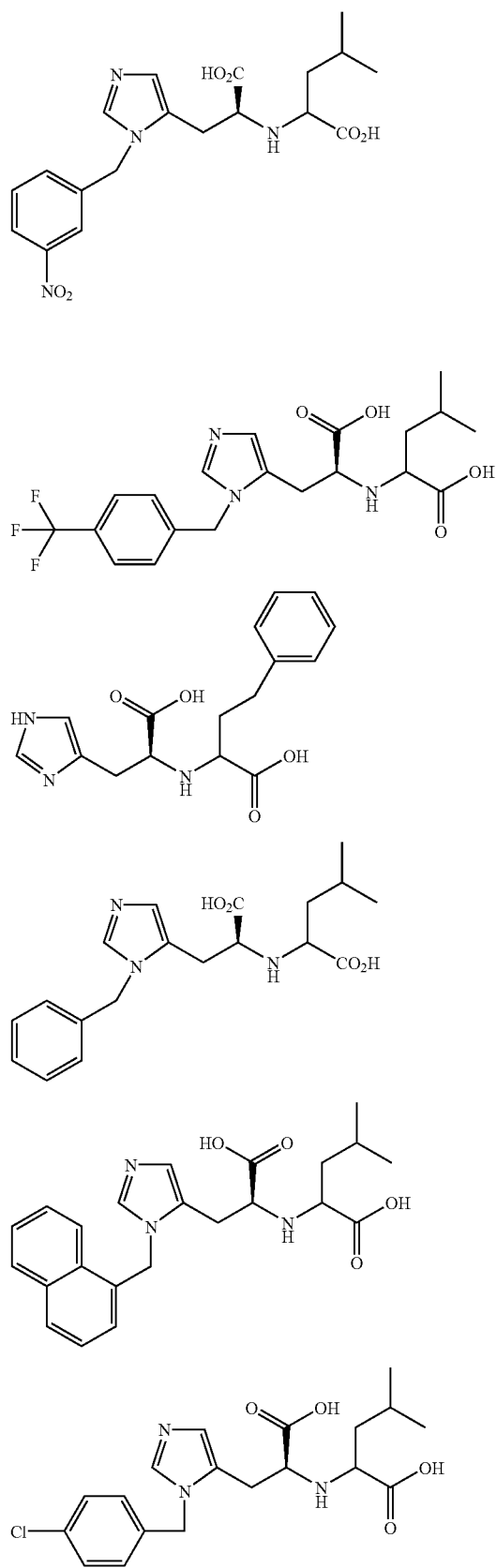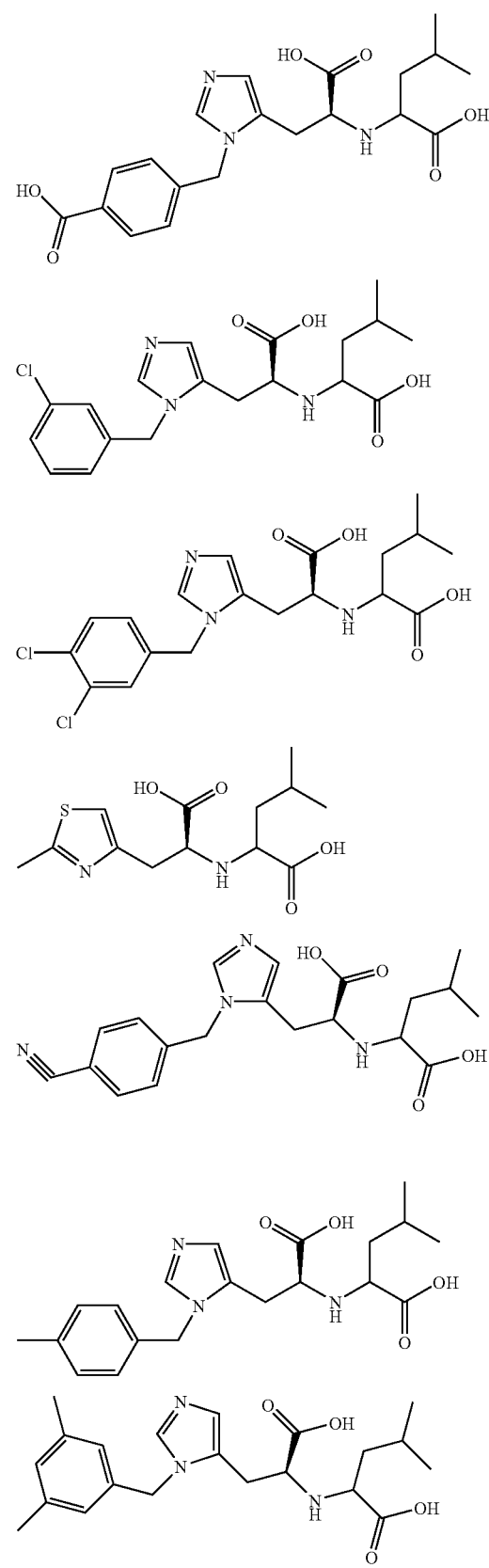

641
-continued
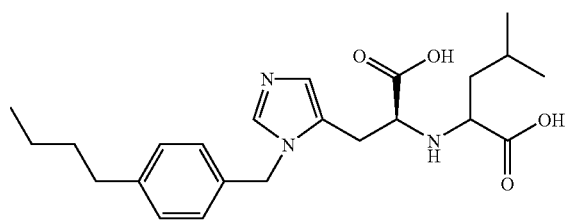
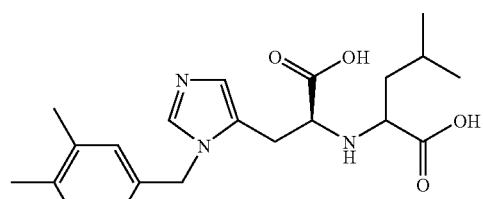
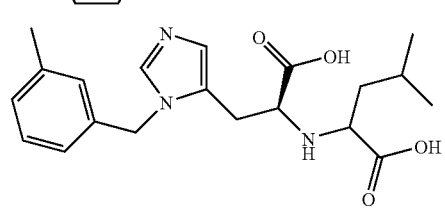
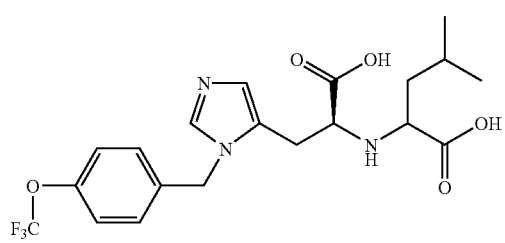
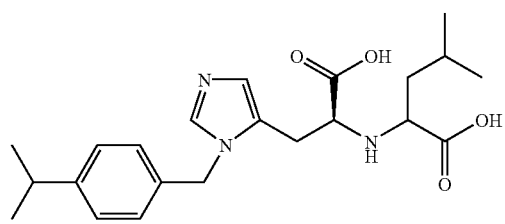
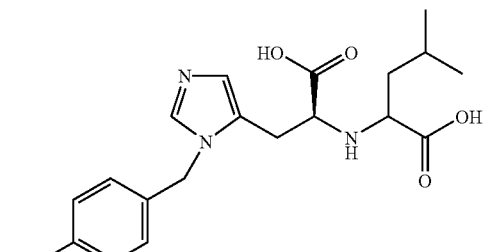
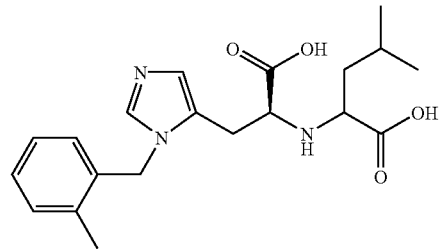
642
-continued
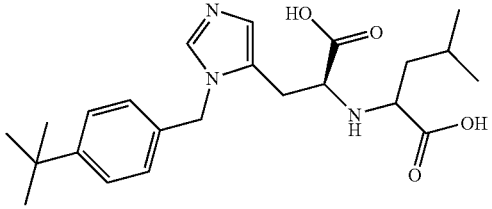
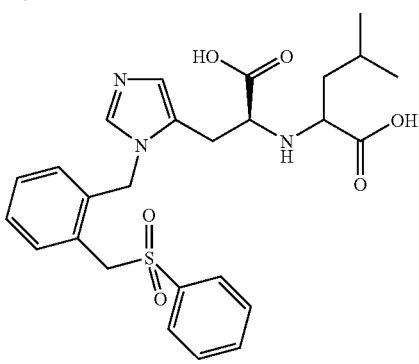
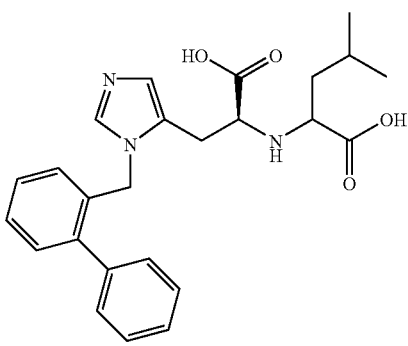
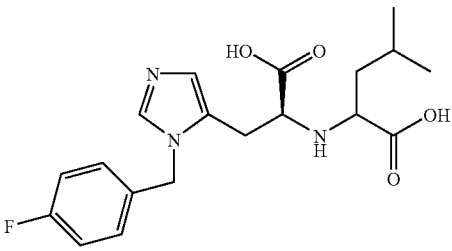
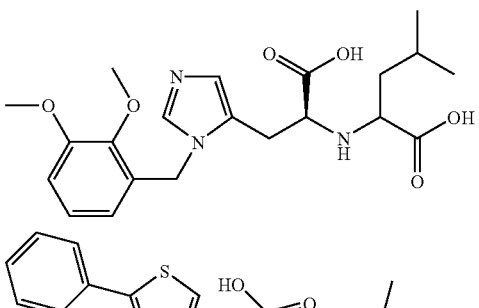
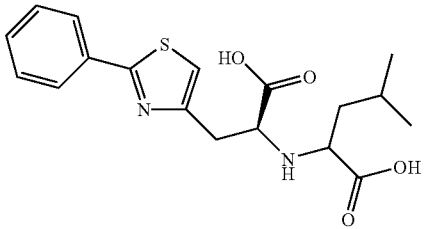

643
-continued
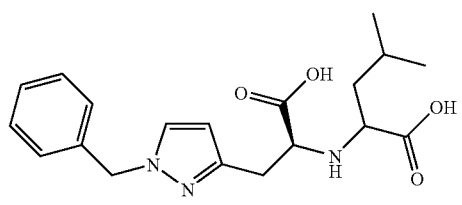
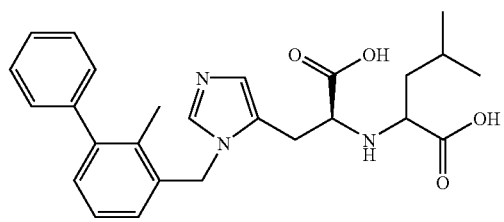
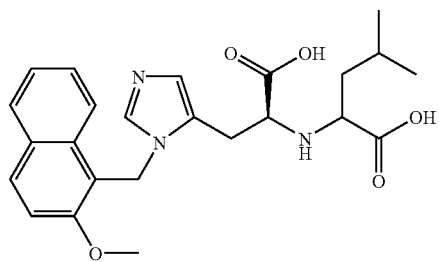
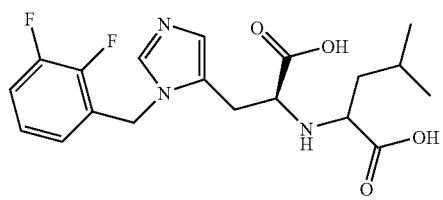
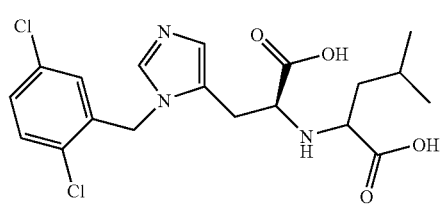
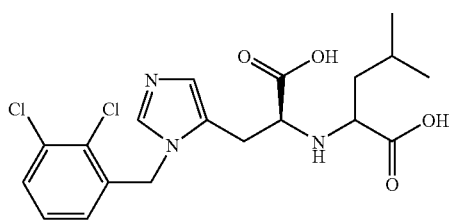
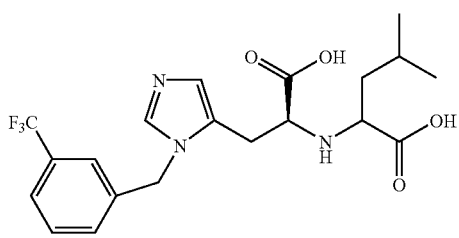
644
-continued
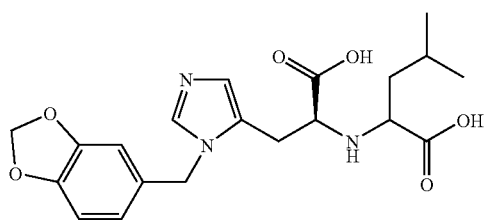
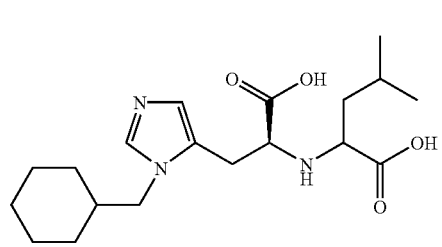
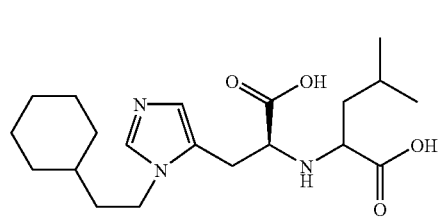
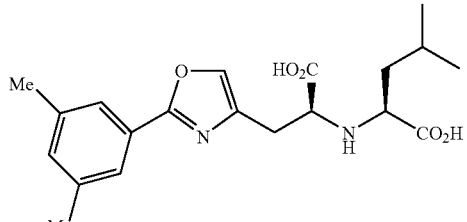
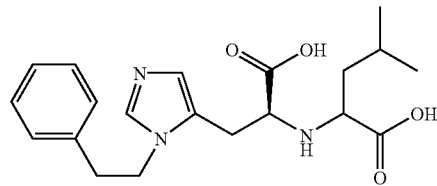
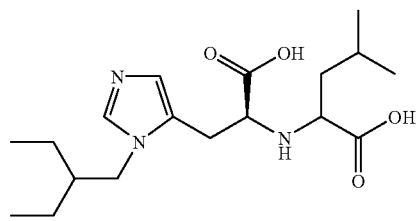
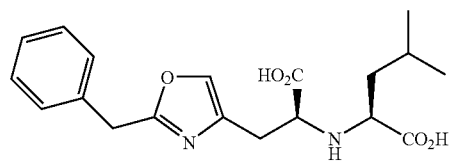

-continued
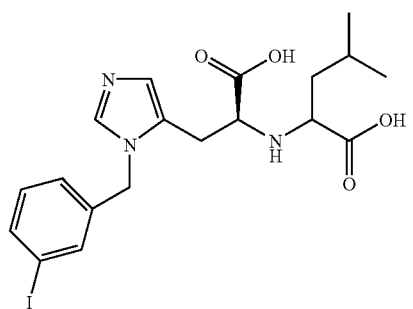
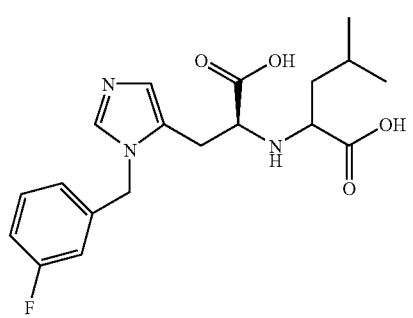
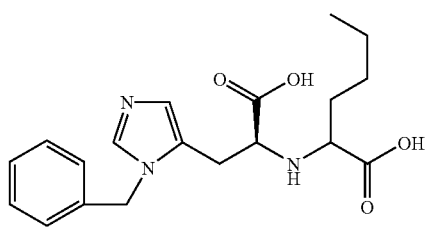
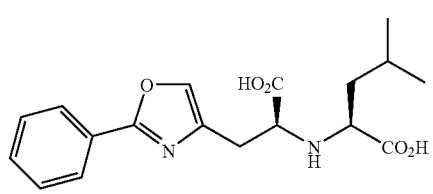
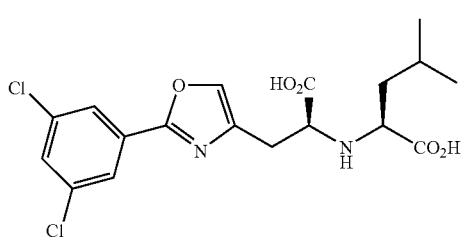
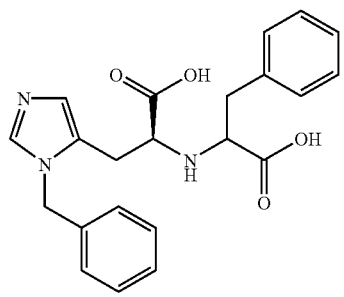
-continued
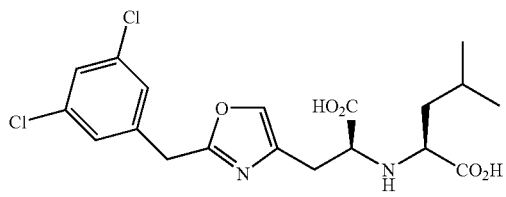
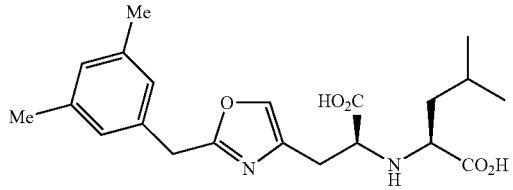
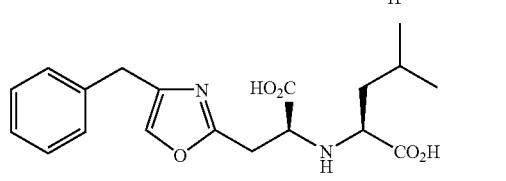
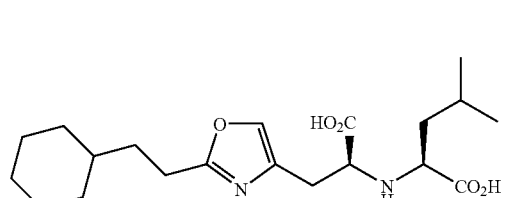
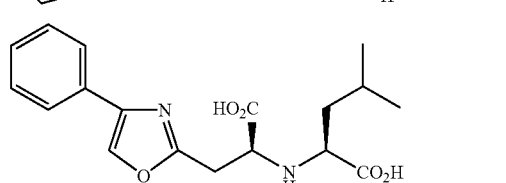
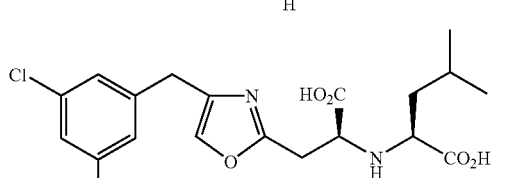
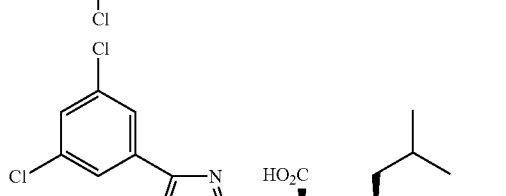
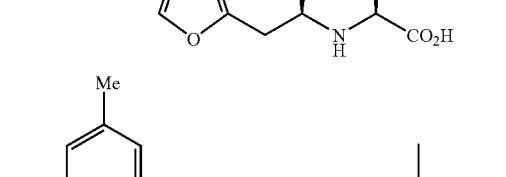
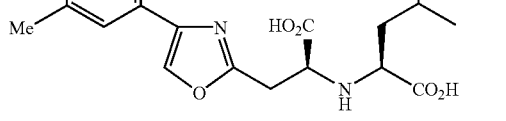

-continued
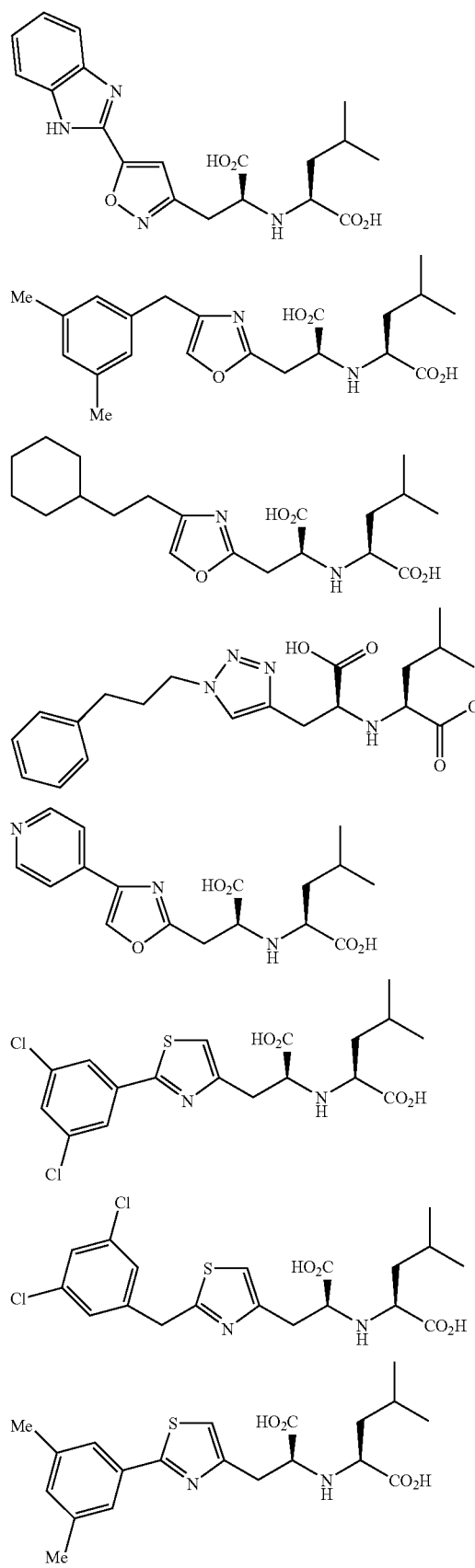
-continued
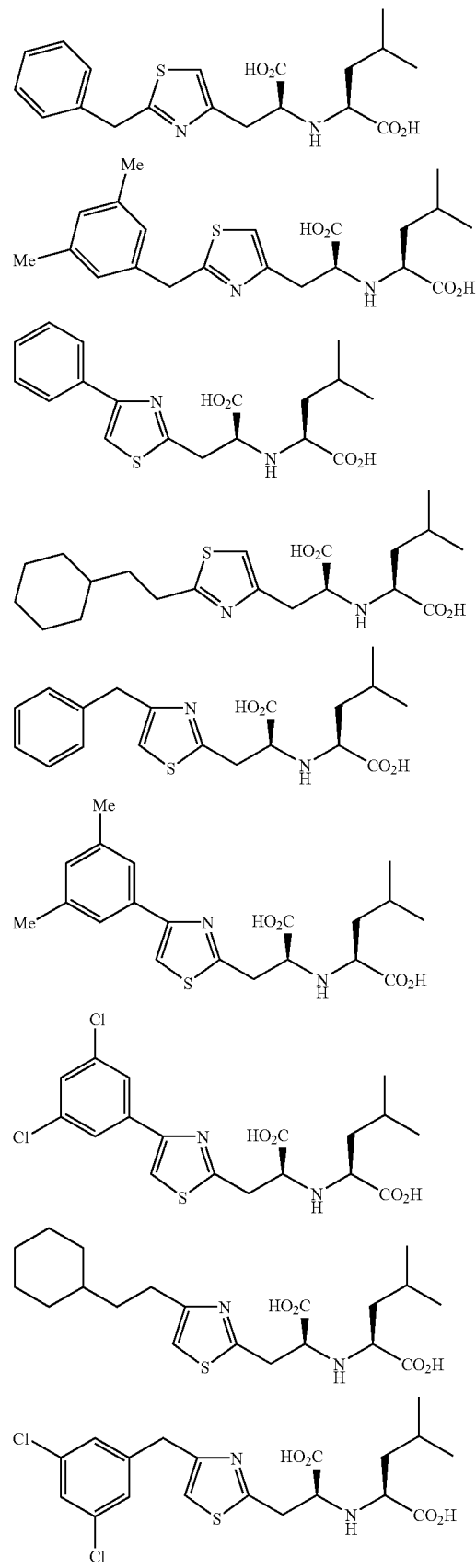

-continued
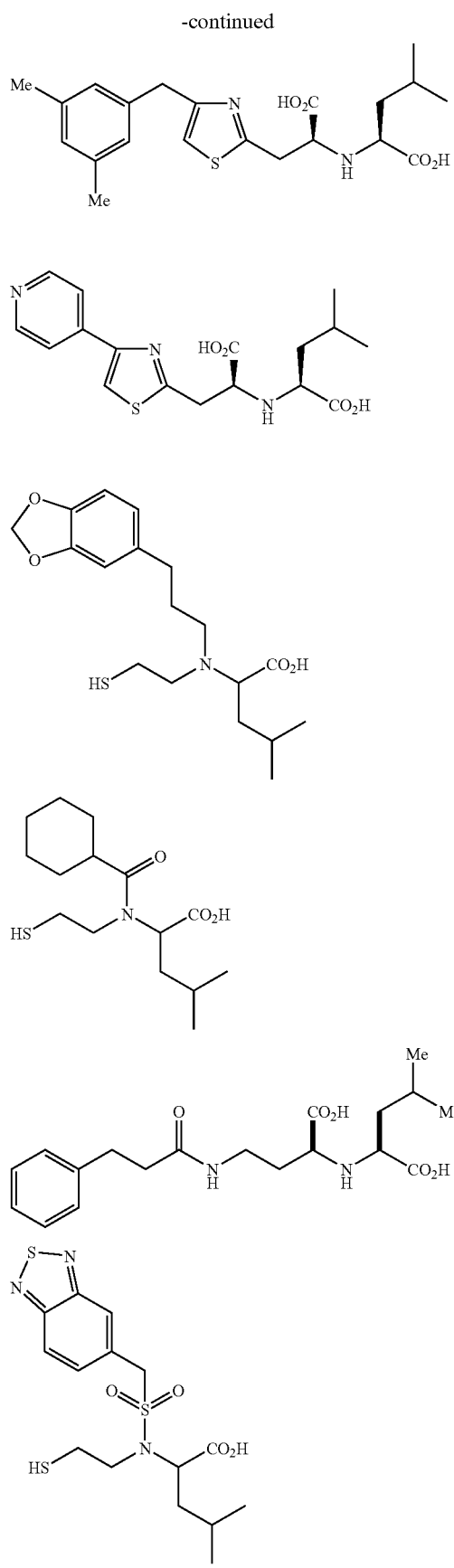
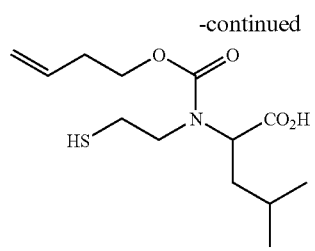

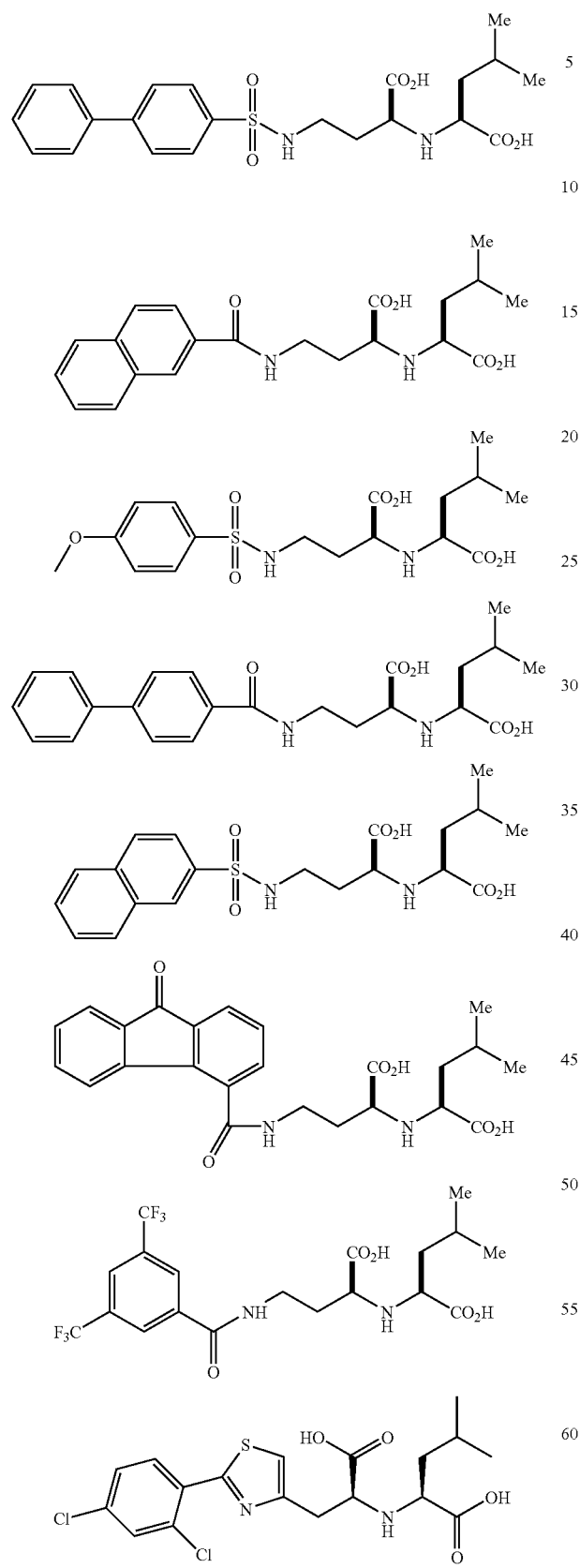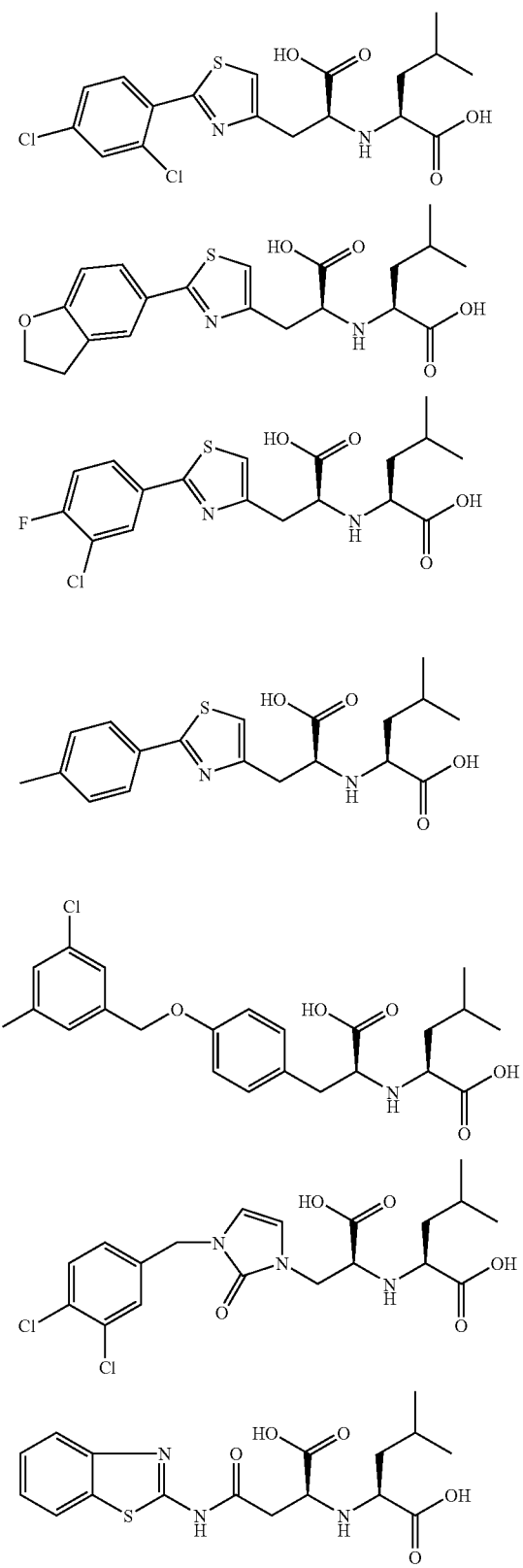

-continued
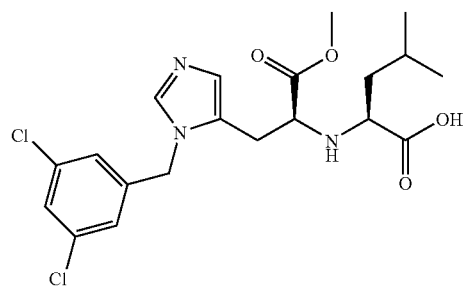
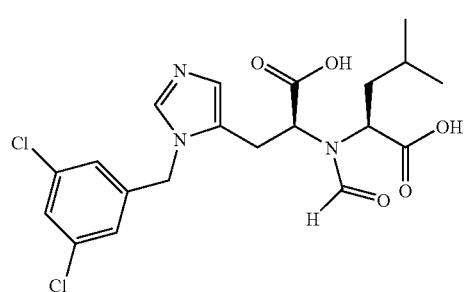
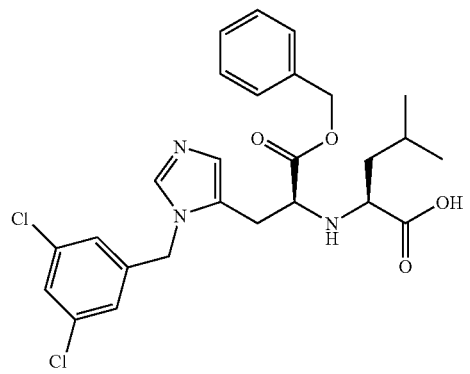
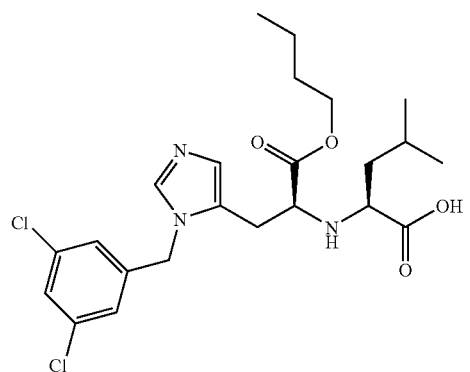
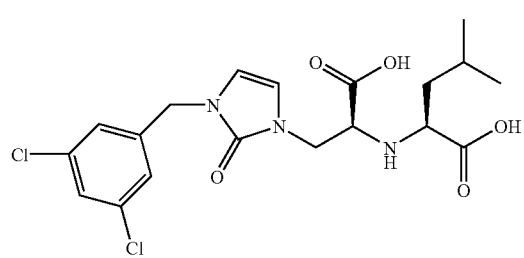
-continued
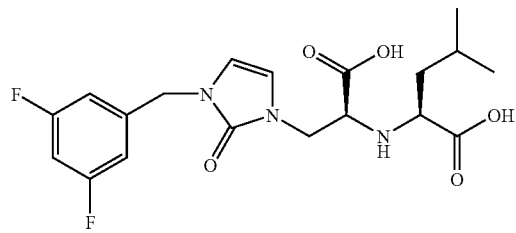
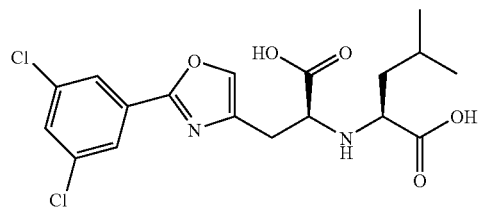
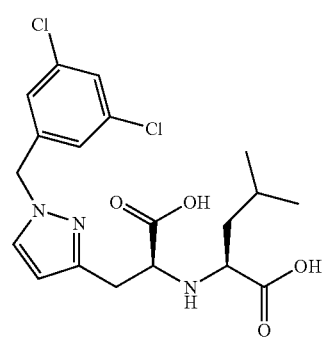
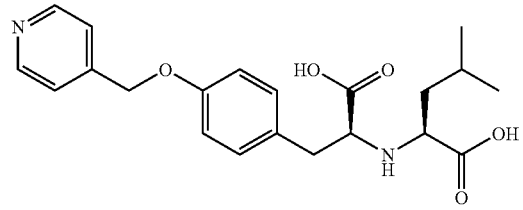
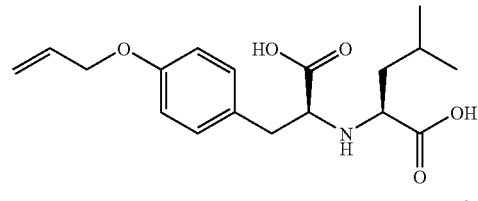
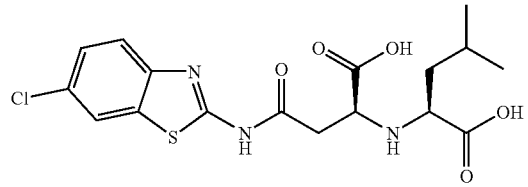
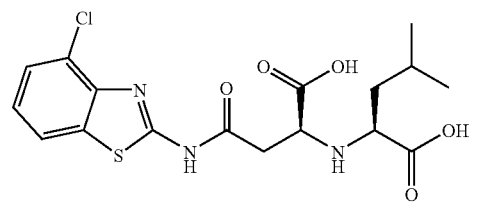

| 655 | 656 |
|---|---|
| -continued | -continued |
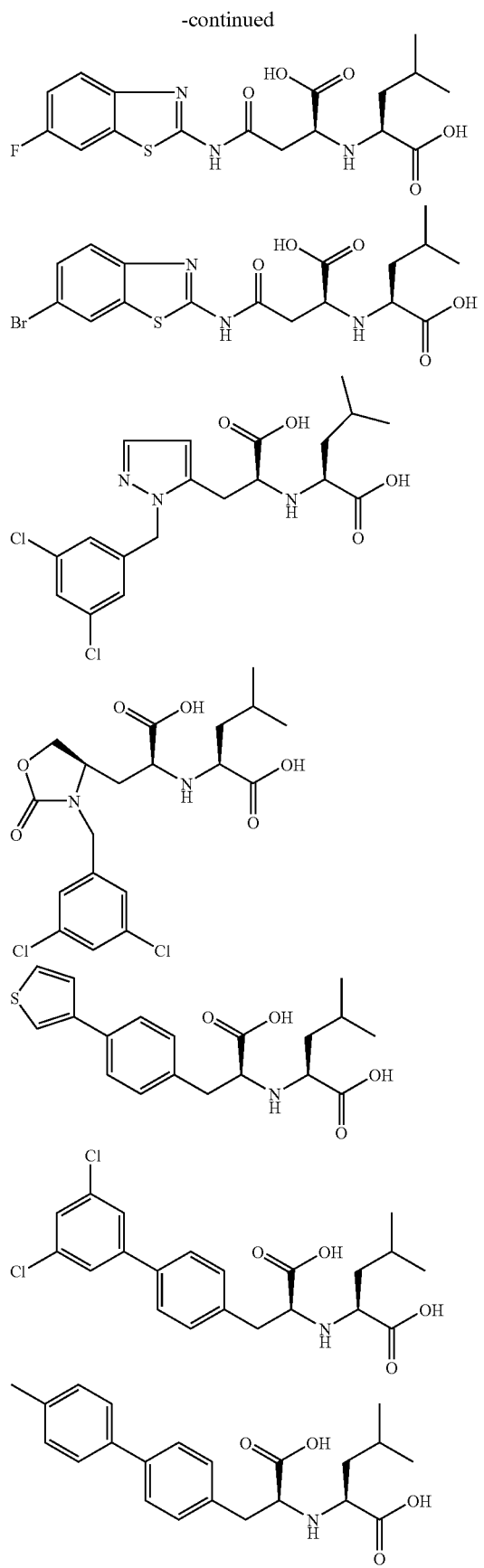
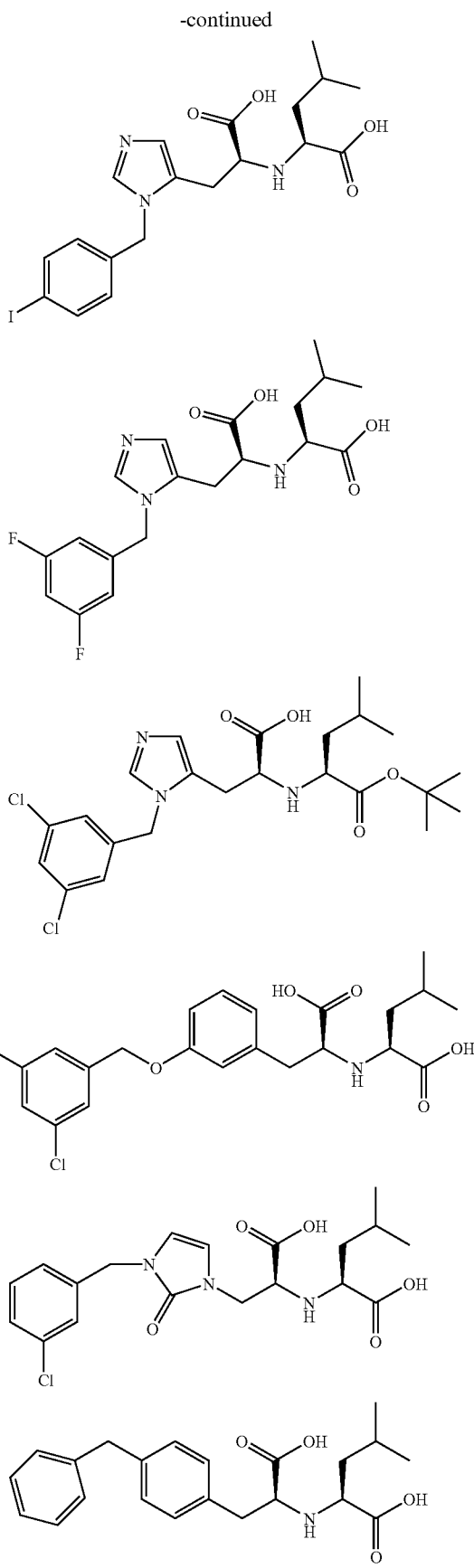

-continued
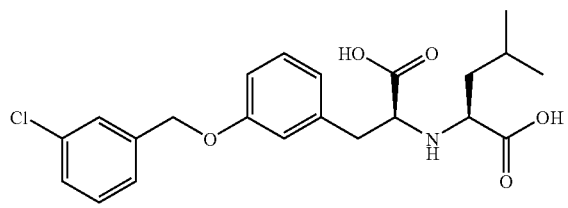
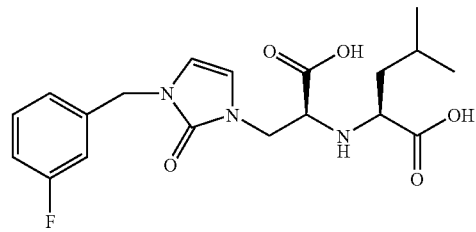
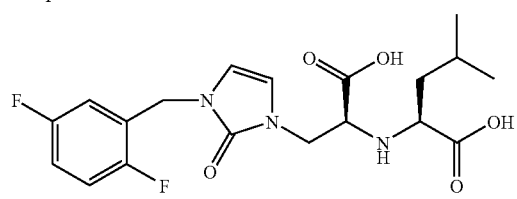
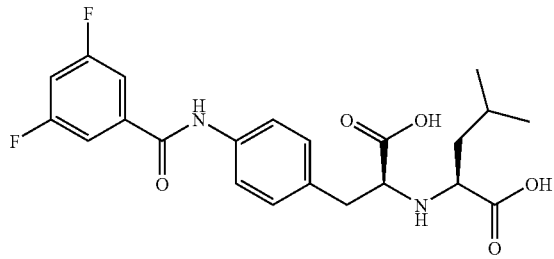
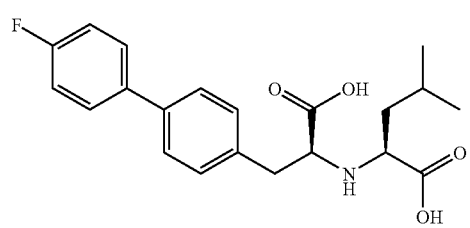
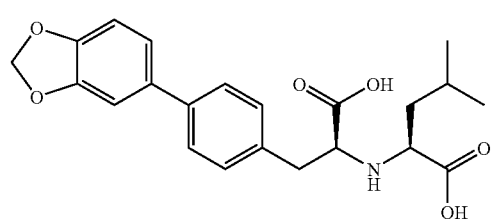
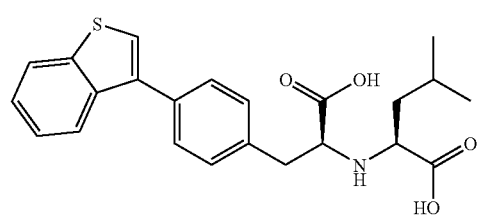
-continued
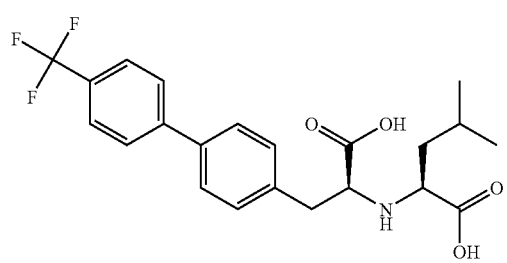
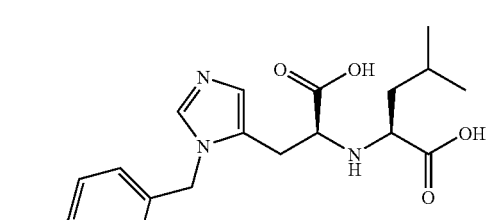
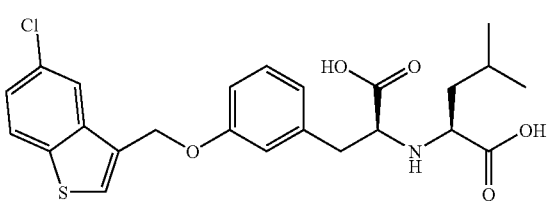
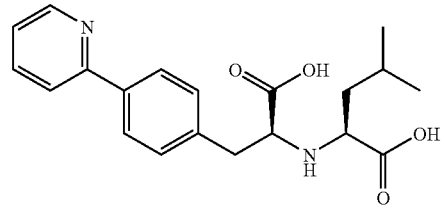
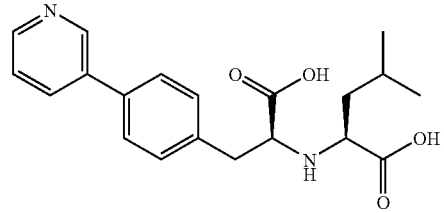
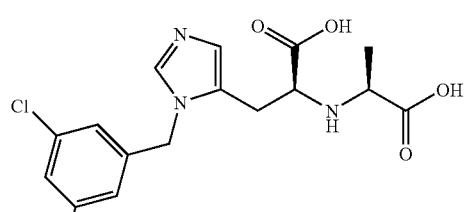

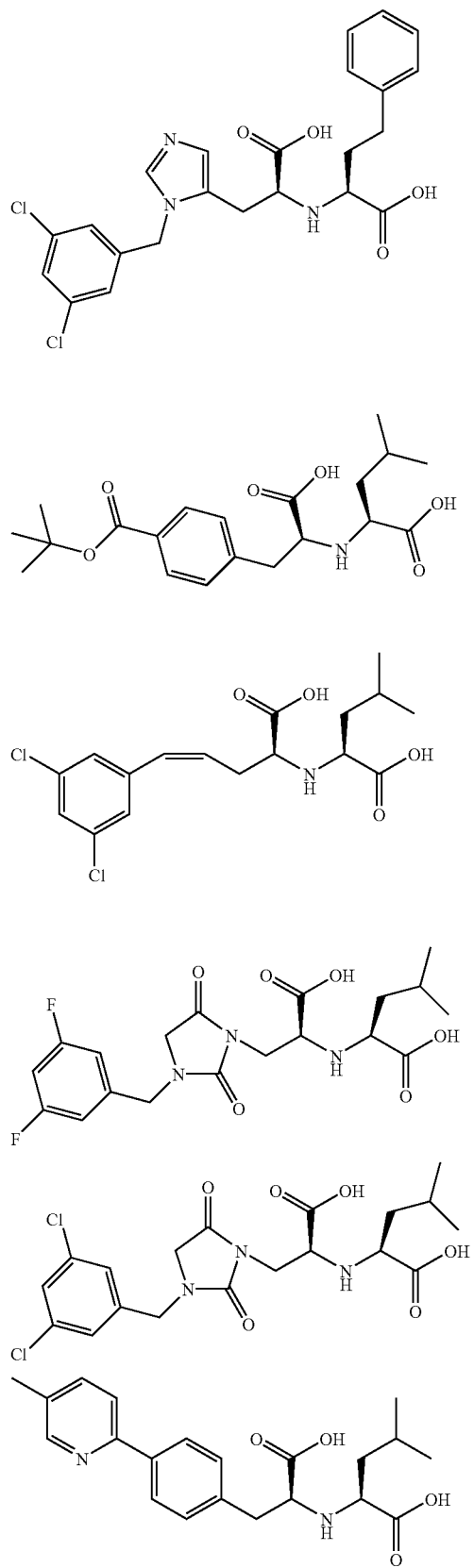
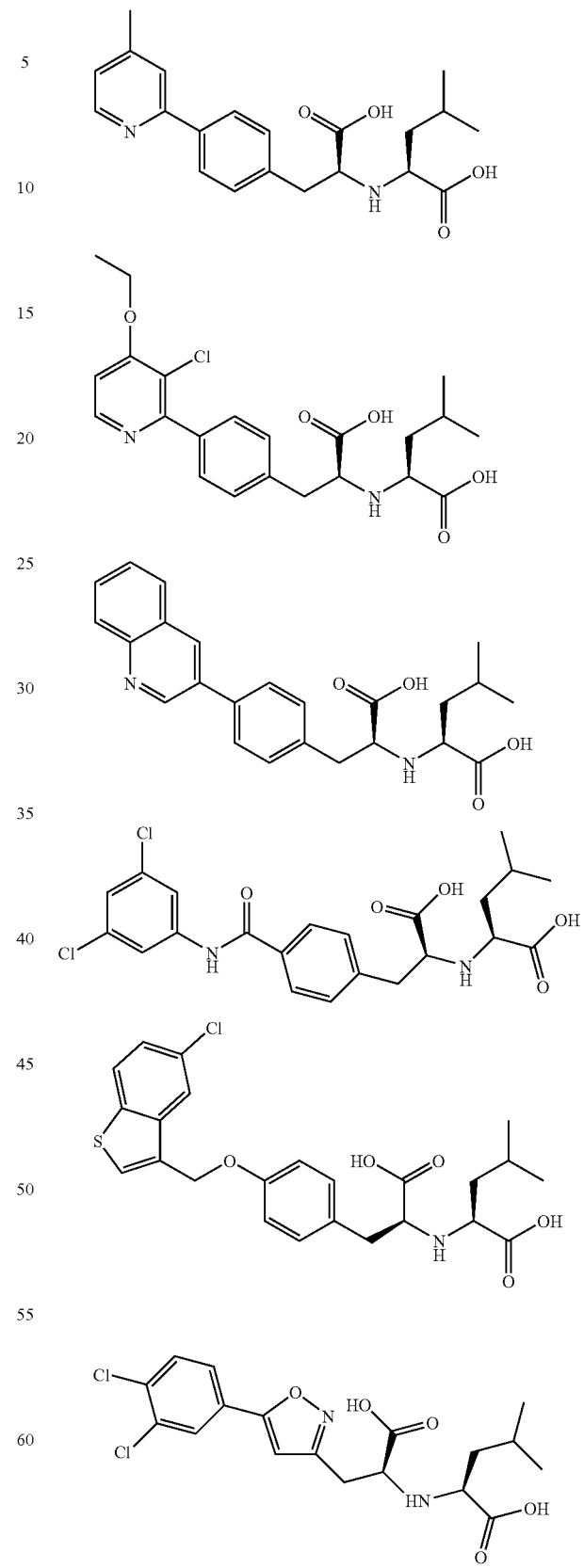

-continued

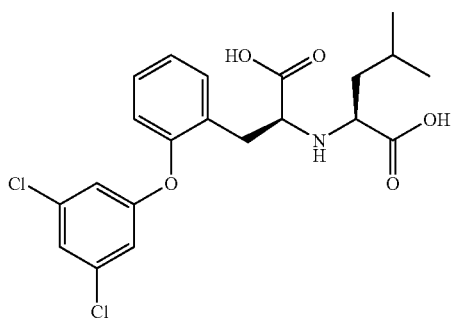

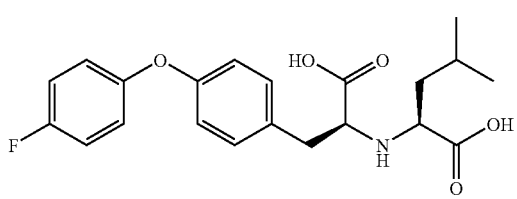

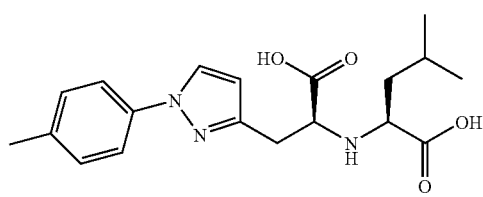

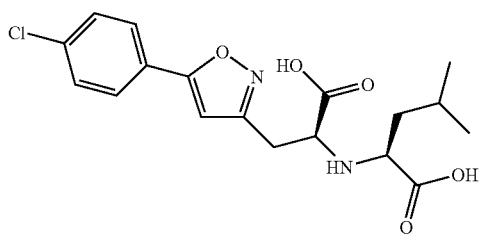

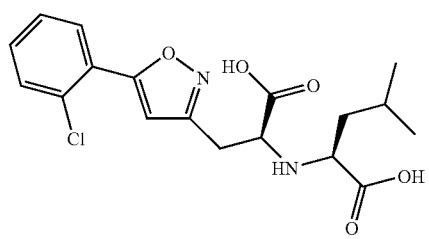

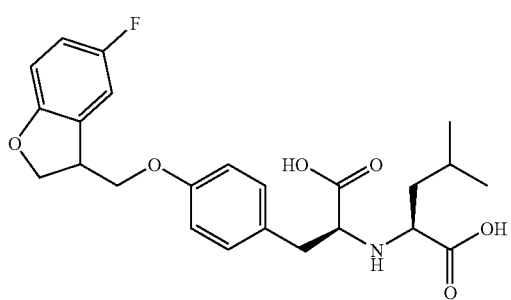

-continued

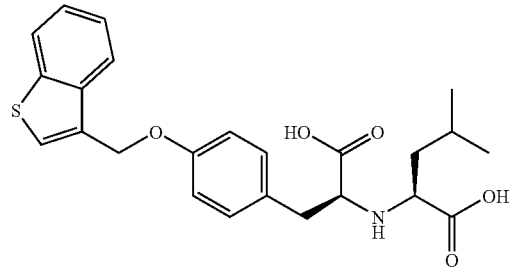

or a pharmaceutically acceptable salt or ester thereof.

34. The method of any one of claims 21–24, further comprising administering a pharmaceutically acceptable carrier.

35. A compound selected from the group consisting of:
2-{1-Carboxy-2-[2-(3-trifluoromethyl-phenyl)-thiazol-4-yl]-ethylamino}-4-methyl-pentanoic acid;
2-{1-Carboxy-3-[(naphthalene-2-carbonyl)-amino]-propylamino}-4-methyl-pentanoic acid;
2-[3-(Biphenyl-4-sulfonylamino)-1-carboxy-propylamino]-4-methyl-pentanoic acid;
2-{1-Carboxy-2-[2-(2,4-dichloro-phenyl)-thiazol-4-yl]-ethylamino}-4-methyl-pentanoic acid;
2-{1-Carboxy-2-[2-(2,3-dihydro-benzofuran-5-yl)-thiazol-4-yl]-ethylamino}-4-methyl-pentanoic acid;

2-{1-Carboxy-2-[2-(3-chloro-4-fluoro-phenyl)-thiazol-4-yl]-ethylamino}-4-methyl-pentanoic acid;
2-[1-Carboxy-2-(2-p-tolyl-thiazol-4-yl)-ethylamino]-4-methyl-pentanoic acid;
2-[1-Carboxy-2-(5-phenyl-isoxazol-3-yl)-ethylamino]-4-methyl-pentanoic acid;
2-(2-Mercapto-3-phenyl-propionylamino)-4-methyl-pentanoic acid;
2-[1-Carboxy-3-(4'-chloro-biphenyl-4-sulfonylamino)-propylamino]-4-methyl-pentanoic acid;
2-[1-Carboxy-3-(3-methoxy-benzoylamino)-propylamino]-4-methyl-pentanoic acid;
2-[1-Carboxy-3-(3-chloro-benzoylamino)-propylamino]-4-methyl-pentanoic acid;
2-[2-(4-Benzyloxy-phenyl)-1-carboxy-ethylamino]-4-methyl-pentanoic acid;
2-[1-Carboxy-2-(4-cyclohexylmethoxy-phenyl)-ethylamino]-4-methyl-pentanoic acid;
2-{1-Carboxy-2-[4-(3,5-dichloro-benzyloxy)-phenyl]-ethylamino}-4-methyl-pentanoic acid;
2-{1-Carboxy-2-[4-(3,5-dimethyl-benzyloxy)-phenyl]-ethylamino}-4-methyl-pentanoic acid;
2-{1-Carboxy-2-[3-(3,4-dichloro-benzyl)-2-oxo-2,3-dihydro-imidazol-1-yl]-ethylamino}-4-methyl-pentanoic acid;
2-[2-(Benzothiazol-2-ylcarbamoyl)-1-carboxy-ethylamino]-4-methyl-pentanoic acid;
2-(1-Carboxy-3-{4-[(4-chloro-phenyl)-phenyl-methyl]-piperazin-1-yl}-3-oxo-propylamino)-4-methyl-pentanoic acid;
2-{2-[3-(3,5-Dichloro-benzyl)-3H-imidazol-4-yl]-1-methoxycarbonyl-ethylamino}-4-methyl-pentanoic acid;
2-({1-Carboxy-2-[3-(3,5-dichloro-benzyl)-3H-imidazol-4-yl]-ethyl}-formyl-amino)-4-methyl-pentanoic acid;
2-{2-[3-(3,5-Dichloro-benzyl)-3H-imidazol-4-yl]-1-methoxycarbonyl-ethylamino}-4-methyl-pentanoic acid benzyl ester;
2-{1-Benzyloxycarbonyl-2-[3-(3,5-dichloro-benzyl)-3H-imidazol-4-yl]-ethylamino}-4-methyl-pentanoic acid;
2-{1-Butoxycarbonyl-2-[3-(3,5-dichloro-benzyl)-3H-imidazol-4-yl]-ethylamino}-4-methyl-pentanoic acid;
2-{1-Carboxy-2-[3-(3,5-dichloro-benzyl)-2-oxo-2,3-dihydro-imidazol-1-yl]-ethylamino}-4-methyl-pentanoic acid;
2-{1-Carboxy-2-[3-(3,5-difluoro-benzyl)-2-oxo-2,3-dihydro-imidazol-1-yl]-ethylamino}-4-methyl-pentanoic acid;
2-{1-Carboxy-2-[2-oxo-3-(1-phenyl-ethyl)-2,3-dihydro-imidazol-1-yl]-ethylamino}-4-methyl-pentanoic acid;
2-[1-Carboxy-2-(3-chloro-benzoylamino)-ethylamino]-4-methyl-pentanoic acid;
2-[1-Carboxy-2-(3,4-dichloro-benzoylamino)-ethylamino]-4-methyl-pentanoic acid;
2-[2-(3-Hydroxy-phenyl)-1-methoxycarbonyl-ethylamino]-4-methyl-pentanoic acid benzyl ester;
2-[1-Carboxy-2-(2-phenyl-oxazol-4-yl)-ethylamino]-4-methyl-pentanoic acid;
2-{1-Carboxy-2-[2-(3,5-dichloro-phenyl)-oxazol-4-yl]-ethylamino}-4-methyl-pentanoic acid;
2-{1-Carboxy-2-[2-(3,5-dichloro-phenyl)-thiazol-4-yl]-ethylamino}-4-methyl-pentanoic acid;
2-{1-Carboxy-2-[1-(3,5-dichloro-benzyl)-1H-pyrazol-3-yl]-ethylamino}-4-methyl-pentanoic acid;
2-{1-Cyclopentyloxycarbonyl-2-[3-(3,5-dichloro-benzyl)-3H-imidazol-4-yl]-ethylamino}-4-methyl-pentanoic acid;
2-{1-Carboxy-2-[3-(3,5-difluoro-benzyl)-2-oxo-imidazolidin-1-yl]-ethylamino}-4-methyl-pentanoic acid;
2-[2-(3-Benzyl-2-oxo-2,3-dihydro-imidazol-1-yl)-1-carboxy-ethylamino]-4-methyl-pentanoic acid;
2-[1-Carboxy-2-(4-phenethyloxy-phenyl)-ethylamino]-4-methyl-pentanoic acid;
2-[2-(4-tert-Butoxy-phenyl)-1-carboxy-ethylamino]-4-methyl-pentanoic acid;
2-{1-Carboxy-2-[4-(pyridin-4-ylmethoxy)-phenyl]-ethylamino}-4-methyl-pentanoic acid;
2-[2-(4-Allyloxy-phenyl)-1-carboxy-ethylamino]-4-methyl-pentanoic acid;
2-{1-Carboxy-2-[4-(pyridin-3-ylmethoxy)-phenyl]-ethylamino}-4-methyl-pentanoic acid;
2-[1-Carboxy-2-(4'-methyl-biphenyl-3-yl)-ethylamino]-4-methyl-pentanoic acid;
2-[1-Carboxy-2-(3-methoxy-benzoylamino)-ethylamino]-4-methyl-pentanoic acid;
2-{1-Carboxy-2-[(naphthalene-1-carbonyl)-amino]-ethylamino}-4-methyl-pentanoic acid;
2-[1-Carboxy-2-(6-chloro-benzothiazol-2-ylcarbamoyl)-ethylamino]-4-methyl-pentanoic acid;
2-[1-Carboxy-2-(5,6-dimethyl-benzothiazol-2-ylcarbamoyl)-ethylamino]-4-methyl-pentanoic acid;
2-[1-Carboxy-2-(4-chloro-benzothiazol-2-ylcarbamoyl)-ethylamino]-4-methyl-pentanoic acid;
2-{1-Carboxy-2-[3-(2-cyclohexyl-ethyl)-2-oxo-2,3-dihydro-imidazol-1-yl]-ethylamino}-4-methyl-pentanoic acid;
2-{1-Carboxy-2-[2-oxo-3-(1-phenyl-ethyl)-2,3-dihydro-imidazol-1-yl]-ethylamino}-4-methyl-pentanoic acid;
2-[1-Carboxy-2-(5,6-dichloro-benzothiazol-2-ylcarbamoyl)-ethylamino]-4-methyl-pentanoic acid;
2-[1-Carboxy-2-(3-cyclopropylmethyl-2-oxo-2,3-dihydro-imidazol-1-yl)-ethylamino]-4-methyl-pentanoic acid;
2-[1-Carboxy-2-(3',5'-dichloro-biphenyl-3-yl)-ethylamino]-4-methyl-pentanoic acid;
2-[1-Carboxy-2-(3-thiophen-3-yl-phenyl)-ethylamino]-4-methyl-pentanoic acid;
2-[1-Carboxy-2-(3',5'-dimethoxy-biphenyl-3-yl)-ethylamino]-4-methyl-pentanoic acid;
3-[2-(1-Benzyloxycarbonyl-3-methyl-butylamino)-2-methoxycarbonyyl-ethyl]-pyrazole-1-carboxylic acid tert-butyl ester;
2-{2-[3-(3,5-Dichloro-benzyl)-3H-imidazol-4-yl]-1-methoxycarbonyl-ethylamino}-4-methyl-pentanoic acid methyl ester;
2-[1-Carboxy-2-(3-cyclohexyl-2-oxo-2,3-dihydro-imidazol-1-yl)-ethylamino]-4-methyl-pentanoic acid;
2-[1-Carboxy-2-(6-methoxy-benzothiazol-2-ylcarbamoyl)-ethylamino]-4-methyl-pentanoic acid;
2-[1-Carboxy-2-(6-ethoxy-benzothiazol-2-ylcarbamoyl)-ethylamino]-4-methyl-pentanoic acid;
2-[1-Carboxy-2-(6-fluoro-benzothiazol-2-ylcarbamoyl)-ethylamino]-4-methyl-pentanoic acid;
2-[2-(6-Bromo-benzothiazol-2-ylcarbamoyl)-1-carboxy-ethylamino]-4-methyl-pentanoic acid;
2-{1-Carboxy-2-[3-(3,5-difluoro-phenyl)-2-oxo-2,3-dihydro-imidazol-1-yl]-ethylamino}-4-methyl-pentanoic acid;
2-{1-Carboxy-2-[(naphthalene-2-carbonyl)-amino]-ethylamino}-4-methyl-pentanoic acid;
2-[1-Carboxy-2-(naphthalene-2-sulfonylamino)-ethylamino]-4-methyl-pentanoic acid;
2-{1-Carboxy-2-[2-(3,5-dichloro-benzyl)-2H-pyrazol-3-yl]-ethylamino}-4-methyl-pentanoic acid;

2-[1-Carboxy-2-(3-naphthalen-1-yl-phenyl)-ethylamino]-4-methyl-pentanoic acid;
2-{1-Carboxy-2-[3-(3,5-dichloro-benzyl)-3H-imidazol-4-yl]-ethylamino}-4-methyl-pentanoic acid;
2-{1-Carboxy-2-[3-(3,5-difluoro-benzyloxy)-phenyl]-ethylamino}-4-methyl-pentanoic acid;
2-[2-(3-Allyloxy-phenyl)-1-carboxy-ethylamino]-4-methyl-pentanoic acid;
2-{1-Carboxy-2-[3-(3,5-difluoro-phenyl)-2-oxo-imidazolidin-1-yl]-ethylamino}-4-methyl-pentanoic acid;
2-{1-Carboxy-2-[(5-chloro-1H-indole-2-carbonyl)-amino]-ethylamino}-4-methyl-pentanoic acid;
2-{1-Carboxy-2-[3-(3,5-dichloro-benzyl)-2-oxo-oxazolidin-4-yl]-ethylamino}-4-methyl-pentanoic acid;
2-[1-Carboxy-2-(4-thiophen-3-yl-phenyl)-ethylamino]-4-methyl-pentanoic acid;
2-[1-Carboxy-2-(3',5'-dichloro-biphenyl-4-yl)-ethylamino]-4-methyl-pentanoic acid;
2-[1-Carboxy-2-(4'-methyl-biphenyl-4-yl)-ethylamino]-4-methyl-pentanoic acid;
2-{1-Carboxy-2-[3-(4-iodo-benzyl)-3H-imidazol-4-yl]-ethylamino}-4-methyl-pentanoic acid;
2-{1-Carboxy-2-[3-(3,5-difluoro-benzyl)-3H-imidazol-4-yl]-ethylamino}-4-methyl-pentanoic acid;
2-(1-Carboxy-2-{3-[2-(4-fluoro-phenyl)-ethyl]-2-oxo-2,3-dihydro-imidazol-1-yl}-ethylamino)-4-methyl-pentanoic acid;
2-[1-Carboxy-2-(3-cyclohexylmethyl-2-oxo-2,3-dihydro-imidazol-1-yl)-ethylamino]-4-methyl-pentanoic acid;
2-{1-Carboxy-2-[3-(3,5-dichloro-benzyl)-3H-imidazol-4-yl]-ethylamino}-4-methyl-pentanoic acid tert-butyl ester;
2-{1-Carboxy-2-[3-(3,5-dichloro-benzyl)-2-oxo-oxazolidin-4-yl]-ethylamino}-4-methyl-pentanoic acid;
2-[1-Carboxy-2-(5-p-tolyl-furan-2-yl)-ethylamino]-4-methyl-pentanoic acid;
2-(1-Carboxy-2-{3-[2-(3-fluoro-phenyl)-ethyl]-2-oxo-2,3-dihydro-imidazol-1-yl}-ethylamino)-4-methyl-pentanoic acid;
2-[1-Carboxy-2-(5-phenyl-furan-2-yl)-ethylamino]-4-methyl-pentanoic acid;
2-{1-Carboxy-2-[5-(3,5-dichloro-phenyl)-furan-2-yl]-ethylamino}-4-methyl-pentanoic acid;
2-{1-Carboxy-2-[5-(3,5-dimethyl-phenyl)-furan-2-yl]-ethylamino}-4-methyl-pentanoic acid;
2-{1-Carboxy-2-[5-(3,5-difluoro-phenyl)-furan-2-yl]-ethylamino}-4-methyl-pentanoic acid;
2-[1-Carboxy-2-(5-thiophen-3-yl-furan-2-yl)-ethylamino]-4-methyl-pentanoic acid;
2-[1-Carboxy-2-(6-methyl-benzothiazol-2-ylcarbamoyl)-ethylamino]-4-methyl-pentanoic acid;
2-[1-Carboxy-2-(4-hydroxy-phenyl)-ethylamino]-4-methyl-pentanoic acid;
2-{1-Carboxy-2-[3-(3,5-dichloro-benzyloxy)-phenyl]-ethylamino}-4-methyl-pentanoic acid;
2-{1-Carboxy-2-[3-(pyridin-4-ylmethoxy)-phenyl]-ethylamino}-4-methyl-pentanoic acid;
2-{1-Carboxy-2-[3-(3,5-dimethyl-benzyloxy)-phenyl]-ethylamino}-4-methyl-pentanoic acid;
2-{1-Carboxy-2-[3-(4-chloro-benzyloxy)-phenyl]-ethylamino}-4-methyl-pentanoic acid;
2-{2-[3-(2,4-Bis-trifluoromethyl-benzyloxy)-phenyl]-1-carboxy-ethylamino}-4-methyl-pentanoic acid;
2-[1-Carboxy-2-(1-phenyl-1H-pyrazol-3-yl)-ethylamino]-4-methyl-pentanoic acid;
2-{1-Carboxy-2-[3-(3-chloro-benzyl)-2-oxo-2,3-dihydro-imidazol-1-yl]-ethylamino}-4-methyl-pentanoic acid;
2-{1-Carboxy-2-[4-(3,5-dichloro-benzyl)-phenyl]-ethylamino}-4-methyl-pentanoic acid;
2-[2-(4-Benzyl-phenyl)-1-carboxy-ethylamino]-4-methyl-pentanoic acid;
2-[1-Carboxy-2-(4-phenyl-thiazol-2-ylcarbamoyl)-ethylamino]-4-methyl-pentanoic acid;
2-{1-Carboxy-2-[5-(4-methoxy-phenyl)-furan-2-yl]-ethylamino}-4-methyl-pentanoic acid;
2-[2-(5-Benzo[1,3]dioxol-5-yl-furan-2-yl)-1-carboxy-ethylamino]-4-methyl-pentanoic acid;
2-[1-Carboxy-2-(5-naphthalen-1-yl-furan-2-yl)-ethylamino]-4-methyl-pentanoic acid;
2-{1-Carboxy-2-[5-(4-chloro-phenyl)-furan-2-yl]-ethylamino}-4-methyl-pentanoic acid;
2-{1-Carboxy-2-[5-(4-trifluoromethyl-phenyl)-furan-2-yl]-ethylamino}-4-methyl-pentanoic acid;
2-[1-Carboxy-2-(3-isobutoxy-phenyl)-ethylamino]-4-methyl-pentanoic acid;
2-{1-Carboxy-2-[3-(3-chloro-benzyloxy)-phenyl]-ethylamino}-4-methyl-pentanoic acid;
2-{1-Carboxy-2-[3-(2-chloro-benzyloxy)-phenyl]-ethylamino}-4-methyl-pentanoic acid;
2-[3-(4-Benzyloxy-phenyl)-1-carboxy-propylamino]-4-methyl-pentanoic acid;
2-{1-Carboxy-2-[5-(3-chloro-phenyl)-furan-2-yl]-ethylamino}-4-methyl-pentanoic acid;
2-{1-Carboxy-2-[3-(3-fluoro-benzyl)-2-oxo-2,3-dihydro-imidazol-1-yl]-ethylamino}-4-methyl-pentanoic acid;
2-{1-Carboxy-2-[3-(3,4-difluoro-benzyl)-2-oxo-2,3-dihydro-imidazol-1-yl]-ethylamino}-4-methyl-pentanoic acid;
2-[1-Carboxy-3-(6-fluoro-benzothiazol-2-ylcarbamoyl)-propylamino]-4-methyl-pentanoic acid;
2-{1-Carboxy-2-[3-(2,5-difluoro-benzyl)-2-oxo-2,3-dihydro-imidazol-1-yl]-ethylamino}-4-methyl-pentanoic acid;
2-{1-Carboxy-2-[4-(3,5-difluoro-benzoylamino)-phenyl]-ethylamino}-4-methyl-pentanoic acid;
2-[1-Carboxy-2-(4'-fluoro-biphenyl-4-yl)-ethylamino]-4-methyl-pentanoic acid;
2-[2-(4-Benzo[1,3]dioxol-5-yl-phenyl)-1-carboxy-ethylamino]-4-methyl-pentanoic acid;
2-[2-(4-Benzo[b]thiophen-3-yl-phenyl)-1-carboxy-ethylamino]-4-methyl-pentanoic acid;
2-[2-(3-Benzyl-phenyl)-1-carboxy-ethylamino]-4-methyl-pentanoic acid;
2-[1-Carboxy-2-(4'-trifluoromethyl-biphenyl-4-yl)-ethylamino]-4-methyl-pentanoic acid;
2-(1-Carboxy-2-{3-[2-(3-chloro-phenyl)-ethyl]-2-oxo-2,3-dihydro-imidazol-1-yl}-ethylamino)-4-methylpentanoic acid;
2-{2-[3-(4-Bromo-benzyl)-3H-imidazol-4-yl]-1-carboxy-ethylamino}-4-methyl-pentanoic acid;
2-[2-(4-Benzenesulfonylamino-phenyl)-1-carboxy-ethylamino]-4-methyl-pentanoic acid;
2-{1-Carboxy-2-[3-(3-chloro-benzyl)-phenyl]-ethylamino}-4-methyl-pentanoic acid;
2-{1-Carboxy-2-[3-(3,5-dichloro-benzyl)-phenyl]-ethylamino}-4-methyl-pentanoic acid;
2-{1-Carboxy-2-[3-(5-chloro-benzo[b]thiophen-3-ylmethoxy)-phenyl]-ethylamino}-4-methyl-pentanoic acid;
2-[1-Carboxy-2-(4-pyridin-2-yl-phenyl)-ethylamino]-4-methyl-pentanoic acid;
2-[1-Carboxy-2-(4-pyridin-3-yl-phenyl)-ethylamino]-4-methyl-pentanoic acid;

2-[1-Carboxy-2-(4-pyridin-4-yl-phenyl)-ethylamino]-4-methyl-pentanoic acid;
2-(1-Carboxy-ethylamino)-3-[3-(3,5-dichloro-benzyl)-3H-imidazol-4-yl]-propionic acid;
2-{1-Carboxy-2-[3-(3,5-dichloro-benzyl)-3H-imidazol-4-yl]-ethylamino}-4-phenyl-butyric acid;
2-(1-Carboxy-2-{3-[2-(2-fluoro-phenyl)-ethyl]-2-oxo-2,3-dihydro-imidazol-1-yl}-ethylamino)-4-methyl-pentanoic acid;
2-[1-Carboxy-2-(4-pyrrol-1-yl-phenyl)-ethylamino]-4-methyl-pentanoic acid;
2-(1-Carboxy-3-methyl-butylamino)-5-(3,5-dichloro-phenyl)-pent-4-ynoic acid;
2-{1-Carboxy-2-[4-(3,5-difluoro-phenoxy)-phenyl]-ethylamino}-4-methyl-pentanoic acid;
2-[1-Carboxy-2-(3',5'-dichloro-biphenyl-2-yl)-ethylamino]-4-methyl-pentanoic acid;
4-[2-Carboxy-2-(1-carboxy-3-methyl-butylamino)-ethyl]-benzoic acid tert-butyl ester;
2-(1-Carboxy-3-methyl-butylamino)-5-(3,5-dichloro-phenyl)-pent-4-enoic acid;
2-{1-Carboxy-2-[3-(3,5-difluoro-benzyl)-2,5-dioxo-imidazolidin-1-yl]-ethylamino}-4-methyl-pentanoic acid;
2-{1-Carboxy-2-[3-(3,5-dichloro-benzyl)-2,5-dioxo-imidazolidin-1-yl]-ethylamino}-4-methyl-pentanoic acid;
2-{2-[3-(2,4-Bis-trifluoromethyl-benzyl)-2,5-dioxo-imidazolidin-1-yl]-1-carboxy-ethylamino}-4-methyl-pentanoic acid;
2-{1-Carboxy-2-[4-(5-methyl-pyridin-2-yl)-phenyl]-ethylamino}-4-methyl-pentanoic acid;
2-{1-Carboxy-2-[4-(4-methyl-pyridin-2-yl)-phenyl]-ethylamino}-4-methyl-pentanoic acid;
2-{1-Carboxy-2-[4-(3-chloro-4-ethoxy-pyridin-2-yl)-phenyl]-ethylamino}-4-methyl-pentanoic acid;
2-[1-Carboxy-2-(4-quinolin-3-yl-phenyl)-ethylamino]-4-methyl-pentanoic acid;
2-{1-Carboxy-2-[4-(3,5-difluoro-benzylcarbamoyl)-phenyl]-ethylamino}-4-methyl-pentanoic acid;
2-{1-Carboxy-2-[4-(3,5-dichloro-phenylcarbamoyl)-phenyl]-ethylamino}-4-methyl-pentanoic acid;
2-[1-Carboxy-2-(4-phenylcarbamoyl-phenyl)-ethylamino]-4-methyl-pentanoic acid;
2-[1-Carboxy-2-(4-cyclohexylcarbamoyl-phenyl)-ethylamino]-4-methyl-pentanoic acid;
2-[1-Carboxy-2-(2-cyano-phenyl)-ethylamino]-4-methyl-pentanoic acid;
2-[1-Carboxy-2-(4-phenoxy-phenyl)-ethylamino]-4-methyl-pentanoic acid;
2-{1-Carboxy-2-[4-(5-chloro-benzo[b]thiophen-3-ylmethoxy)-phenyl]-ethylamino}-4-methyl-pentanoic acid;
2-{1-Carboxy-2-[5-(3,4-dichloro-phenyl)-isoxazol-3-yl]-ethylamino}-4-methyl-pentanoic acid;
2-{1-Carboxy-2-[4-(3,5-dichloro-phenoxy)-phenyl]-ethylamino}-4-methyl-pentanoic acid;
2-{1-Carboxy-2-[2-(3,5-dichloro-phenoxy)-phenyl]-ethylamino}-4-methyl-pentanoic acid;
2-{1-Carboxy-2-[2-(3-chloro-benzyloxy)-phenyl]-ethylamino}-4-methyl-pentanoic acid;
2-{1-Carboxy-2-[4-(4-fluoro-phenoxy)-phenyl]-ethylamino}-4-methyl-pentanoic acid;
2-[1-Carboxy-2-(1-p-tolyl-1H-pyrazol-3-yl)-ethylamino]-4-methyl-pentanoic acid;
2-{1-Carboxy-2-[4-(cyclopentanecarbonyl-amino)-phenyl]-ethylamino}-4-methyl-pentanoic acid;
2-{1-Carboxy-2-[4-(2,2-dimethyl-propionylamino)-phenyl]-ethylamino}-4-methyl-pentanoic acid;
2-{1-Carboxy-2-[2-(5-chloro-benzo[b]thiophen-3-ylmethoxy)-phenyl]-ethylamino}-4-methyl-pentanoic acid;
2-{1-Carboxy-2-[5-(4-chloro-phenyl)-isoxazol-3-yl]-ethylamino}-4-methyl-pentanoic acid;
2-{1-Carboxy-2-[5-(2-chloro-phenyl)-isoxazol-3-yl]-ethylamino}-4-methyl-pentanoic acid;
2-{1-Carboxy-2-[4-(5-fluoro-2,3-dihydro-benzofuran-3-ylmethoxy)-phenyl]-ethylamino}-4-methyl-pentanoic acid;
2-{2-[4-(Benzo[b]thiophen-3-ylmethoxy)-phenyl]-1-carboxy-ethylamino}-4-methyl-pentanoic acid;
5-[2-Carboxy-2-(1-carboxy-3-methyl-butylamino)-ethyl]-1-(3,5-dichloro-benzyl)-1H-pyrrole-2-carboxylic acid;
2-{1-Carboxy-2-[1-(2-cyclohexyl-ethyl)-5-(2,2,2-trifluoro-acetyl)-1H-pyrrol-2-yl]-ethylamino}-4-methyl-pentanoic acid;
2-[1-Carboxy-2-(4-nitro-phenyl)-ethylamino]-4-methyl-pentanoic acid;
2-{1-Carboxy-2-[4-(2-methoxy-benzoylamino)-phenyl]-ethylamino}-4-methyl-pentanoic acid;
2-[1-Carboxy-2-(2-trifluoromethyl-phenyl)-ethylamino]-4-methyl-pentanoic acid;
2-(2-{4-[Bis-(3,5-difluoro-benzyl)-amino]-phenyl}-1-carboxy-ethylamino)-4-methyl-pentanoic acid;
2-[1-Carboxy-2-(2-p-tolyl-thiazol-4-yl)-ethylamino]-4-phenyl-butyric acid;
2-[1-Carboxy-2-(4-dimethylcarbamoyl-phenyl)-ethylamino]-4-methyl-pentanoic acid;
2-{1-Carboxy-2-[4-(3,5-dimethyl-phenylcarbamoyl)-phenyl]-ethylamino}-4-methyl-pentanoic acid;
2-[2-(4-tert-Butylcarbainoyl-phenyl)-1-carboxy-ethylamino]-4-methyl-pentanoic acid;
4-Methyl-2-{[pyrimidin-2-yl-(2-p-tolyl-thiazol-4-ylmethyl)-amino]-methyl}-pentanoic acid;
2-{1-Carboxy-2-[1-(3,5-dichloro-benzyl)-1H-pyrrol-2-yl]-ethylamino}-4-methyl-pentanoic acid;
2-[1-Carboxy-2-(4-isopropylcarbamoyl-phenyl)-ethylamino]-4-methyl-pentanoic acid;
2-{1-Carboxy-2-[4-(morpholine-4-carbonyl)-phenyl]-ethylamino}-4-methyl-pentanoic acid;
2-{1-Carboxy-2-[4-(3,4-dihydro-1H-isoquinoline-2-carbonyl)-phenyl]-ethylamino}-4-methyl-pentanoic acid; or a pharmaceutically acceptable salt, prodrug, or ester thereof.

36. A compound of the formula:

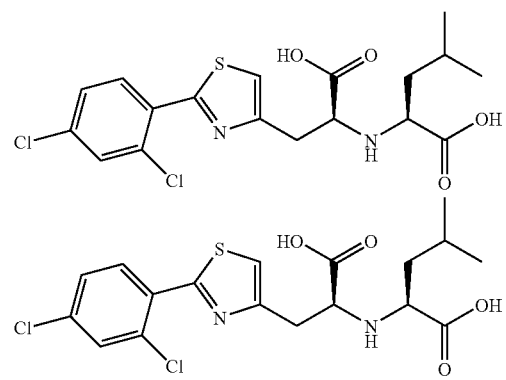

669
-continued
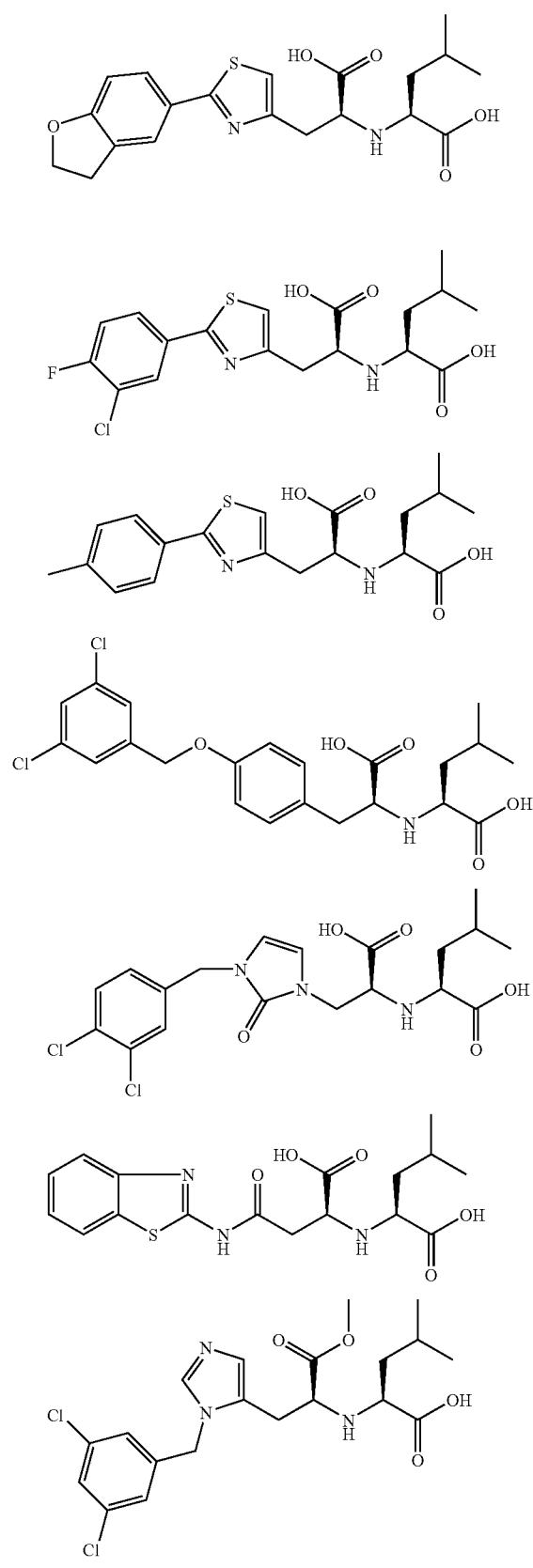
670
-continued
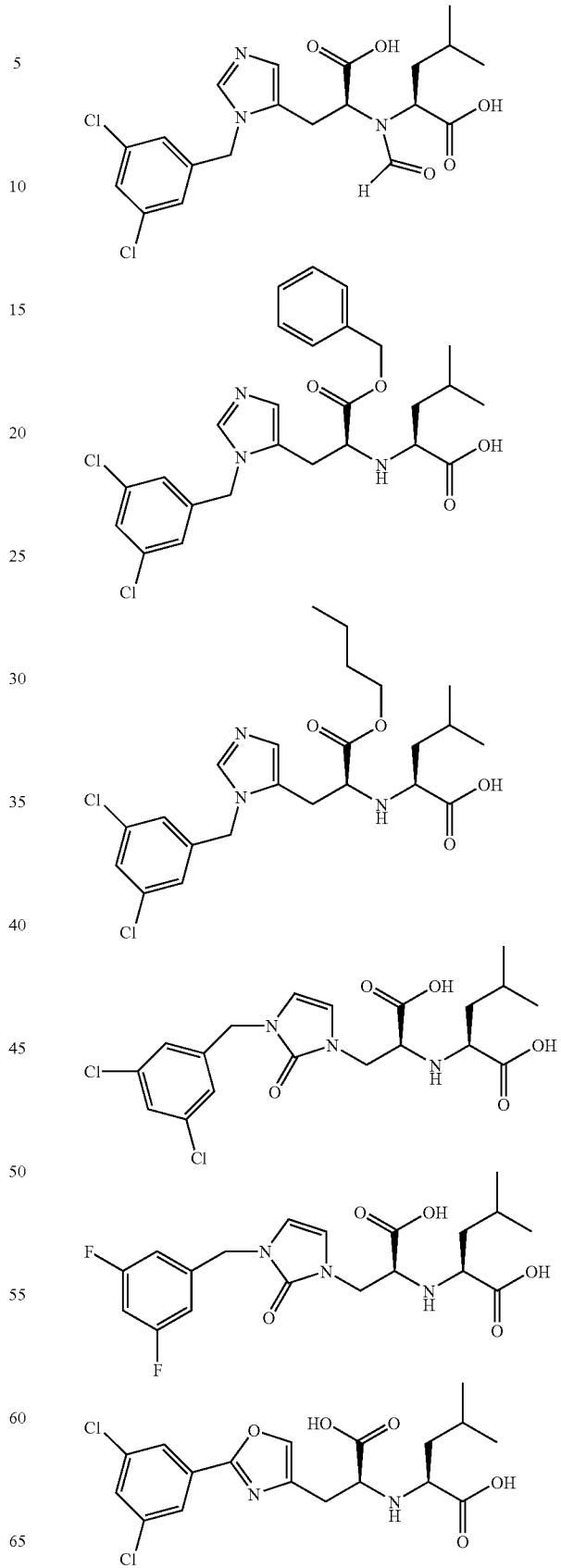

-continued
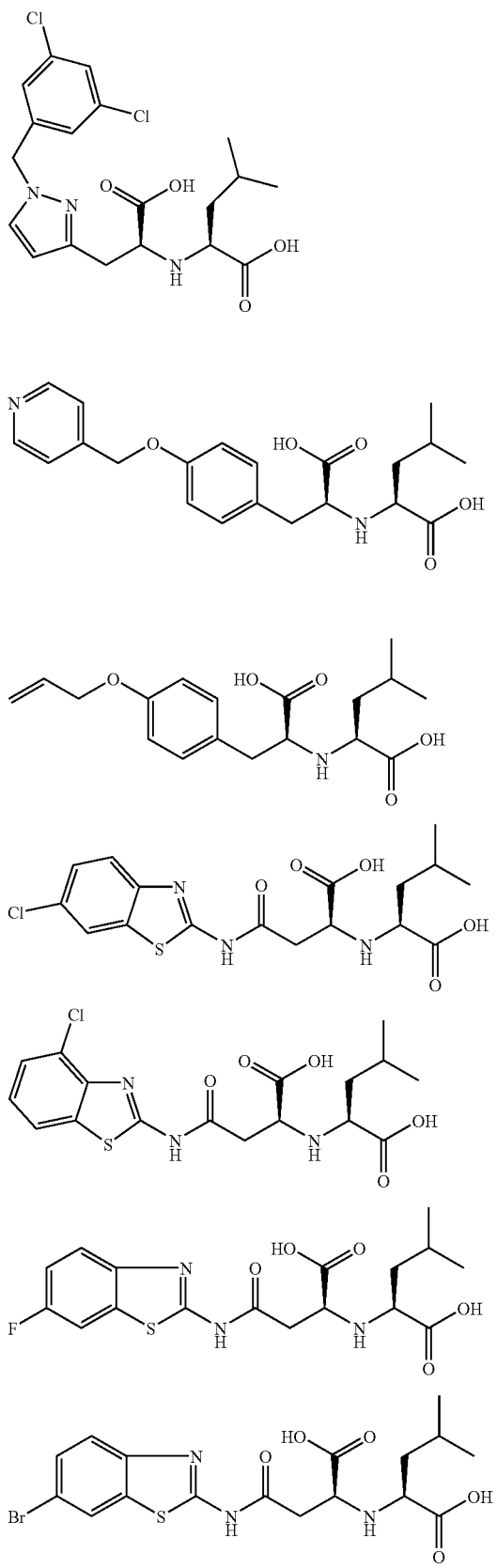
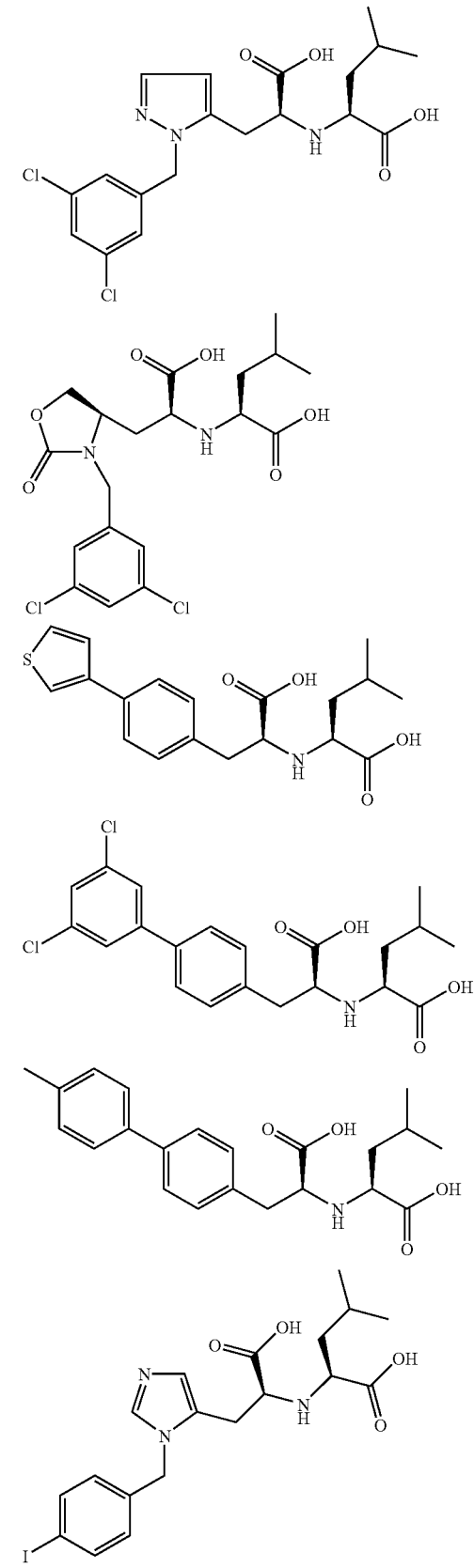

-continued
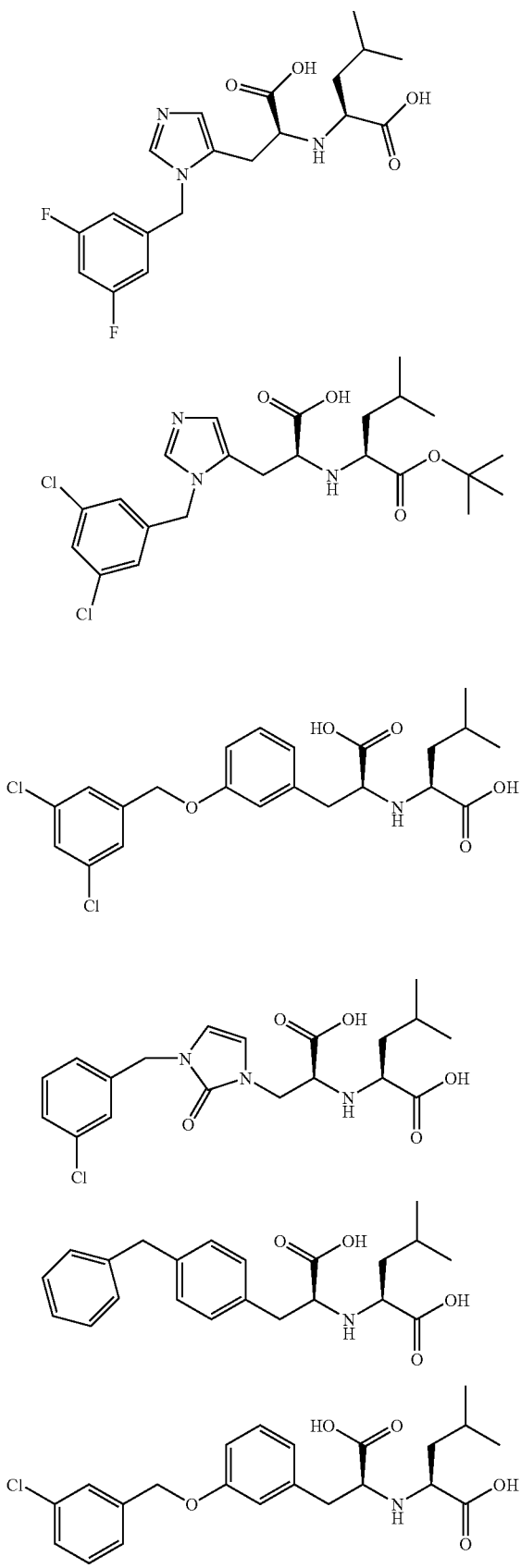
-continued
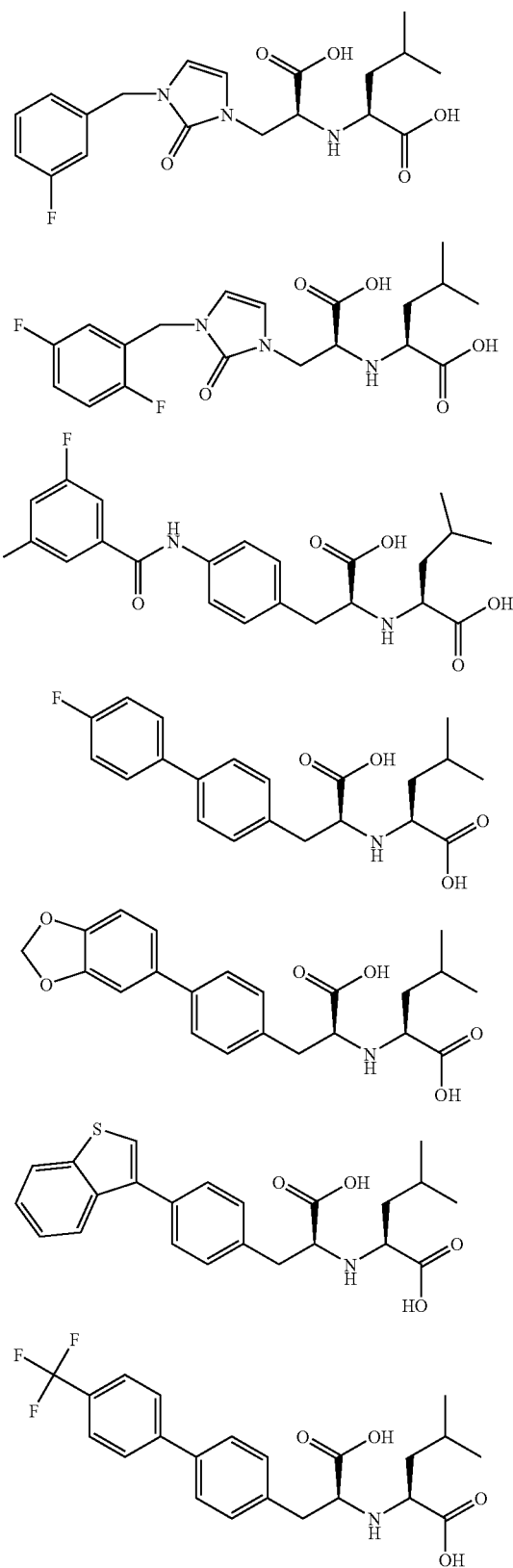

675
-continued
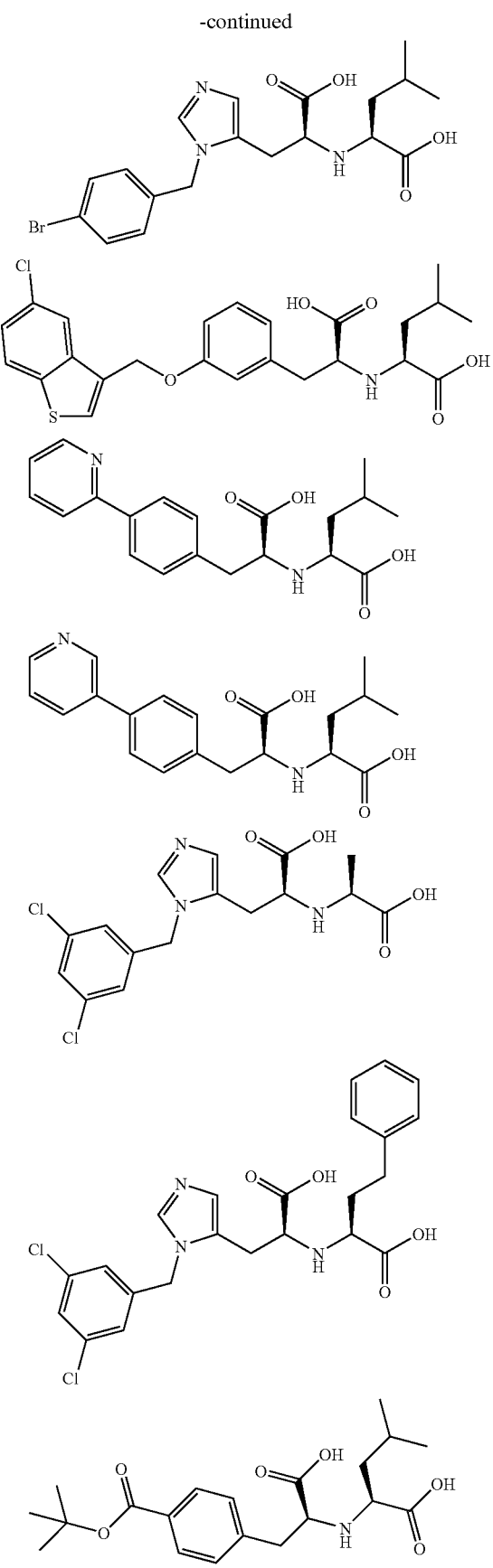
676
-continued
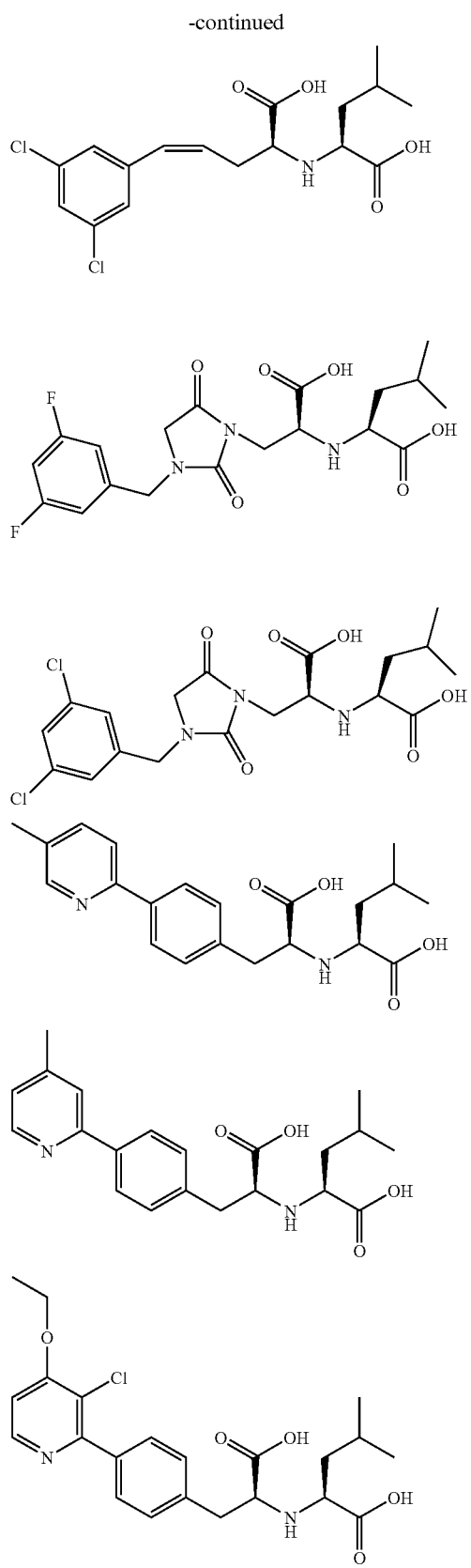

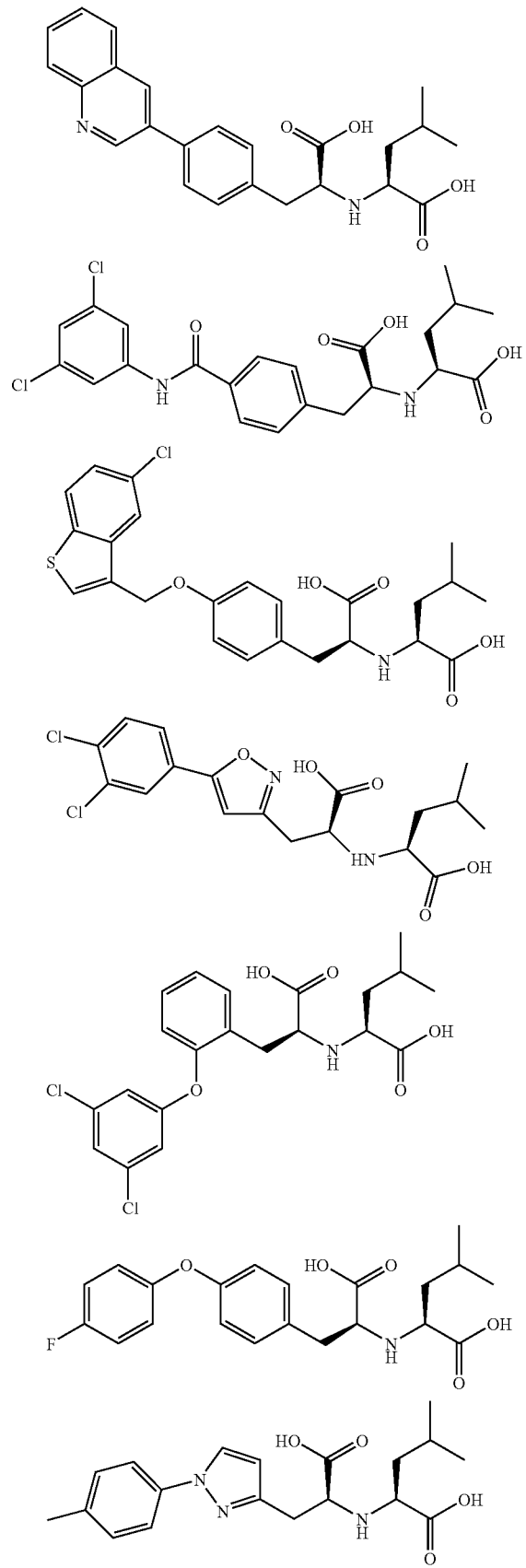
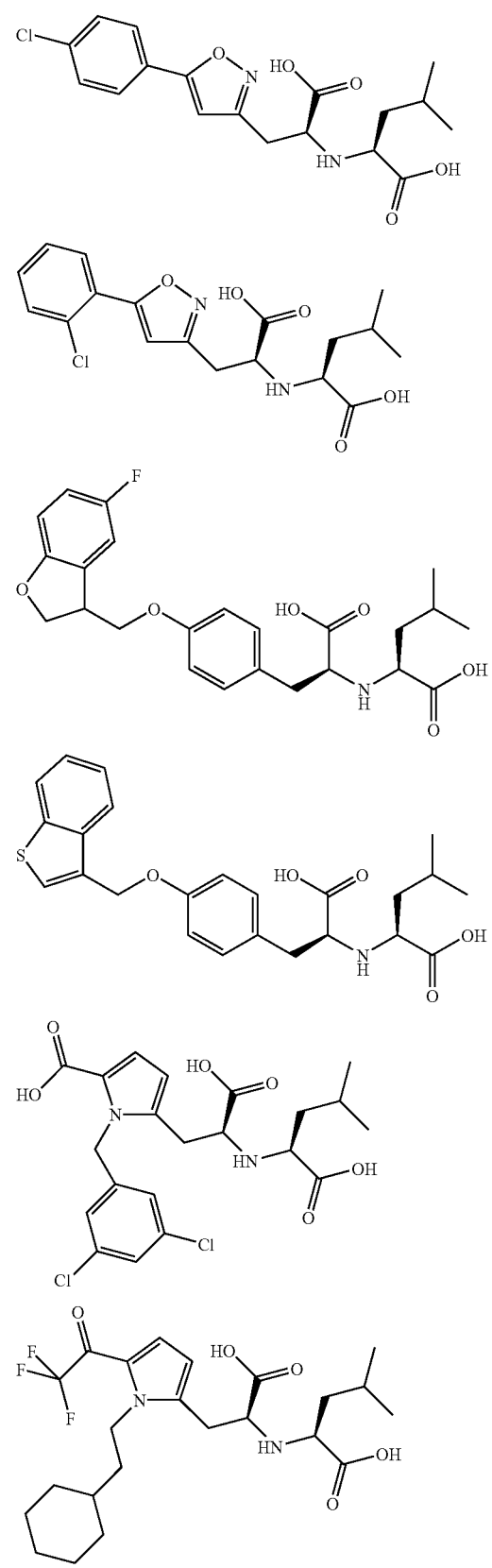

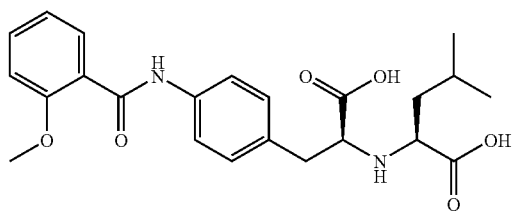

or a pharmaceutically acceptable salt, prodrug, or ester thereof.

37. A pharmaceutical composition comprising a compound of claim 35 or 36 and a pharmaceutically acceptable carrier.

38. A method for treating an ACE-2 associated state in a subject, comprising modulating ACE-2 in said subject by administering an effective amount of an ACE-2 inhibitor, such that said ACE-2 associated state is treated, wherein said ACE-2 inhibitor is a compound of claim 35 or 36, and wherein the ACE-2 associated state is a body weight disorder, increased appetite, decreased muscle mass, increased body weight, diabetes, or a disorder associated with aberrant lipid metabolism.

39. The method of claim 38, wherein said subject is a human.

40. A method for modulating ACE-2, comprising contacting ACE-2 with an ACE-2 inhibitor, such that ACE-2 is modulated, wherein said inhibitor is a compound of claim 35 or 36.

* * * * *

SEQUENCE LISTING

<160> NUMBER OF SEQ ID NOS: 34

<210> SEQ ID NO 1
<211> LENGTH: 3396
<212> TYPE: DNA
<213> ORGANISM: Homo sapiens
<220> FEATURE:
<221> NAME/KEY: CDS
<222> LOCATION: (82)..(2496)

<400> SEQUENCE: 1

```
gaattcggct tccatcctaa tacgactcac tatagggctc gagcggccgc ccggggcagg         60
tatcttggct cacagggac g atg tca agc tct tcc tgg ctc ctt ctc agc          111
                      Met Ser Ser Ser Ser Trp Leu Leu Leu Ser
                       1               5                  10 ctt gtt gct gta act gct gct cag tcc acc att gag gaa cag gcc aag         159
Leu Val Ala Val Thr Ala Ala Gln Ser Thr Ile Glu Glu Gln Ala Lys
             15                  20                  25 aca ttt ttg gac aag ttt aac cac gaa gcc gaa gac ctg ttc tat caa         207
Thr Phe Leu Asp Lys Phe Asn His Glu Ala Glu Asp Leu Phe Tyr Gln
         30                  35                  40 agt tca ctt gct tct tgg aat tat aac acc aat att act gaa gag aat         255
Ser Ser Leu Ala Ser Trp Asn Tyr Asn Thr Asn Ile Thr Glu Glu Asn
     45                  50                  55 gtc caa aac atg aat aat gct ggg gac aaa tgg tct gcc ttt tta aag         303
Val Gln Asn Met Asn Asn Ala Gly Asp Lys Trp Ser Ala Phe Leu Lys
 60                  65                  70 gaa cag tcc aca ctt gcc caa atg tat cca cta caa gaa att cag aat         351
Glu Gln Ser Thr Leu Ala Gln Met Tyr Pro Leu Gln Glu Ile Gln Asn
 75                  80                  85                  90 ctc aca gtc aag ctt cag ctg cag gct ctt cag caa aat ggg tct tca         399
Leu Thr Val Lys Leu Gln Leu Gln Ala Leu Gln Gln Asn Gly Ser Ser
                 95                 100                 105 gtg ctg tca gaa gac aag agc aaa cgg ttg aac aca att cta aat aca         447
Val Leu Ser Glu Asp Lys Ser Lys Arg Leu Asn Thr Ile Leu Asn Thr
            110                 115                 120 atg agc acc atc tac agt act gga aaa gtt tgt aac cca gat aat cca         495
Met Ser Thr Ile Tyr Ser Thr Gly Lys Val Cys Asn Pro Asp Asn Pro
        125                 130                 135 caa gaa tgc tta tta ctt gaa cca ggt tta aat gaa ata atg gca aac         543
Gln Glu Cys Leu Leu Leu Glu Pro Gly Leu Asn Glu Ile Met Ala Asn
    140                 145                 150 agt tta gac tac aat gag agg ctc tgg gct tgg gaa agc tgg aga tct         591
Ser Leu Asp Tyr Asn Glu Arg Leu Trp Ala Trp Glu Ser Trp Arg Ser
155                 160                 165                 170 gag gtc ggc aag cag ctg agg cca tta tat gaa gag tat gtg gtc ttg         639
Glu Val Gly Lys Gln Leu Arg Pro Leu Tyr Glu Glu Tyr Val Val Leu
                175                 180                 185 aaa aat gag atg gca aga gca aat cat tat gag gac tat ggg gat tat         687
Lys Asn Glu Met Ala Arg Ala Asn His Tyr Glu Asp Tyr Gly Asp Tyr
            190                 195                 200 tgg aga gga gac tat gaa gta aat ggg gta gat ggc tat gac tac agc         735
Trp Arg Gly Asp Tyr Glu Val Asn Gly Val Asp Gly Tyr Asp Tyr Ser
        205                 210                 215 cgc ggc cag ttg att gaa gat gtg gaa cat acc ttt gaa gag att aaa         783
Arg Gly Gln Leu Ile Glu Asp Val Glu His Thr Phe Glu Glu Ile Lys
    220                 225                 230 cca tta tat gaa cat ctt cat gcc tat gtg agg gca aag ttg atg aat         831
Pro Leu Tyr Glu His Leu His Ala Tyr Val Arg Ala Lys Leu Met Asn
```

```
                235                 240                 245                 250
gcc tat cct tcc tat atc agt cca att gga tgc ctc cct gct cat ttg      879
Ala Tyr Pro Ser Tyr Ile Ser Pro Ile Gly Cys Leu Pro Ala His Leu
                    255                 260                 265 ctt ggt gat atg tgg ggt aga ttt tgg aca aat ctg tac tct ttg aca      927
Leu Gly Asp Met Trp Gly Arg Phe Trp Thr Asn Leu Tyr Ser Leu Thr
                270                 275                 280 gtt ccc ttt gga cag aaa cca aac ata gat gtt act gat gca atg gtg      975
Val Pro Phe Gly Gln Lys Pro Asn Ile Asp Val Thr Asp Ala Met Val
            285                 290                 295 gac cag gcc tgg gat gca cag aga ata ttc aag gag gcc gag aag ttc     1023
Asp Gln Ala Trp Asp Ala Gln Arg Ile Phe Lys Glu Ala Glu Lys Phe
        300                 305                 310 ttt gta tct gtt ggt ctt cct aat atg act caa gga ttc tgg gaa aat     1071
Phe Val Ser Val Gly Leu Pro Asn Met Thr Gln Gly Phe Trp Glu Asn
315                 320                 325                 330 tcc atg cta acg gac cca gga aat gtt cag aaa gca gtc tgc cat ccc     1119
Ser Met Leu Thr Asp Pro Gly Asn Val Gln Lys Ala Val Cys His Pro
                    335                 340                 345 aca gct tgg gac ctg ggg aag ggc gac ttc agg atc ctt atg tgc aca     1167
Thr Ala Trp Asp Leu Gly Lys Gly Asp Phe Arg Ile Leu Met Cys Thr
                350                 355                 360 aag gtg aca atg gac gac ttc ctg aca gct cat cat gag atg ggg cat     1215
Lys Val Thr Met Asp Asp Phe Leu Thr Ala His His Glu Met Gly His
            365                 370                 375 atc cag tat gat atg gca tat gct gca caa cct ttt ctg cta aga aat     1263
Ile Gln Tyr Asp Met Ala Tyr Ala Ala Gln Pro Phe Leu Leu Arg Asn
        380                 385                 390 gga gct aat gaa gga ttc cat gaa gct gtt ggg gaa atc atg tca ctt     1311
Gly Ala Asn Glu Gly Phe His Glu Ala Val Gly Glu Ile Met Ser Leu
395                 400                 405                 410 tct gca gcc aca cct aag cat tta aaa tcc att ggt ctt ctg tca ccc     1359
Ser Ala Ala Thr Pro Lys His Leu Lys Ser Ile Gly Leu Leu Ser Pro
                    415                 420                 425 gat ttt caa gaa gac aat gaa aca gaa ata aac ttc ctg ctc aaa caa     1407
Asp Phe Gln Glu Asp Asn Glu Thr Glu Ile Asn Phe Leu Leu Lys Gln
                430                 435                 440 gca ctc acg att gtt ggg act ctg cca ttt act tac atg tta gag aag     1455
Ala Leu Thr Ile Val Gly Thr Leu Pro Phe Thr Tyr Met Leu Glu Lys
            445                 450                 455 tgg agg tgg atg gtc ttt aaa ggg gaa att ccc aaa gac cag tgg atg     1503
Trp Arg Trp Met Val Phe Lys Gly Glu Ile Pro Lys Asp Gln Trp Met
        460                 465                 470 aaa aag tgg tgg gag atg aag cga gag ata gtt ggg gtg gtg gaa cct     1551
Lys Lys Trp Trp Glu Met Lys Arg Glu Ile Val Gly Val Val Glu Pro
475                 480                 485                 490 gtg ccc cat gat gaa aca tac tgt gac ccc gca tct ctg ttc cat gtt     1599
Val Pro His Asp Glu Thr Tyr Cys Asp Pro Ala Ser Leu Phe His Val
                    495                 500                 505 tct aat gat tac tca ttc att cga tat tac aca agg acc ctt tac caa     1647
Ser Asn Asp Tyr Ser Phe Ile Arg Tyr Tyr Thr Arg Thr Leu Tyr Gln
                510                 515                 520 ttc cag ttt caa gaa gca ctt tgt caa gca gct aaa cat gaa ggc cct     1695
Phe Gln Phe Gln Glu Ala Leu Cys Gln Ala Ala Lys His Glu Gly Pro
            525                 530                 535 ctg cac aaa tgt gac atc tca aac tct aca gaa gct gga cag aaa ctg     1743
Leu His Lys Cys Asp Ile Ser Asn Ser Thr Glu Ala Gly Gln Lys Leu
        540                 545                 550 ttc aat atg ctg agg ctt gga aaa tca gaa ccc tgg acc cta gca ttg     1791
```

-continued

| | | |
|---|---|---|
| Phe Asn Met Leu Arg Leu Gly Lys Ser Glu Pro Trp Thr Leu Ala Leu<br>555                560                565                570 | | |
| gaa aat gtt gta gga gca aag aac atg aat gta agg cca ctg ctc aac<br>Glu Asn Val Val Gly Ala Lys Asn Met Asn Val Arg Pro Leu Leu Asn<br>                575                580                585 | | 1839 |
| tac ttt gag ccc tta ttt acc tgg ctg aaa gac cag aac aag aat tct<br>Tyr Phe Glu Pro Leu Phe Thr Trp Leu Lys Asp Gln Asn Lys Asn Ser<br>            590                595                600 | | 1887 |
| ttt gtg gga tgg agt acc gac tgg agt cca tat gca gac caa agc atc<br>Phe Val Gly Trp Ser Thr Asp Trp Ser Pro Tyr Ala Asp Gln Ser Ile<br>        605                610                615 | | 1935 |
| aaa gtg agg ata agc cta aaa tca gct ctt gga gat aaa gca tat gaa<br>Lys Val Arg Ile Ser Leu Lys Ser Ala Leu Gly Asp Lys Ala Tyr Glu<br>620                625                630 | | 1983 |
| tgg aac gac aat gaa atg tac ctg ttc cga tca tct gtt gca tat gct<br>Trp Asn Asp Asn Glu Met Tyr Leu Phe Arg Ser Ser Val Ala Tyr Ala<br>635                640                645                650 | | 2031 |
| atg agg cag tac ttt tta aaa gta aaa aat cag atg att ctt ttt ggg<br>Met Arg Gln Tyr Phe Leu Lys Val Lys Asn Gln Met Ile Leu Phe Gly<br>            655                660                665 | | 2079 |
| gag gag gat gtg cga gtg gct aat ttg aaa cca aga atc tcc ttt aat<br>Glu Glu Asp Val Arg Val Ala Asn Leu Lys Pro Arg Ile Ser Phe Asn<br>        670                675                680 | | 2127 |
| ttc ttt gtc act gca cct aaa aat gtg tct gat atc att cct aga act<br>Phe Phe Val Thr Ala Pro Lys Asn Val Ser Asp Ile Ile Pro Arg Thr<br>685                690                695 | | 2175 |
| gaa gtt gaa aag gcc atc agg atg tcc cgg agc cgt atc aat gat gct<br>Glu Val Glu Lys Ala Ile Arg Met Ser Arg Ser Arg Ile Asn Asp Ala<br>700                705                710 | | 2223 |
| ttc cgt ctg aat gac aac agc cta gag ttt ctg ggg ata cag cca aca<br>Phe Arg Leu Asn Asp Asn Ser Leu Glu Phe Leu Gly Ile Gln Pro Thr<br>715                720                725                730 | | 2271 |
| ctt gga cct cct aac cag ccc cct gtt tcc ata tgg ctg att gtt ttt<br>Leu Gly Pro Pro Asn Gln Pro Pro Val Ser Ile Trp Leu Ile Val Phe<br>            735                740                745 | | 2319 |
| gga gtt gtg atg gga gtg ata gtg gtt ggc att gtc atc ctg atc ttc<br>Gly Val Val Met Gly Val Ile Val Val Gly Ile Val Ile Leu Ile Phe<br>        750                755                760 | | 2367 |
| act ggg atc aga gat cgg aag aag aaa aat aaa gca aga agt gga gaa<br>Thr Gly Ile Arg Asp Arg Lys Lys Lys Asn Lys Ala Arg Ser Gly Glu<br>765                770                775 | | 2415 |
| aat cct tat gcc tcc atc gat att agc aaa gga gaa aat aat cca gga<br>Asn Pro Tyr Ala Ser Ile Asp Ile Ser Lys Gly Glu Asn Asn Pro Gly<br>780                785                790 | | 2463 |
| ttc caa aac act gat gat gtt cag acc tcc ttt tagaaaaatc tatgtttttc<br>Phe Gln Asn Thr Asp Asp Val Gln Thr Ser Phe<br>795                800                805 | | 2516 |
| ctcttgaggt gattttgttg tatgtaaatg ttaatttcat ggtatagaaa atataagatg | | 2576 |
| ataaagatat cattaaatgt caaaactatg actctgttca gaaaaaaaat tgtccaaaga | | 2636 |
| caacatggcc aaggagagag catcttcatt gacattgctt tcagtattta tttctgtctc | | 2696 |
| tggatttgac ttctgttctg tttcttaata aggatttgt attagagtat attagggaaa | | 2756 |
| gtgtgtattt ggtctcacag gctgttcagg gataatctaa atgtaaatgt ctgttgaatt | | 2816 |
| tctgaagttg aaaacaagga tatatcattg gagcaagtgt tggatcttgt atggaatatg | | 2876 |
| gatggatcac ttgtaaggac agtgcctggg aactggtgta gctgcaagga ttgagaatgg | | 2936 |
| catgcattag ctcactttca tttaatccat tgtcaaggat gacatgcttt cttcacagta | | 2996 |

```
actcagttca agtactatgg tgatttgcct acagtgatgt ttggaatcga tcatgctttc   3056
ttcaaggtga caggtctaaa gagagaagaa tccagggaac aggtagagga cattgctttt   3116
tcacttccaa ggtgcttgat caacatctcc ctgacaacac aaaactagag ccagggggcct  3176 ccgtgaactc ccagagcatg cctgataaa actcatttct actgttctct aactgtggag    3236
tgaatggaaa ttccaactgt atgttcaccc tctgaagtgg gtacccagtc tcttaaatct   3296
tttgtatttg ctcacagtgt ttgagcagtg ctgagcacaa agcagacact caataaatgc   3356
tagatttaca cactcaaaaa aaaaaaaaaa gggcggccgc                          3396
```

<210> SEQ ID NO 2
<211> LENGTH: 805
<212> TYPE: PRT
<213> ORGANISM: Homo sapiens

<400> SEQUENCE: 2

```
Met Ser Ser Ser Trp Leu Leu Leu Ser Leu Val Ala Val Thr Ala
 1               5                  10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300
```

```
Gln Arg Ile Phe Lys Glu Ala Glu Lys Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
            610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
            645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
            690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
```

```
                        725                 730                 735
Pro Pro Val Ser Ile Trp Leu Ile Val Phe Gly Val Met Gly Val
            740                 745                 750
Ile Val Val Gly Ile Val Ile Leu Ile Phe Thr Gly Ile Arg Asp Arg
                755                 760                 765
Lys Lys Lys Asn Lys Ala Arg Ser Gly Glu Asn Pro Tyr Ala Ser Ile
        770                 775                 780
Asp Ile Ser Lys Gly Glu Asn Asn Pro Gly Phe Gln Asn Thr Asp Asp
785                 790                 795                 800
Val Gln Thr Ser Phe
                805
```

<210> SEQ ID NO 3
<211> LENGTH: 9
<212> TYPE: PRT
<213> ORGANISM: Homo sapiens

<400> SEQUENCE: 3

```
Ile Ala Arg Arg His Pro Tyr Phe Leu
1               5
```

<210> SEQ ID NO 4
<211> LENGTH: 7
<212> TYPE: PRT
<213> ORGANISM: Homo sapiens

<400> SEQUENCE: 4

```
Tyr Val Ala Asp Ala Pro Lys
1               5
```

<210> SEQ ID NO 5
<211> LENGTH: 7
<212> TYPE: PRT
<213> ORGANISM: Homo sapiens

<400> SEQUENCE: 5

```
Tyr Val Ala Asp Ala Pro Lys
1               5
```

<210> SEQ ID NO 6
<211> LENGTH: 19
<212> TYPE: PRT
<213> ORGANISM: Homo sapiens

<400> SEQUENCE: 6

```
Asn Thr Asn Ile Thr Glu Glu Asn Val Gln Asn Met Asn Asn Ala Gly
1               5                   10                  15
Asp Lys Trp
```

<210> SEQ ID NO 7
<211> LENGTH: 21
<212> TYPE: PRT
<213> ORGANISM: Homo sapiens

<400> SEQUENCE: 7

```
Asn His Tyr Glu Asp Tyr Gly Asp Tyr Trp Arg Gly Asp Tyr Glu Val
1               5                   10                  15
Asn Gly Val Asp Gly
            20
```

<210> SEQ ID NO 8

```
<211> LENGTH: 20
<212> TYPE: PRT
<213> ORGANISM: Homo sapiens

<400> SEQUENCE: 8

Glu Pro Val Pro His Asp Glu Thr Tyr Cys Asp Pro Ala Ser Leu Phe
 1               5                  10                  15

His Val Ser Asn
            20

<210> SEQ ID NO 9
<211> LENGTH: 20
<212> TYPE: PRT
<213> ORGANISM: Homo sapiens

<400> SEQUENCE: 9

Ile Arg Met Ser Arg Ser Arg Ile Asn Asp Ala Phe Arg Leu Asn Asp
 1               5                  10                  15

Asn Ser Leu Glu
            20

<210> SEQ ID NO 10
<211> LENGTH: 18
<212> TYPE: PRT
<213> ORGANISM: Homo sapiens

<400> SEQUENCE: 10

Asp Ile Ser Lys Gly Glu Asn Asn Pro Gly Phe Gln Asn Thr Asp Asp
 1               5                  10                  15

Val Gln

<210> SEQ ID NO 11
<211> LENGTH: 30
<212> TYPE: DNA
<213> ORGANISM: Homo sapiens

<400> SEQUENCE: 11
ttaagttcta gatttctgat tatgagacac                                      30

<210> SEQ ID NO 12
<211> LENGTH: 30
<212> TYPE: DNA
<213> ORGANISM: Homo sapiens

<400> SEQUENCE: 12
gctatacatt ctagacatta actctcattg                                      30

<210> SEQ ID NO 13
<211> LENGTH: 66
<212> TYPE: DNA
<213> ORGANISM: Homo sapiens

<400> SEQUENCE: 13
aagtaagatt cactttaatc ttgtccgttt ttatgcagaa tcaagcgaca agcttctcga     60
gatctg                                                                66

<210> SEQ ID NO 14
<211> LENGTH: 69
<212> TYPE: DNA
<213> ORGANISM: Homo sapiens

<400> SEQUENCE: 14
```

```
caaaagaaaa attaccgcta tcttcttgaa aatcggatgg cagaatcgac ctgcagccaa    60
ataacttcg                                                            69
```

<210> SEQ ID NO 15
<211> LENGTH: 10
<212> TYPE: PRT
<213> ORGANISM: Homo sapiens

<400> SEQUENCE: 15

Asp Arg Val Tyr Ile His Pro Phe His Leu
 1               5                  10

<210> SEQ ID NO 16
<211> LENGTH: 9
<212> TYPE: PRT
<213> ORGANISM: Homo sapiens

<400> SEQUENCE: 16

Asp Arg Val Tyr Ile His Pro Phe His
 1               5

<210> SEQ ID NO 17
<211> LENGTH: 8
<212> TYPE: PRT
<213> ORGANISM: Homo sapiens

<400> SEQUENCE: 17

Asp Arg Val Tyr Ile His Pro Phe
 1               5

<210> SEQ ID NO 18
<211> LENGTH: 13
<212> TYPE: PRT
<213> ORGANISM: Homo sapiens

<400> SEQUENCE: 18

Gln Arg Pro Arg Leu Ser His Lys Gly Pro Met Pro Phe
 1               5                  10

<210> SEQ ID NO 19
<211> LENGTH: 13
<212> TYPE: PRT
<213> ORGANISM: Homo sapiens

<400> SEQUENCE: 19

Gln Arg Pro Arg Leu Ser His Lys Gly Pro Met Pro Phe
 1               5                  10

<210> SEQ ID NO 20
<211> LENGTH: 9
<212> TYPE: PRT
<213> ORGANISM: Homo sapiens

<400> SEQUENCE: 20

Arg Pro Pro Gly Phe Ser Pro Phe Arg
 1               5

<210> SEQ ID NO 21
<211> LENGTH: 8
<212> TYPE: PRT
<213> ORGANISM: Homo sapiens

<400> SEQUENCE: 21

Arg Pro Pro Gly Phe Ser Pro Phe

-continued

<210> SEQ ID NO 22
<211> LENGTH: 9
<212> TYPE: PRT
<213> ORGANISM: Homo sapiens

<400> SEQUENCE: 22

Lys Arg Pro Pro Gly Phe Ser Pro Phe
1               5

<210> SEQ ID NO 23
<211> LENGTH: 7
<212> TYPE: PRT
<213> ORGANISM: Homo sapiens

<400> SEQUENCE: 23

Tyr Pro Phe Val Glu Pro Ile
1               5

<210> SEQ ID NO 24
<211> LENGTH: 13
<212> TYPE: PRT
<213> ORGANISM: Homo sapiens

<400> SEQUENCE: 24

Tyr Gly Gly Phe Leu Arg Arg Ile Arg Pro Lys Leu Lys
1               5                   10

<210> SEQ ID NO 25
<211> LENGTH: 12
<212> TYPE: PRT
<213> ORGANISM: Homo sapiens

<400> SEQUENCE: 25

Glu Ser Lys Lys Pro Pro Ala Lys Leu Gln Pro Arg
1               5                   10

<210> SEQ ID NO 26
<211> LENGTH: 7
<212> TYPE: PRT
<213> ORGANISM: Homo sapiens

<400> SEQUENCE: 26

Leu Tyr Glu Asn Lys Pro Arg
1               5

<210> SEQ ID NO 27
<211> LENGTH: 10
<212> TYPE: PRT
<213> ORGANISM: Homo sapiens

<400> SEQUENCE: 27

Asp Arg Val Tyr Ile His Pro Phe His Leu
1               5                   10

<210> SEQ ID NO 28
<211> LENGTH: 8
<212> TYPE: PRT
<213> ORGANISM: Homo sapiens

<400> SEQUENCE: 28

Asp Arg Val Tyr Ile His Pro Phe
1               5

-continued

<210> SEQ ID NO 29
<211> LENGTH: 13
<212> TYPE: PRT
<213> ORGANISM: Homo sapiens

<400> SEQUENCE: 29

Gln Arg Pro Arg Leu Ser His Lys Gly Pro Met Pro Phe
1 5 10

<210> SEQ ID NO 30
<211> LENGTH: 7
<212> TYPE: PRT
<213> ORGANISM: Homo sapiens

<400> SEQUENCE: 30

Tyr Pro Phe Val Glu Pro Ile
1 5

<210> SEQ ID NO 31
<211> LENGTH: 8
<212> TYPE: PRT
<213> ORGANISM: Homo sapiens

<400> SEQUENCE: 31

Arg Pro Pro Gly Phe Ser Pro Phe
1 5

<210> SEQ ID NO 32
<211> LENGTH: 9
<212> TYPE: PRT
<213> ORGANISM: Homo sapiens

<400> SEQUENCE: 32

Lys Arg Pro Pro Gly Phe Ser Pro Phe
1 5

<210> SEQ ID NO 33
<211> LENGTH: 13
<212> TYPE: PRT
<213> ORGANISM: Homo sapiens

<400> SEQUENCE: 33

Tyr Gly Gly Phe Leu Arg Arg Ile Arg Pro Lys Leu Lys
1 5 10

<210> SEQ ID NO 34
<211> LENGTH: 7
<212> TYPE: PRT
<213> ORGANISM: Homo sapiens

<400> SEQUENCE: 34

Leu Tyr Glu Asn Lys Pro Arg
1 5